(12) United States Patent
Garcia-Calvo

(10) Patent No.: US 7,901,893 B2
(45) Date of Patent: Mar. 8, 2011

(54) NPC1L1 (NPC3) AND METHODS OF IDENTIFYING LIGANDS THEREOF

(75) Inventor: Maria Margarita Garcia-Calvo, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 874 days.

(21) Appl. No.: 10/586,310

(22) PCT Filed: Jan. 14, 2005

(86) PCT No.: PCT/US2005/001469
§ 371 (c)(1),
(2), (4) Date: May 31, 2007

(87) PCT Pub. No.: WO2005/069900
PCT Pub. Date: Aug. 4, 2005

(65) Prior Publication Data
US 2010/0009461 A1     Jan. 14, 2010

Related U.S. Application Data

(60) Provisional application No. 60/537,341, filed on Jan. 16, 2004.

(51) Int. Cl.
G01N 33/53     (2006.01)
G01N 33/532    (2006.01)
C07D 205/08    (2006.01)

(52) U.S. Cl. .......... 435/7.1; 435/7.93; 436/544; 548/953

(58) Field of Classification Search .................. None
See application file for complete search history.

(56) References Cited

U.S. PATENT DOCUMENTS

| | | |
|---|---|---|
| 5,306,817 A | 4/1994 | Thiruvengadam et al. |
| 5,561,227 A | 10/1996 | Thiruvengadam et al. |
| 5,618,707 A | 4/1997 | Homann et al. |
| 5,624,920 A | 4/1997 | McKittrick et al. |
| 5,627,176 A | 5/1997 | Kirkup et al. |
| 5,631,365 A | 5/1997 | Rosenblum et al. |
| 5,633,246 A | 5/1997 | McKittrick et al. |
| 5,656,624 A | 8/1997 | Vaccaro et al. |
| 5,661,145 A | 8/1997 | Davis |
| 5,688,785 A | 11/1997 | Vaccaro |
| 5,688,787 A | 11/1997 | Burnett et al. |
| 5,688,990 A | 11/1997 | Shankar |
| 5,698,548 A | 12/1997 | Dugar et al. |
| 5,728,827 A | 3/1998 | Thiruvengadam et al. |
| 5,739,321 A | 4/1998 | Wu et al. |
| 5,744,467 A | 4/1998 | McKittrick et al. |
| 5,756,470 A | 5/1998 | Yumibe et al. |
| 5,767,115 A | 6/1998 | Rosenblum et al. |
| 5,846,966 A | 12/1998 | Rosenblum et al. |
| 5,856,473 A | 1/1999 | Shankar |
| 5,886,171 A | 3/1999 | Wu et al. |
| 5,919,672 A | 7/1999 | Homann et al. |
| 6,093,812 A | 7/2000 | Thiruvengadam et al. |
| 6,096,883 A | 8/2000 | Wu et al. |
| 6,133,001 A | 10/2000 | Homann et al. |
| 6,207,822 B1 | 3/2001 | Thiruvengadam et al. |
| RE37,721 E | 5/2002 | Rosenblum et al. |
| 6,426,198 B1 | 7/2002 | Carstea et al. |
| 6,593,078 B1 | 7/2003 | Altmann et al. |
| 6,627,757 B2 | 9/2003 | Fu et al. |
| 6,632,933 B2 | 10/2003 | Altmann et al. |
| 7,135,556 B2 * | 11/2006 | Altmann et al. ............. 530/395 |
| 2002/0151536 A1 | 10/2002 | Davis et al. |
| 2004/0093629 A1 | 5/2004 | Altmann et al. |
| 2004/0132058 A1 | 7/2004 | Altmann et al. |
| 2004/0137467 A1 | 7/2004 | Altmann et al. |
| 2004/0161838 A1 | 8/2004 | Altmann et al. |

FOREIGN PATENT DOCUMENTS

| | | |
|---|---|---|
| WO | WO 00/20623 | 4/2000 |
| WO | WO 00/34240 | 6/2000 |
| WO | WO 00/60107 | 10/2000 |
| WO | WO 00/63703 | 10/2000 |
| WO | WO 01/57190 | 8/2001 |
| WO | WO 01/70974 | 9/2001 |
| WO | WO 01/75067 A2 | 10/2001 |
| WO | WO 01/75067 A3 | 10/2001 |
| WO | WO 02/079174 | 10/2002 |
| WO | WO 03/100094 | 12/2003 |
| WO | WO 2004/009772 A | 1/2004 |
| WO | WO2004/014947 A1 | 2/2004 |
| WO | WO2004/032716 A2 | 4/2004 |
| WO | WO2005/069900 | 8/2005 |
| WO | WO2006015365 A1 | 2/2006 |

OTHER PUBLICATIONS

Heek et al. Comparison of the activity and diposition of the novel cholesterol absorption inhibitor, SCH58235, and its glucuronide, SCH60663. British Journal of Pharmacology 2000, vol. 129, pp. 1748-1754.*

Burnett, D. A. et al., "Synthesis of iodinated biochemical tools related to the 2-azetidinone class of cholesterol absorption inhibitors", *Bioorganic & Medicinal Chemistry Letters*, vol. 12, pp. 311-314, (2002).

Burnett D. A. et al., "Synthesis of fluorescent biochemical tools related to the 2-azetidinone class of cholesterol absorption inhibitors", *Bioorganic & Medicinal Chemistry Letters*, vol. 12, pp. 315-318, (2002).

Garcia-Calvo, Margarita et al., "The target of ezetimibe is Niemann-Pick C1-Like 1 (NPC1L1)", *Proceedings of the National Academy of Sciences of USA*, National Academy of Science, Washington, D.C., vol. 102, No. 23, pp. 8132-8137, (Jun. 7, 2005).

Erickson et al., J. Neuroscience Research, Jun. 2002, pp. 738-744, vol. 68.

Erickson et al., J. Inher. Metab. Dis., Feb. 2000, pp. 54-62, vol. 23.

Erickson et al., Molecular Reproduction and Development, 2002, pp. 167-173, vol. 62.

Altmann et al., Science., Feb. 2004, pp. 1201-1204, vol. 303.

Davies et al., The Journal of Biological Chemistry, Apr. 1, 2005, pp. 12710-12720, vol. 280, No. 13.

(Continued)

*Primary Examiner* — Shafiqul Haq
(74) *Attorney, Agent, or Firm* — Carol S. Quagliato; Catherine D. Fitch

(57) ABSTRACT

The present invention provides human, rat and mouse NPC1L1 polypeptides and polynucleotides encoding the polypeptides. Methods for detecting ligands which bind to NPC1L1 and block intestinal cholesterol absorption are provided. Also included is a method of identifying ligands which bind to NPC1L1 using membranes derived from brush border membrane preparations. Compounds that bind to NPC1L1 can be used for inhibiting intestinal cholesterol absorption in a subject.

10 Claims, 15 Drawing Sheets

OTHER PUBLICATIONS

Ioannou, Nat. Rev. Molecular Cell Biology, Sep. 2001, pp. 657-668, vol. 2.
Blom et al., Human Molecular Genetics, 2003, pp. 257-272, vol. 12, No. 3.
Minhas, Br. J. Cardiol., 2003, pp. 59-68, vol. 10.
Abstracts 1-79, The International Conference on Niemann-Pick Type C Disease, May 29-31, 2003; Tuscon, Arizona.
Carstea et al., Science, 1997, vol. 277, pp. 228-231.
Davies et al., Genomics, 2000, pp. 137-145, vol. 65, Issue 2.
Ioannou et al., Mol. Genet. Metab., 2000, pp. 175-181, vol. 71, No. 1-2.
Altmann et al., Biochim. Biophys. ACTA, 2002, pp. 77-93, vol. 1580.
Deninno et al., J. Med. Chem., 1997, vol. 40, pp. 2547-2554, No. 16.
Kramer et al., Falk Symposium 129, 2002, pp. 147-160, vol. 129.
Amigo et al., Hepatology, 2002, vol. 36, pp. 819-828, No. 4.
Repa et al. Journal of Lipid Research, 2002, pp. 1864-1874, vol. 43.
Hauser et al., Biochemistry, 1998, vol. 37, pp. 17843-17850, No. 51.
Acton et al., The Journal of Biological Chemistry, 1994, vol. 269, pp. 21003-21009, No. 33.
Hernandez et al., Biochimica et Biophysica Acta, 2000, pp. 232-242, vol. 1486.
Detmers et al., Biochimica et Biophysica Acta, 2000, pp. 243-252, vol. 1486.
Smart et al., Proc. Natl. Acad. Sci., 2004, pp. 3450-3455, vol. 101, No. 10.
Dawson et al., Curr. Opin. Lipidol, 1999, pp. 315-320, vol. 10, No. 14.
Allayee et al., Science, 2000, pp. 1709-1711, vol. 290, No. 5497.
Berge et al., Science, 2000, pp. 1771-1775, vol. 290, No. 5497.
Jourdheuil-Rahmani et al., Biochem Biophys Res. Commun., 2002, pp. 390-395, vol. 292, No. .2.
Werder et al., Biochemistry, 2001, pp. 11643-11650, vol. 40, No. 38.
GenBank Sequence Disclosure; Accession No. AF192522.1 (2003).
GenBank Sequence Disclosure; Accession No. AF002020.1 (1997).
GenRank Sequence Disclosure; Accession No. AK078947.1 (2008).
Zetia™ Product Information Sheet (2009).
Mouse Gene Informatics (MGI) web page Gene Detail for NPC1L1 gene; [Internet] http://www.informatics.jax.org/searches/accession_report.cgi?id=MGI:2685089 (2010).

* cited by examiner

Figure 1. Equilibrium binding of EZE-glucuronide to rhesus BBMVs

Figure 2. Equilibrium binding of EZE-glucuronide to rat BBMV.

Figure 3. Association and dissociation kinetics of $^3$H-EZE-glucuronide in rat BBMV.

Figure 4. Association and Dissociation kinetics of $^3$H-EZE-glucuronide in rhesus BBMV.

Figure 5. Displacement of 3H-EZE-glucuronide by EZE-glucuronide and compound 2 in rhesus and rat BBMV.

Figure 6. Displacement of $^{35}$S-labeled compound $\underline{2}$ by EZE-glucuronide and compound $\underline{2}$ in mouse BBMV.

Figure 7. Intestinal distribution of ezetimibe binding sites.

Figure 8. Displacement of $^{35}$S-labeled compound 2 by EZE-glucuronide and analogs in transfected CHO cells expressing rat NPC1L1

Figure 9. Displacement of $^{35}$S-labeled compound 2 by EZE-glucuronide and analogs in transfected CHO cells expressing human NPC1L1

Figure 10. $^{35}$S-labeled compound 2 binding with brush border membranes from intestinal mucosal scrapings of male wild type (A) and NPC1L1 knockout (-/-) mice (B).

Figure 11. Displacement of ³⁵S-labeled compound 2 by compound 2 in mouse wild type and knockout mouse NPC1L1 (-/-) BBMV.

FIGURE 12
Competition
A
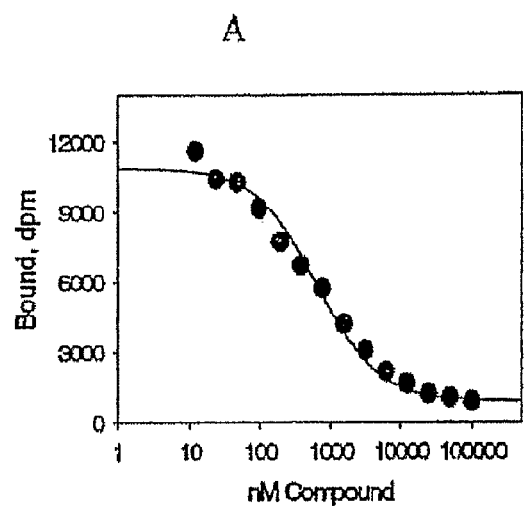
B
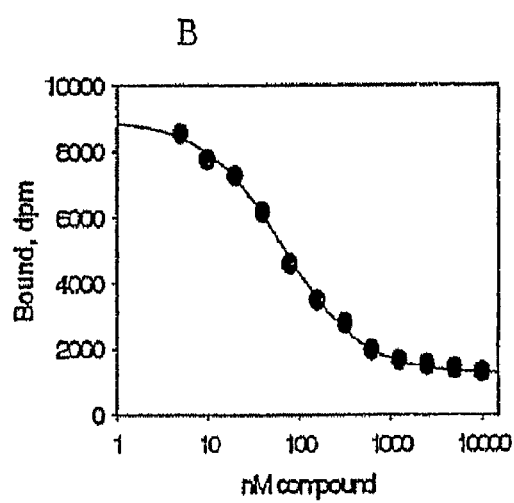

FIGURE 13
Panel 1
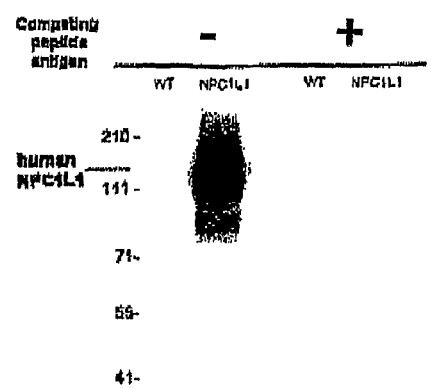
Panel 2
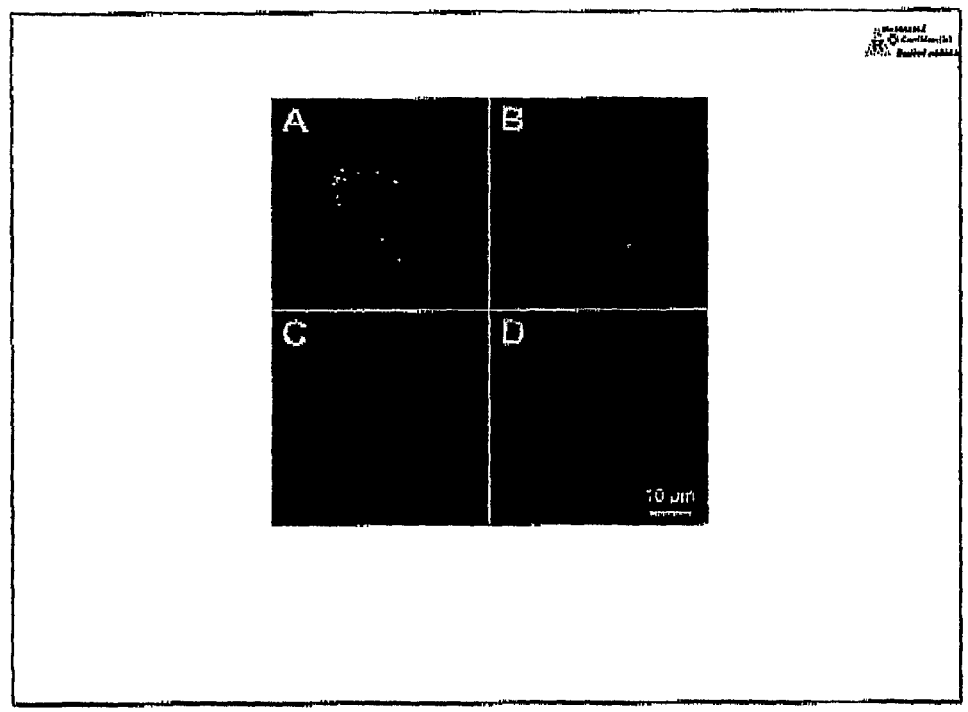

NPC1L1 (NPC3) AND METHODS OF IDENTIFYING LIGANDS THEREOF

This application claims priority to Ser. No. 60/537,341, filed Jan. 16, 2004.

The invention claimed herein was made on behalf of Merck & Co., Inc. and Schering-Plough Corporation, parties to a joint research agreement that was in effect on or before the date the claimed invention was made.

FIELD OF THE INVENTION

The present invention includes NPC1L1 polypeptides and polynucleotides which encode the polypeptides, methods of use and methods of identifying modulators and ligands thereof.

BACKGROUND OF THE INVENTION

A factor leading to development of vascular disease, a leading cause of death in industrialized nations, is elevated serum cholesterol. It is estimated that 19% of Americans between the ages of 20 and 74 years of age have high serum cholesterol. The most prevalent form of vascular disease is arteriosclerosis, a condition associated with the thickening and hardening of the arterial wall. Arteriosclerosis of the large vessels is referred to as atherosclerosis. Atherosclerosis is the predominant underlying factor in vascular disorders such as coronary artery disease, aortic aneurysm, arterial disease of the lower extremities and cerebrovascular disease.

Cholesteryl esters are a major component of atherosclerotic lesions and the major storage form of cholesterol in arterial wall cells. Formation of cholesteryl esters is also a step in the intestinal absorption of dietary cholesterol. Thus, inhibition of cholesteryl ester formation and reduction of serum cholesterol can inhibit the progression of atherosclerotic lesion formation, decrease the accumulation of cholesteryl esters in the arterial wall, and block the intestinal absorption of dietary cholesterol.

The regulation of whole-body cholesterol homeostasis in mammals and animals involves the regulation of intestinal cholesterol absorption, cellular cholesterol trafficking, dietary cholesterol and modulation of cholesterol biosynthesis, bile acid biosynthesis, steroid biosynthesis and the catabolism of the cholesterol-containing plasma lipoproteins. Regulation of intestinal cholesterol absorption has proven to be an effective means by which to regulate serum cholesterol levels. For example, a cholesterol absorption inhibitor, ezetimibe

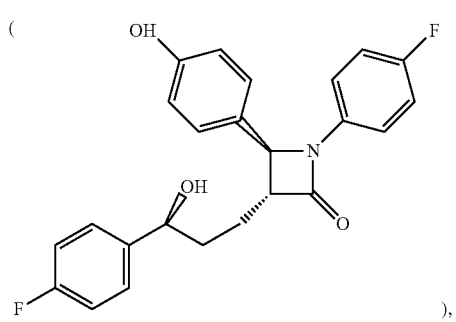

has been shown to be effective in this regard. A pharmaceutical composition containing ezetimibe is commercially available from Merck/Schering-Plough Pharmaceuticals, Inc. under the trade name Zetia®. Identification of a gene target through which ezetimibe acts is important to understanding the process of cholesterol absorption and to the development of other, novel absorption inhibitors. The present invention addresses this need by providing a rat and a mouse homologue of human NPC1L1 (also known as NPC3; Genbank Accession No. AF192522; Davies, et al., (2000) Genomics 65(2): 137-45 and Ioannou, (2000) Mol. Genet. Metab. 71(1-2): 175-81), an ezetimibe target.

NPC1L1 is an N-glycosylated protein comprising a YQRL (SEQ ID NO: 38) motif (i.e., a trans-golgi network to plasma membrane transport signal; see Bos, et al., (1993) EMBO J. 12: 2219-2228; Humphrey, et al., (1993) J. Cell. Biol. 120: 1123-1135; Ponnambalam, et al., (1994) J. Cell. Biol. 125: 253-268 and Rothman, et al., (1996) Science 272: 227-234) which exhibits limited tissue distribution and gastrointestinal abundance. Also, the human NPC1L1 promoter includes a Sterol Regulated Element Binding Protein 1 (SREBP1) binding consensus sequence (Athanikar, et al., (1998) Proc. Natl. Acad. Sci. USA 95: 4935-4940; Ericsson, et al., (1996) Proc. Natl. Acad. Sci. USA 93: 945-950; Metherall, et al., (1989) J. Biol. Chem. 264: 15634-15641; Smith, et al., (1990) J. Biol. Chem. 265: 2306-2310; Bennett, et al., (1999) J. Biol. Chem. 274: 13025-13032 and Brown, et al., (1997) Cell 89: 331-340). NPC1L1 has 42% amino acid sequence homology to human NPC1 (Genbank Accession No. AF002020), a receptor responsible for Niemann-Pick C1 disease (Carstea, et al., (1997) Science 277: 228-231). Niemann-Pick C1 disease is a rare genetic disorder in humans which results in accumulation of low density lipoprotein (LDL)-derived unesterified cholesterol in lysosomes (Pentchev, et al., (1994) Biochim. Biophys. Acta. 1225: 235-243 and Vanier, et al., (1991) Biochim. Biophys. Acta. 1096: 328-337). In addition, cholesterol accumulates in the trans-golgi network of npc1⁻ cells, and relocation of cholesterol, to and from the plasma membrane, is delayed. NPC1 and NPC1L1 each possess 13 transmembrane spanning segments as well as a sterol-sensing domain (SSD). Several other proteins, including HMG-CoA Reductase (HMG-R), Patched (PTC) and Sterol Regulatory Element Binding Protein Cleavage-Activation Protein (SCAP), include an SSD which is involved in sensing cholesterol levels possibly by a mechanism which involves direct cholesterol binding (Gil, et al., (1985) Cell 41: 249-258; Kumagai, et al., (1995) J. Biol. Chem. 270: 19107-19113; Hua, et al., (1996) Cell 87: 415-426; and Radhakrishnan, A., et al., "Direct binding of cholesterol to the purified membrane region of SCAP: Mechanism for a sterol-sensing domain," Mol. Cell. 15, 259-268 (2004)).

SUMMARY OF THE INVENTION

The present invention is based on the discovery that NPC1L1 is the target through which ezetimibe acts, and consequently plays a critical role in the regulation of sterol and 5α-stanol intestinal transport and absorption, e.g. cholesterol absorption. Accordingly, this invention provides for the use of NPC1L1 in an assay for identifying ligands that block NPC1L1-mediated sterol and 5α-stanol intestinal transport. The present invention provides methods for identifying ligands of NPC1L1 which involve contacting NPC1L1 with a detectably labeled substituted 2-azetidinone, preferably substituted 2-azetidinone-glucuronide, and a candidate compound, and determining whether the candidate compound binds to NPC1 L1. The modulation of the binding of the substituted 2-azetidinone to NPC1L1 by the binding of the candidate compound to NPC1L1 indicates that the candidate compound is a ligand that binds to NPC1L1 and is an inhibitor of sterol and 5α-stanol absorption.

The present invention also provides a method for identifying a ligand of NPC1L1 comprising contacting NPC1L1 with a detectably labeled substituted 2-azetidinone, preferably substituted 2-azetidinone-glucuronide, and measuring the binding of detectably labeled substituted 2-azetidinone to NPC1L1 in the presence and absence of a candidate compound, wherein decreased binding of the detectably labeled substituted 2-azetidinone to the NPC1L1 in the presence of the candidate compound indicates that said candidate compound is a ligand of NPC1L1 and is an inhibitor of sterol and 5α-stanol absorption.

The present invention also provides for a method for identifying a compound that inhibits intestinal sterol or 5α-stanol absorption mediated by NPC1L1 involving contacting NPC1L1 with a detectably labeled ligand and the candidate compound and determining whether the candidate compound binds to NPC1L1, wherein binding of said candidate compound to NPC1L1 modulates binding of said ligand to NPC1L1, wherein said modulation indicates that the candidate compound is an intestinal sterol or 5α-stanol absorption inhibitor.

The present invention provides methods for identifying an ligand of NPC1L1 comprising (a) contacting a host cell (e.g., human embryonic kidney (HEK) 293 cells, chinese hamster ovary (CHO) cell, a J774 cell, a macrophage cell or a Caco2 cell) expressing a polypeptide comprising the amino acid sequence of SEQ ID NO: 2 or SEQ ID NO: 4 or SEQ ID NO: 12 or a functional fragment thereof on a cell surface, in the presence of a known amount of a detectably labeled (e.g., with $^3$H, $^{14}$C, $^{125}$I, $^{35}$S or fluorescence labeling) substituted azetidinone (e.g., ezetimibe), with a sample to be tested for the presence of an NPC1L1 ligand; and (b) measuring the amount of detectably labeled substituted azetidinone (e.g., ezetimibe) specifically bound to the polypeptide; wherein an NPC1L1 ligand in the sample is identified by measuring substantially reduced binding of the detectably labeled substituted azetidinone (e.g., ezetimibe) to the polypeptide, compared to what would be measured in the absence of such a ligand.

Another method for identifying a ligand of NPC1L1 is also provided. The method comprises (a) placing, in an aqueous suspension, a plurality of support particles, impregnated with a fluorescer (e.g., yttrium silicate, yttrium oxide, diphenyloxazole and polyvinyltoluene), to which a host cell (e.g., chinese hamster ovary (CHO) cell, a J774 cell, a macrophage cell or a Caco2 cell) expressing a polypeptide comprising the amino acid sequence of SEQ ID NO: 2 or SEQ ID NO: 4 or SEQ ID NO: 12 or a functional fragment thereof on a cell surface are attached; (b) adding, to the suspension, a radiolabeled (e.g., with $^3$H, $^{14}$C or $^{125}$I) substituted azetidinone (e.g., ezetimibe) and a sample to be tested for the presence of a ligand, wherein the radiolabel emits radiation energy capable of activating the fluorescer upon the binding of the substituted azetidinone (e.g., ezetimibe) to the polypeptide to produce light energy, whereas radiolabeled substituted azetidinone (e.g., ezetimibe) that does not bind to the polypeptide is, generally, too far removed from the support particles to enable the radioactive energy to activate the fluorescer; and (c) measuring the light energy emitted by the fluorescer in the suspension; wherein an NPC1L1 ligand in the sample is identified by measuring substantially reduced light energy emission, compared to what would be measured in the absence of such a ligand.

Also provided is a method for identifying a ligand of NPC1L1 comprising (a) contacting a host cell (e.g., Chinese hamster ovary (CHO) cell, a J774 cell, a macrophage cell or a Caco2 cell) expressing a polypeptide comprising an amino acid sequence of SEQ ID NO: 2 or SEQ ID NO: 4 or SEQ ID NO: 12 or a functional fragment thereof on a cell surface with detectably labeled (e.g., with $^3$H, $^{14}$C or $^{125}$I) sterol (e.g., cholesterol) or 5α-stanol and with a sample to be tested for the presence of an ligand; and (b) measuring the amount of detectably labeled sterol (e.g., cholesterol) or 5α-stanol in the cell; wherein an NPC1L1 antagonist in the sample is identified by measuring substantially reduced detectably labeled sterol (e.g., cholesterol) or 5α-stanol within the host cell, compared to what would be measured in the absence of such an antagonist and wherein an NPC1L1 agonist in the sample is identified by measuring substantially increased detectably labeled sterol (e.g., cholesterol) or 5α-stanol within the host cell, compared to what would be measured in the absence of such an agonist.

The present invention includes methods for inhibiting NPC1L1-mediated intestinal sterol (e.g., cholesterol) or 5α-stanol uptake, in a subject, by administering a substance identified by the screening methods described herein to the subject. Such substances include compounds such as small molecule antagonists of NPC1L1 other than ezetimibe. Also contemplated are methods for antagonizing NPC1L1-mediated sterol (e.g., cholesterol) or 5α-stanol absorption by administering anti-NPC1L1 antibodies. NPC1L1-mediated absorption of sterol (e.g., cholesterol) or 5α-stanol can also be antagonized by any method which reduces expression of NPC1L1 in an organism. For example, NPC1L1 expression can be reduced by introduction of anti-sense NPC1L1 mRNA into a cell of an organism or by genetic mutation of the NPC1L1 gene in an organism (e.g., by complete knockout, disruption, truncation or by introduction of one or more point mutations).

Also included in the present invention is a mutant transgenic mammal (e.g., mouse, rat, dog, rabbit, pig, guinea pig, cat, horse), preferably a mouse comprising a homozygous or heterozygous mutation (e.g., disruption, truncation, one or more point mutations, knock out) of endogenous, chromosomal NPC1L1 wherein, preferably, the mouse does not produce any functional NPC1L1 protein. Preferably, the mutant mouse, lacking functional NPC1L1, exhibits a reduced level of intestinal sterol (e.g., cholesterol) or 5α-stanol absorption and/or a reduced level of serum sterol (e.g., cholesterol) or 5α-stanol and/or a reduced level of liver sterol (e.g., cholesterol) or 5α-stanol as compared to that of a non-mutant mouse comprising functional NPC1L1. Preferably, in the mutant mouse chromosome, the region of NPC1L1 (SEQ ID NO: 45) deleted is from nucleotide 790 to nucleotide 998. In one embodiment, NPC1L1 (SEQ ID NO: 11) is deleted from nucleotide 767 to nucleotide 975. Any offspring or progeny of a parent NPC1L1 mutant mouse (i.e., npc1l1) of the invention which has inherited an npc1l1 mutant allele is also part of the present invention.

The scope of the present invention also includes a method for screening a sample for an intestinal sterol (e.g., cholesterol) or 5α-stanol absorption antagonist comprising (a) feeding a sterol (e.g., cholesterol) or 5α-stanol-containing substance (e.g., comprising radiolabeled cholesterol, such as $^{14}$C-cholesterol or $^3$H-cholesterol) to a first and second mouse comprising a functional NPC1L1 gene and to a third, mutant mouse lacking a functional NPC1L1; (b) administering the sample to the first mouse comprising a functional NPC1L1 but not to the second mouse; (c) measuring the amount of sterol (e.g., cholesterol) or 5α-stanol absorption in the intestine of said first, second and third mouse (e.g., by measuring serum cholesterol); and (d) comparing the levels of intestinal sterol (e.g., cholesterol) or 5α-stanol absorption in each mouse; wherein the sample is determined to contain the intestinal sterol (e.g., cholesterol) or 5α-stanol absorption antagonist when the level of intestinal sterol (e.g., cholesterol) or 5α-stanol absorption in the first mouse and third mouse are less than the amount of intestinal sterol (e.g., cholesterol) or 5α-stanol absorption in the second mouse.

The present invention also encompasses a kit comprising (a) a substituted azetidinone (e.g., ezetimibe) in a pharmaceutical dosage form (e.g., a pill or tablet comprising 10 mg substituted azetidinone (e.g., ezetimibe)); and (b) information, for example in the form of an insert, indicating that NPC1L1 is a target of ezetimibe. The kit may also include simvastatin in a pharmaceutical dosage form (e.g., a pill or tablet comprising 5 mg, 10 mg, 20 mg, 40 mg or 80 mg simvastatin). The simvastatin in pharmaceutical dosage form and the ezetimibe in pharmaceutical dosage form can be associated in a single pill or tablet or in separate pills or tablets.

The present invention also provides any isolated mammalian cell (e.g., isolated mouse cell, isolated rat cell or isolated human cell) which lacks a gene which encodes or can produce a functional NPC1L1 polypeptide. The isolated cell can be isolated from a mutant mouse comprising a homozygous mutation of endogenous, chromosomal NPC1L1 wherein the mouse does not produce any functional NPC1L1 protein. Further, the mutation can be in a gene which when un-mutated encodes an amino acid sequence of SEQ ID NO: 12 (e.g., comprising a nucleotide sequence of SEQ ID NO: 11). The cell can be isolated or derived from duodenum, gall bladder, liver, small intestine or stomach tissue. The cell can be an enterocyte.

BRIEF DESCRIPTION OF THE FIGURES

FIG. 12A shows equilibrium determination of $K_D$ for ezetimibe glucuronide by competition of unlabeled compound against 1 in rat enterocyte brush border membranes. Membranes (1.5 mg/ml protein) were incubated with 1 (50 nM) and the indicated concentrations of ezetimibe glucuronide for 1 hour to ensure equilibrium. $K_D$ at equilibrium is 600 nM. FIG. 12B shows the corresponding measurement for rhesus monkey, which were conducted between 0.5 and 1.25 mg/ml protein and 22-50 nM 1, with incubation time of more than 3 hours. $K_D$ at equilibrium is 38.6 nM.

FIG. 13 shows the expression of NPC1L1 in HEK-293 cells using Western blot analysis (Panel 1) and immunofluorescence (Panel 2).

DETAILED DESCRIPTION OF THE INVENTION

Figure 1:
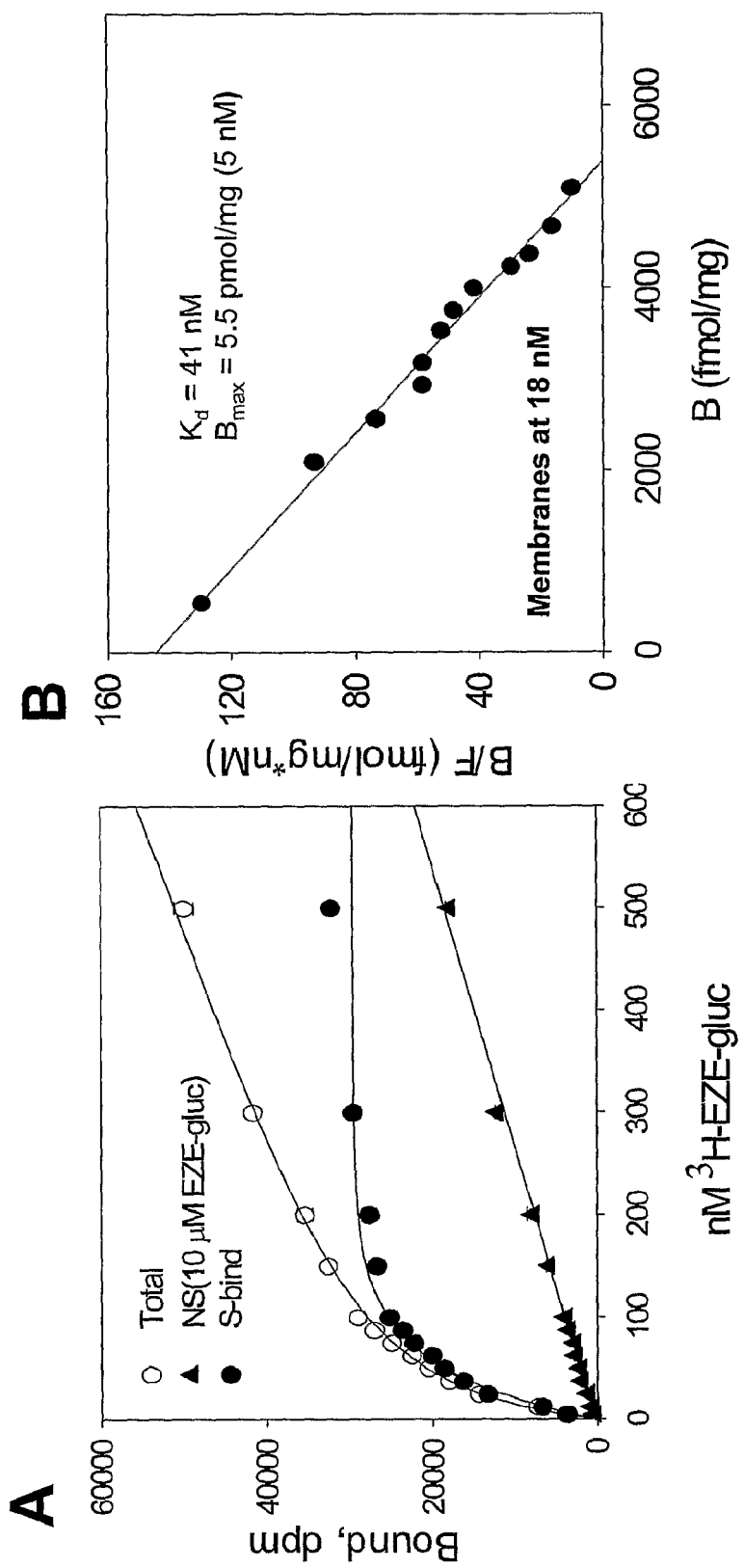
FIG. 1A shows an equilibrium saturation binding plot exhibiting the binding of $^3$H-EZE-glucuronide to rhesus brush border membrane (BBM) vesicles. Observed total binding (Total) is shown as open circles; nonspecific binding (NS) as triangles, and specific binding (S-bind) as solid circles.
FIG. 1B shows a scatchard analysis of $^3$H-EZE-glucuronide binding to rhesus brush border membrane vesicles.

The present invention includes NPC1L1 polypeptides from rat, human and mouse, along with polynucleotides encoding the respective polypeptides. Preferably, the rat NPC1L1 polypeptide comprises the amino acid sequence set forth in SEQ ID NO: 2, the human NPC1L1 comprises the amino acid sequence set forth in SEQ ID NO: 4 and the mouse NPC1L1 polypeptide comprises the amino acid sequence set forth in SEQ ID NO: 12. The rat NPC1L1 polynucleotide of SEQ ID NO: 1 or 10 encodes the rat NPC1L1 polypeptide. The human NPC1L1 polynucleotide of SEQ ID NO: 3 encodes the human NPC1L1 polypeptide. The mouse NPC1L1 polynucleotide of SEQ ID NO: 11 or 13 encodes the mouse NPC1L1 polypeptide.

The present invention includes any isolated polynucleotide or isolated polypeptide comprising a nucleotide or amino acid sequence referred to, below, in Table 1.

TABLE 1

Polynucleotides and Polypeptides of the Invention.

| Polynucleotide or Polypeptide | Sequence Identifier |
|---|---|
| Rat NPC1L1 polynucleotide | SEQ ID NO: 1 |
| Rat NPC1L1 polypeptide | SEQ ID NO: 2 |
| Human NPC1L1 polynucleotide | SEQ ID NO: 3 |
| Human NPC1L1 polypeptide | SEQ ID NO: 4 |
| Rat NPC1L1 expressed sequence tag 603662080F1 (partial sequence) | SEQ ID NO: 5 |
| Rat NPC1L1 expressed sequence tag 603665037F1 (partial sequence) | SEQ ID NO: 6 |
| Rat NPC1L1 expressed sequence tag 604034587F1 (partial sequence) | SEQ ID NO: 7 |
| EST 603662080F1 with downstream sequences added | SEQ ID NO: 8 |
| EST 603662080F1 with upstream and downstream sequences added | SEQ ID NO: 9 |
| Back-translated polynucleotide sequence of rat NPC1L1 | SEQ ID NO: 10 |
| Mouse NPC1L1 polynucleotide | SEQ ID NO: 11 |
| Mouse NPC1L1 polypeptide | SEQ ID NO: 12 |
| Back-translated polynucleotide sequence of mouse NPC1L1 | SEQ ID NO: 13 |
| Back-translated polynucleotide sequence of human NPC1L1 | SEQ ID NO: 51 |

A human NPC1L1 is also disclosed under Genbank Accession Number AF192522. As discussed below, the nucleotide sequence of the rat NPC1L1 set forth in SEQ ID NO: 1 was obtained from an expressed sequence tag (EST) from a rat jejunum enterocyte cDNA library. SEQ ID NOs: 5-7 include partial nucleotide sequences of three independent cDNA clones. The downstream sequence of the SEQ ID NO: 5 EST (603662080F1) were determined; the sequencing data from these experiments are set forth in SEQ ID NO: 8. The upstream sequences were also determined; these data are set forth in SEQ ID NO: 9.

SEQ ID NOs: 43 and 44 are the nucleotide and amino acid sequence, respectively, of human NPC1L1 which is disclosed under Genbank Accession No.: AF192522 (see Davies, et al., (2000) Genomics 65(2): 137-45).

SEQ ID NO: 45 is the nucleotide sequence of a mouse NPC1L1 which is disclosed under Genbank Accession No. AK078947.

NPC1L1 mediates intestinal sterol (e.g., cholesterol) or 5α-stanol absorption. Inhibition of NPC1L1 in a patient is a useful method for reducing intestinal sterol (e.g., cholesterol) or 5α-stanol absorption and serum sterol (e.g., cholesterol) or 5α-stanol in the patient. Reducing the level of intestinal sterol (e.g., cholesterol) or 5α-stanol absorption and serum sterol (e.g., cholesterol) or 5α-stanol in a patient is a useful way in which to treat or prevent the occurrence of atherosclerosis, particularly diet-induced atherosclerosis.

As used herein, the term "sterol" includes, but is not limited to, cholesterol and phytosterols (including, but not limited to, sitosterol, campesterol, stigmasterol and avenosterol).

As used herein, the term "5α-stanol" includes, but is not limited to, cholestanol, 5α-campestanol and 5α-sitostanol.

Without being limited by the present hypothesis, the examples present a better understanding of the putative molecular interaction between NPC1L1 and cholesterol. In this regard, one of the more interesting features of NPC1L1 is that it contains the sterol-sensing domain (SSD) originally observed in SCAP (SREBP cleavage-activating protein).

SCAP controls activation of sterol regulatory element binding proteins (SREBP), a transcription factor which controls more than 35 genes related to lipid and cholesterol homeostasis (Brown, M. S. & Goldstein, J. L. A proteolytic pathway that controls the cholesterol content of membranes, cells, and blood. *Proc. Natl. Acad. Sci. U.S.A.* 96, 11041-11048 (1999)). The SSD, consisting of ~180 amino acids in a packet of 5 putative membrane-spanning helices, also serves a regulatory function in two key enzymes on the cholesterol biosynthesis pathway and is present in the receptor Patched. Recently, high affinity binding of cholesterol to the SSD on SCAP has been demonstrated (Radhakrishnan, A., Sun, L., Kwon, H. J., Brown, M. S. & Goldstein, J. L., "Direct binding of cholesterol to the purified membrane region of SCAP: Mechanism for a sterol-sensing domain," *Mol. Cell.* 15, 259-268 (2004)), suggesting that cholesterol may similarly bind to the SSD of NPC1L1, and raising the possibility that ezetimibe may compete with cholesterol for binding at this site.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait, ed. 1984); *Nucleic Acid Hybridization* (B. D. Hames & S. J. Higgins, eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

The back-translated sequences of SEQ ID NO: 10 and of SEQ ID NO: 13 uses the single-letter code shown in Table 1 of Annex C, Appendix 2 of the PCT Administrative Instruction in the Manual of Patent Examination Procedure.

A "polynucleotide", "nucleic acid" or "nucleic acid molecule" may refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

The present invention includes nucleic acid fragments of any of SEQ ID NOs: 1, 5-11 or 13. A nucleic acid "fragment" includes at least about 30 (e.g., 31, 32, 33, 34), preferably at least about 35 (e.g, 25, 26, 27, 28, 29, 30, 31, 32, 33 or 34), more preferably at least about 45 (e.g., 35, 36, 37, 38, 39, 40, 41, 42, 43 or 44), and most preferably at least about 126 or more contiguous nucleotides (e.g., 130, 131, 132, 133, 134, 135, 136, 137, 138, 139, 140, 150, 160, 170, 180, 190, 200, 300, 400, 500, 1000 or 1200) from any of SEQ ID NOs: 1, 5-11 or 13.

The present invention also includes nucleic acid fragments consisting of at least about 7 (e.g., 9, 12, 17, 19), preferably at least about 20 (e.g., 30, 40, 50, 60), more preferably about 70 (e.g., 80, 90, 95), yet more preferably at least about 100 (e.g., 105, 110, 114) and even more preferably at least about 115 (e.g., 117, 119, 120, 122, 124, 125, 126) contiguous nucleotides from any of SEQ ID NOs: 1, 5-11 or 13.

As used herein, the term "oligonucleotide" refers to a nucleic acid, generally of no more than about 100 nucleotides (e.g., 30, 40, 50, 60, 70, 80, or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" may refer to a series of two or more amino acids in a protein, peptide or polypeptide.

"Protein", "peptide" or "polypeptide" includes a contiguous string of two or more amino acids. Preferred peptides of the invention include those set forth in any of SEQ ID NOs: 2 or 12 as well as variants and fragments thereof. Such fragments preferably comprise at least about 10 (e.g., 11, 12, 13, 14, 15, 16, 17, 18 or 19), more preferably at least about 20 (e.g., 21, 22, 23, 24, 25, 26, 27, 28, 29, 30, 35, 40), and yet more preferably at least about 42 (e.g., 43, 44, 45, 46, 47, 48, 49, 50, 60, 70, 80, 90, 100, 110, 120 or 130) or more contiguous amino acid residues from any of SEQ ID NOs: 2 or 12.

The present invention also includes polypeptides, preferably antigenic polypeptides, consisting of at least about 7 (e.g., 9, 10, 13, 15, 17, 19), preferably at least about 20 (e.g., 22, 24, 26, 28), yet more preferably at least about 30 (e.g., 32, 34, 36, 38) and even more preferably at least about 40 (e.g., 41, 42) contiguous amino acids from any of SEQ ID NOs: 2 or 12.

The polypeptides of the invention can be produced by proteolytic cleavage of an intact peptide, by chemical synthesis or by the application of recombinant DNA technology and are not limited to polypeptides delineated by proteolytic cleavage sites. The polypeptides, either alone or cross-linked or conjugated to a carrier molecule to render them more immunogenic, are useful as antigens to elicit the production of antibodies and fragments thereof. The antibodies can be used, e.g., in immunoassays for immunoaffinity purification or for inhibition of NPC1L1, etc.

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"Amplification" of DNA as used herein may denote the use of polymerase chain reaction (PCR) to increase the concentration of a particular DNA sequence within a mixture of DNA sequences. For a description of PCR see Saiki, et al., Science (1988) 239: 487.

The term "host cell" includes any cell of any organism that is selected, modified, transfected, transformed, grown, or used or manipulated in any way, for the production of a substance by the cell, for example, the expression or replication, by the cell, of a gene, a DNA or RNA sequence or a protein. Preferred host cells include HEK-293 cells, chinese hamster ovary (CHO) cells, murine macrophage J774 cells or any other macrophage cell line and human intestinal epithelial Caco2 cells.

The nucleotide sequence of a nucleic acid may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74: 560), in which DNA is randomly cleaved using individual base-specific reactions. "Enzymatic sequencing" of DNA includes methods such as that of Sanger (Sanger, et al., (1977) Proc. Natl. Acad. Sci. USA 74: 5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290: 304-310), the promoter contained in the 3' long terminal repeat of Rous sarcoma virus (Yamamoto, et al., (1980) Cell 22: 787-797), the herpes thymidine kinase promoter (Wagner, et al., (1981) Proc. Natl. Acad. Sci. USA 78: 1441-1445), the regulatory sequences of the metallothionein gene (Brinster, et al., (1982) Nature 296: 39-42); prokaryotic expression vectors such as the β-lactamase promoter (Villa-Komaroff, et al., (1978) Proc. Natl. Acad. Sci. USA 75: 3727-3731), or the tac promoter (DeBoer, et al., (1983) Proc. Natl. Acad. Sci. USA 80: 21-25); see also "Useful proteins from recombinant bacteria" in Scientific American (1980) 242:

74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

Expression of nucleic acids encoding the NPC1L1 polypeptides of this invention can be carried out by conventional methods in either prokaryotic or eukaryotic cells. Although *E. coli* host cells are employed most frequently in prokaryotic systems, many other bacteria, such as various strains of *Pseudomonas* and *Bacillus*, are known in the art and can be used as well. Suitable host cells for expressing nucleic acids encoding the NPC1L1 polypeptides include prokaryotes and higher eukaryotes. Prokaryotes include both gram-negative and gram-positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. A representative vector for amplifying DNA is pBR322 or many of its derivatives (e.g., pUC18 or 19). Vectors that can be used to express the NPC1L1 polypeptides include, but are not limited to, those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses*, 1988, Buttersworth, Boston, pp. 205-236. Many polypeptides can be expressed, at high levels, in an *E. coli*/T7 expression system as disclosed in U.S. Pat. Nos. 4,952,496; 5,693,489 and 5,869,320 and in Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.

Higher eukaryotic tissue culture cells may also be used for the recombinant production of the NPC1L1 polypeptides of the invention. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, chinese hamster ovary (CHO) cell lines, J774 cells, HEK-293 cells, Caco2 cells, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pCR®3.1, pcDNA1, pCD (Okayama, et al., (1985) Mol. Cell. Biol. 5: 1136), pMC1neo Poly-A (Thomas, et al., (1987) Cell 51: 503), pREP8, pSVSPORT and derivatives thereof, and baculovirus vectors such as pAC373 or pAC610. One embodiment of the invention includes membrane bound NPC1L1. In this embodiment, NPC1L1 can be expressed in the cell membrane of a eukaryotic cell and the membrane bound protein can be isolated from the cell by conventional methods which are known in the art.

The present invention also includes fusions which include the NPC1L1 polypeptides and NPC1L1 polynucleotides of the present invention and a second polypeptide or polynucleotide moiety, which may be referred to as a "tag". The fusions of the present invention may comprise any of the polynucleotides or polypeptides set forth in Table 1 or any subsequence or fragment thereof (discussed above). The fused polypeptides of the invention may be conveniently constructed, for example, by insertion of a polynucleotide of the invention or fragment thereof into an expression vector. The fusions of the invention may include tags which facilitate purification or detection. Such tags include glutathione-S-transferase (GST), hexahistidine (His6) tags (SEQ ID NO: 52), maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation is desired, a polypeptide can be expressed in a glycosylating host, generally a eukaryotic cell. Insect cells often carry out post-translational glycosylations which are similar to those of mammalian cells. For this reason, insect cell expression systems have been developed to express, efficiently, mammalian proteins having native patterns of glycosylation. An insect cell which may be used in this invention is any cell derived from an organism of the class Insecta. Preferably, the insect is *Spodoptera fruigiperda* (Sf9 or Sf21) or *Trichoplusia ni* (High 5). Examples of insect expression systems that can be used with the present invention, for example to produce NPC1L1 polypeptide, include Bac-To-Bac (Invitrogen Corporation, Carlsbad, Calif.) or Gateway (Invitrogen Corporation, Carlsbad, Calif.). If desired, deglycosylation enzymes can be used to remove carbohydrates attached during production in eukaryotic expression systems.

Other modifications may also include addition of aliphatic esters or amides to the polypeptide carboxyl terminus. The present invention also includes analogs of the NPC1L1 polypeptides which contain modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties. For example, the NPC1L1 polypeptides of the invention may be appended with a polymer which increases the half-life of the peptide in the body of a subject. Preferred polymers include polyethylene glycol (PEG) (e.g., PEG with a molecular weight of 2 kDa, 5 kDa, 10 kDa, 12 kDa, 20 kDa, 30 kDa and 40 kDa), dextran and monomethoxypolyethylene glycol (mPEG).

The peptides of the invention may also be cyclized. Specifically, the amino- and carboxy-terminal residues of an NPC1L1 polypeptide or two internal residues of an NPC1L1 polypeptide of the invention can be fused to create a cyclized peptide. Methods for cyclizing peptides are conventional and very well known in the art; for example, see Gurrath, et al., (1992) Eur. J. Biochem. 210: 911-921.

The present invention contemplates any superficial or slight modification to the amino acid or nucleotide sequences which correspond to the polypeptides of the invention. In particular, the present invention contemplates sequence conservative variants of the nucleic acids which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention are also contemplated by the present invention. "Function-conservative variants" are those in which one or more amino acid residues in a protein or enzyme have been changed without altering the overall conformation and function of the polypeptide, including, but, by no means limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids, which may be interchangeable include aspartic acid and glutamic acid and basic amino acids, which may be interchangeable include histidine, lysine and arginine.

The present invention includes polynucleotides encoding rat, human or mouse NPC1L1 and fragments thereof as well as nucleic acids which hybridize to the polynucleotides. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions are 55° C., 5×SSC, 0.1% SDS, 0.25% milk, and no formamide at 42° C.; or 30% formamide, 5×SSC, 0.5% SDS at 42° C. Typical, moderate stringency hybridization conditions are similar to the low stringency conditions except the hybridization is carried out in 40% formamide, with 5× or 6×SSC at 42° C. High stringency hybridization conditions are similar to low stringency conditions except the hybridization conditions are carried out in 50% formamide, 5× or 6×SSC and, optionally, at a higher temperature (e.g., higher than 42° C.: 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra).

Also included in the present invention are polynucleotides comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference rat NPC1L1 nucleotide (e.g., any of SEQ ID NOs: 1 or 5-10) and amino acid sequences (e.g., SEQ ID NO: 2), reference human NPC1L1 nucleotide (e.g., SEQ ID NO: 3) and amino acid sequences (e.g., SEQ ID NO: 4) or the reference mouse NPC1L1 nucleotide (e.g., any of SEQ ID NOs: 11 or 13) and amino acid sequences (e.g., SEQ ID NO: 12), when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference rat NPC1L1 amino acid sequence of SEQ ID NO: 2, reference human NPC1L1 amino acid sequence of SEQ ID NO: 4 or the reference mouse NPC1L1 amino acid sequence of SEQ ID NO: 12, when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215: 403-410; Gish, W., et al., (1993) Nature Genet. 3: 266-272; Madden, T. L., et al., (1996) Meth. Enzymol. 266: 131-141; Altschul, S. F., et al., (1997) Nucleic Acids Res. 25: 3389-3402; Zhang, J., et al., (1997) Genome Res. 7: 649-656; Wootton, J. C., et al., (1993) Comput. Chem. 17: 149-163; Hancock, J. M., et al., (1994) Comput. Appl. Biosci. 10: 67-70; ALIGNMENT SCORING SYSTEMS: Dayhoff, M. O., et al., "A model of evolutionary change in proteins" in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships" in *Atlas of Protein Sequence and Structure*, (1978) vol. 5, suppl. 3. M. O. Dayhoff (ed.), pp. 353-358, Natl. Biomed. Res. Found., Washington, D.C.; Altschul, S. F., (1991) J. Mol. Biol. 219: 555-565; States, D. J., et al., (1991) Methods 3: 66-70; Henikoff, S., et al., (1992) Proc. Natl. Acad. Sci. USA 89: 10915-10919; Altschul, S. F., et al., (1993) J. Mol. Evol. 36: 290-300; ALIGNMENT STATISTICS: Karlin, S., et al., (1990) Proc. Natl. Acad. Sci. USA 87: 2264-2268; Karlin, S., et al., (1993) Proc. Natl. Acad. Sci. USA 90: 5873-5877; Dembo, A., et al., (1994) Ann. Prob. 22: 2022-2039; and Altschul, S. F. "Evaluating the statistical significance of multiple distinct local alignments" in *Theoretical and Computational Methods in Genome Research* (S. Suhai, ed.), (1997) pp. 1-14, Plenum, New York.

Protein Purification

The proteins, polypeptides and antigenic fragments of this invention can be purified by standard methods, including, but not limited to, salt or alcohol precipitation, affinity chromatography (e.g., used in conjunction with a purification tagged NPC1L1 polypeptide as discussed above), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "Guide to Protein Purification", *Methods in Enzymology*, Vol. 182, M. Deutscher, Ed., 1990, Academic Press, New York, N.Y.

Purification steps can be followed by performance of assays for receptorbinding activity as described below. Particularly where an NPC1L1 polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Antibody Molecules

Antigenic (including immunogenic) fragments of the NPC1L1 polypeptides of the invention are within the scope of the present invention (e.g., 42 or more contiguous amino acids from SEQ ID NO: 2, 4 or 12). The antigenic peptides may be useful, inter alia, for preparing isolated antibody molecules which recognize NPC1L11. Isolated anti-NPC1L1 antibody molecules are useful NPC1L1 ligands.

An antigen is any molecule that can bind specifically to an antibody. Some antigens cannot, by themselves, elicit antibody production. Those that can induce antibody production are immunogens.

Preferably, isolated anti-NPC1L1 antibodies recognize an antigenic peptide comprising an amino acid sequence selected from SEQ ID NOs: 39-42 (e.g., an antigen derived from rat NPC1L1). More preferably, the antibody is A0715, A0716, A0717, A0718, A0867, A0868, A1801 or A1802.

The term "antibody molecule" includes, but is not limited to, antibodies and fragments (preferably antigen-binding fragments) thereof. The term includes monoclonal antibodies, polyclonal antibodies, bispecific antibodies, Fab antibody fragments, $F(ab)_2$ antibody fragments, Fv antibody fragments (e.g., $V_H$ or $V_L$), single chain Fv antibody fragments and dsFv antibody fragments. Furthermore, the antibody molecules of the invention may be fully human antibodies, mouse antibodies, rat antibodies, rabbit antibodies, goat antibodies, chicken antibodies, humanized antibodies or chimeric antibodies.

Although it is not always necessary, when NPC1L1 polypeptides are used as antigens to elicit antibody production in an immunologically competent host, smaller antigenic fragments are, preferably, first rendered more immunogenic by cross-linking or concatenation, or by coupling to an immunogenic carrier molecule (i.e., a macromolecule having the property of independently eliciting an immunological response in a host animal, such as diphtheria toxin or tetanus). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Carrier molecules include, e.g., proteins and natural or synthetic polymeric compounds such as polypeptides, polysaccharides, lipopolysaccharides, etc. Protein carrier molecules are especially preferred, including, but not limited to, keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the invention can be coupled, e.g., using water-soluble carbodiimides such as dicyclohexylcarbodiimide or glutaraldehyde.

Coupling agents, such as these, can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregation.

Adjuvants for the vaccination of animals include, but are not limited to, Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis (2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, *Practice and Theory of Enzyme Immunoassays,* 3rd Edition, 1987, Elsevier, New York. Other useful references covering methods for preparing polyclonal antisera include *Microbiology,* 1969, Hoeber Medical Division, Harper and Row; Landsteiner, *Specificity of Serological Reactions,* 1962, Dover Publications, New York, and Williams, et al., *Methods in Immunology and Immunochemistry, Vol.* 1, 1967, Academic Press, New York.

The anti-NPC1L1 antibody molecules of the invention preferably recognize human, mouse or rat NPC1L1; however, the present invention includes antibody molecules which recognize NPC1L1 from any species, preferably mammals (e.g., cat, sheep or horse). The present invention also includes complexes comprising an NPC1L1 polypeptide of the invention and an anti-NPC1L1 antibody molecule. Such complexes can be made by simply contacting the antibody molecule with its cognate polypeptide.

Various methods may be used to make the antibody molecules of the invention. Human antibodies can be made, for example, by methods which are similar to those disclosed in U.S. Pat. Nos. 5,625,126; 5,877,397; 6,255,458; 6,023,010 and 5,874,299.

Hybridoma cells which produce the monoclonal anti-NPC1L1 antibodies may be produced by methods which are commonly known in the art. These methods include, but are not limited to, the hybridoma technique originally developed by Kohler, et al., (1975) (Nature 256: 495-497), as well as the trioma technique (Hering, et al., (1988) Biomed. Biochim. Acta. 47: 211-216 and Hagiwara, et al., (1993) Hum. Antibod. Hybridomas 4: 15), the human B-cell hybridoma technique (Kozbor, et al., (1983) Immunology Today 4: 72 and Cote, et al., (1983) Proc. Natl. Acad. Sci. U.S.A 80: 2026-2030), and the EBV-hybridoma technique (Cole, et al., in *Monoclonal Antibodies and Cancer Therapy,* Alan R. Liss, Inc., pp. 77-96, 1985). ELISA may be used to determine if hybridoma cells are expressing anti-NPC1L1 antibodies.

The anti-NPC1L1 antibody molecules of the present invention may also be produced recombinantly (e.g., in an *E. coli*/T7 expression system as discussed above). In this embodiment, nucleic acids encoding the antibody molecules of the invention (e.g., $V_H$ or $V_L$) may be inserted into a pet-based plasmid and expressed in the *E. coli*/T7 system. There are several methods by which to produce recombinant antibodies which are known in the art. An example of a method for recombinant production of antibodies is disclosed in U.S. Pat. No. 4,816,567. See also Skerra, A., et al., (1988) Science 240: 1038-1041; Better, M., et al., (1988) Science 240: 1041-1043 and Bird, R. E., et al., (1988) Science 242: 423-426.

The term "monoclonal antibody," includes an antibody obtained from a population of substantially homogeneous antibodies, i.e., the individual antibodies comprising the population are identical except for possible, naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being obtained from a substantially homogeneous population of antibodies, and is not to be construed as requiring production of the antibody by any particular method. The monoclonal antibodies to be used in accordance with the present invention may be made by the hybridoma method as described by Kohler, et al., (1975) Nature 256: 495.

The term "polyclonal antibody" includes an antibody which was produced among or in the presence of one or more other, non-identical antibodies. In general, polyclonal antibodies are produced from a B-lymphocyte in the presence of several other B-lymphocytes which produced non-identical antibodies. Typically, polyclonal antibodies are obtained directly from an immunized animal (e.g., a rabbit).

A "bispecific antibody" comprises two different antigen binding regions which bind to distinct antigens. Bispecific antibodies, as well as methods of making and using the antibodies, are conventional and very well known in the art.

Anti-idiotypic antibodies or anti-idiotypes are antibodies directed against the antigen-combining region or variable region (called the idiotype) of another antibody molecule. As disclosed by Jerne (Jerne, N. K., (1974) Ann. Immunol. (Paris) 125c: 373 and Jerne, N. K., et al., (1982) EMBO 1: 234), immunization with an antibody molecule expressing a paratope (antigen-combining site) for a given antigen (e.g., NPC1L1) will produce a group of anti-antibodies, some of which share, with the antigen, a complementary structure to the paratope. Immunization with a subpopulation of the anti-idiotypic antibodies will, in turn, produce a subpopulation of antibodies or immune cell subsets that are reactive to the initial antigen.

The term "fully human antibody" refers to an antibody which comprises human immunoglobulin sequences only. Similarly, "mouse antibody" refers to an antibody which comprises mouse immunoglobulin sequences only.

"Human/mouse chimeric antibody" refers to an antibody which comprises a mouse variable region ($V_H$ and $V_L$) fused to a human constant region.

"Humanized" anti-NPC1L1 antibodies are also within the scope of the present invention. Humanized forms of non-human (e.g., murine) antibodies are chimeric immunoglobulins, which contain minimal sequence derived from non-human immunoglobulin. For the most part, humanized antibodies are human immunoglobulins (recipient antibody) in which residues from a complementary determining region of the recipient are replaced by residues from a complementary determining region of a nonhuman species (donor antibody), such as mouse, rat or rabbit, having a desired specificity, affinity and capacity. In some instances, Fv framework residues of the human immunoglobulin are also replaced by corresponding non-human residues.

"Single-chain Fv" or "sFv" antibody fragments include the $V_H$ and/or $V_L$ domains of an antibody, wherein these domains are present in a single polypeptide chain. Generally, the sFv polypeptide further comprises a polypeptide linker between the $V_H$ and $V_L$ domains which enables the sFv to form the desired structure for antigen binding. Techniques described for the production of single chain antibodies (U.S. Pat. Nos. 5,476,786; 5,132,405 and 4,946,778) can be adapted to produce anti-NPC1L1 specific, single chain antibodies. For a review of sFv see Pluckthun in *The Pharmacology of Monoclonal Antibodies,* vol. 113, Rosenburg and Moore, eds., Springer-Verlag, N.Y., pp. 269-315 (1994).

"Disulfide stabilized Fv fragments" and "dsFv" include molecules having a variable heavy chain ($V_H$) and/or a variable light chain ($V_L$) which are linked by a disulfide bridge.

Antibody fragments within the scope of the present invention also include F(ab)$_2$ fragments which may be produced by enzymatic cleavage of an IgG by, for example, pepsin. Fab fragments may be produced by, for example, reduction of F(ab)$_2$ with dithiothreitol or mercaptoethylamine.

An FV fragment is a $V_L$ or $V_H$ region.

Depending on the amino acid sequences of the constant domain of their heavy chains, immunoglobulins can be assigned to different classes. There are at least five major classes of immunoglobulins: IgA, IgD, IgE, IgG and IgM, and several of these may be further divided into subclasses (isotypes), e.g., IgG-1, IgG-2, IgG-3 and IgG-4; IgA-1 and IgA-2.

The anti-NPC1L1 antibody molecules of the invention may also be conjugated to a chemical moiety. The chemical moiety may be, inter alia, a polymer, a radionuclide or a cytotoxic factor. Preferably, the chemical moiety is a polymer which increases the half-life of the antibody molecule in the body of a subject. Suitable polymers include, but are by no means limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Methods for producing PEGylated anti-IL8 antibodies which are described in U.S. Pat. No. 6,133,426 can be applied to the production of PEGylated anti-NPC1L1 antibodies of the invention. Lee, et al., (1999) (Bioconj. Chem. 10: 973-981) discloses PEG conjugated single-chain antibodies. Wen, et al., (2001) (Bioconj. Chem. 12: 545-553) discloses conjugating antibodies with PEG which is attached to a radiometal chelator (diethylenetriaminpentaacetic acid (DTPA)).

The antibody molecules of the invention may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$Cu, $^{217}$Ci, $^{211}$At, $^{212}$Pb, $^{47}$Sc, $^{109}$Pd, $^{234}$Th, $^{40}$K, $^{157}$Gd, $^{55}$Mn, $^{52}$Tr or $^{56}$Fe.

The antibody molecules of the invention may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diphtheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca ammericana* proteins PAPI, PAPII, and PAP-S, *momordica charantia* inhibitor, curcin, crotin, *saponaria officinialis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144: 945; David, et al., (1974) Biochemistry 13: 1014; Pain, et al., (1981) J. Immunol. Meth. 40: 219; and Nygren, J., (1982) Histochem. and Cytochem. 30: 407.

Methods for conjugating antibodies are conventional and very well known in the art.

Screening Assays

The invention allows the identification of selective ligands of NPC1L1 (e.g., SEQ ID NO: 2, 4 or 12) that may be useful in treatment and management of a variety of medical conditions, including elevated serum sterol (e.g., cholesterol) or 5α-stanol. Thus, NPC1L1 of this invention can be employed in screening systems to identify ligands. These ligands may be agonists or antagonists of NPC1L1. Essentially, these assays provide methods for identifying ligands of NPC1L1 by using (1) NPC1L1, (2) an appropriate known NPC1L1 ligand, agonist or antagonist, for example, a sterol (such as cholesterol, phytosterols, including, but not limited to, sitosterol, campesterol, stigmasterol and avenosterol), a cholesterol oxidation product, a 5α-stanol (including, but not limited to, cholestanol, 5α-campestanol and 5α-sitostanol), a substituted azetidinone (e.g., ezetimibe), BODIPY-ezetimibe (Altmann, et al., (2002) Biochim. Biophys. Acta 1580(1): 77-93) or 4",6"-bis[(2-fluorophenyl)carbamoyl]-beta-D-cellobiosyl derivative of 11-ketotigogenin as described in DeNinno, et al., (1997) (J. Med. Chem. 40(16): 2547-54) or any substituted azetidinone, and (3) a sample to be tested for the presence of a candidate NPC1L1 ligand.

The term "specific" when used to describe binding of, for example, a ligand of NPC1L1 in a screening assay is a term of art which refers to the extent by which the ligand or antagonist (e.g., substituted azetidinone, ezetimibe, sterol (such as cholesterol) or 5α-stanol) binds preferentially to NPC1L1 in comparison to other proteins in the assay system. For example, detection of the specific binding of a ligand of NPC1L1 binds specifically to NPC1L1 is made apparent when a signal generated in the assay to indicate such binding exceeds, to any extent, a signal generated in a negative control wherein, for example, NPC1L1 or ligand is absent. Furthermore, "specific binding" includes binding of a ligand either directly to NPC1L1 or indirectly, for example via another moiety, in a complex of which NPC1L1 is a part. The moiety to which an NPC1L1 ligand binds can be another protein or a post-translational modification of NPC1L1 (e.g., a lipid chain or a carbohydrate chain).

Non-limiting examples of suitable substituted azetidinones for use in the screening assays include those disclosed in U.S. Pat. Nos. RE 37,721; 5,631,365; 5,767,115; 5,846,966; 5,688,990; 5,656,624; 5,624,920; 5,698,548; 5,756,470; 5,688,787; 5,306,817; 5,633,246; 5,627,176; 5,688,785; 5,744,467; 5,846,966; 5,728,827; 6,632,933 and U.S. Patent Application Publication No 2003/0105028—each of which is herein incorporated by reference in its entirety.

The present invention provides for a method by which to evaluate whether a sample contains an NPC1L1 ligand by determining whether the sample contains a candidate compound which competes for binding between the known ligand (e.g., ezetimibe, ezetimibe-glucuronide, compound 2, etc.) and NPC1L1. The ligand may be an agonist or antagonist. In an embodiment of the invention, the binding of the known ligand (e.g., ezetimibe, ezetimibe-glucuronide, compound 2 etc.) to NPC1L1 is disrupted. The term "known ligand" refers to a compound which is known to bind to NPC1L1 and which can be detectably labeled for use in the screening assays and methods described herein. "Known ligands" include the substituted 2-azetidinone glucuronides which can be detectably labeled for use in screening assays as described herein.

Ezetimibe can be prepared by a variety of methods well know to those skilled in the art, for example such as are disclosed in U.S. Pat. Nos. 5,631,365, 5,767,115, 5,846,966, 6,207,822, U.S. Patent Application Publication No. 2002/0193607 and PCT Patent Application WO 93/02048, each of which is incorporated herein by reference in its entirety.

"Sample", "candidate compound" or "candidate substance" refers to a compound or composition which is evaluated in a test or assay, for example, for the ability to bind to NPC1L1 (e.g., SEQ ID NO: 2, 4 or 12) or a functional fragment thereof. The composition may comprise candidate compounds, such as small molecules, peptides, nucleotides, polynucleotides, subatomic particles (e.g., α particles, β particles) or antibodies.

The present invention provides methods for identifying ligands of a compound that binds to NPC1L1 which involve contacting NPC1L1 with a detectably labeled substituted 2-azetidinone, preferably substituted 2-azetidinone-glucuronide, and a candidate compound, and determining whether the candidate compound binds to NPC1L1, wherein binding of said candidate compound to NPC1L1 modulates binding of the detectably labeled substituted 2-azetidinone to NPC1L1. The modulation of the binding of the substituted 2-azetidinone to NPC1L1 by the binding of the candidate compound to NPC1L1 indicates that the candidate compound is a ligand that binds to NPC1L1. It is also a good indication that the candidate compound may be an inhibitor of sterol and 5α-stanol absorption in vivo.

The present invention also provides a method for identifying a ligand of NPC1L1 comprising contacting NPC1L1 with a detectably labeled substituted 2-azetidinone, preferably substituted 2-azetidinone-glucuronide, and measuring the binding of NPC1L1 of the detectably labeled substituted 2-azetidinone in the presence and absence of a candidate compound, wherein decreased binding of the detectably labeled substituted 2-azetidinone to the NPC1L1 in the presence of the candidate compound indicates that said candidate compound is a ligand of NPC1L1 and is an inhibitor of sterol and 5α-stanol absorption.

The substituted 2-azetidinone is detectably labeled with $^3H$, $^{35}S$, $^{125}I$, or a fluorescently labeled substituted 2-azetidinone. Preferably, the substituted 2-azetidinone is labeled with $^{35}S$ or $^{125}I$, and particularly $^{35}S$.

Preferably, the substituted 2-azetidinone is substituted 2-azetidinone-glucuronide. Compounds that are substituted 2-azetidinone-glucuronides are those having the following structure (I):

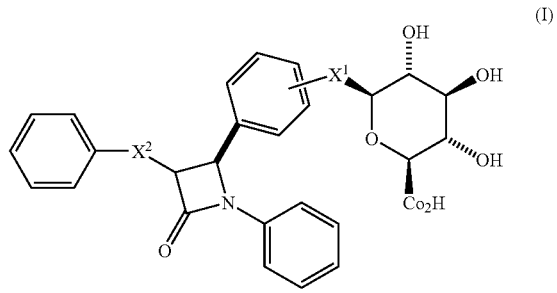

wherein $X^1$ represents a group that links the glucuronide to the 4-phenyl ring, for example but not limited to —O— or —$C_{1-3}$ alkyl-, $X^2$ represents an optionally substituted -alkanediyl-, and wherein any of the phenyl groups may be optionally substituted. Examples of the phenyl-$X^2$-moiety in structure (I) include those represented at the 4-position on the 2-azetidinone structure shown below in structure (II). Additional examples of substituted 2-azetidinone-glucuronides include but are not limited to those described in U.S. Pat. No. 5,756,470, WO02/066464 and US 2002/0137689. Additional examples of substituted 2-azetidinone-glucuronide compounds include those having the structure (II) and pharmaceutically acceptable salts and esters thereof as follows:

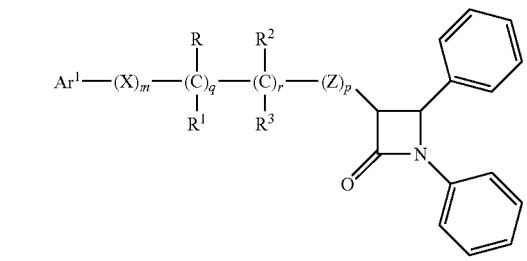

wherein:

$Ar^1$ is selected from the group consisting of aryl and $R^4$-substituted aryl;

X, Y and Z are independently selected from the group consisting of —$CH_2$—, —$CH(C_{1-6}alkyl)$- and —$C(C_{1-6}alkyl)_2$—;

R is selected from the group consisting of —$OR^6$, —$O(CO)R^6$, —$O(CO)OR^9$, —$O(CO)NR^6R^7$, a sugar residue, a disugar residue, a trisugar residue and a tetrasugar residue;

$R^1$ is selected from the group consisting of —H, —$C_{1-6}alkyl$ and aryl, or R and $R^1$ together are oxo;

$R^2$ is selected from the group consisting of —$OR^6$, —$O(CO)R^6$, —$O(CO)OR^9$ and —$O(CO)NR^6R^7$;

$R^3$ is selected from the group consisting of —H, —$C_{1-6}alkyl$ and aryl or $R^2$ and $R^3$ together are oxo;

q, r and t are each independently selected from 0 and 1;

m, n and p are each independently selected from 0, 1, 2, 3 and 4;

$R^4$ is 1-5 substituents independently selected at each occurrence from the group consisting of:
—$OR^5$, —$O(CO)R^5$, —$O(CO)OR^8$, —O—$C_{1-5}$alkyl-$OR^5$, —$O(CO)NR^5R^6$, —$NR^5R^6$, —$NR^5(CO)R^6$, —$NR^5(CO)OR^8$, —$NR^5(CO)NR^6R^7$, —$NR^5SO_2R^8$, —$COOR^5$, —$CONR^5R^6$, —$COR^5$,
—$SO_2NR^5R^6$, —$S(O)_tR^8$, —O—$C_{1-10}$ alkyl-$COOR^5$, —O—$C_{1-10}$ alkyl-$CONR^5R^6$ and fluoro;

$R^5$, $R^6$ and $R^7$ are independently selected at each occurrence from the group consisting of —H, $C_{1-6}alkyl$, aryl and aryl-substituted $C_{1-6}alkyl$;

$R^8$ is independently selected from the group consisting of $C_{1-6}alkyl$, aryl and aryl-substituted $C_{1-6}alkyl$;

$R^9$ is selected from the group consisting of —C≡C—$CH_2$—$NR^{10}R^{11}$, —C≡C—$C(O)R^{13}$, and —$(CH_2)_3$—$NR^{10}R^{14}$;

$R^{10}$ is independently selected at each occurrence from —H and —$C_{1-3}$ alkyl;

$R^{11}$ is selected from the group consisting of —H, —$C_{1-3}alkyl$, —C(O)—$C_{1-3}alkyl$, —C(O)—$NR^{10}R^{10}$, —$SO_2$—$C_{1-3}$ alkyl, and —$SO_2$-phenyl; and $R^{12}$ is selected from

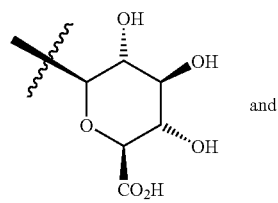 and (referred to herein as "glucuronide")

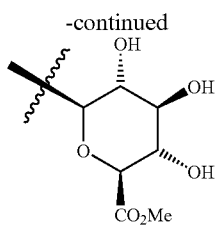

(referred to herein as "methyl ester glucuronide");

$R^{13}$ is selected from the group consisting of —OH and —$NR^{10}R^{11}$; and $R^{14}$ is selected from the group consisting of —C(O)—$C_{1-3}$ alkyl, —C(O)—$NR^{10}R^{10}$, —$SO_2$—$C_{1-3}$alkyl and —$SO_2$-phenyl.

In one embodiment of Formula II are compounds wherein q, r and t are each independently selected from 0 and 1; and m, n and p are each independently selected from 0, 1, 2, 3 and 4; provided that at least one of q and r is 1, and the sum of m, n, p, q are r is 1, 2, 3, 4, 5 or 6; and provided that when p is 0 and r is 1, the sum of m, q and n is 1, 2, 3, 4, or 5. In a second embodiment of Formula II are compounds of Formula IIa,

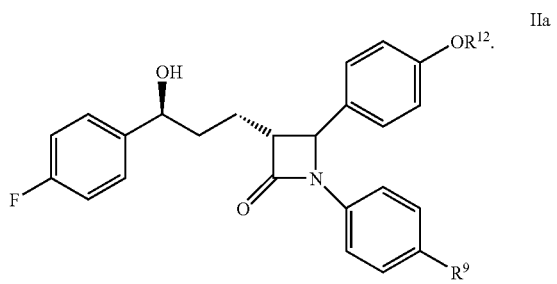

In a class of each of these embodiments are compounds wherein $R^9$ is —C≡C—$CH_2$—$NR^{10}R^{11}$. In another class of each of these embodiments are compounds wherein $R^9$ contains an —$SO_2$— group, i.e., wherein $R^9$ is selected from the group consisting of —C≡C—$CH_2$—$NR^{10}R^{11}$, —C≡C—C(O)$NR^{10}R^{11}$, —($CH_2$)$_3$—$NR^{10}$—$SO_2$—$C_{1-3}$alkyl and —($CH_2$)$_3$—$NR^{10}$—$SO_2$-phenyl, and $R^{11}$ is selected from —$SO_2$—$C_{1-3}$alkyl, and —$SO_2$-phenyl.

The term "alkyl" is intended to include both branched- and straight-chain saturated aliphatic univalent hydrocarbon groups having the specified number of carbon atoms. Examples of alkyl groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like. If there is no specified prefix (such as "n-" for normal, "s-" for sec, "t-" for tert, "i-" for iso) with a named alkyl group, then it is intended that the named alkyl group is an n-alkyl group (i.e., "propyl" is "n-propyl"). The term "aryl" is intended to include phenyl (Ph), naphthyl, indenyl, tetrahydronaphthyl or indanyl. Phenyl is preferred.

Suitable protecting groups (designated as "PG" herein) for the hydroxyl groups of $R^{12}$ when $R^{12}$ is a glucuronide or methyl ester glucuronide include but are not limited to those that are known to be useful as carbohydrate protecting groups, such as for example benzyl, acetyl, benzoyl, tert-butyldiphenylsilyl, trimethylsilyl, para-methoxybenzyl, benzylidine, and methoxy methyl. Conditions required to selectively add and remove such protecting groups are found in standard textbooks such as Greene, T, and Wuts, P. G. M., *Protective Groups in Organic Synthesis*, John Wiley & Sons, Inc., New York, N.Y., 1999.

Compounds of Formula II may contain one or more asymmetric centers and can thus occur as racemates and racemic mixtures, single enantiomers, enantiomeric mixtures, diastereomeric mixtures and individual diastereomers, and all such isomeric forms are within the scope of Formula II.

Radioactive isotopes of the compounds of Formula II are particularly useful in such assays, for example compounds of Formula II wherein sulfur is replaced with "hot"-$^{35}$S—, and particularly wherein the radioactive sulfur isotope is incorporated within the $R^9$ moiety. The use of all such radioactive isotopes of the compounds of Formula II in an assay for identifying NPC1L1 ligands is included within the scope of this invention.

The term "pharmaceutically acceptable salts" means non-toxic salts of the compounds of Formula II which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, morpholine, 2,4,4-trimethyl-2-pentamine and tris (hydroxymethyl)aminomethane.

When the compounds of Formula II are basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Examples of pharmaceutically acceptable esters include, but are not limited to, —$C_{1-4}$ alkyl and —$C_{1-4}$ alkyl substituted with phenyl, dimethylamino and acetylamino. "$C_{1-4}$ alkyl" herein includes straight or branched aliphatic chains containing from 1 to 4 carbon atoms, for example methyl, ethyl, n-propyl, n-butyl, iso-propyl, sec-butyl and tert-butyl.

The compounds of structural Formula II can be prepared according to the procedures of the following Scheme using appropriate materials, and are further exemplified by specific examples which follow. A variety of chromatographic techniques may be employed in the preparation of the compounds of Formula II. These techniques include, but are not limited to: High Performance Liquid Chromatography (including normal- reversed- and chiral-phase); Super Critical Fluid Chromatography; preparative Thin Layer Chromatography; flash chromatography with silica gel or reversed-phase silica gel; ion-exchange chromatography; and radial chromatography. All temperatures are degrees Celsius unless otherwise noted.

Some abbreviations used herein include:
Ac Acyl ($CH_3C(O)$—)
Bn benzyl
calc. Calculated
Celite Celite™ diatomaceous earth
Dess-Martin Periodinane 1,1,1-tris(acetyloxy)-1,1-dihydro-1,2-benzodoxol-3-(1H)-one
DMF N,N-dimethylformamide
equiv. Equivalent(s)

ES-MS Electron Spray Ion-Mass Spectroscopy
EtOAc Ethyl acetate
h Hour(s)
HPLC High performance liquid chromatography
min Minute(s)
m.p. Melting point
MS Mass spectrum
r.t. (or rt) Room temperature
TFA Trifluoroacetic acid
THF Tetrahydrofuran
Tlc Thin layer chromatography corresponding radiolabeled adduct upon reaction with II-1. Conversion of II-3 to II-4 can be achieved using a variety of hydrolytic methods known to those skilled in the art of organic synthesis. For example, a particularly mild hydrolysis protocol involves the treatment of II-3 with a tertiary amine base such as triethylamine, or diisopropylethylamine or the like, in a mixed solvent system comprising methanol and water. The product of the reaction is a compound of structural formula II-4. By utilizing the procedures described herein, one of ordinary skill in the art can readily prepare additional compounds of Formula II.

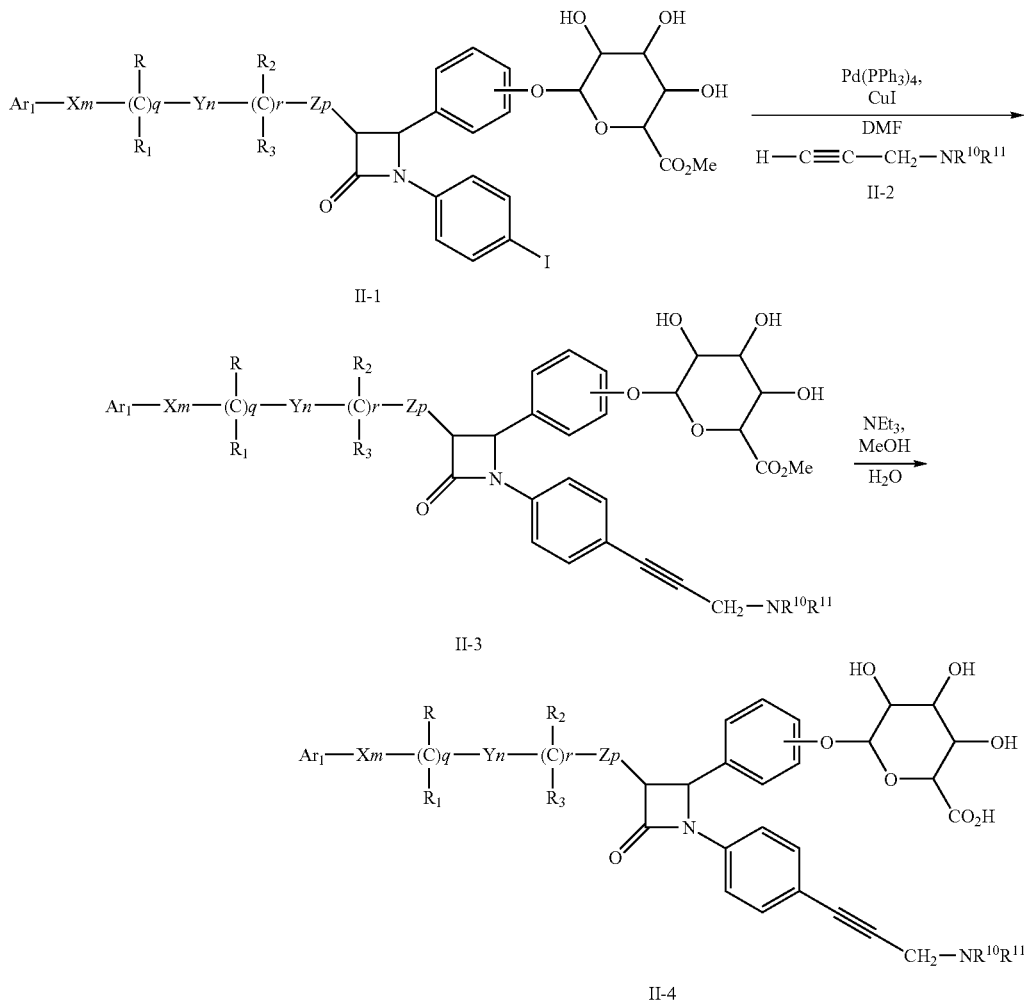

SCHEME

The general Scheme below illustrates a method for the syntheses of compounds of structural formula II-4. All substituents are as defined in Formula II unless indicated otherwise. In this method, II-1 is treated with a terminal alkyne of type II-2 in the presence of a suitable palladium catalyst such as tetrakistriphenylphosphine palladium(0) or [1,1'-bis(diphenylphosphino)ferrocene]dichloropalladium(II) or the like, and copper(I) iodide. The reaction is usually performed in an inert organic solvent such as DMF, between room temperature and 100° C., for a period of 6-48 h, and the product is an internal alkyne of structural formula II-3. Alkyne 11-2 may contain a radioactive atom such as 35S to provide the Two additional types of screening systems that can be used include a labeled-ligand binding assay (e.g., direct binding assay or scintillation proximity assay (SPA)) and a "sterol (e.g., cholesterol) or 5α-stanol uptake" assay. A labeled ligand, for use in the binding assay, can be obtained by labeling a sterol (e.g., cholesterol) or a 5α-stanol or a known NPC1L1 agonist or antagonist with a measurable group (e.g., $^{35}S$, $^{125}I$ or $^{3}H$). Various labeled forms of sterols (e.g., cholesterol) or 5α-stanols are available commercially or can be generated using standard techniques (e.g., Cholesterol-[1,2-$^{3}H(N)$], Cholesterol-[1,2,6,7-$^{3}H(N)$] or Cholesterol-[7-$^{3}H(N)$]; American Radiolabeled Chemicals, Inc; St. Louis, Mo.). In a preferred embodiment, ezetimibe is fluorescently labeled with a BODIPY group (Altmann, et al., (2002) Biochim. Biophys. Acta 1580(1): 77-93) or labeled with a detectable group such as $^{35}S$, $^{125}I$ or $^{3}H$, preferably $^{35}S$.

Direct Binding Assay. Typically, a given amount of NPC1L1 of the invention (e.g., SEQ ID NO: 2, 4 or 12) or a complex including NPC1L1 is contacted with increasing amounts of labeled ligand or known antagonist or agonist (discussed above) and the amount of the bound, labeled ligand or known antagonist or agonist is measured after removing unbound, labeled ligand or known antagonist or agonist by washing. As the amount of the labeled ligand or known agonist or antagonist is increased, a point is eventually reached at which all receptor binding sites are occupied or saturated. Specific receptor binding of the labeled ligand or known agonist or antagonist is abolished by a large excess of unlabeled ligand or known agonist or antagonist.

Preferably, an assay system is used in which non-specific binding of the labeled ligand or known antagonist or agonist to the receptor is minimal. Non-specific binding is typically less than 50%, preferably less than 15%, more preferably less than 10%, and most preferably 5% or less, of the total binding of the labeled ligand or known antagonist or agonist.

In the basic binding assay, the method for identifying an NPC1L1 ligand, agonist or antagonist includes:

(a) contacting NPC1L1 (e.g., SEQ ID NO: 2 or 4 or 12), a fragment thereof or a complex including NPC1L1, in the presence of a known amount of labeled sterol (e.g., cholesterol) or 5α-stanol or known antagonist or agonist (e.g., labeled ezetimibe) with a sample to be tested for the presence of an NPC1L1 ligand, agonist or antagonist; and (b) measuring the amount of labeled sterol (e.g., cholesterol) or 5α-stanol or known antagonist or agonist directly or indirectly bound to NPC1L1.

An NPC1L1 ligand in the sample is identified by measuring substantially reduced direct or indirect binding of the labeled sterol (e.g., cholesterol) or 5α-stanol or known antagonist or agonist to NPC1L1, compared to what would be measured in the absence of such a ligand. For example, reduced direct or indirect binding between [$^{3}H$]-cholesterol and NPC1L1 in the presence of a sample might suggest that the sample contains a substance which is competing against [$^{3}H$]-cholesterol for NPC1L1 binding.

This assay can include a control experiment lacking any NPC1L1-dependent ligand (e.g., sterol such as cholesterol or 5α-stanol) binding. In this assay, for example, a whole cell or cell membrane lacking any functional NPC1L1, for example, a cell or membrane isolated or derived from a transgenic mutant npc1l1⁻ mouse of the invention, is assayed for ligand binding. When screening a sample for the presence of an NPC1L1 antagonist, it is useful to compare the level of binding observed in the presence of a sample being tested with that of a control experiment, as described herein, which completely lacks NPC1L1-dependent binding. Ideally, though by no means necessarily, the level of binding seen in the presence of a sample containing an antagonist will be similar to that of the control experiment.

Alternatively, a sample can be tested directly for binding to NPC1L1 (e.g., SEQ ID NO: 2 or 4 or 12). A basic assay of this type may include the following steps:

(a) contacting NPC1L1 (e.g., SEQ ID NO: 2 or 4 or 12), a fragment thereof or a complex including NPC1L1 with a labeled candidate compound (e.g., [$^{3}H$]-ezetimibe); and (b) detecting direct or indirect binding between the labeled candidate compound and NPC1L1.

Again, these experiment can be performed along with a control experiment wherein NPC1L1-dependent binding is completely lacking. For example, the assay can be performed using a whole cell or cell membrane lacking any functional NPC1L1 (e.g., cell or cell membrane derived from a transgenic, mutant npc1l1⁻ mouse as described herein).

A candidate compound which is found to bind to NPC1L1 may function as ligand, agonist or antagonist of NPC1L1 (e.g., by inhibition of sterol (e.g., cholesterol) or 5α-stanol uptake).

In an embodiment of the invention, the bound candidate compound is quantified after filtration using glass fiber filters. In one aspect of this embodiment, the bound candidate compound is detected after single-tube vacuum filtration of GF/C glass fiber filters, obtained from Whatman. The filters may be pretreated by soaking with 0.5% polyethyleneimine to reduce nonspecific binding. Filtration is accomplished by adding ice cold buffer to the assay tube, pouring the mixture through the filter, and then rinsing the tube and filter twice more with additional buffer. The buffer may be a Tris buffer or MES buffer (120 mM NaCl, 0.1% sodium cholate, and 20 mM MES at pH 6.70). The filters can be counted using scintillation fluid, e.g., Packard DM liquid or Packard Ultima Gold MV.

Alternatively, vacuum filtration of the sample on a Millipore 96-well plate (Whatman GF/C) can also be used to achieve adequate precision in a manner well-known to those skilled in the art.

SPA Assay. NPC1L1 ligands may also be measured using scintillation proximity assays (SPA). SPA assays are conventional and very well known in the art; see, for example, U.S. Pat. No. 4,568,649. In SPA, the target of interest is immobilized to a small microsphere approximately 5 microns in diameter. The microsphere, typically, includes a solid scintillant core which has been coated with a polyhydroxy film, which in turn contains coupling molecules, which allow generic links for assay design. When a radioisotopically labeled molecule binds to the microsphere, the radioisotope is brought into close proximity to the scintillant and effective energy transfer from electrons emitted by the isotope will take place resulting in the emission of light. While the radioisotope remains in free solution, it is too distant from the scintillant and the electron will dissipate the energy into the aqueous medium and therefore remain undetected. Scintillation may be detected with a scintillation counter. In general, $^{3}H$, $^{125}I$ and $^{35}S$ labels are well suited to SPA.

For the assay of receptor-mediated binding events, the lectin wheat germ agglutinin (WGA) may be used as the SPA bead coupling molecule (Amersham Biosciences; Piscataway, N.J.). The WGA coupled bead captures glycosylated, cellular membranes and glycoproteins and has been used for a wide variety of receptor sources and cultured cell membranes. The receptor is immobilized onto the WGA-SPA bead and a signal is generated on binding of an isotopically labeled ligand. Other coupling molecules which may be useful for receptor binding SPA assays include poly-L-lysine and WGA/polyethyleneimine (Amersham Biosciences; Piscataway, N.J.). See, for example, Berry, J. A., et al., (1991) Cardiovascular Pharmacol. 17 (Suppl.7): S143-S145; Hoffman, R., et al., (1992) Anal. Biochem. 203: 70-75; Kienhus, et al., (1992) J. Receptor Research 12: 389-399; Jing, S., et al., (1992) Neuron 9: 1067-1079.

The scintillant contained in SPA beads may include, for example, yttrium silicate (YSi), yttrium oxide (YOx), diphenyloxazole or polyvinyltoluene (PVT) which acts as a solid solvent for diphenylanthracine (DPA).

SPA assays may be used to analyze whether a sample contains an NPC1L1 ligand. In these assays, a host cell which expresses NPC1L1 (e.g., SEQ ID NO: 2 or 4 or 12) on the cell surface or a membrane fraction thereof is incubated with and captured by SPA beads (e.g., WGA coated YOx beads or WGA coated YSi beads). The beads bearing the NPC1L1 are incubated with labeled, known ligand or agonist or antagonist (e.g., $^3$H-cholesterol, $^3$H-ezetimibe, $^{125}$I-ezetimibe or a $^{35}$S-ezetimibe analog). The assay mixture further includes either the sample to be tested or a blank (e.g., water). After an optional incubation, scintillation is measured using a scintillation counter. An NPC1L1 ligand, agonist or antagonist may be identified in the sample by measuring substantially reduced fluorescence, compared to what would be measured in the absence of such ligand, agonist or antagonist (blank). Measuring substantially reduced fluorescence may suggest that the sample contains a substance which competes for direct or indirect NPC1L1 binding with the known ligand, agonist or antagonist.

Alternatively, a sample may be identified as an ligand of NPC1L1 by directly detecting binding in a SPA assay. In this assay, a labeled version of a candidate compound to be tested may be put in contact with the host cell expressing NPC1L1 or a membrane fraction thereof which is bound to the SPA bead. Fluorescence may then be assayed to detect the presence of a complex between the labeled candidate compound and the host cell or membrane fraction expressing NPC1L1 or a complex including NPC1L1. A candidate compound which binds directly or indirectly to NPC1L1 may possess NPC1L1 agonistic or antagonistic activity.

SPA Assays can also be performed along with a control experiment lacking any NPC1L1-dependent binding. The control experiment can be performed, for example, with a cell or cell membrane lacking any functional NPC1L1 (e.g., cell or cell membrane derived from a transgenic, mutant npc1l1-mouse as described herein). When the control experiment is performed, the level of binding observed in the presence of sample being tested for the presence of an antagonist can be compared with that observed in the control experiment.

Sterol/5α-stanol Uptake Assay. Assays may also be performed to determine if a sample can agonize or antagonize NPC1L1 mediated sterol (e.g., cholesterol) or 5α-stanol uptake. In these assays, a host cell expressing NPC1L1 (e.g., SEQ ID NO: 2 or 4 or 12) on the cell surface (discussed above) can be contacted with detectably labeled sterol (e.g., $^3$H-cholesterol or $^{125}$I-cholesterol)) or 5α-stanol along with either a sample or a blank. After an optional incubation, the cells can be washed to remove unabsorbed sterol or 5α-stanol. Sterol or 5α-stanol uptake can be determined by detecting the presence of labeled sterol or 5α-stanol in the host cells. For example, assayed cells or lysates or fractions thereof (e.g., fractions resolved by thin-layer chromatography) can be contacted with a liquid scintillant and scintillation can be measured using a scintillation counter.

In these assays, an NPC1L1 antagonist in the sample may be identified by measuring substantially reduced uptake of labeled sterol (e.g., $^3$H-cholesterol) or 5α-stanol, compared to what would be measured in the absence of such an antagonist and an agonist may be identified by measuring substantially increased uptake of labeled sterol (e.g., $^3$H-cholesterol) or 5α-stanol, compared to what would be measured in the absence of such an agonist.

Uptake assays can also be performed along with a control experiment lacking any NPC1L1-dependent uptake. The control experiment can be performed, for example, with a cell lacking any functional NPC1L1 (e.g., cell derived from a transgenic, mutant npc1l1$^-$ mouse as described herein). When the control experiment is performed, the level of uptake observed in the presence of sample being tested for the presence of an antagonist can be compared with that observed in the control experiment.

Source of NPC1L1. In principle, a binding assay of the invention could be carried out using a soluble NPC1L1 polypeptide of the invention, e.g., following production and refolding by standard methods from an E. coli or other prokaryotic or eukaryotic expression system, and the resulting receptor-labeled ligand complex could be precipitated, e.g., using an antibody against the receptor. The precipitate could then be washed and the amount of the bound, labeled ligand or antagonist or agonist could be measured.

Alternatively, NPC1L1 is membrane-bound. A nucleic acid encoding an NPC1L1 polypeptide of the invention (e.g., SEQ ID NO: 2, 4 or 12) can be transfected into an appropriate host cell, whereby the NPC1L1 will become incorporated into the membrane of the cell. A membrane fraction can then be isolated from the cell and used as a source of NPC1L1 for assay. Alternatively, the whole cell expressing NPC1L1 in the cell surface can be used in an assay. Preferably, specific binding of the labeled ligand or known antagonist or agonist to an untransfected/untransformed host cell or to a membrane fraction from an untransfected/untransformed host cell will be negligible.

Various membranes may be used directly as a source of NPC1L1 for the above-described screening systems, e.g. direct binding, scintillation proximity assay, sterol/5α stanol uptake assay. As described in Examples 5, 6, 7, 8, 9, 17, 27, and 29, NPC1L1 is highly expressed in certain tissues, especially in brush border cells of intestinal tissues. Therefore, brush border membrane (BBM) vesicle preparations may be utilized as a source of NPC1L1. The membranes may be derived from mammalian intestinal tissue from rhesus, rat, mouse or human tissue.

Membranes may be derived from brush border cells of intestinal tissues. Such membranes are conventionally prepared by collecting intestinal tissue from freshly sacrificed animals. The mucosa of the tissue is scraped, collected into buffered solutions, and homogenized. Cellular debris is removed and the membrane fractions are collected by centrifugation. Conventional techniques known to one of skill in the art maybe used for the preparation of brush border membrane vesicles. See Hauser, H., Howell, K., Dawson, R. M. C., Bowyer, D. E. Biochim. Biophys. Acta 602, 567-577 (1980); Kramer, W., Girbig, F., Gutjahr, U., Kowalewski, S., Jouvenal, K., Muller, G., Tripier, D., Wess, G. J. Biol. Chem. 268, 18035-18046 (1993); Rigtrup, K. M., Ong, D. E. Biochemistry 31, 2920-2926 (1992).

The membrane preparation may be in vesicular or non-vesicular form.

Alternatively, liposomes and liposomal preparations comprising NPC1L1 may also be a viable source of NPC1L1 for the screening assays of the present claimed method.

In vitro cultured cells expressing NPC1L1 may also be used. The host cells may be prepared by transforming or transfecting a nucleic acid encoding an NPC1L1 of the invention into an appropriate host cell, whereby the receptor becomes incorporated into the membrane of the cell. A membrane fraction can then be isolated from the cell and used as a source of the receptor for assay. Alternatively, the whole cell expressing the receptor on the cell surface can be used in an assay. Preferably, specific binding of the labeled ligand or known antagonist or agonist to an untransfected/untransformed host cell or membrane fraction from an untransfected/untransformed host cell will be negligible.

Preferred host cells include Chinese Hamster Ovary (CHO) cells, murine macrophage J774 cells, HEK-293 cells or any other macrophage cell line and human intestinal epithelial Caco2 cells.

The present invention provides for a method of identifying a ligand of NPC1L1 using these membrane preparations, for example by contacting membranes comprising NPC1L1, such as brush border membrane vesicle preparations, with detectably labeled substituted azetidinone compounds which are known NPC1L1 ligands, agonists or antagonists, and a candidate compound and determining whether the candidate compound can bind to NPC1L1. The binding of the candidate compound to NPC1L1 may modulate binding of the detectably labeled NPC1L1 ligands, agonists or antagonists to NPC1L1. In addition, a NPC1L1 ligand may be identified by measuring the binding of NPC1L1 with detectably labeled NPC1L1 ligands, agonists or antagonists in the presence and absence of the candidate compound wherein decreased binding of the detectably labeled NPC1L1 ligands, agonists or antagonists to NPC1L1 is an indication that the candidate compound is ligand of NPC1L1.

NPC1L1 may also be obtained by solubilization of membrane fractions comprising NPC1L1. The membranes may be obtained as discussed above, e.g., from mammalian tissue or in vitro cultured cells.

Binding Affinities of NPC1L1 Ligands. The affinity and specificity of the known ligand (e.g., detectably labeled substituted 2-azetidinone-glucuronide) for NPC1L1 are important to the identification of ligands that bind NPC1L1 in a screening assay. It is understood that the known ligand will be labeled for use in the screening assay. In an embodiment of the invention, the binding affinity of the known ligand for human NPC1L1 has a $K_D$ value equivalent or lower than the $K_D$ value of ezetimibe glucuronide 1 for human NPC1L1. In an aspect of this embodiment, the binding affinity of the known ligand for human NPC1L1 has a $K_D$ value of about 200 nM or lower; particularly it has a $K_D$ value of about 100 nM or lower; more particularly it has a $K_D$ value of about 50 nM or lower; even more particularly it has a $K_D$ value of about 20 nM or lower; and most particularly it has a $K_D$ value of about 10 nM or lower. For usefulness in the assay, there is essentially no lower limit on the $K_D$ value of the known ligand and it may, for example, go down into the pM range. As the $K_D$ value decreases, the binding affinity of the ligand for human NPC1L1 increases, which is desirable for the screening assay.

In another embodiment of the invention, the binding affinity of the known ligand for rat NPC1L1 has a $K_D$ value equivalent or lower than the $K_D$ value of ezetimibe glucuronide 1 for rat NPC1L1. In an aspect of this embodiment, the binding affinity of the known ligand for rat NPC1L1 has a $K_D$ value of about 200 nM or lower; particularly it has a $K_D$ value of about 100 nM or lower; more particularly it has a $K_D$ value of about 50 nM or lower; even more particularly it has a $K_D$ value of about 20 nM or lower; and most particularly it has a $K_D$ value of about 10 nM or lower.

In another embodiment of this invention, the known ligand for human NPC1L1 is selected from (a) a sulfur-containing substituted 2-azetidinone-glucuronide that is labeled with $^{35}S$, and particularly a compound of Formula II wherein $R^9$ contains an —$SO_2$— group and (b) a substituted 2-azetidinone-glucuronide labeled with $^{125}I$.

In one aspect of this embodiment, the known ligand for human NPC1L1 is selected from (a) a sulfur-containing substituted 2-azetidinone-glucuronide that is labeled with $^{35}S$, and particularly a compound of Formula II wherein $R^9$ contains an —$SO_2$— group, and (b) a substituted 2-azetidinone-glucuronide labeled with $^{125}I$, and has a $K_D$ value equivalent or lower than the $K_D$ value of ezetimibe glucuronide 1.

In another aspect of this embodiment, the known ligand for human NPC1L1 is selected from (a) a sulfur-containing substituted 2-azetidinone-glucuronide that is labeled with $^{35}S$, and particularly a compound of Formula II wherein $R^9$ contains an —$SO_2$— group, and (b) a substituted 2-azetidinone-glucuronide labeled with $^{125}I$, and has a $K_D$ value of about 200 nM or lower; particularly it has a $K_D$ value of about 100 nM or lower; more particularly it has a $K_D$ value of about 50 nM or lower; even more particularly it has a $K_D$ value of about 20 nM or lower; and most particularly it has a $K_D$ value of about 10 nM or lower.

When using $^3H$-labeled ezetimibe glucuronide in screening to identify NPC1L1 ligands from among the candidate compounds using mouse-derived membranes, candidate compounds identified as NPC1L1 ligands are preferably those candidates that exhibit a binding affinity having a $K_D$ value of about 12,000 nM or lower, preferably about 1000 nM or lower, more preferably about 100 nM or lower, and most preferably about 10 nM or lower. When using $^3H$-labeled ezetimibe glucuronide in screening to identify NPC1L1 ligands using rat-derived membranes or human-derived membranes, candidate compounds identified as NPC1L1 ligands are preferably those candidates that exhibit a binding affinity having a $K_D$ value of about 1000 nM or lower, preferably about 100 nM or lower, and more preferably about 10 nM or lower. When using $^3H$-labeled ezetimibe glucuronide in screening to identify NPC1L1 ligands using rhesus monkey-derived membranes, candidate compounds identified as NPC1L1 ligands are preferably those candidates that exhibit a binding affinity having a $K_D$ value of about 50 nM or lower, and preferably about 10 nM or lower.

When using $^{35}S$-labeled compound 2 in screening to identify NPC1L1 ligands from among the candidate compounds using rat or human-derived membranes, candidate compounds identified as NPC1L1 ligands are preferably those candidates that exhibit a binding affinity having a $K_D$ value in the range from about 10 µM to about 1 nM. When using $^{125}I$-labeled substituted 2-azetidinone glucuronide compounds in the assay with rat or human membranes, candidate compounds identified as NPC1L1 ligands are preferably those candidates that exhibit a binding affinity having a $K_D$ value in the range from about 10 nM to about 10 pM, and preferably from about 100 pM to about 10 pM.

Mouse Assay. The present invention comprises a mutant, transgenic mouse which lacks any functional NPC1L1. This mouse may serve as a convenient control experiment in screening assays for identifying inhibitors of intestinal sterol (e.g., cholesterol) or 5α-stanol absorption, preferably inhibitors of NPC1L1. Preferably, a mouse assay of the present invention would comprise the following steps:

(a) feeding a sterol (e.g., cholesterol) or 5α-stanol-containing substance (e.g., comprising radiolabeled cholesterol, such as $^{14}C$-cholesterol or $^3H$-cholesterol) to a first and second mouse comprising a functional NPC1L1 gene and to a third, mutant mouse lacking a functional NPC1L1 ;

The sterol (e.g., cholesterol) or 5α-stanol containing substance preferably contains labeled cholesterol, such as a radiolabeled cholesterol, for example, $^3H$ or $^{14}C$ labeled cholesterol. The sterol (e.g., cholesterol) or 5α-stanol containing substance may also include cold, unlabeled sterol (e.g., cholesterol) or 5α-stanol such as in corn oil.

In these assays, the third npc1l1⁻ mutant mouse serves as a (+)-control experiment which exhibits low levels of intestinal sterol (e.g., cholesterol) or 5α-stanol absorption and the second mouse serves as a (−)-control experiment which exhibits normal, uninhibited levels of intestinal sterol (e.g., cholesterol) or 5α-stanol absorption. The second mouse is not administered the sample to be tested for an NPC1L1 antagonist. The first mouse is the experiment.

(b) administering the sample to the first mouse comprising a functional NPC1L1 but not to the second mouse;

(c) measuring the amount of sterol (e.g., cholesterol) or 5α-stanol absorption in the intestine of said first, second and third mouse;

Intestinal sterol (e.g., cholesterol) or 5α-stanol absorption may be measured by any method known in the art. For example, the level intestinal absorption can be assayed by measuring the level of serum sterol (e.g., cholesterol) or 5α-stanol.

(d) comparing the levels of intestinal sterol (e.g., cholesterol) or 5α-stanol absorption in each mouse;

wherein the sample is determined to contain the intestinal sterol (e.g., cholesterol) or 5α-stanol absorption antagonist when the level of intestinal sterol (e.g., cholesterol) or 5α-stanol absorption in the first mouse and in the third mouse are less than the amount of intestinal sterol (e.g., cholesterol) or 5α-stanol absorption in the second mouse.

Preferably, if the sample contains an intestinal sterol (e.g., cholesterol) or 5α-stanol absorption inhibitor (e.g., an NPC1L1 inhibitor), the level of sterol (e.g., cholesterol) or 5α-stanol absorption in the first mouse will be similar to that of the third, npc1l1 mutant mouse.

An alternative, (+)-control experiment which may be used in these screening assays is a mouse comprising functional NPC1L1 which is administered a known antagonist of NPC1L1, such as ezetimibe.

Pharmaceutical Compositions

NPC1L1 ligands discovered, for example, by the screening methods described above may be used therapeutically (e.g., in a pharmaceutical composition) to stimulate or block the activity of NPC1L1 and, thereby, to treat any medical condition caused or mediated by NPC1L1. In addition, the antibody molecules of the invention may also be used therapeutically (e.g., in a pharmaceutical composition) to bind NPC1L1 and, thereby, block the ability of NPC1L1 to bind a sterol (e.g., cholesterol) or 5α-stanol. Blocking the binding of a sterol (e.g., cholesterol) or 5α-stanol would prevent absorption of the molecule (e.g., by intestinal cells such as enterocytes). Blocking absorption of sterol (e.g., cholesterol) or 5α-stanol would be a useful way to lower serum sterol (e.g., cholesterol) or 5α-stanol levels in a subject and, thereby, reduce the incidence of, for example, hyperlipidemia, atherosclerosis, coronary heart disease, stroke or arteriosclerosis.

The term "subject" or "patient" includes any organism, preferably animals, more preferably mammals (e.g., mice, rats, rabbits, dogs, horses, primates, cats) and most preferably humans.

The term "pharmaceutical composition" refers to a composition including an active ingredient and a pharmaceutically acceptable carrier and/or adjuvant.

Although the compositions of this invention could be administered in simple solution, they are more typically used in combination with other materials such as carriers, preferably pharmaceutically acceptable carriers. Useful, pharmaceutically acceptable carriers can be any compatible, non-toxic substances suitable for delivering the compositions of the invention to a subject. Sterile water, alcohol, fats, waxes, and inert solids may be included in a pharmaceutically acceptable carrier. Pharmaceutically acceptable adjuvants (buffering agents, dispersing agents) may also be incorporated into the pharmaceutical composition.

Preferably, the pharmaceutical compositions of the invention are in the form of a pill or capsule. Methods for formulating pills and capsules are very well known in the art. For example, for oral administration in the form of tablets or capsules, the active drug component may be combined with any oral, non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

The pharmaceutical compositions of the invention may be administered in conjunction with a second pharmaceutical composition or substance. In preferred embodiments, the second composition includes a cholesterol-lowering drug. When a combination therapy is used, both compositions may be formulated into a single composition for simultaneous delivery or formulated separately into two or more compositions (e.g., a kit).

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications* Dekker, New York; Lieberman et al. (eds.) (1990) *Pharmaceutical Dosage Forms: Tablets* Dekker, New York; and Lieberman et al. (eds.) (1990), *Pharmaceutical Dosage Forms: Disperse Systems* Dekker, New York.

The dosage regimen involved in a therapeutic application may be determined by a physician, considering various factors which may modify the action of the therapeutic substance, e.g., the condition, body weight, sex and diet of the patient, the severity of any infection, time of administration, and other clinical factors. Often, treatment dosages are titrated upward from a low level to optimize safety and efficacy. Dosages may be adjusted to account for the smaller molecular sizes and possibly decreased half-lives (clearance times) following administration.

An "effective amount" of a ligand of the invention may be an amount that will detectably reduce the level of intestinal sterol (e.g., cholesterol) or 5α-stanol absorption or detectably reduce the level of serum sterol (e.g., cholesterol) or 5α-stanol in a subject administered the composition.

Typical protocols for the therapeutic administration of such substances are well known in the art. Pharmaceutical composition of the invention may be administered, for example, by any parenteral or non-parenteral route.

Pills and capsules of the invention can be administered orally. Injectable compositions can be administered with medical devices known in the art; for example, by injection with a hypodermic needle.

Injectable pharmaceutical compositions of the invention may also be administered with a needleless hypodermic injection device; such as the devices disclosed in U.S. Pat. No. 5,399,163; 5,383,851; 5,312,335; 5,064,413; 4,941,880; 4,790,824 or 4,596,556.

Anti-Sense

The present invention also encompasses anti-sense oligonucleotides capable of specifically hybridizing to mRNA encoding NPC1L1 (e.g., any of SEQ ID NOs: 1, 3, 5-11 or 13) having an amino acid sequence defined by, for example, SEQ ID NO: 2 or 4 or 12 or a subsequence thereof so as to prevent translation of the mRNA. Additionally, this invention contemplates anti-sense oligonucleotides capable of specifically hybridizing to the genomic DNA molecule encoding NPC1L1, for example, having an amino acid sequence defined by SEQ ID NO: 2 or 4 or 12 or a subsequence thereof.

This invention further provides pharmaceutical compositions comprising (a) an amount of an oligonucleotide effective to reduce NPC1L1-mediated sterol (e.g., cholesterol) or 5α-stanol absorption by passing through a cell membrane and binding specifically with mRNA encoding NPC1L1 in the cell so as to prevent its translation and (b) a pharmaceutically acceptable carrier capable of passing through a cell membrane. In an embodiment, the oligonucleotide is coupled to a substance that inactivates mRNA. In another embodiment, the substance that inactivates mRNA is a ribozyme.

Reducing the level of NPC1L1 expression by introducing anti-sense NPC1L1 RNA into the cells of a patient is a useful method reducing intestinal sterol (e.g., cholesterol) or 5☐-stanol absorption and serum cholesterol in the patient.

Kits

Kits of the present invention include ezetimibe, preferably combined with a pharmaceutically acceptable carrier, in a pharmaceutical formulation, more preferably in a pharmaceutical dosage form such as a pill, a powder, an injectable liquid, a tablet, dispersible granules, a capsule, a cachet or a suppository. See for example, Gilman et al. (eds.) (1990), The Pharmacological Bases of Therapeutics, 8th Ed., Pergamon Press; and Remington's Pharmaceutical Sciences, supra, Easton, Pa.; Avis et al. (eds.) (1993) Pharmaceutical Dosage Forms: Parenteral Medications Dekker, New York; Lieberman et al. (eds.) (1990) Pharmaceutical Dosage Forms: Tablets Dekker, New York; and Lieberman et al. (eds.) (1990), Pharmaceutical Dosage Forms: Disperse Systems Dekker, New York. Preferably, the dosage form is a Zetia® tablet (Merck/Schering-Plough Corp.). Ezetimibe may be supplied in any convenient form. For example, tablets including ezetimibe may be supplied in bottles of 30, 90 or 500.

The kits of the present invention also include information, for example in the form of a package insert, indicating that the target of ezetimibe is NPC1L1 (NPC3). The term "target of ezetimibe" indicates that ezetimibe reduces intestinal sterol (e.g., cholesterol) or 5α-stanol absorption, either directly or indirectly, by antagonizing NPC1L1. The form of the insert may take any form, such as paper or on electronic media such as a magnetically recorded medium (e.g., floppy disk) or a CD-ROM.

The package insert may also include other information concerning the pharmaceutical compositions and dosage forms in the kit. Generally, such information aids patients and physicians in using the enclosed pharmaceutical compositions and dosage forms effectively and safely. For example, the following information regarding ezetimibe (e.g., Zetia®) and/or simvastatin (e.g., Zocor®) may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references and patent information.

The kits of the invention may also include simvastatin (

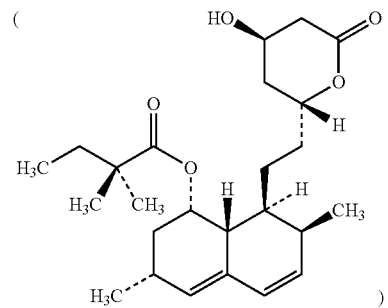

) preferably combined with a pharmaceutically acceptable carrier, in a pharmaceutical formulation, more preferably in a pharmaceutical dosage form such as a pill, a powder, an injectable liquid, a tablet, dispersible granules, a capsule, a cachet or a suppository. Preferably, the dosage form of simvastatin is a Zocor® tablet (Merck & Co.; Whitehouse Station, N.J.).

Tablets or pills comprising simvastatin may be supplied in any convenient form. For example, pills or tablets comprising 5 mg simvastatin can be supplied as follows: bottles of 30, 60, 90, 100 or 1000. Pills or tablets comprising 10 mg simvastatin may be supplied as follows: bottles of 30, 60, 90, 100, 1000 or 10,000. Pills or tablets comprising 20 mg simvastatin may be supplied as follows: bottles of 30, 60, 90, 100, 1000 or 10,000. Pills or tablets comprising 40 mg simvastatin may be supplied as follows: bottles of 30, 60, 90, 100 or 1000. Pills or tablets comprising 80 mg simvastatin may be supplied as follows: bottles of 30, 60, 90, 100, 1000 or 10,000.

Ezetimibe and simvastatin may be supplied, in the kit, as separate compositions or combined into a single composition. For example, ezetimibe and simvastatin may be supplied within a single, common pharmaceutical dosage form (e.g., pill or tablet) as in separate pharmaceutical dosage forms (e.g., two separate pills or tablets).

npc1l1⁻ Cells

The present invention provides any isolated mammalian cell, (e.g., an isolated mouse cell, an isolated rat cell or an isolated human cell) which lacks an NPC1L1 gene which encodes or can produce a functional NPC1L1 protein. Included within this embodiment are mutant npc1l1 genes comprising a point mutation, truncation or deletion of the genetic coding region or of any regulatory element (e.g., a promoter).

For example, the cell can be isolated from a mutant mouse comprising a homozygous mutation of endogenous, chromosomal NPC1L1 wherein the mouse does not produce any functional NPC1L1 protein (e.g., the mouse described below in Example 22). Moreover, the present invention comprises any cell, tissue, organ, fluid, nucleic acid, peptide or other biological substance derived or isolated from such a mutant mouse, particularly a mutant, transgenic mouse which does not produce any functional NPC1L1, wherein the region of endogenous, chromosomal NPC1L1 deleted, in the mouse, corresponds to nucleotides 790-998 of the nucleotide sequence set forth in SEQ ID NO: 45.

The isolated cell can be isolated or derived, for example, from the duodenum, gall bladder, liver, small intestine or stomach of the mutant mouse. Further, the cell can be an enterocyte.

The npc1l1⁻ mutant cells are useful, for example, for use in control experiments in screening assays (see e.g., supra) since they lack any NPC1L1-dependent uptake or binding of sterol, 5α-stanol or ezetimibe. The level of inhibition caused by a particular sample, in a screening assay, can be compared to that of an assay performed with the mutant cell. Ideally, though by no means necessarily, in a screening assay, for example, as described herein, the same amount of binding will be observed by a non-mutant cell or cell membrane, in the presence of an antagonist, as is observed in connection with a mutant npc1l1 cell or cell membrane alone.

EXAMPLES

The following examples are provided to more clearly describe the present invention and should not be construed to limit the scope of the invention in any way.

Example 1

Cloning and Expression of Rat, Mouse and Human NPC1L1

Rat NPC1L1, mouse NPC1L1 or human NPC1L1 can all conveniently be amplified using polymerase chain reaction (PCR). In this approach, DNA from a rat, mouse or human cDNA library can be amplified using appropriate primers and standard PCR conditions. Design of primers and optimal amplification conditions constitute standard techniques which are commonly known in the art.

An amplified NPC1L1 gene may conveniently be expressed, again, using methods which are commonly known in the art. For example, NPC1L1 may be inserted into a pET-based plasmid vector (Stratagene; La Joola, Calif.), downstream of the T7 RNA polymerase promoter. The plasmid may then be transformed into a T7 expression system (e.g., BL21DE3 $E.\ coli$ cells), grown in a liquid culture and induced (e.g., by adding IPTG to the bacterial culture).

Example 2

Direct Binding Assay

Membrane preparation: Caco2 cells transfected with an expression vector containing a polynucleotide encoding NPC1L1 (e.g., SEQ ID NO: 2, 4 or 12) are harvested by incubating in 5 mM EDTA/phosphate-buffered saline followed by repeated pipetting. The cells are centrifuged 5 min at 1000×g. The EDTA/PBS is decanted and an equal volume of ice-cold 50 mM Tris-HCl, pH 7.5 is added and cells are broken up with a Polytron (PT10 tip, setting 5, 30 sec). Nuclei and unbroken cells are sedimented at 1000×g for 10 min and then the supernatant is centrifuged at 50,000×g for 10 min. The supernatant is decanted, the pellet is resuspended by Polytron, a sample is taken for protein assay (bicinchoninic acid, Pierce), and the tissue is again centrifuged at 50,000×g. Pellets are stored frozen at −20° C.

Binding assay: For saturation binding, four concentrations of [³H]-ezetimibe (15 Ci/mmol) are incubated without and with $10^{-5}$ M ezetimibe in triplicate with 50 μg of membrane protein in a total volume of 200 μl of 50 mM Tris-HCl, pH 7.5, for 30 min at 30° C. Samples are filtered on GF/B filters and washed three times with 2 ml of cold Tris buffer. Filters are dried in a microwave oven, impregnated with Meltilex wax scintillant, and counted at 45% efficiency. For competition binding assays, five concentrations of a sample are incubated in triplicate with 18 nM [³H]-ezetimibe and 70 μg of membrane protein under the conditions described above. Curves are fit to the data with Prism (GraphPad Software) nonlinear least-squares curve-fitting program and $K_i$ values are derived from $IC_{50}$ values according to Cheng and Prusoff (Cheng, Y. C., et al., (1973) Biochem. Pharmacol. 22: 3099-3108).

Example 3A

SPA Assay

For each well of a 96 well plate, a reaction mixture of 10 μg human, mouse or rat NPC1L1-CHO overexpressing membranes (Biosignal) and 200 μg/well YSi-WGA-SPA beads (Amersham) in 100 μl is prepared in NPC1L1 assay buffer (25 mM HEPES, pH 7.8, 2 mM $CaCl_2$, 1 mM $MgCl_2$, 125 mM NaCl, 0.1% BSA). A 0.4 nM stock of ligand-[¹²⁵I]-ezetimibe-is prepared in the NPC1L1 assay buffer. The above solutions are added to a 96-well assay plate as follows: 50 μl NPC1L1 assay buffer, 100 μl of reaction mixture, 50 μl of ligand stock (final ligand concentration is 0.1 nM). The assay plates are shaken for 5 minutes on a plate shaker, then incubated for 8 hours before cpm/well are determined in Microbeta Trilux counter (PerkinElmer).

These assays will indicate that [¹²⁵I]-ezetimibe binds to the cell membranes expressing human, mouse or rat NPC1L1. Similar results will be obtained if the same experiment is performed with radiolabeled cholesterol (e.g., ¹²⁵I-cholesterol).

Example 3A

Alternate SPA Assay

The final concentrations should be: 1 nM ³⁵S-2 (Km ~2.5 nM, ~50,000 dpm/assay);

1 μg membranes (~1-2 nM receptor); 0.007%-0.03% taurocholate (0.140 μl 1% stock); 0.010%-0.05% digitonin (0.200 μl 1% stock); 5% DMSO (1.00 μl inhibitors).

In each well of a 96 well plate is put 1 μl DMSO inhibitor solution, and then the radioligand and detergents are added as a 2× solution in 10 μl buffer A. Shake for a minute to be sure the inhibitor and ligand are mixed, before initiating with 9 μl diluted receptor solution in buffer A. After shaking again, the plate is incubated at 37° C. for 2 hours. Then WGA beads (0.3 mg) are added as a 3 μl suspension in buffer A, then shake for 30 minutes. Similar results are obtained if membranes are pre-incubated with beads for 30 minutes before adding ligands. Finally, dilute to 300 μl with buffer A, cover the plate, spin at 3,000 rpm×5 min, and read at 2 minutes per well in the "Microbeta" counter.

Stocks

Ligand: ³⁵S-2 is 525.42 nM, 0616 μCi/μl, in acetonitrile; spec. act.=$3.8916×10^{-4}$ fmol/dpm; 1168 Ci/mmol)

Membranes: 3$^{rd}$ batch recombinant human expressed in HEK-293 cells; 20.2 ug/μl stock; ~20-40 pmol NPC1L1/mg protein Buffer A: 26 mM $NaHCO_3$; 0.96 mN $NaH_2PO_4$; 5 mM HEPES; optional addition of 5.5 mM glucose; 117 mM NaCl; 5.4 mM KCl

Example 4

Cholesterol Uptake Assay

CHO cells expressing either SR-B1 or three different clones of rat NPC1L1 or one clone of mouse NPC1L1 were starved overnight in cholesterol free media then dosed with [3H]-cholesterol in a mixed synthetic micelle emulsion for 4 min, 8 min, 12 min or 24 m in the absence or presence of 10 □M ezetimibe. The cells were harvested and the lipids were organically extracted. The extracted lipids were spotted on thin-layer chromatography (TLC) plates and resolved within an organic vapor phase. The free cholesterol bands for each assay were isolated and counted in a scintillation counter.

The SR-B1 expressing cells exhibited an increase in [$^3$H]-cholesterol uptake as early as 4 min which was also inhibited by ezetimibe. The three rat clones and the one mouse clone appeared to give background levels of [$^3$H]-cholesterol uptake which was similar to that of the untransformed CHO cell.

These experiments will yield data demonstrating that CHO cells can perform mouse, rat and human NPC1L1-dependent uptake of [$^3$H]-cholesterol when more optimal experimental conditions are developed.

Example 5

Expression of Rat NPC1L1 in Wistar Rat Tissue

In these experiments, the expression of rat NPC1L1 mRNA, in several rat tissues, was evaluated. The tissues evaluated were esophagus, stomach, duodenum, jejunum, ileum, proximal colon, distal colon, liver, pancreas, heart, aorta, spleen, lung, kidney, brain, muscle, testes, ovary, uterus, adrenal gland and thyroid gland. Total RNA samples were isolated from at least 3 male and 3 female animals and pooled. The samples were then subjected to real time quantitative PCR using Taqman analysis using standard dual-labeled fluorogenic oligonucleotide probes. Typical probe design incorporated a 5' reporter dye (e.g., 6FAM (6-carboxyfluorescein) or VIC) and a 3' quenching dye (e.g., TAMRA (6-carboxytetramethyl-rhodamine)).

```
rat NPC1L1:
                                         (SEQ ID NO: 14)
Forward:   TCTTCACCCTTGCTCTTTGC (SEQ ID NO: 15)
Reverse:   AATGATGGAGAGTAGGTTGAGGAT (SEQ ID NO: 16)
Probe:     [6FAM]TGCCCACCTTTGTTGTCTGCTACC[TAMRA]

rat β-actin:
                                         (SEQ ID NO: 17)
Forward:   ATCGCTGACAGGATGCAGAAG (SEQ ID NO: 18)
Reverse:   TCAGGAGGAGCAATGATCTTGA (SEQ ID NO: 19)
Probe:     [VIC]AGATTACTGCCCTGGCTCCTAGCACCAT[TAMRA]
```

PCR reactions were run in 96-well format with 25 μl reaction mixture in each well containing: Platinum SuperMix (12.5 μl), ROX Reference Dye (0.5 μl), 50 mM magnesium chloride (2 μl), cDNA from RT reaction (0.2 μl). Multiplex reactions contained gene specific primers at 200 nM each and FAM labeled probe at 100 nM and gene specific primers at 100 nM each and VIC labeled probe at 50 nM. Reactions were run with a standard 2-step cycling program, 95° C. for 15 sec and 60° C. for 1 min, for 40 cycles.

The highest levels of expression were observed in the duodenum, jejunum and ileum tissue. These data indicate that NPC1L1 plays a role in cholesterol absorption in the intestine.

Example 6

Expression of Mouse NPC1L1 in Mouse Tissue

In these experiments, the expression of mouse NPC1L1 mRNA, in several tissues, was evaluated. The tissues evaluated were adrenal gland, BM, brain, heart, islets of langerhans, LI, small intestine, kidney, liver, lung, MLN, PLN, muscle, ovary, pituitary gland, placenta, Peyers Patch, skin, spleen, stomach, testes, thymus, thyroid gland, uterus and trachea. Total RNA samples were isolate from at least 3 male and 3 female animals and pooled. The samples were then subjected to real time quantitative PCR using Taqman analysis using the following primers and probes:

```
mouse NPC1L1:
                                         (SEQ ID NO: 20)
Forward: ATCCTCATCCTGGGCTTTGC (SEQ ID NO: 21)
Reverse: GCAAGGTGATCAGGAGGTTGA (SEQ ID NO: 22)
Probe:   [6FAM]CCCAGCTTATCCAGATTTTCTTCTTCCGC[TAMRA]
```

The highest levels of expression were observed in the Peyer's Patch, small intestine, gall bladder and stomach tissue. These data are consistent with a cholesterol absorption role for NPC1L1 which takes place in the digestive system.

Example 7

Expression of Human NPC1L1 in Human Tissue

In these experiments, the expression level of human NPC1L1 mRNA was evaluated in 2045 samples representing 46 normal tissues. Microarray-based gene expression analysis was performed on the Affymetrix HG-U95 GeneChip using a cRNA probe corresponding to base pairs 4192-5117 (SEQ ID NO: 43) in strict accordance to Affymetrix's established protocols. Gene Chips were scanned under low photo multiplier tube (PMT), and data were normalized using either Affymetrix MAS 4.0 or MAS 5.0 algorithms. In addition "spike ins" for most samples were used to construct a standard curve and obtain RNA concentration values according Gene Logic algorithms and procedures. A summary of these results are indicated, below, in Table 2.

TABLE 2

Expression level of NPC1L1 mRNA in various human tissues.

| Tissue | Present | Absent | Lower 25% | Median | Upper 75% |
|---|---|---|---|---|---|
| Adipose | 2 of 32 | 30 of 32 | -2.45 | 1.16 | 12.23 |
| Adrenal Gland | 0 of 12 | 12 of 12 | -23.54 | -4.47 | 10.51 |
| Appendix | 0 of 3 | 3 of 3 | -8.02 | -6.69 | 38.19 |
| Artery | 0 of 3 | 3 of 3 | -6.59 | -4.67 | 9.68 |
| Bladder | 1 of 5 | 4 of 5 | -22 | -7.95 | -1.99 |
| Bone | 0 of 3 | 3 of 3 | -1.64 | 3.3 | 19.53 |
| Breast | 4 of 80 | 76 of 80 | -4.07 | 3.13 | 14.67 |
| Cerebellum | 0 of 5 | 5 of 5 | -3.04 | 3.24 | 15.38 |
| Cervix | 3 of 101 | 98 of 101 | -7.56 | -0.07 | 20.89 |
| Colon | 9 of 151 | 142 of 151 | -10.19 | 0.31 | 18.36 |
| Cortex Frontal Lobe | 0 of 7 | 7 of 7 | 1.4 | 8.46 | 11.75 |
| Cortex Temporal Lobe | 0 of 3 | 3 of 3 | 7.1 | 8.5 | 15.87 |
| Duodenum | 59 of 61 | 2 of 61 | 519.23 | 827.43 | 1101.67 |
| Endometrium | 0 of 21 | 21 of 21 | -14.43 | -6.39 | 2.79 |
| Esophagus | 1 of 27 | 26 of 27 | -10.93 | -4.97 | 12.48 |
| Fallopian Tube | 3 of 51 | 48 of 51 | 5.02 | 13.24 | 26.77 |
| Gall Bladder | 8 of 8 | 0 of 8 | 205.76 | 273.39 | 422.8 |
| Heart | 0 of 3 | 3 of 3 | 3.33 | 11.19 | 11.66 |
| Hippocampus | 0 of 5 | 5 of 5 | 8.25 | 9.11 | 19.83 |
| Kidney | 4 of 86 | 82 of 86 | -8.36 | 3.41 | 16.46 |
| Larynx | 0 of 4 | 4 of 4 | -13.76 | -0.81 | 8.54 |
| Left Atrium | 2 of 141 | 139 of 141 | -18.9 | -4.58 | 6.84 |
| Left Ventricle | 0 of 15 | 15 of 15 | -21.19 | -9.59 | 17.7 |
| Liver | 32 of 34 | 2 of 34 | 325.74 | 427.77 | 540.1 |
| Lung | 2 of 93 | 91 of 93 | -3.47 | 11.03 | 22.34 |
| Lymph Node | 0 of 11 | 11 of 11 | -1.78 | -0.19 | 1.34 |
| Muscles | 0 of 39 | 39 of 39 | -21.57 | 8.25 | 26.73 |
| Myometrium | 8 of 106 | 98 of 106 | -3.98 | 4.87 | 17.55 |
| Omentum | 0 of 15 | 15 of 15 | -14.25 | -1.6 | 19.58 |
| Ovary | 1 of 74 | 73 of 74 | 0.5 | 17.51 | 38.28 |
| Pancreas | 0 of 34 | 34 of 34 | -87.08 | -53.2 | -24.14 |
| Placenta | 0 of 5 | 5 of 5 | -20.4 | -3.44 | 18.91 |
| Prostate | 0 of 32 | 32 of 32 | 1.08 | 15.56 | 27.24 |
| Rectum | 1 of 43 | 42 of 43 | -9.26 | -1.49 | 9.8 |
| Right Atrium | 4 of 169 | 165 of 169 | -19.32 | -6.58 | 7.72 |
| Right Ventricle | 1 of 160 | 159 of 160 | -24.01 | -6.49 | 10.06 |
| Skin | 0 of 59 | 59 of 59 | -12.68 | 1.5 | 22.77 |
| Small Intestine | 46 of 68 | 22 of 68 | 21.21 | 493.93 | 939.2 |
| Soft Tissues | 1 of 6 | 5 of 6 | -1.99 | 2.6 | 5.32 |
| Spleen | 0 of 31 | 31 of 31 | -9.41 | -0.31 | 9.5 |
| Stomach | 7 of 47 | 40 of 47 | 19.02 | 52.29 | 117.09 |
| Testis | 0 of 5 | 5 of 5 | -4.51 | 1.22 | 11.2 |
| Thymus | 1 of 71 | 70 of 71 | -6.26 | 2.51 | 11.67 |
| Thyroid Gland | 1 of 18 | 17 of 18 | -12.22 | 2.84 | 17.86 |
| Uterus | 0 of 58 | 58 of 58 | -10.67 | 1.59 | 16.01 |
| WBC | 3 of 40 | 37 of 40 | -16.45 | -0.72 | 25.18 |

Shaded data corresponds to tissues wherein the highest levels of NPC1L1 mRNA was detected. The "Present" column indicates the proportion of specified tissue samples evaluated wherein NPC1L1 mRNA was detected. The "Absent" column indicates the proportion of specified tissue samples evaluated wherein NPC1L1 RNA was not detected. The "lower 25%", "median" and "upper 75%" columns indicate statistical distribution of the relative NPC1L1 signal intensities observed for each set of tissue evaluated.

Example 8

Distribution of Rat NPC1L1, Rat IBAT or Rat SR-B1 mRNA in Rat Small Intestine

In these experiments, the distribution of rat NPC1L1 mRNA along the proximal-distal axis of rat small intestines was evaluated. Intestines were isolated from five independent animals and divided into 10 sections of approximately equal length. Total RNA was isolated and analyzed, by real time quantitative PCR using Taqman analysis, for localized expression levels of rat NPC1L1, rat IBAT (ileal bile acid transporter) or rat SR-B1 mRNA. The primers and probes used in the analysis were:

rat NPC1L1:

Forward:  TCTTCACCCTTGCTCTTTGC
(SEQ ID NO: 23)

Reverse:  AATGATGGAGAGTAGGTTGAGGAT
(SEQ ID NO: 24)

Probe:    [6FAM]TGCCCACCTTTGTTGTCTGCTACC[TAMRA]
(SEQ ID NO: 25)

rat Villin:

Forward:  AGCACCTGTCCACTGAAGATTTC
(SEQ ID NO: 26)

Reverse:  TGGACGCTGAGCTTCAGTTCT
(SEQ ID NO: 27)

Probe:    [VIC]CTTCTCTGCGCTGCCTCGATGGAA[TAMRA]
(SEQ ID NO: 28)

rat SR-B1:

Forward:  AGTAAAAAGGGCTCGCAGGAT
(SEQ ID NO: 29)

Reverse:  GGCAGCTGGTGACATCAGAGA
(SEQ ID NO: 30)

Probe:    [6FAM]AGGAGGCCATGCAGGCCTACTCTGA[TAMRA]
(SEQ ID NO: 31)

rat IBAT:

Forward:  GAGTCCACGGTCAGTCCATGT
(SEQ ID NO: 32)

Reverse:  TTATGAACAACAATGCCAAGCAA
(SEQ ID NO: 33)

Probe:    [6FAM]AGTCCTTAGGTAGTGGCTTAGTCCCTGGAAGCTC[TAMRA]
(SEQ ID NO: 34)

The mRNA expression levels of each animal intestinal section were analyzed separately, then the observed expression level was normalized to the observed level of villin mRNA in that intestinal section. The observed, normalized mRNA expression levels for each section where then averaged.

The expression level of NPC1L1 and SR-B1 were highest in the jejunum (sections 2-5) as compared to that of the more distal ileum sections. Since the jejunum is believed to be the site of cholesterol absorption, these data suggest such a role for rat NPC1L1. IBAT distribution favoring the ileum is well document and served as a control for the experiment.

Example 9

In Situ Analysis of Rat NPC1L1 mRNA in Rat Jejunum Tissue

The localization of rat NPC1L1 mRNA was characterized by in situ hybridization analysis of rat jejunum serial sections. The probes used in this analysis were:

```
T7-sense probe:
GTAATACGACTCACTATAGGGCCCTGACGGT    (SEQ ID NO: 35)
CCTTCCTGAGGGAATCTTCAC T7-antisense probe:
GTAATACGACTCACTATAGGGCCTGGGAA      (SEQ ID NO: 36)
GTTGGTCATGGCCACTCCAGC
```

The RNA probes were synthesized using T7 RNA polymerase amplification of a PCR amplified DNA fragment corresponding rat NPC1L1 nucleotides 3318 to 3672 (SEQ ID NO 1). Sense and anti-sense digoxigenin-UTP labeled cRNA probes were generated from the T7 promoter using the DIG RNA Labeling Kit following the manufacturer's instructions. Serial cryosections rat jejunum were hybridized with the sense and antisense probes. Digoxigenin labeling was detected with the DIG Nucleic Acid Detection Kit based on previous methods. A positive signal is characterized by the deposition of a red reaction product at the site of hybridization.

The anti-sense probe showed strong staining of epithelium along the crypt-villus axis under low magnification (40×). The observed rat NPC1L1 mRNA expression levels may have been somewhat greater in the crypts than in the villus tips. Under high magnification (200×), staining was observed in the enterocytes but not in the goblet cells. A lack of staining observed with the sense probe (control) confirmed the high specificity of the NPC1L1 anti-sense signal. These data provided further evidence of the role of rat NPC1L1 in intestinal cholesterol absorption.

Example 10

FACS Analysis of Fluorescently Labeled Ezetimibe Binding to Transiently Transfected CHO Cells In these experiments, the ability of BODIPY-labeled ezetimibe (Altmann, et al., (2002) Biochim. Biophys. Acta 1580(1): 77-93) to bind to NPC1L1 and SR-B1 was evaluated. "BODIPY" is a fluorescent group which was used to detect the BODIPY-ezetimibe. Chinese hamster ovary (CHO) cells were transiently transfected with rat NPC1L1 DNA (rNPC1L1/CHO), mouse NPC1L1 DNA (mNPC1L1/CHO), mouse SR-B1 DNA (mSRBI/CHO) or EGFP DNA (EGFP/CHO). EGFP is enhanced green fluorescent protein which was used as a positive control. The transfected CHO cells or untransfected CHO cells were then stained with 100 nM BODIPY-labeled ezetimibe and analyzed by FACS. Control experiments were also performed wherein the cells were not labeled with the BODIPY-ezetimibe and wherein untransfected CHO cells were labeled with the BODIPY-ezetimibe.

No staining was observed in the untransfected CHO, rNPC1L1/CHO or mNPC1L1/CHO cells. Fluorescence was detected in the positive-control EGFP/CHO cells. Staining was also detected in the mouse SR-B1/CHO cells. These data show that, under the conditions tested, BODIPY-ezetimibe is capable of binding to SR-B1 and that such binding is not ablated by the presence of the fluorescent BODIPY group. When more optimal conditions are determined, BODIPY-ezetimibe will be shown to label the rNPC1L1/CHO and mNPC1L1/CHO cells.

Example 11

FACS Analysis of Transiently Transfected CHO Cells Labeled with Anti-FLAG Antibody M2

In these experiments, the expression of FLAG-tagged NPC1L1 on CHO cells was evaluated. CHO cells were transiently transfected with mouse NPC1L1 DNA, rat NPC1L1 DNA, FLAG-rat NPC1L1 DNA or FLAG-mouse NPC1L1 DNA. The 8 amino acid FLAG tag used was DYKDDDDK (SEQ ID NO: 37) which was inserted on the amino-terminal extracellular loop just past the secretion signal sequence. The cells were incubated with commercially available anti-FLAG monoclonal mouse antibody M2 followed by a BODIPY-tagged anti-mouse secondary antibody. The treated cells were then analyzed by FACS.

The M2 antibody stained the CHO cells transfected with FLAG-rat NPC1L1 DNA and with FLAG-mouse NPC1L1. No staining was observed in the CHO cells transfected with mouse NPC1L1 DNA and with rat NPC1L1 DNA. These data showed that rat NPC1L1 and mouse NPC1L1 possess no significant, inherent fluorescence and are not bound by the anti-FLAG antibody. The observed, FLAG-dependent labeling of the cells indicated that the FLAG-mouse NPC1L1 and FLAG-rat NPC1L1 proteins are localized at the cell membrane of the CHO cells.

Example 12

FACS Analysis of FLAG-Rat NPC1L1-EGFP Chimera in Transiently Transfected CHO Cells In these experiments, the surface and cytoplasmic localization of rat NPC1L1 in CHO cells was evaluated. CHO cells were transiently transfected with FLAG-rat NPC1L1 DNA or with FLAG-rat NPC1L1-EGFP DNA. In these fusions, the FLAG tag is at amino-terminus of rat NPC1L1 and EGFP fusion is at the carboxy-terminus of rat NPC1L1. The cells were then stained with the M2 anti-FLAG mouse (primary) antibody followed by secondary staining with a BODIPY-labeled anti-mouse antibody. In control experiments, cells were stained with only the secondary antibody and not with the primary antibody (M2). The stained cells were then analyzed by FACS.

In a control experiment, FLAG-rat NPC1L1 transfected cells were stained with BODIPY anti-mouse secondary antibody but not with the primary antibody. The data demonstrated that the secondary, anti-mouse antibody possesses no significant specificity for FLAG-rat NPC1L1 and that the FLAG-rat NPC1L1, itself, possesses no significant fluorescence.

In another control experiment, unlabeled FLAG-rat NPC1L1-EGFP cells were FACS analyzed. In these experiments, autofluorescence of the enhanced green fluorescent protein (EGFP) was detected.

FLAG-rat NPC1L1 cells were stained with anti-FLAG mouse antibody M2 and with the BODIPY-labeled anti-mouse secondary antibody and FACS analyzed. The data from this analysis showed that the cells were labeled with the secondary, BODIPY-labeled antibody which indicated expression of the FLAG-rat NPC1L1 protein on the surface of the CHO cells.

FLAG-rat NPC1L1-EGFP cells were stained with anti-FLAG mouse antibody M2 and with the BODIPY-labeled anti-mouse secondary antibody and FACS analyzed. The data from this analysis showed that both markers (BODIPY and EGFP) were present indicating surface expression of the chimeric protein. The data also indicated that a portion of the protein was located within the cells and may be associated with transport vesicles. These data supported a role for rat NPC1L1 in vesicular transport of cholesterol or protein expressed in subcellular organelles such as the rough endoplasmic reticulum.

Example 13

FACS Analysis and Fluorescent Microscopy of FLAG-Rat NPC1L1-EGFP Chimera in a Cloned CHO Cell Line In these experiments, the cellular localization of rat NPC1L1 was evaluated by FACS analysis and by immunohistochemistry. CHO cells were transfected with FLAG-rat NPC1L1-EGFP DNA and stained with anti-FLAG mouse antibody M2 and then with a BODIPY-labeled anti-mouse secondary antibody. In the fusion, the FLAG tag is at the amino-terminus of rat NPC1L1 and the enhanced green fluorescent protein (EGFP) tag is located at the carboxy-terminus of the rat NPC1L1. The stained cells were then analyzed by FACS and by fluorescence microscopy.

Cells transfected with FLAG-rat NPC1L1-EGFP DNA were stained with the anti-FLAG mouse antibody M2 and then with the BODIPY-labeled anti-mouse secondary antibody. FACS analysis of the cells detected both markers indicating surface expression of the chimeric protein.

FLAG-rat NPC1L1-EGFP transfected cells were analyzed by fluorescent microscopy at 63× magnification. Fluorescent microscopic analysis of the cells indicated non-nuclear staining with significant perinuclear organelle staining. Resolution of the image could not confirm the presence of vesicular associated protein. These data indicated that the fusion protein was expressed on the cell membrane of CHO cells.

Example 14

Generation of Polyclonal Anti-Rat NPC1L1 Rabbit Antibodies

Synthetic peptides (SEQ ID NO: 39-42) containing an amino- or carboxy-terminal cysteine residue were coupled to keyhole limpet hemocyanin (KLH) carrier protein through a disulfide linkage and used as antigen to raise polyclonal antiserum in New Zealand white rabbits (range 3-9 months in age). The KLH-peptide was emulsified by mixing with an equal volume of Freund's Adjuvant, and injected into three subcutaneous dorsal sites. Prior to the 16 week immunization schedule a pre-immune sera sample was collected which was followed by a primary injection of 0.25 mg KLH-peptide and 3 scheduled booster injections of 0.1 mg KLH-peptide. Animals were bled from the auricular artery and the blood was allowed to clot and the serum was then collected by centrifugation The anti-peptide antibody titer was determined with an enzyme linked immunosorbent assay (ELISA) with free peptide bound in solid phase (1 µg/well). Results are expressed as the reciprocal of the serum dilution that resulted in an $OD_{450}$ of 0.2. Detection was obtained using the biotinylated anti-rabbit IgG, horse radish peroxidase-streptavidin (HRP-SA) conjugate, and ABTS.

Example 15

FACS Analysis of Rat NPC1L1 Expression in CHO Cells Transiently Transfected with Rat NPC1L1 DNA Using Rabbit Anti-Rat NPC1L1 Antisera In these experiments, the expression of rat NPC1L1 on the surface of CHO cells was evaluated. CHO cells were transfected with rat NPC1L1 DNA, then incubated with either rabbit preimmune serum or with 10 week anti-rat NPC1L1 serum described, above, in Example 14 (i.e., A0715, A0716, A0867 or A0868). Cells labeled with primary antisera were then stained with a BODIPY-modified anti-rabbit secondary antibody followed by FACS analysis.

No antibody surface labeling was observed for any of the pre-immune sera samples. Specific cell surface labeling of rat NPC1L1 transfected cells was observed for both A0715 and A0868. Antisera A0716 and A0867 did not recognize rat NPC1L1 surface expression in this assay format. This indicates that the native, unfused rat NPC1L1 protein is expressed in the CHO cells and localized to the CHO cell membranes. Cell surface expression of NPC1L1 is consistent with a role in intestinal cholesterol absorption.

Example 16

FACS Analysis of CHO Cells Transiently Transfected with FLAG-Mouse NPC1L1 DNA or FLAG-Rat NPC1L1 DNA or Untransfected CHO Cells Using Rabbit Anti-Rat NPC1L1 Antisera In these experiments, the expression of FLAG-mouse NPC1L1 and FLAG-rat NPC1L1 in CHO cells was evaluated. CHO cells were transiently transfected with FLAG-mouse NPC1L1 DNA or with FLAG-rat NPC1L1 DNA. The FLAG-mouse NPC1L1 and FLAG-rat NPC1L1 transfected cells were labeled with either A0801, A0802, A0715 or A0868 sera (see Example 14) or with anti-FLAG antibody, M2. The labeled cells were then stained with BODIPY-labeled anti-rabbit secondary antibody and FACS analyzed. The untransfected CHO cells were analyzed in the same manner as the transfected cell lines.

Positive staining of the untransfected CHO cells was not observed for any of the antisera tested. Serum A0801-dependent labeling of FLAG-rat NPC1L1 transfected cells was observed but such labeling of FLAG-mouse NPC1L1 transfected cells was not observed. Serum A0802-dependent labeling of FLAG-mouse NPC1L1 or FLAG-rat NPC1L1 transfected cells was not observed. Strong serum A0715-dependent labeling of FLAG-rat NPC1L1 transfected cells was observed and weak serum A0715-dependent labeling of FLAG-mouse NPC1L1 transfected cells was observed. Weak serum A0868-dependent labeling of rat NPC1L1 and mouse NPC1L1 transfected cells was observed. Strong Anti-FLAG M2 antibody-dependent labeling of FLAG-rat NPC1L1 and FLAG-mouse NPC1L1 transfected cells was observed. The strong M2 staining is likely to be due to the fact that M2 is an affinity-purified, monoclonal antibody of known concentration. In contrast, the respective antisera are polyclonal, unpurified and contain an uncertain concentration of anti-rat NPC1L1 antibody. These date provide further evidence that the FLAG-mouse NPC1L1 and FLAG-rat NPC1L1 proteins are expressed in CHO cells and localized to the CHO cell membranes. Cell surface expression of NPC1L1 is consistent with a role in intestinal cholesterol absorption.

Example 17

Immunohistochemical Analysis of Rat Jejunum Tissue with Rabbit Anti-Rat NPC1L1 Antisera A0715

In these experiments, the localization of rat NPC1L1 in rat jejunum was analyzed by immunohistochemistry. Rat jejunum was removed, immediately embedded in O.C.T. compound and frozen in liquid nitrogen. Sections (6 µm) were cut with a cryostat microtome and mounted on glass slides. Sections were air dried at room temperature and then fixed in Bouin's fixative. Streptavidin-biotin-peroxidase immunostaining was carried out using Histostain-SP kit. Endogenous tissue peroxidase activity was blocked with a 10 minute incubation in 3% $H_2O_2$ in methanol, and nonspecific antibody binding was minimized by a 45 minute incubation in 10% nonimmune rabbit serum. Sections were incubated with a rabbit anti-rat NPC1L1 antisera A0715 or A0868 at a 1:500 dilution at 4° C., followed by incubation with biotinylated goat anti-rabbit IgG and with streptavidin-peroxidase. Subsequently, the sections were developed in an aminoethyl carbazole (AEC)-$H_2O_2$ staining system and counterstained with hematoxylin and examined by microscopy. A positive reaction using this protocol is characterized by the deposition of a red reaction product at the site of the antigen-antibody reaction. Nuclei appeared blue from the hematoxylin counterstain. Controls were performed simultaneously on the neighboring sections from the same tissue block. Control procedures consisted of the following: (1) substitute the primary antibody with the pre-immune serum, (2) substitute the primary antibody with the non-immune rabbit serum, (3) substitute the primary antibody with PBS, (4) substitute the second antibody with PBS.

The example shows tissue stained with anti-rat NPC1L1 sera A0715 or with the preimmune sera analyzed at low magnification (40×) and at high magnification (200×). The A0715-stained tissue, at low magnification, showed positive, strong staining of the villi epithelial layer (enterocytes). The A0715-stained tissue at high magnification showed positive, strong staining of the enterocyte apical membranes. No staining was observed in tissue treated only with preimmune sera. Similar results were obtained with sera A0868. These data indicate that rat NPC1L1 is expressed in rat jejunum which is consistent with a role in intestinal cholesterol absorption.

Example 18

Labeled Cholesterol Uptake Assay

In this example, the ability of CHO cells stably transfected with rat NPC1L1 to take up labeled cholesterol was evaluated. In these assays, cholesterol uptake, at a single concentration, was evaluated in a pulse-chase experiment. The data generated in these experiments are set forth, below, in Table 3.

Cells:
A. CHO cells stably transfected with rat NPC1L1 cDNA
B. CHO background (no transfection)
Cells were seeded at 500,000 cells/well (mL) in 12-well plates.

Procedure:

All reagents and culture plates were maintained at 37° C. unless otherwise noted.

Starve. The maintenance media (F12 HAMS, 1% Pen/Strep, 10% FCS) was removed and the cells were rinsed with serum-free HAMS media. The serum-free media was then replaced with 1 mL "starve" media (F12 HAMS, Pen/Strep, 5% lipoprotein deficient serum (LPDS).

One plate of each cell line was starved overnight. The remaining 2 plates were designated "No Starve" (see below).

Pre-Incubation. Media was removed from all plates, rinsed with serum-free HAMS and replaced with starve media for 30 minutes.

$^3$H-Cholesterol Pulse. The following was added directly to each well.

0.5 µCi $^3$H-cholesterol (~$1.1 \times 10^6$ dpm/well) in 50 µl of a mixed bile salt micelle.
4.8 mM sodium taurocholate (2.581 mg/mL)
0.6 mM sodium oleate (0.183 mg/mL)
0.25 mM cholesterol (0.1 mg/mL)
Dispersed in "starve" media by ultrasonic vibration
Final media cholesterol concentration=5 µg/mL Labeled cholesterol pulse time points were 0, 4, 12 and 24 minutes. Triplicate wells for each treatment were prepared.

Wash. At the designated times, media was aspirated and the cells were washed once with Hobbs Buffer A (50 mM Tris, 0.9% NaCl, 0.2% BSA, pH 7.4) and once with Hobbs Buffer B (50 mM Tris, 0.9% NaCl, pH 7.4 (no BSA)) at 37° C.

Processing/Analysis. Cells were digested overnight with 0.2N NaOH, 2 mL/well at room temperature. One 1.5 mL aliquot was removed from each well, neutralized & counted for radioactivity by scintillation counting. Two additional 50 µl aliquots from all wells are assayed for total protein by the Pierce micro BCA method. The quantity of labeled cholesterol observed in the cells was normalized by the quantity of protein in the cells.

TABLE 3

Uptake of 3H-cholesterol by CHO cells transfected with rat NPC1L1 or mouse SR-B1 or untransfected CHO cells.

| Time, min After $^3$H-Cholesterol | Total Cholesterol, dpm protein ± sem | | Total Cholesterol, dpm/mg protein ± sem | |
|---|---|---|---|---|
| | NPC1L1 | CHO | NPC1L1 | CHO |
| No Starve | | | | |
| 0 | 2067 ± 46 | 4568 ± 1937 | 10754 ± 166 | 22881 ± 9230 |
| 4 | 2619 ± 130 | 2868 ± 193 | 15366 ± 938 | 15636 ± 1471 |

TABLE 3-continued

Uptake of 3H-cholesterol by CHO cells transfected with rat NPC1L1 or mouse SR-B1 or untransfected CHO cells.

| Time, min | Total Cholesterol, dpm protein ± sem | | Total Cholesterol, dpm/mg protein ± sem | |
|---|---|---|---|---|
| After³H-Cholesterol | NPC1L1 | CHO | NPC1L1 | CHO |
| 12 | 2868 ± 193 | 4459 ± 170 | 15636 ± 1471 | 24622 ± 966 |
| 24 | 7010 ± 89 | 7204 ± 173 | 41129 ± 685 | 39361 ± 1207 |
| | | Starve | | |
| 0 | 1937 ± 273 | 2440 ± 299 | 10909 ± 1847 | 12429 ± 1673 |
| 4 | 3023 ± 308 | 2759 ± 105 | 17278 ± 1650 | 14307 ± 781 |
| 12 | 2759 ± 105 | 4857 ± 186 | 14307 ± 781 | 26270 ± 1473 |
| 24 | 6966 ± 72 | 7344 ± 65 | 39196 ± 174 | 38381 ± 161 | dpm = disintegrations per minute
sem = standard error of the mean

Example 19

Effect of Ezetimibe on Cholesterol Uptake

The effect of ezetimibe on the ability of CHO cells stably transfected with mouse or rat NPC1L1 or mouse SR-B1 to take up $^3$H-labeled cholesterol was evaluated in pulse-chase experiments. One cDNA clone of mouse NPC1L1 (C7) and three clones of rat NPC1L1 (C7, C17 and C21) were evaluated. The ability of CHO cells stably transfected with mouse SR-B1, mouse NPC1L1 and rat NPC1L1 to take up labeled cholesterol, in the absence of ezetimibe, was also evaluated in the pulse-chase experiments. Data generated in these experiments are set forth, below, in Tables 4 and 5. Additionally, the quantity of total cholesterol taken up by transfected and untransfected CHO cells in the presence of four different unlabeled cholesterol concentrations was also evaluated. The data from these experiments is set forth, below, in Table 6.

Cells:

A. CHO cells stably transfected with rat or mouse NPC1L1 cDNA

B. CHO background (no transfection)

C. SR-B1 transfected CHO cells

Cells seeded at 500,000 cells/well (mL) in 12-well plates.

Procedure:

All reagents and culture plates were maintained at 37° C. unless otherwise noted.

Starve. The maintenance media (F12 HAMS, 1% Pen/Strep, 10% FCS) was removed and the cells were rinsed with serum-free HAMS media. The serum-free media was then replaced with 1 mL "starve" media (F12 HAMS, Pen/Strep, 5% lipoprotein deficient serum (LPDS). The cells were then starved overnight.

Pre-Incubation/pre-dose. Media was removed from all plates and replaced with fresh starve media and preincubated for 30 minutes. Half of the wells received media containing ezetimibe (stock soln in EtOH; final conc.=10 µM).

$^3$H-Cholesterol Pulse. The following was added directly to each well:

0.5 µCi $^3$H-cholesterol (~1.1×106 dpm/well) in 50 µl of a mixed bile salt micelle 4.8 mM sodium taurocholate (2.581 mg/mL)

0.6 mM sodium oleate (0.183 mg/mL)

0.25 mM cholesterol (0.1 mg/mL)

Dispersed in "starve" media by ultrasonic vibration

Final media cholesterol concentration=5 µg/mL

Labeled cholesterol pulse time points were 4, 12, 24 minutes and 4 hours. Triplicate wells were prepared for each treatment.

Wash. At designated times, media was aspirated and cells were washed once with Hobbs Buffer A (50 mM Tris, 0.9% NaCl, 0.2% bovine serum albumin (BSA), pH 7.4) and once with Hobbs Buffer B (50 mM Tris, 0.9% NaCl, pH 7.4 (no BSA)) at 37° C.

Processing/Analysis.

A. 4, 12, 24 minute time points: Cells were digested overnight with 0.2N NaOH, 2 mL/well, room temperature. One 1.5 mL aliquot was removed from each well, neutralized & counted for radioactivity by scintillation counting.

B. 4 hour time point: The digested cells were analyzed by thin-layer chromatography to determine the content of cholesterol ester in the cells.

Extracts were spotted onto TLC plates and run for 30 minutes in 2 ml hexane:isopropanol (3:2) mobile phase for 30 minutes, followed by a second run in 1 ml hexane:isopropanol (3:2) mobile phase for 15 minutes.

C. Protein determination of cell extracts. Plates containing a sample of the cell extracts were placed on orbital shaker at 120 rpm for indicated times and then extracts are pooled into 12×75 tubes. Plates were dried and NaOH (2 ml/well) added. The protein content of the samples were then determined. Two additional 50 µl aliquots from all wells were assayed for total protein by the Pierce micro BCA method. The quantity of labeled cholesterol observed in the cells was normalized to the quantity of protein in the cells.

TABLE 4

Total Cholesterol in Transfected CHO Cells in the Presence and Absence of Ezetimibe.

| Clones: | Total Cholesterol, dpm ± sem | | Total Cholesterol, dpm/mg protein ± sem | |
|---|---|---|---|---|
| | Vehicle | EZ (10 µM) | Vehicle | EZ (10 µM) |
| 4 Min Pulse | | | | |
| CHO Control | 3413 ± 417 | 3222 ± 26 | 33443 ± 4070 | 31881 ± 483 |
| SR-BI | 14207 ± 51 | 10968 ± 821 | 118242 ± 1261 | 92474 ± 2902 |
| mNPC1L1(C7) | 4043 ± 419 | 4569 ± 222 | 30169 ± 3242 | 30916 ± 1137 |
| rNPC1L1(C21) | 3283 ± 288 | 3769 ± 147 | 23728 ± 2111 | 27098 ± 689 |
| rNPC1L1(C17) | 3188 ± 232 | 3676 ± 134 | 24000 ± 832 | 28675 ± 527 |
| rNPC1L1(C7) | 1825 ± 806 | 3268 ± 121 | 15069 ± 6794 | 27285 ± 968 |
| 12 Min Pulse | | | | |
| CHO Control | 4710 ± 246 | 4532 ± 165 | 44208 ± 2702 | 43391 ± 1197 |
| SR-BI | 16970 ± 763 | 12349 ± 298 | 140105 ± 6523 | 98956 ± 4447 |
| mNPC1L1(C7) | 6316 ± 85 | 6120 ± 755 | 45133 ± 342 | 41712 ± 4054 |
| rNPC1L1(C21) | 5340 ± 12 | 4703 ± 231 | 40018 ± 1181 | 33985 ± 1928 |
| rNPC1L1(C17) | 4831 ± 431 | 4579 ± 257 | 37378 ± 3461 | 34063 ± 1619 |
| rNPC1L1(C7) | 4726 ± 272 | 4664 ± 63 | 39100 ± 2350 | 38581 ± 784 |
| 24 Min Pulse | | | | |
| CHO Control | 7367 ± 232 | 6678 ± 215 | 65843 ± 1281 | 61764 ± 2131 |
| SR-BI | 39166 ± 2152 | 23558 ± 1310 | 324126 ± 11848 | 198725 ± 11713 |
| mNPC1L1(C7) | 10616 ± 121 | 9749 ± 482 | 77222 ± 1040 | 74041 ± 3670 |
| rNPC1L1(C21) | 9940 ± 587 | 8760 ± 293 | 76356 ± 9618 | 66165 ± 2181 |
| rNPC1L1(C17) | 8728 ± 721 | 8192 ± 237 | 70509 ± 5189 | 62279 ± 4352 |
| rNPC1L1(C7) | 8537 ± 148 | 7829 ± 204 | 72134 ± 1305 | 63482 ± 368 |

EZ = ezetimibe

TABLE 5

Cholesterol Ester in CHO cells in the Presence or Absence of Ezetimibe.

| Clones: | Cholesteryl Ester, dpm ± sem | | Cholesteryl Ester, dpm/mg protein ± sem | |
|---|---|---|---|---|
| | Vehicle | EZ (10 µM) | Vehicle | EZ (10 µM) |
| 4 Hour Pulse | | | | |
| CHO Control | 652 ± 13 | 208 ± 9 | 5647 ± 55 | 1902 ± 87 |
| SR-BI | 47608 ± 1292 | 9305 ± 401 | 391067 ± 14391 | 72782 ± 3181 |
| mNPC1L1(C7) | 732 ± 127 | 453 ± 118 | 4994 ± 827 | 3057 ± 776 |
| rNPC1L1(C21) | 2667 ± 90 | 454 ± 33 | 18655 ± 1032 | 3193 ± 265 |
| rNPC1L1(C17) | 751 ± 74 | 202 ± 10 | 5379 ± 481 | 1510 ± 62 |
| rNPC1L1(C7) | 462 ± 25 | 191 ± 54 | 3597 ± 193 | 1496 ± 403 |

| | Free Cholesterol, dpm ± sem | | Free Cholesterol, dpm/mg protein ± sem | |
|---|---|---|---|---|
| | Vehicle | EZ (10 µM) | Vehicle | EZ (10 µM) |
| 4 Hour Pulse | | | | |
| CHO Control | 61612 ± 1227 | 56792 ± 568 | 533876 ± 17770 | 519607 ± 16203 |
| SR-BI | 214678 ± 4241 | 194519 ± 474 | 1762873 ± 46607 | 1521341 ± 4185 |
| mNPC1L1(C7) | 79628 ± 793 | 77516 ± 1910 | 544661 ± 1269 | 523803 ± 10386 |
| rNPC1L1(C21) | 71352 ± 1343 | 69106 ± 711 | 498016 ± 8171 | 485460 ± 4410 |
| rNPC1L1(C17) | 78956 ± 3782 | 71646 ± 446 | 566456 ± 29204 | 536651 ± 7146 |
| rNPC1L1(C7) | 75348 ± 2093 | 70628 ± 212 | 586127 ± 13932 | 556855 ± 7481 |

EZ = ezetimibe

TABLE 6

Uptake of labeled cholesterol in the presence of increasing amounts of unlabeled cholesterol.

| Cold Cholesterol | Total Cholesterol, dpm ± sem | | | |
|---|---|---|---|---|
| | CHO Control | SR-BI | mNPC1L1(C7) | rNPC1L1(C21) |
| | 24 Min Pulse | | | |
| 3 µg/mL | 12271 ± 430 | 49603 ± 2428 | 14250 ± 1628 | 10656 ± 1233 |
| 10 µg/mL | 16282 ± 2438 | 79967 ± 8151 | 25465 ± 3037 | 13225 ± 4556 |
| 30 µg/mL | 14758 ± 1607 | 71925 ± 3863 | 19001 ± 1530 | 13218 ± 1149 |
| 100 µg/mL | 16458 ± 1614 | 58185 ± 4548 | 15973 ± 1665 | 11560 ± 1132 |

| Cold Cholesterol | Total Cholesterol, dpm/mg protein ± sem | | | |
|---|---|---|---|---|
| | CHO Control | SR-BI | mNPC1L1(C7) | rNPC1L1(C21) |
| | 24 Min Pulse | | | |
| 3 µg/mL | 108936 ± 5413 | 541562 ± 13785 | 140764 ± 14433 | 94945 ± 12916 |
| 10 µg/mL | 151283 ± 23345 | 880224 ± 82254 | 250985 ± 27481 | 123433 ± 34092 |
| 30 µg/mL | 135109 ± 12106 | 796236 ± 18952 | 180436 ± 12112 | 111522 ± 6941 |
| 100 µg/mL | 149559 ± 17977 | 630143 ± 3718 | 147717 ± 8261 | 101328 ± 7191 |

| | Cholesteryl Ester, dpm ± sem | | | |
|---|---|---|---|---|
| | CHO Control | SR-BI | mNPC1L1(C7) | rNPC1L1(C21) |
| | 4 Hour Pulse | | | |
| 3 µg/mL | 2737 ± 114 | 39596 ± 1241 | 1561 ± 1 | 4015 ± 47 |
| 10 µg/mL | 1646 ± 76 | 17292 ± 362 | 998 ± 36 | 1866 ± 33 |
| 30 µg/mL | 970 ± 46 | 6642 ± 153 | 537 ± 82 | 970 ± 9 |
| 100 µg/mL | 895 ± 156 | 4777 ± 27 | 405 ± 7 | 777 ± 16 |

| | Cholesteryl Ester, dpm/mg protein ± sem | | | |
|---|---|---|---|---|
| | CHO Control | SR-BI | mNPC1L1(C7) | rNPC1L1(C21) |
| | 4 Hour Pulse | | | |
| 3 µg/mL | 22050 ± 978 | 382641 ± 5955 | 13684 ± 217 | 32020 ± 641 |
| 10 µg/mL | 13323 ± 606 | 157914 ± 3400 | 8917 ± 467 | 14849 ± 127 |
| 30 µg/mL | 7627 ± 325 | 63547 ± 1760 | 4885 ± 748 | 7741 ± 100 |
| 100 µg/mL | 7135 ± 1230 | 45088 ± 1526 | 3663 ± 68 | 6005 ± 198 |

| | Free Cholesterol, dpm ± sem | | | |
|---|---|---|---|---|
| | CHO Control | SR-BI | mNPC1L1(C7) | rNPC1L1(C21) |
| | 4 Hour Pulse | | | |
| 3 µg/mL | 89013 ± 3724 | 211783 ± 3268 | 104343 ± 2112 | 92244 ± 987 |
| 10 µg/mL | 136396 ± 8566 | 278216 ± 10901 | 196173 ± 4721 | 125144 ± 877 |
| 30 µg/mL | 131745 ± 2922 | 224429 ± 2556 | 149172 ± 19689 | 117143 ± 4976 |
| 100 µg/mL | 79336 ± 4011 | 231470 ± 4221 | 114599 ± 2803 | 93538 ± 1588 |

| | Free Cholesterol, dpm/mg protein ± sem | | | |
|---|---|---|---|---|
| | CHO Control | SR-BI | mNPC1L1(C7) | rNPC1L1(C21) |
| | 4 Hour Pulse | | | |
| 3 µg/mL | 717308 ± 34130 | 2047695 ± 16213 | 914107 ± 5869 | 735498 ± 11209 |
| 10 µg/mL | 1105118 ± 76074 | 2540130 ± 92471 | 1753072 ± 86578 | 996824 ± 27850 |
| 30 µg/mL | 1036195 ± 21142 | 2149315 ± 78068 | 1357136 ± 180264 | 934772 ± 43202 |
| 100 µg/mL | 632965 ± 29756 | 2182022 ± 36793 | 1035979 ± 30329 | 723225 ± 21694 |

| | Cholesteryl Ester, dpm ± sem | | | |
|---|---|---|---|---|
| | CHO Control | SR-BI | mNPC1L1(C7) | rNPC1L1(C21) |
| | 24 Hour Pulse | | | |
| 3 µg/mL | 57373 ± 2704 | 162296 ± 1644 | 22986 ± 940 | 59377 ± 953 |
| 10 µg/mL | 33730 ± 1296 | 112815 ± 373 | 14836 ± 552 | 31797 ± 525 |
| 30 µg/mL | 19193 ± 100 | 58668 ± 1413 | 8878 ± 355 | 18963 ± 380 |
| 100 µg/mL | 16761 ± 398 | 31280 ± 1270 | 8784 ± 946 | 14933 ± 311 |

TABLE 6-continued

Uptake of labeled cholesterol in the presence of increasing amounts of unlabeled cholesterol.

| | Cholesteryl Ester, dpm/mg protein ± sem | | | |
|---|---|---|---|---|
| | CHO Control | SR-BI | mNPC1L1(C7) | rNPC1L1(C21) |
| | 24 Hour Pulse | | | |
| 3 μg/mL | 357629 ± 14639 | 1248900 ± 18565 | 160328 ± 6565 | 401315 ± 5557 |
| 10 μg/mL | 215004 ± 5942 | 830231 ± 12764 | 98594 ± 4205 | 200451 ± 5239 |
| 30 μg/mL | 122071 ± 1271 | 446581 ± 3472 | 59091 ± 2697 | 119728 ± 2131 |
| 100 μg/mL | 103235 ± 1739 | 272796 ± 13392 | 60670 ± 4597 | 96215 ± 1023 |
| | Free Cholesterol, dpm ± sem | | | |
| | CHO Control | SR-BI | mNPC1L1(C7) | rNPC1L1(C21) |
| | 24 Hour Pulse | | | |
| 3 μg/mL | 248985 ± 4207 | 357819 ± 4519 | 285610 ± 5187 | 227244 ± 1016 |
| 10 μg/mL | 231208 ± 8927 | 269822 ± 5872 | 311777 ± 8227 | 231666 ± 6198 |
| 30 μg/mL | 203566 ± 6008 | 225273 ± 5932 | 279604 ± 6612 | 209372 ± 3386 |
| 100 μg/mL | 178424 ± 2379 | 167082 ± 2211 | 229832 ± 4199 | 182678 ± 7709 |
| | Free Cholesterol, dpm/mg protein ± sem | | | |
| | CHO Control | SR-BI | mNPC1L1(C7) | rNPC1L1(C21) |
| | 24 Hour Pulse | | | |
| 3 μg/mL | 1552637 ± 18954 | 2752957 ± 24984 | 1993256 ± 56968 | 1536023 ± 10304 |
| 10 μg/mL | 1477414 ± 85954 | 1984473 ± 18420 | 2069980 ± 25517 | 1461157 ± 58517 |
| 30 μg/mL | 1294878 ± 41819 | 1716066 ± 52581 | 1859476 ± 29507 | 1321730 ± 5452 |
| 100 μg/mL | 1099648 ± 25160 | 1455799 ± 9885 | 1599244 ± 76938 | 1177546 ± 51191 |

Example 20

Labeled Cholesterol Uptake Assay

In this example, the ability of CHO cells transiently transfected with rat NPC1L1 or mouse SR-B1 to take up labeled cholesterol was evaluated. Also evaluated was the ability of rat NPC1L1 to potentiate the ability of CHO cells transfected with mouse SR-B1 to take up labeled cholesterol. In these assays, cholesterol uptake, at a single concentration, was evaluated in pulse-chase experiments. The data generated in these experiments are set forth, below, in Table 7.

Cells:
A. CHO background cells (mock transfection).
B. CHO cells transiently transfected with mouse SR-B1.
C. CHO transiently transfected with rat NPC1L1 cDNAs (n=8 clones).

Transiently transfected cells were seeded at 300,000 cells/well (mL) in 12-well plates.

Procedure:

All reagents and culture plates were maintained at 37° C. unless otherwise noted.

Starve. The maintenance media (F12 HAMS, 1% Pen/Strep, 10% FCS) was removed from the cells and replaced with 1 mL "starve" media (F12 HAMS, Pen/Strep, 5% lipoprotein deficient serum (LPDS). Cells were starved for 1 hour.

$^3$H-Cholesterol Pulse. The following was added directly to each well.

0.5 μCi $^3$H-cholesterol (~1.1×106 dpm/well) in 50 μl of a mixed bile salt micelle.
4.8 mM sodium taurocholate (2.581 mg/mL)
0.6 mM sodium oleate (0.183 mg/mL)
0.25 mM cholesterol (0.1 mg/mL)
Dispersed in "starve" media by ultrasonic vibration
Final media cholesterol concentration=5 μg/mL Labeled cholesterol pulse time points were 24 Min and 4 hours. Triplicate wells for each treatment.

Wash. At the designated times, media was aspirated and cells were washed once with Hobbs Buffer A (50 mM Tris, 0.9% NaCl, 0.2% BSA, pH 7.4) and once with Hobbs Buffer B (50 mM Tris, 0.9% NaCl, pH 7.4 (no BSA)) at 37° C.

Processing/Analysis.

A. 24 minute time point: Cells were digested overnight with 0.2N NaOH, 2 mL/well at room temp. One 1.5 mL aliquot was removed from each well, neutralized & counted for radioactivity by scintillation counting.

B. 4 hour time point: The digested cells were analyzed by thin-layer chromatography to determine the content of cholesterol ester in the cells.

The extracts were spotted onto thin layer chromatography plates and run in 2 ml hexane:isopropanol (3:2) containing mobile phase for 30 minutes, followed by a second run in 1 ml hexane:isopropanol (3:2) containing mobile phase for 15 min.

C. Protein determination of cell extracts: Plates containing a sample of the cell extracts were placed on orbital shaker at 120 rpm for indicated times and then extracts are pooled into 12×75 tubes. Plates were dried and NaOH (2 ml/well) added. The protein content of the samples were then determined. Two additional 50 μl aliquots from all wells were assayed for total protein by the Pierce micro BCA method. The quantity of labeled cholesterol observed in the cells was normalized to the quantity of protein in the cells.

TABLE 7

Labeled cholesterol uptake in transiently transfected CHO cells.

| Transfection | dpm | dpm/mg protein |
|---|---|---|
| Total Cholesterol, ± sem 24 Min Pulse | | |
| CHO Control (mock) | 4721 ± 436 | 49024 ± 4328 |
| SR-BI(Transient) | 5842 ± 82 | 59445 ± 1099 |
| NPC1L1 (Transient) | 4092 ± 377 | 47026 ± 2658 |
| SR-BI/NPC1L1 (trans) | 3833 ± 158 | 52132 ± 3071 |
| Cholesteryl Ester, ± sem 4 Hour Pulse | | |
| CHO Control (mock) | 2132 ± 40 | 20497 ± 640 |
| SR-BI(Transient) | 5918 ± 237 | 51812 ± 1417 |
| NPC1L1 (Transient) | 1944 ± 93 | 19788 ± 642 |
| SR-BI/NPC1L1 (trans) | 4747 ± 39 | 58603 ± 1156 |
| Free Cholesterol, ± sem 4 Hour Pulse | | |
| CHO Control (mock) | 45729 ± 328 | 439346 ± 5389 |
| SR-BI(Transient) | 50820 ± 2369 | 444551 ± 9785 |
| NPC1L1 (Transient) | 39913 ± 1211 | 406615 ± 6820 |
| SR-BI/NPC1L1 (trans) | 37269 ± 1225 | 459509 ± 6195 |

Example 21

Expression of Rat, Mouse and Human NPC1L1

In this example, NPC1L1 was introduced into cells and expressed. Species specific NPC1L1 expression constructs were cloned into the plasmid pCDNA3 using clone specific PCR primers to generate the ORF flanked by appropriate restriction sites compatible with the polylinker of the vector. For all three species of NPC1L1, small intestine total tissue RNA was used as a template for reverse transcriptase-polymerase chain reaction (RT-PCR) using oligo dT as the template primer. The rat NPC1L1 was cloned as an EcoRI fragment, human NPC1L1 was cloned as a XbaI/NotI fragment and mouse NPC1L1 was cloned as an EcoRI fragment. Forward and reverse strand sequencing of each clone was performed to confirm sequence integrity. Standard transient transfection procedures were used with CHO cells. In a 6-well plate CHO cells were plated 1 day before transfection at a plating density of $2\times10^5$ cells/well. The following day, cells were incubated with 2 µg plasmid DNA and 6 µL Lipofectamine for 5 hours followed a fresh media change. Forty-eight hours later, cells were analyzed for NPC1L1 expression using anti-NPC1L1 antisera by either FACS or western blot. To establish stable long term cell lines expressing NPC1L1, transfected CHO cells were selected in the presence of geneticin (G418, 0.8 mg/ml) as recommended by the manufacturer (Life Technologies). Following one month of selection in culture, the cell population was stained with anti-NPC1L1 antisera and sorted by FACS. Individual positive staining cells were cloned after isolation by limiting dilution and then maintained in selective media containing geneticin (0.5 mg/ml).

Other cell types less susceptible to transfection procedures have been generated using adenoviral vector systems. This system used to express NPC1L1 is derived from Ad 5, a type C adenovirus. This recombinant replication-defective adenoviral vector is made defective through modifications of the E1, E2 and E4 regions. The vector also has additional modifications to the E3 region generally affecting the E3b region genes RIDa and RIDb. NPC1L1 expression was driven using the CMV promoter as an expression cassette substituted in the E3 region of the adenovirus. Rat and mouse NPC1L1 were amplified using clone specific primers flanked by restriction sites compatible with the adenovirus vector Adenovirus infective particles were produced from 293-D22 cells in titers of $5\times10^{10}$ P/mL. Viral lysates were used to infect cells resistant to standard transfection methodologies. In Caco2 cells, which are highly resistant to heterologous protein expression, adenovirus mediated expression of NPC1L1 has been shown by western blot analysis to persist at least 21 days post-infection.

Example 22

NPC1L1 Knock-Out Transgenic Mouse

NPC1L1 knockout mice were constructed via targeted mutagenesis. This methodology utilized a targeting construct designed to delete a specific region of the mouse NPC1L1 gene. During the targeting process the *E. coli* lacZ reporter gene was inserted under the control of the endogenous NPC1L1 promoter. The region in NPC1L1 (SEQ ID NO: 45) being deleted is from nucleotide 790 to nucleotide 998. The targeting vector contains the LacZ-Neo cassette flanked by 1.9 kb 5' arm ending with nucleotide 789 and a 3.2 kb 3' arm starting with nucleotide 999. Genomic DNA from the recombinant embryonic stem cell line was assayed for homologous recombination using PCR. Amplified DNA fragments were visualized by agarose gel electrophoresis. The test PCRs employed a gene specific primer, which lies outside of and adjacent to the targeting vector arm, paired with one of three primers specific to the LacZ-Neo cassette sequence. For 5' PCR reconfirmation, the NPC1L1 specific oligonucleotide ATGTTAGGTGAGTCTGAACCTACCC (SEQ ID NO: 46) and for 3'PCR reconfirmation the NPC1L1 specific oligonucleotide GGATTGCATTTCCTTCAAGAAAGCC (SEQ ID NO: 47) were used. Genotyping of the F2 mice was performed by multiplex PCR using the NPC1L1 specific forward primer TATGGCTCTGCCCTCTGCAATGCTC (SEQ ID NO: 48) the LacZ-Neo cassette specific forward primer TCAGCAGCCTCTGTTCCACATACACTTC (SEQ ID NO: 49) in combination with the NPC1L1 gene specific reverse primer GTTCCACAGGGTCTGTGGTGAGTTC (SEQ ID NO: 50) allowed for determination of both the targeted and endogenous alleles. Analysis of the PCR products by agarose gel electrophoresis distinguished the wild-type, heterozygote and homozygote null mouse from each other.

Example 23

Acute Cholesterol Absorption in NPC1L1-Deficient Mice

To determine whether NPC1L1 plays a role in cholesterol absorption, NPC1L1 deficient mice were studied.

Mice deficient in NPC1L1 (−/−) were generated by breeding heterozygote mice (+/) to obtain wild-type (+/+) and NPC1L1 deficient mice (−/−). Non-fasted mice (6.5-9 weeks old, mixed 129 and C57BL/6 background) were weighed and grouped (n=2−/− and n=4+/+). All animals were gavaged (Feeding needles, 24G×1 inch, Popper and Sons, NY) with 0.1 ml corn oil (Sigma; St. Louis, Mo.) containing 1 µCi $^{14}$C-cholesterol (New England Nuclear, [$4-^{14}$C] Cholesterol, NEC-018) and 0.1 mg carrier cholesterol mass (Sigma; St. Louis, Mo.). Two hours later, blood was collected by heart puncture. The liver was removed, weighed, and three samples were placed into 20 ml counting vials. Tissues were digested in 1 ml of 1N NaOH at 60° C. overnight. The tissue digests were acidified by addition of 250 µl of 4N HCl prior to liquid scintillation counting (LSC). Plasma was isolated by centrifugation at 10,000 rpm for 5 minutes in a microfuge and duplicate 100 µl aliquots of plasma were taken for LSC.

Cholesterol absorption, evaluated by this acute technique and expressed as the total amount of radioactive cholesterol in the plasma and liver, demonstrated that the wild type mice (+/+) absorbed an average of 11,773 dpm and NPC1L1 deficient mice absorbed 992 dpm of the 14C-cholesterol. These results indicate that the NPC1L1 deficient mice have a 92% reduction in cholesterol absorption. These data confirm the role of NPC1L1 in intestinal cholesterol absorption. Inhibition of NPC1L1-mediated cholesterol absorption, in a subject, by administering NPC1L1 antagonists, such as ezetimibe, to the subject, are a useful way to reduce serum cholesterol levels and the occurrence of atherosclerosis in the subject.

Example 24

Cholesterol Absorption in NPC1L1 (NPC3) Knockout Mice (Fecal Ratio Method: Cholesterol/Sitostanol)

In this example, cholesterol absorption and the activity of ezetimibe was determined in the NPC1L1 knockout mice (−/−), heterozygous mice (+/−), and age matched wild-type mice (+/+).

Cholesterol absorption in the mice was determined by the dual fecal isotope ratio method as described by Altmann et al. (Biochim. Biophys. Acta. 1580(1): 77-93 (2002)). Mice (n—4-6/group) were fed a standard rodent chow diet and in some groups treated daily with a maximally effective dose of ezetimibe (10 mg/kg). Mice were gavaged with $^{14}$C-cholesterol (1 µCi, 0.1 mg unlabeled cholesterol) and $^{3}$H-sitostanol (2 µCi) in 0.1 ml corn oil. Feces were collected for 2 days and fecal $^{14}$C-cholesterol and $^{3}$H-sitostanol levels were determined by combustion in a Packard Oxidizer. The fraction of cholesterol absorbed, as evaluated by the fecal dual isotope technique, was similar in wild type (+/+) and heterozygous mice (+/−) fed a chow diet (heterozygous mice absorbed 46±5% and age matched wild type mice absorbed 51±3% of the dose of $^{14}$C-cholesterol). The NPC1L1 knockout mice (−/−) absorbed 15.6±0.4% of the $^{14}$C-cholesterol, which was similar to the wild type mice treated with a maximally effective dose of ezetimibe (16.1±0.3%), and reduced by 69% compared to wild type mice (p<0.001). In NPC1L1 knockout treated with ezetimibe at 10 mg/kg/day, cholesterol absorption was similar to that seen in the untreated knockout mice (16.2±0.6% compared to 15.6%±0.4%, respectively). Thus, the majority of cholesterol absorption is dependent on the presence of NPC1L1 and the residual cholesterol absorption in mice lacking NPC1L1 is insensitive to ezetimibe treatment. These results indicate that NPC1L1 is involved in the small intestinal enterocyte uptake and absorption of cholesterol and is in the ezetimibe sensitive pathway.

Example 25

Mouse Screening Assay (Acute Cholesterol Absorption)

The following screening assay is used to identify the presence of an NPC1L1 antagonist in a sample.

Mice deficient in NPC1L1 (−/−) are generated by breeding heterozygote mice (+/) to obtain wild-type (+/+) and NPC1L1 deficient mice (−/−).

In a first set of experiments, non-fasted mice (6.5-9 weeks old, mixed 129 and C57BL/6 background) are weighed and grouped (n=1 to 4−/− and n=1 to 4+/+). All animals are gavaged (Feeding needles, 24G×1 inch, Popper and Sons, NY) with 0.1 ml corn oil (Sigma; St. Louis, Mo.) containing 1 µCi $^{14}$C-cholesterol (New England Nuclear, [$^{4-14}$C] Cholesterol, NEC-018) and 0.1 mg carrier cholesterol mass (Sigma; St. Louis, Mo.).

In another set of experiments, 1 to 4 wild-type NPC1L1 mice (+/+) are treated identically to the mice in the first set of experiments, above, except that the mice are additionally fed a sample to be tested for the presence of an NPC1L1 antagonist.

Two hours later, blood is collected from each mouse by heart puncture. The liver is removed, weighed, and three samples are placed into 20 ml counting vials. Tissues are digested in 1 ml of 1N NaOH at 60° C. overnight. The tissue digests are acidified by addition of 250 µl of 4N HCl prior to liquid scintillation counting (LSC). Plasma is isolated by centrifugation at 10,000 rpm for 5 minutes in a microfuge and duplicate 100 µl aliquots of plasma are taken for LSC.

Cholesterol absorption, evaluated by this acute technique is expressed as the total amount of radioactive cholesterol in the plasma and liver. The sample tested is determined to contain an NPC1L1 antagonist when the level of cholesterol absorption (as measured by the above described methods) in the wild-type NPC1L1 mouse (+/+) which was fed the sample and in the NPC1L1 deficient mouse (−/−) are less than the amount of cholesterol absorption in the wild-type NPC1L1 mouse (+/+) which was not fed the sample.

Example 26

Mouse Screening Assay (Fecal Ratio Method: Cholesterol/Sitostanol)

The following screening assay is used to identify the presence of an NPC1L1 antagonist in a sample.

Cholesterol absorption in the mice is determined by the dual fecal isotope ratio method as described by Altmann et al. (Biochim. Biophys. Acta. 1580(1): 77-93 (2002)).

Three groups of mice (n=1-6/group) are assembled. Two separate groups comprise wild-type NPC1L1 mice (+/+) and one group comprises NPC1L1 deficient mice (−/−).

Each group is fed a standard rodent chow diet and in some groups treated daily. Mice are gavaged with $^{14}$C-cholesterol (1 µCi, 0.1 mg unlabeled cholesterol) and $^{3}$H-sitostanol (2 µCi) in 0.1 ml corn oil. One group of mice, which comprise wild-type NPC1L1 mice (+/+) are further fed a sample to be tested for the presence of an NPC1L1 antagonist. Feces are collected for 2 days and fecal $^{14}$C-cholesterol and $^{3}$H-sitostanol levels are determined by combustion in a Packard Oxidizer.

The sample tested is determined to contain an NPC1L1 antagonist when the level of cholesterol and/or sitostanol absorption (as measured by the above described methods) in the wild-type NPC1L1 mouse (+/+) which was fed the sample and in the NPC1L1 deficient mouse (−/−) are less than the amount of cholesterol and/or sitostanol absorption in the wild-type NPC1L1 mouse (+/+) which was not fed the sample.

Example 27

Binding Analysis Using Brush Border Membrane Vesicles

The following screening assay may be used to identify the presence of an NPC1L1 ligand in a sample.

Materials. The following two compounds were synthesized for the binding assay described herein, $^3$H-ezetimibe glucuronide 1 (34.5 Ci/mmol) and its $^{35}$S-propargyl-sulfonamide derivative 2 (800-1100 Ci/mmol).

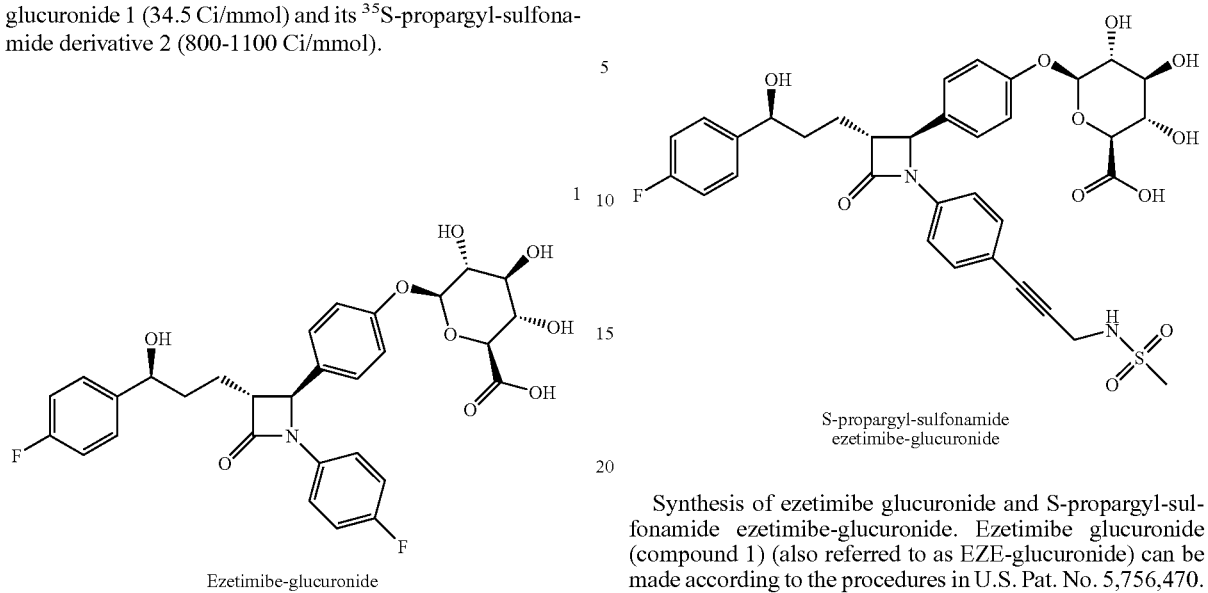

Ezetimibe-glucuronide

S-propargyl-sulfonamide ezetimibe-glucuronide

Synthesis of ezetimibe glucuronide and S-propargyl-sulfonamide ezetimibe-glucuronide. Ezetimibe glucuronide (compound 1) (also referred to as EZE-glucuronide) can be made according to the procedures in U.S. Pat. No. 5,756,470. The general scheme below illustrates a method for the synthesis of compound 2 and radiolabel led $^{35}$S-2.

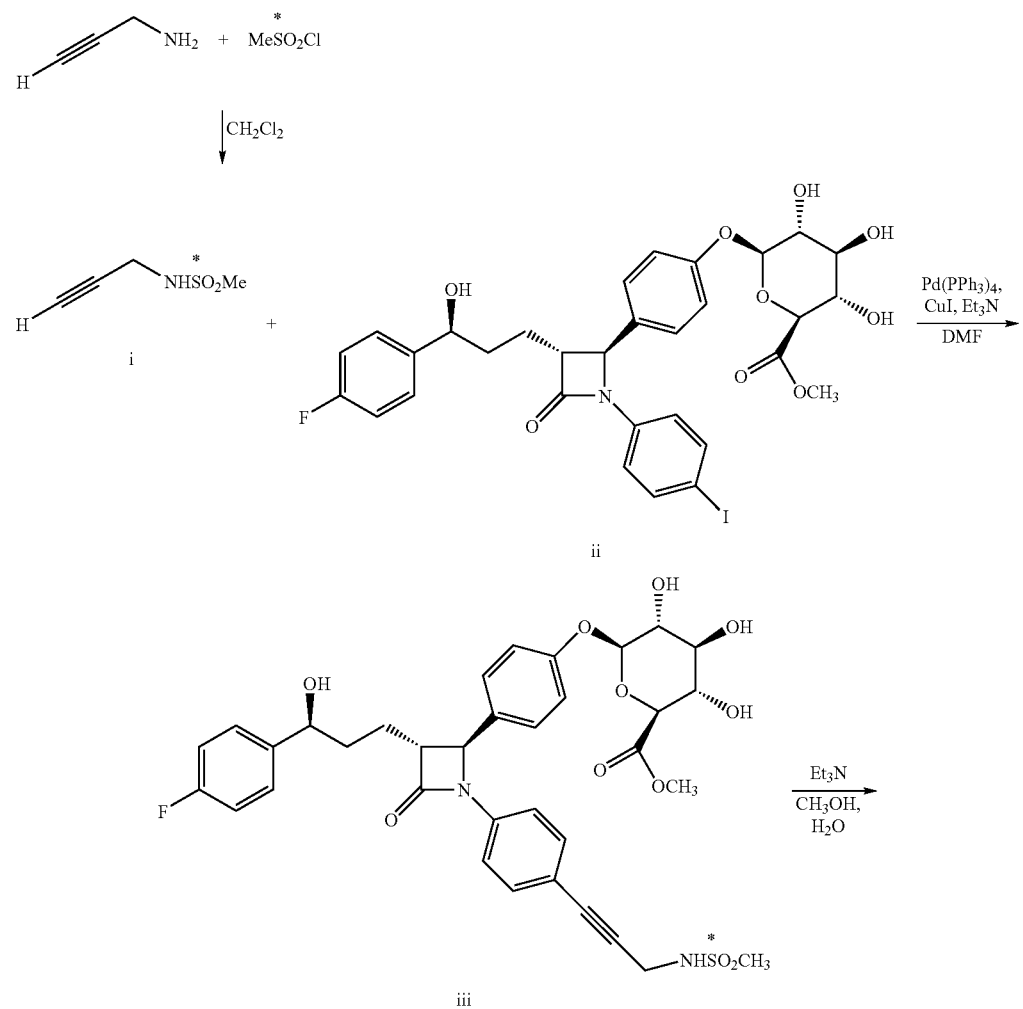

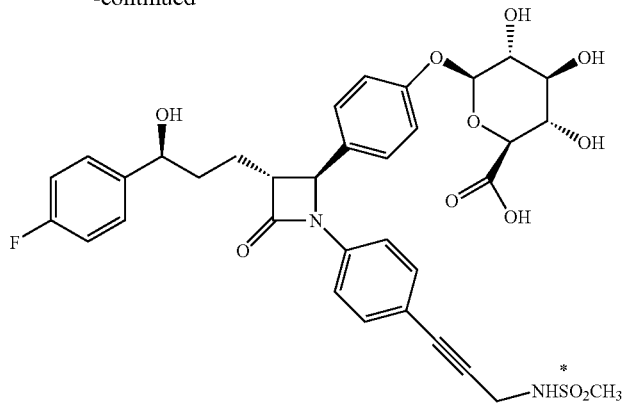

$^{35}$S-2

(* denotes $^{35}$S)

Preparation of Compound $^{35}$S-2 (Compound 2 with Radiolabelled $^{35}$S)

Step A: Preparation of [$^{35}$S]N-prop-2-yn-1-ylmethanesulfonamide (i). The appropriate volume of [$^{35}$S]methane sulfonyl chloride (see Dean, D. C.; et al., *J. Med. Chem.* 1996, 39, 1767) totaling 3.5 mCi was removed from a stock solution in methylene chloride and placed in a 5 mL conical flask. It was then distilled at atmospheric pressure until the volume was approximately 50 μL. To this solution was immediately added 50 μL of propargylamine. After 15 min, the reaction mixture was diluted with 10 mL of ethyl acetate, washed with saturated sodium bicarbonate solution (3×2 mL), and dried over sodium sulfate. After filtration the resulting solution had a count of 3.3 mCi and a radiochemical purity of 99.9% by HPLC (Zorbax XDB C8 column, 4.6×150 mm, 5% acetonitrile:H$_2$O (0.1% TFA) to 100% acetonitrile, 15 min linear gradient, 1 mL/min, $t_R$=4.4 min).

Step B: Preparation of [$^{35}$S]-4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl methyl β-D-glucopyranosiduronate ([$^{35}$S]) (iii). Dissolved 3.0 mCi of [$^{35}$S]N-prop-2-yn-1-ylmethanesulfonamide, 1 mg of compound ii (prepared according to Burnett, D. S. et al., *Bioorg. Med. Chem. Lett.* (2002), vol. 12, p. 311), and 1 μL of triethylamine in 100 μL of dimethylformamide inside a plastic microcentrifuge tube. To this solution was added 10 μL of a stock solution containing 8.1 mg of tetrakis(triphenylphosphine)palladium(0) and 1.4 mg of copper iodide in 1 mL of dimethylformamide. Stirred at room temperature for sixty hours at which time HPLC indicated 55% conversion. This reaction mixture, which had a radiochemical purity of 44.4% by HPLC (Zorbax XDB C8 column, 4.6×150 mm, 5% acetonitrile:H$_2$O (0.1% TFA) to 100% acetonitrile, 15 min linear gradient, 1 mL/min, $t_R$=9.3 min) was taken on directly to the next step.

Step C: Preparation of [$^{35}$S]-4-[(2S,3R)-3-[(3S)-3-(4-fluorophenyl)-3-hydroxypropyl]-1-(4-{3-[(methylsulfonyl)amino]prop-1-yn-1-yl}phenyl)-4-oxoazetidin-2-yl]phenyl β-D-glucopyranosiduronic acid $^{35}$S-2. The crude reaction mixture containing compound iii was treated with 25 μL of methanol, 90 μL of water, and 30 μL of triethylamine and stirred at room temperature for one hour at which time it was concentrated to near dryness under a slow stream of nitrogen. The residue was dissolved in 1:1 acetonitrile:H$_2$O and subjected to semi-preparative chromatography (Zorbax XDB C8 250×9.4 mm column, 70:30 acetonitrile:H$_2$O (0.1% TFA) 4 mL/min, 1×0.2 mL injections). 540 μCi of product was obtained which had a radiochemical purity of 99.9% by HPLC (Zorbax XDB C8 column, 4.6×150 mm, 70:30 acetonitrile:H$_2$O (0.1% TFA), 1 mL/min, $t_R$=10.4 min) and coeluted with an authentic sample of compound 2. LC/MS m/z=508 (product-glucuronide-H$_2$O), SA=769 Ci/mmol.

Alternate Preparation of $^{35}$S-2.

Step A: Preparation of iii. The appropriate volume of [$^{35}$S] methane sulfonyl chloride (see Dean, D. C.; et al., *J. Med. Chem.* 1996, 39, 1767) totaling 1.3 mCi was removed from a stock solution in methylene chloride and placed in a 5 mL conical flask. It was then distilled at atmospheric pressure until the volume was approximately 50 μL. To this solution was immediately added a solution of 1 mg of v in 5 μL of pyridine (freshly distilled over calcium hydride).

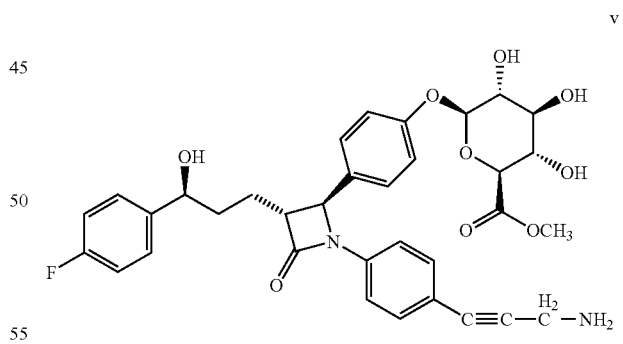

v

The solution was stirred at room temperature for five minutes at which time it was concentrated to near dryness under a slow stream of nitrogen. This reaction mixture, which had a radiochemical purity of 80.1% by HPLC (Zorbax XDB C8 column, 4.6×150 mm, 5% acetonitrile:H$_2$O (0.1% TFA) to 100% acetonitrile, 15 min linear gradient, 1 mL/min, $t_R$=9.3 min) was taken on directly to the next step.

Step B: Preparation of $^{35}$S-2. The crude reaction mixture containing iii was treated with 25 μL of methanol, 90 μL of water, and 30 μL of triethylamine and stirred at room temperature for one hour at which time it was concentrated to near dryness under a slow stream of nitrogen. The residue was dissolved in 1:1 acetonitrile:$H_2O$ and subjected to semi-preparative chromatography (Zorbax XDB C8 250×9.4 mm column, 70:30 acetonitrile:$H_2O$ (0.1% TFA) 4 mL/min, 1×0.2 mL injections). 350 µCi of product was obtained which had a radiochemical purity of 98.4% by HPLC (Zorbax XDB C8 column, 4.6×150 mm, 70:30 acetonitrile:$H_2O$ (0.1% TFA), 1 mL/min, $t_R$=10.4 min) and coeluted with an authentic sample of 2. LC/MS m/z=508 (product-glucuronide-$H_2O$), SA=911 Ci/mmol.

Following the same general procedure for synthesis of $^{35}$S-2, except omitting the radiolabelling, compounds 2 and iv can be prepared.

Preparation of Brush Border Membrane Vesicles (BBMV).

Membranes were prepared from Rhesus macaque (*Macaca mulatta*), rat (male Sprague-Dawley), and mouse (male C57BL/6J) intestines, using $Mg^{++}$ precipitation method described in the following references and with modifications described below (Hauser, H., Howell, K., Dawson, R. M. C., Bowyer, D. E. Biochim. Biophys. Acta 602, 567-577 (1980); Kramer, W., Girbig, F., Gutjahr, U., Kowalewski, S., Jouvenal, K., Muller, G., Tripier, D., Wess, G. J. Biol. Chem. 268, 18035-18046 (1993); Rigtrup, K. M., Ong, D. E. Biochemistry 31, 2920-2926 (1992)).

The intestines from freshly sacrificed animals were cut into segments, perfused with ice-cold saline buffer (Buffer A: 26 mM $NaHCO_3$, 0.96 mM $NaH_2PO_4$, 5 mM HEPES, 5.5 mM glucose, 117 mM NaCl, 5.4 mM KCl, pH=7.4), placed on cold glass plates, opened longitudinally, and the mucosa scraped with glass microscope slips. This mucosa could be used fresh or frozen with identical results. To prepare the membranes, the mucosal scrapings were resuspended in 20 volumes of cold buffer consisting of 300 mM D-mannitol, 5 mM EGTA, 12 mM Tris, pH 7.4 with HCl, and containing 0.1 mM PMSF and a 1% dilution of a protease inhibitor cocktail (set 1, Calbiochem). They were homogenized using a Polytron at medium speed on ice until inspection with a microscope indicated complete cell lysis. Then, solid $MgCl_2$ was added slowly with stirring to a final concentration of 10 mM, and the solution was kept stirring on ice for 15 min. Cellular debris was removed by centrifugation for 15 min at 3,000 g, and the membranes were recovered by centrifugation for 60 min at 48,000 g. The membranes were further rinsed by re-suspension in a buffer containing 50 mM D-mannitol, 5 mM EGTA, and 2 mM Tris at pH 7.40, and centrifugation for 60 min at 48,000 g. The final pellet was resuspended in 120 mM NaCl and 20 mM Tris at pH 7.40 to a concentration of ~10-20 mg protein/ml, aliquoted, frozen in liquid nitrogen, and stored at −80 C. The activity was stable indefinitely and could be freeze-thawed with minimal loss of activity.

Membrane protein was measured by the Bradford assay (Bradford, M. M. Anal. Biochem. 72, 248-254 (1976)) using bovine serum albumin as standard. The enrichment in brush border membranes was assessed using gamma-glutamyl-transferase as a marker enzyme (Kramer, W., Girbig, F., Gutjahr, U., Kowalewski, S., Jouvenal, K., Muller, G., Tripier, D., Wess, G. J. Biol. Chem. 268, 18035-18046 (1993)), which indicated a 6-fold enrichment over the initial homogenate.

Binding assay. Assays were conducted in 12×75 mm glass test tubes and total volume 20-100 ul. In general, frozen membranes were diluted in buffer A or buffer A containing 0.03% taurocholate and 0.05% digitonin to a final concentration of 0.02 to 5 mg/ml. Radiolabeled ligands were typically 25-50 nM for $^3$H-ezetimibe (EZE)glucuronide 1, and 3-5 nM for its $^{35}$S analog 2, in the assay, and they were delivered as DMSO or $CH_3CN$ solutions. Competing ligands were likewise added as DMSO solutions to give a total 2-10% organic solvent content. Nonspecific binding was defined by competition with 100 uM ezetimibe glucuronide. At least 2 components of buffer A, the bicarbonate and phosphate salts, were later found to be inconsequential and were routinely omitted. To ensure equilibrium was established, the reactions with compound 1 were incubated at least 3 hours for rhesus membranes and at least one hour for rat membranes at room temperature, and with compound 2 as long as 2 hours at 37° C. with rhesus and rat brush membranes. Additionally, reactions with compound 2 were incubated as long as 2 hours at 37° C. with membranes from HEK-293 cells expressing mouse, rat or human NPC1L1.

Bound ligand was quantified by single-tube vacuum filtration using GF/C glass fiber filters. Glass fiber filters (GF/C) were obtained from Whatman. The filters were pretreated by soaking with 0.5% polyethyleneimine to reduce nonspecific binding. Filtration was accomplished by adding 2.5 ml of ice cold buffer (120 mM NaCl, 0.1% sodium cholate, and 20 mM MES at pH 6.70) to the assay tube, pouring the mixture through the filter, and then rinsing the tube and filter twice more with another 2×2.5 ml buffer. The filters were counted in 7 ml vials using Packard DM liquid scintillation fluid. Where triplicate assays were performed, the standard error was typically <4%. As an example, a 100 µl assay of rat brush border membranes at 2 mg/ml in the presence of 400,000 dpm (50 nM) $^3$H-ezetimibe glucuronide gave 15,000 dpm specific and 3,000 dpm nonspecific binding. The filters contributed most of the nonspecific binding (2,000 dpm).

Alternatively, vacuum filtration of compound 2 on a Millipore 96-well plate (Whatman GF/C) can also be used to achieve adequate precision.

Data analysis. Data from saturation experiments were subjected to a Scatchard analysis, and linear regression was performed to yield the equilibrium dissociation constant ($K_d$) and maximum receptor concentration ($B_{max}$). Correlation coefficients for these determinations were typically greater than 0.96. Data from competition experiments were analyzed and $IC_{50}$ values determined from Hill plots of the binding data. The kinetic data for ligand association and dissociation were subjected to the analysis of Weiland and Molinoff (Weiland, G., Molinoff, B. Life Sci. 29, 313-330 (1981)). The dissociation rate constant for ($k_{-1}$) was determined directly for a first order plot of ligand dissociation versus time. The rate of ligand association ($k_1$) was determined from the equation $k_1=k_{obs}([LR_e]/([L][LR]_{max}))$ where [L] is the concentration of ligand, $[LR_e]$ is the concentration of the complex at equilibrium, $[LR]_{max}$ is the maximum number of receptors present, and $k_{obs}$ is the slope of the pseudo-first order plot $L_n([LE]_e/([LR]_e-[LR]_t))$ versus time.

Binding analysis. Ezetimibe is rapidly converted to its glucuronide in vivo, and this metabolite is thought to be largely if not exclusively responsible for inhibition of cholesterol uptake. Accordingly, both $^3$H-ezetimibe and its corresponding glucuronide derivative (1) were prepared and tested for binding to intestinal brush border membrane preparations, using a single-tube vacuum filtration technique. As a result of the hydrophobic nature of $^3$H-ezetimibe, high nonspecific binding was observed, precluding its use as a radioligand for the binding assay. However, due to the improved physical properties of the glucuronide derivative (1), specific binding was observed with this radioligand and it was used to assess binding in rhesus, rat, and mouse intestinal brush border membranes.

Figure 2:
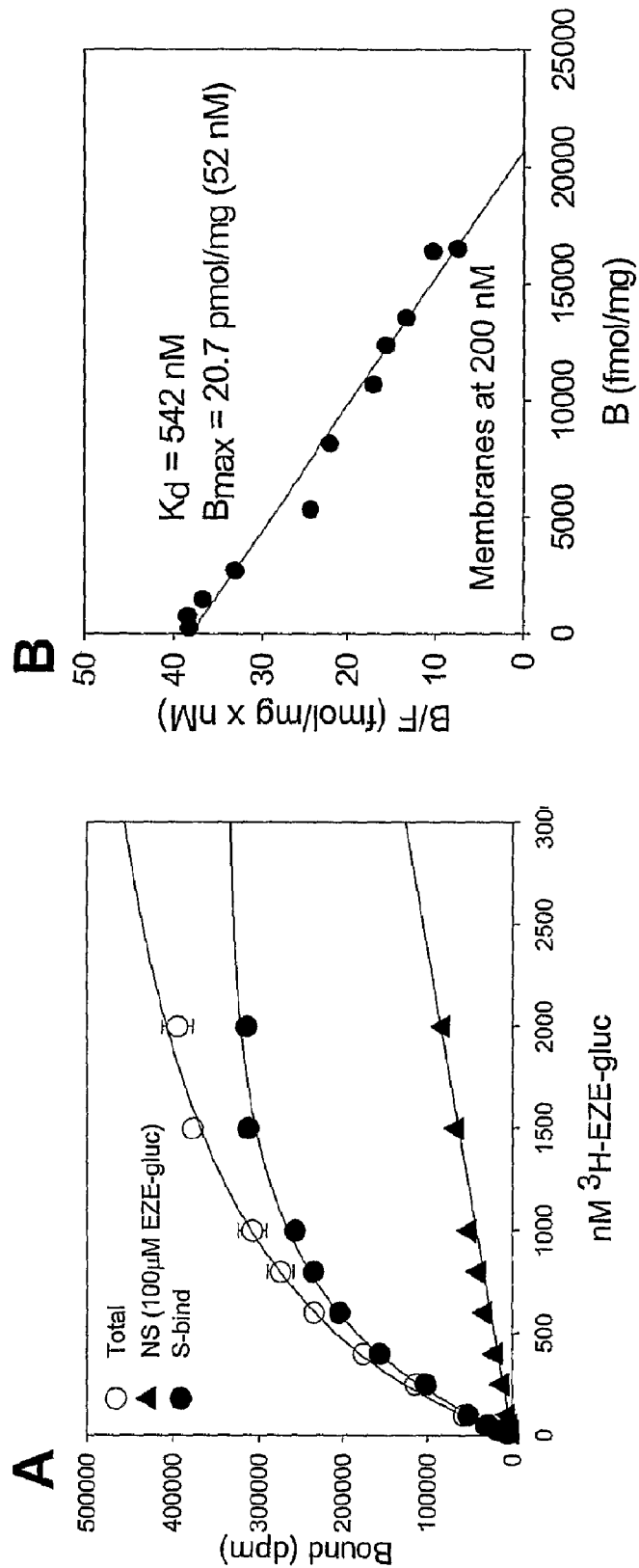
FIG. 2A shows an equilibrium saturation binding plot exhibiting the binding of $^3$H-EZE-glucuronide (1) to rat brush border membrane vesicles. Observed total binding (open circles) and nonspecific binding (triangles), determined in the presence of 100 μM unlabeled ezetimibe glucuronide, are included; specific binding (solid circles) was assessed from the difference between total and nonspecific binding. Binding was measured at 2.5 mg protein/ml in a volume of 100 μl after 1 hour incubation. Data were fit by nonlinear regression as described in Methods.
FIG. 2B shows scatchard analysis of $^3$H-EZE-glucuronide binding to rat brush border membrane vesicles. The binding data identify a single high-affinity site with $K_D$=542 nM and Bmax=20.7 pmol/mg protein.

Rhesus, rat, and mouse intestinal scrapings were homogenized and the brush border membranes isolated. Specific binding was observed exclusively in the membrane fraction. Plots of total, nonspecific, and specific binding to rhesus (FIG. 1) and rat (FIG. 2) brush border membranes. Aliquots of rhesus BBMV (83 µg/assay) or rat BBMV (250 µg/assay) were incubated with increasing concentrations of $^3$H-EZE-glucuronide. Total binding and nonspecific binding determined in the presence of 10-100 uM EZE-glucuronide are shown. Specific binding was calculated from the difference between total and nonspecific binding. Data were fit by nonlinear regression as described above, and the linear Scatchard plot is shown. In rhesus membranes, the data correspond to a single binding site with $K_d$=41 nM and a concentration of 5.5 pmol/mg membrane protein. The affinity is ~10-fold lower in rat membranes ($K_d$=540 nM). $^3$H-EZE-glucuronide is not the best ligand for a binding assay for the mouse target due to the compounds low affinity in mouse membrane. These potencies correlate roughly with the sensitivity of these species to ezetimibe inhibition of cholesterol uptake.

Rate constants for binding and dissociation. Ezetimibe-glucuronide is slow to bind, and forms a relatively long-lived complex with its receptor. Indeed, this was key to detecting the interaction in a traditional filter-binding assay, as ligand/receptor interactions with $K_d$ values greater than 100 nM often go unrecognized because of the typical fast off-rates of the ligands. Rate constants for association ($k_{on}$) and dissociation $k_{off}$) of compound 1 were determined for rat and rhesus membranes, and used as an alternative method to calculate the dissociation constant ($K_d$) according to the relationship $K_d$=$k_{off}$/$k_{on}$. 300 µg/assay of rat brush border membrane vesicles were incubated with 25 nM $^3$H-EZE-glucuronide at room temperature for up to three hours for the association kinetic studies. 83 µg/assay of rhesus brush border membrane vesicles were incubated with 25 nM $^3$H-EZE-glucuronide at room temperature for up to five hours for the association kinetic studies. Nonspecific binding measured in the presence of 100 µM EZE-glucuronide was subtracted from the total binding to calculate the specific binding shown in FIGS. 3A and 4A. For the dissociation kinetic study, rat brush border membrane vesicles were incubated with 25 nM $^3$H-EZE-glucuronide for 2 hours at room temperature and ligand dissociation was initiated by the addition of 100 µM EZE-glucuronide. Rhesus brush border membrane vesicles were incubated with 42 nM $^3$H-EZE-glucuronide for 4 hours at room temperature and ligand dissociation was initiated by the addition of 100 µM EZE-glucuronide. For both rat and rhesus dissociation studies, samples were collected at various times and radiolabel was detected. Dissociation curves are shown in FIGS. 3B (rat) and 4B (rhesus).

Figure 3:
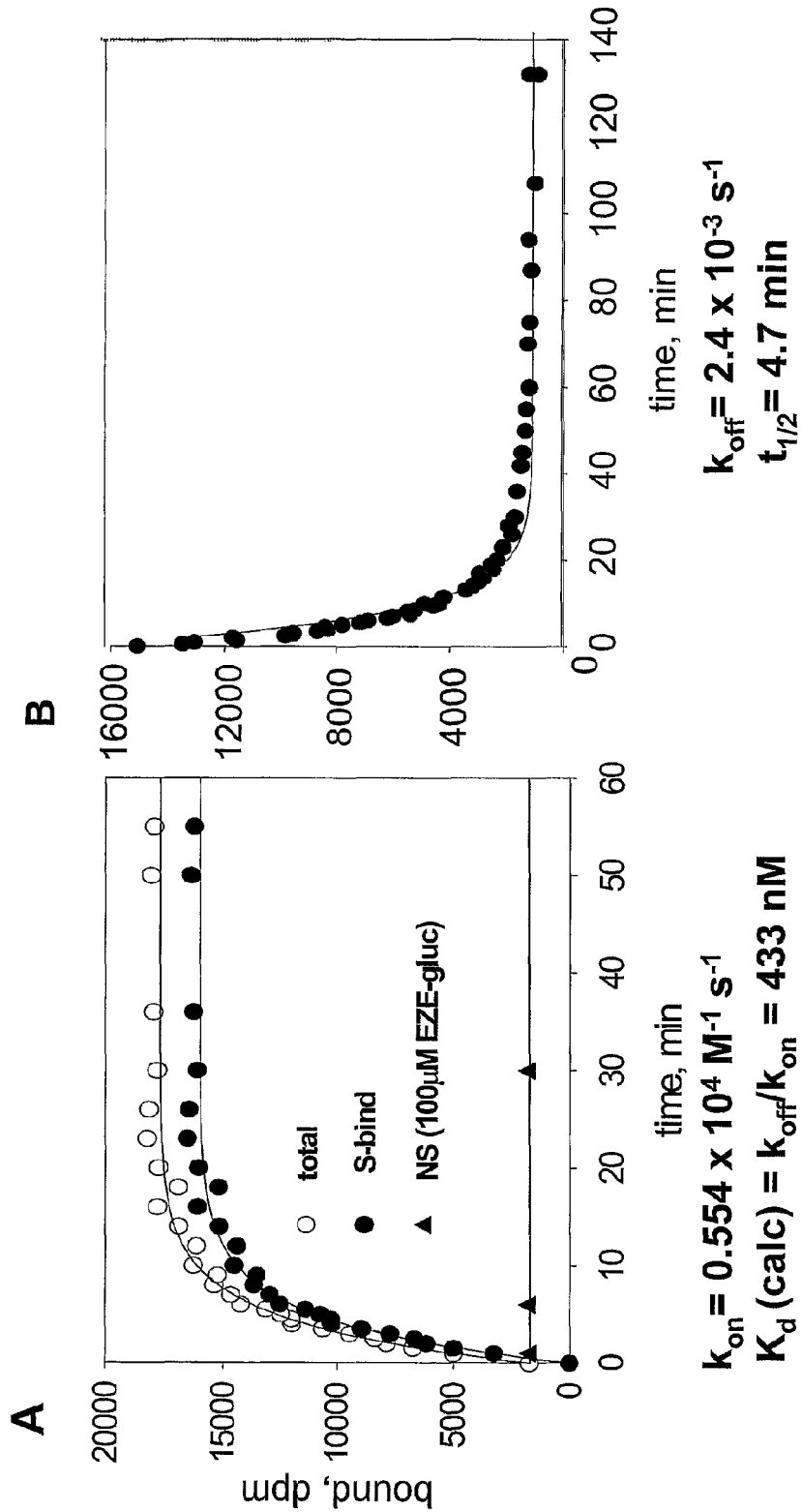
FIG. 3A shows association kinetic analysis of $^3$H-EZE-glucuronide in rat brush border membrane vesicles. Conditions were 25 nM of 1 and 3 mg/ml protein at 25° C. The second-order rate constant $k_{on}$ (0.55×10$^{-4}$ M$^{-1}$ s$^{-1}$) was calculated from $k_{obs}$ (0.004 s$^{-1}$) as described in Methods.
FIG. 3B shows dissociation kinetic analysis of $^3$H-EZE-glucuronide 1 in rat brush border membrane vesicles. After the complex was formed by incubating 25 nM of 1 and 3 mg/ml protein for 1 hour, dissociation was initiated by competition with 100 μM unlabeled ezetimibe glucuronide. The curve is theoretical for $k_{off}$=0.0024 s$^{-1}$.

For rat membranes, the rate constant for association is $k_{on}$=5,540 M$^{-1}$ s$^{-1}$ (compared to 10$^8$ to 10$^9$ M$^{-1}$ s$^{-1}$ for diffusion controlled encounter), and the rate constant for dissociation is $k_{off}$=2.4×10$^{-3}$ s$^{-1}$, corresponding to a half-life of 4.7 min. The data are shown in FIG. 3, where the solid lines are theoretical for these rate constants. The $K_d$ value predicted from these rate constants ($K_d$=$k_{off}$/$k_{on}$=440 nM) agrees well with that measured at equilibrium ($K_d$=540 nM).

Figure 4:
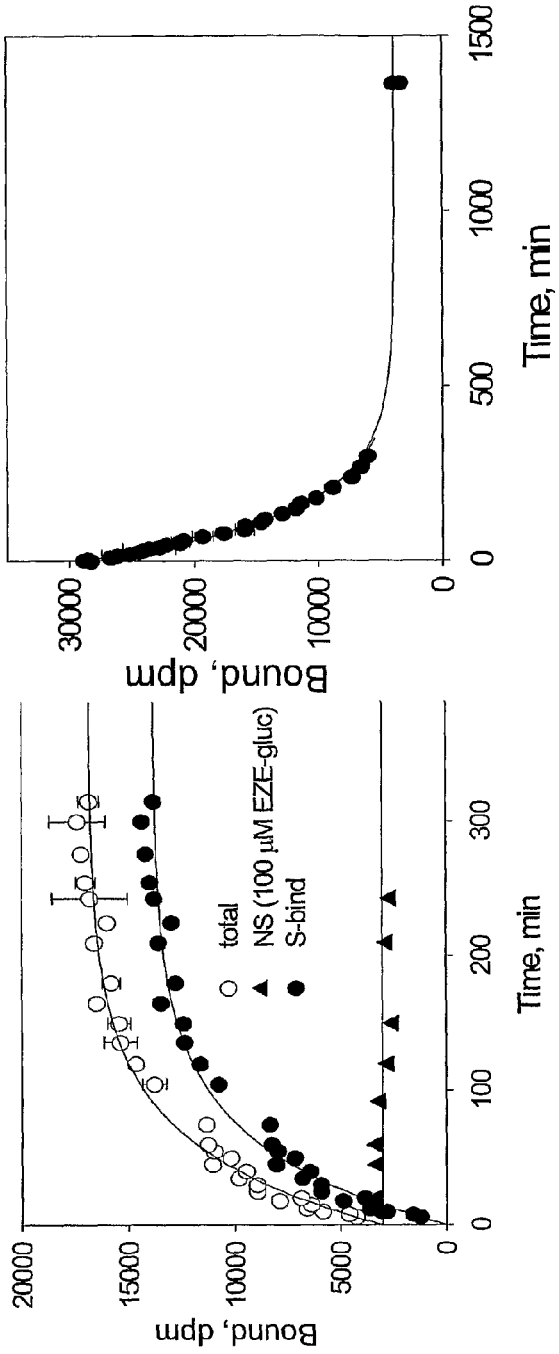
FIG. 4A shows association kinetic analysis of $^3$H-EZE-glucuronide in rhesus brush border membrane vesicles.
FIG. 4B shows dissociation kinetic analysis of $^3$H-EZE-glucuronide in rhesus brush border membrane vesicles.

For rhesus membranes, where $^3$H-ezetimibe glucuronide is at least 10-fold more potent (as described above), the association rate remains the same but the half-life for dissociation of the complex increases to ~90 min. These data are shown in FIG. 4, where the theoretical lines correspond to $k_{on}$=3,900 M$^{-1}$ s$^{-1}$ and $k_{off}$=1.23×10$^{-4}$ s$^{-1}$, and predict $K_d$=32 nM compared to that measured at equilibrium ($K_d$=41 nM).

Example 28

Binding Analysis of a Potent NPC1L1 Ligand

A $^{35}$S-labeled propargyl-sulfonamide analogue of ezetimibe glucuronide ($^{35}$S-2) was identified as a potential NPC1L1 antagonist. Compound 2 was prepared as described in Example 27 and found to have markedly improved affinity for some species of brush border membranes vesicles. For rhesus brush border membranes vesicles, 56 µg protein/assay were incubated with 25 nM $^3$H-EZE-glucuronide in the presence of increasing concentrations of EZE-glucuronide and 2. For rat brush border membranes vesicles, 150 µg protein/assay were incubated with 50 nM $^3$H-EZE-glucuronide in the presence of increasing concentrations of EZE-glucuronide and 2. For mouse brush border membranes vesicles, 20 µg protein/assay were incubated with 3 nM $^{35}$S-2 in the presence of increasing concentrations of EZE-glucuronide and 2.

Figure 5:
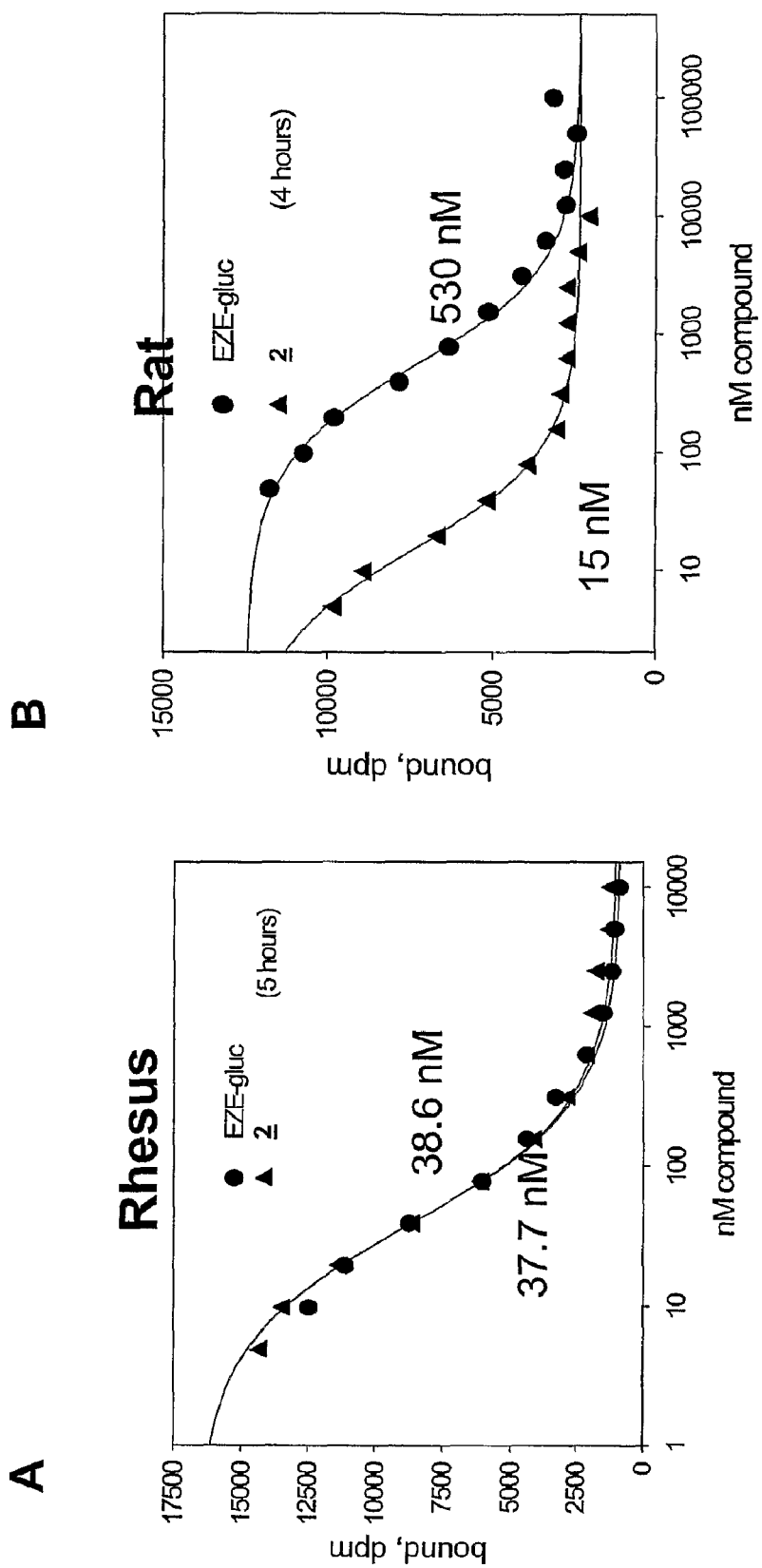
FIG. 5 shows the results of a binding assay where $^3$H-EZE-glucuronide is dissociated by EZE-glucuronide and compound 2 from rhesus (A) and rat (B) brush border membrane vesicles.
Figure 6:
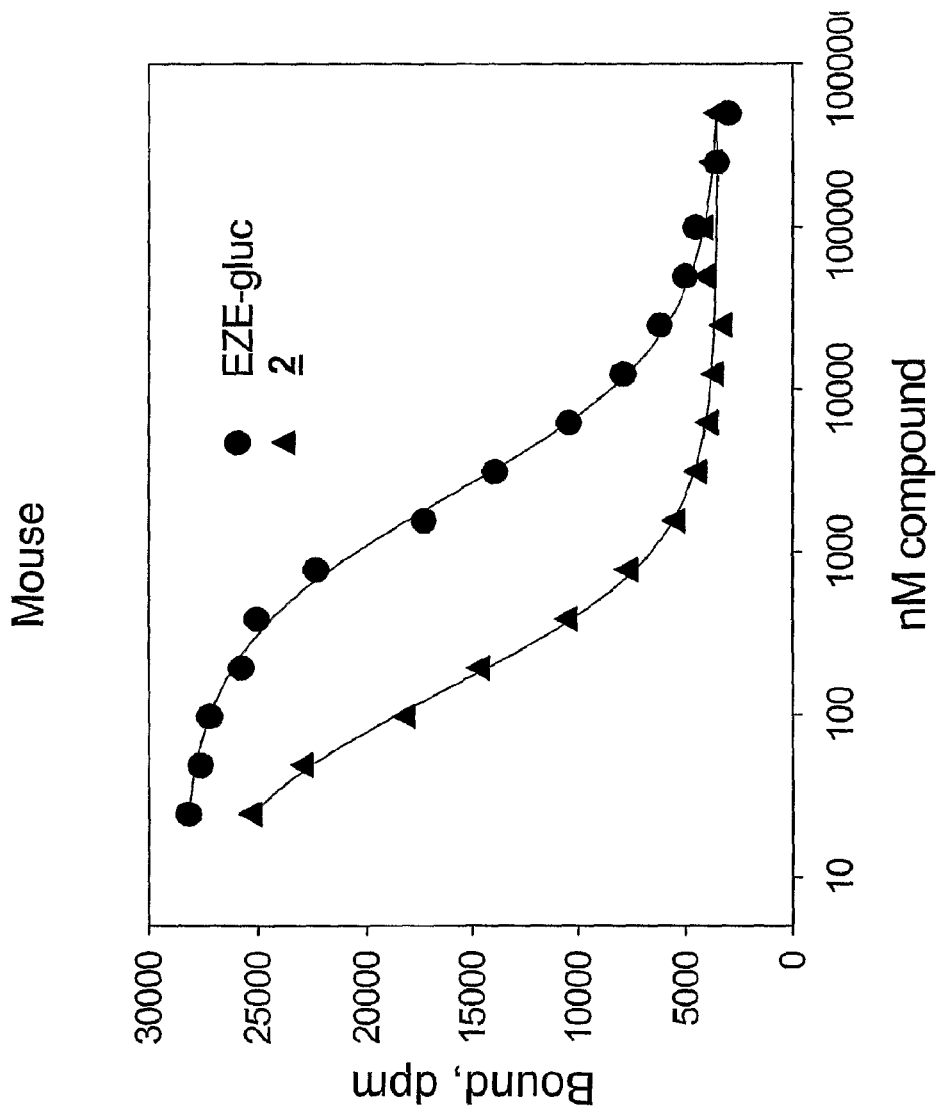
FIG. 6 shows the results of a binding assay where $^{35}$S-2 is dissociated by EZE-glucuronide and 2 from mouse brush border membrane vesicles.

2 is more potent against enterocyte brush border membrane preparations from rats (35-fold), but is equipotent with ezetimibe glucuronide for rhesus membrane preparations (FIG. 5, Table 8). It also has enhanced affinity for mouse membranes (FIG. 6, Table 8).

TABLE 8

Summary of inhibition constants ($K_i$) for binding of ezetimibe glucuronide 1 and its propargyl-sulfonamide derivative 2 to rhesus, rat, and mouse intestinal brush border membranes.

| Compound | Rhesus | Rat | Mouse |
| --- | --- | --- | --- |
| 1 | 39 | 530 | 2,300 |
| 2 | 38 | 15 | 144 |

$K_i$ values are nM.

Example 29

Distribution of $^3$H-Ezetimibe Glucuronide (1) Binding to Intestinal Tissues

Previous studies have established that cholesterol absorption occurs primarily in the jejunum, and is substantially lower in the ileum and duodenum. To determine if the binding activity is similarly distributed, the binding assay using $^3$H-ezetimibe glucuronide ($^3$H-1) as a radioligand was used to determine the distribution of binding sites in sections from rhesus and rat intestines.

For the rhesus studies, 10 cm corresponding to the ileum of a rhesus small intestine was separated and the remaining intestine was divided into three segments, (proximal, middle and distal) of equal length (70 cm each). For the rat studies, 10 cm corresponding to the ileum of a rhesus small intestine was separated and the remaining intestine was divided into three segments, (proximal, middle and distal) of equal length (36 cm each). Brush border membrane vesicles were prepared as described in Example 27. Aliquots of vesicles (100-200 µg) protein/assay were incubated with 50 nM $^3$H-EZE-glucuronide in the absence and presence of 100 µM EZE-glucuronide.

Figure 7:
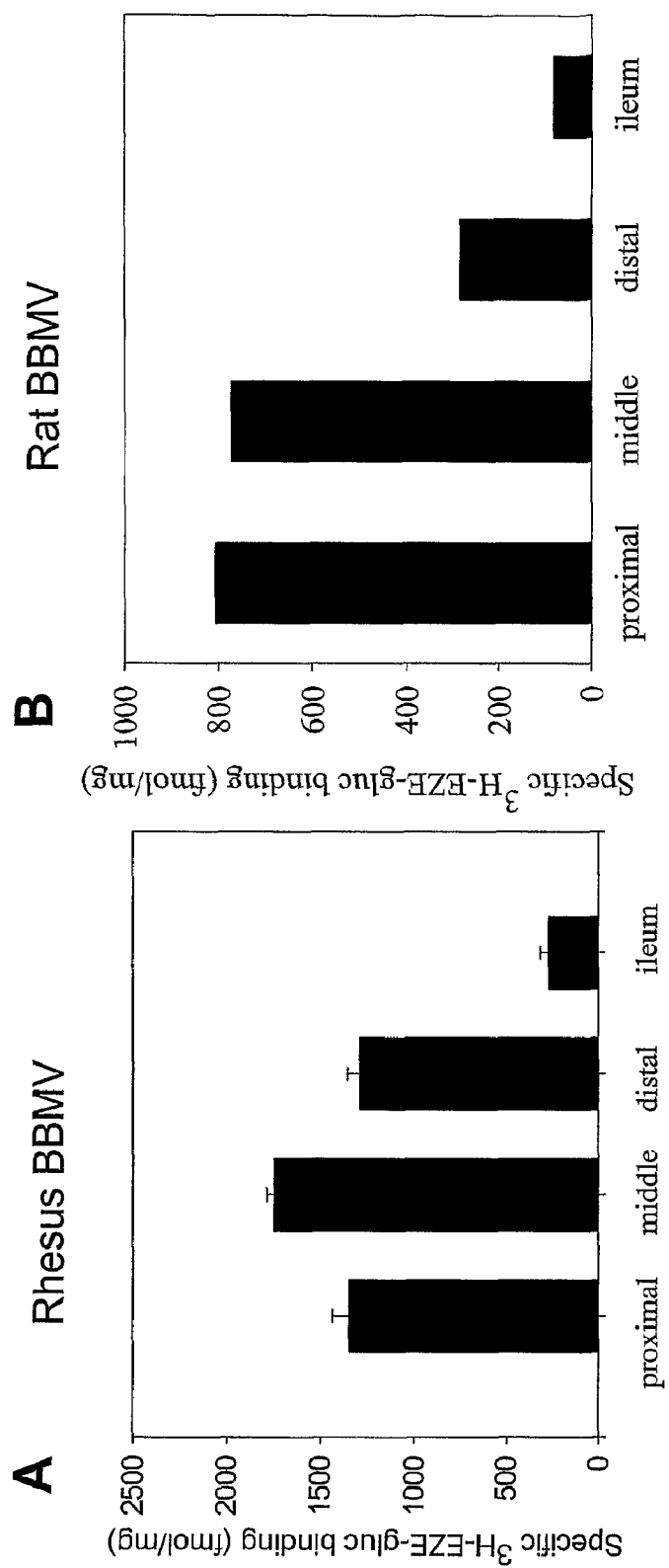
FIG. 7 shows the distribution of $^3$H-EZE-glucuronide binding to rhesus (A) and rat (B) brush border membranes prepared from various portions of rhesus (A) and rat (B) intestinal tissue.
Figure 8:
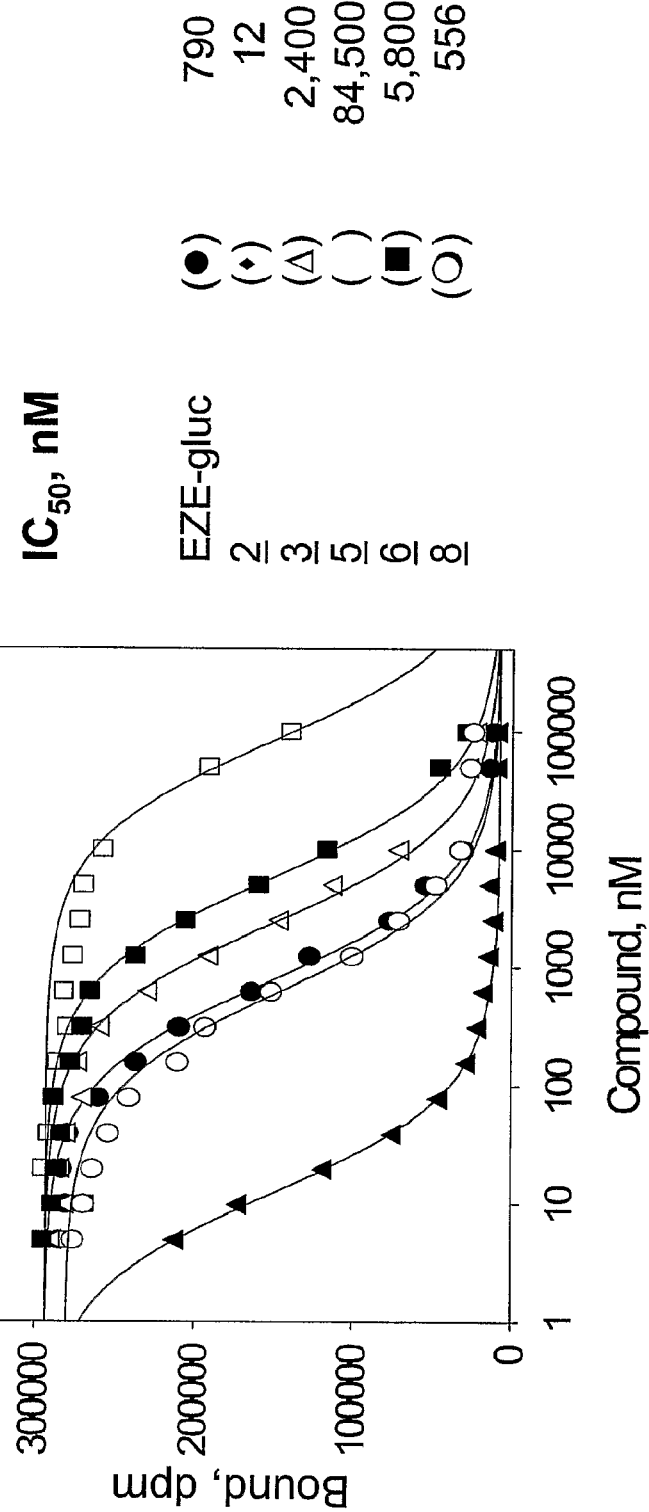
FIG. 8 shows the results of a binding assay where $^{35}$S-2 is dissociated by EZE-glucuronide and various analogs from CHO cells transfected with rat NPC1L1.

As shown in FIG. 7, specific binding for $^3$H-ezetimibe glucuronide peaks in the jejunum in both species, consistent with the previously observed pattern of cholesterol absorption.

Example 30

Correlation of In Vitro and In Vivo Binding Activity of NPC1L1

To determine if in vitro binding activity is predictive of in vivo efficacy, the enantiomer of ezetimibe glucuronide and several close structural analogues of ezetimibe glucuronide that were tested in the rat membrane binding assay were tested in an acute rat cholesterol absorption study as described in Examples 23-26. The selected analogs had a range of in vitro potencies, and were anticipated to have similar physical properties to ezetimibe glucuronide (Tables 9 and 12). The enantiomer, which has a Kd>100,000 nM for the rat target, was inactive in the in vivo assay. For the other analogs, the same rank order of potency is observed in the in vitro and in vivo assays, further evidence that the observed binding is due to the target of ezetimibe.

TABLE 9

IC$_{50}$ values of EZE-gluc and analogs to inhibit binding of 3H-EZE-gluc to rat brush border membrane vesicles.

| Compound Name | R$^1$ | X | Y | RAT IC$_{50}$ (nM) |
|---|---|---|---|---|
| 3 | H | H2 | F | 2,300 |
| EZE-gluc 1 | H | (S)-OH | F | 530 |
| EZE-gluc enantiomer 4 | H | (R)-OH | F | >100000 |
| 5 | H | (R)-OH | F | 3,900 |
| 6 | H | =O | F | 70,000 |
| 7 | OH | (S)-OH | F | 252 |

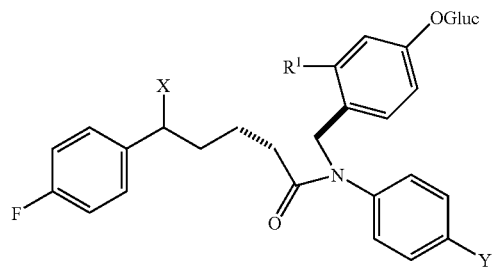

compounds 1, 3, 5, 6 and 7.

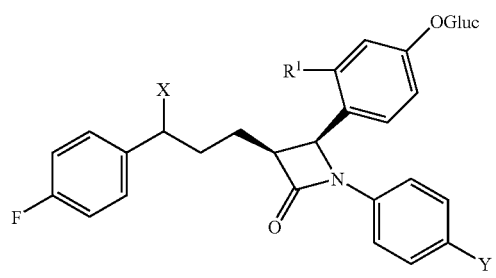

Backbone structure for compound 4.

Example 31

Binding Affinities of Ezetimibe Glucuronide and its Analogs to Recombinant NPC1L1

NPC1L1 was identified as a candidate target of ezetimibe from a search of genetic databases for cholesterol binding motifs. Subsequently, NPC1L1 deficient mice were found to have 80% reduction of cholesterol absorption, and did not respond to ezetimibe treatment, strongly suggesting that this protein is required for ezetimibe efficacy. To determine if NPC1L1 is the direct target of ezetimibe, binding affinities were compared for ezetimibe glucuronide and several analogs to NPC1L1 transfected cells and rat brush border membrane vesicles.

Rat NPC1L1 transfected CHO cells (~500,000 cells/assay) were incubated with 5 nM $^{35}$S-2 (~1 million dpm/assay) for 2 hours at 37° C. in the absence or presence of increasing concentrations of EZE-glucuronide (compound 1), compounds 2, 3, 5, 6, or 8. Compound 8 is an analog of compound 2 wherein the hydroxyl group in the 3-hydroxylpropyl moiety of 2 is replaced with an oxo group.

Human NPC1L1 transfected CHO cells (~600,000 cells/assay) were incubated with 5 nM $^{35}$S-2 (~1 million dpm/assay) in buffer A for 2 hours at 37° C. in the absence or presence of increasing concentrations of EZE-glucuronide (compound 1), compounds 2, 3, 5, 6, or 8.

Figure 9:
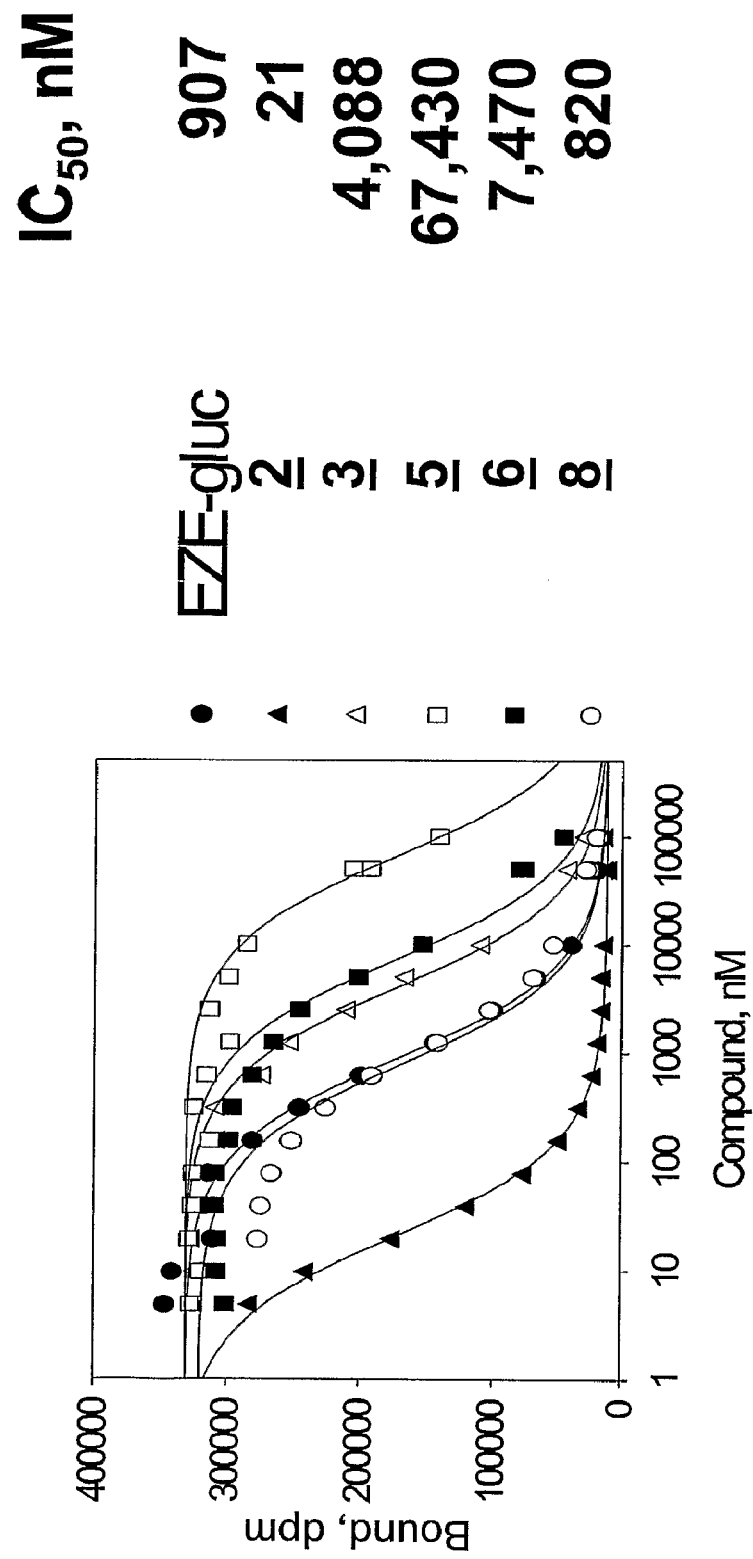
FIG. 9 shows the results of a binding assay where $^{35}$S-2 is dissociated by EZE-glucuronide and various analogs from CHO cells transfected with human NPC1L1.

As shown in FIGS. 9 and 12, and Table 10, the affinities for the recombinant and native proteins are virtually identical, providing compelling evidence that NPC1L1 is the direct target of ezetimibe in mammalian tissues, and that other proteins are not required for binding.

Affinities of ezetimibe glucuronide and analogues thereof were also determined for human recombinant NPC1L1. The results, shown in FIG. 9, indicate that ezetimibe glucuronide (1) has an affinity for the human protein of 907 nM. The propargyl-sulfonamide analogue (2) is approximately 50-fold more potent, with a K$_d$=21 nM, suggesting that this compound has the potential for enhanced potency of cholesterol absorption inhibition in man.

TABLE 10

Comparison of inhibition constants (Ki) for binding to native rat intestinal brush border membranes and membranes from rat NPC1L1 transfected cells.

| Analog | Recombinant rat NPC1L1 Ki, nM | Rat BBMV Ki, nM |
|---|---|---|
| EZE-glucuronide 1 | 790 | 600 |
| 2 | 12 | 15 |
| 3 | 2400 | 2300 |
| 6 | 84500 | 70000 |
| 5 | 5800 | 3900 |
| 8 | 556 | 818 |

Example 32

Binding of $^{35}$S-2 to Membranes from Wild Type and NPC1L1 Deficient Mice

Final confirmation that NPC1L1 is the target of ezetimibe was provided by binding studies with $^{35}$S-2 in intestinal brush border membranes from NPC1L1 deficient and control mice.

Brush border membranes vesicles were prepared from intestinal tissues of wild type and NPC1L1 knockout (−/−) mice. 15, 30 and 60 μg protein/assay of brush border membranes vesicles were incubated with 4 nM $^{35}$S-2 in buffer A for 3 hours at 37° C. in the presence and absence of 100 μM EZE-glucuronide.

Figure 10:
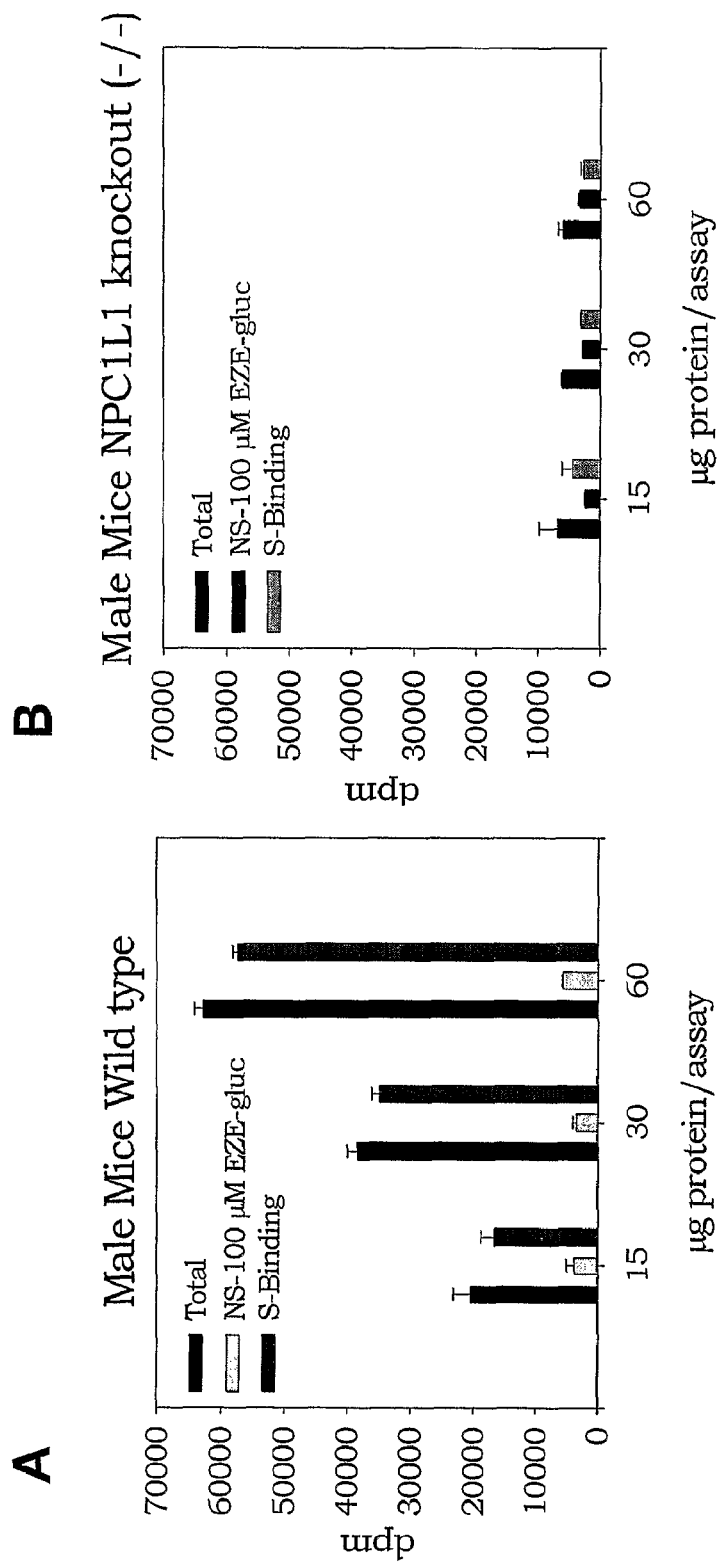
FIG. 10 shows the binding of $^{35}$S-2 to brush border membrane vesicles prepared from wild type (A) and NPC1L1 knockout (−/−) mice.
Figure 11:
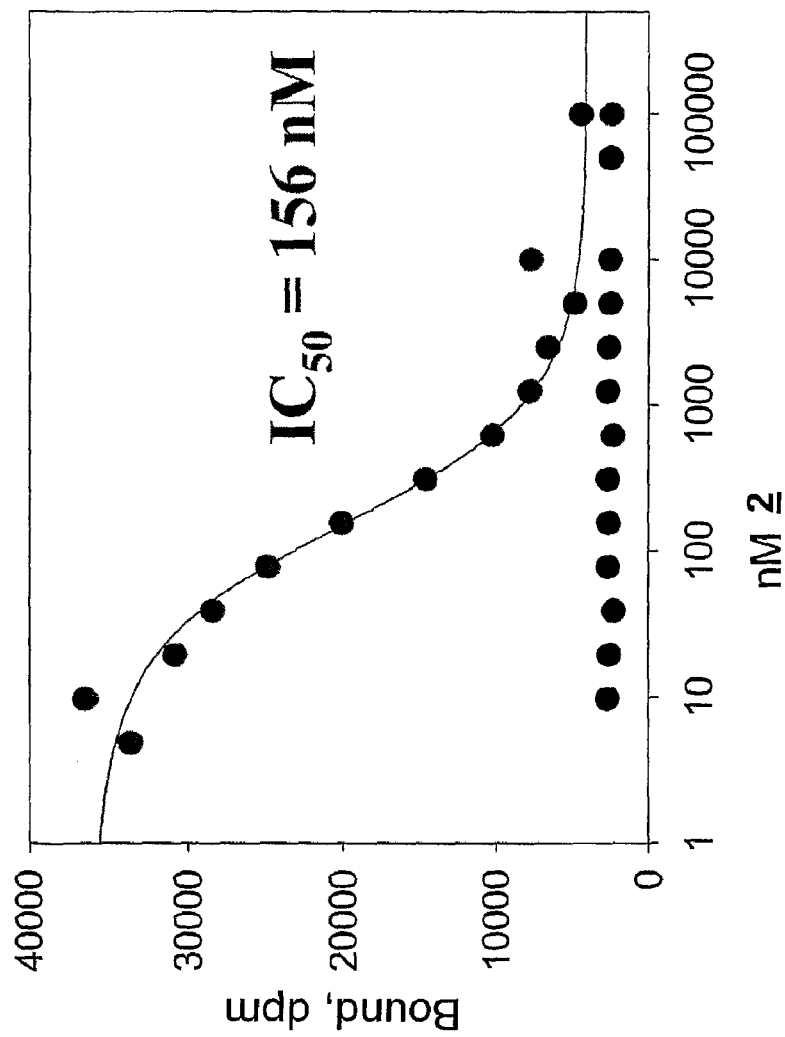
FIG. 11 shows the results of a binding assay where $^{35}$S-2 is dissociated by compound 2 from mouse wild type and NPC1L1 knockout (−/−) brush border membrane vesicles.

The results, shown in FIG. 10, indicate that no detectable binding is observed in membranes from NPC1L1 deficient mice, whereas age matched wild type control membranes have detectable binding. The binding affinity observed in this experiment in control mouse membranes (K$_d$=156 nM) was virtually identical to that observed in previous studies (FIG. 11).

Example 33

Binding Analysis Using Brush Border Membrane Vesicles from Rat Mouse and Rhesus Monkey Binding studies were performed to compare the relative binding affinity of ezetimibe glucuronide to various brush border membrane vesicles.

³H-ezetimibe glucuronide 1 was prepared as described in Example 27. The brush border membranes were prepared as described in Example 27.

Binding Assay. Assays were conducted in 12×75 mm glass test tubes and total volume 20-100 µl. In general, frozen membranes were diluted in buffer A or buffer A containing 0.03% taurocholate and 0.05% digitonin to a final concentration of 0.5 to 5 mg/ml (Buffer A: 26 mM NaHCO$_3$, 0.96 mM NaH$_2$PO$_4$, 5 mM HEPES, 5.5 mM glucose, 117 mM NaCl, 5.4 mM KCl, pH=7.4). Final concentrations of [³H]ezetimibe glucuronide 1 were typically 25-50 nM, and were delivered as DMSO or CH$_3$CN solutions. Competing ligands were likewise added as DMSO solutions to give a total 1-5% organic solvent content. Nonspecific binding was defined by competition with 100-500 µM ezetimibe glucuronide. At least three components of buffer A, the bicarbonate and phosphate salts, and glucose, were later found to be inconsequential and were routinely omitted. Reactions were incubated until equilibrium was achieved (one hour for rat or three hours for rhesus membranes).

Bound ligand was recovered by single-tube vacuum filtration on Whatman GF/C glass fiber filters. The filters were pretreated by soaking with 0.5% polyethyleneimine to reduce nonspecific binding. Filtration was accomplished by adding 2.5 ml of ice cold buffer (120 mM NaCl, 0.1% sodium cholate, and 20 mM MES at pH 6.7) to the assay tube, pouring the mixture through the filter, and then rinsing the tube and filter twice more with another 2×2.5 ml buffer. The filters were counted in 7 ml vials using Ultima Gold MV liquid scintillation fluid from Packard. Where triplicate assays were performed, the standard error was typically <4%. As an example, a 100 µl assay of rat brush border membranes at 2 mg/ml in the presence of 400,000 dpm (50 nM) [³H]ezetimibe glucuronide gave 15,000 dpm specific and 3,000 dpm nonspecific binding. The filters contributed most of the nonspecific binding (2,000 dpm).

Data Analysis. After correction for nonspecific binding, saturation-binding data were fit by nonlinear regression (Sigma Plot) to the single-site expression $[B]=B_{max}\times[L]/([L]+K_D)$. Linear Scatchard plots are shown for illustration. Data on $K_i$ from competition experiments were analyzed by nonlinear regression to the expression $[B]=[B_O]/(1+[I]/K_i^{obs})$, and where required were corrected for radioligand competition as $K_i=K_i^{obs}/(1+[L^*]/K_D)$.

First-order rate constants ($k_{obs}$ and $k_{off}$) were determined by nonlinear regression to the first order rate equation $A=A_o e^{-kt}$. Kinetic data for $k_{on}$ were analyzed according to Weiland and Molinoff (32), using the equation $k_{on}=k_{obs}([LR]_e/([L][LR]_{max}))$, where [L] is the concentration of ligand, $[LR]_e$ is the concentration of the complex at equilibrium, $[LR]_{max}$ is the maximum number of receptors present, and $k_{obs}$ is the apparent first-order rate constant.

Binding analysis. Binding studies using the [³H]ezetimibe glucuronide a traditional rapid-filtration assay on glass fiber filters using enterocyte brush border membrane preparations from rat, mouse and rhesus monkey were performed (Table 11). Table 11 shows the binding affinities of [³H]ezetimibe glucuronide to the membranes in the absence of detergents. The observed binding was specific, saturable, and consistent with a single molecular site. Scatchard analyses and the specific/nonspecific binding windows for rat and monkey are shown in FIG. 12. The binding affinity is relatively weak in rat membranes ($K_D$=542 nM) and even weaker in murine membranes ($K_D$=10,000 nM). In contrast, binding affinity in rhesus monkey membranes is approximately 10-fold greater ($K_D$=41 nM). The number of binding sites varied from 5-20 pmol/mg membrane protein depending on species and preparation.

The rates for binding and dissociation of [³H]ezetimibe glucuronide were determined and found to be slow relative to those typically observed for protein-ligand interactions. For example, the rate constants for association to rat and monkey brush border membranes are $k_{on}$=5.54 and 3.90×10 M$^{-1}$ s$^{-1}$ (FIG. 12). These are 100,000-fold smaller than those typically observed for a diffusion controlled encounter, $10^8$ to $10^9$ M$^{-1}$ s$^{-1}$. Similarly, these complexes are unusually long-lived, dissociating with rate constants of $k_{off}$=2.4×10$^{-3}$ s$^{-1}$ and 1.2×10$^{-4}$ s$^{-1}$ at 25 C, equivalent to half-lives of 4.7 and 96 min for the rat and monkey complexes, respectively. In comparison, half lives are normally <1 sec for dissociation of common diffusion controlled, 100 nanopolar $K_D$ ligands. These rate constants predict $K_D$ values ($K_D$=$k_{off}/k_{on}$) of 440 and 32 nM, respectively, which agree well with those measured by equilibrium titration (FIG. 12), and by saturation as described earlier. Such slow-forming, long-lived complexes suggest that conformational changes in the protein are rate limiting.

TABLE 11

Comparison of ezetimibe binding affinity and cross species efficacy

| Species | $K_D$ (nM) | ED$_{50}$ (mg/Kg) |
|---------|-----------|-------------------|
| mouse   | 12,000    | 0.5000            |
| rat     | 542       | 0.0300            |
| monkey  | 41        | 0.0005            |

Table 11 also shows a correlation between in vitro and in vivo binding of [³H]ezetimibe glucuronide in various enterocyte brush border membrane preparations from rat, mouse and rhesus monkey. The in vivo ED$_{50}$ values are derived from cholesterol absorption and cholesterol feeding studies. The rank order of ezetimibe potency (ED$_{50}$) in vivo as follows: rhesus (0.0005 mpk)>rat (0.03 mpk)>mouse (0.5 mpk) is the same as the order of in vitro binding affinity (IC$_{50}$) as follows: rhesus monkey (41 nM)<rat (542 nM)<mouse (12,000 nM).

The binding affinities of 1 to brush border membranes correlate well across species with the sensitivity to ezetimibe inhibition of cholesterol uptake in vivo (mouse<rat<monkey) (Clader, J. W. The discovery of ezetimibe; A view from outside the receptor. *J. Med. Chem.* 47, 1-9 (2004); Davis, H. R. Jr., Compton, D. S., Hoos, L. & Tetzloff, G. Ezetimibe, a potent cholesterol absorption inhibitor, inhibits the development of atherosclerosis in ApoE knockout mice. *Arterioscler. Thromb. Vasc. Biol.* 21, 2032-2038 (2001); Burnett, D. A. Beta-lactam cholesterol absorption inhibitors. *Curr. Med. Chem.* 11, 1873-1887 (2004), consistent with the hypothesis that the assay is relevant to the target of ezetimibe in vivo (Table 11). As evidence that this interaction is very specific, the glucuronide of the enantiomer of ezetimibe was prepared and found to be completely inactive in vitro ($K_i$>100×$K_D$ for ezetimibe glucuronide in all species), consistent with its lack of activity in vivo in a rat acute cholesterol absorption model (see Table 12 in which the enantiomer is analyzed).

Example 34

NPC1L1 as the Target of Ezetimibe in NPC1L1-Expressing HEK293 Cells

This example demonstrates that ezetimibe binds specifically to NPC1L1-expressing HEK293 cells.

Transient expression of NPC1L1. Plasmid pCR3.1 expressing rat NPC1L1 (Genbank AY437867) or human NPC1L1 (Genbank AY437865) were prepared using standard molecular biology protocols. HEK-293 cells (ATCC) were seeded at 10×10$^6$ cells per T-225 flask (Corning) in DMEM containing 10% fetal calf serum, 4.5 g/L D-glucose and L-glutamine, 18 hours prior to transfection. They were transiently transfected with 25 μg of DNA using Fugene transfection reagent (Roche Biochemical) at a ratio of 6:1 Fugene:DNA. Following transfection, the cells were incubated at 37° C. and 5% $CO_2$ for 48 hours, and then harvested using PBS based cell dissociation buffer (Gibco), pelleted at 500×g, snap frozen on dry ice, and stored at −80° C.

Membrane preparation from HEK-293 cells. Membranes were prepared by resuspending the frozen cell pellets in ten volumes of 20 mM HEPES/Tris buffer at pH 7.40 containing 8% sucrose, and sonicating the suspensions with a probe sonicator on ice until most of the cells were lysed. To isolate the membranes, the sonicates were centrifuged at 1600×g for 10 min to remove cell debris, and then the supernatants were centrifuged at 125,000×g for 1 hour to recover the membranes. These membranes were resuspended in 20 mM HEPES/Tris buffer at pH 7.40 containing 160 mM NaCl and 5% glycerol, and stored at 10-20 mg/ml protein at −80° C.

Pursuing the recent evidence indicating that NPC1L1 is an important component of the pathway inhibited by ezetimibe, recombinant rat and human NPC1L1 were expressed in human embryonic kidney (HEK) 293 cells (FIG. 13, Panel 1). Cell lysates from HEK-293 cells expressing NPC1L1 (Lanes 1 and 3 of Panel 1 FIG. 13) and wild-type cells (Lanes 2 and 4 of Panel 1 FIG. 13) were analyzed by gel electrophoresis and Western blot with an anti-NPC1L1 antibody A1801. An excess of NPC1L1-specific peptide was included to assess specificity of the antibody for NPC1L1 (Lane 3 and 4 of Panel 1 FIG. 13). Preliminary binding studies using 1 revealed specific binding to membrane preparations from cells expressing NPC1L1, and no specific binding to membranes from mock transfected cells (not shown).

Binding to NPC1L1 expressing cells was also observed with a BODIPY-labeled fluorescent ezetimibe glucuronide analog (SCH354909) (FIG. 13, Panel 2A). Panel 2 of FIG. 13 shows confocal microscope images of a fluorescent ezetimibe glucuronide analog (SCH354909) bound to the surface of NPC1L1-293 cells (Panel 2A), nonspecific binding of SCH354909 to NPC1L1-293 cells in the presence of 100 μM unlabeled ezetimibe glucuronide (Panel 2B), binding of SCH354909 to wild type HEK 293 cells (Panel 2C), and nonspecific binding of SCH354909 to wild type HEK 293 cells in the presence of 100 μM unlabeled ezetimibe glucuronide (Panel 2D). In each case, plated cells were incubated in culture media with 500 nM SCH354909 for 4 hours at 37° C. Cells were subsequently washed with PBS and fluorescence was detected using confocal microscopy.

Binding of SCH345909 was clearly evident at the cell surface membrane of the NPC1L1-expressing cells and was completely abolished in the presence of excess unlabeled ezetimibe glucuronide (FIG. 13, Panel 2C). No binding was observed in wild type HEK 293 cells (FIG. 13, Panels 2B and 2D). These results demonstrated that ezetimibe glucuronide binds specifically to NPC1L1.

Example 35

NPC1L1 as the In Vivo Target of Ezetimibe

To obtain evidence that NPC1L1 is the direct binding target of ezetimibe in vivo, binding affinities of 1 and several key analogs were determined for recombinant rat and human NPC1L1 expressed in HEK-293 cell membranes and compared to those for native rat and rhesus intestinal enterocyte brush border membranes. A series of ezetimibe analogs was selected with subtle structural diversity, but with no binding affinities to native brush border membranes that covered a range of 1000-fold.

Table 12 shows a comparison of binding affinities ($K_i$ values) for recombinant NPC1L1-293 cell membranes and native brush border membranes Selected analogs of ezetimibe glucuronide are compared against recombinant rat and human NPC1L1 membranes prepared from transiently transfected HEK-293 cells compared to native rat and rhesus brush border membranes. The binding assays were conducted in a final volume of 20 μl in the presence of 0.03% sodium taurocholate and 0.05% digitonin until equilibrium was achieved. 1.25 mg protein/ml and 100 nM 1 were used for native rat, recombinant rat, and recombinant human experiments, and 1.25 mg protein/ml and 20 nM 1 were used for native rhesus monkey experiments. Observed total and non-specific binding, respectively, in the absence of inhibition were native rat: 7,700 & 1,100, recombinant rat: 33,000 & 1,100, native rhesus monkey: 7,300 & 367, and recombinant human: 19,200 & 1,000 dpm. Analog structures are defined in Table 12. Compound 4 has the stereochemical configuration 3S,4R, and is the glucuronide of the enantiomer of ezetimibe. These determinations were conducted in buffer containing 0.03% taurocholate and 0.05% digitonin, levels below the critical micelle concentrations of these detergents. These conditions enhanced apparent binding by as much as 20-fold for the recombinant preparations (principally a $B_{max}$ effect), and greatly facilitated a quantitative comparison of $K_i$ values for 1 and its analogs.

As shown in Table 12, the $K_i$ values for recombinant rat NPC1L1 and native rat brush border membranes are virtually identical, strongly suggesting that NPC1L1 is the molecular target of ezetimibe in vivo. In the case of membranes from cells expressing recombinant human NPC1L1, the binding affinities also parallel those observed in rat membranes, whereas binding affinities for native rhesus brush border membranes are uniformly ~10-fold more potent. This result is consistent with the finding that ezetimibe is an order of magnitude more potent in monkey than in human or rat (Clader, J. W. The discovery of ezetimibe; A view from outside the receptor. *J. Med. Chem.* 47, 1-9 (2004); Jeu, L. & Cheng, J. W. Pharmacology and therapeutics of ezetimibe (SCH 58235), a cholesterol-absorption inhibitor. *Clin. Ther.* 25, 2352-2387 (2003)).

TABLE 12

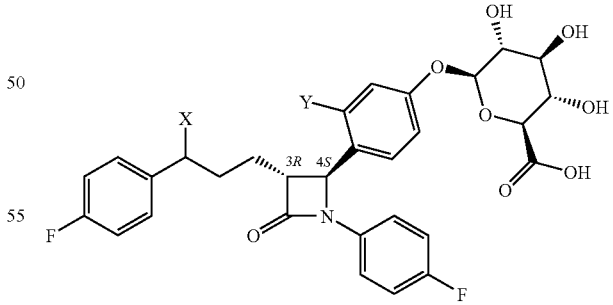

| Analog | X | Y | Rat BBM Ki (nM) | Rat NPC1L1 Ki (nM) | Human NPC1L1 Ki (nM) | Monkey BBM Ki (nM) |
|---|---|---|---|---|---|---|
| EZE-gluc 1 | OH (S) | H | 390 | 210 | 220 | 15 |
| 4* | OH (R) | H | 130,000 | 74,000 | 130,000 | 22,000 |
| 3 | H | H | 1,600 | 820 | 1,000 | 150 |

TABLE 12-continued

[Chemical structure showing ezetimibe glucuronide analog with X, Y substituents, 3R,4S stereochemistry, two fluorophenyl groups, and glucuronide moiety]

| Analog | X | Y | Rat BBM Ki (nM) | Rat NPC1L1 Ki (nM) | Human NPC1L1 Ki (nM) | Monkey BBM Ki (nM) |
|---|---|---|---|---|---|---|
| 6 | =O | H | 33,000 | 23,000 | 14,000 | 3,300 |
| 5 | OH (R) | H | 2,800 | 1,700 | 1,300 | 120 |
| 7 | OH (S) | OH | 280 | 360 | 210 | 60 |

Figure 14:
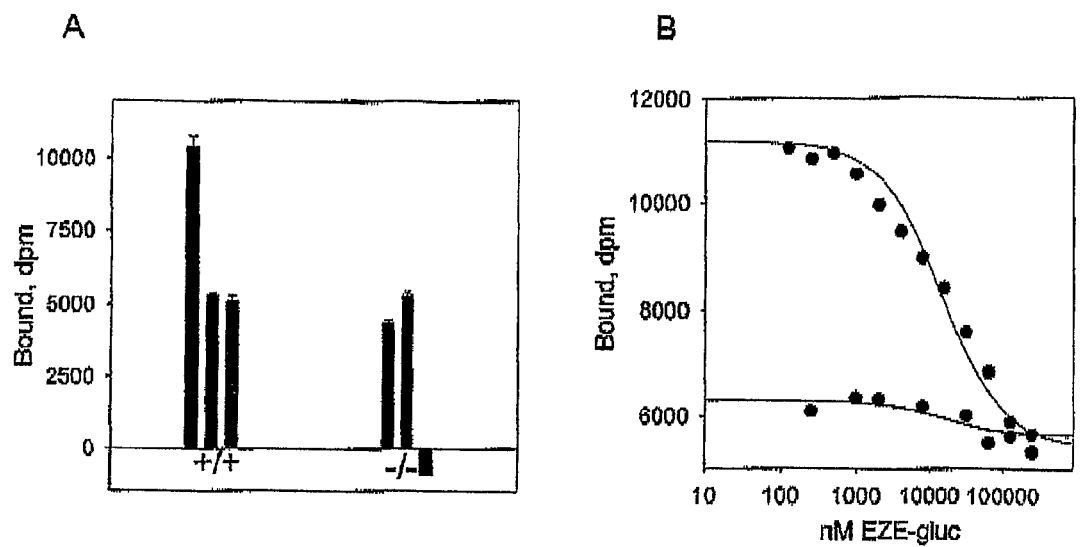
FIG. 14A shows binding of $^3$H-ezetimibe glucuronide to enterocyte brush border membranes from wild type mice and NPC1L1 deficient mice in the presence of detergent.
FIG. 14B shows competition studies of unlabeled ezetimibe glucuronide against labeled ezetimibe glucuronide.

*glucuronide of the enantiomer of ezetimibe has stereochemical configuration 3S, 4R Conclusive evidence that NPC1L1 is the target of ezetimibe was provided by studies with tissues from NPC1L1 deficient mice. Enterocyte brush border membranes prepared from NPC1L1 deficient mice showed no detectable specific binding affinity for 1, whereas membranes from age-matched wild-type mice showed a high level of specific binding with a $K_D=12$ µM (FIG. 14).

For FIG. 14A, enterocyte brush border membranes were prepared from NPC1L1 deficient male mice and same sex wild-type littermates, and tested for binding of 1. Conditions for binding were 5 mg/ml protein and 500 nM 1 in a volume of 20 µl and in the presence of 0.03% sodium taurocholate and 0.05% digitonin. Membranes from wild type mice are on the left and from NPC1L1 deficient mice on the right. The bar graphs indicate total binding (left bar), nonspecific binding in the presence of 500 µM cold ezetimibe glucuronide (middle bar), and specific (right bar) binding, respectively for each of wild type and NPC1L1 deficient mice, and error bars represent triplicate measurements. The graphs show that although specific binding is readily detectable in wild-type mice, it is absent in NPC1L1-deficient mice.

FIG. 14B shows a plot demonstrating competition of unlabeled ezetimibe glucuronide against 1. Membranes from wild-type mice (upper curve) gave $K_i=12,000$ nM, while specific binding was virtually undetectable in membranes from the knockout animals (lower curve). Conditions were those described in FIG. 14A.

The present studies involve a quantitative comparison of binding between recombinant proteins and brush border membranes. SR-B1 (scavenger receptor type B1) was previously identified as a potential target using an expression cloning strategy employing ezetimibe binding to candidate proteins; this hypothesis was readily dismissed when neither cholesterol absorption nor ezetimibe activity were affected in SR-B1 deficient mice (Altmann, S. W. et al The identification of intestinal scavenger receptor class B, type 1 (SR-B1) by expression cloning and its role in cholesterol absorption. *Biochem. Biophs. Acta* 1580, 77-93 (2002)). The results show that ezetimibe binds to native intestinal membranes and cells expressing recombinant NPC1L1 with comparable affinity, and does not bind to membranes from NPC1L1 deficient mice, indicating a specific binding interaction between NPC1L1 and ezetimibe. Together with the previously published findings that mice deficient in NPC1L1 are defective in intestinal cholesterol uptake, and are no longer responsive to ezetimibe (Altmann, S. W. et al. Niemann-Pick C1 Like 1 protein is critical for intestinal cholesterol absorption. *Science* 303, 1201-1204 (2004)), these data definitively establish NPC1L1 as the direct target of ezetimibe.

Example 36

Effect of Detergents on [³H]Ezetimibe Glucuronide Binding

Figure 15:
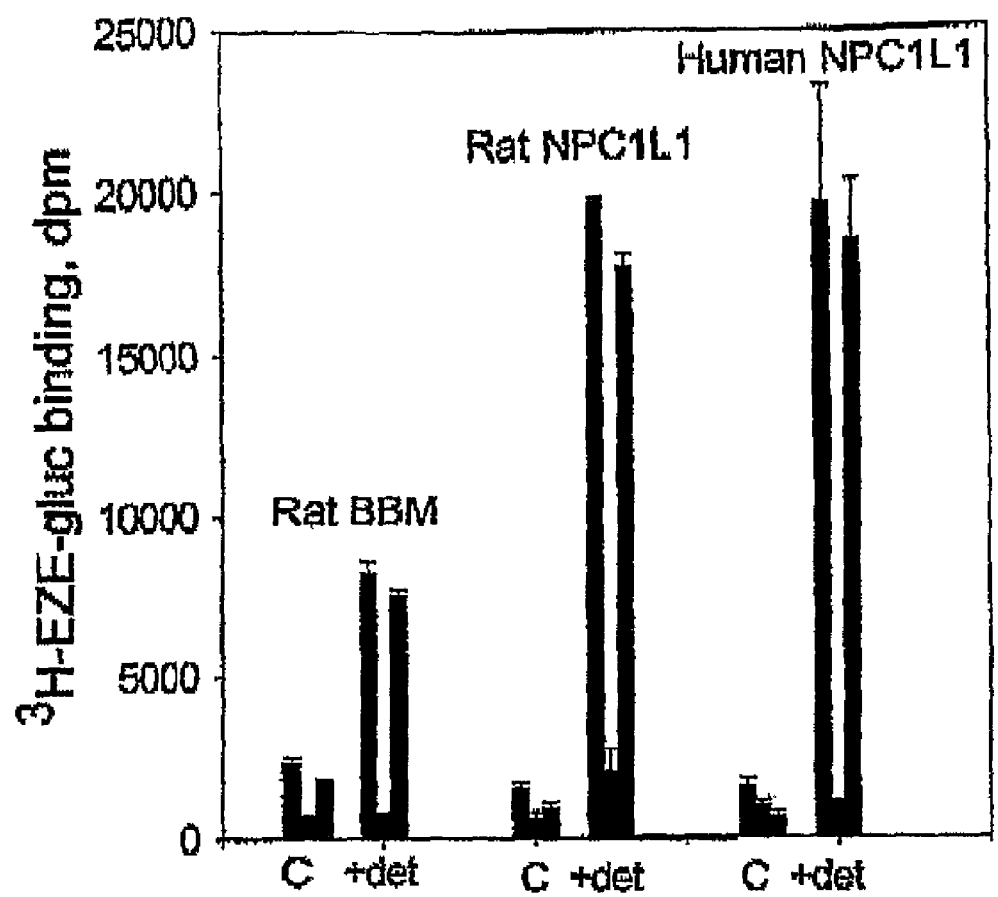
FIG. 15 shows the effect of detergents, taurocholate and digitonin, on [$^3$H]ezetimibe glucuronide binding.

A practical aspect of work with the recombinant protein was that the number of binding sites in transfected NPC1L1-293 cell membranes initially appeared quite low. The influence of a combination of 0.03% taurocholate and 0.05% digitonin on specific binding to these and native enterocyte brush border membrane preparations is dramatic as illustrated in FIG. 15.

Equal amounts (25 µg protein) of rat brush border membranes, membranes from HEK-293 cells transiently expressing recombinant rat and human NPC1L1, were incubated with 25 nM 1 in a final volume of 20 µl until equilibrium was achieved. The incubation conditions were buffer A with and without sodium taurocholate and digitonin to a final concentration of 0.03% and 0.05%, respectively. On the x-axis, "C" denotes controls in the absence of detergent, and "+det" the response in the presence of both detergents. The results are shown in 3 bar groupings; Total binding (left bar in each 3 bar group), nonspecific binding in the presence of 100 µM unlabeled ezetimibe glucuronide (middle bar in each 3 bar group), and specific binding (right bar in each 3 bar group) are shown.

Example 37

Binding Affinities of Ezetimibe Glucuronide and Various Analogues NPC1L1 in Rat and Rhesus Monkey Membranes As determined from binding assay results using ³H-ezetimibe glucuronide with rat brush border membrane, representative tested compounds of Formula II were determined to have $IC_{50}$'s of about 13,000 nM or lower, and particularly certain tested compounds had $IC_{50}$'s of about 1900 nM or lower, more particularly certain tested compounds had $IC_{50}$'s of about 1000 nM or lower, and most particularly certain tested compounds had $IC_{50}$'s of less than 100 nM. As determined from binding assay results using ³H-ezetimibe glucuronide with rhesus brush border membrane, representative tested compounds of Formula II were determined to have $IC_{50}$'s of about 4200 nM or lower, and particularly certain tested compounds had $IC_{50}$'s of about 165 nM or lower, more particularly certain tested compounds had $IC_{50}$'s of less than 100 nM, and most particularly certain tested compounds had $IC_{50}$'s of less than 50 nM.

The designations below are used in the Examples that follow for certain repetitively used intermediates:

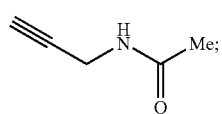

i-1

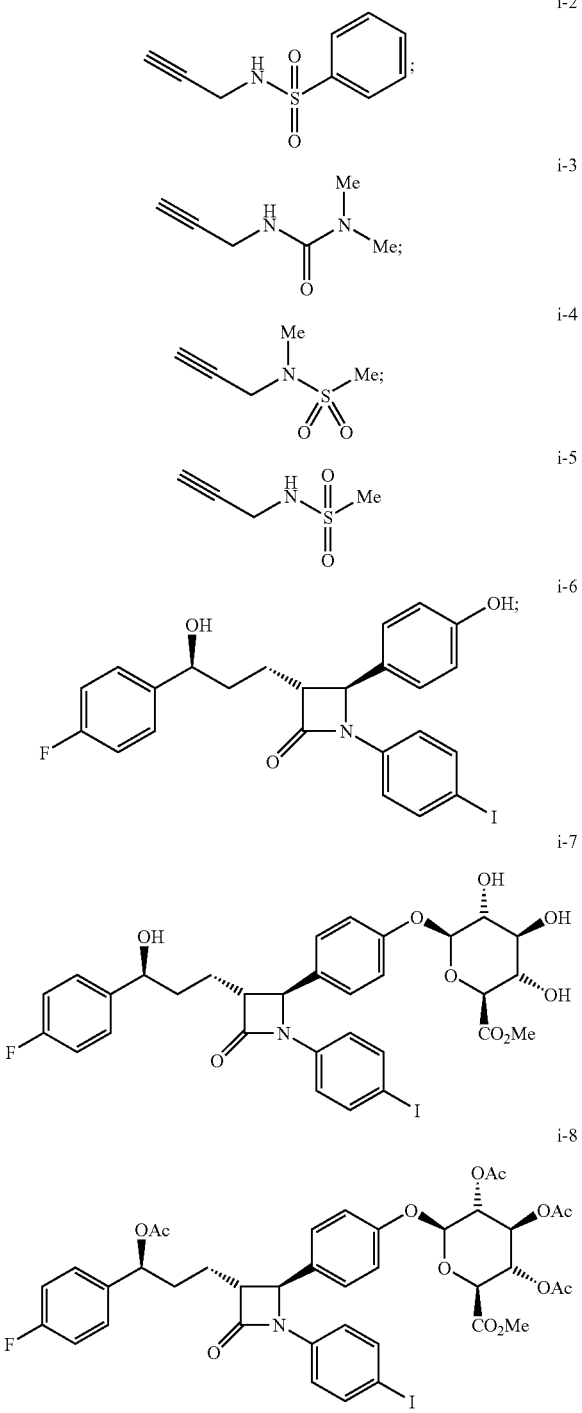

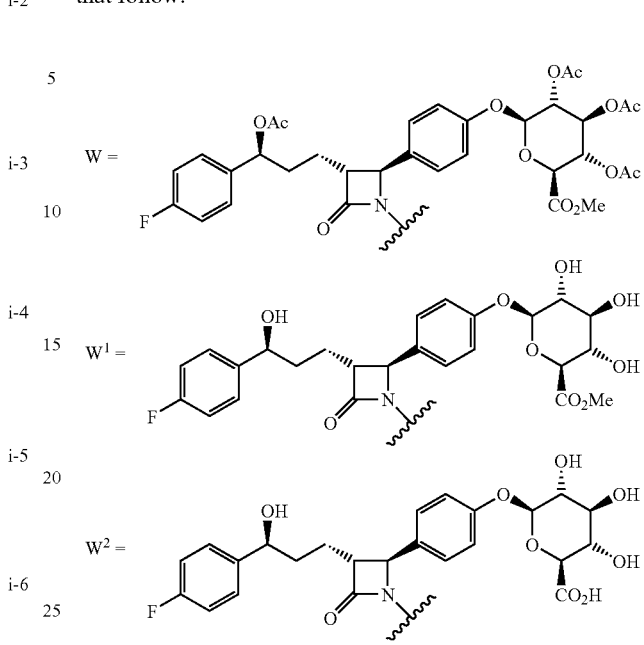

The compounds (3R,4S)-3-[(3S)-3-(4-fluorophenyl)-3-hydroxypropyl]-4-(4-hydroxyphenyl)-1-(4-iodophenyl)azetidin-2-one (i-6) and 4-[(2S,3R)-3-[(3S)-3-(4-fluorophenyl)-3-hydroxypropyl]-1-(4-iodophenyl)-4-oxoazetidin-2-yl]phenyl methyl β-D-glucopyranosiduronate (i-7) were prepared according to Burnett, D. S.; Caplen, M. A.; Domalski, M. S.; Browne, M. E.; Davis, H. R. Jr.; Clader, J. W. Bioorg. Med. Chem. Lett. (2002), 12, 311. Compound i-8 is the hydroxy-protected analog of i-7, where the protecting group is acyl.

The following definitions are also used in the Examples that follow:

Example 38

Preparation of N-prop-2-yn-1-ylacetamide (i-1)

Acetyl chloride (0.52 mL, 7.3 mmol) was added to a stirred solution of propargylamine (0.5 mL, 7.3 mmol) and dimethylaminopyridine (18 mg, 0.14 mmol) in pyridine (2.5 mL) at 0° C., and the resulting mixture was allowed to warm to ambient temperature. After approximately 15 h, the reaction mixture was diluted with ethyl acetate and washed successively with 1N HCl and brine. The organic phase was dried ($Na_2SO_4$), filtered and concentrated in vacuo to afford the title compound (i-1), which was used without further purification.

Example 39

Preparation of N-prop-2-yn-1-ylbenzenesulfonamide (i-2)

Benzene sulfonyl chloride (1.16 mL, 9.1 mmol) was added to stirred solution of propargylamine (0.62 mL, 9.1 mmol) and dimethylaminopyridine (22 mg, 0.18 mmol) in pyridine (5 mL) at room temperature. The resulting solution was aged at ambient temperature for approximately 15 h. The reaction mixture was diluted with ethyl acetate and washed successively with 1N HCl and brine. The organic phase was dried ($Na_2SO_4$), filtered and concentrated in vacuo to furnish the title compound (i-2), which was used without further purification.

Example 40

Preparation of N,N-Dimethyl-N'-prop-2-yn-1-ylurea (i-3)

Dimethyl carbamylchloride (0.84 mL, 9.1 μmmol) was added to a stirred solution of propargylamine (0.62 mL, 9.1 mmol) and dimethylaminopyridine (22 mg, 0.18 mmol) in pyridine (5 mL) at room temperature. The resulting suspension was stirred at ambient temperature for approximately 15 h. The reaction mixture was diluted with ethyl acetate and washed successively with 1N HCl and brine. The organic phase was dried (Na$_2$SO$_4$), filtered and concentrated in vacuo to afford the title compound (i-3), which was used without further purification.

Example 41

Preparation of N-Methyl-N-prop-2-yn-1-ylmethanesulfonamide (i-4)

Methanesulfonylchloride (1.12 mL, 14.5 mmol) was added to a stirred solution of N-methylpropargylamine (1.22 mL, 14.5 mmol) and dimethylaminopyridine (35 mg, 0.30 mmol) in pyridine (10 mL) at room temperature. After aging for approximately 15 h, the reaction mixture was poured into ethyl acetate and washed successively with 1N HCl and brine. The organic phase was dried (Na$_2$SO$_4$), filtered and concentrated in vacuo, to afford the title compound (i-4), which was used without further purification.

Example 42

Preparation of N-prop-2-yn-1-ylmethanesulfonamide (i-5)

Methanesulfonylchloride (1.40 mL, 18.1 μmmol) was added dropwise to a stirred solution of propargylamine (1.00 g, 18.1 mmol) and dimethylaminopyridine (44.0 mg, 0.36 mmol) in pyridine (10 mL) at 0° C. After aging for approximately 15 h, the reaction mixture was poured into 1N HCl and extracted twice with ethyl acetate. The combined organic extracts were washed with saturated aqueous sodium bicarbonate, brine, dried (MgSO$_4$), filtered and concentrated in vacuo, to afford the title compound i-5. Crude i-5 crystallized on standing and was used without further purification.

Example 43

Preparation of N-(3-{4-[(2S,3R)-3-[(3S)-3-(4-fluorophenyl)-3-hydroxypropyl]-2-(4-hydroxyphenyl)-4-oxoazetidin-1-yl]phenyl}prop-2-yn-1-yl)methanesulfonamide (Compound 6a)

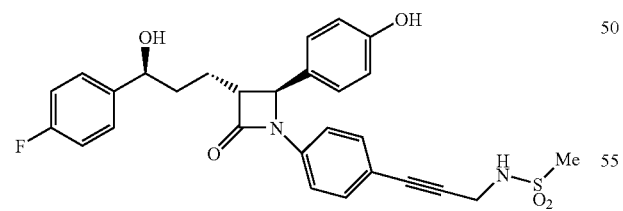

6a

Triethylamine (7 equivalents) is added to a solution of (3R,4S)-3-[(3S)-3-(4-fluorophenyl)-3-hydroxypropyl]-4-(4-hydroxyphenyl)-1-(4-iodophenyl)azetidin-2-one (i-6) (1.00 equivalent), N-prop-2-yn-1-ylmethanesulfonamide (i-5) (1.50 equivalents), tetrakistriphenylphosphine palladium(0) (0.15 equivalents) and copper(I) iodide (0.30 equivalents) in DMF (0.1 M concentration with respect to final product) under a nitrogen atmosphere and the resulting solution aged at room temperature. After completion of reaction, the volatiles are evaporated in vacuo and the crude residue can be purified by flash chromatography on silica gel to afford the title compound.

Example 44

Step A: Preparation of 4-[(2S,3R)-3-[(3S-3 (4-fluorophenyl)-3-hydroxypropyl]-1-(4-{3-[(methylsulfonyl)amino]prop-1-n-1-yl}phenyl)-4-oxoazetidin-2-yl]phenyl methyl β-D-glucopyranosiduronate (Compound 7a)

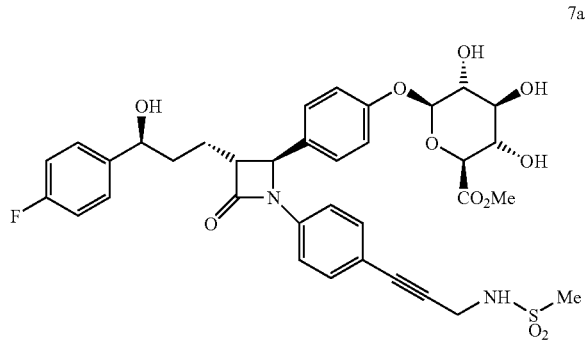

7a

Triethylamine (0.07 mL, 0.502 mmol) was added to a stirred solution of 4-[(2S,3R)-3-[(3S)-3-(4-fluorophenyl)-3-hydroxypropyl]-1-(4-iodophenyl)-4-oxoazetidin-2-yl]phenyl methyl β-D-glucopyranosiduronate (i-7) (0.050 g, 0.071 mmol), N-prop-2-yn-1-ylmethanesulfonamide (i-5) (0.014 g, 0.105 mmol), tetrakistriphenylphosphine palladium(0) (0.012 g, 0.010 mmol) and copper iodide (0.005 g, 0.026 mmol) in DMF (0.5 mL) under a nitrogen atmosphere and the resulting solution aged at room temperature for 18 h. The volatiles were evaporated in vacuo and the crude residue purified by flash chromatography on silica gel (gradient elution; 0-25% methanol/methylene chloride as eluent) to afford the title compound; m/z (ES) 713 (MH$^+$), 505.

Step B: Preparation of 4-[(2S,3R)-3-[(3S)-3 (4-fluorophenyl)-3-hydroxypropyl]-1-(4-{3-[(methylsulfonyl)amino]prop-1-yn-1-yl}phenyl)-4-oxoazetidin-2-yl]phenyl β-D-glucopyranosiduronic acid (Compound 7b, also referred to herein as compound 2)

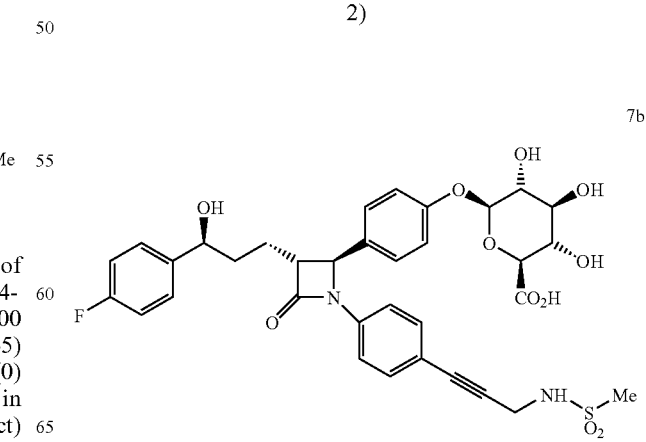

7b

A solution of compound 7a in methanol/water/triethylamine (1:7:2; 1 mL) was stirred at room temperature for approximately 1.5 h. The volatiles were evaporated in vacuo and the crude residue purified by preparative reversed phase high performance liquid chromatography on YMC Pack Pro C18 phase (gradient elution; 10-65% acetonitrile/water as eluent, 0.1% TFA modifier) to give the title compound (7b); m/z (ES) 699 (MH$^+$), 505; HRMS (ES) m/z calcd for $C_{34}H_{36}FN_2O_{11}S$ (MH$^+$) 699.2024, found 699.2016.

Example 45

Compounds 6B to 6G and 7C to 7N

The following compounds of Formula IIa have been prepared (as indicated by MS data provided) or can be prepared using the general synthetic procedures described in Example 43 (shown in Table 13) or Example 44 (shown in Table 14).

TABLE 13

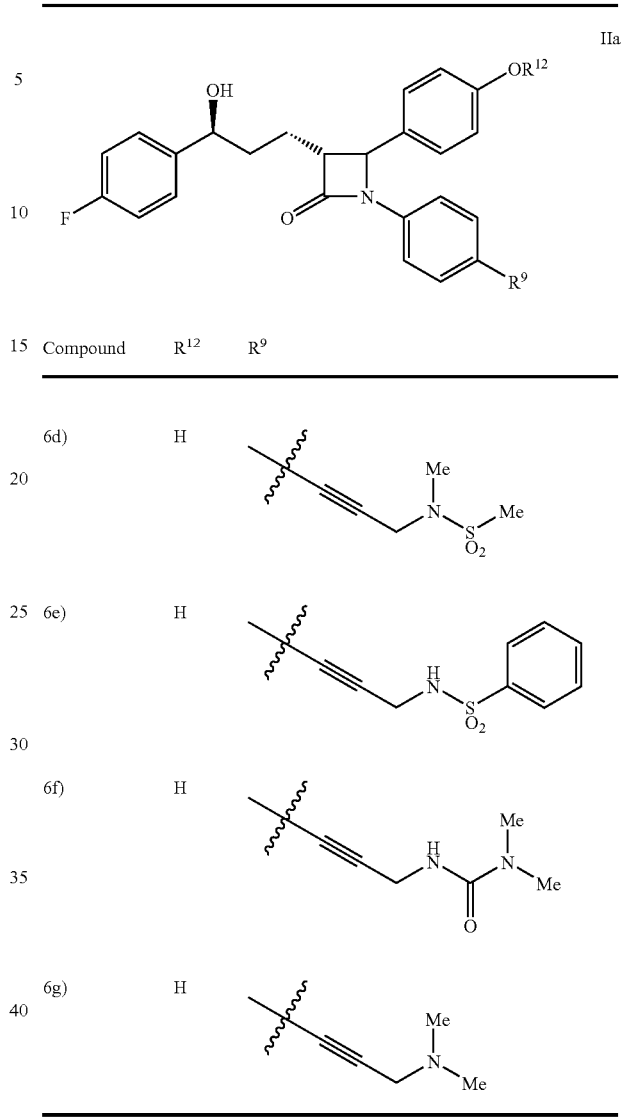

| Compound | R$^{12}$ | R$^9$ |
|---|---|---|
| 6b) | H | ~~~≡~~NH$_2$ |
| 6c) | H | ~~~≡~~NHC(O)Me |
| 6d) | H | ~~~≡~~CH$_2$N(Me)S(O)$_2$Me |
| 6e) | H | ~~~≡~~CH$_2$NHS(O)$_2$Ph |
| 6f) | H | ~~~≡~~CH$_2$NHC(O)N(Me)Me |
| 6g) | H | ~~~≡~~CH$_2$N(Me)Me |

TABLE 14

| Compound | R$^{12}$ | R$^9$ | m/z (ES) | HRMS m/z (ES) |
|---|---|---|---|---|
| 7c) | methyl ester glucuronide | ~~~≡≡~~CH$_2$NH$_2$ | 658 (MNa$^+$) | |
| 7d) | glucuronide | ~~~≡≡~~CH$_2$NH$_2$ | 621 (MH$^+$) | (MH$^+$) Calcd 621.2249 Found 621.2223 |
| 7e) | methyl ester glucuronide | ~~~≡~~CH$_2$NHC(O)Me | 677 (MH$^+$) | |

TABLE 14-continued

| Compound | R¹² | R⁹ | m/z (ES) | HRMS m/z (ES) |
|---|---|---|---|---|
| 7f) | glucuronide | —CH₂—C≡C—CH₂—NH—C(=O)—CH₃ | 663 (MH⁺) | (MH⁺) Calcd 663.2354 Found 663.2331 |
| 7g) | methyl ester glucuronide | —CH₂—C≡C—CH₂—N(Me)—SO₂—Me | 749 (MNa⁺) | |
| 7h) | glucuronide | —CH₂—C≡C—CH₂—N(Me)—SO₂—Me | 735 (MNa⁺) | (MH⁺) Calcd 713.2180 Found 713.2170 |
| 7i) | methyl ester glucuronide | —CH₂—C≡C—CH₂—NH—SO₂—Ph | 797 (MNa⁺) | |
| 7j) | glucuronide | —CH₂—C≡C—CH₂—NH—SO₂—Ph | 783 (MNa⁺) | (MH⁺) Calcd 761.2180 Found 761.2193 |
| 7k) | methyl ester glucuronide | —CH₂—C≡C—CH₂—NH—C(=O)—N(Me)₂ | 706 (MH⁺) | |
| 7l) | glucuronide | —CH₂—C≡C—CH₂—NH—C(=O)—N(Me)₂ | 692 (MH⁺) | (MH⁺) Calcd 692.2620 Found 692.2618 |
| 7m) | methyl ester glucuronide | —CH₂—C≡C—CH₂—N(Me)₂ | 663 (MH⁺) | |
| 7n) | glucuronide | —CH₂—C≡C—CH₂—N(Me)₂ | 649 (MH⁺) | (MH⁺) Calcd 649.2562 Found 649.2532 |

Example 46

Step A: Preparation of 4-((2S,3R)-3-[(3S)-3-(4-fluorophenyl)-3-hydroxypropyl]-4-oxo-1-{4-[(trimethylsilyl)ethynyl]phenyl}azetidin-2-yl)phenyl methyl β-D-glucopyranosiduronate (8a)

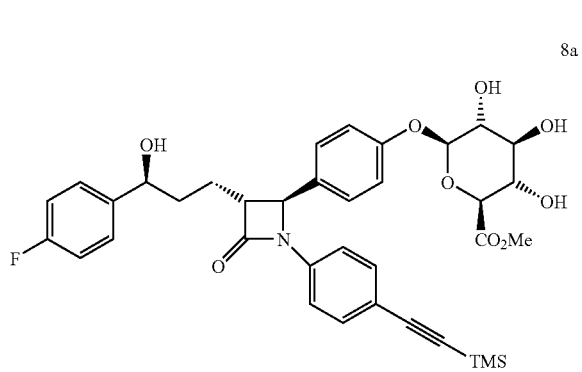

8a

Triethylamine (69.0 μL, 0.495 mmol) was added to a stirred solution of i-7 (50.0 mg, 0.071 mmol), trimethylsilylacetylene (12.0 μL, 0.085 mmol), tetrakistriphenylphosphine palladium(0) (13.0 mg, 0.011 mmol) and copper iodide (5.10 mg, 0.028 mmol) in DMF (0.5 mL) under a nitrogen atmosphere and the resulting solution aged at room temperature for 18 h. The volatiles were evaporated in vacuo and the crude residue purified by flash chromatography on silica gel (gradient elution; 0-25% methanol/methylene chloride as eluent) to afford the title compound (8a); m/z (ES) 660 (M-OH)$^+$, 470.

Step B: Preparation of 4-{(2S,3R)-1-(4-ethynylphenyl)-3-[(3S)-3-(4-fluorophenyl)-3-hydroxypropyl]-4-oxoazetidin-2-yl}phenyl β-D-glucopyranosiduronic acid (8b)

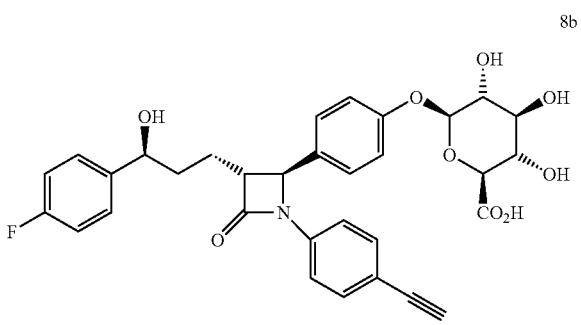

8b

A solution of 8a in methanol/water/triethylamine (0.25 mL:1.10 mL:0.40 mL) was stirred at room temperature for approximately 6 h. The volatiles were evaporated in vacuo and the crude residue purified by preparative reversed phase high performance liquid chromatography on YMC Pack Pro C18 phase (gradient elution; 10-65% acetonitrile/water as eluent, 0.1% TFA modifier) to give the title compound (8b); m/z (ES) 574 (M-OH)$^+$, 398; HRMS (ES) m/z calc'd for $C_{32}H_{31}FNO_9$ (MH$^+$) 592.1983, found 592.1985.

Example 47

Step A: Preparation of 4-[(2S,3R)-3-[(3S)-3-(4-fluorophenyl)-3-hydroxypropyl]-1-(4-{3-[(methylsulfonyl)amino]propyl}phenyl)-4-oxoazetidin-2-yl]phenyl methyl β-D-glucopyranosiduronate (9a)

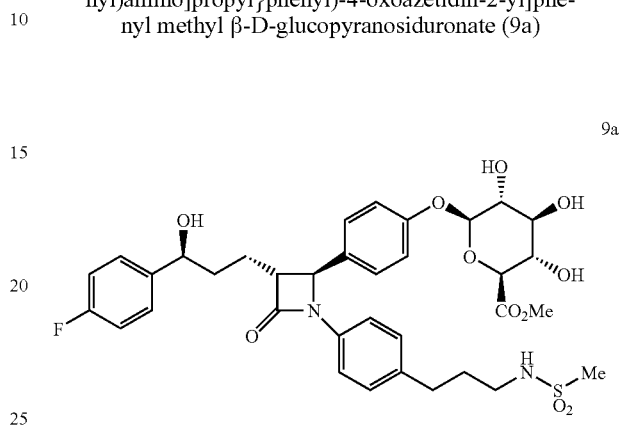

9a

A mixture of 7a (40.0 mg, 0.056 mmol) and palladium (~8 mg of 10 wt. % (dry basis) on activated carbon) in methanol (2 mL) was hydrogenated at atmospheric pressure for approximately 1 h. The reaction mixture was filtered through a short plug of celite, eluting copiously with methanol, and the filtrate evaporated in vacuo to afford the title compound (9a); m/z (ES) 509 (M-sugar-OH)$^+$.

Step B: Preparation of 4-[(2S,3R)-3-[(3S)-3-(4-fluorophenyl)-3-hydroxypropyl]-1-(4-{3-[(methylsulfonyl)amino]propyl}phenyl)-4-oxoazetidin-2-yl]phenyl β-D-glucopyranosiduronic acid (9b)

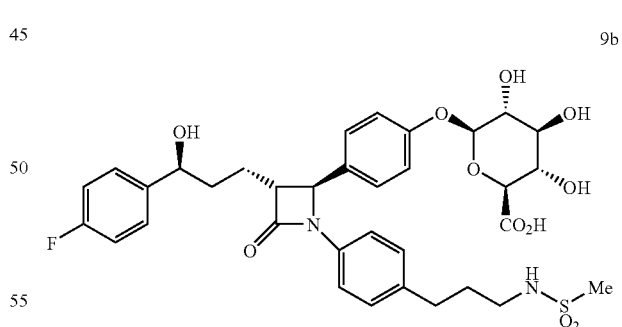

9b

A solution of 9a in methanol/water/triethylamine (1:7:2, 1 mL) was stirred at room temperature for approximately 1 h. The volatiles were evaporated in vacuo and the crude residue purified by preparative reversed phase high performance liquid chromatography on YMC Pack Pro C18 phase (gradient elution; 10-65% acetonitrile/water as eluent, 0.1% TFA modifier) to give the title compound (9b); m/z (ES) 735

(M+Na)⁺, 685 (M-OH)⁺, 509 (M-sugar-OH)⁺; HRMS (ES) m/z calc'd for $C_{34}H_{39}FN_2O_{11}S$ (MH⁺) 703.2337, found 703.2337.

Example 48

Step A: Preparation of 4-{(2S,3R)-3-[(3S)-3-acetoxy)-3-(4-fluorophenyl)propyl]-1-[4-(3-{[tert-butyl(dimethylsilyl]oxy}prop-1-yn-1-yl)phenyl]-4-oxoazetidin-2-yl}phenyl methyl 2,3,4-tri-O-acetyl-β-D-glucopyranosiduronate (10a)

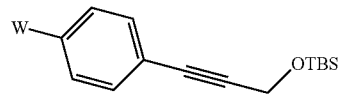

10a

Triethylamine (170 µL, 1.25 mmol) was added to a solution of i-8 (156 mg, 0.178 mmol), tert-butyldimethyl(2-propynyloxy)silane (43.0 µL, 0.214 mmol), dichlorobistriphenylphosphine palladium(II) (12.0 mg, 0.018 mmol) and copper iodide (7.00 mg, 0.036 mmol) in DMF (1.3 mL) under a nitrogen atmosphere and the resulting solution aged at room temperature for approximately 20 h. The reaction mixture was poured into saturated aqueous sodium bicarbonate and extracted twice with diethyl ether. The combined organic extracts were washed with water, brine, dried (MgSO₄), filtered and the filtrate concentrated in vacuo. Purification of the crude residue by flash chromatography on silica gel (gradient elution; 15-40% ethyl acetate/hexanes as eluent) afforded the title compound 10a.

Step B: Preparation of 4-{(2S,3R)-3-[(3S)-3-(acetyloxy)-3-(4-fluorophenyl)propyl]-1-[4-(3-hydroxyprop-1-yn-1-yl)phenyl]-4-oxoazetidin-2-yl}phenyl methyl 2,3,4-tri-O-acetyl-β-D-glucopyranosiduronate (10b)

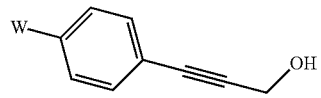

10b

Tetrabutylammonium fluoride hydrate (39.0 mg, 0.148 mmol) was added to 10a (136 mg, 0.148 mmol) in tetrahydrofuran (1.5 mL), and the resulting solution aged at room temperature for 1 h. The reaction mixture was poured into saturated aqueous ammonium chloride and extracted twice with ether. The combined organic extracts were washed with saturated sodium bicarbonate, brine, dried (MgSO₄), filtered and concentrated in vacuo. Purification of the crude residue by flash chromatography on silica gel (50% ethyl acetate/hexanes) afforded the title compound 10b.

Step C: Preparation of 4-{(2S,3R)-3-[(3S)-3-(acetyloxy)-3-(4-fluorophenyl)propyl]-4-oxo-1-[4-(3-oxoprop-1-yn-1-yl)phenyl]azetidin-2-yl}phenyl methyl 2,3,4-tri-O-acetyl-β-D-glucopyranosiduronate (10c)

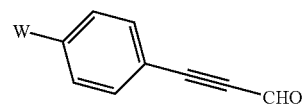

10c

Dess-Martin periodinane (33.0 mg, 0.077 mmol) was added to a solution of 10b (62.0 mg, 0.077 mmol) and pyridine (31.0 µL, 0.386 mmol) in dichloromethane (1 mL) at room temperature. After 30 min, the reaction mixture was poured into saturated aqueous sodium bicarbonate, and extracted twice with ethyl acetate. The combined organic extracts were washed with water, brine, dried (MgSO₄), filtered and concentrated in vacuo. Purification of the crude residue by flash chromatography on silica gel (gradient elution; 20-40% ethyl acetate/hexanes) afforded the title compound 10c.

Step D: Preparation of 4-{(2S,3R)-3-[(3S)-3-(acetyloxy)-3-(4-fluorophenyl)propyl]-1-[4-(carboxyethynyl)phenyl]-4-oxoazetidin-2-yl}phenyl methyl 2,3,4-tri-O-acetyl-β-D-glucopyranosiduronate (10d)

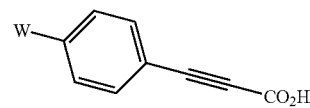

10d

An aqueous solution (0.1 mL) of sodium dihydrogenphosphate (9.00 mg, 0.065 mmol) and sodium chlorite (5.00 mg, 0.055 mmol) was added to a solution of 10c (37.0 mg, 0.046 mmol) in tert-butyl alcohol (0.4 mL), dioxane (0.2 mL) and isobutylene (~0.1 mL) at room temperature. After 1.5 h, the reaction mixture was concentrated in vacuo and the crude residue triturated repeatedly with ethyl acetate. The organic washings were dried (Na₂SO₄), filtered and concentrated in vacuo to afford the title compound 10d.

Step E: Preparation of 4-{(2S,3R)-1-[4-(carboxyethynyl)phenyl]-3-[(3S)-3-(4-fluorophenyl)-3-hydroxypropyl]-4-oxoazetidin-2-yl}phenyl β-D-glucopyranosiduronic acid (10e)

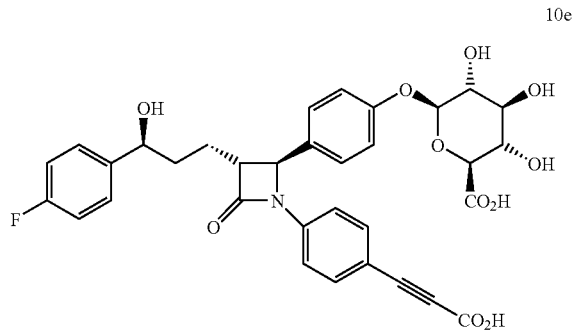

10e

A solution of 4-{(2S,3R)-3-[(3S)-3-(acetyloxy)-3-(4-fluorophenyl)propyl]-1-[4-(carboxyethynyl)phenyl]-4-oxoazetidin-2-yl}phenyl methyl 2,3,4-tri-O-acetyl-β-D-glucopyranosiduronate (10d) and sodium cyanide (~1 mg, 0.020 mmol) in methanol (3 mL) was heated to 45° C. After 22 h, the reaction mixture was concentrated under reduced pressure and dissolved in methanol/water/triethylamine (1:7:2, 1 mL). After stirring at room temperature for approximately 1 h, the volatiles were evaporated in vacuo and the crude residue purified by preparative reversed phase high performance liquid chromatography on YMC Pack Pro C18 phase (gradient elution; 10-60% acetonitrile/water as eluent, 0.1% TFA modifier) to give the title compound (10e), m/z (ES) 442.0 (M-sugar-OH)⁺, 618.0 (M-OH)⁺; HRMS (ES) m/z calcd. for C₃₃H₃₁FNO₁₁ (MH⁺) 636.1881, found 636.1889

Example 49

Step A: Preparation of 4-((2S,3R)-3-[(3S)-3-(acetyloxy)-3-(4-fluorophenyl)propyl]-1-{4-(3-(ethylamino)-3-oxoprop-1-yn-1-yl]phenyl}-4-oxoazetidin-2-yl)phenyl methyl 2,3,4-tri-O-acetyl-β-D-glucopyranosiduronate (11a)

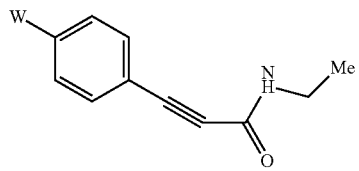

11a

A 1M solution of ethylamine hydrochloride and diisopropylethylamine in DMF (40.0 µL, 0.40 mmol) was added to 4-{(2S,3R)-3-[(3s)-3-(acetyloxy)-3-(4-fluorophenyl)propyl]-1-[4-(carboxyethynyl)phenyl]-4-oxoazetidin-2-yl}phenyl methyl 2,3,4-tri-O-acetyl-β-D-glucopyranosiduronate (10d) (27.0 mg, 0.033 mmol), 1-[3-(dimethylamino)propyl]-3-ethylcarbodiimide hydrochloride (19.0 mg, 0.099 mmol) and 1-hydroxybenzotriazole (8.00 mg, 0.059 mmol) in DMF (0.25 mL). After 4.5 h, the reaction mixture was poured into ethyl acetate and washed successively with water and brine. The organic layer was dried, filtered and concentrated under reduced pressure. Purification of the crude residue by flash chromatography on silica gel (gradient elution; 50-60% ethyl acetate/hexanes) afforded the title compound 11a.

Step B: Preparation of 4-{(2S,3R)-1-{4-[3-(ethylamino)-3-oxoprop-1-yn-1-yl]phenyl}-3-[(3S)-3-(4-fluorophenyl)-3-hydroxypropyl]-4-oxoazetidin-2-yl}phenyl β-D-glucopyranosiduronic acid (11b)

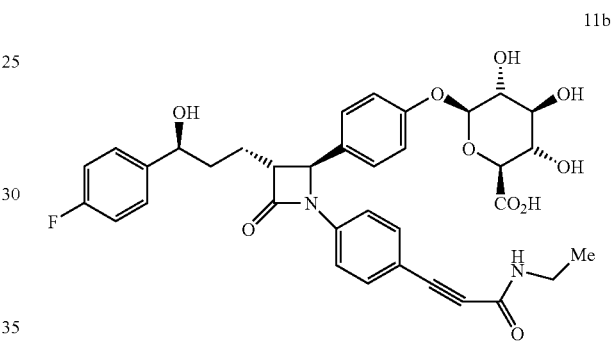

11b

A solution of 4-((2S,3R)-3-[(3S)-3-(acetyloxy)-3-(4-fluorophenyl)propyl]-1-{4-(3-(ethylamino)-3-oxoprop-1-yn-1-yl]phenyl}-4-oxoazetidin-2-yl)phenyl methyl 2,3,4-tri-O-acetyl-β-D-glucopyranosiduronate (11a) (22.0 mg, 0.026 mmol) and sodium cyanide (~1 mg, 0.020 mmol) in methanol (3 mL) was heated to 45° C. After 18 h, the reaction mixture was concentrated under reduced pressure and dissolved in methanol/water/triethylamine (1:3:1, 2.5 mL). After stirring at room temperature for approximately 1 h, the volatiles were evaporated in vacuo, and the crude residue purified by preparative reversed phase high performance liquid chromatography on YMC Pack Pro C18 phase (gradient elution; 10-60% acetonitrile/water as eluent, 0.1% TFA modifier) to give the title compound (11b) m/z (ES) 663.0 (M+H)⁺; HRMS (ES) m/z calcd. for C₃₅H₃₆FN₂O₁₀ (MH⁺) 663.2354, found 663.2341.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, Genbank Accession Numbers and protocols are cited throughout this application, the disclosures of which are incorporated herein by reference in their entireties for all purposes.

The invention claimed is:

1. A method for identifying a ligand of NPC1L1 comprising:
(a) contacting human NPC1L1 with a candidate compound and a detectably labeled substituted 2-azetidinone glucuronide compound selected from the group consisting of compound 1, compound 8

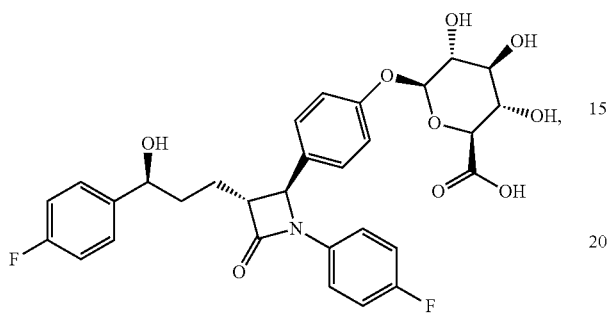

and a compound of Formula IIa

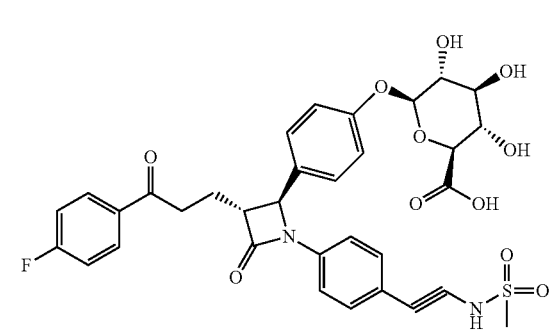

wherein,
R⁹ is selected from the group consisting of —C≡C—CH₂—NR¹⁰R¹¹ wherein R¹¹ is selected from the group consisting of —H, —C₁₋₃alkyl, —C(O)—C₁₋₃alkyl, —C(O)—NR¹⁰R¹⁰, —SO₂—C₁₋₃alkyl and —SO₂-phenyl; —C≡C(O)NR¹⁰—SO₂—C₁₋₃alkyl; —C≡C—C(O)NR¹⁰—SO₂—phenyl; —(CH₂)₃—NR¹⁰—SO₂—phenyl;

R¹⁰ is independently selected at each occurrence from —H and —C₁₋₃alkyl; and

R¹² is selected from

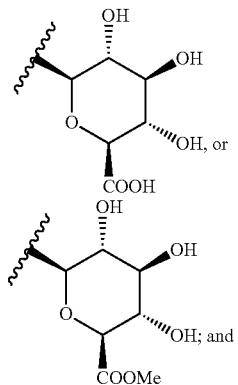

(b) measuring the amount of detectably labeled substituted 2-azetidinone glucuronide compound that is bound to NPC1L1,
wherein binding of said candidate compound to human NPC1L1 decreases binding of said detectably labeled substituted 2-azetidinone glucuronide to human NPC1L1, and indicates that the candidate compound is a ligand of human NPC1L1.

2. The method of claim 1, wherein the substituted 2-azetidinone-glucuronide comprises a detectable label from the group consisting of ³H, ³⁵S and ¹²⁵I.

3. The method of claim 2, wherein the substituted 2-azetidinone-glucuronide is a compound of Formula IIa.

4. The method of claim 3, wherein the substituted 2-azetidinone-glucuronide is a compound of Formula IIa, wherein R⁹ is selected from the group consisting of —C≡C—CH₂—NR¹⁰R¹¹, —C≡C—C(O)NR¹⁰R¹¹, —(CH₂)₃—NR¹⁰—SO₂—C₁₋₃alkyl and —(CH₂)₃—NR¹⁰—SO₂-phenyl, and R¹¹ is selected from —SO₂—C₁₋₃alkyl and —SO₂-phenyl.

5. The method of claim 4, wherein the substituted 2-azetidinone-glucuronide of Formula IIa is labeled with ³⁵S.

6. The method of claim 5 wherein R⁹ is —C≡C—CH₂—NR¹⁰R¹¹.

7. The method of claim 1 wherein the detectably labeled substituted 2-azetidinone glucuronide is ³⁵S-labeled compound 2

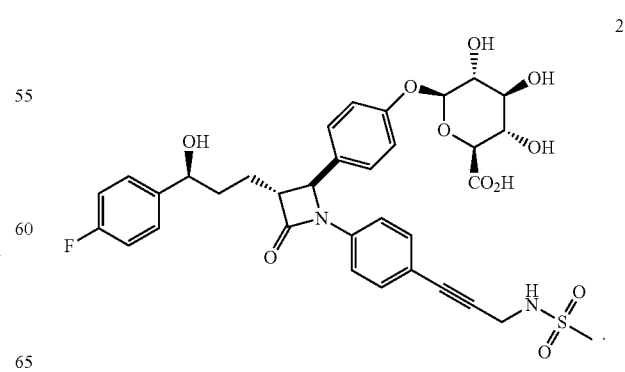

8. The method of claim 1 wherein $R^{12}$ is

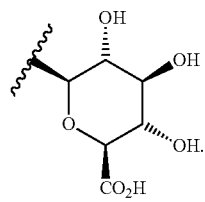

9. The method of claim 1 wherein the detectably labeled substituted 2-azetidinone glucuronide is selected from the group consisting of compound 1, and compound 8.

10. The method of claim 9 wherein the detectably labeled substituted 2-azetidinone glucuronide comprises a detectable label selected from the group consisting of $^3H$ and $^{125}I$.

* * * * *

SEQUENCE LISTING

<160> NUMBER OF SEQ ID NOS: 52

<210> SEQ ID NO 1
<211> LENGTH: 3996
<212> TYPE: DNA
<213> ORGANISM: Rattus sp.
<220> FEATURE:
<221> NAME/KEY: CDS
<222> LOCATION: (1)..(3996)

<400> SEQUENCE: 1

| | | | | | | | | | | | | | | | | |
|---|---|---|---|---|---|---|---|---|---|---|---|---|---|---|---|---|
| atg | gca | gct | gcc | tgg | ctg | gga | tgg | ctg | ctc | tgg | gcc | ctg | ctc | ctg | agc | 48 |
| Met | Ala | Ala | Ala | Trp | Leu | Gly | Trp | Leu | Leu | Trp | Ala | Leu | Leu | Leu | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcg | gcc | cag | ggt | gag | cta | tac | aca | ccc | aaa | cac | gaa | gct | ggg | gtc | tgc | 96 |
| Ala | Ala | Gln | Gly | Glu | Leu | Tyr | Thr | Pro | Lys | His | Glu | Ala | Gly | Val | Cys | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | ttt | tac | gaa | gag | tgc | ggg | aaa | aac | cca | gag | ctc | tct | gga | ggc | ctc | 144 |
| Thr | Phe | Tyr | Glu | Glu | Cys | Gly | Lys | Asn | Pro | Glu | Leu | Ser | Gly | Gly | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| acg | tca | cta | tcc | aat | gta | tcc | tgc | ctg | tct | aac | acc | ccg | gcc | cgc | cac | 192 |
| Thr | Ser | Leu | Ser | Asn | Val | Ser | Cys | Leu | Ser | Asn | Thr | Pro | Ala | Arg | His | |
| | 50 | | | | | 55 | | | | | 60 | | | | | |

| | | | | | | | | | | | | | | | | |
|---|---|---|---|---|---|---|---|---|---|---|---|---|---|---|---|---|
| gtc | acg | ggt | gaa | cac | ctg | gct | ctt | ctc | cag | cgc | atc | tgt | ccc | cgc | ctg | 240 |
| Val | Thr | Gly | Glu | His | Leu | Ala | Leu | Leu | Gln | Arg | Ile | Cys | Pro | Arg | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tac | aac | ggc | ccc | aat | acc | act | ttt | gcc | tgt | tgc | tct | acc | aag | cag | ctg | 288 |
| Tyr | Asn | Gly | Pro | Asn | Thr | Thr | Phe | Ala | Cys | Cys | Ser | Thr | Lys | Gln | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | tcc | tta | gaa | agc | agc | atg | tcc | atc | acc | aag | gcc | ctt | ctc | acg | cgc | 336 |
| Leu | Ser | Leu | Glu | Ser | Ser | Met | Ser | Ile | Thr | Lys | Ala | Leu | Leu | Thr | Arg | |
| | | | | 100 | | | | | 105 | | | | | 110 | | |

| | | | | | | | | | | | | | | | | |
|---|---|---|---|---|---|---|---|---|---|---|---|---|---|---|---|---|
| tgc | ccg | gcc | tgc | tct | gac | aat | ttt | gtg | agc | tta | cac | tgc | cac | aac | act | 384 |
| Cys | Pro | Ala | Cys | Ser | Asp | Asn | Phe | Val | Ser | Leu | His | Cys | His | Asn | Thr | |
| | | | 115 | | | | | 120 | | | | | 125 | | | |

| | | | | | | | | | | | | | | | | |
|---|---|---|---|---|---|---|---|---|---|---|---|---|---|---|---|---|
| tgc | agc | cct | gac | cag | agc | ctc | ttc | atc | aac | gtc | acc | cgg | gtg | gtt | gag | 432 |
| Cys | Ser | Pro | Asp | Gln | Ser | Leu | Phe | Ile | Asn | Val | Thr | Arg | Val | Val | Glu | |
| | | 130 | | | | | 135 | | | | | 140 | | | | |

| | | | | | | | | | | | | | | | | |
|---|---|---|---|---|---|---|---|---|---|---|---|---|---|---|---|---|
| cgg | ggc | gct | gga | gag | cct | cct | gcc | gtg | gtg | gcc | tat | gag | gcc | ttt | tat | 480 |
| Arg | Gly | Ala | Gly | Glu | Pro | Pro | Ala | Val | Val | Ala | Tyr | Glu | Ala | Phe | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cag | cgc | agc | ttt | gct | gag | aag | gcc | tat | gag | tcc | tgc | agc | cag | gtg | cgc | 528 |
| Gln | Arg | Ser | Phe | Ala | Glu | Lys | Ala | Tyr | Glu | Ser | Cys | Ser | Gln | Val | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| atc | cct | gcg | gcc | gct | tcc | ttg | gcc | gtg | ggc | agc | atg | tgt | gga | gtg | tat | 576 |
| Ile | Pro | Ala | Ala | Ala | Ser | Leu | Ala | Val | Gly | Ser | Met | Cys | Gly | Val | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| ggc | tcc | gcc | ctc | tgc | aat | gct | cag | cgc | tgg | ctc | aac | ttc | caa | gga | gac | 624 |
| Gly | Ser | Ala | Leu | Cys | Asn | Ala | Gln | Arg | Trp | Leu | Asn | Phe | Gln | Gly | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| aca | ggg | aat | ggc | ctg | gct | ccg | ctg | gat | atc | acc | ttc | cac | ctc | ttg | gag | 672 |
| Thr | Gly | Asn | Gly | Leu | Ala | Pro | Leu | Asp | Ile | Thr | Phe | His | Leu | Leu | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| cct | ggc | cag | gcc | cta | ccg | gat | ggg | atc | cag | cca | ctg | aat | ggg | aag | atc | 720 |
| Pro | Gly | Gln | Ala | Leu | Pro | Asp | Gly | Ile | Gln | Pro | Leu | Asn | Gly | Lys | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gca | ccc | tgc | aac | gag | tct | cag | ggt | gat | gac | tca | gca | gtc | tgc | tcc | tgc | 768 |
| Ala | Pro | Cys | Asn | Glu | Ser | Gln | Gly | Asp | Asp | Ser | Ala | Val | Cys | Ser | Cys | |
| | | | | 245 | | | | | 250 | | | | | 255 | | |

| | | | | | | | | | | | | | | | | |
|---|---|---|---|---|---|---|---|---|---|---|---|---|---|---|---|---|
| cag | gac | tgt | gcg | gcg | tcc | tgc | cct | gtc | atc | cct | ccg | ccc | gag | gcc | ttg | 816 |

-continued

```
    Gln Asp Cys Ala Ala Ser Cys Pro Val Ile Pro Pro Glu Ala Leu
                260                 265                 270 cgc cct tcc ttc tac atg ggt cgc atg cca ggc tgg ctg gcc ctc atc       864
Arg Pro Ser Phe Tyr Met Gly Arg Met Pro Gly Trp Leu Ala Leu Ile
            275                 280                 285 atc atc ttc act gct gtc ttt gtg ttg ctc tct gca gtc ctt gtg cgt       912
Ile Ile Phe Thr Ala Val Phe Val Leu Leu Ser Ala Val Leu Val Arg
            290                 295                 300 ctc cga gtg gtt tcc aac agg aac aag aac aag gca gaa ggc ccc cag       960
Leu Arg Val Val Ser Asn Arg Asn Lys Asn Lys Ala Glu Gly Pro Gln
305                 310                 315                 320 gaa gcc ccc aaa ctc cct cat aag cac aaa ctc tca ccc cat acc atc      1008
Glu Ala Pro Lys Leu Pro His Lys His Lys Leu Ser Pro His Thr Ile
                325                 330                 335 ctg ggc cgg ttc ttc cag aac tgg ggc aca agg gtg gcc tcg tgg cca      1056
Leu Gly Arg Phe Phe Gln Asn Trp Gly Thr Arg Val Ala Ser Trp Pro
                340                 345                 350 ctc acc gtc tta gca ctg tcc ttc atc gtt gtg ata gcc tta gca gca      1104
Leu Thr Val Leu Ala Leu Ser Phe Ile Val Val Ile Ala Leu Ala Ala
                355                 360                 365 ggc ctg acc ttt att gaa ctc acc aca gac cct gtg gaa ctg tgg tcg      1152
Gly Leu Thr Phe Ile Glu Leu Thr Thr Asp Pro Val Glu Leu Trp Ser
370                 375                 380 gcc ccc aag agc cag gcc cgg aaa gag aag tct ttc cat gat gag cat      1200
Ala Pro Lys Ser Gln Ala Arg Lys Glu Lys Ser Phe His Asp Glu His
385                 390                 395                 400 ttc ggc ccc ttc ttt cga acc aac cag att ttc gtg aca gct cgg aac      1248
Phe Gly Pro Phe Phe Arg Thr Asn Gln Ile Phe Val Thr Ala Arg Asn
                405                 410                 415 agg tcc agc tac aag tac gac tcc cta ctg cta ggg tcc aag aac ttc      1296
Arg Ser Ser Tyr Lys Tyr Asp Ser Leu Leu Leu Gly Ser Lys Asn Phe
                420                 425                 430 agt ggg atc ctg tcc ctg gac ttc ctg ctg gag ctg ctg gag ctt cag      1344
Ser Gly Ile Leu Ser Leu Asp Phe Leu Leu Glu Leu Leu Glu Leu Gln
                435                 440                 445 gag agg ctt cga cac ctg caa gtg tgg tcc cct gag gca gag cgc aac      1392
Glu Arg Leu Arg His Leu Gln Val Trp Ser Pro Glu Ala Glu Arg Asn
450                 455                 460 atc tcc ctc cag gac atc tgc tat gcc ccc ctc aac cca tat aac acc      1440
Ile Ser Leu Gln Asp Ile Cys Tyr Ala Pro Leu Asn Pro Tyr Asn Thr
465                 470                 475                 480 agc ctc tcc gac tgc tgt gtc aac agc ctc ctt cag tac ttc cag aac      1488
Ser Leu Ser Asp Cys Cys Val Asn Ser Leu Leu Gln Tyr Phe Gln Asn
                485                 490                 495 aac cgc acc ctc ctg atg ctc acg gcc aac cag act ctg aat ggc cag      1536
Asn Arg Thr Leu Leu Met Leu Thr Ala Asn Gln Thr Leu Asn Gly Gln
                500                 505                 510 acc tcc ctg gtg gac tgg aag gac cat ttc ctc tac tgt gca aat gcc      1584
Thr Ser Leu Val Asp Trp Lys Asp His Phe Leu Tyr Cys Ala Asn Ala
                515                 520                 525 cct ctc acg ttc aaa gat ggc acg tct ctg gcc ctg agc tgc atg gct      1632
Pro Leu Thr Phe Lys Asp Gly Thr Ser Leu Ala Leu Ser Cys Met Ala
530                 535                 540 gac tac ggg gct cct gtc ttc ccc ttc ctt gct gtt gga gga tac caa      1680
Asp Tyr Gly Ala Pro Val Phe Pro Phe Leu Ala Val Gly Gly Tyr Gln
545                 550                 555                 560 ggc acg gac tat tcc gag gca gaa gcg ctg atc ata acc ttc tct ctc      1728
Gly Thr Asp Tyr Ser Glu Ala Glu Ala Leu Ile Ile Thr Phe Ser Leu
                565                 570                 575 aat aac tac ccc gct gat gat ccc cgc atg gcc cag gcc aag ctc tgg      1776
```

-continued

| | |
|---|---|
| Asn Asn Tyr Pro Ala Asp Asp Pro Arg Met Ala Gln Ala Lys Leu Trp<br>          580                 585                 590 | |
| gag gag gct ttc ttg aag gaa atg gaa tcc ttc cag agg aac aca agt<br>Glu Glu Ala Phe Leu Lys Glu Met Glu Ser Phe Gln Arg Asn Thr Ser<br>        595                 600                 605 | 1824 |
| gac aag ttc cag gtt gcg ttc tca gct gag cgc tct ctg gag gat gag<br>Asp Lys Phe Gln Val Ala Phe Ser Ala Glu Arg Ser Leu Glu Asp Glu<br>610                 615                 620 | 1872 |
| atc aac cgc acc acc atc cag gac ctg cct gtc ttt gcc gtc agc tac<br>Ile Asn Arg Thr Thr Ile Gln Asp Leu Pro Val Phe Ala Val Ser Tyr<br>625                 630                 635                 640 | 1920 |
| att atc gtc ttc ctg tac atc tcc ctg gcc ctg ggc agc tac tcc aga<br>Ile Ile Val Phe Leu Tyr Ile Ser Leu Ala Leu Gly Ser Tyr Ser Arg<br>                645                 650                 655 | 1968 |
| tgc agc cga gta gcg gtg gag tcc aag gct act ctg ggc cta ggt ggg<br>Cys Ser Arg Val Ala Val Glu Ser Lys Ala Thr Leu Gly Leu Gly Gly<br>            660                 665                 670 | 2016 |
| gtg att gtt gtg ctg gga gca gtt ctg gct gcc atg ggc ttc tac tcc<br>Val Ile Val Val Leu Gly Ala Val Leu Ala Ala Met Gly Phe Tyr Ser<br>        675                 680                 685 | 2064 |
| tac ctg ggt gtc ccc tct tct ctg gtt atc atc caa gtg gta cct ttc<br>Tyr Leu Gly Val Pro Ser Ser Leu Val Ile Ile Gln Val Val Pro Phe<br>690                 695                 700 | 2112 |
| ctg gtg cta gct gtg gga gct gac aac atc ttc atc ttt gtt ctt gag<br>Leu Val Leu Ala Val Gly Ala Asp Asn Ile Phe Ile Phe Val Leu Glu<br>705                 710                 715                 720 | 2160 |
| tac cag agg cta cct agg atg cct ggg gaa cag cga gag gct cac att<br>Tyr Gln Arg Leu Pro Arg Met Pro Gly Glu Gln Arg Glu Ala His Ile<br>                725                 730                 735 | 2208 |
| ggc cgc acc ctg ggc agt gtg gcc ccc agc atg ctg ctg tgc agc ctc<br>Gly Arg Thr Leu Gly Ser Val Ala Pro Ser Met Leu Leu Cys Ser Leu<br>            740                 745                 750 | 2256 |
| tct gag gcc atc tgc ttc ttt cta ggg gcc ctg acc ccc atg cca gct<br>Ser Glu Ala Ile Cys Phe Phe Leu Gly Ala Leu Thr Pro Met Pro Ala<br>        755                 760                 765 | 2304 |
| gtg agg acc ttc gcc ttg acc tct ggc tta gca att atc ctc gac ttc<br>Val Arg Thr Phe Ala Leu Thr Ser Gly Leu Ala Ile Ile Leu Asp Phe<br>770                 775                 780 | 2352 |
| ctg ctc cag atg act gcc ttt gtg gcc ctg ctc tcc ctg gat agc aag<br>Leu Leu Gln Met Thr Ala Phe Val Ala Leu Leu Ser Leu Asp Ser Lys<br>785                 790                 795                 800 | 2400 |
| agg cag gag gcc tct cgc ccg gat gtc tta tgc tgc ttt tca acc cgg<br>Arg Gln Glu Ala Ser Arg Pro Asp Val Leu Cys Cys Phe Ser Thr Arg<br>                805                 810                 815 | 2448 |
| aag ctg ccc cca cct aaa gaa aaa gaa ggc ctc tta ctc cgc ttc ttc<br>Lys Leu Pro Pro Pro Lys Glu Lys Glu Gly Leu Leu Leu Arg Phe Phe<br>            820                 825                 830 | 2496 |
| cgc aag ata tac gct cct ttc ctg ctg cac aga ttc atc cgc cct gtt<br>Arg Lys Ile Tyr Ala Pro Phe Leu Leu His Arg Phe Ile Arg Pro Val<br>        835                 840                 845 | 2544 |
| gtg atg ctg ctg ttt ctg acc ctg ttt gga gca aat ctc tac tta atg<br>Val Met Leu Leu Phe Leu Thr Leu Phe Gly Ala Asn Leu Tyr Leu Met<br>850                 855                 860 | 2592 |
| tgc aac atc aac gtg ggg cta gac cag gag ctg gct ctg ccc aag gac<br>Cys Asn Ile Asn Val Gly Leu Asp Gln Glu Leu Ala Leu Pro Lys Asp<br>865                 870                 875                 880 | 2640 |
| tcg tac ttg ata gac tac ttc ctc ttt ctg aac cga tac ctt gaa gtg<br>Ser Tyr Leu Ile Asp Tyr Phe Leu Phe Leu Asn Arg Tyr Leu Glu Val<br>                885                 890                 895 | 2688 |
| ggg cct cca gtg tac ttt gtc acc acc tcg ggc ttc aac ttc tcc agc<br> | 2736 |

-continued

```
            Gly Pro Pro Val Tyr Phe Val Thr Thr Ser Gly Phe Asn Phe Ser Ser
                        900                 905                 910 gag gca ggc atg aac gcc act tgc tct agc gca ggc tgt aag agc ttc       2784
Glu Ala Gly Met Asn Ala Thr Cys Ser Ser Ala Gly Cys Lys Ser Phe
            915                 920                 925 tcc cta acc cag aaa atc cag tat gcc agt gaa ttc cct gac cag tct       2832
Ser Leu Thr Gln Lys Ile Gln Tyr Ala Ser Glu Phe Pro Asp Gln Ser
            930                 935                 940 tac gtg gct att gct gca tcc tcc tgg gta gat gac ttc atc gac tgg       2880
Tyr Val Ala Ile Ala Ala Ser Ser Trp Val Asp Asp Phe Ile Asp Trp
945                 950                 955                 960 ctg acc ccg tcc tcc tcc tgc tgt cgc ctt tat ata cgt ggc ccc cat       2928
Leu Thr Pro Ser Ser Ser Cys Cys Arg Leu Tyr Ile Arg Gly Pro His
                965                 970                 975 aag gat gag ttc tgt ccc tca acg gat act tcc ttc aac tgc tta aaa       2976
Lys Asp Glu Phe Cys Pro Ser Thr Asp Thr Ser Phe Asn Cys Leu Lys
            980                 985                 990 aac tgc atg aac cgc act ctg ggt cct gtg agg ccc aca gcg gaa cag       3024
Asn Cys Met Asn Arg Thr Leu Gly Pro Val Arg Pro Thr Ala Glu Gln
            995                 1000                1005 ttt cat aag tac ctg ccc tgg ttc ctg aat gat ccg ccc aat atc           3069
Phe His Lys Tyr Leu Pro Trp Phe Leu Asn Asp Pro Pro Asn Ile
            1010                1015                1020 aga tgt ccc aaa ggg ggt cta gca gcg tat aga acg tct gtg aat           3114
Arg Cys Pro Lys Gly Gly Leu Ala Ala Tyr Arg Thr Ser Val Asn
            1025                1030                1035 ttg agc tca gat ggc cag gtt ata gcc tcc cag ttc atg gcc tac           3159
Leu Ser Ser Asp Gly Gln Val Ile Ala Ser Gln Phe Met Ala Tyr
            1040                1045                1050 cac aag ccc tta agg aac tca cag gac ttc aca gaa gct ctc cgg           3204
His Lys Pro Leu Arg Asn Ser Gln Asp Phe Thr Glu Ala Leu Arg
            1055                1060                1065 gcg tcc cgg ttg cta gca gcc aac atc aca gct gac cta cgg aag           3249
Ala Ser Arg Leu Leu Ala Ala Asn Ile Thr Ala Asp Leu Arg Lys
            1070                1075                1080 gtg cct ggg aca gat cca aac ttt gag gtc ttc cct tac acg atc           3294
Val Pro Gly Thr Asp Pro Asn Phe Glu Val Phe Pro Tyr Thr Ile
            1085                1090                1095 tcc aac gtg ttc tac cag caa tac ctg acg gtc ctt cct gag gga           3339
Ser Asn Val Phe Tyr Gln Gln Tyr Leu Thr Val Leu Pro Glu Gly
            1100                1105                1110 atc ttc acc ctt gct ctt tgc ttt gtg ccc acc ttt gtt gtc tgc           3384
Ile Phe Thr Leu Ala Leu Cys Phe Val Pro Thr Phe Val Val Cys
            1115                1120                1125 tac ctc cta ctg ggc ctg gac atg tgc tca ggg atc ctc aac cta           3429
Tyr Leu Leu Leu Gly Leu Asp Met Cys Ser Gly Ile Leu Asn Leu
            1130                1135                1140 ctc tcc atc att atg att ctc gtg gac acc att ggc ctc atg gct           3474
Leu Ser Ile Ile Met Ile Leu Val Asp Thr Ile Gly Leu Met Ala
            1145                1150                1155 gtg tgg ggt atc agc tat aat gcg gta tcc ctc atc aac ctt gtc           3519
Val Trp Gly Ile Ser Tyr Asn Ala Val Ser Leu Ile Asn Leu Val
            1160                1165                1170 acg gca gtg ggc atg tct gtg gag ttt gtg tcc cac atc act cgg           3564
Thr Ala Val Gly Met Ser Val Glu Phe Val Ser His Ile Thr Arg
            1175                1180                1185 tcc ttt gct gta agc acc aag cct acc cgg ctg gag agg gct aaa           3609
Ser Phe Ala Val Ser Thr Lys Pro Thr Arg Leu Glu Arg Ala Lys
            1190                1195                1200 gat gct act gtc ttc atg ggc agt gcg gtg ttt gct gga gtg gcc           3654
```

-continued

| | | | | | | | | | | | | | | |
|---|---|---|---|---|---|---|---|---|---|---|---|---|---|---|
| Asp | Ala | Thr | Val | Phe | Met | Gly | Ser | Ala | Val | Phe | Ala | Gly | Val | Ala |
| | 1205 | | | | 1210 | | | | | 1215 | | | | |

```
atg  acc  aac  ttc  cca  ggc  atc  ctc  atc  ttg  ggc  ttt  gcc  caa  gcc       3699
Met  Thr  Asn  Phe  Pro  Gly  Ile  Leu  Ile  Leu  Gly  Phe  Ala  Gln  Ala
     1220                     1225                     1230 cag  ctt  att  cag  atc  ttc  ttc  ttc  cgc  ctc  aac  ctt  ctg  atc  acc       3744
Gln  Leu  Ile  Gln  Ile  Phe  Phe  Phe  Arg  Leu  Asn  Leu  Leu  Ile  Thr
     1235                     1240                     1245 ttg  ctg  ggt  ctg  ctg  cat  ggc  ctg  gtc  ttc  ctg  ccg  gtt  gtc  ctc       3789
Leu  Leu  Gly  Leu  Leu  His  Gly  Leu  Val  Phe  Leu  Pro  Val  Val  Leu
     1250                     1255                     1260 agc  tat  ctg  gga  cca  gat  gtt  aac  caa  gct  ctg  gta  cag  gag  gag       3834
Ser  Tyr  Leu  Gly  Pro  Asp  Val  Asn  Gln  Ala  Leu  Val  Gln  Glu  Glu
     1265                     1270                     1275 aaa  cta  gcc  agc  gag  gca  gca  gtg  gcc  cca  gag  cct  tct  tgc  cca       3879
Lys  Leu  Ala  Ser  Glu  Ala  Ala  Val  Ala  Pro  Glu  Pro  Ser  Cys  Pro
     1280                     1285                     1290 cag  tac  ccc  tcc  cct  gct  gat  gcg  gat  gcc  aat  gtt  aac  tac  ggc       3924
Gln  Tyr  Pro  Ser  Pro  Ala  Asp  Ala  Asp  Ala  Asn  Val  Asn  Tyr  Gly
     1295                     1300                     1305 ttt  gcc  cca  gaa  ctt  gcc  cac  gga  gct  aat  gct  gct  aga  agc  tct       3969
Phe  Ala  Pro  Glu  Leu  Ala  His  Gly  Ala  Asn  Ala  Ala  Arg  Ser  Ser
     1310                     1315                     1320 ttg  ccc  aaa  agt  gac  caa  aag  ttc  taa                                     3996
Leu  Pro  Lys  Ser  Asp  Gln  Lys  Phe
     1325                     1330
```

<210> SEQ ID NO 2
<211> LENGTH: 1331
<212> TYPE: PRT
<213> ORGANISM: Rattus sp.

<400> SEQUENCE: 2

Met Ala Ala Ala Trp Leu Gly Trp Leu Leu Trp Ala Leu Leu Leu Ser
1               5                   10                  15

Ala Ala Gln Gly Glu Leu Tyr Thr Pro Lys His Glu Ala Gly Val Cys
                20                  25                  30

Thr Phe Tyr Glu Glu Cys Gly Lys Asn Pro Glu Leu Ser Gly Gly Leu
            35                  40                  45

Thr Ser Leu Ser Asn Val Ser Cys Leu Ser Asn Thr Pro Ala Arg His
        50                  55                  60

Val Thr Gly Glu His Leu Ala Leu Leu Gln Arg Ile Cys Pro Arg Leu
65                  70                  75                  80

Tyr Asn Gly Pro Asn Thr Thr Phe Ala Cys Cys Ser Thr Lys Gln Leu
                85                  90                  95

Leu Ser Leu Glu Ser Ser Met Ser Ile Thr Lys Ala Leu Leu Thr Arg
            100                 105                 110

Cys Pro Ala Cys Ser Asp Asn Phe Val Ser Leu His Cys His Asn Thr
        115                 120                 125

Cys Ser Pro Asp Gln Ser Leu Phe Ile Asn Val Thr Arg Val Val Glu
    130                 135                 140

Arg Gly Ala Gly Glu Pro Pro Ala Val Val Ala Tyr Glu Ala Phe Tyr
145                 150                 155                 160

Gln Arg Ser Phe Ala Glu Lys Tyr Glu Ser Cys Ser Gln Val Arg
                165                 170                 175

Ile Pro Ala Ala Ala Ser Leu Ala Val Gly Ser Met Cys Gly Val Tyr
            180                 185                 190

Gly Ser Ala Leu Cys Asn Ala Gln Arg Trp Leu Asn Phe Gln Gly Asp

```
                195                 200                 205
Thr Gly Asn Gly Leu Ala Pro Leu Asp Ile Thr Phe His Leu Leu Glu
    210                 215                 220

Pro Gly Gln Ala Leu Pro Asp Gly Ile Gln Pro Leu Asn Gly Lys Ile
225                 230                 235                 240

Ala Pro Cys Asn Glu Ser Gln Gly Asp Asp Ser Ala Val Cys Ser Cys
                245                 250                 255

Gln Asp Cys Ala Ala Ser Cys Pro Val Ile Pro Pro Glu Ala Leu
            260                 265                 270

Arg Pro Ser Phe Tyr Met Gly Arg Met Pro Gly Trp Leu Ala Leu Ile
        275                 280                 285

Ile Ile Phe Thr Ala Val Phe Val Leu Leu Ser Ala Val Leu Val Arg
    290                 295                 300

Leu Arg Val Val Ser Asn Arg Asn Lys Asn Lys Ala Glu Gly Pro Gln
305                 310                 315                 320

Glu Ala Pro Lys Leu Pro His Lys His Lys Leu Ser Pro His Thr Ile
                325                 330                 335

Leu Gly Arg Phe Phe Gln Asn Trp Gly Thr Arg Val Ala Ser Trp Pro
            340                 345                 350

Leu Thr Val Leu Ala Leu Ser Phe Ile Val Val Ile Ala Leu Ala Ala
        355                 360                 365

Gly Leu Thr Phe Ile Glu Leu Thr Thr Asp Pro Val Glu Leu Trp Ser
    370                 375                 380

Ala Pro Lys Ser Gln Ala Arg Lys Glu Lys Ser Phe His Asp Glu His
385                 390                 395                 400

Phe Gly Pro Phe Phe Arg Thr Asn Gln Ile Phe Val Thr Ala Arg Asn
                405                 410                 415

Arg Ser Ser Tyr Lys Tyr Asp Ser Leu Leu Leu Gly Ser Lys Asn Phe
            420                 425                 430

Ser Gly Ile Leu Ser Leu Asp Phe Leu Leu Glu Leu Leu Glu Leu Gln
        435                 440                 445

Glu Arg Leu Arg His Leu Gln Val Trp Ser Pro Glu Ala Glu Arg Asn
    450                 455                 460

Ile Ser Leu Gln Asp Ile Cys Tyr Ala Pro Leu Asn Pro Tyr Asn Thr
465                 470                 475                 480

Ser Leu Ser Asp Cys Cys Val Asn Ser Leu Leu Gln Tyr Phe Gln Asn
                485                 490                 495

Asn Arg Thr Leu Leu Met Leu Thr Ala Asn Gln Thr Leu Asn Gly Gln
            500                 505                 510

Thr Ser Leu Val Asp Trp Lys Asp His Phe Leu Tyr Cys Ala Asn Ala
        515                 520                 525

Pro Leu Thr Phe Lys Asp Gly Thr Ser Leu Ala Leu Ser Cys Met Ala
    530                 535                 540

Asp Tyr Gly Ala Pro Val Phe Pro Phe Leu Ala Val Gly Gly Tyr Gln
545                 550                 555                 560

Gly Thr Asp Tyr Ser Glu Ala Glu Ala Leu Ile Ile Thr Phe Ser Leu
                565                 570                 575

Asn Asn Tyr Pro Ala Asp Asp Pro Arg Met Ala Gln Ala Lys Leu Trp
            580                 585                 590

Glu Glu Ala Phe Leu Lys Glu Met Glu Ser Phe Gln Arg Asn Thr Ser
        595                 600                 605

Asp Lys Phe Gln Val Ala Phe Ser Ala Glu Arg Ser Leu Glu Asp Glu
    610                 615                 620
```

-continued

Ile Asn Arg Thr Thr Ile Gln Asp Leu Pro Val Phe Ala Val Ser Tyr
625                 630                 635                 640

Ile Ile Val Phe Leu Tyr Ile Ser Leu Ala Leu Gly Ser Tyr Ser Arg
            645                 650                 655

Cys Ser Arg Val Ala Val Glu Ser Lys Ala Thr Leu Gly Leu Gly Gly
        660                 665                 670

Val Ile Val Val Leu Gly Ala Val Leu Ala Ala Met Gly Phe Tyr Ser
    675                 680                 685

Tyr Leu Gly Val Pro Ser Ser Leu Val Ile Gln Val Val Pro Phe
690                 695                 700

Leu Val Leu Ala Val Gly Ala Asp Asn Ile Phe Ile Phe Val Leu Glu
705                 710                 715                 720

Tyr Gln Arg Leu Pro Arg Met Pro Gly Glu Gln Arg Glu Ala His Ile
                725                 730                 735

Gly Arg Thr Leu Gly Ser Val Ala Pro Ser Met Leu Leu Cys Ser Leu
            740                 745                 750

Ser Glu Ala Ile Cys Phe Phe Leu Gly Ala Leu Thr Pro Met Pro Ala
        755                 760                 765

Val Arg Thr Phe Ala Leu Thr Ser Gly Leu Ala Ile Ile Leu Asp Phe
    770                 775                 780

Leu Leu Gln Met Thr Ala Phe Val Ala Leu Leu Ser Leu Asp Ser Lys
785                 790                 795                 800

Arg Gln Glu Ala Ser Arg Pro Asp Val Leu Cys Cys Phe Ser Thr Arg
                805                 810                 815

Lys Leu Pro Pro Pro Lys Glu Lys Glu Gly Leu Leu Leu Arg Phe Phe
            820                 825                 830

Arg Lys Ile Tyr Ala Pro Phe Leu Leu His Arg Phe Ile Arg Pro Val
        835                 840                 845

Val Met Leu Leu Phe Leu Thr Leu Phe Gly Ala Asn Leu Tyr Leu Met
    850                 855                 860

Cys Asn Ile Asn Val Gly Leu Asp Gln Glu Leu Ala Leu Pro Lys Asp
865                 870                 875                 880

Ser Tyr Leu Ile Asp Tyr Phe Leu Phe Leu Asn Arg Tyr Leu Glu Val
                885                 890                 895

Gly Pro Pro Val Tyr Phe Val Thr Thr Ser Gly Phe Asn Phe Ser Ser
            900                 905                 910

Glu Ala Gly Met Asn Ala Thr Cys Ser Ser Ala Gly Cys Lys Ser Phe
        915                 920                 925

Ser Leu Thr Gln Lys Ile Gln Tyr Ala Ser Glu Phe Pro Asp Gln Ser
    930                 935                 940

Tyr Val Ala Ile Ala Ala Ser Ser Trp Val Asp Asp Phe Ile Asp Trp
945                 950                 955                 960

Leu Thr Pro Ser Ser Ser Cys Cys Arg Leu Tyr Ile Arg Gly Pro His
                965                 970                 975

Lys Asp Glu Phe Cys Pro Ser Thr Thr Ser Phe Asn Cys Leu Lys
            980                 985                 990

Asn Cys Met Asn Arg Thr Leu Gly Pro Val Arg Pro Thr Ala Glu Gln
        995                 1000                1005

Phe His Lys Tyr Leu Pro Trp Phe Leu Asn Asp Pro Pro Asn Ile
    1010                1015                1020

Arg Cys Pro Lys Gly Gly Leu Ala Ala Tyr Arg Thr Ser Val Asn
    1025                1030                1035

Leu Ser Ser Asp Gly Gln Val Ile Ala Ser Gln Phe Met Ala Tyr
    1040                1045                1050

| | | | | | | | | | | | |
|---|---|---|---|---|---|---|---|---|---|---|---|
|His|Lys|Pro|Leu|Arg|Asn|Ser|Gln|Asp|Phe|Thr|Glu Ala Leu Arg|
|1055| | | |1060| | | |1065| | | |

Ala Ser Arg Leu Leu Ala Ala Asn Ile Thr Ala Asp Leu Arg Lys
1070            1075            1080

Val Pro Gly Thr Asp Pro Asn Phe Glu Val Phe Pro Tyr Thr Ile
1085            1090            1095

Ser Asn Val Phe Tyr Gln Gln Tyr Leu Thr Val Leu Pro Glu Gly
1100            1105            1110

Ile Phe Thr Leu Ala Leu Cys Phe Val Pro Thr Phe Val Val Cys
1115            1120            1125

Tyr Leu Leu Leu Gly Leu Asp Met Cys Ser Gly Ile Leu Asn Leu
1130            1135            1140

Leu Ser Ile Ile Met Ile Leu Val Asp Thr Ile Gly Leu Met Ala
1145            1150            1155

Val Trp Gly Ile Ser Tyr Asn Ala Val Ser Leu Ile Asn Leu Val
1160            1165            1170

Thr Ala Val Gly Met Ser Val Glu Phe Val Ser His Ile Thr Arg
1175            1180            1185

Ser Phe Ala Val Ser Thr Lys Pro Thr Arg Leu Glu Arg Ala Lys
1190            1195            1200

Asp Ala Thr Val Phe Met Gly Ser Ala Val Phe Ala Gly Val Ala
1205            1210            1215

Met Thr Asn Phe Pro Gly Ile Leu Ile Leu Gly Phe Ala Gln Ala
1220            1225            1230

Gln Leu Ile Gln Ile Phe Phe Phe Arg Leu Asn Leu Leu Ile Thr
1235            1240            1245

Leu Leu Gly Leu Leu His Gly Leu Val Phe Leu Pro Val Val Leu
1250            1255            1260

Ser Tyr Leu Gly Pro Asp Val Asn Gln Ala Leu Val Gln Glu Glu
1265            1270            1275

Lys Leu Ala Ser Glu Ala Ala Val Ala Pro Glu Pro Ser Cys Pro
1280            1285            1290

Gln Tyr Pro Ser Pro Ala Asp Ala Asp Ala Asn Val Asn Tyr Gly
1295            1300            1305

Phe Ala Pro Glu Leu Ala His Gly Ala Asn Ala Ala Arg Ser Ser
1310            1315            1320

Leu Pro Lys Ser Asp Gln Lys Phe
1325            1330

```
<210> SEQ ID NO 3
<211> LENGTH: 3999
<212> TYPE: DNA
<213> ORGANISM: Homo sapiens
<220> FEATURE:
<221> NAME/KEY: CDS
<222> LOCATION: (1)..(3999)

<400> SEQUENCE: 3
``` atg gcg gag gcc ggc ctg agg ggc tgg ctg ctg tgg gcc ctg ctc ctg    48
Met Ala Glu Ala Gly Leu Arg Gly Trp Leu Leu Trp Ala Leu Leu Leu
1               5                   10                  15 cgc ttg gcc cag agt gag cct tac aca acc atc cac cag cct ggc tac    96
Arg Leu Ala Gln Ser Glu Pro Tyr Thr Thr Ile His Gln Pro Gly Tyr
            20                  25                  30 tgc gcc ttc tat gac gaa tgt ggg aag aac cca gag ctg tct gga agc   144
Cys Ala Phe Tyr Asp Glu Cys Gly Lys Asn Pro Glu Leu Ser Gly Ser
        35                  40                  45

| | | |
|---|---|---|
| ctc atg aca ctc tcc aac gtg tcc tgc ctg tcc aac acg ccg gcc cgc<br>Leu Met Thr Leu Ser Asn Val Ser Cys Leu Ser Asn Thr Pro Ala Arg<br>50                         55                    60 | | 192 |
| aag atc aca ggt gat cac ctg atc cta tta cag aag atc tgc ccc cgc<br>Lys Ile Thr Gly Asp His Leu Ile Leu Leu Gln Lys Ile Cys Pro Arg<br>65                         70                    75                    80 | | 240 |
| ctc tac acc ggc ccc aac acc caa gcc tgc tgc tcc gcc aag cag ctg<br>Leu Tyr Thr Gly Pro Asn Thr Gln Ala Cys Cys Ser Ala Lys Gln Leu<br>                       85                    90                    95 | | 288 |
| gta tca ctg gaa gcg agt ctg tcg atc acc aag gcc ctc ctc acc cgc<br>Val Ser Leu Glu Ala Ser Leu Ser Ile Thr Lys Ala Leu Leu Thr Arg<br>             100                        105                    110 | | 336 |
| tgc cca gcc tgc tct gac aat ttt gtg aac ctg cac tgc cac aac acg<br>Cys Pro Ala Cys Ser Asp Asn Phe Val Asn Leu His Cys His Asn Thr<br>             115                        120                    125 | | 384 |
| tgc agc ccc aat cag agc ctc ttc atc aat gtg acc cgc gtg gcc cag<br>Cys Ser Pro Asn Gln Ser Leu Phe Ile Asn Val Thr Arg Val Ala Gln<br>130                        135                    140 | | 432 |
| cta ggg gct gga caa ctc cca gct gtg gtg gcc tat gag gcc ttc tac<br>Leu Gly Ala Gly Gln Leu Pro Ala Val Val Ala Tyr Glu Ala Phe Tyr<br>145                       150                    155                    160 | | 480 |
| cag cat agc ttt gcc gag cag agc tat gac tcc tgc agc cgt gtg cgc<br>Gln His Ser Phe Ala Glu Gln Ser Tyr Asp Ser Cys Ser Arg Val Arg<br>                       165                    170                    175 | | 528 |
| gtc cct gca gct gcc acg ctg gct gtg ggc acc atg tgt ggc gtg tat<br>Val Pro Ala Ala Ala Thr Leu Ala Val Gly Thr Met Cys Gly Val Tyr<br>                  180                        185                    190 | | 576 |
| ggc tct gcc ctt tgc aat gcc cag cgc tgg ctc aac ttc cag gga gac<br>Gly Ser Ala Leu Cys Asn Ala Gln Arg Trp Leu Asn Phe Gln Gly Asp<br>                       195                    200                    205 | | 624 |
| aca ggc aat ggt ctg gcc cca ctg gac atc acc ttc cac ctc ttg gag<br>Thr Gly Asn Gly Leu Ala Pro Leu Asp Ile Thr Phe His Leu Leu Glu<br>210                        215                    220 | | 672 |
| cct ggc cag gcc gtg ggg agt ggg att cag cct ctg aat gag ggg gtt<br>Pro Gly Gln Ala Val Gly Ser Gly Ile Gln Pro Leu Asn Glu Gly Val<br>225                       230                    235                    240 | | 720 |
| gca cgt tgc aat gag tcc caa ggt gac gac gtg gcg acc tgc tcc tgc<br>Ala Arg Cys Asn Glu Ser Gln Gly Asp Asp Val Ala Thr Cys Ser Cys<br>                       245                    250                    255 | | 768 |
| caa gac tgt gct gca tcc tgt cct gcc ata gcc cgc ccc cag gcc ctc<br>Gln Asp Cys Ala Ala Ser Cys Pro Ala Ile Ala Arg Pro Gln Ala Leu<br>                  260                        265                    270 | | 816 |
| gac tcc acc ttc tac ctg ggc cag atg ccg ggc agt ctg gtc ctc atc<br>Asp Ser Thr Phe Tyr Leu Gly Gln Met Pro Gly Ser Leu Val Leu Ile<br>                     275                    280                    285 | | 864 |
| atc atc ctc tgc tct gtc ttc gct gtg gtc acc atc ctg ctt gtg gga<br>Ile Ile Leu Cys Ser Val Phe Ala Val Val Thr Ile Leu Leu Val Gly<br>290                        295                    300 | | 912 |
| ttc cgt gtg gcc ccc gcc agg gac aaa agc aag atg gtg gac ccc aag<br>Phe Arg Val Ala Pro Ala Arg Asp Lys Ser Lys Met Val Asp Pro Lys<br>305                       310                    315                    320 | | 960 |
| aag ggc acc agc ctc tct gac aag ctc agc ttc tcc acc cac acc ctc<br>Lys Gly Thr Ser Leu Ser Asp Lys Leu Ser Phe Ser Thr His Thr Leu<br>                     325                    330                    335 | | 1008 |
| ctt ggc cag ttc ttc cag ggc tgg ggc acg tgg gtg gct tcg tgg cct<br>Leu Gly Gln Phe Phe Gln Gly Trp Gly Thr Trp Val Ala Ser Trp Pro<br>                     340                    345                    350 | | 1056 |
| ctg acc atc ttg gtg cta tct gtc atc ccg gtg gtg gcc ttg gca gcg<br>Leu Thr Ile Leu Val Leu Ser Val Ile Pro Val Val Ala Leu Ala Ala<br>                  355                        360                    365 | | 1104 |

```
ggc ctg gtc ttt aca gaa ctc act acg gac ccc gtg gag ctg tgg tcg      1152
Gly Leu Val Phe Thr Glu Leu Thr Thr Asp Pro Val Glu Leu Trp Ser
370                 375                 380 gcc ccc aac agc caa gcc cgg agt gag aaa gct ttc cat gac cag cat      1200
Ala Pro Asn Ser Gln Ala Arg Ser Glu Lys Ala Phe His Asp Gln His
385                 390                 395                 400 ttc ggc ccc ttc ttc cga acc aac cag gtg atc ctg acg gct cct aac      1248
Phe Gly Pro Phe Phe Arg Thr Asn Gln Val Ile Leu Thr Ala Pro Asn
                405                 410                 415 cgg tcc agc tac agg tat gac tct ctg ctg ctg ggg ccc aag aac ttc      1296
Arg Ser Ser Tyr Arg Tyr Asp Ser Leu Leu Leu Gly Pro Lys Asn Phe
        420                 425                 430 agc gga atc ctg gac ctg gac ttg ctg ctg gag ctg cta gag ctg cag      1344
Ser Gly Ile Leu Asp Leu Asp Leu Leu Leu Glu Leu Leu Glu Leu Gln
    435                 440                 445 gag agg ctg cgg cac ctc cag gta tgg tcg ccc gaa gca cag cgc aac      1392
Glu Arg Leu Arg His Leu Gln Val Trp Ser Pro Glu Ala Gln Arg Asn
450                 455                 460 atc tcc ctg cag gac atc tgc tac gcc ccc ctc aat ccg gac aat acc      1440
Ile Ser Leu Gln Asp Ile Cys Tyr Ala Pro Leu Asn Pro Asp Asn Thr
465                 470                 475                 480 agt ctc tac gac tgc tgc atc aac agc ctc ctg cag tat ttc cag aac      1488
Ser Leu Tyr Asp Cys Cys Ile Asn Ser Leu Leu Gln Tyr Phe Gln Asn
                485                 490                 495 aac cgc acg ctc ctg ctc cta gcc aac cag aca ctg atg ggg cag      1536
Asn Arg Thr Leu Leu Leu Leu Thr Ala Asn Gln Thr Leu Met Gly Gln
                500                 505                 510 acc tcc caa gtc gac tgg aag gac cat ttt ctg tac tgt gcc aat gcc      1584
Thr Ser Gln Val Asp Trp Lys Asp His Phe Leu Tyr Cys Ala Asn Ala
        515                 520                 525 ccg ctc acc ttc aag gat ggc aca gcc ctg gcc ctg agc tgc atg gct      1632
Pro Leu Thr Phe Lys Asp Gly Thr Ala Leu Ala Leu Ser Cys Met Ala
    530                 535                 540 gac tac ggg gcc cct gtc ttc ccc ttc ctt gcc att ggg ggg tac aaa      1680
Asp Tyr Gly Ala Pro Val Phe Pro Phe Leu Ala Ile Gly Gly Tyr Lys
545                 550                 555                 560 gga aag gac tat tct gag gca gag gcc ctg atc atg acg ttc tcc ctc      1728
Gly Lys Asp Tyr Ser Glu Ala Glu Ala Leu Ile Met Thr Phe Ser Leu
                565                 570                 575 aac aat tac cct gcc ggg gac ccc cgt ctg gcc cag gcc aag ctg tgg      1776
Asn Asn Tyr Pro Ala Gly Asp Pro Arg Leu Ala Gln Ala Lys Leu Trp
                580                 585                 590 gag gag gcc ttc tta gag gaa atg cga gcc ttc cag cgt cgg atg gct      1824
Glu Glu Ala Phe Leu Glu Glu Met Arg Ala Phe Gln Arg Arg Met Ala
        595                 600                 605 ggc atg ttc cag gtc acg ttc acg gct gag cgc tct ctg gaa gac gag      1872
Gly Met Phe Gln Val Thr Phe Thr Ala Glu Arg Ser Leu Glu Asp Glu
    610                 615                 620 atc aat cgc acc aca gct gaa gac ctg ccc atc ttt gcc acc agc tac      1920
Ile Asn Arg Thr Thr Ala Glu Asp Leu Pro Ile Phe Ala Thr Ser Tyr
625                 630                 635                 640 att gtc ata ttc ctg tac atc tct ctg gcc ctg ggc agc tat tcc agc      1968
Ile Val Ile Phe Leu Tyr Ile Ser Leu Ala Leu Gly Ser Tyr Ser Ser
                645                 650                 655 tgg agc cga gtg atg gtg gac tcc aag gcc acg ctg ggc ctg ggc ggg      2016
Trp Ser Arg Val Met Val Asp Ser Lys Ala Thr Leu Gly Leu Gly Gly
                660                 665                 670 gtg gcc gtg gtc ctg gga gca gtc atg gct gcc atg ggc ttc ttc tcc      2064
Val Ala Val Val Leu Gly Ala Val Met Ala Ala Met Gly Phe Phe Ser
        675                 680                 685
```

-continued

| | | | | | | | | | | | | | | | |
|---|---|---|---|---|---|---|---|---|---|---|---|---|---|---|---|
| tac | ttg | ggt | atc | cgc | tcc | tcc | ctg | gtc | atc | ctg | caa | gtg | gtt | cct | ttc | 2112 |
| Tyr | Leu | Gly | Ile | Arg | Ser | Ser | Leu | Val | Ile | Leu | Gln | Val | Val | Pro | Phe | |
| | 690 | | | | 695 | | | | 700 | | | | | | | |

| ctg | gtg | ctg | tcc | gtg | ggg | gct | gat | aac | atc | ttc | atc | ttt | gtt | ctc | gag | 2160 |
| Leu | Val | Leu | Ser | Val | Gly | Ala | Asp | Asn | Ile | Phe | Ile | Phe | Val | Leu | Glu | |
| 705 | | | | 710 | | | | 715 | | | | | 720 | | | |

| tac | cag | agg | ctg | ccc | cgg | agg | cct | ggg | gag | cca | cga | gag | gtc | cac | att | 2208 |
| Tyr | Gln | Arg | Leu | Pro | Arg | Arg | Pro | Gly | Glu | Pro | Arg | Glu | Val | His | Ile | |
| | | | | 725 | | | | 730 | | | | | 735 | | | |

| ggg | cga | gcc | cta | ggc | agg | gtg | gct | ccc | agc | atg | ctg | ttg | tgc | agc | ctc | 2256 |
| Gly | Arg | Ala | Leu | Gly | Arg | Val | Ala | Pro | Ser | Met | Leu | Leu | Cys | Ser | Leu | |
| | | | 740 | | | | 745 | | | | 750 | | | | | |

| tct | gag | gcc | atc | tgc | ttc | ttc | cta | ggg | gcc | ctg | acc | ccc | atg | cca | gct | 2304 |
| Ser | Glu | Ala | Ile | Cys | Phe | Phe | Leu | Gly | Ala | Leu | Thr | Pro | Met | Pro | Ala | |
| | | 755 | | | | 760 | | | | 765 | | | | | | |

| gtg | cgg | acc | ttt | gcc | ctg | acc | tct | ggc | ctt | gca | gtg | atc | ctt | gac | ttc | 2352 |
| Val | Arg | Thr | Phe | Ala | Leu | Thr | Ser | Gly | Leu | Ala | Val | Ile | Leu | Asp | Phe | |
| | 770 | | | | 775 | | | | 780 | | | | | | | |

| ctc | ctg | cag | atg | tca | gcc | ttt | gtg | gcc | ctg | ctc | tcc | ctg | gac | agc | aag | 2400 |
| Leu | Leu | Gln | Met | Ser | Ala | Phe | Val | Ala | Leu | Leu | Ser | Leu | Asp | Ser | Lys | |
| 785 | | | | 790 | | | | 795 | | | | 800 | | | | |

| agg | cag | gag | gcc | tcc | cgg | ttg | gac | gtc | tgc | tgc | tgt | gtc | aag | ccc | cag | 2448 |
| Arg | Gln | Glu | Ala | Ser | Arg | Leu | Asp | Val | Cys | Cys | Cys | Val | Lys | Pro | Gln | |
| | | | | 805 | | | | 810 | | | | | 815 | | | |

| gag | ctg | ccc | ccg | cct | ggc | cag | gga | gag | ggg | ctc | ctg | ctt | ggc | ttc | ttc | 2496 |
| Glu | Leu | Pro | Pro | Pro | Gly | Gln | Gly | Glu | Gly | Leu | Leu | Leu | Gly | Phe | Phe | |
| | | | 820 | | | | 825 | | | | 830 | | | | | |

| caa | aag | gct | tat | gcc | ccc | ttc | ctg | ctg | cac | tgg | atc | act | cga | ggt | gtt | 2544 |
| Gln | Lys | Ala | Tyr | Ala | Pro | Phe | Leu | Leu | His | Trp | Ile | Thr | Arg | Gly | Val | |
| | | 835 | | | | 840 | | | | 845 | | | | | | |

| gtg | ctg | ctg | ctg | ttt | ctc | gcc | ctg | ttc | gga | gtg | agc | ctc | tac | tcc | atg | 2592 |
| Val | Leu | Leu | Leu | Phe | Leu | Ala | Leu | Phe | Gly | Val | Ser | Leu | Tyr | Ser | Met | |
| | 850 | | | | 855 | | | | 860 | | | | | | | |

| tgc | cac | atc | agc | gtg | gga | ctg | gac | cag | gag | ctg | gcc | ctg | ccc | aag | gac | 2640 |
| Cys | His | Ile | Ser | Val | Gly | Leu | Asp | Gln | Glu | Leu | Ala | Leu | Pro | Lys | Asp | |
| 865 | | | | 870 | | | | 875 | | | | 880 | | | | |

| tcg | tac | ctg | ctt | gac | tat | ttc | ctc | ttt | ctg | aac | cgc | tac | ttc | gag | gtg | 2688 |
| Ser | Tyr | Leu | Leu | Asp | Tyr | Phe | Leu | Phe | Leu | Asn | Arg | Tyr | Phe | Glu | Val | |
| | | | 885 | | | | 890 | | | | 895 | | | | | |

| ggg | gcc | ccg | gtg | tac | ttt | gtt | acc | acc | ttg | ggc | tac | aac | ttc | tcc | agc | 2736 |
| Gly | Ala | Pro | Val | Tyr | Phe | Val | Thr | Thr | Leu | Gly | Tyr | Asn | Phe | Ser | Ser | |
| | | 900 | | | | 905 | | | | 910 | | | | | | |

| gag | gct | ggg | atg | aat | gcc | atc | tgc | tcc | agt | gca | ggc | tgc | aac | aac | ttc | 2784 |
| Glu | Ala | Gly | Met | Asn | Ala | Ile | Cys | Ser | Ser | Ala | Gly | Cys | Asn | Asn | Phe | |
| | 915 | | | | 920 | | | | 925 | | | | | | | |

| tcc | ttc | acc | cag | aag | atc | cag | tat | gcc | aca | gag | ttc | cct | gag | cag | tct | 2832 |
| Ser | Phe | Thr | Gln | Lys | Ile | Gln | Tyr | Ala | Thr | Glu | Phe | Pro | Glu | Gln | Ser | |
| | 930 | | | | 935 | | | | 940 | | | | | | | |

| tac | ctg | gcc | atc | cct | gcc | tcc | tcc | tgg | gtg | gat | gac | ttc | att | gac | tgg | 2880 |
| Tyr | Leu | Ala | Ile | Pro | Ala | Ser | Ser | Trp | Val | Asp | Asp | Phe | Ile | Asp | Trp | |
| 945 | | | | 950 | | | | 955 | | | | 960 | | | | |

| ctg | acc | ccg | tcc | tcc | tgc | tgc | cgc | ctt | tat | ata | tct | ggc | ccc | aat | aag | 2928 |
| Leu | Thr | Pro | Ser | Ser | Cys | Cys | Arg | Leu | Tyr | Ile | Ser | Gly | Pro | Asn | Lys | |
| | | | | 965 | | | | 970 | | | | 975 | | | | |

| gac | aag | ttc | tgc | ccc | tcg | acc | gtc | aac | tct | ctg | aac | tgc | cta | aag | aac | 2976 |
| Asp | Lys | Phe | Cys | Pro | Ser | Thr | Val | Asn | Ser | Leu | Asn | Cys | Leu | Lys | Asn | |
| | | | 980 | | | | 985 | | | | 990 | | | | | |

| tgc | atg | agc | atc | acg | atg | ggc | tct | | gtg | agg | ccc | tcg | gtg | gag | cag | ttc | 3024 |
| Cys | Met | Ser | Ile | Thr | Met | Gly | Ser | | Val | Arg | Pro | Ser | Val | Glu | Gln | Phe |
| | 995 | | | | | 1000 | | | | | 1005 | | | | | |

```
cat aag tat ctt ccc tgg ttc ctg aac gac cgg ccc aac atc aaa      3069
His Lys Tyr Leu Pro Trp Phe Leu Asn Asp Arg Pro Asn Ile Lys
    1010            1015                1020 tgt ccc aaa ggc ggc ctg gca gca tac agc acc tct gtg aac ttg      3114
Cys Pro Lys Gly Gly Leu Ala Ala Tyr Ser Thr Ser Val Asn Leu
1025            1030                1035 act tca gat ggc cag gtt tta gcc tcc agg ttc atg gcc tat cac      3159
Thr Ser Asp Gly Gln Val Leu Ala Ser Arg Phe Met Ala Tyr His
    1040            1045                1050 aag ccc ctg aaa aac tca cag gat tac aca gaa gct ctg cgg gca      3204
Lys Pro Leu Lys Asn Ser Gln Asp Tyr Thr Glu Ala Leu Arg Ala
1055            1060                1065 gct cga gag ctg gca gcc aac atc act gct gac ctg cgg aaa gtg      3249
Ala Arg Glu Leu Ala Ala Asn Ile Thr Ala Asp Leu Arg Lys Val
    1070            1075                1080 cct gga aca gac ccg gct ttt gag gtc ttc ccc tac acg atc acc      3294
Pro Gly Thr Asp Pro Ala Phe Glu Val Phe Pro Tyr Thr Ile Thr
1085            1090                1095 aat gtg ttt tat gag cag tac ctg acc atc ctc cct gag ggg ctc      3339
Asn Val Phe Tyr Glu Gln Tyr Leu Thr Ile Leu Pro Glu Gly Leu
    1100            1105                1110 ttc atg ctc agc ctc tgc ctt gtg ccc acc ttc gct gtc tcc tgc      3384
Phe Met Leu Ser Leu Cys Leu Val Pro Thr Phe Ala Val Ser Cys
1115            1120                1125 ctc ctg ctg ggc ctg gac ctg cgc tcc ggc ctc ctc aac ctg ctc      3429
Leu Leu Leu Gly Leu Asp Leu Arg Ser Gly Leu Leu Asn Leu Leu
    1130            1135                1140 tcc att gtc atg atc ctc gtg gac act gtc ggc ttc atg gcc ctg      3474
Ser Ile Val Met Ile Leu Val Asp Thr Val Gly Phe Met Ala Leu
1145            1150                1155 tgg gac atc agt tac aat gct gtg tcc ctc atc aac ctg gtc tcg      3519
Trp Asp Ile Ser Tyr Asn Ala Val Ser Leu Ile Asn Leu Val Ser
    1160            1165                1170 gcg gtg ggc atg tct gtg gag ttt gtg tcc cac att acc cgc tcc      3564
Ala Val Gly Met Ser Val Glu Phe Val Ser His Ile Thr Arg Ser
1175            1180                1185 ttt gcc atc agc acc aag ccc acc tgg ctg gag agg gcc aaa gag      3609
Phe Ala Ile Ser Thr Lys Pro Thr Trp Leu Glu Arg Ala Lys Glu
    1190            1195                1200 gcc acc atc tct atg gga agt gcg gtg ttt gca ggt gtg gcc atg      3654
Ala Thr Ile Ser Met Gly Ser Ala Val Phe Ala Gly Val Ala Met
1205            1210                1215 acc aac ctg cct ggc atc ctt gtc ctg ggc ctc gcc aag gcc cag      3699
Thr Asn Leu Pro Gly Ile Leu Val Leu Gly Leu Ala Lys Ala Gln
    1220            1225                1230 ctc att cag atc ttc ttc ttc cgc ctc aac ctc ctg atc act ctg      3744
Leu Ile Gln Ile Phe Phe Phe Arg Leu Asn Leu Leu Ile Thr Leu
1235            1240                1245 ctg ggc ctg ctg cat ggc ttg gtc ttc ctg ccc gtc atc ctc agc      3789
Leu Gly Leu Leu His Gly Leu Val Phe Leu Pro Val Ile Leu Ser
    1250            1255                1260 tac gtg ggg cct gac gtt aac ccg gct ctg gca ctg gag cag aag      3834
Tyr Val Gly Pro Asp Val Asn Pro Ala Leu Ala Leu Glu Gln Lys
1265            1270                1275 cgg gct gag gag gcg gtg gca gca gtc atg gtg gcc tct tgc cca      3879
Arg Ala Glu Glu Ala Val Ala Ala Val Met Val Ala Ser Cys Pro
    1280            1285                1290 aat cac ccc tcc cga gtc tcc aca gct gac aac atc tat gtc aac      3924
Asn His Pro Ser Arg Val Ser Thr Ala Asp Asn Ile Tyr Val Asn
1295            1300                1305
```

```
cac agc ttt gaa ggt tct atc aaa ggt gct ggt gcc atc agc aac      3969
His Ser Phe Glu Gly Ser Ile Lys Gly Ala Gly Ala Ile Ser Asn
    1310                1315                1320 ttc ttg ccc aac aat ggg cgg cag ttc tga                          3999
Phe Leu Pro Asn Asn Gly Arg Gln Phe
    1325                1330

<210> SEQ ID NO 4
<211> LENGTH: 1332
<212> TYPE: PRT
<213> ORGANISM: Homo sapiens

<400> SEQUENCE: 4

Met Ala Glu Ala Gly Leu Arg Gly Trp Leu Leu Trp Ala Leu Leu Leu
1               5                   10                  15

Arg Leu Ala Gln Ser Glu Pro Tyr Thr Thr Ile His Gln Pro Gly Tyr
            20                  25                  30

Cys Ala Phe Tyr Asp Glu Cys Gly Lys Asn Pro Glu Leu Ser Gly Ser
        35                  40                  45

Leu Met Thr Leu Ser Asn Val Ser Cys Leu Ser Asn Thr Pro Ala Arg
    50                  55                  60

Lys Ile Thr Gly Asp His Leu Ile Leu Leu Gln Lys Ile Cys Pro Arg
65                  70                  75                  80

Leu Tyr Thr Gly Pro Asn Thr Gln Ala Cys Cys Ser Ala Lys Gln Leu
                85                  90                  95

Val Ser Leu Glu Ala Ser Leu Ser Ile Thr Lys Ala Leu Leu Thr Arg
            100                 105                 110

Cys Pro Ala Cys Ser Asp Asn Phe Val Asn Leu His Cys His Asn Thr
        115                 120                 125

Cys Ser Pro Asn Gln Ser Leu Phe Ile Asn Val Thr Arg Val Ala Gln
    130                 135                 140

Leu Gly Ala Gly Gln Leu Pro Ala Val Val Ala Tyr Glu Ala Phe Tyr
145                 150                 155                 160

Gln His Ser Phe Ala Glu Gln Ser Tyr Asp Ser Cys Ser Arg Val Arg
                165                 170                 175

Val Pro Ala Ala Ala Thr Leu Ala Val Gly Thr Met Cys Gly Val Tyr
            180                 185                 190

Gly Ser Ala Leu Cys Asn Ala Gln Arg Trp Leu Asn Phe Gln Gly Asp
        195                 200                 205

Thr Gly Asn Gly Leu Ala Pro Leu Asp Ile Thr Phe His Leu Leu Glu
    210                 215                 220

Pro Gly Gln Ala Val Gly Ser Gly Ile Gln Pro Leu Asn Glu Gly Val
225                 230                 235                 240

Ala Arg Cys Asn Glu Ser Gly Asp Asp Val Ala Thr Cys Ser Cys
                245                 250                 255

Gln Asp Cys Ala Ala Ser Cys Pro Ala Ile Ala Arg Pro Gln Ala Leu
            260                 265                 270

Asp Ser Thr Phe Tyr Leu Gly Gln Met Pro Gly Ser Leu Val Leu Ile
        275                 280                 285

Ile Ile Leu Cys Ser Val Phe Ala Val Val Thr Ile Leu Leu Val Gly
    290                 295                 300

Phe Arg Val Ala Pro Ala Arg Asp Lys Ser Lys Met Val Asp Pro Lys
305                 310                 315                 320

Lys Gly Thr Ser Leu Ser Asp Lys Leu Ser Phe Ser Thr His Thr Leu
                325                 330                 335
```

-continued

```
Leu Gly Gln Phe Phe Gln Gly Trp Gly Thr Trp Val Ala Ser Trp Pro
                340                 345                 350

Leu Thr Ile Leu Val Leu Ser Val Ile Pro Val Val Ala Leu Ala Ala
            355                 360                 365

Gly Leu Val Phe Thr Glu Leu Thr Thr Asp Pro Val Glu Leu Trp Ser
        370                 375                 380

Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                405                 410                 415

Arg Ser Ser Tyr Arg Tyr Asp Ser Leu Leu Gly Pro Lys Asn Phe
            420                 425                 430

Ser Gly Ile Leu Asp Leu Asp Leu Leu Glu Leu Glu Leu Gln
        435                 440                 445

Glu Arg Leu Arg His Leu Gln Val Trp Ser Pro Glu Ala Gln Arg Asn
                450                 455                 460

Ile Ser Leu Gln Asp Ile Cys Tyr Ala Pro Leu Asn Pro Asp Asn Thr
465                 470                 475                 480

Ser Leu Tyr Asp Cys Cys Ile Asn Ser Leu Leu Gln Tyr Phe Gln Asn
                485                 490                 495

Asn Arg Thr Leu Leu Leu Leu Thr Ala Asn Gln Thr Leu Met Gly Gln
            500                 505                 510

Thr Ser Gln Val Asp Trp Lys Asp His Phe Leu Tyr Cys Ala Asn Ala
        515                 520                 525

Pro Leu Thr Phe Lys Asp Gly Thr Ala Leu Ala Leu Ser Cys Met Ala
        530                 535                 540

Asp Tyr Gly Ala Pro Val Phe Pro Phe Leu Ala Ile Gly Gly Tyr Lys
545                 550                 555                 560

Gly Lys Asp Tyr Ser Glu Ala Glu Ala Leu Ile Met Thr Phe Ser Leu
                565                 570                 575

Asn Asn Tyr Pro Ala Gly Asp Pro Arg Leu Ala Gln Ala Lys Leu Trp
            580                 585                 590

Glu Glu Ala Phe Leu Glu Met Arg Ala Phe Gln Arg Arg Met Ala
        595                 600                 605

Gly Met Phe Gln Val Thr Phe Thr Ala Glu Arg Ser Leu Glu Asp Glu
        610                 615                 620

Ile Asn Arg Thr Thr Ala Glu Asp Leu Pro Ile Phe Ala Thr Ser Tyr
625                 630                 635                 640

Ile Val Ile Phe Leu Tyr Ile Ser Leu Ala Leu Gly Ser Tyr Ser Ser
                645                 650                 655

Trp Ser Arg Val Met Val Asp Ser Lys Ala Thr Leu Gly Leu Gly Gly
            660                 665                 670

Val Ala Val Val Leu Gly Ala Val Met Ala Ala Met Gly Phe Phe Ser
        675                 680                 685

Tyr Leu Gly Ile Arg Ser Ser Leu Val Ile Leu Gln Val Val Pro Phe
        690                 695                 700

Leu Val Leu Ser Val Gly Ala Asp Asn Ile Phe Ile Phe Val Leu Glu
705                 710                 715                 720

Tyr Gln Arg Leu Pro Arg Arg Pro Gly Glu Pro Arg Glu Val His Ile
                725                 730                 735

Gly Arg Ala Leu Gly Arg Val Ala Pro Ser Met Leu Leu Cys Ser Leu
            740                 745                 750

Ser Glu Ala Ile Cys Phe Phe Leu Gly Ala Leu Thr Pro Met Pro Ala
        755                 760                 765
```

```
Val Arg Thr Phe Ala Leu Thr Ser Gly Leu Ala Val Ile Leu Asp Phe
770                 775                 780

Leu Leu Gln Met Ser Ala Phe Val Ala Leu Leu Ser Leu Asp Ser Lys
785                 790                 795                 800

Arg Gln Glu Ala Ser Arg Leu Asp Val Cys Cys Cys Val Lys Pro Gln
            805                 810                 815

Glu Leu Pro Pro Pro Gly Gln Gly Glu Gly Leu Leu Leu Gly Phe Phe
            820                 825                 830

Gln Lys Ala Tyr Ala Pro Phe Leu Leu His Trp Ile Thr Arg Gly Val
            835                 840                 845

Val Leu Leu Leu Phe Leu Ala Leu Phe Gly Val Ser Leu Tyr Ser Met
850                 855                 860

Cys His Ile Ser Val Gly Leu Asp Gln Glu Leu Ala Leu Pro Lys Asp
865                 870                 875                 880

Ser Tyr Leu Leu Asp Tyr Phe Leu Phe Leu Asn Arg Tyr Phe Glu Val
            885                 890                 895

Gly Ala Pro Val Tyr Phe Val Thr Thr Leu Gly Tyr Asn Phe Ser Ser
            900                 905                 910

Glu Ala Gly Met Asn Ala Ile Cys Ser Ser Ala Gly Cys Asn Asn Phe
            915                 920                 925

Ser Phe Thr Gln Lys Ile Gln Tyr Ala Thr Glu Phe Pro Glu Gln Ser
930                 935                 940

Tyr Leu Ala Ile Pro Ala Ser Ser Trp Val Asp Asp Phe Ile Asp Trp
945                 950                 955                 960

Leu Thr Pro Ser Ser Cys Cys Arg Leu Tyr Ile Ser Gly Pro Asn Lys
            965                 970                 975

Asp Lys Phe Cys Pro Ser Thr Val Asn Ser Leu Asn Cys Leu Lys Asn
            980                 985                 990

Cys Met Ser Ile Thr Met Gly Ser Val Arg Pro Ser Val Glu Gln Phe
            995                 1000                1005

His Lys Tyr Leu Pro Trp Phe Leu Asn Asp Arg Pro Asn Ile Lys
    1010                1015                1020

Cys Pro Lys Gly Gly Leu Ala Ala Tyr Ser Thr Ser Val Asn Leu
    1025                1030                1035

Thr Ser Asp Gly Gln Val Leu Ala Ser Arg Phe Met Ala Tyr His
    1040                1045                1050

Lys Pro Leu Lys Asn Ser Gln Asp Tyr Thr Glu Ala Leu Arg Ala
    1055                1060                1065

Ala Arg Glu Leu Ala Ala Asn Ile Thr Ala Asp Leu Arg Lys Val
    1070                1075                1080

Pro Gly Thr Asp Pro Ala Phe Glu Val Phe Pro Tyr Thr Ile Thr
    1085                1090                1095

Asn Val Phe Tyr Glu Gln Tyr Leu Thr Ile Leu Pro Glu Gly Leu
    1100                1105                1110

Phe Met Leu Ser Leu Cys Leu Val Pro Thr Phe Ala Val Ser Cys
    1115                1120                1125

Leu Leu Leu Gly Leu Asp Leu Arg Ser Gly Leu Leu Asn Leu Leu
    1130                1135                1140

Ser Ile Val Met Ile Leu Val Asp Thr Val Gly Phe Met Ala Leu
    1145                1150                1155

Trp Asp Ile Ser Tyr Asn Ala Val Ser Leu Ile Asn Leu Val Ser
    1160                1165                1170

Ala Val Gly Met Ser Val Glu Phe Val Ser His Ile Thr Arg Ser
```

|   |   |   |   |   | 1175 |   |   |   | 1180 |   |   |   |   | 1185 |   |
|---|---|---|---|---|------|---|---|---|------|---|---|---|---|------|---|

Phe Ala Ile Ser Thr Lys Pro Thr Trp Leu Glu Arg Ala Lys Glu
             1190                1195                    1200

Ala Thr Ile Ser Met Gly Ser Ala Val Phe Ala Gly Val Ala Met
        1205                1210                1215

Thr Asn Leu Pro Gly Ile Leu Val Leu Gly Leu Ala Lys Ala Gln
    1220                1225                1230

Leu Ile Gln Ile Phe Phe Phe Arg Leu Asn Leu Leu Ile Thr Leu
    1235                1240                1245

Leu Gly Leu Leu His Gly Leu Val Phe Leu Pro Val Ile Leu Ser
    1250                1255                1260

Tyr Val Gly Pro Asp Val Asn Pro Ala Leu Ala Leu Glu Gln Lys
    1265                1270                1275

Arg Ala Glu Glu Ala Val Ala Ala Val Met Val Ala Ser Cys Pro
    1280                1285                1290

Asn His Pro Ser Arg Val Ser Thr Ala Asp Asn Ile Tyr Val Asn
    1295                1300                1305

His Ser Phe Glu Gly Ser Ile Lys Gly Ala Gly Ala Ile Ser Asn
    1310                1315                1320

Phe Leu Pro Asn Asn Gly Arg Gln Phe
    1325                1330

```
<210> SEQ ID NO 5
<211> LENGTH: 885
<212> TYPE: DNA
<213> ORGANISM: Rattus sp.

<400> SEQUENCE: 5
ccacgcgtcc gcacctgcaa gtgtggtccc ctgaggcaga gcgcaacatc tccctccagg      60
acatctgcta tgccccctc aacccatata caccagcct ctccgactgc tgtgtcaaca     120
gcctccttca gtacttccag aacaaccgca ccctcctgat gctcacggcc aaccagactc     180
tgaatggcca gacctccctg gtggactgga aggaccattt cctctactgt gcaaatgccc     240
ctctcacgtt caaagatggc acgtctctgg ccctgagctg catggctgac tacggggctc     300
ctgtcttccc cttccttgct gttgggggat accaaggcac ggactattcc gaggcagaag     360
cgctgatcat aaccttctct ctcaataact acccgctga tgatccccgc atggcccagg     420
ccaagctctg ggaggaggct ttcttgaagg aaatggaatc cttccagagg aacacaagtg     480
acaagttcca ggttgcgttc tcagctgagc gctctctgga ggatgagatc aaccgcacca     540
ccatccagga cctgcctgtc tttgccgtca gctacattat cgtcttcctg tacatctccc     600
tggccctggg cagctactcc agatgcagcc gagtagcgt ggagtccaag gctactctgg     660
gcctaggtgg ggtgatagtg tgctgggagc agttctggct tgcatggggc ttctaactcc     720
tacctgggtg tccctcttc tctggttatc atccaagtgg tacctttcct ggtgcttaag     780
ctgtgggagc tggacacatc tacatcctag acttgagtac cagaggtacc taggaagccg     840
cggaacagcg aaaaggacac attgggcgca ccctgggcat gtggc                     885

<210> SEQ ID NO 6
<211> LENGTH: 458
<212> TYPE: DNA
<213> ORGANISM: Rattus sp.

<400> SEQUENCE: 6
gaccagatgt taaccaagct ctggtacagg aggagaaact agccagcgag gcagcagtgg      60
```

```
cccccagagcc ttcttgccca cagtaccccct ccctgctga tgcggatgcc aatgttaact    120
acggctttgc cccagaactt gcccacggag ctaatgctgc tagaagctct ttgcccaaaa    180
gtgaccaaaa gttctaatgg agtaggagct tgtccatgct tctgctgatg agggatcatg    240
aaggtcttcc ctctggttgt cctcaaggcc tgggggagg ttgttcagag aaaaatggct    300
ggcattcctg ccacgaggca accggcagct tggcactgac tccttggtct cataggtccc    360
taaggcttgg tcagattact cctcatggag agactatctt aagtatctaa gctatcgatt    420
gggatgcatc gctgttcatt aaaaaggcta tggctatg                            458

<210> SEQ ID NO 7
<211> LENGTH: 896
<212> TYPE: DNA
<213> ORGANISM: Rattus sp.

<400> SEQUENCE: 7
ccacgcgtcc gcagtttcat aagtacctgc cctggttcct gaatgatccg cccaatatca     60
gatgtcccaa aggggtcta gcagcgtata gaacgtctgt gaatttgagc tcagatggcc    120
aggttatagc ctcccagttc atggcctacc acaagccctt aaggaactca caggacttca    180
cagaagctct ccgggcgtcc cggttgctag cagccaacat cacagctgac ctacggaagg    240
tgcctgggac agatccaaac tttgaggtct cccttacac gatctccaac gtgttctacc    300
agcaatacct gacggtcctt cctgagggaa tcttcaccct tgctcttgc tttgtgccca    360 cctttgttgt ctgctacctc ctactgggcc tggacatgtg ctcagggatc ctcaacctac    420
tctccatcat tatgattctc gtggacacca ttggcctcat ggctgtgtgg ggtatcagct    480
ataatgcggt atccctcatc aaccttgtca cggcagtggg catgtctgtg gagttttgtgt    540 cccacatcac tcggtccttt gcttgtaagc accaagccta cccggctgga gagggctaaa    600
agatgctact gtcttcatgg gcagtgcggt gtttgctgga gtggccatga ccaacttccc    660
aggcatcctc atcttggggg ctttgcccca gcccaggct tattcagatc ttcttcttcc    720
gcctcaacct tctgatcacc tttgctgggg tctgctgcat ggctggtctt cctgcccggt    780
ttgtcctcag ctatctggga ccagatgtaa ccaaggctct gctacccgga ggagaaaacta    840 gccagcgagg gcagcagtgg ccccagagac ttcttgccca caagtaccct tccctg        896

<210> SEQ ID NO 8
<211> LENGTH: 3124
<212> TYPE: DNA
<213> ORGANISM: Rattus sp.

<400> SEQUENCE: 8
tgcaagtgtg gtcccctgag gcagagcgca acatctccct ccaggacatc tgctatgccc     60
ccctcaaccc atataacacc agcctctccg actgctgtgt caacagcctc cttcagtact    120
tccagaacaa ccgcaccctc ctgatgctca cggccaacca gactctgaat ggccagacct    180
ccctggtgga ctggaaggac catttcctct actgtgcaaa tgcccctctc acgttcaaag    240
atggcacgtc tctggccctg agctgcatgg ctgactacgg ggctcctgtc ttcccttcc    300 ttgctgtttgg gggataccaa ggcacggact attccgaggc agaagcgctg atcataacct    360
tctctctcaa taactacccc gctgatgatc cccgcatggc ccaggccaag ctctgggagg    420 aggcttttctt gaaggaaatg gaatccttcc agaggaacac aagtgacaag ttccaggttg    480
cgttctcagc tgagcgctct ctggaggatg agatcaaccg caccaccatc caggacctgc    540
ctgtctttgc cgtcagctac attatcgtct tcctgtacat ctccctggcc ctgggcagct    600
```

```
actccagatg cagccgagta gcggtggagt ccaaggctac tctgggccta ggtgggtga       660 ttgttgtgct gggagcagtt ctggctgcca tgggcttcta ctcctacctg ggtgtccct       720 cttctctggt tatcatccaa gtggtacctt cctggtgct agctgtggga gctgacaaca       780
tcttcatctt tgttcttgag taccagaggc tacctaggat gcctgggaa cagcgagagg       840 ctcacattgg ccgcaccctg ggcagtgtgg ccccagcat gctgctgtgc agcctctctg       900
aggccatctg cttcttttcta ggggccctga ccccatgcc agctgtgagg accttcgcct       960
tgacctctgg cttagcaatt atcctcgact tcctgctcca gatgactgcc tttgtggccc      1020
tgctctccct ggatagcaag aggcaggagg cctctcgccc ggatgtctta tgctgctttt      1080
caacccggaa gctgccccca cctaaagaaa aagaaggcct cttactccgc ttcttccgca      1140
agatatacgc tccttttcctg ctgcacagat tcatccgccc tgttgtgatg ctgctgtttc      1200
tgaccctgtt tggagcaaat ctctacttaa tgtgcaacat caacgtgggg ctagaccagg      1260
agctggctct gcccaaggac tcgtacttga tagactactt cctctttctg aaccgatacc      1320
ttgaagtggg gcctccagtg tactttgtca ccacctcggg cttcaacttc tccagcgagg      1380
caggcatgaa cgccacttgc tctagcgcag gctgtaagag cttctcccta acccagaaaa      1440
tccagtatgc cagtgaattc cctgaccagt cttacgtggc tattgctgca tcctcctggg      1500
tagatgactt catcgactgg ctgacccgt cctcctcctg ctgtcgcctt tatatacgtg      1560
gcccccataa ggatgagttc tgtccctcaa cggatacttc cttcaactgc ttaaaaaact      1620
gcatgaaccg cactctgggt cctgtgaggc ccacagcgga acagtttcat aagtacctgc      1680
cctggttcct gaatgatccg cccaatatca gatgtcccaa agggggtcta gcagcgtata      1740
gaacgtctgt gaatttgagc tcagatggc aggttatagc ctcccagttc atggcctacc      1800
acaagccctt aaggaactca caggacttca cagaagctct ccgggcgtcc cggttgctag      1860
cagccaacat cacagctgac ctacggaagg tgcctgggac agatccaaac tttgaggtct      1920
tcccttacac gatctccaac gtgttctacc agcaatacct gacggtcctt cctgagggaa      1980
tcttcaccct tgctctttgc tttgtgccca cctttgttgt ctgctacctc ctactgggcc      2040
tggacatgtg ctcagggatc ctcaacctac tctccatcat tatgattctc gtggacacca      2100
ttggcctcat ggctgtgtgg ggtatcagct ataatgcggt atccctcatc aaccttgtca      2160
cggcagtggg catgtctgtg gagtttgtgt cccacatcac tcggtccttt gctgtaagca      2220
ccaagcctac ccggctggag agggctaaag atgctactgt cttcatgggc agtgcggtgt      2280
ttgctggagt ggccatgacc aacttcccag gcatcctcat cttgggcttt gcccaagccc      2340
agcttattca gatcttcttc ttccgcctca accttctgat caccttgctg ggtctgctgc      2400
atggcctggt cttcctgccg gttgtcctca gctatctggg accagatgtt aaccaagctc      2460
tggtacagga ggagaaacta gccagcgagg cagcagtggc cccagagcct tcttgcccac      2520 agtaccctc cctgctgat gcggatgcca atgttaacta cggctttgcc ccagaacttg      2580
cccacggagc taatgctgct agaagctctt tgcccaaaag tgaccaaaag ttctaatgga      2640
gtaggagctt gtccatgctt cttgctgatg agggatcatg aaggtcttcc ctctggttgt      2700
cctcaaggcc tgggggagg ttgtttcaga gaaaaatggc tggcattcct gccacgaggc      2760
aaccggcagc attggcactg acctccttgc tctcataggt ccctaaggcc ttggtcagat      2820
tacctcctcc atggagagac tatcttaagt atcttaagta tcgtatggga tgcatcgcct      2880
gtcaattaaa aaggctatgg cctatggctc aggcagggcc atccggaaga agagaggatt      2940
ctgggataaa gccaggtggg agattcgcct ggggaaaatg tgacaatggt tcctgagcat      3000
```

-continued

| | |
|---|---|
| gggcaatcag ccatgtggca aatgtaaat taatataaat gggttgtctt aagttatgat | 3060 |
| tctagctggg gaggagccta gctgtgtagc aagatatttt gtaaatataa aaaaaaaaaa | 3120 |
| aaaa | 3124 |

<210> SEQ ID NO 9
<211> LENGTH: 4484
<212> TYPE: DNA
<213> ORGANISM: Rattus sp.

<400> SEQUENCE: 9

| | |
|---|---|
| atggcagctg cctggctggg atggctgctc tgggccctgc tcctgagcgc ggcccagggt | 60 |
| gagctataca cacccaaaca cgaagctggg gtctgcacct tttacgaaga gtgcgggaaa | 120 |
| aacccagagc tctctggagg cctcacgtca ctatccaatg tatcctgcct gtctaacacc | 180 |
| ccggcccgcc acgtcacggg tgaacacctg gctcttctcc agcgcatctg tccccgcctg | 240 |
| tacaacggcc ccaataccac ttttgcctgt tgctctacca gcagctgct gtccttagaa | 300 |
| agcagcatgt ccatcaccaa ggcccttctc acgcgctgcc cggcctgctc tgacaatttt | 360 |
| gtgagcttac actgccacaa cacttgcagc cctgaccaga gcctcttcat caacgtcacc | 420 |
| cgggtggttg agcggggcgc tggagagcct cctgccgtgg tggcctatga ggccttttat | 480 |
| cagcgcagct ttgctgagaa ggcctatgag tcctgcagcc aggtgcgcat ccctgcggcc | 540 |
| gcttccttgg ccgtgggcag catgtgtgga gtgtatggct ccgccctctg caatgctcag | 600 |
| cgctggctca acttccaagg agacacaggg aatggcctgg ctccgctgga tatcaccttc | 660 |
| cacctcttgg agcctggcca ggccctaccg gatgggatcc agccactgaa tgggaagatc | 720 |
| gcaccctgca acgagtctca gggtgatgac tcagcagtct gctcctgcca ggactgtgcg | 780 |
| gcgtcctgcc ctgtcatccc tccgcccgag gccttgcgcc cttccttcta catgggtcgc | 840 |
| atgccaggct ggctggccct catcatcatc ttcactgctg tctttgtgtt gctctctgca | 900 |
| gtccttgtgc gtctccgagt ggtttccaac aggaacaaga caaggcaga aggcccccag | 960 |
| gaagccccca aactccctca taagcacaaa ctctcacccc ataccatcct gggccggttc | 1020 |
| ttccagaact ggggcacaag ggtggcctcg tggccactca ccgtcttagc actgtccttc | 1080 |
| atcgttgtga tagccttagc agcaggcctg acctttattg aactcaccac agaccctgtg | 1140 |
| gaactgtggt cggcccccaa gagccaggcc cggaaagaga gtctttcca tgatgagcat | 1200 |
| ttcggcccct ctttcgaac caaccagatt ttcgtgacag ctcggaacag gtccagctac | 1260 |
| aagtacgact ccctactgct agggtccaag aacttcagtg ggatcctgtc cctggacttc | 1320 |
| ctgctggagc tgctggagct tcaggagagg cttcgacacc tgcaagtgtg gtcccctgag | 1380 |
| gcagagcgca acatctccct ccaggacatc tgctatgccc ccctcaaccc atataacacc | 1440 |
| agcctctccg actgctgtgt caacagcctc cttcagtact tccagaacaa ccgcaccctc | 1500 |
| ctgatgctca cggccaacca gactctgaat ggccagacct ccctggtgga ctggaaggac | 1560 |
| catttcctct actgtgcaaa tgcccctctc acgttcaaag atggcacgtc tctggccctg | 1620 |
| agctgcatgg ctgactacgg ggctcctgtc ttccccttcc ttgctgttgg gggataccaa | 1680 |
| ggcacggact attccgaggc agaagcgctg atcataacct tctctctcaa taactacccc | 1740 |
| gctgatgatc cccgcatggc ccaggccaag ctctgggagg aggctttctt gaaggaaatg | 1800 |
| gaatccttcc agaggaacac aagtgacaag ttccaggttg cgttctcagc tgagcgctct | 1860 |
| ctggaggatg agatcaaccg caccaccatc caggacctgc ctgtctttgc cgtcagctac | 1920 |
| attatcgtct tcctgtacat ctccctggcc ctgggcagct actccagatg cagccgagta | 1980 |

```
gcggtggagt ccaaggctac tctgggccta ggtggggtga ttgttgtgct gggagcagtt    2040
ctggctgcca tgggcttcta ctcctacctg ggtgtcccct cttctctggt tatcatccaa    2100
gtggtacctt tcctggtgct agctgtggga gctgacaaca tcttcatctt tgttcttgag    2160
taccagaggc tacctaggat gcctggggaa cagcgagagg ctcacattgg ccgcaccctg    2220
ggcagtgtgg cccccagcat gctgctgtgc agcctctctg aggccatctg cttctttcta    2280
ggggccctga cccccatgcc agctgtgagg accttcgcct tgacctctgg cttagcaatt    2340
atcctcgact tcctgctcca gatgactgcc tttgtggccc tgctctccct ggatagcaag    2400
aggcaggagg cctctcgccc ggatgtctta tgctgctttt caacccggaa gctgccccca    2460
cctaaagaaa aagaaggcct cttactccgc ttcttccgca agatatacgc tcctttcctg    2520
ctgcacagat tcatccgccc tgttgtgatg ctgctgtttc tgaccctgtt tggagcaaat    2580
ctctacttaa tgtgcaacat caacgtgggg ctagaccagg agctggctct gcccaaggac    2640
tcgtacttga tagactactt cctctttctg aaccgatacc ttgaagtggg gcctccagtg    2700
tactttgtca ccacctcggg cttcaacttc tccagcgagg caggcatgaa cgccacttgc    2760
tctagcgcag gctgtaagag cttctcccta acccagaaaa tccagtatgc cagtgaattc    2820
cctgaccagt cttacgtggc tattgctgca tcctcctggg tagatgactt catcgactgg    2880
ctgaccccgt cctcctcctg ctgtcgcctt tatatacgtg gccccataa ggatgagttc    2940 tgtccctcaa cggatacttc cttcaactgc ttaaaaaact gcatgaaccg cactctgggt    3000
cctgtgaggc ccacagcgga acagtttcat aagtacctgc cctggttcct gaatgatccg    3060
cccaatatca gatgtcccaa aggggggtcta gcagcgtata aacgtctgt gaatttgagc    3120 tcagatggcc aggttatagc ctcccagttc atggcctacc acaagcccct aaggaactca    3180
caggacttca cagaagctct ccgggcgtcc cggttgctag cagccaacat cacagctgac    3240
ctacggaagg tgcctgggac agatccaaac tttgaggtct cccttacac gatctccaac    3300 gtgttctacc agcaatacct gacggtcctt cctgagggaa tcttcaccct tgctctttgc    3360
tttgtgccca cctttgttgt ctgctacctc ctactgggcc tggacatgtg ctcagggatc    3420
ctcaacctac tctccatcat tatgattctc gtggacacca ttggcctcat ggctgtgtgg    3480
ggtatcagct ataatgcggt atccctcatc aaccttgtca cggcagtggg catgtctgtg    3540
gagtttgtgt cccacatcac tcggtccttt gctgtaagca ccaagcctac ccggctggag    3600
agggctaaag atgctactgt cttcatgggc agtgcggtgt ttgctggagt ggccatgacc    3660
aacttcccag gcatcctcat cttgggcttt gcccaagccc agcttattca gatcttcttc    3720
ttccgcctca accttctgat caccttgctg ggtctgctgc atggcctggt cttcctgccg    3780
gttgtcctca gctatctggg accagatgtt aaccaagctc tggtacagga ggagaaaacta    3840 gccagcgagg cagcagtggc cccagagcct tcttgcccac agtacccctc ccctgctgat    3900
gcggatgcca atgttaacta cggctttgcc ccagaacttg cccacggagc taatgctgct    3960
agaagctctt tgcccaaaag tgaccaaaag ttctaatgga gtaggagctt gtccatgctt    4020
cttgctgatg agggatcatg aaggtcttcc ctctggttgt cctcaaggcc tgggggggagg    4080 ttgtttcaga gaaaaatggc tggcattcct gccacgaggc aaccggcagc attggcactg    4140
acctccttgc tctcataggt ccctaaggcc ttggtcagat tacctcctcc atggagagac    4200
tatcttaagt atcttaagta tcgtatggga tgcatcgcct gtcaattaaa aaggctatgg    4260
cctatggctc aggcagggcc atccggaaga agagaggatt ctgggataaa gccaggtggg    4320
agattcgcct ggggaaaatg tgacaatggt tcctgagcat gggcaatcag ccatgtggca    4380
```

-continued

```
gaatgtaaat taatataaat gggttgtctt aagttatgat tctagctggg gaggagccta    4440
gctgtgtagc caagatattt gtaaatataa aaaaaaaaaa aaaa                     4484

<210> SEQ ID NO 10
<211> LENGTH: 3993
<212> TYPE: DNA
<213> ORGANISM: Rattus sp.
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (30)..(30)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other
<220> FEATURE:
<221> NAME/KEY: modified_base
<222> LOCATION: (39)..(39)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (45)..(45)
<223> OTHER INFORMATION: a, c, g, t, unknown or other
<220> FEATURE:
<221> NAME/KEY: modified_base
<222> LOCATION: (48)..(48)
<223> OTHER INFORMATION: a, c, g, t, unknown or other
<220> FEATURE:
<221> NAME/KEY: modified_base
<222> LOCATION: (51)..(51)
<223> OTHER INFORMATION: a, c, g, t, unknown or other
<220> FEATURE:
<221> NAME/KEY: modified_base
<222> LOCATION: (54)..(54)
<223> OTHER INFORMATION: a, c, g, t, unknown or other
<220> FEATURE:
<221> NAME/KEY: modified_base
<222> LOCATION: (60)..(60)
<223> OTHER INFORMATION: a, c, g, t, unknown or other
<220> FEATURE:
<221> NAME/KEY: modified_base
<222> LOCATION: (66)..(66)
<223> OTHER INFORMATION: a, c, g, t, unknown or other
<220> FEATURE:
<221> NAME/KEY: modified_base
<222> LOCATION: (72)..(72)
<223> OTHER INFORMATION: a, c, g, t, unknown or other
<220> FEATURE:
<221> NAME/KEY: modified_base
<222> LOCATION: (75)..(75)
```

```
<223> OTHER INFORMATION: a, c, g, t, unknown or other
<220> FEATURE:
<221> NAME/KEY: modified_base
<222> LOCATION: (87)..(87)
<223> OTHER INFORMATION: a, c, g, t, unknown or other
<220> FEATURE:
<221> NAME/KEY: modified_base
<222> LOCATION: (90)..(90)
<223> OTHER INFORMATION: a, c, g, t, unknown or other
<220> FEATURE:
<221> NAME/KEY: modified_base
<222> LOCATION: (93)..(93)
<223> OTHER INFORMATION: a, c, g, t, unknown or other
<220> FEATURE:
<221> NAME/KEY: modified_base
<222> LOCATION: (99)..(99)
<223> OTHER INFORMATION: a, c, g, t, unknown or other
<220> FEATURE:
<221> NAME/KEY: modified_base
<222> LOCATION: (117)..(117)
<223> OTHER INFORMATION: a, c, g, t, unknown or other
<220> FEATURE:
<221> NAME/KEY: modified_base
<222> LOCATION: (126)..(126)
<223> OTHER INFORMATION: a, c, g, t, unknown or other
<220> FEATURE:
<221> NAME/KEY: modified_base
<222> LOCATION: (132)..(132)
<223> OTHER INFORMATION: a, c, g, t, unknown or other
<220> FEATURE:
<221> NAME/KEY: modified_base
<222> LOCATION: (135)..(135)
<223> OTHER INFORMATION: a, c, g, t, unknown or other
<220> FEATURE:
<221> NAME/KEY: modified_base
<222> LOCATION: (138)..(138)
<223> OTHER INFORMATION: a, c, g, t, unknown or other
<220> FEATURE:
<221> NAME/KEY: modified_base
<222> LOCATION: (141)..(141)
<223> OTHER INFORMATION: a, c, g, t, unknown or other
<220> FEATURE:
<221> NAME/KEY: modified_base
<222> LOCATION: (144)..(144)
<223> OTHER INFORMATION: a, c, g, t, unknown or other
<220> FEATURE:
<221> NAME/KEY: modified_base
<222> LOCATION: (147)..(147)
<223> OTHER INFORMATION: a, c, g, t, unknown or other
<220> FEATURE:
<221> NAME/KEY: modified_base
<222> LOCATION: (150)..(150)
<223> OTHER INFORMATION: a, c, g, t, unknown or other
<220> FEATURE:
<221> NAME/KEY: modified_base
<222> LOCATION: (153)..(153)
<223> OTHER INFORMATION: a, c, g, t, unknown or other
<220> FEATURE:
<221> NAME/KEY: modified_base
<222> LOCATION: (156)..(156)
<223> OTHER INFORMATION: a, c, g, t, unknown or other
<220> FEATURE:
<221> NAME/KEY: modified_base
<222> LOCATION: (162)..(162)
<223> OTHER INFORMATION: a, c, g, t, unknown or other
<220> FEATURE:
<221> NAME/KEY: modified_base
<222> LOCATION: (165)..(165)
<223> OTHER INFORMATION: a, c, g, t, unknown or other
<220> FEATURE:
<221> NAME/KEY: modified_base
<222> LOCATION: (171)..(171)
<223> OTHER INFORMATION: a, c, g, t, unknown or other
<220> FEATURE:
<221> NAME/KEY: modified_base
<222> LOCATION: (174)..(174)
<223> OTHER INFORMATION: a, c, g, t, unknown or other
<220> FEATURE:
<221> NAME/KEY: modified_base
<222> LOCATION: (180)..(180)
```

-continued

```
<223> OTHER INFORMATION: a, c, g, t, unknown or other
<220> FEATURE:
<221> NAME/KEY: modified_base
<222> LOCATION: (183)..(183)
<223> OTHER INFORMATION: a, c, g, t, unknown or other
<220> FEATURE:
<221> NAME/KEY: modified_base
<222> LOCATION: (186)..(186)
<223> OTHER INFORMATION: a, c, g, t, unknown or other
<220> FEATURE:
<221> NAME/KEY: modified_base
<222> LOCATION: (189)..(189)
<223> OTHER INFORMATION: a, c, g, t, unknown or other
<220> FEATURE:
<221> NAME/KEY: modified_base
<222> LOCATION: (195)..(195)
<223> OTHER INFORMATION: a, c, g, t, unknown or other
<220> FEATURE:
<221> NAME/KEY: modified_base
<222> LOCATION: (198)..(198)
<223> OTHER INFORMATION: a, c, g, t, unknown or other
<220> FEATURE:
<221> NAME/KEY: modified_base
<222> LOCATION: (201)..(201)
<223> OTHER INFORMATION: a, c, g, t, unknown or other
<220> FEATURE:
<221> NAME/KEY: modified_base
<222> LOCATION: (210)..(210)
<223> OTHER INFORMATION: a, c, g, t, unknown or other
<220> FEATURE:
<221> NAME/KEY: modified_base
<222> LOCATION: (213)..(213)
<223> OTHER INFORMATION: a, c, g, t, unknown or other
<220> FEATURE:
<221> NAME/KEY: modified_base
<222> LOCATION: (216)..(216)
<223> OTHER INFORMATION: a, c, g, t, unknown or other
<220> FEATURE:
<221> NAME/KEY: modified_base
<222> LOCATION: (219)..(219)
<223> OTHER INFORMATION: a, c, g, t, unknown or other
<220> FEATURE:
<221> NAME/KEY: modified_base
<222> LOCATION: (225)..(225)
<223> OTHER INFORMATION: a, c, g, t, unknown or other
<220> FEATURE:
<221> NAME/KEY: modified_base
<222> LOCATION: (234)..(234)
<223> OTHER INFORMATION: a, c, g, t, unknown or other
<220> FEATURE:
<221> NAME/KEY: modified_base
<222> LOCATION: (237)..(237)
<223> OTHER INFORMATION: a, c, g, t, unknown or other
<220> FEATURE:
<221> NAME/KEY: modified_base
<222> LOCATION: (240)..(240)
<223> OTHER INFORMATION: a, c, g, t, unknown or other
<220> FEATURE:
<221> NAME/KEY: modified_base
<222> LOCATION: (249)..(249)
<223> OTHER INFORMATION: a, c, g, t, unknown or other
<220> FEATURE:
<221> NAME/KEY: modified_base
<222> LOCATION: (252)..(252)
<223> OTHER INFORMATION: a, c, g, t, unknown or other
<220> FEATURE:
<221> NAME/KEY: modified_base
<222> LOCATION: (258)..(258)
<223> OTHER INFORMATION: a, c, g, t, unknown or other
<220> FEATURE:
<221> NAME/KEY: modified_base
<222> LOCATION: (261)..(261)
<223> OTHER INFORMATION: a, c, g, t, unknown or other
<220> FEATURE:
<221> NAME/KEY: modified_base
<222> LOCATION: (267)..(267)
<223> OTHER INFORMATION: a, c, g, t, unknown or other
<220> FEATURE:
<221> NAME/KEY: modified_base
<222> LOCATION: (276)..(276)
```

-continued

```
<223> OTHER INFORMATION: a, c, g, t, unknown or other
<220> FEATURE:
<221> NAME/KEY: modified_base
<222> LOCATION: (279)..(279)
<223> OTHER INFORMATION: a, c, g, t, unknown or other
<220> FEATURE:
<221> NAME/KEY: modified_base
<222> LOCATION: (288)..(288)
<223> OTHER INFORMATION: a, c, g, t, unknown or other
<220> FEATURE:
<221> NAME/KEY: modified_base
<222> LOCATION: (291)..(291)
<223> OTHER INFORMATION: a, c, g, t, unknown or other
<220> FEATURE:
<221> NAME/KEY: modified_base
<222> LOCATION: (294)..(294)
<223> OTHER INFORMATION: a, c, g, t, unknown or other
<220> FEATURE:
<221> NAME/KEY: modified_base
<222> LOCATION: (297)..(297)
<223> OTHER INFORMATION: a, c, g, t, unknown or other
<220> FEATURE:
<221> NAME/KEY: modified_base
<222> LOCATION: (303)..(303)
<223> OTHER INFORMATION: a, c, g, t, unknown or other
<220> FEATURE:
<221> NAME/KEY: modified_base
<222> LOCATION: (306)..(306)
<223> OTHER INFORMATION: a, c, g, t, unknown or other
<220> FEATURE:
<221> NAME/KEY: modified_base
<222> LOCATION: (312)..(312)
<223> OTHER INFORMATION: a, c, g, t, unknown or other
<220> FEATURE:
<221> NAME/KEY: modified_base
<222> LOCATION: (318)..(318)
<223> OTHER INFORMATION: a, c, g, t, unknown or other
<220> FEATURE:
<221> NAME/KEY: modified_base
<222> LOCATION: (324)..(324)
<223> OTHER INFORMATION: a, c, g, t, unknown or other
<220> FEATURE:
<221> NAME/KEY: modified_base
<222> LOCATION: (327)..(327)
<223> OTHER INFORMATION: a, c, g, t, unknown or other
<220> FEATURE:
<221> NAME/KEY: modified_base
<222> LOCATION: (330)..(330)
<223> OTHER INFORMATION: a, c, g, t, unknown or other
<220> FEATURE:
<221> NAME/KEY: modified_base
<222> LOCATION: (333)..(333)
<223> OTHER INFORMATION: a, c, g, t, unknown or other
<220> FEATURE:
<221> NAME/KEY: modified_base
<222> LOCATION: (336)..(336)
<223> OTHER INFORMATION: a, c, g, t, unknown or other
<220> FEATURE:
<221> NAME/KEY: modified_base
<222> LOCATION: (342)..(342)
<223> OTHER INFORMATION: a, c, g, t, unknown or other
<220> FEATURE:
<221> NAME/KEY: modified_base
<222> LOCATION: (345)..(345)
<223> OTHER INFORMATION: a, c, g, t, unknown or other
<220> FEATURE:
<221> NAME/KEY: modified_base
<222> LOCATION: (351)..(351)
<223> OTHER INFORMATION: a, c, g, t, unknown or other
<220> FEATURE:
<221> NAME/KEY: modified_base
<222> LOCATION: (363)..(363)
<223> OTHER INFORMATION: a, c, g, t, unknown or other
<220> FEATURE:
<221> NAME/KEY: modified_base
<222> LOCATION: (366)..(366)
<223> OTHER INFORMATION: a, c, g, t, unknown or other
<220> FEATURE:
<221> NAME/KEY: modified_base
<222> LOCATION: (369)..(369)
```

-continued

```
<223> OTHER INFORMATION: a, c, g, t, unknown or other
<220> FEATURE:
<221> NAME/KEY: modified_base
<222> LOCATION: (384)..(384)
<223> OTHER INFORMATION: a, c, g, t, unknown or other
<220> FEATURE:
<221> NAME/KEY: modified_base
<222> LOCATION: (390)..(390)
<223> OTHER INFORMATION: a, c, g, t, unknown or other
<220> FEATURE:
<221> NAME/KEY: modified_base
<222> LOCATION: (393)..(393)
<223> OTHER INFORMATION: a, c, g, t, unknown or other
<220> FEATURE:
<221> NAME/KEY: modified_base
<222> LOCATION: (402)..(402)
<223> OTHER INFORMATION: a, c, g, t, unknown or other
<220> FEATURE:
<221> NAME/KEY: modified_base
<222> LOCATION: (405)..(405)
<223> OTHER INFORMATION: a, c, g, t, unknown or other
<220> FEATURE:
<221> NAME/KEY: modified_base
<222> LOCATION: (417)..(417)
<223> OTHER INFORMATION: a, c, g, t, unknown or other
<220> FEATURE:
<221> NAME/KEY: modified_base
<222> LOCATION: (420)..(420)
<223> OTHER INFORMATION: a, c, g, t, unknown or other
<220> FEATURE:
<221> NAME/KEY: modified_base
<222> LOCATION: (423)..(423)
<223> OTHER INFORMATION: a, c, g, t, unknown or other
<220> FEATURE:
<221> NAME/KEY: modified_base
<222> LOCATION: (426)..(426)
<223> OTHER INFORMATION: a, c, g, t, unknown or other
<220> FEATURE:
<221> NAME/KEY: modified_base
<222> LOCATION: (429)..(429)
<223> OTHER INFORMATION: a, c, g, t, unknown or other
<220> FEATURE:
<221> NAME/KEY: modified_base
<222> LOCATION: (435)..(435)
<223> OTHER INFORMATION: a, c, g, t, unknown or other
<220> FEATURE:
<221> NAME/KEY: modified_base
<222> LOCATION: (438)..(438)
<223> OTHER INFORMATION: a, c, g, t, unknown or other
<220> FEATURE:
<221> NAME/KEY: modified_base
<222> LOCATION: (441)..(441)
<223> OTHER INFORMATION: a, c, g, t, unknown or other
<220> FEATURE:
<221> NAME/KEY: modified_base
<222> LOCATION: (444)..(444)
<223> OTHER INFORMATION: a, c, g, t, unknown or other
<220> FEATURE:
<221> NAME/KEY: modified_base
<222> LOCATION: (450)..(450)
<223> OTHER INFORMATION: a, c, g, t, unknown or other
<220> FEATURE:
<221> NAME/KEY: modified_base
<222> LOCATION: (453)..(453)
<223> OTHER INFORMATION: a, c, g, t, unknown or other
<220> FEATURE:
<221> NAME/KEY: modified_base
<222> LOCATION: (456)..(456)
<223> OTHER INFORMATION: a, c, g, t, unknown or other
<220> FEATURE:
<221> NAME/KEY: modified_base
<222> LOCATION: (459)..(459)
<223> OTHER INFORMATION: a, c, g, t, unknown or other
<220> FEATURE:
<221> NAME/KEY: modified_base
<222> LOCATION: (462)..(462)
<223> OTHER INFORMATION: a, c, g, t, unknown or other
<220> FEATURE:
<221> NAME/KEY: modified_base
<222> LOCATION: (465)..(465)
```

-continued

```
<223> OTHER INFORMATION: a, c, g, t, unknown or other
<220> FEATURE:
<221> NAME/KEY: modified_base
<222> LOCATION: (474)..(474)
<223> OTHER INFORMATION: a, c, g, t, unknown or other
<220> FEATURE:
<221> NAME/KEY: modified_base
<222> LOCATION: (486)..(486)
<223> OTHER INFORMATION: a, c, g, t, unknown or other
<220> FEATURE:
<221> NAME/KEY: modified_base
<222> LOCATION: (489)..(489)
<223> OTHER INFORMATION: a, c, g, t, unknown or other
<220> FEATURE:
<221> NAME/KEY: modified_base
<222> LOCATION: (495)..(495)
<223> OTHER INFORMATION: a, c, g, t, unknown or other
<220> FEATURE:
<221> NAME/KEY: modified_base
<222> LOCATION: (504)..(504)
<223> OTHER INFORMATION: a, c, g, t, unknown or other
<220> FEATURE:
<221> NAME/KEY: modified_base
<222> LOCATION: (513)..(513)
<223> OTHER INFORMATION: a, c, g, t, unknown or other
<220> FEATURE:
<221> NAME/KEY: modified_base
<222> LOCATION: (519)..(519)
<223> OTHER INFORMATION: a, c, g, t, unknown or other
<220> FEATURE:
<221> NAME/KEY: modified_base
<222> LOCATION: (525)..(525)
<223> OTHER INFORMATION: a, c, g, t, unknown or other
<220> FEATURE:
<221> NAME/KEY: modified_base
<222> LOCATION: (528)..(528)
<223> OTHER INFORMATION: a, c, g, t, unknown or other
<220> FEATURE:
<221> NAME/KEY: modified_base
<222> LOCATION: (534)..(534)
<223> OTHER INFORMATION: a, c, g, t, unknown or other
<220> FEATURE:
<221> NAME/KEY: modified_base
<222> LOCATION: (537)..(537)
<223> OTHER INFORMATION: a, c, g, t, unknown or other
<220> FEATURE:
<221> NAME/KEY: modified_base
<222> LOCATION: (540)..(540)
<223> OTHER INFORMATION: a, c, g, t, unknown or other
<220> FEATURE:
<221> NAME/KEY: modified_base
<222> LOCATION: (543)..(543)
<223> OTHER INFORMATION: a, c, g, t, unknown or other
<220> FEATURE:
<221> NAME/KEY: modified_base
<222> LOCATION: (546)..(546)
<223> OTHER INFORMATION: a, c, g, t, unknown or other
<220> FEATURE:
<221> NAME/KEY: modified_base
<222> LOCATION: (549)..(549)
<223> OTHER INFORMATION: a, c, g, t, unknown or other
<220> FEATURE:
<221> NAME/KEY: modified_base
<222> LOCATION: (552)..(552)
<223> OTHER INFORMATION: a, c, g, t, unknown or other
<220> FEATURE:
<221> NAME/KEY: modified_base
<222> LOCATION: (555)..(555)
<223> OTHER INFORMATION: a, c, g, t, unknown or other
<220> FEATURE:
<221> NAME/KEY: modified_base
<222> LOCATION: (558)..(558)
<223> OTHER INFORMATION: a, c, g, t, unknown or other
<220> FEATURE:
<221> NAME/KEY: modified_base
<222> LOCATION: (561)..(561)
<223> OTHER INFORMATION: a, c, g, t, unknown or other
<220> FEATURE:
<221> NAME/KEY: modified_base
<222> LOCATION: (570)..(570)
```

-continued

```
<223> OTHER INFORMATION: a, c, g, t, unknown or other
<220> FEATURE:
<221> NAME/KEY: modified_base
<222> LOCATION: (573)..(573)
<223> OTHER INFORMATION: a, c, g, t, unknown or other
<220> FEATURE:
<221> NAME/KEY: modified_base
<222> LOCATION: (579)..(579)
<223> OTHER INFORMATION: a, c, g, t, unknown or other
<220> FEATURE:
<221> NAME/KEY: modified_base
<222> LOCATION: (582)..(582)
<223> OTHER INFORMATION: a, c, g, t, unknown or other
<220> FEATURE:
<221> NAME/KEY: modified_base
<222> LOCATION: (585)..(585)
<223> OTHER INFORMATION: a, c, g, t, unknown or other
<220> FEATURE:
<221> NAME/KEY: modified_base
<222> LOCATION: (588)..(588)
<223> OTHER INFORMATION: a, c, g, t, unknown or other
<220> FEATURE:
<221> NAME/KEY: modified_base
<222> LOCATION: (597)..(597)
<223> OTHER INFORMATION: a, c, g, t, unknown or other
<220> FEATURE:
<221> NAME/KEY: modified_base
<222> LOCATION: (603)..(603)
<223> OTHER INFORMATION: a, c, g, t, unknown or other
<220> FEATURE:
<221> NAME/KEY: modified_base
<222> LOCATION: (609)..(609)
<223> OTHER INFORMATION: a, c, g, t, unknown or other
<220> FEATURE:
<221> NAME/KEY: modified_base
<222> LOCATION: (621)..(621)
<223> OTHER INFORMATION: a, c, g, t, unknown or other
<220> FEATURE:
<221> NAME/KEY: modified_base
<222> LOCATION: (627)..(627)
<223> OTHER INFORMATION: a, c, g, t, unknown or other
<220> FEATURE:
<221> NAME/KEY: modified_base
<222> LOCATION: (630)..(630)
<223> OTHER INFORMATION: a, c, g, t, unknown or other
<220> FEATURE:
<221> NAME/KEY: modified_base
<222> LOCATION: (636)..(636)
<223> OTHER INFORMATION: a, c, g, t, unknown or other
<220> FEATURE:
<221> NAME/KEY: modified_base
<222> LOCATION: (639)..(639)
<223> OTHER INFORMATION: a, c, g, t, unknown or other
<220> FEATURE:
<221> NAME/KEY: modified_base
<222> LOCATION: (642)..(642)
<223> OTHER INFORMATION: a, c, g, t, unknown or other
<220> FEATURE:
<221> NAME/KEY: modified_base
<222> LOCATION: (645)..(645)
<223> OTHER INFORMATION: a, c, g, t, unknown or other
<220> FEATURE:
<221> NAME/KEY: modified_base
<222> LOCATION: (648)..(648)
<223> OTHER INFORMATION: a, c, g, t, unknown or other
<220> FEATURE:
<221> NAME/KEY: modified_base
<222> LOCATION: (657)..(657)
<223> OTHER INFORMATION: a, c, g, t, unknown or other
<220> FEATURE:
<221> NAME/KEY: modified_base
<222> LOCATION: (666)..(666)
<223> OTHER INFORMATION: a, c, g, t, unknown or other
<220> FEATURE:
<221> NAME/KEY: modified_base
<222> LOCATION: (669)..(669)
<223> OTHER INFORMATION: a, c, g, t, unknown or other
<220> FEATURE:
<221> NAME/KEY: modified_base
<222> LOCATION: (675)..(675)
```

-continued

```
<223> OTHER INFORMATION: a, c, g, t, unknown or other
<220> FEATURE:
<221> NAME/KEY: modified_base
<222> LOCATION: (678)..(678)
<223> OTHER INFORMATION: a, c, g, t, unknown or other
<220> FEATURE:
<221> NAME/KEY: modified_base
<222> LOCATION: (684)..(684)
<223> OTHER INFORMATION: a, c, g, t, unknown or other
<220> FEATURE:
<221> NAME/KEY: modified_base
<222> LOCATION: (687)..(687)
<223> OTHER INFORMATION: a, c, g, t, unknown or other
<220> FEATURE:
<221> NAME/KEY: modified_base
<222> LOCATION: (690)..(690)
<223> OTHER INFORMATION: a, c, g, t, unknown or other
<220> FEATURE:
<221> NAME/KEY: modified_base
<222> LOCATION: (696)..(696)
<223> OTHER INFORMATION: a, c, g, t, unknown or other
<220> FEATURE:
<221> NAME/KEY: modified_base
<222> LOCATION: (705)..(705)
<223> OTHER INFORMATION: a, c, g, t, unknown or other
<220> FEATURE:
<221> NAME/KEY: modified_base
<222> LOCATION: (708)..(708)
<223> OTHER INFORMATION: a, c, g, t, unknown or other
<220> FEATURE:
<221> NAME/KEY: modified_base
<222> LOCATION: (714)..(714)
<223> OTHER INFORMATION: a, c, g, t, unknown or other
<220> FEATURE:
<221> NAME/KEY: modified_base
<222> LOCATION: (723)..(723)
<223> OTHER INFORMATION: a, c, g, t, unknown or other
<220> FEATURE:
<221> NAME/KEY: modified_base
<222> LOCATION: (726)..(726)
<223> OTHER INFORMATION: a, c, g, t, unknown or other
<220> FEATURE:
<221> NAME/KEY: modified_base
<222> LOCATION: (738)..(738)
<223> OTHER INFORMATION: a, c, g, t, unknown or other
<220> FEATURE:
<221> NAME/KEY: modified_base
<222> LOCATION: (744)..(744)
<223> OTHER INFORMATION: a, c, g, t, unknown or other
<220> FEATURE:
<221> NAME/KEY: modified_base
<222> LOCATION: (753)..(753)
<223> OTHER INFORMATION: a, c, g, t, unknown or other
<220> FEATURE:
<221> NAME/KEY: modified_base
<222> LOCATION: (756)..(756)
<223> OTHER INFORMATION: a, c, g, t, unknown or other
<220> FEATURE:
<221> NAME/KEY: modified_base
<222> LOCATION: (759)..(759)
<223> OTHER INFORMATION: a, c, g, t, unknown or other
<220> FEATURE:
<221> NAME/KEY: modified_base
<222> LOCATION: (765)..(765)
<223> OTHER INFORMATION: a, c, g, t, unknown or other
<220> FEATURE:
<221> NAME/KEY: modified_base
<222> LOCATION: (780)..(780)
<223> OTHER INFORMATION: a, c, g, t, unknown or other
<220> FEATURE:
<221> NAME/KEY: modified_base
<222> LOCATION: (783)..(783)
<223> OTHER INFORMATION: a, c, g, t, unknown or other
<220> FEATURE:
<221> NAME/KEY: modified_base
<222> LOCATION: (786)..(786)
<223> OTHER INFORMATION: a, c, g, t, unknown or other
<220> FEATURE:
<221> NAME/KEY: modified_base
<222> LOCATION: (792)..(792)
```

-continued

```
<223> OTHER INFORMATION: a, c, g, t, unknown or other
<220> FEATURE:
<221> NAME/KEY: modified_base
<222> LOCATION: (795)..(795)
<223> OTHER INFORMATION: a, c, g, t, unknown or other
<220> FEATURE:
<221> NAME/KEY: modified_base
<222> LOCATION: (801)..(801)
<223> OTHER INFORMATION: a, c, g, t, unknown or other
<220> FEATURE:
<221> NAME/KEY: modified_base
<222> LOCATION: (804)..(804)
<223> OTHER INFORMATION: a, c, g, t, unknown or other
<220> FEATURE:
<221> NAME/KEY: modified_base
<222> LOCATION: (807)..(807)
<223> OTHER INFORMATION: a, c, g, t, unknown or other
<220> FEATURE:
<221> NAME/KEY: modified_base
<222> LOCATION: (813)..(813)
<223> OTHER INFORMATION: a, c, g, t, unknown or other
<220> FEATURE:
<221> NAME/KEY: modified_base
<222> LOCATION: (816)..(816)
<223> OTHER INFORMATION: a, c, g, t, unknown or other
<220> FEATURE:
<221> NAME/KEY: modified_base
<222> LOCATION: (819)..(819)
<223> OTHER INFORMATION: a, c, g, t, unknown or other
<220> FEATURE:
<221> NAME/KEY: modified_base
<222> LOCATION: (822)..(822)
<223> OTHER INFORMATION: a, c, g, t, unknown or other
<220> FEATURE:
<221> NAME/KEY: modified_base
<222> LOCATION: (825)..(825)
<223> OTHER INFORMATION: a, c, g, t, unknown or other
<220> FEATURE:
<221> NAME/KEY: modified_base
<222> LOCATION: (837)..(837)
<223> OTHER INFORMATION: a, c, g, t, unknown or other
<220> FEATURE:
<221> NAME/KEY: modified_base
<222> LOCATION: (840)..(840)
<223> OTHER INFORMATION: a, c, g, t, unknown or other
<220> FEATURE:
<221> NAME/KEY: modified_base
<222> LOCATION: (846)..(846)
<223> OTHER INFORMATION: a, c, g, t, unknown or other
<220> FEATURE:
<221> NAME/KEY: modified_base
<222> LOCATION: (849)..(849)
<223> OTHER INFORMATION: a, c, g, t, unknown or other
<220> FEATURE:
<221> NAME/KEY: modified_base
<222> LOCATION: (855)..(855)
<223> OTHER INFORMATION: a, c, g, t, unknown or other
<220> FEATURE:
<221> NAME/KEY: modified_base
<222> LOCATION: (858)..(858)
<223> OTHER INFORMATION: a, c, g, t, unknown or other
<220> FEATURE:
<221> NAME/KEY: modified_base
<222> LOCATION: (861)..(861)
<223> OTHER INFORMATION: a, c, g, t, unknown or other
<220> FEATURE:
<221> NAME/KEY: modified_base
<222> LOCATION: (876)..(876)
<223> OTHER INFORMATION: a, c, g, t, unknown or other
<220> FEATURE:
<221> NAME/KEY: modified_base
<222> LOCATION: (879)..(879)
<223> OTHER INFORMATION: a, c, g, t, unknown or other
<220> FEATURE:
<221> NAME/KEY: modified_base
<222> LOCATION: (882)..(882)
<223> OTHER INFORMATION: a, c, g, t, unknown or other
<220> FEATURE:
<221> NAME/KEY: modified_base
<222> LOCATION: (888)..(888)
```

-continued

```
<223> OTHER INFORMATION: a, c, g, t, unknown or other
<220> FEATURE:
<221> NAME/KEY: modified_base
<222> LOCATION: (891)..(891)
<223> OTHER INFORMATION: a, c, g, t, unknown or other
<220> FEATURE:
<221> NAME/KEY: modified_base
<222> LOCATION: (894)..(894)
<223> OTHER INFORMATION: a, c, g, t, unknown or other
<220> FEATURE:
<221> NAME/KEY: modified_base
<222> LOCATION: (897)..(897)
<223> OTHER INFORMATION: a, c, g, t, unknown or other
<220> FEATURE:
<221> NAME/KEY: modified_base
<222> LOCATION: (900)..(900)
<223> OTHER INFORMATION: a, c, g, t, unknown or other
<220> FEATURE:
<221> NAME/KEY: modified_base
<222> LOCATION: (903)..(903)
<223> OTHER INFORMATION: a, c, g, t, unknown or other
<220> FEATURE:
<221> NAME/KEY: modified_base
<222> LOCATION: (906)..(906)
<223> OTHER INFORMATION: a, c, g, t, unknown or other
<220> FEATURE:
<221> NAME/KEY: modified_base
<222> LOCATION: (909)..(909)
<223> OTHER INFORMATION: a, c, g, t, unknown or other
<220> FEATURE:
<221> NAME/KEY: modified_base
<222> LOCATION: (912)..(912)
<223> OTHER INFORMATION: a, c, g, t, unknown or other
<220> FEATURE:
<221> NAME/KEY: modified_base
<222> LOCATION: (915)..(915)
<223> OTHER INFORMATION: a, c, g, t, unknown or other
<220> FEATURE:
<221> NAME/KEY: modified_base
<222> LOCATION: (918)..(918)
<223> OTHER INFORMATION: a, c, g, t, unknown or other
<220> FEATURE:
<221> NAME/KEY: modified_base
<222> LOCATION: (921)..(921)
<223> OTHER INFORMATION: a, c, g, t, unknown or other
<220> FEATURE:
<221> NAME/KEY: modified_base
<222> LOCATION: (924)..(924)
<223> OTHER INFORMATION: a, c, g, t, unknown or other
<220> FEATURE:
<221> NAME/KEY: modified_base
<222> LOCATION: (927)..(927)
<223> OTHER INFORMATION: a, c, g, t, unknown or other
<220> FEATURE:
<221> NAME/KEY: modified_base
<222> LOCATION: (933)..(933)
<223> OTHER INFORMATION: a, c, g, t, unknown or other
<220> FEATURE:
<221> NAME/KEY: modified_base
<222> LOCATION: (948)..(948)
<223> OTHER INFORMATION: a, c, g, t, unknown or other
<220> FEATURE:
<221> NAME/KEY: modified_base
<222> LOCATION: (954)..(954)
<223> OTHER INFORMATION: a, c, g, t, unknown or other
<220> FEATURE:
<221> NAME/KEY: modified_base
<222> LOCATION: (957)..(957)
<223> OTHER INFORMATION: a, c, g, t, unknown or other
<220> FEATURE:
<221> NAME/KEY: modified_base
<222> LOCATION: (966)..(966)
<223> OTHER INFORMATION: a, c, g, t, unknown or other
<220> FEATURE:
<221> NAME/KEY: modified_base
<222> LOCATION: (969)..(969)
<223> OTHER INFORMATION: a, c, g, t, unknown or other
<220> FEATURE:
<221> NAME/KEY: modified_base
<222> LOCATION: (975)..(975)
```

-continued

```
<223> OTHER INFORMATION: a, c, g, t, unknown or other
<220> FEATURE:
<221> NAME/KEY: modified_base
<222> LOCATION: (978)..(978)
<223> OTHER INFORMATION: a, c, g, t, unknown or other
<220> FEATURE:
<221> NAME/KEY: modified_base
<222> LOCATION: (993)..(993)
<223> OTHER INFORMATION: a, c, g, t, unknown or other
<220> FEATURE:
<221> NAME/KEY: modified_base
<222> LOCATION: (996)..(996)
<223> OTHER INFORMATION: a, c, g, t, unknown or other
<220> FEATURE:
<221> NAME/KEY: modified_base
<222> LOCATION: (999)..(999)
<223> OTHER INFORMATION: a, c, g, t, unknown or other
<220> FEATURE:
<221> NAME/KEY: modified_base
<222> LOCATION: (1005)..(1005)
<223> OTHER INFORMATION: a, c, g, t, unknown or other
<220> FEATURE:
<221> NAME/KEY: modified_base
<222> LOCATION: (1011)..(1011)
<223> OTHER INFORMATION: a, c, g, t, unknown or other
<220> FEATURE:
<221> NAME/KEY: modified_base
<222> LOCATION: (1014)..(1014)
<223> OTHER INFORMATION: a, c, g, t, unknown or other
<220> FEATURE:
<221> NAME/KEY: modified_base
<222> LOCATION: (1017)..(1017)
<223> OTHER INFORMATION: a, c, g, t, unknown or other
<220> FEATURE:
<221> NAME/KEY: modified_base
<222> LOCATION: (1035)..(1035)
<223> OTHER INFORMATION: a, c, g, t, unknown or other
<220> FEATURE:
<221> NAME/KEY: modified_base
<222> LOCATION: (1038)..(1038)
<223> OTHER INFORMATION: a, c, g, t, unknown or other
<220> FEATURE:
<221> NAME/KEY: modified_base
<222> LOCATION: (1041)..(1041)
<223> OTHER INFORMATION: a, c, g, t, unknown or other
<220> FEATURE:
<221> NAME/KEY: modified_base
<222> LOCATION: (1044)..(1044)
<223> OTHER INFORMATION: a, c, g, t, unknown or other
<220> FEATURE:
<221> NAME/KEY: modified_base
<222> LOCATION: (1047)..(1047)
<223> OTHER INFORMATION: a, c, g, t, unknown or other
<220> FEATURE:
<221> NAME/KEY: modified_base
<222> LOCATION: (1050)..(1050)
<223> OTHER INFORMATION: a, c, g, t, unknown or other
<220> FEATURE:
<221> NAME/KEY: modified_base
<222> LOCATION: (1056)..(1056)
<223> OTHER INFORMATION: a, c, g, t, unknown or other
<220> FEATURE:
<221> NAME/KEY: modified_base
<222> LOCATION: (1059)..(1059)
<223> OTHER INFORMATION: a, c, g, t, unknown or other
<220> FEATURE:
<221> NAME/KEY: modified_base
<222> LOCATION: (1062)..(1062)
<223> OTHER INFORMATION: a, c, g, t, unknown or other
<220> FEATURE:
<221> NAME/KEY: modified_base
<222> LOCATION: (1065)..(1065)
<223> OTHER INFORMATION: a, c, g, t, unknown or other
<220> FEATURE:
<221> NAME/KEY: modified_base
<222> LOCATION: (1068)..(1068)
<223> OTHER INFORMATION: a, c, g, t, unknown or other
<220> FEATURE:
<221> NAME/KEY: modified_base
<222> LOCATION: (1071)..(1071)
```

```
<223> OTHER INFORMATION: a, c, g, t, unknown or other
<220> FEATURE:
<221> NAME/KEY: modified_base
<222> LOCATION: (1074)..(1074)
<223> OTHER INFORMATION: a, c, g, t, unknown or other
<220> FEATURE:
<221> NAME/KEY: modified_base
<222> LOCATION: (1077)..(1077)
<223> OTHER INFORMATION: a, c, g, t, unknown or other
<220> FEATURE:
<221> NAME/KEY: modified_base
<222> LOCATION: (1086)..(1086)
<223> OTHER INFORMATION: a, c, g, t, unknown or other
<220> FEATURE:
<221> NAME/KEY: modified_base
<222> LOCATION: (1089)..(1089)
<223> OTHER INFORMATION: a, c, g, t, unknown or other
<220> FEATURE:
<221> NAME/KEY: modified_base
<222> LOCATION: (1095)..(1095)
<223> OTHER INFORMATION: a, c, g, t, unknown or other
<220> FEATURE:
<221> NAME/KEY: modified_base
<222> LOCATION: (1098)..(1098)
<223> OTHER INFORMATION: a, c, g, t, unknown or other
<220> FEATURE:
<221> NAME/KEY: modified_base
<222> LOCATION: (1101)..(1101)
<223> OTHER INFORMATION: a, c, g, t, unknown or other
<220> FEATURE:
<221> NAME/KEY: modified_base
<222> LOCATION: (1104)..(1104)
<223> OTHER INFORMATION: a, c, g, t, unknown or other
<220> FEATURE:
<221> NAME/KEY: modified_base
<222> LOCATION: (1107)..(1107)
<223> OTHER INFORMATION: a, c, g, t, unknown or other
<220> FEATURE:
<221> NAME/KEY: modified_base
<222> LOCATION: (1110)..(1110)
<223> OTHER INFORMATION: a, c, g, t, unknown or other
<220> FEATURE:
<221> NAME/KEY: modified_base
<222> LOCATION: (1113)..(1113)
<223> OTHER INFORMATION: a, c, g, t, unknown or other
<220> FEATURE:
<221> NAME/KEY: modified_base
<222> LOCATION: (1125)..(1125)
<223> OTHER INFORMATION: a, c, g, t, unknown or other
<220> FEATURE:
<221> NAME/KEY: modified_base
<222> LOCATION: (1128)..(1128)
<223> OTHER INFORMATION: a, c, g, t, unknown or other
<220> FEATURE:
<221> NAME/KEY: modified_base
<222> LOCATION: (1131)..(1131)
<223> OTHER INFORMATION: a, c, g, t, unknown or other
<220> FEATURE:
<221> NAME/KEY: modified_base
<222> LOCATION: (1137)..(1137)
<223> OTHER INFORMATION: a, c, g, t, unknown or other
<220> FEATURE:
<221> NAME/KEY: modified_base
<222> LOCATION: (1140)..(1140)
<223> OTHER INFORMATION: a, c, g, t, unknown or other
<220> FEATURE:
<221> NAME/KEY: modified_base
<222> LOCATION: (1146)..(1146)
<223> OTHER INFORMATION: a, c, g, t, unknown or other
<220> FEATURE:
<221> NAME/KEY: modified_base
<222> LOCATION: (1152)..(1152)
<223> OTHER INFORMATION: a, c, g, t, unknown or other
<220> FEATURE:
<221> NAME/KEY: modified_base
<222> LOCATION: (1155)..(1155)
<223> OTHER INFORMATION: a, c, g, t, unknown or other
<220> FEATURE:
<221> NAME/KEY: modified_base
<222> LOCATION: (1158)..(1158)
```

```
-continued

<223> OTHER INFORMATION: a, c, g, t, unknown or other
<220> FEATURE:
<221> NAME/KEY: modified_base
<222> LOCATION: (1164)..(1164)
<223> OTHER INFORMATION: a, c, g, t, unknown or other
<220> FEATURE:
<221> NAME/KEY: modified_base
<222> LOCATION: (1170)..(1170)
<223> OTHER INFORMATION: a, c, g, t, unknown or other
<220> FEATURE:
<221> NAME/KEY: modified_base
<222> LOCATION: (1173)..(1173)
<223> OTHER INFORMATION: a, c, g, t, unknown or other
<220> FEATURE:
<221> NAME/KEY: modified_base
<222> LOCATION: (1185)..(1185)
<223> OTHER INFORMATION: a, c, g, t, unknown or other
<220> FEATURE:
<221> NAME/KEY: modified_base
<222> LOCATION: (1206)..(1206)
<223> OTHER INFORMATION: a, c, g, t, unknown or other
<220> FEATURE:
<221> NAME/KEY: modified_base
<222> LOCATION: (1209)..(1209)
<223> OTHER INFORMATION: a, c, g, t, unknown or other
<220> FEATURE:
<221> NAME/KEY: modified_base
<222> LOCATION: (1218)..(1218)
<223> OTHER INFORMATION: a, c, g, t, unknown or other
<220> FEATURE:
<221> NAME/KEY: modified_base
<222> LOCATION: (1221)..(1221)
<223> OTHER INFORMATION: a, c, g, t, unknown or other
<220> FEATURE:
<221> NAME/KEY: modified_base
<222> LOCATION: (1236)..(1236)
<223> OTHER INFORMATION: a, c, g, t, unknown or other
<220> FEATURE:
<221> NAME/KEY: modified_base
<222> LOCATION: (1239)..(1239)
<223> OTHER INFORMATION: a, c, g, t, unknown or other
<220> FEATURE:
<221> NAME/KEY: modified_base
<222> LOCATION: (1242)..(1242)
<223> OTHER INFORMATION: a, c, g, t, unknown or other
<220> FEATURE:
<221> NAME/KEY: modified_base
<222> LOCATION: (1245)..(1245)
<223> OTHER INFORMATION: a, c, g, t, unknown or other
<220> FEATURE:
<221> NAME/KEY: modified_base
<222> LOCATION: (1251)..(1251)
<223> OTHER INFORMATION: a, c, g, t, unknown or other
<220> FEATURE:
<221> NAME/KEY: modified_base
<222> LOCATION: (1254)..(1254)
<223> OTHER INFORMATION: a, c, g, t, unknown or other
<220> FEATURE:
<221> NAME/KEY: modified_base
<222> LOCATION: (1257)..(1257)
<223> OTHER INFORMATION: a, c, g, t, unknown or other
<220> FEATURE:
<221> NAME/KEY: modified_base
<222> LOCATION: (1272)..(1272)
<223> OTHER INFORMATION: a, c, g, t, unknown or other
<220> FEATURE:
<221> NAME/KEY: modified_base
<222> LOCATION: (1275)..(1275)
<223> OTHER INFORMATION: a, c, g, t, unknown or other
<220> FEATURE:
<221> NAME/KEY: modified_base
<222> LOCATION: (1278)..(1278)
<223> OTHER INFORMATION: a, c, g, t, unknown or other
<220> FEATURE:
<221> NAME/KEY: modified_base
<222> LOCATION: (1281)..(1281)
<223> OTHER INFORMATION: a, c, g, t, unknown or other
<220> FEATURE:
<221> NAME/KEY: modified_base
<222> LOCATION: (1284)..(1284)
```

-continued

```
<223> OTHER INFORMATION: a, c, g, t, unknown or other
<220> FEATURE:
<221> NAME/KEY: modified_base
<222> LOCATION: (1287)..(1287)
<223> OTHER INFORMATION: a, c, g, t, unknown or other
<220> FEATURE:
<221> NAME/KEY: modified_base
<222> LOCATION: (1299)..(1299)
<223> OTHER INFORMATION: a, c, g, t, unknown or other
<220> FEATURE:
<221> NAME/KEY: modified_base
<222> LOCATION: (1302)..(1302)
<223> OTHER INFORMATION: a, c, g, t, unknown or other
<220> FEATURE:
<221> NAME/KEY: modified_base
<222> LOCATION: (1308)..(1308)
<223> OTHER INFORMATION: a, c, g, t, unknown or other
<220> FEATURE:
<221> NAME/KEY: modified_base
<222> LOCATION: (1311)..(1311)
<223> OTHER INFORMATION: a, c, g, t, unknown or other
<220> FEATURE:
<221> NAME/KEY: modified_base
<222> LOCATION: (1314)..(1314)
<223> OTHER INFORMATION: a, c, g, t, unknown or other
<220> FEATURE:
<221> NAME/KEY: modified_base
<222> LOCATION: (1323)..(1323)
<223> OTHER INFORMATION: a, c, g, t, unknown or other
<220> FEATURE:
<221> NAME/KEY: modified_base
<222> LOCATION: (1326)..(1326)
<223> OTHER INFORMATION: a, c, g, t, unknown or other
<220> FEATURE:
<221> NAME/KEY: modified_base
<222> LOCATION: (1332)..(1332)
<223> OTHER INFORMATION: a, c, g, t, unknown or other
<220> FEATURE:
<221> NAME/KEY: modified_base
<222> LOCATION: (1335)..(1335)
<223> OTHER INFORMATION: a, c, g, t, unknown or other
<220> FEATURE:
<221> NAME/KEY: modified_base
<222> LOCATION: (1341)..(1341)
<223> OTHER INFORMATION: a, c, g, t, unknown or other
<220> FEATURE:
<221> NAME/KEY: modified_base
<222> LOCATION: (1350)..(1350)
<223> OTHER INFORMATION: a, c, g, t, unknown or other
<220> FEATURE:
<221> NAME/KEY: modified_base
<222> LOCATION: (1353)..(1353)
<223> OTHER INFORMATION: a, c, g, t, unknown or other
<220> FEATURE:
<221> NAME/KEY: modified_base
<222> LOCATION: (1356)..(1356)
<223> OTHER INFORMATION: a, c, g, t, unknown or other
<220> FEATURE:
<221> NAME/KEY: modified_base
<222> LOCATION: (1362)..(1362)
<223> OTHER INFORMATION: a, c, g, t, unknown or other
<220> FEATURE:
<221> NAME/KEY: modified_base
<222> LOCATION: (1368)..(1368)
<223> OTHER INFORMATION: a, c, g, t, unknown or other
<220> FEATURE:
<221> NAME/KEY: modified_base
<222> LOCATION: (1374)..(1374)
<223> OTHER INFORMATION: a, c, g, t, unknown or other
<220> FEATURE:
<221> NAME/KEY: modified_base
<222> LOCATION: (1377)..(1377)
<223> OTHER INFORMATION: a, c, g, t, unknown or other
<220> FEATURE:
<221> NAME/KEY: modified_base
<222> LOCATION: (1383)..(1383)
<223> OTHER INFORMATION: a, c, g, t, unknown or other
<220> FEATURE:
<221> NAME/KEY: modified_base
<222> LOCATION: (1389)..(1389)
```

-continued

```
<223> OTHER INFORMATION: a, c, g, t, unknown or other
<220> FEATURE:
<221> NAME/KEY: modified_base
<222> LOCATION: (1398)..(1398)
<223> OTHER INFORMATION: a, c, g, t, unknown or other
<220> FEATURE:
<221> NAME/KEY: modified_base
<222> LOCATION: (1401)..(1401)
<223> OTHER INFORMATION: a, c, g, t, unknown or other
<220> FEATURE:
<221> NAME/KEY: modified_base
<222> LOCATION: (1419)..(1419)
<223> OTHER INFORMATION: a, c, g, t, unknown or other
<220> FEATURE:
<221> NAME/KEY: modified_base
<222> LOCATION: (1422)..(1422)
<223> OTHER INFORMATION: a, c, g, t, unknown or other
<220> FEATURE:
<221> NAME/KEY: modified_base
<222> LOCATION: (1425)..(1425)
<223> OTHER INFORMATION: a, c, g, t, unknown or other
<220> FEATURE:
<221> NAME/KEY: modified_base
<222> LOCATION: (1431)..(1431)
<223> OTHER INFORMATION: a, c, g, t, unknown or other
<220> FEATURE:
<221> NAME/KEY: modified_base
<222> LOCATION: (1440)..(1440)
<223> OTHER INFORMATION: a, c, g, t, unknown or other
<220> FEATURE:
<221> NAME/KEY: modified_base
<222> LOCATION: (1443)..(1443)
<223> OTHER INFORMATION: a, c, g, t, unknown or other
<220> FEATURE:
<221> NAME/KEY: modified_base
<222> LOCATION: (1446)..(1446)
<223> OTHER INFORMATION: a, c, g, t, unknown or other
<220> FEATURE:
<221> NAME/KEY: modified_base
<222> LOCATION: (1449)..(1449)
<223> OTHER INFORMATION: a, c, g, t, unknown or other
<220> FEATURE:
<221> NAME/KEY: modified_base
<222> LOCATION: (1461)..(1461)
<223> OTHER INFORMATION: a, c, g, t, unknown or other
<220> FEATURE:
<221> NAME/KEY: modified_base
<222> LOCATION: (1467)..(1467)
<223> OTHER INFORMATION: a, c, g, t, unknown or other
<220> FEATURE:
<221> NAME/KEY: modified_base
<222> LOCATION: (1470)..(1470)
<223> OTHER INFORMATION: a, c, g, t, unknown or other
<220> FEATURE:
<221> NAME/KEY: modified_base
<222> LOCATION: (1473)..(1473)
<223> OTHER INFORMATION: a, c, g, t, unknown or other
<220> FEATURE:
<221> NAME/KEY: modified_base
<222> LOCATION: (1494)..(1494)
<223> OTHER INFORMATION: a, c, g, t, unknown or other
<220> FEATURE:
<221> NAME/KEY: modified_base
<222> LOCATION: (1497)..(1497)
<223> OTHER INFORMATION: a, c, g, t, unknown or other
<220> FEATURE:
<221> NAME/KEY: modified_base
<222> LOCATION: (1500)..(1500)
<223> OTHER INFORMATION: a, c, g, t, unknown or other
<220> FEATURE:
<221> NAME/KEY: modified_base
<222> LOCATION: (1503)..(1503)
<223> OTHER INFORMATION: a, c, g, t, unknown or other
<220> FEATURE:
<221> NAME/KEY: modified_base
<222> LOCATION: (1509)..(1509)
<223> OTHER INFORMATION: a, c, g, t, unknown or other
<220> FEATURE:
<221> NAME/KEY: modified_base
<222> LOCATION: (1512)..(1512)
```

-continued

```
<223> OTHER INFORMATION: a, c, g, t, unknown or other
<220> FEATURE:
<221> NAME/KEY: modified_base
<222> LOCATION: (1515)..(1515)
<223> OTHER INFORMATION: a, c, g, t, unknown or other
<220> FEATURE:
<221> NAME/KEY: modified_base
<222> LOCATION: (1524)..(1524)
<223> OTHER INFORMATION: a, c, g, t, unknown or other
<220> FEATURE:
<221> NAME/KEY: modified_base
<222> LOCATION: (1527)..(1527)
<223> OTHER INFORMATION: a, c, g, t, unknown or other
<220> FEATURE:
<221> NAME/KEY: modified_base
<222> LOCATION: (1533)..(1533)
<223> OTHER INFORMATION: a, c, g, t, unknown or other
<220> FEATURE:
<221> NAME/KEY: modified_base
<222> LOCATION: (1539)..(1539)
<223> OTHER INFORMATION: a, c, g, t, unknown or other
<220> FEATURE:
<221> NAME/KEY: modified_base
<222> LOCATION: (1542)..(1542)
<223> OTHER INFORMATION: a, c, g, t, unknown or other
<220> FEATURE:
<221> NAME/KEY: modified_base
<222> LOCATION: (1545)..(1545)
<223> OTHER INFORMATION: a, c, g, t, unknown or other
<220> FEATURE:
<221> NAME/KEY: modified_base
<222> LOCATION: (1548)..(1548)
<223> OTHER INFORMATION: a, c, g, t, unknown or other
<220> FEATURE:
<221> NAME/KEY: modified_base
<222> LOCATION: (1569)..(1569)
<223> OTHER INFORMATION: a, c, g, t, unknown or other
<220> FEATURE:
<221> NAME/KEY: modified_base
<222> LOCATION: (1578)..(1578)
<223> OTHER INFORMATION: a, c, g, t, unknown or other
<220> FEATURE:
<221> NAME/KEY: modified_base
<222> LOCATION: (1584)..(1584)
<223> OTHER INFORMATION: a, c, g, t, unknown or other
<220> FEATURE:
<221> NAME/KEY: modified_base
<222> LOCATION: (1587)..(1587)
<223> OTHER INFORMATION: a, c, g, t, unknown or other
<220> FEATURE:
<221> NAME/KEY: modified_base
<222> LOCATION: (1590)..(1590)
<223> OTHER INFORMATION: a, c, g, t, unknown or other
<220> FEATURE:
<221> NAME/KEY: modified_base
<222> LOCATION: (1593)..(1593)
<223> OTHER INFORMATION: a, c, g, t, unknown or other
<220> FEATURE:
<221> NAME/KEY: modified_base
<222> LOCATION: (1605)..(1605)
<223> OTHER INFORMATION: a, c, g, t, unknown or other
<220> FEATURE:
<221> NAME/KEY: modified_base
<222> LOCATION: (1608)..(1608)
<223> OTHER INFORMATION: a, c, g, t, unknown or other
<220> FEATURE:
<221> NAME/KEY: modified_base
<222> LOCATION: (1611)..(1611)
<223> OTHER INFORMATION: a, c, g, t, unknown or other
<220> FEATURE:
<221> NAME/KEY: modified_base
<222> LOCATION: (1614)..(1614)
<223> OTHER INFORMATION: a, c, g, t, unknown or other
<220> FEATURE:
<221> NAME/KEY: modified_base
<222> LOCATION: (1617)..(1617)
<223> OTHER INFORMATION: a, c, g, t, unknown or other
<220> FEATURE:
<221> NAME/KEY: modified_base
<222> LOCATION: (1620)..(1620)
```

-continued

```
<223> OTHER INFORMATION: a, c, g, t, unknown or other
<220> FEATURE:
<221> NAME/KEY: modified_base
<222> LOCATION: (1623)..(1623)
<223> OTHER INFORMATION: a, c, g, t, unknown or other
<220> FEATURE:
<221> NAME/KEY: modified_base
<222> LOCATION: (1632)..(1632)
<223> OTHER INFORMATION: a, c, g, t, unknown or other
<220> FEATURE:
<221> NAME/KEY: modified_base
<222> LOCATION: (1641)..(1641)
<223> OTHER INFORMATION: a, c, g, t, unknown or other
<220> FEATURE:
<221> NAME/KEY: modified_base
<222> LOCATION: (1644)..(1644)
<223> OTHER INFORMATION: a, c, g, t, unknown or other
<220> FEATURE:
<221> NAME/KEY: modified_base
<222> LOCATION: (1647)..(1647)
<223> OTHER INFORMATION: a, c, g, t, unknown or other
<220> FEATURE:
<221> NAME/KEY: modified_base
<222> LOCATION: (1650)..(1650)
<223> OTHER INFORMATION: a, c, g, t, unknown or other
<220> FEATURE:
<221> NAME/KEY: modified_base
<222> LOCATION: (1656)..(1656)
<223> OTHER INFORMATION: a, c, g, t, unknown or other
<220> FEATURE:
<221> NAME/KEY: modified_base
<222> LOCATION: (1662)..(1662)
<223> OTHER INFORMATION: a, c, g, t, unknown or other
<220> FEATURE:
<221> NAME/KEY: modified_base
<222> LOCATION: (1665)..(1665)
<223> OTHER INFORMATION: a, c, g, t, unknown or other
<220> FEATURE:
<221> NAME/KEY: modified_base
<222> LOCATION: (1668)..(1668)
<223> OTHER INFORMATION: a, c, g, t, unknown or other
<220> FEATURE:
<221> NAME/KEY: modified_base
<222> LOCATION: (1671)..(1671)
<223> OTHER INFORMATION: a, c, g, t, unknown or other
<220> FEATURE:
<221> NAME/KEY: modified_base
<222> LOCATION: (1674)..(1674)
<223> OTHER INFORMATION: a, c, g, t, unknown or other
<220> FEATURE:
<221> NAME/KEY: modified_base
<222> LOCATION: (1683)..(1683)
<223> OTHER INFORMATION: a, c, g, t, unknown or other
<220> FEATURE:
<221> NAME/KEY: modified_base
<222> LOCATION: (1686)..(1686)
<223> OTHER INFORMATION: a, c, g, t, unknown or other
<220> FEATURE:
<221> NAME/KEY: modified_base
<222> LOCATION: (1695)..(1695)
<223> OTHER INFORMATION: a, c, g, t, unknown or other
<220> FEATURE:
<221> NAME/KEY: modified_base
<222> LOCATION: (1701)..(1701)
<223> OTHER INFORMATION: a, c, g, t, unknown or other
<220> FEATURE:
<221> NAME/KEY: modified_base
<222> LOCATION: (1707)..(1707)
<223> OTHER INFORMATION: a, c, g, t, unknown or other
<220> FEATURE:
<221> NAME/KEY: modified_base
<222> LOCATION: (1710)..(1710)
<223> OTHER INFORMATION: a, c, g, t, unknown or other
<220> FEATURE:
<221> NAME/KEY: modified_base
<222> LOCATION: (1719)..(1719)
<223> OTHER INFORMATION: a, c, g, t, unknown or other
<220> FEATURE:
<221> NAME/KEY: modified_base
<222> LOCATION: (1725)..(1725)
```

```
<223> OTHER INFORMATION: a, c, g, t, unknown or other
<220> FEATURE:
<221> NAME/KEY: modified_base
<222> LOCATION: (1728)..(1728)
<223> OTHER INFORMATION: a, c, g, t, unknown or other
<220> FEATURE:
<221> NAME/KEY: modified_base
<222> LOCATION: (1740)..(1740)
<223> OTHER INFORMATION: a, c, g, t, unknown or other
<220> FEATURE:
<221> NAME/KEY: modified_base
<222> LOCATION: (1743)..(1743)
<223> OTHER INFORMATION: a, c, g, t, unknown or other
<220> FEATURE:
<221> NAME/KEY: modified_base
<222> LOCATION: (1752)..(1752)
<223> OTHER INFORMATION: a, c, g, t, unknown or other
<220> FEATURE:
<221> NAME/KEY: modified_base
<222> LOCATION: (1755)..(1755)
<223> OTHER INFORMATION: a, c, g, t, unknown or other
<220> FEATURE:
<221> NAME/KEY: modified_base
<222> LOCATION: (1761)..(1761)
<223> OTHER INFORMATION: a, c, g, t, unknown or other
<220> FEATURE:
<221> NAME/KEY: modified_base
<222> LOCATION: (1767)..(1767)
<223> OTHER INFORMATION: a, c, g, t, unknown or other
<220> FEATURE:
<221> NAME/KEY: modified_base
<222> LOCATION: (1773)..(1773)
<223> OTHER INFORMATION: a, c, g, t, unknown or other
<220> FEATURE:
<221> NAME/KEY: modified_base
<222> LOCATION: (1785)..(1785)
<223> OTHER INFORMATION: a, c, g, t, unknown or other
<220> FEATURE:
<221> NAME/KEY: modified_base
<222> LOCATION: (1791)..(1791)
<223> OTHER INFORMATION: a, c, g, t, unknown or other
<220> FEATURE:
<221> NAME/KEY: modified_base
<222> LOCATION: (1806)..(1806)
<223> OTHER INFORMATION: a, c, g, t, unknown or other
<220> FEATURE:
<221> NAME/KEY: modified_base
<222> LOCATION: (1815)..(1815)
<223> OTHER INFORMATION: a, c, g, t, unknown or other
<220> FEATURE:
<221> NAME/KEY: modified_base
<222> LOCATION: (1821)..(1821)
<223> OTHER INFORMATION: a, c, g, t, unknown or other
<220> FEATURE:
<221> NAME/KEY: modified_base
<222> LOCATION: (1824)..(1824)
<223> OTHER INFORMATION: a, c, g, t, unknown or other
<220> FEATURE:
<221> NAME/KEY: modified_base
<222> LOCATION: (1839)..(1839)
<223> OTHER INFORMATION: a, c, g, t, unknown or other
<220> FEATURE:
<221> NAME/KEY: modified_base
<222> LOCATION: (1842)..(1842)
<223> OTHER INFORMATION: a, c, g, t, unknown or other
<220> FEATURE:
<221> NAME/KEY: modified_base
<222> LOCATION: (1848)..(1848)
<223> OTHER INFORMATION: a, c, g, t, unknown or other
<220> FEATURE:
<221> NAME/KEY: modified_base
<222> LOCATION: (1851)..(1851)
<223> OTHER INFORMATION: a, c, g, t, unknown or other
<220> FEATURE:
<221> NAME/KEY: modified_base
<222> LOCATION: (1857)..(1857)
<223> OTHER INFORMATION: a, c, g, t, unknown or other
<220> FEATURE:
<221> NAME/KEY: modified_base
<222> LOCATION: (1860)..(1860)
```

```
<223> OTHER INFORMATION: a, c, g, t, unknown or other
<220> FEATURE:
<221> NAME/KEY: modified_base
<222> LOCATION: (1863)..(1863)
<223> OTHER INFORMATION: a, c, g, t, unknown or other
<220> FEATURE:
<221> NAME/KEY: modified_base
<222> LOCATION: (1881)..(1881)
<223> OTHER INFORMATION: a, c, g, t, unknown or other
<220> FEATURE:
<221> NAME/KEY: modified_base
<222> LOCATION: (1884)..(1884)
<223> OTHER INFORMATION: a, c, g, t, unknown or other
<220> FEATURE:
<221> NAME/KEY: modified_base
<222> LOCATION: (1887)..(1887)
<223> OTHER INFORMATION: a, c, g, t, unknown or other
<220> FEATURE:
<221> NAME/KEY: modified_base
<222> LOCATION: (1899)..(1899)
<223> OTHER INFORMATION: a, c, g, t, unknown or other
<220> FEATURE:
<221> NAME/KEY: modified_base
<222> LOCATION: (1902)..(1902)
<223> OTHER INFORMATION: a, c, g, t, unknown or other
<220> FEATURE:
<221> NAME/KEY: modified_base
<222> LOCATION: (1905)..(1905)
<223> OTHER INFORMATION: a, c, g, t, unknown or other
<220> FEATURE:
<221> NAME/KEY: modified_base
<222> LOCATION: (1911)..(1911)
<223> OTHER INFORMATION: a, c, g, t, unknown or other
<220> FEATURE:
<221> NAME/KEY: modified_base
<222> LOCATION: (1914)..(1914)
<223> OTHER INFORMATION: a, c, g, t, unknown or other
<220> FEATURE:
<221> NAME/KEY: modified_base
<222> LOCATION: (1917)..(1917)
<223> OTHER INFORMATION: a, c, g, t, unknown or other
<220> FEATURE:
<221> NAME/KEY: modified_base
<222> LOCATION: (1929)..(1929)
<223> OTHER INFORMATION: a, c, g, t, unknown or other
<220> FEATURE:
<221> NAME/KEY: modified_base
<222> LOCATION: (1935)..(1935)
<223> OTHER INFORMATION: a, c, g, t, unknown or other
<220> FEATURE:
<221> NAME/KEY: modified_base
<222> LOCATION: (1944)..(1944)
<223> OTHER INFORMATION: a, c, g, t, unknown or other
<220> FEATURE:
<221> NAME/KEY: modified_base
<222> LOCATION: (1947)..(1947)
<223> OTHER INFORMATION: a, c, g, t, unknown or other
<220> FEATURE:
<221> NAME/KEY: modified_base
<222> LOCATION: (1950)..(1950)
<223> OTHER INFORMATION: a, c, g, t, unknown or other
<220> FEATURE:
<221> NAME/KEY: modified_base
<222> LOCATION: (1953)..(1953)
<223> OTHER INFORMATION: a, c, g, t, unknown or other
<220> FEATURE:
<221> NAME/KEY: modified_base
<222> LOCATION: (1956)..(1956)
<223> OTHER INFORMATION: a, c, g, t, unknown or other
<220> FEATURE:
<221> NAME/KEY: modified_base
<222> LOCATION: (1959)..(1959)
<223> OTHER INFORMATION: a, c, g, t, unknown or other
<220> FEATURE:
<221> NAME/KEY: modified_base
<222> LOCATION: (1965)..(1965)
<223> OTHER INFORMATION: a, c, g, t, unknown or other
<220> FEATURE:
<221> NAME/KEY: modified_base
<222> LOCATION: (1968)..(1968)
```

-continued

```
<223> OTHER INFORMATION: a, c, g, t, unknown or other
<220> FEATURE:
<221> NAME/KEY: modified_base
<222> LOCATION: (1974)..(1974)
<223> OTHER INFORMATION: a, c, g, t, unknown or other
<220> FEATURE:
<221> NAME/KEY: modified_base
<222> LOCATION: (1977)..(1977)
<223> OTHER INFORMATION: a, c, g, t, unknown or other
<220> FEATURE:
<221> NAME/KEY: modified_base
<222> LOCATION: (1980)..(1980)
<223> OTHER INFORMATION: a, c, g, t, unknown or other
<220> FEATURE:
<221> NAME/KEY: modified_base
<222> LOCATION: (1983)..(1983)
<223> OTHER INFORMATION: a, c, g, t, unknown or other
<220> FEATURE:
<221> NAME/KEY: modified_base
<222> LOCATION: (1986)..(1986)
<223> OTHER INFORMATION: a, c, g, t, unknown or other
<220> FEATURE:
<221> NAME/KEY: modified_base
<222> LOCATION: (1992)..(1992)
<223> OTHER INFORMATION: a, c, g, t, unknown or other
<220> FEATURE:
<221> NAME/KEY: modified_base
<222> LOCATION: (1998)..(1998)
<223> OTHER INFORMATION: a, c, g, t, unknown or other
<220> FEATURE:
<221> NAME/KEY: modified_base
<222> LOCATION: (2001)..(2001)
<223> OTHER INFORMATION: a, c, g, t, unknown or other
<220> FEATURE:
<221> NAME/KEY: modified_base
<222> LOCATION: (2004)..(2004)
<223> OTHER INFORMATION: a, c, g, t, unknown or other
<220> FEATURE:
<221> NAME/KEY: modified_base
<222> LOCATION: (2007)..(2007)
<223> OTHER INFORMATION: a, c, g, t, unknown or other
<220> FEATURE:
<221> NAME/KEY: modified_base
<222> LOCATION: (2010)..(2010)
<223> OTHER INFORMATION: a, c, g, t, unknown or other
<220> FEATURE:
<221> NAME/KEY: modified_base
<222> LOCATION: (2013)..(2013)
<223> OTHER INFORMATION: a, c, g, t, unknown or other
<220> FEATURE:
<221> NAME/KEY: modified_base
<222> LOCATION: (2016)..(2016)
<223> OTHER INFORMATION: a, c, g, t, unknown or other
<220> FEATURE:
<221> NAME/KEY: modified_base
<222> LOCATION: (2019)..(2019)
<223> OTHER INFORMATION: a, c, g, t, unknown or other
<220> FEATURE:
<221> NAME/KEY: modified_base
<222> LOCATION: (2025)..(2025)
<223> OTHER INFORMATION: a, c, g, t, unknown or other
<220> FEATURE:
<221> NAME/KEY: modified_base
<222> LOCATION: (2028)..(2028)
<223> OTHER INFORMATION: a, c, g, t, unknown or other
<220> FEATURE:
<221> NAME/KEY: modified_base
<222> LOCATION: (2031)..(2031)
<223> OTHER INFORMATION: a, c, g, t, unknown or other
<220> FEATURE:
<221> NAME/KEY: modified_base
<222> LOCATION: (2034)..(2034)
<223> OTHER INFORMATION: a, c, g, t, unknown or other
<220> FEATURE:
<221> NAME/KEY: modified_base
<222> LOCATION: (2037)..(2037)
<223> OTHER INFORMATION: a, c, g, t, unknown or other
<220> FEATURE:
<221> NAME/KEY: modified_base
<222> LOCATION: (2040)..(2040)
```

-continued

```
<223> OTHER INFORMATION: a, c, g, t, unknown or other
<220> FEATURE:
<221> NAME/KEY: modified_base
<222> LOCATION: (2043)..(2043)
<223> OTHER INFORMATION: a, c, g, t, unknown or other
<220> FEATURE:
<221> NAME/KEY: modified_base
<222> LOCATION: (2046)..(2046)
<223> OTHER INFORMATION: a, c, g, t, unknown or other
<220> FEATURE:
<221> NAME/KEY: modified_base
<222> LOCATION: (2049)..(2049)
<223> OTHER INFORMATION: a, c, g, t, unknown or other
<220> FEATURE:
<221> NAME/KEY: modified_base
<222> LOCATION: (2055)..(2055)
<223> OTHER INFORMATION: a, c, g, t, unknown or other
<220> FEATURE:
<221> NAME/KEY: modified_base
<222> LOCATION: (2064)..(2064)
<223> OTHER INFORMATION: a, c, g, t, unknown or other
<220> FEATURE:
<221> NAME/KEY: modified_base
<222> LOCATION: (2070)..(2070)
<223> OTHER INFORMATION: a, c, g, t, unknown or other
<220> FEATURE:
<221> NAME/KEY: modified_base
<222> LOCATION: (2073)..(2073)
<223> OTHER INFORMATION: a, c, g, t, unknown or other
<220> FEATURE:
<221> NAME/KEY: modified_base
<222> LOCATION: (2076)..(2076)
<223> OTHER INFORMATION: a, c, g, t, unknown or other
<220> FEATURE:
<221> NAME/KEY: modified_base
<222> LOCATION: (2079)..(2079)
<223> OTHER INFORMATION: a, c, g, t, unknown or other
<220> FEATURE:
<221> NAME/KEY: modified_base
<222> LOCATION: (2082)..(2082)
<223> OTHER INFORMATION: a, c, g, t, unknown or other
<220> FEATURE:
<221> NAME/KEY: modified_base
<222> LOCATION: (2085)..(2085)
<223> OTHER INFORMATION: a, c, g, t, unknown or other
<220> FEATURE:
<221> NAME/KEY: modified_base
<222> LOCATION: (2088)..(2088)
<223> OTHER INFORMATION: a, c, g, t, unknown or other
<220> FEATURE:
<221> NAME/KEY: modified_base
<222> LOCATION: (2091)..(2091)
<223> OTHER INFORMATION: a, c, g, t, unknown or other
<220> FEATURE:
<221> NAME/KEY: modified_base
<222> LOCATION: (2103)..(2103)
<223> OTHER INFORMATION: a, c, g, t, unknown or other
<220> FEATURE:
<221> NAME/KEY: modified_base
<222> LOCATION: (2106)..(2106)
<223> OTHER INFORMATION: a, c, g, t, unknown or other
<220> FEATURE:
<221> NAME/KEY: modified_base
<222> LOCATION: (2109)..(2109)
<223> OTHER INFORMATION: a, c, g, t, unknown or other
<220> FEATURE:
<221> NAME/KEY: modified_base
<222> LOCATION: (2115)..(2115)
<223> OTHER INFORMATION: a, c, g, t, unknown or other
<220> FEATURE:
<221> NAME/KEY: modified_base
<222> LOCATION: (2118)..(2118)
<223> OTHER INFORMATION: a, c, g, t, unknown or other
<220> FEATURE:
<221> NAME/KEY: modified_base
<222> LOCATION: (2121)..(2121)
<223> OTHER INFORMATION: a, c, g, t, unknown or other
<220> FEATURE:
<221> NAME/KEY: modified_base
<222> LOCATION: (2124)..(2124)
```

-continued

```
<223> OTHER INFORMATION: a, c, g, t, unknown or other
<220> FEATURE:
<221> NAME/KEY: modified_base
<222> LOCATION: (2127)..(2127)
<223> OTHER INFORMATION: a, c, g, t, unknown or other
<220> FEATURE:
<221> NAME/KEY: modified_base
<222> LOCATION: (2130)..(2130)
<223> OTHER INFORMATION: a, c, g, t, unknown or other
<220> FEATURE:
<221> NAME/KEY: modified_base
<222> LOCATION: (2133)..(2133)
<223> OTHER INFORMATION: a, c, g, t, unknown or other
<220> FEATURE:
<221> NAME/KEY: modified_base
<222> LOCATION: (2154)..(2154)
<223> OTHER INFORMATION: a, c, g, t, unknown or other
<220> FEATURE:
<221> NAME/KEY: modified_base
<222> LOCATION: (2157)..(2157)
<223> OTHER INFORMATION: a, c, g, t, unknown or other
<220> FEATURE:
<221> NAME/KEY: modified_base
<222> LOCATION: (2169)..(2169)
<223> OTHER INFORMATION: a, c, g, t, unknown or other
<220> FEATURE:
<221> NAME/KEY: modified_base
<222> LOCATION: (2172)..(2172)
<223> OTHER INFORMATION: a, c, g, t, unknown or other
<220> FEATURE:
<221> NAME/KEY: modified_base
<222> LOCATION: (2175)..(2175)
<223> OTHER INFORMATION: a, c, g, t, unknown or other
<220> FEATURE:
<221> NAME/KEY: modified_base
<222> LOCATION: (2178)..(2178)
<223> OTHER INFORMATION: a, c, g, t, unknown or other
<220> FEATURE:
<221> NAME/KEY: modified_base
<222> LOCATION: (2184)..(2184)
<223> OTHER INFORMATION: a, c, g, t, unknown or other
<220> FEATURE:
<221> NAME/KEY: modified_base
<222> LOCATION: (2187)..(2187)
<223> OTHER INFORMATION: a, c, g, t, unknown or other
<220> FEATURE:
<221> NAME/KEY: modified_base
<222> LOCATION: (2196)..(2196)
<223> OTHER INFORMATION: a, c, g, t, unknown or other
<220> FEATURE:
<221> NAME/KEY: modified_base
<222> LOCATION: (2202)..(2202)
<223> OTHER INFORMATION: a, c, g, t, unknown or other
<220> FEATURE:
<221> NAME/KEY: modified_base
<222> LOCATION: (2211)..(2211)
<223> OTHER INFORMATION: a, c, g, t, unknown or other
<220> FEATURE:
<221> NAME/KEY: modified_base
<222> LOCATION: (2214)..(2214)
<223> OTHER INFORMATION: a, c, g, t, unknown or other
<220> FEATURE:
<221> NAME/KEY: modified_base
<222> LOCATION: (2217)..(2217)
<223> OTHER INFORMATION: a, c, g, t, unknown or other
<220> FEATURE:
<221> NAME/KEY: modified_base
<222> LOCATION: (2220)..(2220)
<223> OTHER INFORMATION: a, c, g, t, unknown or other
<220> FEATURE:
<221> NAME/KEY: modified_base
<222> LOCATION: (2223)..(2223)
<223> OTHER INFORMATION: a, c, g, t, unknown or other
<220> FEATURE:
<221> NAME/KEY: modified_base
<222> LOCATION: (2226)..(2226)
<223> OTHER INFORMATION: a, c, g, t, unknown or other
<220> FEATURE:
<221> NAME/KEY: modified_base
<222> LOCATION: (2229)..(2229)
```

```
<223> OTHER INFORMATION: a, c, g, t, unknown or other
<220> FEATURE:
<221> NAME/KEY: modified_base
<222> LOCATION: (2232)..(2232)
<223> OTHER INFORMATION: a, c, g, t, unknown or other
<220> FEATURE:
<221> NAME/KEY: modified_base
<222> LOCATION: (2235)..(2235)
<223> OTHER INFORMATION: a, c, g, t, unknown or other
<220> FEATURE:
<221> NAME/KEY: modified_base
<222> LOCATION: (2238)..(2238)
<223> OTHER INFORMATION: a, c, g, t, unknown or other
<220> FEATURE:
<221> NAME/KEY: modified_base
<222> LOCATION: (2244)..(2244)
<223> OTHER INFORMATION: a, c, g, t, unknown or other
<220> FEATURE:
<221> NAME/KEY: modified_base
<222> LOCATION: (2247)..(2247)
<223> OTHER INFORMATION: a, c, g, t, unknown or other
<220> FEATURE:
<221> NAME/KEY: modified_base
<222> LOCATION: (2253)..(2253)
<223> OTHER INFORMATION: a, c, g, t, unknown or other
<220> FEATURE:
<221> NAME/KEY: modified_base
<222> LOCATION: (2256)..(2256)
<223> OTHER INFORMATION: a, c, g, t, unknown or other
<220> FEATURE:
<221> NAME/KEY: modified_base
<222> LOCATION: (2259)..(2259)
<223> OTHER INFORMATION: a, c, g, t, unknown or other
<220> FEATURE:
<221> NAME/KEY: modified_base
<222> LOCATION: (2265)..(2265)
<223> OTHER INFORMATION: a, c, g, t, unknown or other
<220> FEATURE:
<221> NAME/KEY: modified_base
<222> LOCATION: (2280)..(2280)
<223> OTHER INFORMATION: a, c, g, t, unknown or other
<220> FEATURE:
<221> NAME/KEY: modified_base
<222> LOCATION: (2283)..(2283)
<223> OTHER INFORMATION: a, c, g, t, unknown or other
<220> FEATURE:
<221> NAME/KEY: modified_base
<222> LOCATION: (2286)..(2286)
<223> OTHER INFORMATION: a, c, g, t, unknown or other
<220> FEATURE:
<221> NAME/KEY: modified_base
<222> LOCATION: (2289)..(2289)
<223> OTHER INFORMATION: a, c, g, t, unknown or other
<220> FEATURE:
<221> NAME/KEY: modified_base
<222> LOCATION: (2292)..(2292)
<223> OTHER INFORMATION: a, c, g, t, unknown or other
<220> FEATURE:
<221> NAME/KEY: modified_base
<222> LOCATION: (2295)..(2295)
<223> OTHER INFORMATION: a, c, g, t, unknown or other
<220> FEATURE:
<221> NAME/KEY: modified_base
<222> LOCATION: (2301)..(2301)
<223> OTHER INFORMATION: a, c, g, t, unknown or other
<220> FEATURE:
<221> NAME/KEY: modified_base
<222> LOCATION: (2304)..(2304)
<223> OTHER INFORMATION: a, c, g, t, unknown or other
<220> FEATURE:
<221> NAME/KEY: modified_base
<222> LOCATION: (2307)..(2307)
<223> OTHER INFORMATION: a, c, g, t, unknown or other
<220> FEATURE:
<221> NAME/KEY: modified_base
<222> LOCATION: (2310)..(2310)
<223> OTHER INFORMATION: a, c, g, t, unknown or other
<220> FEATURE:
<221> NAME/KEY: modified_base
<222> LOCATION: (2313)..(2313)
```

-continued

```
<223> OTHER INFORMATION: a, c, g, t, unknown or other
<220> FEATURE:
<221> NAME/KEY: modified_base
<222> LOCATION: (2319)..(2319)
<223> OTHER INFORMATION: a, c, g, t, unknown or other
<220> FEATURE:
<221> NAME/KEY: modified_base
<222> LOCATION: (2322)..(2322)
<223> OTHER INFORMATION: a, c, g, t, unknown or other
<220> FEATURE:
<221> NAME/KEY: modified_base
<222> LOCATION: (2325)..(2325)
<223> OTHER INFORMATION: a, c, g, t, unknown or other
<220> FEATURE:
<221> NAME/KEY: modified_base
<222> LOCATION: (2328)..(2328)
<223> OTHER INFORMATION: a, c, g, t, unknown or other
<220> FEATURE:
<221> NAME/KEY: modified_base
<222> LOCATION: (2331)..(2331)
<223> OTHER INFORMATION: a, c, g, t, unknown or other
<220> FEATURE:
<221> NAME/KEY: modified_base
<222> LOCATION: (2334)..(2334)
<223> OTHER INFORMATION: a, c, g, t, unknown or other
<220> FEATURE:
<221> NAME/KEY: modified_base
<222> LOCATION: (2337)..(2337)
<223> OTHER INFORMATION: a, c, g, t, unknown or other
<220> FEATURE:
<221> NAME/KEY: modified_base
<222> LOCATION: (2346)..(2346)
<223> OTHER INFORMATION: a, c, g, t, unknown or other
<220> FEATURE:
<221> NAME/KEY: modified_base
<222> LOCATION: (2355)..(2355)
<223> OTHER INFORMATION: a, c, g, t, unknown or other
<220> FEATURE:
<221> NAME/KEY: modified_base
<222> LOCATION: (2358)..(2358)
<223> OTHER INFORMATION: a, c, g, t, unknown or other
<220> FEATURE:
<221> NAME/KEY: modified_base
<222> LOCATION: (2367)..(2367)
<223> OTHER INFORMATION: a, c, g, t, unknown or other
<220> FEATURE:
<221> NAME/KEY: modified_base
<222> LOCATION: (2370)..(2370)
<223> OTHER INFORMATION: a, c, g, t, unknown or other
<220> FEATURE:
<221> NAME/KEY: modified_base
<222> LOCATION: (2376)..(2376)
<223> OTHER INFORMATION: a, c, g, t, unknown or other
<220> FEATURE:
<221> NAME/KEY: modified_base
<222> LOCATION: (2379)..(2379)
<223> OTHER INFORMATION: a, c, g, t, unknown or other
<220> FEATURE:
<221> NAME/KEY: modified_base
<222> LOCATION: (2382)..(2382)
<223> OTHER INFORMATION: a, c, g, t, unknown or other
<220> FEATURE:
<221> NAME/KEY: modified_base
<222> LOCATION: (2385)..(2385)
<223> OTHER INFORMATION: a, c, g, t, unknown or other
<220> FEATURE:
<221> NAME/KEY: modified_base
<222> LOCATION: (2388)..(2388)
<223> OTHER INFORMATION: a, c, g, t, unknown or other
<220> FEATURE:
<221> NAME/KEY: modified_base
<222> LOCATION: (2391)..(2391)
<223> OTHER INFORMATION: a, c, g, t, unknown or other
<220> FEATURE:
<221> NAME/KEY: modified_base
<222> LOCATION: (2397)..(2397)
<223> OTHER INFORMATION: a, c, g, t, unknown or other
<220> FEATURE:
<221> NAME/KEY: modified_base
<222> LOCATION: (2403)..(2403)
```

-continued

```
<223> OTHER INFORMATION: a, c, g, t, unknown or other
<220> FEATURE:
<221> NAME/KEY: modified_base
<222> LOCATION: (2412)..(2412)
<223> OTHER INFORMATION: a, c, g, t, unknown or other
<220> FEATURE:
<221> NAME/KEY: modified_base
<222> LOCATION: (2415)..(2415)
<223> OTHER INFORMATION: a, c, g, t, unknown or other
<220> FEATURE:
<221> NAME/KEY: modified_base
<222> LOCATION: (2418)..(2418)
<223> OTHER INFORMATION: a, c, g, t, unknown or other
<220> FEATURE:
<221> NAME/KEY: modified_base
<222> LOCATION: (2421)..(2421)
<223> OTHER INFORMATION: a, c, g, t, unknown or other
<220> FEATURE:
<221> NAME/KEY: modified_base
<222> LOCATION: (2427)..(2427)
<223> OTHER INFORMATION: a, c, g, t, unknown or other
<220> FEATURE:
<221> NAME/KEY: modified_base
<222> LOCATION: (2430)..(2430)
<223> OTHER INFORMATION: a, c, g, t, unknown or other
<220> FEATURE:
<221> NAME/KEY: modified_base
<222> LOCATION: (2442)..(2442)
<223> OTHER INFORMATION: a, c, g, t, unknown or other
<220> FEATURE:
<221> NAME/KEY: modified_base
<222> LOCATION: (2445)..(2445)
<223> OTHER INFORMATION: a, c, g, t, unknown or other
<220> FEATURE:
<221> NAME/KEY: modified_base
<222> LOCATION: (2448)..(2448)
<223> OTHER INFORMATION: a, c, g, t, unknown or other
<220> FEATURE:
<221> NAME/KEY: modified_base
<222> LOCATION: (2454)..(2454)
<223> OTHER INFORMATION: a, c, g, t, unknown or other
<220> FEATURE:
<221> NAME/KEY: modified_base
<222> LOCATION: (2457)..(2457)
<223> OTHER INFORMATION: a, c, g, t, unknown or other
<220> FEATURE:
<221> NAME/KEY: modified_base
<222> LOCATION: (2460)..(2460)
<223> OTHER INFORMATION: a, c, g, t, unknown or other
<220> FEATURE:
<221> NAME/KEY: modified_base
<222> LOCATION: (2463)..(2463)
<223> OTHER INFORMATION: a, c, g, t, unknown or other
<220> FEATURE:
<221> NAME/KEY: modified_base
<222> LOCATION: (2478)..(2478)
<223> OTHER INFORMATION: a, c, g, t, unknown or other
<220> FEATURE:
<221> NAME/KEY: modified_base
<222> LOCATION: (2481)..(2481)
<223> OTHER INFORMATION: a, c, g, t, unknown or other
<220> FEATURE:
<221> NAME/KEY: modified_base
<222> LOCATION: (2484)..(2484)
<223> OTHER INFORMATION: a, c, g, t, unknown or other
<220> FEATURE:
<221> NAME/KEY: modified_base
<222> LOCATION: (2487)..(2487)
<223> OTHER INFORMATION: a, c, g, t, unknown or other
<220> FEATURE:
<221> NAME/KEY: modified_base
<222> LOCATION: (2490)..(2490)
<223> OTHER INFORMATION: a, c, g, t, unknown or other
<220> FEATURE:
<221> NAME/KEY: modified_base
<222> LOCATION: (2499)..(2499)
<223> OTHER INFORMATION: a, c, g, t, unknown or other
<220> FEATURE:
<221> NAME/KEY: modified_base
<222> LOCATION: (2511)..(2511)
```

-continued

```
<223> OTHER INFORMATION: a, c, g, t, unknown or other
<220> FEATURE:
<221> NAME/KEY: modified_base
<222> LOCATION: (2514)..(2514)
<223> OTHER INFORMATION: a, c, g, t, unknown or other
<220> FEATURE:
<221> NAME/KEY: modified_base
<222> LOCATION: (2520)..(2520)
<223> OTHER INFORMATION: a, c, g, t, unknown or other
<220> FEATURE:
<221> NAME/KEY: modified_base
<222> LOCATION: (2523)..(2523)
<223> OTHER INFORMATION: a, c, g, t, unknown or other
<220> FEATURE:
<221> NAME/KEY: modified_base
<222> LOCATION: (2529)..(2529)
<223> OTHER INFORMATION: a, c, g, t, unknown or other
<220> FEATURE:
<221> NAME/KEY: modified_base
<222> LOCATION: (2538)..(2538)
<223> OTHER INFORMATION: a, c, g, t, unknown or other
<220> FEATURE:
<221> NAME/KEY: modified_base
<222> LOCATION: (2541)..(2541)
<223> OTHER INFORMATION: a, c, g, t, unknown or other
<220> FEATURE:
<221> NAME/KEY: modified_base
<222> LOCATION: (2544)..(2544)
<223> OTHER INFORMATION: a, c, g, t, unknown or other
<220> FEATURE:
<221> NAME/KEY: modified_base
<222> LOCATION: (2547)..(2547)
<223> OTHER INFORMATION: a, c, g, t, unknown or other
<220> FEATURE:
<221> NAME/KEY: modified_base
<222> LOCATION: (2553)..(2553)
<223> OTHER INFORMATION: a, c, g, t, unknown or other
<220> FEATURE:
<221> NAME/KEY: modified_base
<222> LOCATION: (2556)..(2556)
<223> OTHER INFORMATION: a, c, g, t, unknown or other
<220> FEATURE:
<221> NAME/KEY: modified_base
<222> LOCATION: (2562)..(2562)
<223> OTHER INFORMATION: a, c, g, t, unknown or other
<220> FEATURE:
<221> NAME/KEY: modified_base
<222> LOCATION: (2565)..(2565)
<223> OTHER INFORMATION: a, c, g, t, unknown or other
<220> FEATURE:
<221> NAME/KEY: modified_base
<222> LOCATION: (2568)..(2568)
<223> OTHER INFORMATION: a, c, g, t, unknown or other
<220> FEATURE:
<221> NAME/KEY: modified_base
<222> LOCATION: (2574)..(2574)
<223> OTHER INFORMATION: a, c, g, t, unknown or other
<220> FEATURE:
<221> NAME/KEY: modified_base
<222> LOCATION: (2577)..(2577)
<223> OTHER INFORMATION: a, c, g, t, unknown or other
<220> FEATURE:
<221> NAME/KEY: modified_base
<222> LOCATION: (2583)..(2583)
<223> OTHER INFORMATION: a, c, g, t, unknown or other
<220> FEATURE:
<221> NAME/KEY: modified_base
<222> LOCATION: (2589)..(2589)
<223> OTHER INFORMATION: a, c, g, t, unknown or other
<220> FEATURE:
<221> NAME/KEY: modified_base
<222> LOCATION: (2607)..(2607)
<223> OTHER INFORMATION: a, c, g, t, unknown or other
<220> FEATURE:
<221> NAME/KEY: modified_base
<222> LOCATION: (2610)..(2610)
<223> OTHER INFORMATION: a, c, g, t, unknown or other
<220> FEATURE:
<221> NAME/KEY: modified_base
<222> LOCATION: (2613)..(2613)
```

-continued

```
<223> OTHER INFORMATION: a, c, g, t, unknown or other
<220> FEATURE:
<221> NAME/KEY: modified_base
<222> LOCATION: (2625)..(2625)
<223> OTHER INFORMATION: a, c, g, t, unknown or other
<220> FEATURE:
<221> NAME/KEY: modified_base
<222> LOCATION: (2628)..(2628)
<223> OTHER INFORMATION: a, c, g, t, unknown or other
<220> FEATURE:
<221> NAME/KEY: modified_base
<222> LOCATION: (2631)..(2631)
<223> OTHER INFORMATION: a, c, g, t, unknown or other
<220> FEATURE:
<221> NAME/KEY: modified_base
<222> LOCATION: (2634)..(2634)
<223> OTHER INFORMATION: a, c, g, t, unknown or other
<220> FEATURE:
<221> NAME/KEY: modified_base
<222> LOCATION: (2643)..(2643)
<223> OTHER INFORMATION: a, c, g, t, unknown or other
<220> FEATURE:
<221> NAME/KEY: modified_base
<222> LOCATION: (2649)..(2649)
<223> OTHER INFORMATION: a, c, g, t, unknown or other
<220> FEATURE:
<221> NAME/KEY: modified_base
<222> LOCATION: (2664)..(2664)
<223> OTHER INFORMATION: a, c, g, t, unknown or other
<220> FEATURE:
<221> NAME/KEY: modified_base
<222> LOCATION: (2670)..(2670)
<223> OTHER INFORMATION: a, c, g, t, unknown or other
<220> FEATURE:
<221> NAME/KEY: modified_base
<222> LOCATION: (2676)..(2676)
<223> OTHER INFORMATION: a, c, g, t, unknown or other
<220> FEATURE:
<221> NAME/KEY: modified_base
<222> LOCATION: (2682)..(2682)
<223> OTHER INFORMATION: a, c, g, t, unknown or other
<220> FEATURE:
<221> NAME/KEY: modified_base
<222> LOCATION: (2688)..(2688)
<223> OTHER INFORMATION: a, c, g, t, unknown or other
<220> FEATURE:
<221> NAME/KEY: modified_base
<222> LOCATION: (2691)..(2691)
<223> OTHER INFORMATION: a, c, g, t, unknown or other
<220> FEATURE:
<221> NAME/KEY: modified_base
<222> LOCATION: (2694)..(2694)
<223> OTHER INFORMATION: a, c, g, t, unknown or other
<220> FEATURE:
<221> NAME/KEY: modified_base
<222> LOCATION: (2697)..(2697)
<223> OTHER INFORMATION: a, c, g, t, unknown or other
<220> FEATURE:
<221> NAME/KEY: modified_base
<222> LOCATION: (2700)..(2700)
<223> OTHER INFORMATION: a, c, g, t, unknown or other
<220> FEATURE:
<221> NAME/KEY: modified_base
<222> LOCATION: (2709)..(2709)
<223> OTHER INFORMATION: a, c, g, t, unknown or other
<220> FEATURE:
<221> NAME/KEY: modified_base
<222> LOCATION: (2712)..(2712)
<223> OTHER INFORMATION: a, c, g, t, unknown or other
<220> FEATURE:
<221> NAME/KEY: modified_base
<222> LOCATION: (2715)..(2715)
<223> OTHER INFORMATION: a, c, g, t, unknown or other
<220> FEATURE:
<221> NAME/KEY: modified_base
<222> LOCATION: (2718)..(2718)
<223> OTHER INFORMATION: a, c, g, t, unknown or other
<220> FEATURE:
<221> NAME/KEY: modified_base
<222> LOCATION: (2721)..(2721)
```

-continued

```
<223> OTHER INFORMATION: a, c, g, t, unknown or other
<220> FEATURE:
<221> NAME/KEY: modified_base
<222> LOCATION: (2733)..(2733)
<223> OTHER INFORMATION: a, c, g, t, unknown or other
<220> FEATURE:
<221> NAME/KEY: modified_base
<222> LOCATION: (2736)..(2736)
<223> OTHER INFORMATION: a, c, g, t, unknown or other
<220> FEATURE:
<221> NAME/KEY: modified_base
<222> LOCATION: (2742)..(2742)
<223> OTHER INFORMATION: a, c, g, t, unknown or other
<220> FEATURE:
<221> NAME/KEY: modified_base
<222> LOCATION: (2745)..(2745)
<223> OTHER INFORMATION: a, c, g, t, unknown or other
<220> FEATURE:
<221> NAME/KEY: modified_base
<222> LOCATION: (2754)..(2754)
<223> OTHER INFORMATION: a, c, g, t, unknown or other
<220> FEATURE:
<221> NAME/KEY: modified_base
<222> LOCATION: (2757)..(2757)
<223> OTHER INFORMATION: a, c, g, t, unknown or other
<220> FEATURE:
<221> NAME/KEY: modified_base
<222> LOCATION: (2763)..(2763)
<223> OTHER INFORMATION: a, c, g, t, unknown or other
<220> FEATURE:
<221> NAME/KEY: modified_base
<222> LOCATION: (2766)..(2766)
<223> OTHER INFORMATION: a, c, g, t, unknown or other
<220> FEATURE:
<221> NAME/KEY: modified_base
<222> LOCATION: (2769)..(2769)
<223> OTHER INFORMATION: a, c, g, t, unknown or other
<220> FEATURE:
<221> NAME/KEY: modified_base
<222> LOCATION: (2772)..(2772)
<223> OTHER INFORMATION: a, c, g, t, unknown or other
<220> FEATURE:
<221> NAME/KEY: modified_base
<222> LOCATION: (2781)..(2781)
<223> OTHER INFORMATION: a, c, g, t, unknown or other
<220> FEATURE:
<221> NAME/KEY: modified_base
<222> LOCATION: (2787)..(2787)
<223> OTHER INFORMATION: a, c, g, t, unknown or other
<220> FEATURE:
<221> NAME/KEY: modified_base
<222> LOCATION: (2790)..(2790)
<223> OTHER INFORMATION: a, c, g, t, unknown or other
<220> FEATURE:
<221> NAME/KEY: modified_base
<222> LOCATION: (2793)..(2793)
<223> OTHER INFORMATION: a, c, g, t, unknown or other
<220> FEATURE:
<221> NAME/KEY: modified_base
<222> LOCATION: (2811)..(2811)
<223> OTHER INFORMATION: a, c, g, t, unknown or other
<220> FEATURE:
<221> NAME/KEY: modified_base
<222> LOCATION: (2814)..(2814)
<223> OTHER INFORMATION: a, c, g, t, unknown or other
<220> FEATURE:
<221> NAME/KEY: modified_base
<222> LOCATION: (2823)..(2823)
<223> OTHER INFORMATION: a, c, g, t, unknown or other
<220> FEATURE:
<221> NAME/KEY: modified_base
<222> LOCATION: (2832)..(2832)
<223> OTHER INFORMATION: a, c, g, t, unknown or other
<220> FEATURE:
<221> NAME/KEY: modified_base
<222> LOCATION: (2838)..(2838)
<223> OTHER INFORMATION: a, c, g, t, unknown or other
<220> FEATURE:
<221> NAME/KEY: modified_base
<222> LOCATION: (2841)..(2841)
```

-continued

```
<223> OTHER INFORMATION: a, c, g, t, unknown or other
<220> FEATURE:
<221> NAME/KEY: modified_base
<222> LOCATION: (2847)..(2847)
<223> OTHER INFORMATION: a, c, g, t, unknown or other
<220> FEATURE:
<221> NAME/KEY: modified_base
<222> LOCATION: (2850)..(2850)
<223> OTHER INFORMATION: a, c, g, t, unknown or other
<220> FEATURE:
<221> NAME/KEY: modified_base
<222> LOCATION: (2853)..(2853)
<223> OTHER INFORMATION: a, c, g, t, unknown or other
<220> FEATURE:
<221> NAME/KEY: modified_base
<222> LOCATION: (2856)..(2856)
<223> OTHER INFORMATION: a, c, g, t, unknown or other
<220> FEATURE:
<221> NAME/KEY: modified_base
<222> LOCATION: (2862)..(2862)
<223> OTHER INFORMATION: a, c, g, t, unknown or other
<220> FEATURE:
<221> NAME/KEY: modified_base
<222> LOCATION: (2883)..(2883)
<223> OTHER INFORMATION: a, c, g, t, unknown or other
<220> FEATURE:
<221> NAME/KEY: modified_base
<222> LOCATION: (2886)..(2886)
<223> OTHER INFORMATION: a, c, g, t, unknown or other
<220> FEATURE:
<221> NAME/KEY: modified_base
<222> LOCATION: (2889)..(2889)
<223> OTHER INFORMATION: a, c, g, t, unknown or other
<220> FEATURE:
<221> NAME/KEY: modified_base
<222> LOCATION: (2892)..(2892)
<223> OTHER INFORMATION: a, c, g, t, unknown or other
<220> FEATURE:
<221> NAME/KEY: modified_base
<222> LOCATION: (2895)..(2895)
<223> OTHER INFORMATION: a, c, g, t, unknown or other
<220> FEATURE:
<221> NAME/KEY: modified_base
<222> LOCATION: (2898)..(2898)
<223> OTHER INFORMATION: a, c, g, t, unknown or other
<220> FEATURE:
<221> NAME/KEY: modified_base
<222> LOCATION: (2907)..(2907)
<223> OTHER INFORMATION: a, c, g, t, unknown or other
<220> FEATURE:
<221> NAME/KEY: modified_base
<222> LOCATION: (2910)..(2910)
<223> OTHER INFORMATION: a, c, g, t, unknown or other
<220> FEATURE:
<221> NAME/KEY: modified_base
<222> LOCATION: (2919)..(2919)
<223> OTHER INFORMATION: a, c, g, t, unknown or other
<220> FEATURE:
<221> NAME/KEY: modified_base
<222> LOCATION: (2922)..(2922)
<223> OTHER INFORMATION: a, c, g, t, unknown or other
<220> FEATURE:
<221> NAME/KEY: modified_base
<222> LOCATION: (2925)..(2925)
<223> OTHER INFORMATION: a, c, g, t, unknown or other
<220> FEATURE:
<221> NAME/KEY: modified_base
<222> LOCATION: (2946)..(2946)
<223> OTHER INFORMATION: a, c, g, t, unknown or other
<220> FEATURE:
<221> NAME/KEY: modified_base
<222> LOCATION: (2949)..(2949)
<223> OTHER INFORMATION: a, c, g, t, unknown or other
<220> FEATURE:
<221> NAME/KEY: modified_base
<222> LOCATION: (2952)..(2952)
<223> OTHER INFORMATION: a, c, g, t, unknown or other
<220> FEATURE:
<221> NAME/KEY: modified_base
<222> LOCATION: (2958)..(2958)
```

-continued

```
<223> OTHER INFORMATION: a, c, g, t, unknown or other
<220> FEATURE:
<221> NAME/KEY: modified_base
<222> LOCATION: (2961)..(2961)
<223> OTHER INFORMATION: a, c, g, t, unknown or other
<220> FEATURE:
<221> NAME/KEY: modified_base
<222> LOCATION: (2973)..(2973)
<223> OTHER INFORMATION: a, c, g, t, unknown or other
<220> FEATURE:
<221> NAME/KEY: modified_base
<222> LOCATION: (2991)..(2991)
<223> OTHER INFORMATION: a, c, g, t, unknown or other
<220> FEATURE:
<221> NAME/KEY: modified_base
<222> LOCATION: (2994)..(2994)
<223> OTHER INFORMATION: a, c, g, t, unknown or other
<220> FEATURE:
<221> NAME/KEY: modified_base
<222> LOCATION: (2997)..(2997)
<223> OTHER INFORMATION: a, c, g, t, unknown or other
<220> FEATURE:
<221> NAME/KEY: modified_base
<222> LOCATION: (3000)..(3000)
<223> OTHER INFORMATION: a, c, g, t, unknown or other
<220> FEATURE:
<221> NAME/KEY: modified_base
<222> LOCATION: (3003)..(3003)
<223> OTHER INFORMATION: a, c, g, t, unknown or other
<220> FEATURE:
<221> NAME/KEY: modified_base
<222> LOCATION: (3006)..(3006)
<223> OTHER INFORMATION: a, c, g, t, unknown or other
<220> FEATURE:
<221> NAME/KEY: modified_base
<222> LOCATION: (3009)..(3009)
<223> OTHER INFORMATION: a, c, g, t, unknown or other
<220> FEATURE:
<221> NAME/KEY: modified_base
<222> LOCATION: (3012)..(3012)
<223> OTHER INFORMATION: a, c, g, t, unknown or other
<220> FEATURE:
<221> NAME/KEY: modified_base
<222> LOCATION: (3015)..(3015)
<223> OTHER INFORMATION: a, c, g, t, unknown or other
<220> FEATURE:
<221> NAME/KEY: modified_base
<222> LOCATION: (3018)..(3018)
<223> OTHER INFORMATION: a, c, g, t, unknown or other
<220> FEATURE:
<221> NAME/KEY: modified_base
<222> LOCATION: (3039)..(3039)
<223> OTHER INFORMATION: a, c, g, t, unknown or other
<220> FEATURE:
<221> NAME/KEY: modified_base
<222> LOCATION: (3042)..(3042)
<223> OTHER INFORMATION: a, c, g, t, unknown or other
<220> FEATURE:
<221> NAME/KEY: modified_base
<222> LOCATION: (3051)..(3051)
<223> OTHER INFORMATION: a, c, g, t, unknown or other
<220> FEATURE:
<221> NAME/KEY: modified_base
<222> LOCATION: (3060)..(3060)
<223> OTHER INFORMATION: a, c, g, t, unknown or other
<220> FEATURE:
<221> NAME/KEY: modified_base
<222> LOCATION: (3063)..(3063)
<223> OTHER INFORMATION: a, c, g, t, unknown or other
<220> FEATURE:
<221> NAME/KEY: modified_base
<222> LOCATION: (3072)..(3072)
<223> OTHER INFORMATION: a, c, g, t, unknown or other
<220> FEATURE:
<221> NAME/KEY: modified_base
<222> LOCATION: (3078)..(3078)
<223> OTHER INFORMATION: a, c, g, t, unknown or other
<220> FEATURE:
<221> NAME/KEY: modified_base
<222> LOCATION: (3084)..(3084)
```

-continued

```
<223> OTHER INFORMATION: a, c, g, t, unknown or other
<220> FEATURE:
<221> NAME/KEY: modified_base
<222> LOCATION: (3087)..(3087)
<223> OTHER INFORMATION: a, c, g, t, unknown or other
<220> FEATURE:
<221> NAME/KEY: modified_base
<222> LOCATION: (3090)..(3090)
<223> OTHER INFORMATION: a, c, g, t, unknown or other
<220> FEATURE:
<221> NAME/KEY: modified_base
<222> LOCATION: (3093)..(3093)
<223> OTHER INFORMATION: a, c, g, t, unknown or other
<220> FEATURE:
<221> NAME/KEY: modified_base
<222> LOCATION: (3096)..(3096)
<223> OTHER INFORMATION: a, c, g, t, unknown or other
<220> FEATURE:
<221> NAME/KEY: modified_base
<222> LOCATION: (3102)..(3102)
<223> OTHER INFORMATION: a, c, g, t, unknown or other
<220> FEATURE:
<221> NAME/KEY: modified_base
<222> LOCATION: (3105)..(3105)
<223> OTHER INFORMATION: a, c, g, t, unknown or other
<220> FEATURE:
<221> NAME/KEY: modified_base
<222> LOCATION: (3108)..(3108)
<223> OTHER INFORMATION: a, c, g, t, unknown or other
<220> FEATURE:
<221> NAME/KEY: modified_base
<222> LOCATION: (3111)..(3111)
<223> OTHER INFORMATION: a, c, g, t, unknown or other
<220> FEATURE:
<221> NAME/KEY: modified_base
<222> LOCATION: (3117)..(3117)
<223> OTHER INFORMATION: a, c, g, t, unknown or other
<220> FEATURE:
<221> NAME/KEY: modified_base
<222> LOCATION: (3120)..(3120)
<223> OTHER INFORMATION: a, c, g, t, unknown or other
<220> FEATURE:
<221> NAME/KEY: modified_base
<222> LOCATION: (3123)..(3123)
<223> OTHER INFORMATION: a, c, g, t, unknown or other
<220> FEATURE:
<221> NAME/KEY: modified_base
<222> LOCATION: (3129)..(3129)
<223> OTHER INFORMATION: a, c, g, t, unknown or other
<220> FEATURE:
<221> NAME/KEY: modified_base
<222> LOCATION: (3135)..(3135)
<223> OTHER INFORMATION: a, c, g, t, unknown or other
<220> FEATURE:
<221> NAME/KEY: modified_base
<222> LOCATION: (3141)..(3141)
<223> OTHER INFORMATION: a, c, g, t, unknown or other
<220> FEATURE:
<221> NAME/KEY: modified_base
<222> LOCATION: (3144)..(3144)
<223> OTHER INFORMATION: a, c, g, t, unknown or other
<220> FEATURE:
<221> NAME/KEY: modified_base
<222> LOCATION: (3156)..(3156)
<223> OTHER INFORMATION: a, c, g, t, unknown or other
<220> FEATURE:
<221> NAME/KEY: modified_base
<222> LOCATION: (3168)..(3168)
<223> OTHER INFORMATION: a, c, g, t, unknown or other
<220> FEATURE:
<221> NAME/KEY: modified_base
<222> LOCATION: (3171)..(3171)
<223> OTHER INFORMATION: a, c, g, t, unknown or other
<220> FEATURE:
<221> NAME/KEY: modified_base
<222> LOCATION: (3174)..(3174)
<223> OTHER INFORMATION: a, c, g, t, unknown or other
<220> FEATURE:
<221> NAME/KEY: modified_base
<222> LOCATION: (3180)..(3180)
```

-continued

```
<223> OTHER INFORMATION: a, c, g, t, unknown or other
<220> FEATURE:
<221> NAME/KEY: modified_base
<222> LOCATION: (3192)..(3192)
<223> OTHER INFORMATION: a, c, g, t, unknown or other
<220> FEATURE:
<221> NAME/KEY: modified_base
<222> LOCATION: (3198)..(3198)
<223> OTHER INFORMATION: a, c, g, t, unknown or other
<220> FEATURE:
<221> NAME/KEY: modified_base
<222> LOCATION: (3201)..(3201)
<223> OTHER INFORMATION: a, c, g, t, unknown or other
<220> FEATURE:
<221> NAME/KEY: modified_base
<222> LOCATION: (3204)..(3204)
<223> OTHER INFORMATION: a, c, g, t, unknown or other
<220> FEATURE:
<221> NAME/KEY: modified_base
<222> LOCATION: (3207)..(3207)
<223> OTHER INFORMATION: a, c, g, t, unknown or other
<220> FEATURE:
<221> NAME/KEY: modified_base
<222> LOCATION: (3210)..(3210)
<223> OTHER INFORMATION: a, c, g, t, unknown or other
<220> FEATURE:
<221> NAME/KEY: modified_base
<222> LOCATION: (3213)..(3213)
<223> OTHER INFORMATION: a, c, g, t, unknown or other
<220> FEATURE:
<221> NAME/KEY: modified_base
<222> LOCATION: (3216)..(3216)
<223> OTHER INFORMATION: a, c, g, t, unknown or other
<220> FEATURE:
<221> NAME/KEY: modified_base
<222> LOCATION: (3219)..(3219)
<223> OTHER INFORMATION: a, c, g, t, unknown or other
<220> FEATURE:
<221> NAME/KEY: modified_base
<222> LOCATION: (3222)..(3222)
<223> OTHER INFORMATION: a, c, g, t, unknown or other
<220> FEATURE:
<221> NAME/KEY: modified_base
<222> LOCATION: (3225)..(3225)
<223> OTHER INFORMATION: a, c, g, t, unknown or other
<220> FEATURE:
<221> NAME/KEY: modified_base
<222> LOCATION: (3234)..(3234)
<223> OTHER INFORMATION: a, c, g, t, unknown or other
<220> FEATURE:
<221> NAME/KEY: modified_base
<222> LOCATION: (3237)..(3237)
<223> OTHER INFORMATION: a, c, g, t, unknown or other
<220> FEATURE:
<221> NAME/KEY: modified_base
<222> LOCATION: (3243)..(3243)
<223> OTHER INFORMATION: a, c, g, t, unknown or other
<220> FEATURE:
<221> NAME/KEY: modified_base
<222> LOCATION: (3246)..(3246)
<223> OTHER INFORMATION: a, c, g, t, unknown or other
<220> FEATURE:
<221> NAME/KEY: modified_base
<222> LOCATION: (3252)..(3252)
<223> OTHER INFORMATION: a, c, g, t, unknown or other
<220> FEATURE:
<221> NAME/KEY: modified_base
<222> LOCATION: (3255)..(3255)
<223> OTHER INFORMATION: a, c, g, t, unknown or other
<220> FEATURE:
<221> NAME/KEY: modified_base
<222> LOCATION: (3258)..(3258)
<223> OTHER INFORMATION: a, c, g, t, unknown or other
<220> FEATURE:
<221> NAME/KEY: modified_base
<222> LOCATION: (3261)..(3261)
<223> OTHER INFORMATION: a, c, g, t, unknown or other
<220> FEATURE:
<221> NAME/KEY: modified_base
<222> LOCATION: (3267)..(3267)
```

-continued

```
<223> OTHER INFORMATION: a, c, g, t, unknown or other
<220> FEATURE:
<221> NAME/KEY: modified_base
<222> LOCATION: (3279)..(3279)
<223> OTHER INFORMATION: a, c, g, t, unknown or other
<220> FEATURE:
<221> NAME/KEY: modified_base
<222> LOCATION: (3285)..(3285)
<223> OTHER INFORMATION: a, c, g, t, unknown or other
<220> FEATURE:
<221> NAME/KEY: modified_base
<222> LOCATION: (3291)..(3291)
<223> OTHER INFORMATION: a, c, g, t, unknown or other
<220> FEATURE:
<221> NAME/KEY: modified_base
<222> LOCATION: (3297)..(3297)
<223> OTHER INFORMATION: a, c, g, t, unknown or other
<220> FEATURE:
<221> NAME/KEY: modified_base
<222> LOCATION: (3303)..(3303)
<223> OTHER INFORMATION: a, c, g, t, unknown or other
<220> FEATURE:
<221> NAME/KEY: modified_base
<222> LOCATION: (3321)..(3321)
<223> OTHER INFORMATION: a, c, g, t, unknown or other
<220> FEATURE:
<221> NAME/KEY: modified_base
<222> LOCATION: (3324)..(3324)
<223> OTHER INFORMATION: a, c, g, t, unknown or other
<220> FEATURE:
<221> NAME/KEY: modified_base
<222> LOCATION: (3327)..(3327)
<223> OTHER INFORMATION: a, c, g, t, unknown or other
<220> FEATURE:
<221> NAME/KEY: modified_base
<222> LOCATION: (3330)..(3330)
<223> OTHER INFORMATION: a, c, g, t, unknown or other
<220> FEATURE:
<221> NAME/KEY: modified_base
<222> LOCATION: (3333)..(3333)
<223> OTHER INFORMATION: a, c, g, t, unknown or other
<220> FEATURE:
<221> NAME/KEY: modified_base
<222> LOCATION: (3339)..(3339)
<223> OTHER INFORMATION: a, c, g, t, unknown or other
<220> FEATURE:
<221> NAME/KEY: modified_base
<222> LOCATION: (3348)..(3348)
<223> OTHER INFORMATION: a, c, g, t, unknown or other
<220> FEATURE:
<221> NAME/KEY: modified_base
<222> LOCATION: (3351)..(3351)
<223> OTHER INFORMATION: a, c, g, t, unknown or other
<220> FEATURE:
<221> NAME/KEY: modified_base
<222> LOCATION: (3354)..(3354)
<223> OTHER INFORMATION: a, c, g, t, unknown or other
<220> FEATURE:
<221> NAME/KEY: modified_base
<222> LOCATION: (3357)..(3357)
<223> OTHER INFORMATION: a, c, g, t, unknown or other
<220> FEATURE:
<221> NAME/KEY: modified_base
<222> LOCATION: (3366)..(3366)
<223> OTHER INFORMATION: a, c, g, t, unknown or other
<220> FEATURE:
<221> NAME/KEY: modified_base
<222> LOCATION: (3369)..(3369)
<223> OTHER INFORMATION: a, c, g, t, unknown or other
<220> FEATURE:
<221> NAME/KEY: modified_base
<222> LOCATION: (3372)..(3372)
<223> OTHER INFORMATION: a, c, g, t, unknown or other
<220> FEATURE:
<221> NAME/KEY: modified_base
<222> LOCATION: (3378)..(3378)
<223> OTHER INFORMATION: a, c, g, t, unknown or other
<220> FEATURE:
<221> NAME/KEY: modified_base
<222> LOCATION: (3381)..(3381)
```

-continued

```
<223> OTHER INFORMATION: a, c, g, t, unknown or other
<220> FEATURE:
<221> NAME/KEY: modified_base
<222> LOCATION: (3390)..(3390)
<223> OTHER INFORMATION: a, c, g, t, unknown or other
<220> FEATURE:
<221> NAME/KEY: modified_base
<222> LOCATION: (3393)..(3393)
<223> OTHER INFORMATION: a, c, g, t, unknown or other
<220> FEATURE:
<221> NAME/KEY: modified_base
<222> LOCATION: (3396)..(3396)
<223> OTHER INFORMATION: a, c, g, t, unknown or other
<220> FEATURE:
<221> NAME/KEY: modified_base
<222> LOCATION: (3399)..(3399)
<223> OTHER INFORMATION: a, c, g, t, unknown or other
<220> FEATURE:
<221> NAME/KEY: modified_base
<222> LOCATION: (3402)..(3402)
<223> OTHER INFORMATION: a, c, g, t, unknown or other
<220> FEATURE:
<221> NAME/KEY: modified_base
<222> LOCATION: (3414)..(3414)
<223> OTHER INFORMATION: a, c, g, t, unknown or other
<220> FEATURE:
<221> NAME/KEY: modified_base
<222> LOCATION: (3417)..(3417)
<223> OTHER INFORMATION: a, c, g, t, unknown or other
<220> FEATURE:
<221> NAME/KEY: modified_base
<222> LOCATION: (3423)..(3423)
<223> OTHER INFORMATION: a, c, g, t, unknown or other
<220> FEATURE:
<221> NAME/KEY: modified_base
<222> LOCATION: (3429)..(3429)
<223> OTHER INFORMATION: a, c, g, t, unknown or other
<220> FEATURE:
<221> NAME/KEY: modified_base
<222> LOCATION: (3432)..(3432)
<223> OTHER INFORMATION: a, c, g, t, unknown or other
<220> FEATURE:
<221> NAME/KEY: modified_base
<222> LOCATION: (3435)..(3435)
<223> OTHER INFORMATION: a, c, g, t, unknown or other
<220> FEATURE:
<221> NAME/KEY: modified_base
<222> LOCATION: (3450)..(3450)
<223> OTHER INFORMATION: a, c, g, t, unknown or other
<220> FEATURE:
<221> NAME/KEY: modified_base
<222> LOCATION: (3453)..(3453)
<223> OTHER INFORMATION: a, c, g, t, unknown or other
<220> FEATURE:
<221> NAME/KEY: modified_base
<222> LOCATION: (3459)..(3459)
<223> OTHER INFORMATION: a, c, g, t, unknown or other
<220> FEATURE:
<221> NAME/KEY: modified_base
<222> LOCATION: (3465)..(3465)
<223> OTHER INFORMATION: a, c, g, t, unknown or other
<220> FEATURE:
<221> NAME/KEY: modified_base
<222> LOCATION: (3468)..(3468)
<223> OTHER INFORMATION: a, c, g, t, unknown or other
<220> FEATURE:
<221> NAME/KEY: modified_base
<222> LOCATION: (3474)..(3474)
<223> OTHER INFORMATION: a, c, g, t, unknown or other
<220> FEATURE:
<221> NAME/KEY: modified_base
<222> LOCATION: (3477)..(3477)
<223> OTHER INFORMATION: a, c, g, t, unknown or other
<220> FEATURE:
<221> NAME/KEY: modified_base
<222> LOCATION: (3483)..(3483)
<223> OTHER INFORMATION: a, c, g, t, unknown or other
<220> FEATURE:
<221> NAME/KEY: modified_base
<222> LOCATION: (3489)..(3489)
```

-continued

```
<223> OTHER INFORMATION: a, c, g, t, unknown or other
<220> FEATURE:
<221> NAME/KEY: modified_base
<222> LOCATION: (3498)..(3498)
<223> OTHER INFORMATION: a, c, g, t, unknown or other
<220> FEATURE:
<221> NAME/KEY: modified_base
<222> LOCATION: (3501)..(3501)
<223> OTHER INFORMATION: a, c, g, t, unknown or other
<220> FEATURE:
<221> NAME/KEY: modified_base
<222> LOCATION: (3504)..(3504)
<223> OTHER INFORMATION: a, c, g, t, unknown or other
<220> FEATURE:
<221> NAME/KEY: modified_base
<222> LOCATION: (3507)..(3507)
<223> OTHER INFORMATION: a, c, g, t, unknown or other
<220> FEATURE:
<221> NAME/KEY: modified_base
<222> LOCATION: (3516)..(3516)
<223> OTHER INFORMATION: a, c, g, t, unknown or other
<220> FEATURE:
<221> NAME/KEY: modified_base
<222> LOCATION: (3519)..(3519)
<223> OTHER INFORMATION: a, c, g, t, unknown or other
<220> FEATURE:
<221> NAME/KEY: modified_base
<222> LOCATION: (3522)..(3522)
<223> OTHER INFORMATION: a, c, g, t, unknown or other
<220> FEATURE:
<221> NAME/KEY: modified_base
<222> LOCATION: (3525)..(3525)
<223> OTHER INFORMATION: a, c, g, t, unknown or other
<220> FEATURE:
<221> NAME/KEY: modified_base
<222> LOCATION: (3528)..(3528)
<223> OTHER INFORMATION: a, c, g, t, unknown or other
<220> FEATURE:
<221> NAME/KEY: modified_base
<222> LOCATION: (3531)..(3531)
<223> OTHER INFORMATION: a, c, g, t, unknown or other
<220> FEATURE:
<221> NAME/KEY: modified_base
<222> LOCATION: (3537)..(3537)
<223> OTHER INFORMATION: a, c, g, t, unknown or other
<220> FEATURE:
<221> NAME/KEY: modified_base
<222> LOCATION: (3540)..(3540)
<223> OTHER INFORMATION: a, c, g, t, unknown or other
<220> FEATURE:
<221> NAME/KEY: modified_base
<222> LOCATION: (3549)..(3549)
<223> OTHER INFORMATION: a, c, g, t, unknown or other
<220> FEATURE:
<221> NAME/KEY: modified_base
<222> LOCATION: (3552)..(3552)
<223> OTHER INFORMATION: a, c, g, t, unknown or other
<220> FEATURE:
<221> NAME/KEY: modified_base
<222> LOCATION: (3561)..(3561)
<223> OTHER INFORMATION: a, c, g, t, unknown or other
<220> FEATURE:
<221> NAME/KEY: modified_base
<222> LOCATION: (3564)..(3564)
<223> OTHER INFORMATION: a, c, g, t, unknown or other
<220> FEATURE:
<221> NAME/KEY: modified_base
<222> LOCATION: (3567)..(3567)
<223> OTHER INFORMATION: a, c, g, t, unknown or other
<220> FEATURE:
<221> NAME/KEY: modified_base
<222> LOCATION: (3573)..(3573)
<223> OTHER INFORMATION: a, c, g, t, unknown or other
<220> FEATURE:
<221> NAME/KEY: modified_base
<222> LOCATION: (3576)..(3576)
<223> OTHER INFORMATION: a, c, g, t, unknown or other
<220> FEATURE:
<221> NAME/KEY: modified_base
<222> LOCATION: (3579)..(3579)
```

-continued

```
<223> OTHER INFORMATION: a, c, g, t, unknown or other
<220> FEATURE:
<221> NAME/KEY: modified_base
<222> LOCATION: (3582)..(3582)
<223> OTHER INFORMATION: a, c, g, t, unknown or other
<220> FEATURE:
<221> NAME/KEY: modified_base
<222> LOCATION: (3588)..(3588)
<223> OTHER INFORMATION: a, c, g, t, unknown or other
<220> FEATURE:
<221> NAME/KEY: modified_base
<222> LOCATION: (3591)..(3591)
<223> OTHER INFORMATION: a, c, g, t, unknown or other
<220> FEATURE:
<221> NAME/KEY: modified_base
<222> LOCATION: (3594)..(3594)
<223> OTHER INFORMATION: a, c, g, t, unknown or other
<220> FEATURE:
<221> NAME/KEY: modified_base
<222> LOCATION: (3597)..(3597)
<223> OTHER INFORMATION: a, c, g, t, unknown or other
<220> FEATURE:
<221> NAME/KEY: modified_base
<222> LOCATION: (3603)..(3603)
<223> OTHER INFORMATION: a, c, g, t, unknown or other
<220> FEATURE:
<221> NAME/KEY: modified_base
<222> LOCATION: (3606)..(3606)
<223> OTHER INFORMATION: a, c, g, t, unknown or other
<220> FEATURE:
<221> NAME/KEY: modified_base
<222> LOCATION: (3615)..(3615)
<223> OTHER INFORMATION: a, c, g, t, unknown or other
<220> FEATURE:
<221> NAME/KEY: modified_base
<222> LOCATION: (3618)..(3618)
<223> OTHER INFORMATION: a, c, g, t, unknown or other
<220> FEATURE:
<221> NAME/KEY: modified_base
<222> LOCATION: (3621)..(3621)
<223> OTHER INFORMATION: a, c, g, t, unknown or other
<220> FEATURE:
<221> NAME/KEY: modified_base
<222> LOCATION: (3630)..(3630)
<223> OTHER INFORMATION: a, c, g, t, unknown or other
<220> FEATURE:
<221> NAME/KEY: modified_base
<222> LOCATION: (3633)..(3633)
<223> OTHER INFORMATION: a, c, g, t, unknown or other
<220> FEATURE:
<221> NAME/KEY: modified_base
<222> LOCATION: (3636)..(3636)
<223> OTHER INFORMATION: a, c, g, t, unknown or other
<220> FEATURE:
<221> NAME/KEY: modified_base
<222> LOCATION: (3639)..(3639)
<223> OTHER INFORMATION: a, c, g, t, unknown or other
<220> FEATURE:
<221> NAME/KEY: modified_base
<222> LOCATION: (3645)..(3645)
<223> OTHER INFORMATION: a, c, g, t, unknown or other
<220> FEATURE:
<221> NAME/KEY: modified_base
<222> LOCATION: (3648)..(3648)
<223> OTHER INFORMATION: a, c, g, t, unknown or other
<220> FEATURE:
<221> NAME/KEY: modified_base
<222> LOCATION: (3651)..(3651)
<223> OTHER INFORMATION: a, c, g, t, unknown or other
<220> FEATURE:
<221> NAME/KEY: modified_base
<222> LOCATION: (3654)..(3654)
<223> OTHER INFORMATION: a, c, g, t, unknown or other
<220> FEATURE:
<221> NAME/KEY: modified_base
<222> LOCATION: (3660)..(3660)
<223> OTHER INFORMATION: a, c, g, t, unknown or other
<220> FEATURE:
<221> NAME/KEY: modified_base
<222> LOCATION: (3669)..(3669)
```

-continued

```
<223> OTHER INFORMATION: a, c, g, t, unknown or other
<220> FEATURE:
<221> NAME/KEY: modified_base
<222> LOCATION: (3672)..(3672)
<223> OTHER INFORMATION: a, c, g, t, unknown or other
<220> FEATURE:
<221> NAME/KEY: modified_base
<222> LOCATION: (3678)..(3678)
<223> OTHER INFORMATION: a, c, g, t, unknown or other
<220> FEATURE:
<221> NAME/KEY: modified_base
<222> LOCATION: (3684)..(3684)
<223> OTHER INFORMATION: a, c, g, t, unknown or other
<220> FEATURE:
<221> NAME/KEY: modified_base
<222> LOCATION: (3687)..(3687)
<223> OTHER INFORMATION: a, c, g, t, unknown or other
<220> FEATURE:
<221> NAME/KEY: modified_base
<222> LOCATION: (3693)..(3693)
<223> OTHER INFORMATION: a, c, g, t, unknown or other
<220> FEATURE:
<221> NAME/KEY: modified_base
<222> LOCATION: (3699)..(3699)
<223> OTHER INFORMATION: a, c, g, t, unknown or other
<220> FEATURE:
<221> NAME/KEY: modified_base
<222> LOCATION: (3705)..(3705)
<223> OTHER INFORMATION: a, c, g, t, unknown or other
<220> FEATURE:
<221> NAME/KEY: modified_base
<222> LOCATION: (3726)..(3726)
<223> OTHER INFORMATION: a, c, g, t, unknown or other
<220> FEATURE:
<221> NAME/KEY: modified_base
<222> LOCATION: (3729)..(3729)
<223> OTHER INFORMATION: a, c, g, t, unknown or other
<220> FEATURE:
<221> NAME/KEY: modified_base
<222> LOCATION: (3735)..(3735)
<223> OTHER INFORMATION: a, c, g, t, unknown or other
<220> FEATURE:
<221> NAME/KEY: modified_base
<222> LOCATION: (3738)..(3738)
<223> OTHER INFORMATION: a, c, g, t, unknown or other
<220> FEATURE:
<221> NAME/KEY: modified_base
<222> LOCATION: (3744)..(3744)
<223> OTHER INFORMATION: a, c, g, t, unknown or other
<220> FEATURE:
<221> NAME/KEY: modified_base
<222> LOCATION: (3747)..(3747)
<223> OTHER INFORMATION: a, c, g, t, unknown or other
<220> FEATURE:
<221> NAME/KEY: modified_base
<222> LOCATION: (3750)..(3750)
<223> OTHER INFORMATION: a, c, g, t, unknown or other
<220> FEATURE:
<221> NAME/KEY: modified_base
<222> LOCATION: (3753)..(3753)
<223> OTHER INFORMATION: a, c, g, t, unknown or other
<220> FEATURE:
<221> NAME/KEY: modified_base
<222> LOCATION: (3756)..(3756)
<223> OTHER INFORMATION: a, c, g, t, unknown or other
<220> FEATURE:
<221> NAME/KEY: modified_base
<222> LOCATION: (3759)..(3759)
<223> OTHER INFORMATION: a, c, g, t, unknown or other
<220> FEATURE:
<221> NAME/KEY: modified_base
<222> LOCATION: (3765)..(3765)
<223> OTHER INFORMATION: a, c, g, t, unknown or other
<220> FEATURE:
<221> NAME/KEY: modified_base
<222> LOCATION: (3768)..(3768)
<223> OTHER INFORMATION: a, c, g, t, unknown or other
<220> FEATURE:
<221> NAME/KEY: modified_base
<222> LOCATION: (3771)..(3771)
```

-continued

```
<223> OTHER INFORMATION: a, c, g, t, unknown or other
<220> FEATURE:
<221> NAME/KEY: modified_base
<222> LOCATION: (3777)..(3777)
<223> OTHER INFORMATION: a, c, g, t, unknown or other
<220> FEATURE:
<221> NAME/KEY: modified_base
<222> LOCATION: (3780)..(3780)
<223> OTHER INFORMATION: a, c, g, t, unknown or other
<220> FEATURE:
<221> NAME/KEY: modified_base
<222> LOCATION: (3783)..(3783)
<223> OTHER INFORMATION: a, c, g, t, unknown or other
<220> FEATURE:
<221> NAME/KEY: modified_base
<222> LOCATION: (3786)..(3786)
<223> OTHER INFORMATION: a, c, g, t, unknown or other
<220> FEATURE:
<221> NAME/KEY: modified_base
<222> LOCATION: (3789)..(3789)
<223> OTHER INFORMATION: a, c, g, t, unknown or other
<220> FEATURE:
<221> NAME/KEY: modified_base
<222> LOCATION: (3792)..(3792)
<223> OTHER INFORMATION: a, c, g, t, unknown or other
<220> FEATURE:
<221> NAME/KEY: modified_base
<222> LOCATION: (3798)..(3798)
<223> OTHER INFORMATION: a, c, g, t, unknown or other
<220> FEATURE:
<221> NAME/KEY: modified_base
<222> LOCATION: (3801)..(3801)
<223> OTHER INFORMATION: a, c, g, t, unknown or other
<220> FEATURE:
<221> NAME/KEY: modified_base
<222> LOCATION: (3804)..(3804)
<223> OTHER INFORMATION: a, c, g, t, unknown or other
<220> FEATURE:
<221> NAME/KEY: modified_base
<222> LOCATION: (3810)..(3810)
<223> OTHER INFORMATION: a, c, g, t, unknown or other
<220> FEATURE:
<221> NAME/KEY: modified_base
<222> LOCATION: (3819)..(3819)
<223> OTHER INFORMATION: a, c, g, t, unknown or other
<220> FEATURE:
<221> NAME/KEY: modified_base
<222> LOCATION: (3822)..(3822)
<223> OTHER INFORMATION: a, c, g, t, unknown or other
<220> FEATURE:
<221> NAME/KEY: modified_base
<222> LOCATION: (3825)..(3825)
<223> OTHER INFORMATION: a, c, g, t, unknown or other
<220> FEATURE:
<221> NAME/KEY: modified_base
<222> LOCATION: (3840)..(3840)
<223> OTHER INFORMATION: a, c, g, t, unknown or other
<220> FEATURE:
<221> NAME/KEY: modified_base
<222> LOCATION: (3843)..(3843)
<223> OTHER INFORMATION: a, c, g, t, unknown or other
<220> FEATURE:
<221> NAME/KEY: modified_base
<222> LOCATION: (3846)..(3846)
<223> OTHER INFORMATION: a, c, g, t, unknown or other
<220> FEATURE:
<221> NAME/KEY: modified_base
<222> LOCATION: (3852)..(3852)
<223> OTHER INFORMATION: a, c, g, t, unknown or other
<220> FEATURE:
<221> NAME/KEY: modified_base
<222> LOCATION: (3855)..(3855)
<223> OTHER INFORMATION: a, c, g, t, unknown or other
<220> FEATURE:
<221> NAME/KEY: modified_base
<222> LOCATION: (3858)..(3858)
<223> OTHER INFORMATION: a, c, g, t, unknown or other
<220> FEATURE:
<221> NAME/KEY: modified_base
<222> LOCATION: (3861)..(3861)
```

-continued

```
<223> OTHER INFORMATION: a, c, g, t, unknown or other
<220> FEATURE:
<221> NAME/KEY: modified_base
<222> LOCATION: (3864)..(3864)
<223> OTHER INFORMATION: a, c, g, t, unknown or other
<220> FEATURE:
<221> NAME/KEY: modified_base
<222> LOCATION: (3870)..(3870)
<223> OTHER INFORMATION: a, c, g, t, unknown or other
<220> FEATURE:
<221> NAME/KEY: modified_base
<222> LOCATION: (3873)..(3873)
<223> OTHER INFORMATION: a, c, g, t, unknown or other
<220> FEATURE:
<221> NAME/KEY: modified_base
<222> LOCATION: (3879)..(3879)
<223> OTHER INFORMATION: a, c, g, t, unknown or other
<220> FEATURE:
<221> NAME/KEY: modified_base
<222> LOCATION: (3888)..(3888)
<223> OTHER INFORMATION: a, c, g, t, unknown or other
<220> FEATURE:
<221> NAME/KEY: modified_base
<222> LOCATION: (3891)..(3891)
<223> OTHER INFORMATION: a, c, g, t, unknown or other
<220> FEATURE:
<221> NAME/KEY: modified_base
<222> LOCATION: (3894)..(3894)
<223> OTHER INFORMATION: a, c, g, t, unknown or other
<220> FEATURE:
<221> NAME/KEY: modified_base
<222> LOCATION: (3897)..(3897)
<223> OTHER INFORMATION: a, c, g, t, unknown or other
<220> FEATURE:
<221> NAME/KEY: modified_base
<222> LOCATION: (3903)..(3903)
<223> OTHER INFORMATION: a, c, g, t, unknown or other
<220> FEATURE:
<221> NAME/KEY: modified_base
<222> LOCATION: (3909)..(3909)
<223> OTHER INFORMATION: a, c, g, t, unknown or other
<220> FEATURE:
<221> NAME/KEY: modified_base
<222> LOCATION: (3915)..(3915)
<223> OTHER INFORMATION: a, c, g, t, unknown or other
<220> FEATURE:
<221> NAME/KEY: modified_base
<222> LOCATION: (3924)..(3924)
<223> OTHER INFORMATION: a, c, g, t, unknown or other
<220> FEATURE:
<221> NAME/KEY: modified_base
<222> LOCATION: (3930)..(3930)
<223> OTHER INFORMATION: a, c, g, t, unknown or other
<220> FEATURE:
<221> NAME/KEY: modified_base
<222> LOCATION: (3933)..(3933)
<223> OTHER INFORMATION: a, c, g, t, unknown or other
<220> FEATURE:
<221> NAME/KEY: modified_base
<222> LOCATION: (3939)..(3939)
<223> OTHER INFORMATION: a, c, g, t, unknown or other
<220> FEATURE:
<221> NAME/KEY: modified_base
<222> LOCATION: (3942)..(3942)
<223> OTHER INFORMATION: a, c, g, t, unknown or other
<220> FEATURE:
<221> NAME/KEY: modified_base
<222> LOCATION: (3948)..(3948)
<223> OTHER INFORMATION: a, c, g, t, unknown or other
<220> FEATURE:
<221> NAME/KEY: modified_base
<222> LOCATION: (3951)..(3951)
<223> OTHER INFORMATION: a, c, g, t, unknown or other
<220> FEATURE:
<221> NAME/KEY: modified_base
<222> LOCATION: (3957)..(3957)
<223> OTHER INFORMATION: a, c, g, t, unknown or other
<220> FEATURE:
<221> NAME/KEY: modified_base
<222> LOCATION: (3960)..(3960)
```

<223> OTHER INFORMATION: a, c, g, t, unknown or other
<220> FEATURE:
<221> NAME/KEY: modified_base
<222> LOCATION: (3963)..(3963)
<223> OTHER INFORMATION: a, c, g, t, unknown or other
<220> FEATURE:
<221> NAME/KEY: modified_base
<222> LOCATION: (3966)..(3966)
<223> OTHER INFORMATION: a, c, g, t, unknown or other
<220> FEATURE:
<221> NAME/KEY: modified_base
<222> LOCATION: (3969)..(3969)
<223> OTHER INFORMATION: a, c, g, t, unknown or other
<220> FEATURE:
<221> NAME/KEY: modified_base
<222> LOCATION: (3972)..(3972)
<223> OTHER INFORMATION: a, c, g, t, unknown or other
<220> FEATURE:
<221> NAME/KEY: modified_base
<222> LOCATION: (3975)..(3975)
<223> OTHER INFORMATION: a, c, g, t, unknown or other
<220> FEATURE:
<221> NAME/KEY: modified_base
<222> LOCATION: (3981)..(3981)
<223> OTHER INFORMATION: a, c, g, t, unknown or other

<400> SEQUENCE: 10
atggcngcng cntggytngg ntggytnytn tgggcnytny tnytnwsngc ngcncarggn 60
garytntaya cnccnaarca ygargcnggn gtntgyacnt tytaygarga rtgyggnaar 120
aayccngary tnwsnggngg nytnacnwsn ytnwsnaayg tnwsntgyyt nwsnaayacn 180
ccngcnmgnc aygtnacngg ngarcayytn gcnytnytnc armgnathtg yccnmgnytn 240
tayaayggnc cnaayacnac nttygcntgy tgywsnacna arcarytnyt nwsnytngar 300
wsnwsnatgw snathacnaa rgcnytnytn acnmgntgyc cngcntgyws ngayaaytty 360
gtnwsnytnc aytgycayaa yacntgywsn ccngaycarw snytnttyat haaygtnacn 420
mgngtngtng armgnggngc nggngarccn ccngcngtng tngcntayga rgcnttytay 480
carmgnwsnt tygcngaraa rgcntaygar wsntgywsnc argtnmgnat hccngcngcn 540
gcnwsnytng cngtnggnws natgtgyggn gtntayggnw sngcnytntg yaaygcncar 600
mgntggytna ayttycargg ngayacnggn aayggnytng cnccnytnga yathacntty 660
cayytnytng arccnggnca rgcnytnccn gayggnathc arccnytnaa yggnaarath 720
gcnccntgya aygarwsnca rggngaygay wsngcngtnt gywsntgyca rgaytgygcn 780
gcnwsntgyc cngtnathcc nccnccngar gcnytnmgnc cnwsnttyta yatgggnmgn 840
atgccnggnt ggytngcnyt nathathath ttyacngcng tnttygtnyt nytnwsngcn 900
gtnytngtnm gnytnmgngt ngtnwsnaay mgnaayaara ayaargcnga rggnccncar 960
gargcnccna arytnccnca yaarcayaar ytnwsnccnc ayacnathyt nggnmgntty 1020
ttycaraayt ggggnacnmg ngtngcnwsn tggccnytna cngtnytngc nytnwsntty 1080
athgtngtna thgcnytngc ngcnggnytn acnttyathg arytnacnac ngayccngtn 1140
garytntggw sngcnccnaa rwsncargcn mgnaargara arwsnttyca ygaygarcay 1200
ttyggnccnt tyttymgnac naaycarath ttygtnacng cnmgnaaymg nwsnwsntay 1260
aartaygayw snytnytnyt nggnwsnaar aayttywsng gnathytnws nytngaytty 1320
ytnytngary tnytngaryt ncargarmgn ytnmgncayy tncargtntg gwsnccngar 1380
gcngarmgna ayathwsnyt ncargayath tgytaygcnc cnytnaaycc ntayaayacn 1440
wsnytnwsng aytgytgygt naaywsnytn ytncartayt tycaraayaa ymgnacnytn 1500
ytnatgytna cngcnaayca racnytnaay ggncaracnw snytngtnga ytggaargay 1560

-continued cayttyytnt aytgygcnaa ygcnccnytn acnttyaarg ayggnacnws nytngcnytn 1620
wsntgyatgg cngaytaygg ngcnccngtn ttyccnttyy tngcngtngg nggntaycar 1680
ggnacngayt aywsngargc ngargcnytn athathacnt tywsnytnaa yaaytayccn 1740
gcngaygayc cnmgnatggc ncargcnaar ytntgggarg argcnttyyt naargaratg 1800
garwsnttyc armgnaayac nwsngayaar ttycargtng cnttywsngc ngarmgnwsn 1860
ytngargayg arathaaymg nacnacnath cargayytnc cngtnttygc ngtnwsntay 1920
athathgtnt tyytntayat hwsnytngcn ytnggnwsnt aywsnmgntg ywsnmgngtn 1980
gcngtngarw snaargcnac nytnggnytn ggnggngtna thgtngtnyt nggngcngtn 2040
ytngcngcna tgggnttyta ywsntayytn ggngtnccnw snwsnytngt nathathcar 2100
gtngtnccnt tyytngtnyt ngcngtnggn gcngayaaya thttyathtt ygtnytngar 2160
taycarmgny tnccnmgnat gccnggngar carmgngarg cncayathgg nmgnacnytn 2220
ggnwsngtng cnccnwsnat gytnytntgy wsnytnwsng argcnathtg yttyttyytn 2280
ggngcnytna cnccnatgcc ngcngtnmgn acnttygcny tnacnwsngg nytngcnath 2340
athytngayt tyytnytnca ratgacngcn ttygtngcny tnytnwsnyt ngaywsnaar 2400
mgncargarg cnwsnmgncc ngaygtnytn tgytgyttyw snacnmgnaa rytnccnccn 2460
ccnaargara argarggnyt nytnytnmgn ttyttymgna arathtaygc nccnttyytn 2520
ytncaymgnt tyathmgncc ngtngtnatg ytnytnttyy tnacnytntt yggngcnaay 2580
ytntayytna tgtgyaayat haaygtnggn ytngaycarg arytngcnyt nccnaargay 2640
wsntayytna thgaytaytt yytnttyytn aaymgntayy tngargtngg nccnccngtn 2700
tayttygtna cnacnwsngg nttyaaytty wsnwsngarg cnggnatgaa ygcnacntgy 2760
wsnwsngcng gntgyaarws nttywsnytn acncaraara thcartaygc nwsngartty 2820
ccngaycarw sntaygtngc nathgcngcn wsnwsntggg tngaygaytt yathgaytgg 2880
ytnacnccnw snwsnwsntg ytgymgnytn tayathmgng gnccncayaa rgaygartty 2940
tgyccnwsna cngayacnws nttyaaytgy ytnaaraayt gyatgaaymg nacnytnggn 3000
ccngtnmgnc cnacngcnga rcarttycay aartayytnc cntggttyyt naaygayccn 3060
ccnaayathm gntgyccnaa rggnggnytn gcngcntaym gnacnwsngt naayytnwsn 3120
wsngayggnc argtnathgc nwsncartty atggcntayc ayaarccnyt nmgnaaywsn 3180
cargayttya cngargcnyt nmgngcnwsn mgnytnytng cngcnaayat hacngcngay 3240
ytnmgnaarg tnccnggnac ngayccnaay ttygargtnt tyccntayac nathwsnaay 3300
gtnttytayc arcartayyt nacngtnytn ccngarggna thttyacnyt ngcnytntgy 3360
ttygtnccna cnttygtngt ntgytayytn ytnytnggny tngayatgtg ywsnggnath 3420
ytnaayytny tnwsnathat hatgathytn gtngayacna thggnytnat ggcngtntgg 3480
ggnathwsnt ayaaygcngt nwsnytnath aayytngtna cngcngtngg natgwsngtn 3540
garttygtnw sncayathac nmgnwsntty gcngtnwsna cnaarccnac nmgnytngar 3600
mgngcnaarg aygcnacngt nttyatgggn wsngcngtnt tygcnggngt ngcnatgacn 3660
aayttyccng gnathytnat hytnggntty gcncargcnc arytnathca rathttytty 3720
ttymgnytna ayytnytnat hacnytnytn ggnytnytnc ayggnytngt nttyytnccn 3780
gtngtnytnw sntayytngg nccngaygtn aaycargcny tngtncarga rgaraarytn 3840
gcnwsngarg cngcngtngc nccngarccn wsntgyccnc artayccnws nccngcngay 3900
gcngaygcna aygtnaayta yggnttygcn ccngarytng cncayggngc naaygcngcn 3960

| | | |
|---|---|---|
| mgnwsnwsny tnccnaarws ngaycaraar tty | | 3993 |

<210> SEQ ID NO 11
<211> LENGTH: 4002
<212> TYPE: DNA
<213> ORGANISM: Mus sp.
<220> FEATURE:
<221> NAME/KEY: CDS
<222> LOCATION: (1)..(4002)

<400> SEQUENCE: 11

| | | |
|---|---|---|
| atg gca gct gcc tgg cag gga tgg ctg ctc tgg gcc ctg ctc ctg aat<br>Met Ala Ala Ala Trp Gln Gly Trp Leu Leu Trp Ala Leu Leu Leu Asn<br>1                       5                     10                  15 | | 48 |
| tcg gcc cag ggt gag ctc tac aca ccc act cac aaa gct ggc ttc tgc<br>Ser Ala Gln Gly Glu Leu Tyr Thr Pro Thr His Lys Ala Gly Phe Cys<br>                20                     25                     30 | | 96 |
| acc ttt tat gaa gag tgt ggg aag aac cca gag ctt tct gga ggc ctc<br>Thr Phe Tyr Glu Glu Cys Gly Lys Asn Pro Glu Leu Ser Gly Gly Leu<br>                35                     40                     45 | | 144 |
| aca tca cta tcc aat atc tcc tgc ttg tct aat acc cca gcc cgc cat<br>Thr Ser Leu Ser Asn Ile Ser Cys Leu Ser Asn Thr Pro Ala Arg His<br>        50                     55                     60 | | 192 |
| gtc aca ggt gac cac ctg gct ctt ctc cag cgc gtc tgt ccc cgc cta<br>Val Thr Gly Asp His Leu Ala Leu Leu Gln Arg Val Cys Pro Arg Leu<br>65                     70                     75                     80 | | 240 |
| tac aat ggc ccc aat gac acc tat gcc tgt tgc tct acc aag cag ctg<br>Tyr Asn Gly Pro Asn Asp Thr Tyr Ala Cys Cys Ser Thr Lys Gln Leu<br>                85                     90                     95 | | 288 |
| gtg tca tta gac agt agc ctg tct atc acc aag gcc ctc ctt aca cgc<br>Val Ser Leu Asp Ser Ser Leu Ser Ile Thr Lys Ala Leu Leu Thr Arg<br>                   100                   105                 110 | | 336 |
| tgc ccg gca tgc tct gaa aat ttt gtg agc ata cac tgt cat aat acc<br>Cys Pro Ala Cys Ser Glu Asn Phe Val Ser Ile His Cys His Asn Thr<br>            115                     120                   125 | | 384 |
| tgc agc cct gac cag agc ctc ttc atc aat gtt act cgc gtg gtt cag<br>Cys Ser Pro Asp Gln Ser Leu Phe Ile Asn Val Thr Arg Val Val Gln<br>        130                     135                     140 | | 432 |
| cgg gac cct gga cag ctt cct gct gtg gtg gcc tat gag gcc ttt tat<br>Arg Asp Pro Gly Gln Leu Pro Ala Val Val Ala Tyr Glu Ala Phe Tyr<br>145                   150                     155                    160 | | 480 |
| caa cgc agt ttt gca gag aag gcc tat gag tcc tgt agc cgg gtg cgc<br>Gln Arg Ser Phe Ala Glu Lys Ala Tyr Glu Ser Cys Ser Arg Val Arg<br>                 165                   170                 175 | | 528 |
| atc cct gca gct gcc tcg ctg gct gtg ggc agc atg tgt gga gtg tat<br>Ile Pro Ala Ala Ala Ser Leu Ala Val Gly Ser Met Cys Gly Val Tyr<br>            180                     185                   190 | | 576 |
| ggc tct gcc ctc tgc aat gct cag cgc tgg ctc aac ttc caa gga gac<br>Gly Ser Ala Leu Cys Asn Ala Gln Arg Trp Leu Asn Phe Gln Gly Asp<br>               195                   200                 205 | | 624 |
| aca ggg aat ggc ctg gct ccg ctg gac atc acc ttc cac ctc ttg gag<br>Thr Gly Asn Gly Leu Ala Pro Leu Asp Ile Thr Phe His Leu Leu Glu<br>        210                     215                     220 | | 672 |
| cct ggc cag gcc ctg gca gat ggg atg aag cca ctg gat ggg aag atc<br>Pro Gly Gln Ala Leu Ala Asp Gly Met Lys Pro Leu Asp Gly Lys Ile<br>225                   230                     235                    240 | | 720 |
| aca ccc tgc aat gag tcc cag ggt gaa gac tcg gca gcc tgt tcc tgc<br>Thr Pro Cys Asn Glu Ser Gln Gly Glu Asp Ser Ala Ala Cys Ser Cys<br>                   245                   250                 255 | | 768 |
| cag gac tgt gca gca tcc tgc cct gtc atc cct ccg ccc ccg gcc ctg<br>Gln Asp Cys Ala Ala Ser Cys Pro Val Ile Pro Pro Pro Pro Ala Leu<br>            260                     265                   270 | | 816 |

-continued

| | | |
|---|---|---|
| cgc cct tct ttc tac atg ggt cga atg cca ggc tgg ctg gct ctc atc<br>Arg Pro Ser Phe Tyr Met Gly Arg Met Pro Gly Trp Leu Ala Leu Ile<br>       275                      280                      285 | 864 | |
| atc atc ttc act gct gtc ttt gta ttg ctc tct gtt gtc ctt gtg tat<br>Ile Ile Phe Thr Ala Val Phe Val Leu Leu Ser Val Val Leu Val Tyr<br>       290                      295                      300 | 912 | |
| ctc cga gtg gct tcc aac agg aac aag aac aag aca gca ggc tcc cag<br>Leu Arg Val Ala Ser Asn Arg Asn Lys Asn Lys Thr Ala Gly Ser Gln<br>305                      310                      315                      320 | 960 | |
| gaa gcc ccc aac ctc cct cgt aag cgc aga ttc tca cct cac act gtc<br>Glu Ala Pro Asn Leu Pro Arg Lys Arg Arg Phe Ser Pro His Thr Val<br>                      325                      330                      335 | 1008 | |
| ctt ggc cgg ttc ttc gag agc tgg gga aca agg gtg gcc tca tgg cca<br>Leu Gly Arg Phe Phe Glu Ser Trp Gly Thr Arg Val Ala Ser Trp Pro<br>       340                      345                      350 | 1056 | |
| ctc act gtc ttg gca ctg tcc ttc ata gtt gtg ata gcc ttg tca gta<br>Leu Thr Val Leu Ala Leu Ser Phe Ile Val Val Ile Ala Leu Ser Val<br>                      355                      360                      365 | 1104 | |
| ggc ctg acc ttt ata gaa ctc acc aca gac cct gtg gaa ctg tgg tcg<br>Gly Leu Thr Phe Ile Glu Leu Thr Thr Asp Pro Val Glu Leu Trp Ser<br>370                      375                      380 | 1152 | |
| gcc cct aaa agc caa gcc cgg aaa gaa aag gct ttc cat gac gag cat<br>Ala Pro Lys Ser Gln Ala Arg Lys Glu Lys Ala Phe His Asp Glu His<br>385                      390                      395                      400 | 1200 | |
| ttt ggc ccc ttc ttc cga acc aac cag att ttt gtg aca gct aag aac<br>Phe Gly Pro Phe Phe Arg Thr Asn Gln Ile Phe Val Thr Ala Lys Asn<br>                      405                      410                      415 | 1248 | |
| agg tcc agc tac aag tac gac tcc ctg ctg cta ggg ccc aag aac ttc<br>Arg Ser Ser Tyr Lys Tyr Asp Ser Leu Leu Leu Gly Pro Lys Asn Phe<br>                      420                      425                      430 | 1296 | |
| agt ggg atc cta tcc ctg gac ttg ctg cag gag ctg ttg gag cta cag<br>Ser Gly Ile Leu Ser Leu Asp Leu Leu Gln Glu Leu Leu Glu Leu Gln<br>                      435                      440                      445 | 1344 | |
| gag aga ctt cga cac ctg caa gtg tgg tcc cat gag gca cag cgc aac<br>Glu Arg Leu Arg His Leu Gln Val Trp Ser His Glu Ala Gln Arg Asn<br>450                      455                      460 | 1392 | |
| atc tcc ctc cag gac atc tgc tat gct ccc ctc aac ccg cat aac acc<br>Ile Ser Leu Gln Asp Ile Cys Tyr Ala Pro Leu Asn Pro His Asn Thr<br>465                      470                      475                      480 | 1440 | |
| agc ctc act gac tgc tgt gtc aac agc ctc ctt caa tac ttc cag aac<br>Ser Leu Thr Asp Cys Cys Val Asn Ser Leu Leu Gln Tyr Phe Gln Asn<br>                      485                      490                      495 | 1488 | |
| aac cac aca ctc ctg ctc aca gcc aat cag act ctg aat ggc cag<br>Asn His Thr Leu Leu Leu Thr Ala Asn Gln Thr Leu Asn Gly Gln<br>                      500                      505                      510 | 1536 | |
| acc tcc ctg gtg gac tgg aag gac cat ttc ctc tac tgt gcc aat gcc<br>Thr Ser Leu Val Asp Trp Lys Asp His Phe Leu Tyr Cys Ala Asn Ala<br>                      515                      520                      525 | 1584 | |
| cct ctc acg tac aaa gat ggc aca gcc ctg gcc ctg agc tgc ata gct<br>Pro Leu Thr Tyr Lys Asp Gly Thr Ala Leu Ala Leu Ser Cys Ile Ala<br>       530                      535                      540 | 1632 | |
| gac tac ggg gca cct gtc ttc ccc ttc ctt gct gtt ggg ggc tac caa<br>Asp Tyr Gly Ala Pro Val Phe Pro Phe Leu Ala Val Gly Gly Tyr Gln<br>545                      550                      555                      560 | 1680 | |
| ggg acg gac tac tcg gag gca gaa gcc ctg atc ata acc ttc tct atc<br>Gly Thr Asp Tyr Ser Glu Ala Glu Ala Leu Ile Ile Thr Phe Ser Ile<br>                      565                      570                      575 | 1728 | |
| aat aac tac ccc gct gat gat ccc cgc atg gcc cac gcc aag ctc tgg<br>Asn Asn Tyr Pro Ala Asp Asp Pro Arg Met Ala His Ala Lys Leu Trp<br>                      580                      585                      590 | 1776 | |

-continued

| | | |
|---|---|---|
| gag gag gct ttc ttg aag gaa atg caa tcc ttc cag aga agc aca gct<br>Glu Glu Ala Phe Leu Lys Glu Met Gln Ser Phe Gln Arg Ser Thr Ala<br>              595                    600                  605 | 1824 |
| gac aag ttc cag att gcg ttc tca gct gag cgt tct ctg gag gac gag<br>Asp Lys Phe Gln Ile Ala Phe Ser Ala Glu Arg Ser Leu Glu Asp Glu<br>610                    615                    620 | 1872 |
| atc aat cgc act acc atc cag gac ctg cct gtc ttt gcc atc agc tac<br>Ile Asn Arg Thr Thr Ile Gln Asp Leu Pro Val Phe Ala Ile Ser Tyr<br>625                    630                    635                  640 | 1920 |
| ctt atc gtc ttc ctg tac atc tcc ctg gcc ctg ggc agc tac tcc aga<br>Leu Ile Val Phe Leu Tyr Ile Ser Leu Ala Leu Gly Ser Tyr Ser Arg<br>              645                    650                    655 | 1968 |
| tgg agc cga gtt gcg gtg gat tcc aag gct act ctg ggc cta ggt ggg<br>Trp Ser Arg Val Ala Val Asp Ser Lys Ala Thr Leu Gly Leu Gly Gly<br>                  660                    665                  670 | 2016 |
| gtg gct gtt gtg ctg gga gca gtc gtc gct gcc atg ggc ttc tac tcc<br>Val Ala Val Val Leu Gly Ala Val Val Ala Ala Met Gly Phe Tyr Ser<br>675                    680                    685 | 2064 |
| tac ctg ggt gtc ccc tcc tct ctg gtc atc att caa gtg gta cct ttc<br>Tyr Leu Gly Val Pro Ser Ser Leu Val Ile Ile Gln Val Val Pro Phe<br>              690                    695                    700 | 2112 |
| ctg gtg ctg gct gtg gga gct gac aac atc ttc atc ttt gtt ctt gag<br>Leu Val Leu Ala Val Gly Ala Asp Asn Ile Phe Ile Phe Val Leu Glu<br>705                    710                    715                  720 | 2160 |
| tac cag agg ctg cct agg atg ccc ggg gag cag cga gag gct cac att<br>Tyr Gln Arg Leu Pro Arg Met Pro Gly Glu Gln Arg Glu Ala His Ile<br>                  725                    730                  735 | 2208 |
| ggc cgc acc ctg ggt agt gtg gcc ccc agc atg ctg ctg tgc agc ctc<br>Gly Arg Thr Leu Gly Ser Val Ala Pro Ser Met Leu Leu Cys Ser Leu<br>740                    745                    750 | 2256 |
| tct gag gcc atc tgc ttc ttt cta ggg gcc ctg acc tcc atg cca gct<br>Ser Glu Ala Ile Cys Phe Phe Leu Gly Ala Leu Thr Ser Met Pro Ala<br>              755                    760                  765 | 2304 |
| gtg agg acc ttt gcc ttg acc tct ggc tta gca atc atc ttt gac ttc<br>Val Arg Thr Phe Ala Leu Thr Ser Gly Leu Ala Ile Ile Phe Asp Phe<br>770                    775                    780 | 2352 |
| ctg ctc cag atg aca gcc ttt gtg gcc ctg ctc tcc ctg gat agc aag<br>Leu Leu Gln Met Thr Ala Phe Val Ala Leu Leu Ser Leu Asp Ser Lys<br>785                    790                    795                  800 | 2400 |
| agg cag gag gcc tct cgc ccc gac gtc gtg tgc tgc ttt tca agc cga<br>Arg Gln Glu Ala Ser Arg Pro Asp Val Val Cys Cys Phe Ser Ser Arg<br>                  805                    810                  815 | 2448 |
| aat ctg ccc cca ccg aaa caa aaa gaa ggc ctc tta ctt tgc ttc ttc<br>Asn Leu Pro Pro Pro Lys Gln Lys Glu Gly Leu Leu Leu Cys Phe Phe<br>820                    825                    830 | 2496 |
| cgc aag ata tac act ccc ttc ctg ctg cac aga ttc atc cgc cct gtt<br>Arg Lys Ile Tyr Thr Pro Phe Leu Leu His Arg Phe Ile Arg Pro Val<br>              835                    840                  845 | 2544 |
| gtg ctg ctg ctc ttt ctg gtc ctg ttt gga gca aac ctc tac tta atg<br>Val Leu Leu Leu Phe Leu Val Leu Phe Gly Ala Asn Leu Tyr Leu Met<br>850                    855                    860 | 2592 |
| tgc aac atc agc gtg ggg ctg gac cag gat ctg gct ctg ccc aag gat<br>Cys Asn Ile Ser Val Gly Leu Asp Gln Asp Leu Ala Leu Pro Lys Asp<br>865                    870                    875                  880 | 2640 |
| tcc tac ctg ata gac tac ttc ctc ttt ctg aac cgg tac ttg gaa gtg<br>Ser Tyr Leu Ile Asp Tyr Phe Leu Phe Leu Asn Arg Tyr Leu Glu Val<br>              885                    890                  895 | 2688 |
| ggg cct cca gtg tac ttt gac acc acc tca ggc tac aac ttt tcc acc<br>Gly Pro Pro Val Tyr Phe Asp Thr Thr Ser Gly Tyr Asn Phe Ser Thr<br>900                    905                    910 | 2736 |

```
gag gca ggc atg aac gcc att tgc tct agt gca ggc tgt gag agc ttc    2784
Glu Ala Gly Met Asn Ala Ile Cys Ser Ser Ala Gly Cys Glu Ser Phe
        915                 920                 925 tcc cta acc cag aaa atc cag tat gcc agt gaa ttc cct aat cag tct    2832
Ser Leu Thr Gln Lys Ile Gln Tyr Ala Ser Glu Phe Pro Asn Gln Ser
    930                 935                 940 tat gtg gct att gct gca tcc tcc tgg gta gat gac ttc atc gac tgg    2880
Tyr Val Ala Ile Ala Ala Ser Ser Trp Val Asp Asp Phe Ile Asp Trp
945                 950                 955                 960 ctg acc cca tcc tcc tcc tgc tgc cgc att tat acc cgt ggc ccc cat    2928
Leu Thr Pro Ser Ser Ser Cys Cys Arg Ile Tyr Thr Arg Gly Pro His
        965                 970                 975 aaa gat gag ttc tgt ccc tca acg gat act tcc ttc aac tgt ctc aaa    2976
Lys Asp Glu Phe Cys Pro Ser Thr Asp Thr Ser Phe Asn Cys Leu Lys
    980                 985                 990 aac tgc atg aac cgc act ctg ggt ccc gtg aga ccc aca aca gaa cag    3024
Asn Cys Met Asn Arg Thr Leu Gly Pro Val Arg Pro Thr Thr Glu Gln
        995                 1000                1005 ttt cat aag tac ctg ccc tgg ttc ctg aat gat acg ccc aac atc        3069
Phe His Lys Tyr Leu Pro Trp Phe Leu Asn Asp Thr Pro Asn Ile
    1010                1015                1020 aga tgt cct aaa ggg ggc cta gca gcg tat aga acc tct gtg aat        3114
Arg Cys Pro Lys Gly Gly Leu Ala Ala Tyr Arg Thr Ser Val Asn
    1025                1030                1035 ttg agc tca gat ggc cag att ata gcc tcc cag ttc atg gcc tac        3159
Leu Ser Ser Asp Gly Gln Ile Ile Ala Ser Gln Phe Met Ala Tyr
    1040                1045                1050 cac aag ccc tta cgg aac tca cag gac ttt aca gaa gct ctc cgg        3204
His Lys Pro Leu Arg Asn Ser Gln Asp Phe Thr Glu Ala Leu Arg
    1055                1060                1065 gca tcc cgg ttg cta gca gcc aac atc aca gct gaa cta cgg aag        3249
Ala Ser Arg Leu Leu Ala Ala Asn Ile Thr Ala Glu Leu Arg Lys
    1070                1075                1080 gtg cct ggg aca gat ccc aac ttt gag gtc ttc cct tac acg atc        3294
Val Pro Gly Thr Asp Pro Asn Phe Glu Val Phe Pro Tyr Thr Ile
    1085                1090                1095 tcc aat gtg ttc tac cag caa tac ctg acg gtt ctc cct gag gga        3339
Ser Asn Val Phe Tyr Gln Gln Tyr Leu Thr Val Leu Pro Glu Gly
    1100                1105                1110 atc ttc act ctt gct ctc tgc ttc gtg ccc acc ttt gtg gtc tgc        3384
Ile Phe Thr Leu Ala Leu Cys Phe Val Pro Thr Phe Val Val Cys
    1115                1120                1125 tac ctc cta ctg ggc ctg gac ata cgc tca ggc atc ctc aac ctg        3429
Tyr Leu Leu Leu Gly Leu Asp Ile Arg Ser Gly Ile Leu Asn Leu
    1130                1135                1140 ctc tcc atc att atg atc ctc gtg gac acc atc ggc ctc atg gct        3474
Leu Ser Ile Ile Met Ile Leu Val Asp Thr Ile Gly Leu Met Ala
    1145                1150                1155 gtg tgg ggt atc agc tac aat gct gtg tcc ctc atc aac ctt gtc        3519
Val Trp Gly Ile Ser Tyr Asn Ala Val Ser Leu Ile Asn Leu Val
    1160                1165                1170 acg gca gtg ggc atg tct gtg gag ttc gtg tcc cac att acc cgg        3564
Thr Ala Val Gly Met Ser Val Glu Phe Val Ser His Ile Thr Arg
    1175                1180                1185 tcc ttt gct gta agc acc aag cct acc cgg ctg gag aga gcc aaa        3609
Ser Phe Ala Val Ser Thr Lys Pro Thr Arg Leu Glu Arg Ala Lys
    1190                1195                1200 gat gct act atc ttc atg ggc agt gcg gtg ttt gct gga gtg gcc        3654
Asp Ala Thr Ile Phe Met Gly Ser Ala Val Phe Ala Gly Val Ala
    1205                1210                1215
```

```
atg acc aac ttc ccg ggc atc ctc atc ctg ggc ttt gct cag gcc    3699
Met Thr Asn Phe Pro Gly Ile Leu Ile Leu Gly Phe Ala Gln Ala
1220            1225                1230 cag ctt atc cag att ttc ttc cgc ctc aac ctc ctg atc acc        3744
Gln Leu Ile Gln Ile Phe Phe Arg Leu Asn Leu Leu Ile Thr
    1235            1240                1245 ttg ctg ggt ctg cta cac ggc ctg gtc ttc ctg ccc gtt gtc ctc    3789
Leu Leu Gly Leu Leu His Gly Leu Val Phe Leu Pro Val Val Leu
1250            1255                1260 agc tat ctg ggg cca gat gtt aac caa gct ctg gta ctg gag gag    3834
Ser Tyr Leu Gly Pro Asp Val Asn Gln Ala Leu Val Leu Glu Glu
1265            1270                1275 aaa cta gcc act gag gca gcc atg gtc tca gag cct tct tgc cca    3879
Lys Leu Ala Thr Glu Ala Ala Met Val Ser Glu Pro Ser Cys Pro
    1280            1285                1290 cag tac ccc ttc ccg gct gat gca aac acc agt gac tat gtt aac    3924
Gln Tyr Pro Phe Pro Ala Asp Ala Asn Thr Ser Asp Tyr Val Asn
1295            1300                1305 tac ggc ttt aat cca gaa ttt atc cct gaa att aat gct gct agc    3969
Tyr Gly Phe Asn Pro Glu Phe Ile Pro Glu Ile Asn Ala Ala Ser
1310            1315                1320 agc tct ctg ccc aaa agt gac caa aag ttc taa                    4002
Ser Ser Leu Pro Lys Ser Asp Gln Lys Phe
    1325            1330

<210> SEQ ID NO 12
<211> LENGTH: 1333
<212> TYPE: PRT
<213> ORGANISM: Mus sp.

<400> SEQUENCE: 12

Met Ala Ala Ala Trp Gln Gly Trp Leu Leu Trp Ala Leu Leu Leu Asn
1               5                   10                  15

Ser Ala Gln Gly Glu Leu Tyr Thr Pro Thr His Lys Ala Gly Phe Cys
            20                  25                  30

Thr Phe Tyr Glu Glu Cys Gly Lys Asn Pro Glu Leu Ser Gly Gly Leu
        35                  40                  45

Thr Ser Leu Ser Asn Ile Ser Cys Leu Ser Thr Pro Ala Arg His
    50                  55                  60

Val Thr Gly Asp His Leu Ala Leu Leu Gln Arg Val Cys Pro Arg Leu
65                  70                  75                  80

Tyr Asn Gly Pro Asn Asp Thr Tyr Ala Cys Cys Ser Thr Lys Gln Leu
                85                  90                  95

Val Ser Leu Asp Ser Ser Leu Ser Ile Thr Lys Ala Leu Leu Thr Arg
            100                 105                 110

Cys Pro Ala Cys Ser Glu Asn Phe Val Ser Ile His Cys His Asn Thr
        115                 120                 125

Cys Ser Pro Asp Gln Ser Leu Phe Ile Asn Val Thr Arg Val Val Gln
    130                 135                 140

Arg Asp Pro Gly Gln Leu Pro Ala Val Val Ala Tyr Glu Ala Phe Tyr
145                 150                 155                 160

Gln Arg Ser Phe Ala Glu Lys Ala Tyr Glu Ser Cys Ser Arg Val Arg
                165                 170                 175

Ile Pro Ala Ala Ala Ser Leu Ala Val Gly Ser Met Cys Gly Val Tyr
            180                 185                 190

Gly Ser Ala Leu Cys Asn Ala Gln Arg Trp Leu Asn Phe Gln Gly Asp
        195                 200                 205
```

```
Thr Gly Asn Gly Leu Ala Pro Leu Asp Ile Thr Phe His Leu Leu Glu
210                 215                 220

Pro Gly Gln Ala Leu Ala Asp Gly Met Lys Pro Leu Asp Gly Lys Ile
225                 230                 235                 240

Thr Pro Cys Asn Glu Ser Gln Gly Glu Asp Ser Ala Ala Cys Ser Cys
                245                 250                 255

Gln Asp Cys Ala Ala Ser Cys Pro Val Ile Pro Pro Pro Ala Leu
            260                 265                 270

Arg Pro Ser Phe Tyr Met Gly Arg Met Pro Gly Trp Leu Ala Leu Ile
        275                 280                 285

Ile Ile Phe Thr Ala Val Phe Val Leu Ser Val Val Leu Val Tyr
290                 295                 300

Leu Arg Val Ala Ser Asn Arg Asn Lys Asn Lys Thr Ala Gly Ser Gln
305                 310                 315                 320

Glu Ala Pro Asn Leu Pro Arg Lys Arg Arg Phe Ser Pro His Thr Val
                325                 330                 335

Leu Gly Arg Phe Phe Glu Ser Trp Gly Thr Arg Val Ala Ser Trp Pro
            340                 345                 350

Leu Thr Val Leu Ala Leu Ser Phe Ile Val Val Ile Ala Leu Ser Val
        355                 360                 365

Gly Leu Thr Phe Ile Glu Leu Thr Thr Asp Pro Val Glu Leu Trp Ser
370                 375                 380

Ala Pro Lys Ser Gln Ala Arg Lys Glu Lys Ala Phe His Asp Glu His
385                 390                 395                 400

Phe Gly Pro Phe Phe Arg Thr Asn Gln Ile Phe Val Thr Ala Lys Asn
                405                 410                 415

Arg Ser Ser Tyr Lys Tyr Asp Ser Leu Leu Leu Gly Pro Lys Asn Phe
            420                 425                 430

Ser Gly Ile Leu Ser Leu Asp Leu Leu Gln Glu Leu Leu Glu Leu Gln
        435                 440                 445

Glu Arg Leu Arg His Leu Gln Val Trp Ser His Glu Ala Gln Arg Asn
450                 455                 460

Ile Ser Leu Gln Asp Ile Cys Tyr Ala Pro Leu Asn Pro His Asn Thr
465                 470                 475                 480

Ser Leu Thr Asp Cys Cys Val Asn Ser Leu Leu Gln Tyr Phe Gln Asn
                485                 490                 495

Asn His Thr Leu Leu Leu Leu Thr Ala Asn Gln Thr Leu Asn Gly Gln
            500                 505                 510

Thr Ser Leu Val Asp Trp Lys Asp His Phe Leu Tyr Cys Ala Asn Ala
        515                 520                 525

Pro Leu Thr Tyr Lys Asp Gly Thr Ala Leu Ala Leu Ser Cys Ile Ala
530                 535                 540

Asp Tyr Gly Ala Pro Val Phe Pro Phe Leu Ala Val Gly Gly Tyr Gln
545                 550                 555                 560

Gly Thr Asp Tyr Ser Glu Ala Glu Ala Leu Ile Ile Thr Phe Ser Ile
                565                 570                 575

Asn Asn Tyr Pro Ala Asp Asp Pro Arg Met Ala His Ala Lys Leu Trp
            580                 585                 590

Glu Glu Ala Phe Leu Lys Glu Met Gln Ser Phe Gln Arg Ser Thr Ala
        595                 600                 605

Asp Lys Phe Gln Ile Ala Phe Ser Ala Glu Arg Ser Leu Glu Asp Glu
610                 615                 620

Ile Asn Arg Thr Thr Ile Gln Asp Leu Pro Val Phe Ala Ile Ser Tyr
625                 630                 635                 640
```

Leu Ile Val Phe Leu Tyr Ile Ser Leu Ala Leu Gly Ser Tyr Ser Arg
                        645                 650                 655

Trp Ser Arg Val Ala Val Asp Ser Lys Ala Thr Leu Gly Leu Gly Gly
            660                 665                 670

Val Ala Val Val Leu Gly Ala Val Ala Ala Met Gly Phe Tyr Ser
            675                 680                 685

Tyr Leu Gly Val Pro Ser Ser Leu Val Ile Ile Gln Val Val Pro Phe
    690                 695                 700

Leu Val Leu Ala Val Gly Ala Asp Asn Ile Phe Ile Phe Val Leu Glu
705                 710                 715                 720

Tyr Gln Arg Leu Pro Arg Met Pro Gly Glu Gln Arg Glu Ala His Ile
                    725                 730                 735

Gly Arg Thr Leu Gly Ser Val Ala Pro Ser Met Leu Leu Cys Ser Leu
                740                 745                 750

Ser Glu Ala Ile Cys Phe Phe Leu Gly Ala Leu Thr Ser Met Pro Ala
            755                 760                 765

Val Arg Thr Phe Ala Leu Thr Ser Gly Leu Ala Ile Ile Phe Asp Phe
    770                 775                 780

Leu Leu Gln Met Thr Ala Phe Val Ala Leu Leu Ser Leu Asp Ser Lys
785                 790                 795                 800

Arg Gln Glu Ala Ser Arg Pro Asp Val Val Cys Cys Phe Ser Ser Arg
                    805                 810                 815

Asn Leu Pro Pro Pro Lys Gln Lys Glu Gly Leu Leu Leu Cys Phe Phe
                820                 825                 830

Arg Lys Ile Tyr Thr Pro Phe Leu Leu His Arg Phe Ile Arg Pro Val
            835                 840                 845

Val Leu Leu Leu Phe Leu Val Leu Phe Gly Ala Asn Leu Tyr Leu Met
    850                 855                 860

Cys Asn Ile Ser Val Gly Leu Asp Gln Asp Leu Ala Leu Pro Lys Asp
865                 870                 875                 880

Ser Tyr Leu Ile Asp Tyr Phe Leu Phe Leu Asn Arg Tyr Leu Glu Val
                    885                 890                 895

Gly Pro Pro Val Tyr Phe Asp Thr Thr Ser Gly Tyr Asn Phe Ser Thr
                900                 905                 910

Glu Ala Gly Met Asn Ala Ile Cys Ser Ser Ala Gly Cys Glu Ser Phe
            915                 920                 925

Ser Leu Thr Gln Lys Ile Gln Tyr Ala Ser Glu Phe Pro Asn Gln Ser
    930                 935                 940

Tyr Val Ala Ile Ala Ala Ser Ser Trp Val Asp Asp Phe Ile Asp Trp
945                 950                 955                 960

Leu Thr Pro Ser Ser Ser Cys Cys Arg Ile Tyr Thr Arg Gly Pro His
                    965                 970                 975

Lys Asp Glu Phe Cys Pro Ser Thr Asp Thr Ser Phe Asn Cys Leu Lys
                980                 985                 990

Asn Cys Met Asn Arg Thr Leu Gly Pro Val Arg Pro Thr Thr Glu Gln
            995                 1000                1005

Phe His Lys Tyr Leu Pro Trp Phe Leu Asn Asp Thr Pro Asn Ile
    1010                1015                1020

Arg Cys Pro Lys Gly Gly Leu Ala Ala Tyr Arg Thr Ser Val Asn
    1025                1030                1035

Leu Ser Ser Asp Gly Gln Ile Ile Ala Ser Gln Phe Met Ala Tyr
    1040                1045                1050

His Lys Pro Leu Arg Asn Ser Gln Asp Phe Thr Glu Ala Leu Arg

```
                 1055                1060                1065

Ala Ser Arg Leu Leu Ala Ala Asn Ile Thr Ala Glu Leu Arg Lys
        1070                1075                1080

Val Pro Gly Thr Asp Pro Asn Phe Glu Val Phe Pro Tyr Thr Ile
    1085                1090                1095

Ser Asn Val Phe Tyr Gln Gln Tyr Leu Thr Val Leu Pro Glu Gly
    1100                1105                1110

Ile Phe Thr Leu Ala Leu Cys Phe Val Pro Thr Phe Val Val Cys
    1115                1120                1125

Tyr Leu Leu Leu Gly Leu Asp Ile Arg Ser Gly Ile Leu Asn Leu
    1130                1135                1140

Leu Ser Ile Ile Met Ile Leu Val Asp Thr Ile Gly Leu Met Ala
    1145                1150                1155

Val Trp Gly Ile Ser Tyr Asn Ala Val Ser Leu Ile Asn Leu Val
    1160                1165                1170

Thr Ala Val Gly Met Ser Val Glu Phe Val Ser His Ile Thr Arg
    1175                1180                1185

Ser Phe Ala Val Ser Thr Lys Pro Thr Arg Leu Glu Arg Ala Lys
    1190                1195                1200

Asp Ala Thr Ile Phe Met Gly Ser Ala Val Phe Ala Gly Val Ala
    1205                1210                1215

Met Thr Asn Phe Pro Gly Ile Leu Ile Leu Gly Phe Ala Gln Ala
    1220                1225                1230

Gln Leu Ile Gln Ile Phe Phe Phe Arg Leu Asn Leu Leu Ile Thr
    1235                1240                1245

Leu Leu Gly Leu Leu His Gly Leu Val Phe Leu Pro Val Val Leu
    1250                1255                1260

Ser Tyr Leu Gly Pro Asp Val Asn Gln Ala Leu Val Leu Glu Glu
    1265                1270                1275

Lys Leu Ala Thr Glu Ala Ala Met Val Ser Glu Pro Ser Cys Pro
    1280                1285                1290

Gln Tyr Pro Phe Pro Ala Asp Ala Asn Thr Ser Asp Tyr Val Asn
    1295                1300                1305

Tyr Gly Phe Asn Pro Glu Phe Ile Pro Glu Ile Asn Ala Ala Ser
    1310                1315                1320

Ser Ser Leu Pro Lys Ser Asp Gln Lys Phe
    1325                1330

<210> SEQ ID NO 13
<211> LENGTH: 3999
<212> TYPE: DNA
<213> ORGANISM: Mus sp.
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (27)..(27)
```

-continued

```
<223> OTHER INFORMATION: a, c, g, t, unknown or other
<220> FEATURE:
<221> NAME/KEY: modified_base
<222> LOCATION: (30)..(30)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other
<220> FEATURE:
<221> NAME/KEY: modified_base
<222> LOCATION: (39)..(39)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (45)..(45)
<223> OTHER INFORMATION: a, c, g, t, unknown or other
<220> FEATURE:
<221> NAME/KEY: modified_base
<222> LOCATION: (51)..(51)
<223> OTHER INFORMATION: a, c, g, t, unknown or other
<220> FEATURE:
<221> NAME/KEY: modified_base
<222> LOCATION: (54)..(54)
<223> OTHER INFORMATION: a, c, g, t, unknown or other
<220> FEATURE:
<221> NAME/KEY: modified_base
<222> LOCATION: (60)..(60)
<223> OTHER INFORMATION: a, c, g, t, unknown or other
<220> FEATURE:
<221> NAME/KEY: modified_base
<222> LOCATION: (66)..(66)
<223> OTHER INFORMATION: a, c, g, t, unknown or other
<220> FEATURE:
<221> NAME/KEY: modified_base
<222> LOCATION: (72)..(72)
<223> OTHER INFORMATION: a, c, g, t, unknown or other
<220> FEATURE:
<221> NAME/KEY: modified_base
<222> LOCATION: (75)..(75)
<223> OTHER INFORMATION: a, c, g, t, unknown or other
<220> FEATURE:
<221> NAME/KEY: modified_base
<222> LOCATION: (78)..(78)
<223> OTHER INFORMATION: a, c, g, t, unknown or other
<220> FEATURE:
<221> NAME/KEY: modified_base
<222> LOCATION: (87)..(87)
<223> OTHER INFORMATION: a, c, g, t, unknown or other
<220> FEATURE:
<221> NAME/KEY: modified_base
<222> LOCATION: (90)..(90)
<223> OTHER INFORMATION: a, c, g, t, unknown or other
<220> FEATURE:
<221> NAME/KEY: modified_base
<222> LOCATION: (99)..(99)
<223> OTHER INFORMATION: a, c, g, t, unknown or other
<220> FEATURE:
<221> NAME/KEY: modified_base
<222> LOCATION: (117)..(117)
<223> OTHER INFORMATION: a, c, g, t, unknown or other
<220> FEATURE:
<221> NAME/KEY: modified_base
<222> LOCATION: (126)..(126)
<223> OTHER INFORMATION: a, c, g, t, unknown or other
<220> FEATURE:
<221> NAME/KEY: modified_base
<222> LOCATION: (132)..(132)
<223> OTHER INFORMATION: a, c, g, t, unknown or other
<220> FEATURE:
<221> NAME/KEY: modified_base
<222> LOCATION: (135)..(135)
<223> OTHER INFORMATION: a, c, g, t, unknown or other
<220> FEATURE:
<221> NAME/KEY: modified_base
<222> LOCATION: (138)..(138)
```

-continued

```
<223> OTHER INFORMATION: a, c, g, t, unknown or other
<220> FEATURE:
<221> NAME/KEY: modified_base
<222> LOCATION: (141)..(141)
<223> OTHER INFORMATION: a, c, g, t, unknown or other
<220> FEATURE:
<221> NAME/KEY: modified_base
<222> LOCATION: (144)..(144)
<223> OTHER INFORMATION: a, c, g, t, unknown or other
<220> FEATURE:
<221> NAME/KEY: modified_base
<222> LOCATION: (147)..(147)
<223> OTHER INFORMATION: a, c, g, t, unknown or other
<220> FEATURE:
<221> NAME/KEY: modified_base
<222> LOCATION: (150)..(150)
<223> OTHER INFORMATION: a, c, g, t, unknown or other
<220> FEATURE:
<221> NAME/KEY: modified_base
<222> LOCATION: (153)..(153)
<223> OTHER INFORMATION: a, c, g, t, unknown or other
<220> FEATURE:
<221> NAME/KEY: modified_base
<222> LOCATION: (156)..(156)
<223> OTHER INFORMATION: a, c, g, t, unknown or other
<220> FEATURE:
<221> NAME/KEY: modified_base
<222> LOCATION: (165)..(165)
<223> OTHER INFORMATION: a, c, g, t, unknown or other
<220> FEATURE:
<221> NAME/KEY: modified_base
<222> LOCATION: (171)..(171)
<223> OTHER INFORMATION: a, c, g, t, unknown or other
<220> FEATURE:
<221> NAME/KEY: modified_base
<222> LOCATION: (174)..(174)
<223> OTHER INFORMATION: a, c, g, t, unknown or other
<220> FEATURE:
<221> NAME/KEY: modified_base
<222> LOCATION: (180)..(180)
<223> OTHER INFORMATION: a, c, g, t, unknown or other
<220> FEATURE:
<221> NAME/KEY: modified_base
<222> LOCATION: (183)..(183)
<223> OTHER INFORMATION: a, c, g, t, unknown or other
<220> FEATURE:
<221> NAME/KEY: modified_base
<222> LOCATION: (186)..(186)
<223> OTHER INFORMATION: a, c, g, t, unknown or other
<220> FEATURE:
<221> NAME/KEY: modified_base
<222> LOCATION: (189)..(189)
<223> OTHER INFORMATION: a, c, g, t, unknown or other
<220> FEATURE:
<221> NAME/KEY: modified_base
<222> LOCATION: (195)..(195)
<223> OTHER INFORMATION: a, c, g, t, unknown or other
<220> FEATURE:
<221> NAME/KEY: modified_base
<222> LOCATION: (198)..(198)
<223> OTHER INFORMATION: a, c, g, t, unknown or other
<220> FEATURE:
<221> NAME/KEY: modified_base
<222> LOCATION: (201)..(201)
<223> OTHER INFORMATION: a, c, g, t, unknown or other
<220> FEATURE:
<221> NAME/KEY: modified_base
<222> LOCATION: (210)..(210)
<223> OTHER INFORMATION: a, c, g, t, unknown or other
<220> FEATURE:
<221> NAME/KEY: modified_base
<222> LOCATION: (213)..(213)
<223> OTHER INFORMATION: a, c, g, t, unknown or other
<220> FEATURE:
<221> NAME/KEY: modified_base
<222> LOCATION: (216)..(216)
<223> OTHER INFORMATION: a, c, g, t, unknown or other
<220> FEATURE:
<221> NAME/KEY: modified_base
<222> LOCATION: (219)..(219)
```

```
<223> OTHER INFORMATION: a, c, g, t, unknown or other
<220> FEATURE:
<221> NAME/KEY: modified_base
<222> LOCATION: (225)..(225)
<223> OTHER INFORMATION: a, c, g, t, unknown or other
<220> FEATURE:
<221> NAME/KEY: modified_base
<222> LOCATION: (228)..(228)
<223> OTHER INFORMATION: a, c, g, t, unknown or other
<220> FEATURE:
<221> NAME/KEY: modified_base
<222> LOCATION: (234)..(234)
<223> OTHER INFORMATION: a, c, g, t, unknown or other
<220> FEATURE:
<221> NAME/KEY: modified_base
<222> LOCATION: (237)..(237)
<223> OTHER INFORMATION: a, c, g, t, unknown or other
<220> FEATURE:
<221> NAME/KEY: modified_base
<222> LOCATION: (240)..(240)
<223> OTHER INFORMATION: a, c, g, t, unknown or other
<220> FEATURE:
<221> NAME/KEY: modified_base
<222> LOCATION: (249)..(249)
<223> OTHER INFORMATION: a, c, g, t, unknown or other
<220> FEATURE:
<221> NAME/KEY: modified_base
<222> LOCATION: (252)..(252)
<223> OTHER INFORMATION: a, c, g, t, unknown or other
<220> FEATURE:
<221> NAME/KEY: modified_base
<222> LOCATION: (261)..(261)
<223> OTHER INFORMATION: a, c, g, t, unknown or other
<220> FEATURE:
<221> NAME/KEY: modified_base
<222> LOCATION: (267)..(267)
<223> OTHER INFORMATION: a, c, g, t, unknown or other
<220> FEATURE:
<221> NAME/KEY: modified_base
<222> LOCATION: (276)..(276)
<223> OTHER INFORMATION: a, c, g, t, unknown or other
<220> FEATURE:
<221> NAME/KEY: modified_base
<222> LOCATION: (279)..(279)
<223> OTHER INFORMATION: a, c, g, t, unknown or other
<220> FEATURE:
<221> NAME/KEY: modified_base
<222> LOCATION: (288)..(288)
<223> OTHER INFORMATION: a, c, g, t, unknown or other
<220> FEATURE:
<221> NAME/KEY: modified_base
<222> LOCATION: (291)..(291)
<223> OTHER INFORMATION: a, c, g, t, unknown or other
<220> FEATURE:
<221> NAME/KEY: modified_base
<222> LOCATION: (294)..(294)
<223> OTHER INFORMATION: a, c, g, t, unknown or other
<220> FEATURE:
<221> NAME/KEY: modified_base
<222> LOCATION: (297)..(297)
<223> OTHER INFORMATION: a, c, g, t, unknown or other
<220> FEATURE:
<221> NAME/KEY: modified_base
<222> LOCATION: (303)..(303)
<223> OTHER INFORMATION: a, c, g, t, unknown or other
<220> FEATURE:
<221> NAME/KEY: modified_base
<222> LOCATION: (306)..(306)
<223> OTHER INFORMATION: a, c, g, t, unknown or other
<220> FEATURE:
<221> NAME/KEY: modified_base
<222> LOCATION: (309)..(309)
<223> OTHER INFORMATION: a, c, g, t, unknown or other
<220> FEATURE:
<221> NAME/KEY: modified_base
<222> LOCATION: (312)..(312)
<223> OTHER INFORMATION: a, c, g, t, unknown or other
<220> FEATURE:
<221> NAME/KEY: modified_base
<222> LOCATION: (318)..(318)
```

-continued

```
<223> OTHER INFORMATION: a, c, g, t, unknown or other
<220> FEATURE:
<221> NAME/KEY: modified_base
<222> LOCATION: (324)..(324)
<223> OTHER INFORMATION: a, c, g, t, unknown or other
<220> FEATURE:
<221> NAME/KEY: modified_base
<222> LOCATION: (327)..(327)
<223> OTHER INFORMATION: a, c, g, t, unknown or other
<220> FEATURE:
<221> NAME/KEY: modified_base
<222> LOCATION: (330)..(330)
<223> OTHER INFORMATION: a, c, g, t, unknown or other
<220> FEATURE:
<221> NAME/KEY: modified_base
<222> LOCATION: (333)..(333)
<223> OTHER INFORMATION: a, c, g, t, unknown or other
<220> FEATURE:
<221> NAME/KEY: modified_base
<222> LOCATION: (336)..(336)
<223> OTHER INFORMATION: a, c, g, t, unknown or other
<220> FEATURE:
<221> NAME/KEY: modified_base
<222> LOCATION: (342)..(342)
<223> OTHER INFORMATION: a, c, g, t, unknown or other
<220> FEATURE:
<221> NAME/KEY: modified_base
<222> LOCATION: (345)..(345)
<223> OTHER INFORMATION: a, c, g, t, unknown or other
<220> FEATURE:
<221> NAME/KEY: modified_base
<222> LOCATION: (351)..(351)
<223> OTHER INFORMATION: a, c, g, t, unknown or other
<220> FEATURE:
<221> NAME/KEY: modified_base
<222> LOCATION: (363)..(363)
<223> OTHER INFORMATION: a, c, g, t, unknown or other
<220> FEATURE:
<221> NAME/KEY: modified_base
<222> LOCATION: (366)..(366)
<223> OTHER INFORMATION: a, c, g, t, unknown or other
<220> FEATURE:
<221> NAME/KEY: modified_base
<222> LOCATION: (384)..(384)
<223> OTHER INFORMATION: a, c, g, t, unknown or other
<220> FEATURE:
<221> NAME/KEY: modified_base
<222> LOCATION: (390)..(390)
<223> OTHER INFORMATION: a, c, g, t, unknown or other
<220> FEATURE:
<221> NAME/KEY: modified_base
<222> LOCATION: (393)..(393)
<223> OTHER INFORMATION: a, c, g, t, unknown or other
<220> FEATURE:
<221> NAME/KEY: modified_base
<222> LOCATION: (402)..(402)
<223> OTHER INFORMATION: a, c, g, t, unknown or other
<220> FEATURE:
<221> NAME/KEY: modified_base
<222> LOCATION: (405)..(405)
<223> OTHER INFORMATION: a, c, g, t, unknown or other
<220> FEATURE:
<221> NAME/KEY: modified_base
<222> LOCATION: (417)..(417)
<223> OTHER INFORMATION: a, c, g, t, unknown or other
<220> FEATURE:
<221> NAME/KEY: modified_base
<222> LOCATION: (420)..(420)
<223> OTHER INFORMATION: a, c, g, t, unknown or other
<220> FEATURE:
<221> NAME/KEY: modified_base
<222> LOCATION: (423)..(423)
<223> OTHER INFORMATION: a, c, g, t, unknown or other
<220> FEATURE:
<221> NAME/KEY: modified_base
<222> LOCATION: (426)..(426)
<223> OTHER INFORMATION: a, c, g, t, unknown or other
<220> FEATURE:
<221> NAME/KEY: modified_base
<222> LOCATION: (429)..(429)
```

-continued

```
<223> OTHER INFORMATION: a, c, g, t, unknown or other
<220> FEATURE:
<221> NAME/KEY: modified_base
<222> LOCATION: (435)..(435)
<223> OTHER INFORMATION: a, c, g, t, unknown or other
<220> FEATURE:
<221> NAME/KEY: modified_base
<222> LOCATION: (441)..(441)
<223> OTHER INFORMATION: a, c, g, t, unknown or other
<220> FEATURE:
<221> NAME/KEY: modified_base
<222> LOCATION: (444)..(444)
<223> OTHER INFORMATION: a, c, g, t, unknown or other
<220> FEATURE:
<221> NAME/KEY: modified_base
<222> LOCATION: (450)..(450)
<223> OTHER INFORMATION: a, c, g, t, unknown or other
<220> FEATURE:
<221> NAME/KEY: modified_base
<222> LOCATION: (453)..(453)
<223> OTHER INFORMATION: a, c, g, t, unknown or other
<220> FEATURE:
<221> NAME/KEY: modified_base
<222> LOCATION: (456)..(456)
<223> OTHER INFORMATION: a, c, g, t, unknown or other
<220> FEATURE:
<221> NAME/KEY: modified_base
<222> LOCATION: (459)..(459)
<223> OTHER INFORMATION: a, c, g, t, unknown or other
<220> FEATURE:
<221> NAME/KEY: modified_base
<222> LOCATION: (462)..(462)
<223> OTHER INFORMATION: a, c, g, t, unknown or other
<220> FEATURE:
<221> NAME/KEY: modified_base
<222> LOCATION: (465)..(465)
<223> OTHER INFORMATION: a, c, g, t, unknown or other
<220> FEATURE:
<221> NAME/KEY: modified_base
<222> LOCATION: (474)..(474)
<223> OTHER INFORMATION: a, c, g, t, unknown or other
<220> FEATURE:
<221> NAME/KEY: modified_base
<222> LOCATION: (486)..(486)
<223> OTHER INFORMATION: a, c, g, t, unknown or other
<220> FEATURE:
<221> NAME/KEY: modified_base
<222> LOCATION: (489)..(489)
<223> OTHER INFORMATION: a, c, g, t, unknown or other
<220> FEATURE:
<221> NAME/KEY: modified_base
<222> LOCATION: (495)..(495)
<223> OTHER INFORMATION: a, c, g, t, unknown or other
<220> FEATURE:
<221> NAME/KEY: modified_base
<222> LOCATION: (504)..(504)
<223> OTHER INFORMATION: a, c, g, t, unknown or other
<220> FEATURE:
<221> NAME/KEY: modified_base
<222> LOCATION: (513)..(513)
<223> OTHER INFORMATION: a, c, g, t, unknown or other
<220> FEATURE:
<221> NAME/KEY: modified_base
<222> LOCATION: (519)..(519)
<223> OTHER INFORMATION: a, c, g, t, unknown or other
<220> FEATURE:
<221> NAME/KEY: modified_base
<222> LOCATION: (522)..(522)
<223> OTHER INFORMATION: a, c, g, t, unknown or other
<220> FEATURE:
<221> NAME/KEY: modified_base
<222> LOCATION: (525)..(525)
<223> OTHER INFORMATION: a, c, g, t, unknown or other
<220> FEATURE:
<221> NAME/KEY: modified_base
<222> LOCATION: (528)..(528)
<223> OTHER INFORMATION: a, c, g, t, unknown or other
<220> FEATURE:
<221> NAME/KEY: modified_base
<222> LOCATION: (534)..(534)
```

-continued

```
<223> OTHER INFORMATION: a, c, g, t, unknown or other
<220> FEATURE:
<221> NAME/KEY: modified_base
<222> LOCATION: (537)..(537)
<223> OTHER INFORMATION: a, c, g, t, unknown or other
<220> FEATURE:
<221> NAME/KEY: modified_base
<222> LOCATION: (540)..(540)
<223> OTHER INFORMATION: a, c, g, t, unknown or other
<220> FEATURE:
<221> NAME/KEY: modified_base
<222> LOCATION: (543)..(543)
<223> OTHER INFORMATION: a, c, g, t, unknown or other
<220> FEATURE:
<221> NAME/KEY: modified_base
<222> LOCATION: (546)..(546)
<223> OTHER INFORMATION: a, c, g, t, unknown or other
<220> FEATURE:
<221> NAME/KEY: modified_base
<222> LOCATION: (549)..(549)
<223> OTHER INFORMATION: a, c, g, t, unknown or other
<220> FEATURE:
<221> NAME/KEY: modified_base
<222> LOCATION: (552)..(552)
<223> OTHER INFORMATION: a, c, g, t, unknown or other
<220> FEATURE:
<221> NAME/KEY: modified_base
<222> LOCATION: (555)..(555)
<223> OTHER INFORMATION: a, c, g, t, unknown or other
<220> FEATURE:
<221> NAME/KEY: modified_base
<222> LOCATION: (558)..(558)
<223> OTHER INFORMATION: a, c, g, t, unknown or other
<220> FEATURE:
<221> NAME/KEY: modified_base
<222> LOCATION: (561)..(561)
<223> OTHER INFORMATION: a, c, g, t, unknown or other
<220> FEATURE:
<221> NAME/KEY: modified_base
<222> LOCATION: (570)..(570)
<223> OTHER INFORMATION: a, c, g, t, unknown or other
<220> FEATURE:
<221> NAME/KEY: modified_base
<222> LOCATION: (573)..(573)
<223> OTHER INFORMATION: a, c, g, t, unknown or other
<220> FEATURE:
<221> NAME/KEY: modified_base
<222> LOCATION: (579)..(579)
<223> OTHER INFORMATION: a, c, g, t, unknown or other
<220> FEATURE:
<221> NAME/KEY: modified_base
<222> LOCATION: (582)..(582)
<223> OTHER INFORMATION: a, c, g, t, unknown or other
<220> FEATURE:
<221> NAME/KEY: modified_base
<222> LOCATION: (585)..(585)
<223> OTHER INFORMATION: a, c, g, t, unknown or other
<220> FEATURE:
<221> NAME/KEY: modified_base
<222> LOCATION: (588)..(588)
<223> OTHER INFORMATION: a, c, g, t, unknown or other
<220> FEATURE:
<221> NAME/KEY: modified_base
<222> LOCATION: (597)..(597)
<223> OTHER INFORMATION: a, c, g, t, unknown or other
<220> FEATURE:
<221> NAME/KEY: modified_base
<222> LOCATION: (603)..(603)
<223> OTHER INFORMATION: a, c, g, t, unknown or other
<220> FEATURE:
<221> NAME/KEY: modified_base
<222> LOCATION: (609)..(609)
<223> OTHER INFORMATION: a, c, g, t, unknown or other
<220> FEATURE:
<221> NAME/KEY: modified_base
<222> LOCATION: (621)..(621)
<223> OTHER INFORMATION: a, c, g, t, unknown or other
<220> FEATURE:
<221> NAME/KEY: modified_base
<222> LOCATION: (627)..(627)
```

-continued

```
<223> OTHER INFORMATION: a, c, g, t, unknown or other
<220> FEATURE:
<221> NAME/KEY: modified_base
<222> LOCATION: (630)..(630)
<223> OTHER INFORMATION: a, c, g, t, unknown or other
<220> FEATURE:
<221> NAME/KEY: modified_base
<222> LOCATION: (636)..(636)
<223> OTHER INFORMATION: a, c, g, t, unknown or other
<220> FEATURE:
<221> NAME/KEY: modified_base
<222> LOCATION: (639)..(639)
<223> OTHER INFORMATION: a, c, g, t, unknown or other
<220> FEATURE:
<221> NAME/KEY: modified_base
<222> LOCATION: (642)..(642)
<223> OTHER INFORMATION: a, c, g, t, unknown or other
<220> FEATURE:
<221> NAME/KEY: modified_base
<222> LOCATION: (645)..(645)
<223> OTHER INFORMATION: a, c, g, t, unknown or other
<220> FEATURE:
<221> NAME/KEY: modified_base
<222> LOCATION: (648)..(648)
<223> OTHER INFORMATION: a, c, g, t, unknown or other
<220> FEATURE:
<221> NAME/KEY: modified_base
<222> LOCATION: (657)..(657)
<223> OTHER INFORMATION: a, c, g, t, unknown or other
<220> FEATURE:
<221> NAME/KEY: modified_base
<222> LOCATION: (666)..(666)
<223> OTHER INFORMATION: a, c, g, t, unknown or other
<220> FEATURE:
<221> NAME/KEY: modified_base
<222> LOCATION: (669)..(669)
<223> OTHER INFORMATION: a, c, g, t, unknown or other
<220> FEATURE:
<221> NAME/KEY: modified_base
<222> LOCATION: (675)..(675)
<223> OTHER INFORMATION: a, c, g, t, unknown or other
<220> FEATURE:
<221> NAME/KEY: modified_base
<222> LOCATION: (678)..(678)
<223> OTHER INFORMATION: a, c, g, t, unknown or other
<220> FEATURE:
<221> NAME/KEY: modified_base
<222> LOCATION: (684)..(684)
<223> OTHER INFORMATION: a, c, g, t, unknown or other
<220> FEATURE:
<221> NAME/KEY: modified_base
<222> LOCATION: (687)..(687)
<223> OTHER INFORMATION: a, c, g, t, unknown or other
<220> FEATURE:
<221> NAME/KEY: modified_base
<222> LOCATION: (690)..(690)
<223> OTHER INFORMATION: a, c, g, t, unknown or other
<220> FEATURE:
<221> NAME/KEY: modified_base
<222> LOCATION: (696)..(696)
<223> OTHER INFORMATION: a, c, g, t, unknown or other
<220> FEATURE:
<221> NAME/KEY: modified_base
<222> LOCATION: (705)..(705)
<223> OTHER INFORMATION: a, c, g, t, unknown or other
<220> FEATURE:
<221> NAME/KEY: modified_base
<222> LOCATION: (708)..(708)
<223> OTHER INFORMATION: a, c, g, t, unknown or other
<220> FEATURE:
<221> NAME/KEY: modified_base
<222> LOCATION: (714)..(714)
<223> OTHER INFORMATION: a, c, g, t, unknown or other
<220> FEATURE:
<221> NAME/KEY: modified_base
<222> LOCATION: (723)..(723)
<223> OTHER INFORMATION: a, c, g, t, unknown or other
<220> FEATURE:
<221> NAME/KEY: modified_base
<222> LOCATION: (726)..(726)
```

-continued

```
<223> OTHER INFORMATION: a, c, g, t, unknown or other
<220> FEATURE:
<221> NAME/KEY: modified_base
<222> LOCATION: (738)..(738)
<223> OTHER INFORMATION: a, c, g, t, unknown or other
<220> FEATURE:
<221> NAME/KEY: modified_base
<222> LOCATION: (744)..(744)
<223> OTHER INFORMATION: a, c, g, t, unknown or other
<220> FEATURE:
<221> NAME/KEY: modified_base
<222> LOCATION: (753)..(753)
<223> OTHER INFORMATION: a, c, g, t, unknown or other
<220> FEATURE:
<221> NAME/KEY: modified_base
<222> LOCATION: (756)..(756)
<223> OTHER INFORMATION: a, c, g, t, unknown or other
<220> FEATURE:
<221> NAME/KEY: modified_base
<222> LOCATION: (759)..(759)
<223> OTHER INFORMATION: a, c, g, t, unknown or other
<220> FEATURE:
<221> NAME/KEY: modified_base
<222> LOCATION: (765)..(765)
<223> OTHER INFORMATION: a, c, g, t, unknown or other
<220> FEATURE:
<221> NAME/KEY: modified_base
<222> LOCATION: (780)..(780)
<223> OTHER INFORMATION: a, c, g, t, unknown or other
<220> FEATURE:
<221> NAME/KEY: modified_base
<222> LOCATION: (783)..(783)
<223> OTHER INFORMATION: a, c, g, t, unknown or other
<220> FEATURE:
<221> NAME/KEY: modified_base
<222> LOCATION: (786)..(786)
<223> OTHER INFORMATION: a, c, g, t, unknown or other
<220> FEATURE:
<221> NAME/KEY: modified_base
<222> LOCATION: (792)..(792)
<223> OTHER INFORMATION: a, c, g, t, unknown or other
<220> FEATURE:
<221> NAME/KEY: modified_base
<222> LOCATION: (795)..(795)
<223> OTHER INFORMATION: a, c, g, t, unknown or other
<220> FEATURE:
<221> NAME/KEY: modified_base
<222> LOCATION: (801)..(801)
<223> OTHER INFORMATION: a, c, g, t, unknown or other
<220> FEATURE:
<221> NAME/KEY: modified_base
<222> LOCATION: (804)..(804)
<223> OTHER INFORMATION: a, c, g, t, unknown or other
<220> FEATURE:
<221> NAME/KEY: modified_base
<222> LOCATION: (807)..(807)
<223> OTHER INFORMATION: a, c, g, t, unknown or other
<220> FEATURE:
<221> NAME/KEY: modified_base
<222> LOCATION: (810)..(810)
<223> OTHER INFORMATION: a, c, g, t, unknown or other
<220> FEATURE:
<221> NAME/KEY: modified_base
<222> LOCATION: (813)..(813)
<223> OTHER INFORMATION: a, c, g, t, unknown or other
<220> FEATURE:
<221> NAME/KEY: modified_base
<222> LOCATION: (816)..(816)
<223> OTHER INFORMATION: a, c, g, t, unknown or other
<220> FEATURE:
<221> NAME/KEY: modified_base
<222> LOCATION: (819)..(819)
<223> OTHER INFORMATION: a, c, g, t, unknown or other
<220> FEATURE:
<221> NAME/KEY: modified_base
<222> LOCATION: (822)..(822)
<223> OTHER INFORMATION: a, c, g, t, unknown or other
<220> FEATURE:
<221> NAME/KEY: modified_base
<222> LOCATION: (825)..(825)
```

-continued

```
<223> OTHER INFORMATION: a, c, g, t, unknown or other
<220> FEATURE:
<221> NAME/KEY: modified_base
<222> LOCATION: (837)..(837)
<223> OTHER INFORMATION: a, c, g, t, unknown or other
<220> FEATURE:
<221> NAME/KEY: modified_base
<222> LOCATION: (840)..(840)
<223> OTHER INFORMATION: a, c, g, t, unknown or other
<220> FEATURE:
<221> NAME/KEY: modified_base
<222> LOCATION: (846)..(846)
<223> OTHER INFORMATION: a, c, g, t, unknown or other
<220> FEATURE:
<221> NAME/KEY: modified_base
<222> LOCATION: (849)..(849)
<223> OTHER INFORMATION: a, c, g, t, unknown or other
<220> FEATURE:
<221> NAME/KEY: modified_base
<222> LOCATION: (855)..(855)
<223> OTHER INFORMATION: a, c, g, t, unknown or other
<220> FEATURE:
<221> NAME/KEY: modified_base
<222> LOCATION: (858)..(858)
<223> OTHER INFORMATION: a, c, g, t, unknown or other
<220> FEATURE:
<221> NAME/KEY: modified_base
<222> LOCATION: (861)..(861)
<223> OTHER INFORMATION: a, c, g, t, unknown or other
<220> FEATURE:
<221> NAME/KEY: modified_base
<222> LOCATION: (876)..(876)
<223> OTHER INFORMATION: a, c, g, t, unknown or other
<220> FEATURE:
<221> NAME/KEY: modified_base
<222> LOCATION: (879)..(879)
<223> OTHER INFORMATION: a, c, g, t, unknown or other
<220> FEATURE:
<221> NAME/KEY: modified_base
<222> LOCATION: (882)..(882)
<223> OTHER INFORMATION: a, c, g, t, unknown or other
<220> FEATURE:
<221> NAME/KEY: modified_base
<222> LOCATION: (888)..(888)
<223> OTHER INFORMATION: a, c, g, t, unknown or other
<220> FEATURE:
<221> NAME/KEY: modified_base
<222> LOCATION: (891)..(891)
<223> OTHER INFORMATION: a, c, g, t, unknown or other
<220> FEATURE:
<221> NAME/KEY: modified_base
<222> LOCATION: (894)..(894)
<223> OTHER INFORMATION: a, c, g, t, unknown or other
<220> FEATURE:
<221> NAME/KEY: modified_base
<222> LOCATION: (897)..(897)
<223> OTHER INFORMATION: a, c, g, t, unknown or other
<220> FEATURE:
<221> NAME/KEY: modified_base
<222> LOCATION: (900)..(900)
<223> OTHER INFORMATION: a, c, g, t, unknown or other
<220> FEATURE:
<221> NAME/KEY: modified_base
<222> LOCATION: (903)..(903)
<223> OTHER INFORMATION: a, c, g, t, unknown or other
<220> FEATURE:
<221> NAME/KEY: modified_base
<222> LOCATION: (906)..(906)
<223> OTHER INFORMATION: a, c, g, t, unknown or other
<220> FEATURE:
<221> NAME/KEY: modified_base
<222> LOCATION: (909)..(909)
<223> OTHER INFORMATION: a, c, g, t, unknown or other
<220> FEATURE:
<221> NAME/KEY: modified_base
<222> LOCATION: (915)..(915)
<223> OTHER INFORMATION: a, c, g, t, unknown or other
<220> FEATURE:
<221> NAME/KEY: modified_base
<222> LOCATION: (918)..(918)
```

-continued

```
<223> OTHER INFORMATION: a, c, g, t, unknown or other
<220> FEATURE:
<221> NAME/KEY: modified_base
<222> LOCATION: (921)..(921)
<223> OTHER INFORMATION: a, c, g, t, unknown or other
<220> FEATURE:
<221> NAME/KEY: modified_base
<222> LOCATION: (924)..(924)
<223> OTHER INFORMATION: a, c, g, t, unknown or other
<220> FEATURE:
<221> NAME/KEY: modified_base
<222> LOCATION: (927)..(927)
<223> OTHER INFORMATION: a, c, g, t, unknown or other
<220> FEATURE:
<221> NAME/KEY: modified_base
<222> LOCATION: (933)..(933)
<223> OTHER INFORMATION: a, c, g, t, unknown or other
<220> FEATURE:
<221> NAME/KEY: modified_base
<222> LOCATION: (948)..(948)
<223> OTHER INFORMATION: a, c, g, t, unknown or other
<220> FEATURE:
<221> NAME/KEY: modified_base
<222> LOCATION: (951)..(951)
<223> OTHER INFORMATION: a, c, g, t, unknown or other
<220> FEATURE:
<221> NAME/KEY: modified_base
<222> LOCATION: (954)..(954)
<223> OTHER INFORMATION: a, c, g, t, unknown or other
<220> FEATURE:
<221> NAME/KEY: modified_base
<222> LOCATION: (957)..(957)
<223> OTHER INFORMATION: a, c, g, t, unknown or other
<220> FEATURE:
<221> NAME/KEY: modified_base
<222> LOCATION: (966)..(966)
<223> OTHER INFORMATION: a, c, g, t, unknown or other
<220> FEATURE:
<221> NAME/KEY: modified_base
<222> LOCATION: (969)..(969)
<223> OTHER INFORMATION: a, c, g, t, unknown or other
<220> FEATURE:
<221> NAME/KEY: modified_base
<222> LOCATION: (975)..(975)
<223> OTHER INFORMATION: a, c, g, t, unknown or other
<220> FEATURE:
<221> NAME/KEY: modified_base
<222> LOCATION: (978)..(978)
<223> OTHER INFORMATION: a, c, g, t, unknown or other
<220> FEATURE:
<221> NAME/KEY: modified_base
<222> LOCATION: (981)..(981)
<223> OTHER INFORMATION: a, c, g, t, unknown or other
<220> FEATURE:
<221> NAME/KEY: modified_base
<222> LOCATION: (987)..(987)
<223> OTHER INFORMATION: a, c, g, t, unknown or other
<220> FEATURE:
<221> NAME/KEY: modified_base
<222> LOCATION: (990)..(990)
<223> OTHER INFORMATION: a, c, g, t, unknown or other
<220> FEATURE:
<221> NAME/KEY: modified_base
<222> LOCATION: (996)..(996)
<223> OTHER INFORMATION: a, c, g, t, unknown or other
<220> FEATURE:
<221> NAME/KEY: modified_base
<222> LOCATION: (999)..(999)
<223> OTHER INFORMATION: a, c, g, t, unknown or other
<220> FEATURE:
<221> NAME/KEY: modified_base
<222> LOCATION: (1005)..(1005)
<223> OTHER INFORMATION: a, c, g, t, unknown or other
<220> FEATURE:
<221> NAME/KEY: modified_base
<222> LOCATION: (1008)..(1008)
<223> OTHER INFORMATION: a, c, g, t, unknown or other
<220> FEATURE:
<221> NAME/KEY: modified_base
<222> LOCATION: (1011)..(1011)
```

-continued

```
<223> OTHER INFORMATION: a, c, g, t, unknown or other
<220> FEATURE:
<221> NAME/KEY: modified_base
<222> LOCATION: (1014)..(1014)
<223> OTHER INFORMATION: a, c, g, t, unknown or other
<220> FEATURE:
<221> NAME/KEY: modified_base
<222> LOCATION: (1017)..(1017)
<223> OTHER INFORMATION: a, c, g, t, unknown or other
<220> FEATURE:
<221> NAME/KEY: modified_base
<222> LOCATION: (1029)..(1029)
<223> OTHER INFORMATION: a, c, g, t, unknown or other
<220> FEATURE:
<221> NAME/KEY: modified_base
<222> LOCATION: (1035)..(1035)
<223> OTHER INFORMATION: a, c, g, t, unknown or other
<220> FEATURE:
<221> NAME/KEY: modified_base
<222> LOCATION: (1038)..(1038)
<223> OTHER INFORMATION: a, c, g, t, unknown or other
<220> FEATURE:
<221> NAME/KEY: modified_base
<222> LOCATION: (1041)..(1041)
<223> OTHER INFORMATION: a, c, g, t, unknown or other
<220> FEATURE:
<221> NAME/KEY: modified_base
<222> LOCATION: (1044)..(1044)
<223> OTHER INFORMATION: a, c, g, t, unknown or other
<220> FEATURE:
<221> NAME/KEY: modified_base
<222> LOCATION: (1047)..(1047)
<223> OTHER INFORMATION: a, c, g, t, unknown or other
<220> FEATURE:
<221> NAME/KEY: modified_base
<222> LOCATION: (1050)..(1050)
<223> OTHER INFORMATION: a, c, g, t, unknown or other
<220> FEATURE:
<221> NAME/KEY: modified_base
<222> LOCATION: (1056)..(1056)
<223> OTHER INFORMATION: a, c, g, t, unknown or other
<220> FEATURE:
<221> NAME/KEY: modified_base
<222> LOCATION: (1059)..(1059)
<223> OTHER INFORMATION: a, c, g, t, unknown or other
<220> FEATURE:
<221> NAME/KEY: modified_base
<222> LOCATION: (1062)..(1062)
<223> OTHER INFORMATION: a, c, g, t, unknown or other
<220> FEATURE:
<221> NAME/KEY: modified_base
<222> LOCATION: (1065)..(1065)
<223> OTHER INFORMATION: a, c, g, t, unknown or other
<220> FEATURE:
<221> NAME/KEY: modified_base
<222> LOCATION: (1068)..(1068)
<223> OTHER INFORMATION: a, c, g, t, unknown or other
<220> FEATURE:
<221> NAME/KEY: modified_base
<222> LOCATION: (1071)..(1071)
<223> OTHER INFORMATION: a, c, g, t, unknown or other
<220> FEATURE:
<221> NAME/KEY: modified_base
<222> LOCATION: (1074)..(1074)
<223> OTHER INFORMATION: a, c, g, t, unknown or other
<220> FEATURE:
<221> NAME/KEY: modified_base
<222> LOCATION: (1077)..(1077)
<223> OTHER INFORMATION: a, c, g, t, unknown or other
<220> FEATURE:
<221> NAME/KEY: modified_base
<222> LOCATION: (1086)..(1086)
<223> OTHER INFORMATION: a, c, g, t, unknown or other
<220> FEATURE:
<221> NAME/KEY: modified_base
<222> LOCATION: (1089)..(1089)
<223> OTHER INFORMATION: a, c, g, t, unknown or other
<220> FEATURE:
<221> NAME/KEY: modified_base
<222> LOCATION: (1095)..(1095)
```

-continued

```
<223> OTHER INFORMATION: a, c, g, t, unknown or other
<220> FEATURE:
<221> NAME/KEY: modified_base
<222> LOCATION: (1098)..(1098)
<223> OTHER INFORMATION: a, c, g, t, unknown or other
<220> FEATURE:
<221> NAME/KEY: modified_base
<222> LOCATION: (1101)..(1101)
<223> OTHER INFORMATION: a, c, g, t, unknown or other
<220> FEATURE:
<221> NAME/KEY: modified_base
<222> LOCATION: (1104)..(1104)
<223> OTHER INFORMATION: a, c, g, t, unknown or other
<220> FEATURE:
<221> NAME/KEY: modified_base
<222> LOCATION: (1107)..(1107)
<223> OTHER INFORMATION: a, c, g, t, unknown or other
<220> FEATURE:
<221> NAME/KEY: modified_base
<222> LOCATION: (1110)..(1110)
<223> OTHER INFORMATION: a, c, g, t, unknown or other
<220> FEATURE:
<221> NAME/KEY: modified_base
<222> LOCATION: (1113)..(1113)
<223> OTHER INFORMATION: a, c, g, t, unknown or other
<220> FEATURE:
<221> NAME/KEY: modified_base
<222> LOCATION: (1125)..(1125)
<223> OTHER INFORMATION: a, c, g, t, unknown or other
<220> FEATURE:
<221> NAME/KEY: modified_base
<222> LOCATION: (1128)..(1128)
<223> OTHER INFORMATION: a, c, g, t, unknown or other
<220> FEATURE:
<221> NAME/KEY: modified_base
<222> LOCATION: (1131)..(1131)
<223> OTHER INFORMATION: a, c, g, t, unknown or other
<220> FEATURE:
<221> NAME/KEY: modified_base
<222> LOCATION: (1137)..(1137)
<223> OTHER INFORMATION: a, c, g, t, unknown or other
<220> FEATURE:
<221> NAME/KEY: modified_base
<222> LOCATION: (1140)..(1140)
<223> OTHER INFORMATION: a, c, g, t, unknown or other
<220> FEATURE:
<221> NAME/KEY: modified_base
<222> LOCATION: (1146)..(1146)
<223> OTHER INFORMATION: a, c, g, t, unknown or other
<220> FEATURE:
<221> NAME/KEY: modified_base
<222> LOCATION: (1152)..(1152)
<223> OTHER INFORMATION: a, c, g, t, unknown or other
<220> FEATURE:
<221> NAME/KEY: modified_base
<222> LOCATION: (1155)..(1155)
<223> OTHER INFORMATION: a, c, g, t, unknown or other
<220> FEATURE:
<221> NAME/KEY: modified_base
<222> LOCATION: (1158)..(1158)
<223> OTHER INFORMATION: a, c, g, t, unknown or other
<220> FEATURE:
<221> NAME/KEY: modified_base
<222> LOCATION: (1164)..(1164)
<223> OTHER INFORMATION: a, c, g, t, unknown or other
<220> FEATURE:
<221> NAME/KEY: modified_base
<222> LOCATION: (1170)..(1170)
<223> OTHER INFORMATION: a, c, g, t, unknown or other
<220> FEATURE:
<221> NAME/KEY: modified_base
<222> LOCATION: (1173)..(1173)
<223> OTHER INFORMATION: a, c, g, t, unknown or other
<220> FEATURE:
<221> NAME/KEY: modified_base
<222> LOCATION: (1185)..(1185)
<223> OTHER INFORMATION: a, c, g, t, unknown or other
<220> FEATURE:
<221> NAME/KEY: modified_base
<222> LOCATION: (1206)..(1206)
```

-continued

```
<223> OTHER INFORMATION: a, c, g, t, unknown or other
<220> FEATURE:
<221> NAME/KEY: modified_base
<222> LOCATION: (1209)..(1209)
<223> OTHER INFORMATION: a, c, g, t, unknown or other
<220> FEATURE:
<221> NAME/KEY: modified_base
<222> LOCATION: (1218)..(1218)
<223> OTHER INFORMATION: a, c, g, t, unknown or other
<220> FEATURE:
<221> NAME/KEY: modified_base
<222> LOCATION: (1221)..(1221)
<223> OTHER INFORMATION: a, c, g, t, unknown or other
<220> FEATURE:
<221> NAME/KEY: modified_base
<222> LOCATION: (1236)..(1236)
<223> OTHER INFORMATION: a, c, g, t, unknown or other
<220> FEATURE:
<221> NAME/KEY: modified_base
<222> LOCATION: (1239)..(1239)
<223> OTHER INFORMATION: a, c, g, t, unknown or other
<220> FEATURE:
<221> NAME/KEY: modified_base
<222> LOCATION: (1242)..(1242)
<223> OTHER INFORMATION: a, c, g, t, unknown or other
<220> FEATURE:
<221> NAME/KEY: modified_base
<222> LOCATION: (1251)..(1251)
<223> OTHER INFORMATION: a, c, g, t, unknown or other
<220> FEATURE:
<221> NAME/KEY: modified_base
<222> LOCATION: (1254)..(1254)
<223> OTHER INFORMATION: a, c, g, t, unknown or other
<220> FEATURE:
<221> NAME/KEY: modified_base
<222> LOCATION: (1257)..(1257)
<223> OTHER INFORMATION: a, c, g, t, unknown or other
<220> FEATURE:
<221> NAME/KEY: modified_base
<222> LOCATION: (1272)..(1272)
<223> OTHER INFORMATION: a, c, g, t, unknown or other
<220> FEATURE:
<221> NAME/KEY: modified_base
<222> LOCATION: (1275)..(1275)
<223> OTHER INFORMATION: a, c, g, t, unknown or other
<220> FEATURE:
<221> NAME/KEY: modified_base
<222> LOCATION: (1278)..(1278)
<223> OTHER INFORMATION: a, c, g, t, unknown or other
<220> FEATURE:
<221> NAME/KEY: modified_base
<222> LOCATION: (1281)..(1281)
<223> OTHER INFORMATION: a, c, g, t, unknown or other
<220> FEATURE:
<221> NAME/KEY: modified_base
<222> LOCATION: (1284)..(1284)
<223> OTHER INFORMATION: a, c, g, t, unknown or other
<220> FEATURE:
<221> NAME/KEY: modified_base
<222> LOCATION: (1287)..(1287)
<223> OTHER INFORMATION: a, c, g, t, unknown or other
<220> FEATURE:
<221> NAME/KEY: modified_base
<222> LOCATION: (1299)..(1299)
<223> OTHER INFORMATION: a, c, g, t, unknown or other
<220> FEATURE:
<221> NAME/KEY: modified_base
<222> LOCATION: (1302)..(1302)
<223> OTHER INFORMATION: a, c, g, t, unknown or other
<220> FEATURE:
<221> NAME/KEY: modified_base
<222> LOCATION: (1308)..(1308)
<223> OTHER INFORMATION: a, c, g, t, unknown or other
<220> FEATURE:
<221> NAME/KEY: modified_base
<222> LOCATION: (1311)..(1311)
<223> OTHER INFORMATION: a, c, g, t, unknown or other
<220> FEATURE:
<221> NAME/KEY: modified_base
<222> LOCATION: (1314)..(1314)
```

-continued

```
<223> OTHER INFORMATION: a, c, g, t, unknown or other
<220> FEATURE:
<221> NAME/KEY: modified_base
<222> LOCATION: (1320)..(1320)
<223> OTHER INFORMATION: a, c, g, t, unknown or other
<220> FEATURE:
<221> NAME/KEY: modified_base
<222> LOCATION: (1323)..(1323)
<223> OTHER INFORMATION: a, c, g, t, unknown or other
<220> FEATURE:
<221> NAME/KEY: modified_base
<222> LOCATION: (1332)..(1332)
<223> OTHER INFORMATION: a, c, g, t, unknown or other
<220> FEATURE:
<221> NAME/KEY: modified_base
<222> LOCATION: (1335)..(1335)
<223> OTHER INFORMATION: a, c, g, t, unknown or other
<220> FEATURE:
<221> NAME/KEY: modified_base
<222> LOCATION: (1341)..(1341)
<223> OTHER INFORMATION: a, c, g, t, unknown or other
<220> FEATURE:
<221> NAME/KEY: modified_base
<222> LOCATION: (1350)..(1350)
<223> OTHER INFORMATION: a, c, g, t, unknown or other
<220> FEATURE:
<221> NAME/KEY: modified_base
<222> LOCATION: (1353)..(1353)
<223> OTHER INFORMATION: a, c, g, t, unknown or other
<220> FEATURE:
<221> NAME/KEY: modified_base
<222> LOCATION: (1356)..(1356)
<223> OTHER INFORMATION: a, c, g, t, unknown or other
<220> FEATURE:
<221> NAME/KEY: modified_base
<222> LOCATION: (1362)..(1362)
<223> OTHER INFORMATION: a, c, g, t, unknown or other
<220> FEATURE:
<221> NAME/KEY: modified_base
<222> LOCATION: (1368)..(1368)
<223> OTHER INFORMATION: a, c, g, t, unknown or other
<220> FEATURE:
<221> NAME/KEY: modified_base
<222> LOCATION: (1374)..(1374)
<223> OTHER INFORMATION: a, c, g, t, unknown or other
<220> FEATURE:
<221> NAME/KEY: modified_base
<222> LOCATION: (1383)..(1383)
<223> OTHER INFORMATION: a, c, g, t, unknown or other
<220> FEATURE:
<221> NAME/KEY: modified_base
<222> LOCATION: (1389)..(1389)
<223> OTHER INFORMATION: a, c, g, t, unknown or other
<220> FEATURE:
<221> NAME/KEY: modified_base
<222> LOCATION: (1398)..(1398)
<223> OTHER INFORMATION: a, c, g, t, unknown or other
<220> FEATURE:
<221> NAME/KEY: modified_base
<222> LOCATION: (1401)..(1401)
<223> OTHER INFORMATION: a, c, g, t, unknown or other
<220> FEATURE:
<221> NAME/KEY: modified_base
<222> LOCATION: (1419)..(1419)
<223> OTHER INFORMATION: a, c, g, t, unknown or other
<220> FEATURE:
<221> NAME/KEY: modified_base
<222> LOCATION: (1422)..(1422)
<223> OTHER INFORMATION: a, c, g, t, unknown or other
<220> FEATURE:
<221> NAME/KEY: modified_base
<222> LOCATION: (1425)..(1425)
<223> OTHER INFORMATION: a, c, g, t, unknown or other
<220> FEATURE:
<221> NAME/KEY: modified_base
<222> LOCATION: (1431)..(1431)
<223> OTHER INFORMATION: a, c, g, t, unknown or other
<220> FEATURE:
<221> NAME/KEY: modified_base
<222> LOCATION: (1440)..(1440)
```

-continued

```
<223> OTHER INFORMATION: a, c, g, t, unknown or other
<220> FEATURE:
<221> NAME/KEY: modified_base
<222> LOCATION: (1443)..(1443)
<223> OTHER INFORMATION: a, c, g, t, unknown or other
<220> FEATURE:
<221> NAME/KEY: modified_base
<222> LOCATION: (1446)..(1446)
<223> OTHER INFORMATION: a, c, g, t, unknown or other
<220> FEATURE:
<221> NAME/KEY: modified_base
<222> LOCATION: (1449)..(1449)
<223> OTHER INFORMATION: a, c, g, t, unknown or other
<220> FEATURE:
<221> NAME/KEY: modified_base
<222> LOCATION: (1461)..(1461)
<223> OTHER INFORMATION: a, c, g, t, unknown or other
<220> FEATURE:
<221> NAME/KEY: modified_base
<222> LOCATION: (1467)..(1467)
<223> OTHER INFORMATION: a, c, g, t, unknown or other
<220> FEATURE:
<221> NAME/KEY: modified_base
<222> LOCATION: (1470)..(1470)
<223> OTHER INFORMATION: a, c, g, t, unknown or other
<220> FEATURE:
<221> NAME/KEY: modified_base
<222> LOCATION: (1473)..(1473)
<223> OTHER INFORMATION: a, c, g, t, unknown or other
<220> FEATURE:
<221> NAME/KEY: modified_base
<222> LOCATION: (1497)..(1497)
<223> OTHER INFORMATION: a, c, g, t, unknown or other
<220> FEATURE:
<221> NAME/KEY: modified_base
<222> LOCATION: (1500)..(1500)
<223> OTHER INFORMATION: a, c, g, t, unknown or other
<220> FEATURE:
<221> NAME/KEY: modified_base
<222> LOCATION: (1503)..(1503)
<223> OTHER INFORMATION: a, c, g, t, unknown or other
<220> FEATURE:
<221> NAME/KEY: modified_base
<222> LOCATION: (1506)..(1506)
<223> OTHER INFORMATION: a, c, g, t, unknown or other
<220> FEATURE:
<221> NAME/KEY: modified_base
<222> LOCATION: (1509)..(1509)
<223> OTHER INFORMATION: a, c, g, t, unknown or other
<220> FEATURE:
<221> NAME/KEY: modified_base
<222> LOCATION: (1512)..(1512)
<223> OTHER INFORMATION: a, c, g, t, unknown or other
<220> FEATURE:
<221> NAME/KEY: modified_base
<222> LOCATION: (1515)..(1515)
<223> OTHER INFORMATION: a, c, g, t, unknown or other
<220> FEATURE:
<221> NAME/KEY: modified_base
<222> LOCATION: (1524)..(1524)
<223> OTHER INFORMATION: a, c, g, t, unknown or other
<220> FEATURE:
<221> NAME/KEY: modified_base
<222> LOCATION: (1527)..(1527)
<223> OTHER INFORMATION: a, c, g, t, unknown or other
<220> FEATURE:
<221> NAME/KEY: modified_base
<222> LOCATION: (1533)..(1533)
<223> OTHER INFORMATION: a, c, g, t, unknown or other
<220> FEATURE:
<221> NAME/KEY: modified_base
<222> LOCATION: (1539)..(1539)
<223> OTHER INFORMATION: a, c, g, t, unknown or other
<220> FEATURE:
<221> NAME/KEY: modified_base
<222> LOCATION: (1542)..(1542)
<223> OTHER INFORMATION: a, c, g, t, unknown or other
<220> FEATURE:
<221> NAME/KEY: modified_base
<222> LOCATION: (1545)..(1545)
```

-continued

```
<223> OTHER INFORMATION: a, c, g, t, unknown or other
<220> FEATURE:
<221> NAME/KEY: modified_base
<222> LOCATION: (1548)..(1548)
<223> OTHER INFORMATION: a, c, g, t, unknown or other
<220> FEATURE:
<221> NAME/KEY: modified_base
<222> LOCATION: (1569)..(1569)
<223> OTHER INFORMATION: a, c, g, t, unknown or other
<220> FEATURE:
<221> NAME/KEY: modified_base
<222> LOCATION: (1578)..(1578)
<223> OTHER INFORMATION: a, c, g, t, unknown or other
<220> FEATURE:
<221> NAME/KEY: modified_base
<222> LOCATION: (1584)..(1584)
<223> OTHER INFORMATION: a, c, g, t, unknown or other
<220> FEATURE:
<221> NAME/KEY: modified_base
<222> LOCATION: (1587)..(1587)
<223> OTHER INFORMATION: a, c, g, t, unknown or other
<220> FEATURE:
<221> NAME/KEY: modified_base
<222> LOCATION: (1590)..(1590)
<223> OTHER INFORMATION: a, c, g, t, unknown or other
<220> FEATURE:
<221> NAME/KEY: modified_base
<222> LOCATION: (1593)..(1593)
<223> OTHER INFORMATION: a, c, g, t, unknown or other
<220> FEATURE:
<221> NAME/KEY: modified_base
<222> LOCATION: (1605)..(1605)
<223> OTHER INFORMATION: a, c, g, t, unknown or other
<220> FEATURE:
<221> NAME/KEY: modified_base
<222> LOCATION: (1608)..(1608)
<223> OTHER INFORMATION: a, c, g, t, unknown or other
<220> FEATURE:
<221> NAME/KEY: modified_base
<222> LOCATION: (1611)..(1611)
<223> OTHER INFORMATION: a, c, g, t, unknown or other
<220> FEATURE:
<221> NAME/KEY: modified_base
<222> LOCATION: (1614)..(1614)
<223> OTHER INFORMATION: a, c, g, t, unknown or other
<220> FEATURE:
<221> NAME/KEY: modified_base
<222> LOCATION: (1617)..(1617)
<223> OTHER INFORMATION: a, c, g, t, unknown or other
<220> FEATURE:
<221> NAME/KEY: modified_base
<222> LOCATION: (1620)..(1620)
<223> OTHER INFORMATION: a, c, g, t, unknown or other
<220> FEATURE:
<221> NAME/KEY: modified_base
<222> LOCATION: (1623)..(1623)
<223> OTHER INFORMATION: a, c, g, t, unknown or other
<220> FEATURE:
<221> NAME/KEY: modified_base
<222> LOCATION: (1632)..(1632)
<223> OTHER INFORMATION: a, c, g, t, unknown or other
<220> FEATURE:
<221> NAME/KEY: modified_base
<222> LOCATION: (1641)..(1641)
<223> OTHER INFORMATION: a, c, g, t, unknown or other
<220> FEATURE:
<221> NAME/KEY: modified_base
<222> LOCATION: (1644)..(1644)
<223> OTHER INFORMATION: a, c, g, t, unknown or other
<220> FEATURE:
<221> NAME/KEY: modified_base
<222> LOCATION: (1647)..(1647)
<223> OTHER INFORMATION: a, c, g, t, unknown or other
<220> FEATURE:
<221> NAME/KEY: modified_base
<222> LOCATION: (1650)..(1650)
<223> OTHER INFORMATION: a, c, g, t, unknown or other
<220> FEATURE:
<221> NAME/KEY: modified_base
<222> LOCATION: (1656)..(1656)
```

-continued

```
<223> OTHER INFORMATION: a, c, g, t, unknown or other
<220> FEATURE:
<221> NAME/KEY: modified_base
<222> LOCATION: (1662)..(1662)
<223> OTHER INFORMATION: a, c, g, t, unknown or other
<220> FEATURE:
<221> NAME/KEY: modified_base
<222> LOCATION: (1665)..(1665)
<223> OTHER INFORMATION: a, c, g, t, unknown or other
<220> FEATURE:
<221> NAME/KEY: modified_base
<222> LOCATION: (1668)..(1668)
<223> OTHER INFORMATION: a, c, g, t, unknown or other
<220> FEATURE:
<221> NAME/KEY: modified_base
<222> LOCATION: (1671)..(1671)
<223> OTHER INFORMATION: a, c, g, t, unknown or other
<220> FEATURE:
<221> NAME/KEY: modified_base
<222> LOCATION: (1674)..(1674)
<223> OTHER INFORMATION: a, c, g, t, unknown or other
<220> FEATURE:
<221> NAME/KEY: modified_base
<222> LOCATION: (1683)..(1683)
<223> OTHER INFORMATION: a, c, g, t, unknown or other
<220> FEATURE:
<221> NAME/KEY: modified_base
<222> LOCATION: (1686)..(1686)
<223> OTHER INFORMATION: a, c, g, t, unknown or other
<220> FEATURE:
<221> NAME/KEY: modified_base
<222> LOCATION: (1695)..(1695)
<223> OTHER INFORMATION: a, c, g, t, unknown or other
<220> FEATURE:
<221> NAME/KEY: modified_base
<222> LOCATION: (1701)..(1701)
<223> OTHER INFORMATION: a, c, g, t, unknown or other
<220> FEATURE:
<221> NAME/KEY: modified_base
<222> LOCATION: (1707)..(1707)
<223> OTHER INFORMATION: a, c, g, t, unknown or other
<220> FEATURE:
<221> NAME/KEY: modified_base
<222> LOCATION: (1710)..(1710)
<223> OTHER INFORMATION: a, c, g, t, unknown or other
<220> FEATURE:
<221> NAME/KEY: modified_base
<222> LOCATION: (1719)..(1719)
<223> OTHER INFORMATION: a, c, g, t, unknown or other
<220> FEATURE:
<221> NAME/KEY: modified_base
<222> LOCATION: (1725)..(1725)
<223> OTHER INFORMATION: a, c, g, t, unknown or other
<220> FEATURE:
<221> NAME/KEY: modified_base
<222> LOCATION: (1740)..(1740)
<223> OTHER INFORMATION: a, c, g, t, unknown or other
<220> FEATURE:
<221> NAME/KEY: modified_base
<222> LOCATION: (1743)..(1743)
<223> OTHER INFORMATION: a, c, g, t, unknown or other
<220> FEATURE:
<221> NAME/KEY: modified_base
<222> LOCATION: (1752)..(1752)
<223> OTHER INFORMATION: a, c, g, t, unknown or other
<220> FEATURE:
<221> NAME/KEY: modified_base
<222> LOCATION: (1755)..(1755)
<223> OTHER INFORMATION: a, c, g, t, unknown or other
<220> FEATURE:
<221> NAME/KEY: modified_base
<222> LOCATION: (1761)..(1761)
<223> OTHER INFORMATION: a, c, g, t, unknown or other
<220> FEATURE:
<221> NAME/KEY: modified_base
<222> LOCATION: (1767)..(1767)
<223> OTHER INFORMATION: a, c, g, t, unknown or other
<220> FEATURE:
<221> NAME/KEY: modified_base
<222> LOCATION: (1773)..(1773)
```

-continued

```
<223> OTHER INFORMATION: a, c, g, t, unknown or other
<220> FEATURE:
<221> NAME/KEY: modified_base
<222> LOCATION: (1785)..(1785)
<223> OTHER INFORMATION: a, c, g, t, unknown or other
<220> FEATURE:
<221> NAME/KEY: modified_base
<222> LOCATION: (1791)..(1791)
<223> OTHER INFORMATION: a, c, g, t, unknown or other
<220> FEATURE:
<221> NAME/KEY: modified_base
<222> LOCATION: (1806)..(1806)
<223> OTHER INFORMATION: a, c, g, t, unknown or other
<220> FEATURE:
<221> NAME/KEY: modified_base
<222> LOCATION: (1815)..(1815)
<223> OTHER INFORMATION: a, c, g, t, unknown or other
<220> FEATURE:
<221> NAME/KEY: modified_base
<222> LOCATION: (1818)..(1818)
<223> OTHER INFORMATION: a, c, g, t, unknown or other
<220> FEATURE:
<221> NAME/KEY: modified_base
<222> LOCATION: (1821)..(1821)
<223> OTHER INFORMATION: a, c, g, t, unknown or other
<220> FEATURE:
<221> NAME/KEY: modified_base
<222> LOCATION: (1824)..(1824)
<223> OTHER INFORMATION: a, c, g, t, unknown or other
<220> FEATURE:
<221> NAME/KEY: modified_base
<222> LOCATION: (1842)..(1842)
<223> OTHER INFORMATION: a, c, g, t, unknown or other
<220> FEATURE:
<221> NAME/KEY: modified_base
<222> LOCATION: (1848)..(1848)
<223> OTHER INFORMATION: a, c, g, t, unknown or other
<220> FEATURE:
<221> NAME/KEY: modified_base
<222> LOCATION: (1851)..(1851)
<223> OTHER INFORMATION: a, c, g, t, unknown or other
<220> FEATURE:
<221> NAME/KEY: modified_base
<222> LOCATION: (1857)..(1857)
<223> OTHER INFORMATION: a, c, g, t, unknown or other
<220> FEATURE:
<221> NAME/KEY: modified_base
<222> LOCATION: (1860)..(1860)
<223> OTHER INFORMATION: a, c, g, t, unknown or other
<220> FEATURE:
<221> NAME/KEY: modified_base
<222> LOCATION: (1863)..(1863)
<223> OTHER INFORMATION: a, c, g, t, unknown or other
<220> FEATURE:
<221> NAME/KEY: modified_base
<222> LOCATION: (1881)..(1881)
<223> OTHER INFORMATION: a, c, g, t, unknown or other
<220> FEATURE:
<221> NAME/KEY: modified_base
<222> LOCATION: (1884)..(1884)
<223> OTHER INFORMATION: a, c, g, t, unknown or other
<220> FEATURE:
<221> NAME/KEY: modified_base
<222> LOCATION: (1887)..(1887)
<223> OTHER INFORMATION: a, c, g, t, unknown or other
<220> FEATURE:
<221> NAME/KEY: modified_base
<222> LOCATION: (1899)..(1899)
<223> OTHER INFORMATION: a, c, g, t, unknown or other
<220> FEATURE:
<221> NAME/KEY: modified_base
<222> LOCATION: (1902)..(1902)
<223> OTHER INFORMATION: a, c, g, t, unknown or other
<220> FEATURE:
<221> NAME/KEY: modified_base
<222> LOCATION: (1905)..(1905)
<223> OTHER INFORMATION: a, c, g, t, unknown or other
<220> FEATURE:
<221> NAME/KEY: modified_base
<222> LOCATION: (1911)..(1911)
```

```
<223> OTHER INFORMATION: a, c, g, t, unknown or other
<220> FEATURE:
<221> NAME/KEY: modified_base
<222> LOCATION: (1917)..(1917)
<223> OTHER INFORMATION: a, c, g, t, unknown or other
<220> FEATURE:
<221> NAME/KEY: modified_base
<222> LOCATION: (1923)..(1923)
<223> OTHER INFORMATION: a, c, g, t, unknown or other
<220> FEATURE:
<221> NAME/KEY: modified_base
<222> LOCATION: (1929)..(1929)
<223> OTHER INFORMATION: a, c, g, t, unknown or other
<220> FEATURE:
<221> NAME/KEY: modified_base
<222> LOCATION: (1935)..(1935)
<223> OTHER INFORMATION: a, c, g, t, unknown or other
<220> FEATURE:
<221> NAME/KEY: modified_base
<222> LOCATION: (1944)..(1944)
<223> OTHER INFORMATION: a, c, g, t, unknown or other
<220> FEATURE:
<221> NAME/KEY: modified_base
<222> LOCATION: (1947)..(1947)
<223> OTHER INFORMATION: a, c, g, t, unknown or other
<220> FEATURE:
<221> NAME/KEY: modified_base
<222> LOCATION: (1950)..(1950)
<223> OTHER INFORMATION: a, c, g, t, unknown or other
<220> FEATURE:
<221> NAME/KEY: modified_base
<222> LOCATION: (1953)..(1953)
<223> OTHER INFORMATION: a, c, g, t, unknown or other
<220> FEATURE:
<221> NAME/KEY: modified_base
<222> LOCATION: (1956)..(1956)
<223> OTHER INFORMATION: a, c, g, t, unknown or other
<220> FEATURE:
<221> NAME/KEY: modified_base
<222> LOCATION: (1959)..(1959)
<223> OTHER INFORMATION: a, c, g, t, unknown or other
<220> FEATURE:
<221> NAME/KEY: modified_base
<222> LOCATION: (1965)..(1965)
<223> OTHER INFORMATION: a, c, g, t, unknown or other
<220> FEATURE:
<221> NAME/KEY: modified_base
<222> LOCATION: (1968)..(1968)
<223> OTHER INFORMATION: a, c, g, t, unknown or other
<220> FEATURE:
<221> NAME/KEY: modified_base
<222> LOCATION: (1974)..(1974)
<223> OTHER INFORMATION: a, c, g, t, unknown or other
<220> FEATURE:
<221> NAME/KEY: modified_base
<222> LOCATION: (1977)..(1977)
<223> OTHER INFORMATION: a, c, g, t, unknown or other
<220> FEATURE:
<221> NAME/KEY: modified_base
<222> LOCATION: (1980)..(1980)
<223> OTHER INFORMATION: a, c, g, t, unknown or other
<220> FEATURE:
<221> NAME/KEY: modified_base
<222> LOCATION: (1983)..(1983)
<223> OTHER INFORMATION: a, c, g, t, unknown or other
<220> FEATURE:
<221> NAME/KEY: modified_base
<222> LOCATION: (1986)..(1986)
<223> OTHER INFORMATION: a, c, g, t, unknown or other
<220> FEATURE:
<221> NAME/KEY: modified_base
<222> LOCATION: (1992)..(1992)
<223> OTHER INFORMATION: a, c, g, t, unknown or other
<220> FEATURE:
<221> NAME/KEY: modified_base
<222> LOCATION: (1998)..(1998)
<223> OTHER INFORMATION: a, c, g, t, unknown or other
<220> FEATURE:
<221> NAME/KEY: modified_base
<222> LOCATION: (2001)..(2001)
```

```
<223> OTHER INFORMATION: a, c, g, t, unknown or other
<220> FEATURE:
<221> NAME/KEY: modified_base
<222> LOCATION: (2004)..(2004)
<223> OTHER INFORMATION: a, c, g, t, unknown or other
<220> FEATURE:
<221> NAME/KEY: modified_base
<222> LOCATION: (2007)..(2007)
<223> OTHER INFORMATION: a, c, g, t, unknown or other
<220> FEATURE:
<221> NAME/KEY: modified_base
<222> LOCATION: (2010)..(2010)
<223> OTHER INFORMATION: a, c, g, t, unknown or other
<220> FEATURE:
<221> NAME/KEY: modified_base
<222> LOCATION: (2013)..(2013)
<223> OTHER INFORMATION: a, c, g, t, unknown or other
<220> FEATURE:
<221> NAME/KEY: modified_base
<222> LOCATION: (2016)..(2016)
<223> OTHER INFORMATION: a, c, g, t, unknown or other
<220> FEATURE:
<221> NAME/KEY: modified_base
<222> LOCATION: (2019)..(2019)
<223> OTHER INFORMATION: a, c, g, t, unknown or other
<220> FEATURE:
<221> NAME/KEY: modified_base
<222> LOCATION: (2022)..(2022)
<223> OTHER INFORMATION: a, c, g, t, unknown or other
<220> FEATURE:
<221> NAME/KEY: modified_base
<222> LOCATION: (2025)..(2025)
<223> OTHER INFORMATION: a, c, g, t, unknown or other
<220> FEATURE:
<221> NAME/KEY: modified_base
<222> LOCATION: (2028)..(2028)
<223> OTHER INFORMATION: a, c, g, t, unknown or other
<220> FEATURE:
<221> NAME/KEY: modified_base
<222> LOCATION: (2031)..(2031)
<223> OTHER INFORMATION: a, c, g, t, unknown or other
<220> FEATURE:
<221> NAME/KEY: modified_base
<222> LOCATION: (2034)..(2034)
<223> OTHER INFORMATION: a, c, g, t, unknown or other
<220> FEATURE:
<221> NAME/KEY: modified_base
<222> LOCATION: (2037)..(2037)
<223> OTHER INFORMATION: a, c, g, t, unknown or other
<220> FEATURE:
<221> NAME/KEY: modified_base
<222> LOCATION: (2040)..(2040)
<223> OTHER INFORMATION: a, c, g, t, unknown or other
<220> FEATURE:
<221> NAME/KEY: modified_base
<222> LOCATION: (2043)..(2043)
<223> OTHER INFORMATION: a, c, g, t, unknown or other
<220> FEATURE:
<221> NAME/KEY: modified_base
<222> LOCATION: (2046)..(2046)
<223> OTHER INFORMATION: a, c, g, t, unknown or other
<220> FEATURE:
<221> NAME/KEY: modified_base
<222> LOCATION: (2049)..(2049)
<223> OTHER INFORMATION: a, c, g, t, unknown or other
<220> FEATURE:
<221> NAME/KEY: modified_base
<222> LOCATION: (2055)..(2055)
<223> OTHER INFORMATION: a, c, g, t, unknown or other
<220> FEATURE:
<221> NAME/KEY: modified_base
<222> LOCATION: (2064)..(2064)
<223> OTHER INFORMATION: a, c, g, t, unknown or other
<220> FEATURE:
<221> NAME/KEY: modified_base
<222> LOCATION: (2070)..(2070)
<223> OTHER INFORMATION: a, c, g, t, unknown or other
<220> FEATURE:
<221> NAME/KEY: modified_base
<222> LOCATION: (2073)..(2073)
```

-continued

```
<223> OTHER INFORMATION: a, c, g, t, unknown or other
<220> FEATURE:
<221> NAME/KEY: modified_base
<222> LOCATION: (2076)..(2076)
<223> OTHER INFORMATION: a, c, g, t, unknown or other
<220> FEATURE:
<221> NAME/KEY: modified_base
<222> LOCATION: (2079)..(2079)
<223> OTHER INFORMATION: a, c, g, t, unknown or other
<220> FEATURE:
<221> NAME/KEY: modified_base
<222> LOCATION: (2082)..(2082)
<223> OTHER INFORMATION: a, c, g, t, unknown or other
<220> FEATURE:
<221> NAME/KEY: modified_base
<222> LOCATION: (2085)..(2085)
<223> OTHER INFORMATION: a, c, g, t, unknown or other
<220> FEATURE:
<221> NAME/KEY: modified_base
<222> LOCATION: (2088)..(2088)
<223> OTHER INFORMATION: a, c, g, t, unknown or other
<220> FEATURE:
<221> NAME/KEY: modified_base
<222> LOCATION: (2091)..(2091)
<223> OTHER INFORMATION: a, c, g, t, unknown or other
<220> FEATURE:
<221> NAME/KEY: modified_base
<222> LOCATION: (2103)..(2103)
<223> OTHER INFORMATION: a, c, g, t, unknown or other
<220> FEATURE:
<221> NAME/KEY: modified_base
<222> LOCATION: (2106)..(2106)
<223> OTHER INFORMATION: a, c, g, t, unknown or other
<220> FEATURE:
<221> NAME/KEY: modified_base
<222> LOCATION: (2109)..(2109)
<223> OTHER INFORMATION: a, c, g, t, unknown or other
<220> FEATURE:
<221> NAME/KEY: modified_base
<222> LOCATION: (2115)..(2115)
<223> OTHER INFORMATION: a, c, g, t, unknown or other
<220> FEATURE:
<221> NAME/KEY: modified_base
<222> LOCATION: (2118)..(2118)
<223> OTHER INFORMATION: a, c, g, t, unknown or other
<220> FEATURE:
<221> NAME/KEY: modified_base
<222> LOCATION: (2121)..(2121)
<223> OTHER INFORMATION: a, c, g, t, unknown or other
<220> FEATURE:
<221> NAME/KEY: modified_base
<222> LOCATION: (2124)..(2124)
<223> OTHER INFORMATION: a, c, g, t, unknown or other
<220> FEATURE:
<221> NAME/KEY: modified_base
<222> LOCATION: (2127)..(2127)
<223> OTHER INFORMATION: a, c, g, t, unknown or other
<220> FEATURE:
<221> NAME/KEY: modified_base
<222> LOCATION: (2130)..(2130)
<223> OTHER INFORMATION: a, c, g, t, unknown or other
<220> FEATURE:
<221> NAME/KEY: modified_base
<222> LOCATION: (2133)..(2133)
<223> OTHER INFORMATION: a, c, g, t, unknown or other
<220> FEATURE:
<221> NAME/KEY: modified_base
<222> LOCATION: (2154)..(2154)
<223> OTHER INFORMATION: a, c, g, t, unknown or other
<220> FEATURE:
<221> NAME/KEY: modified_base
<222> LOCATION: (2157)..(2157)
<223> OTHER INFORMATION: a, c, g, t, unknown or other
<220> FEATURE:
<221> NAME/KEY: modified_base
<222> LOCATION: (2169)..(2169)
<223> OTHER INFORMATION: a, c, g, t, unknown or other
<220> FEATURE:
<221> NAME/KEY: modified_base
<222> LOCATION: (2172)..(2172)
```

-continued

```
<223> OTHER INFORMATION: a, c, g, t, unknown or other
<220> FEATURE:
<221> NAME/KEY: modified_base
<222> LOCATION: (2175)..(2175)
<223> OTHER INFORMATION: a, c, g, t, unknown or other
<220> FEATURE:
<221> NAME/KEY: modified_base
<222> LOCATION: (2178)..(2178)
<223> OTHER INFORMATION: a, c, g, t, unknown or other
<220> FEATURE:
<221> NAME/KEY: modified_base
<222> LOCATION: (2184)..(2184)
<223> OTHER INFORMATION: a, c, g, t, unknown or other
<220> FEATURE:
<221> NAME/KEY: modified_base
<222> LOCATION: (2187)..(2187)
<223> OTHER INFORMATION: a, c, g, t, unknown or other
<220> FEATURE:
<221> NAME/KEY: modified_base
<222> LOCATION: (2196)..(2196)
<223> OTHER INFORMATION: a, c, g, t, unknown or other
<220> FEATURE:
<221> NAME/KEY: modified_base
<222> LOCATION: (2202)..(2202)
<223> OTHER INFORMATION: a, c, g, t, unknown or other
<220> FEATURE:
<221> NAME/KEY: modified_base
<222> LOCATION: (2211)..(2211)
<223> OTHER INFORMATION: a, c, g, t, unknown or other
<220> FEATURE:
<221> NAME/KEY: modified_base
<222> LOCATION: (2214)..(2214)
<223> OTHER INFORMATION: a, c, g, t, unknown or other
<220> FEATURE:
<221> NAME/KEY: modified_base
<222> LOCATION: (2217)..(2217)
<223> OTHER INFORMATION: a, c, g, t, unknown or other
<220> FEATURE:
<221> NAME/KEY: modified_base
<222> LOCATION: (2220)..(2220)
<223> OTHER INFORMATION: a, c, g, t, unknown or other
<220> FEATURE:
<221> NAME/KEY: modified_base
<222> LOCATION: (2223)..(2223)
<223> OTHER INFORMATION: a, c, g, t, unknown or other
<220> FEATURE:
<221> NAME/KEY: modified_base
<222> LOCATION: (2226)..(2226)
<223> OTHER INFORMATION: a, c, g, t, unknown or other
<220> FEATURE:
<221> NAME/KEY: modified_base
<222> LOCATION: (2229)..(2229)
<223> OTHER INFORMATION: a, c, g, t, unknown or other
<220> FEATURE:
<221> NAME/KEY: modified_base
<222> LOCATION: (2232)..(2232)
<223> OTHER INFORMATION: a, c, g, t, unknown or other
<220> FEATURE:
<221> NAME/KEY: modified_base
<222> LOCATION: (2235)..(2235)
<223> OTHER INFORMATION: a, c, g, t, unknown or other
<220> FEATURE:
<221> NAME/KEY: modified_base
<222> LOCATION: (2238)..(2238)
<223> OTHER INFORMATION: a, c, g, t, unknown or other
<220> FEATURE:
<221> NAME/KEY: modified_base
<222> LOCATION: (2244)..(2244)
<223> OTHER INFORMATION: a, c, g, t, unknown or other
<220> FEATURE:
<221> NAME/KEY: modified_base
<222> LOCATION: (2247)..(2247)
<223> OTHER INFORMATION: a, c, g, t, unknown or other
<220> FEATURE:
<221> NAME/KEY: modified_base
<222> LOCATION: (2253)..(2253)
<223> OTHER INFORMATION: a, c, g, t, unknown or other
<220> FEATURE:
<221> NAME/KEY: modified_base
<222> LOCATION: (2256)..(2256)
```

-continued

```
<223> OTHER INFORMATION: a, c, g, t, unknown or other
<220> FEATURE:
<221> NAME/KEY: modified_base
<222> LOCATION: (2259)..(2259)
<223> OTHER INFORMATION: a, c, g, t, unknown or other
<220> FEATURE:
<221> NAME/KEY: modified_base
<222> LOCATION: (2265)..(2265)
<223> OTHER INFORMATION: a, c, g, t, unknown or other
<220> FEATURE:
<221> NAME/KEY: modified_base
<222> LOCATION: (2280)..(2280)
<223> OTHER INFORMATION: a, c, g, t, unknown or other
<220> FEATURE:
<221> NAME/KEY: modified_base
<222> LOCATION: (2283)..(2283)
<223> OTHER INFORMATION: a, c, g, t, unknown or other
<220> FEATURE:
<221> NAME/KEY: modified_base
<222> LOCATION: (2286)..(2286)
<223> OTHER INFORMATION: a, c, g, t, unknown or other
<220> FEATURE:
<221> NAME/KEY: modified_base
<222> LOCATION: (2289)..(2289)
<223> OTHER INFORMATION: a, c, g, t, unknown or other
<220> FEATURE:
<221> NAME/KEY: modified_base
<222> LOCATION: (2292)..(2292)
<223> OTHER INFORMATION: a, c, g, t, unknown or other
<220> FEATURE:
<221> NAME/KEY: modified_base
<222> LOCATION: (2295)..(2295)
<223> OTHER INFORMATION: a, c, g, t, unknown or other
<220> FEATURE:
<221> NAME/KEY: modified_base
<222> LOCATION: (2301)..(2301)
<223> OTHER INFORMATION: a, c, g, t, unknown or other
<220> FEATURE:
<221> NAME/KEY: modified_base
<222> LOCATION: (2304)..(2304)
<223> OTHER INFORMATION: a, c, g, t, unknown or other
<220> FEATURE:
<221> NAME/KEY: modified_base
<222> LOCATION: (2307)..(2307)
<223> OTHER INFORMATION: a, c, g, t, unknown or other
<220> FEATURE:
<221> NAME/KEY: modified_base
<222> LOCATION: (2310)..(2310)
<223> OTHER INFORMATION: a, c, g, t, unknown or other
<220> FEATURE:
<221> NAME/KEY: modified_base
<222> LOCATION: (2313)..(2313)
<223> OTHER INFORMATION: a, c, g, t, unknown or other
<220> FEATURE:
<221> NAME/KEY: modified_base
<222> LOCATION: (2319)..(2319)
<223> OTHER INFORMATION: a, c, g, t, unknown or other
<220> FEATURE:
<221> NAME/KEY: modified_base
<222> LOCATION: (2322)..(2322)
<223> OTHER INFORMATION: a, c, g, t, unknown or other
<220> FEATURE:
<221> NAME/KEY: modified_base
<222> LOCATION: (2325)..(2325)
<223> OTHER INFORMATION: a, c, g, t, unknown or other
<220> FEATURE:
<221> NAME/KEY: modified_base
<222> LOCATION: (2328)..(2328)
<223> OTHER INFORMATION: a, c, g, t, unknown or other
<220> FEATURE:
<221> NAME/KEY: modified_base
<222> LOCATION: (2331)..(2331)
<223> OTHER INFORMATION: a, c, g, t, unknown or other
<220> FEATURE:
<221> NAME/KEY: modified_base
<222> LOCATION: (2334)..(2334)
<223> OTHER INFORMATION: a, c, g, t, unknown or other
<220> FEATURE:
<221> NAME/KEY: modified_base
<222> LOCATION: (2337)..(2337)
```

-continued

```
<223> OTHER INFORMATION: a, c, g, t, unknown or other
<220> FEATURE:
<221> NAME/KEY: modified_base
<222> LOCATION: (2355)..(2355)
<223> OTHER INFORMATION: a, c, g, t, unknown or other
<220> FEATURE:
<221> NAME/KEY: modified_base
<222> LOCATION: (2358)..(2358)
<223> OTHER INFORMATION: a, c, g, t, unknown or other
<220> FEATURE:
<221> NAME/KEY: modified_base
<222> LOCATION: (2367)..(2367)
<223> OTHER INFORMATION: a, c, g, t, unknown or other
<220> FEATURE:
<221> NAME/KEY: modified_base
<222> LOCATION: (2370)..(2370)
<223> OTHER INFORMATION: a, c, g, t, unknown or other
<220> FEATURE:
<221> NAME/KEY: modified_base
<222> LOCATION: (2376)..(2376)
<223> OTHER INFORMATION: a, c, g, t, unknown or other
<220> FEATURE:
<221> NAME/KEY: modified_base
<222> LOCATION: (2379)..(2379)
<223> OTHER INFORMATION: a, c, g, t, unknown or other
<220> FEATURE:
<221> NAME/KEY: modified_base
<222> LOCATION: (2382)..(2382)
<223> OTHER INFORMATION: a, c, g, t, unknown or other
<220> FEATURE:
<221> NAME/KEY: modified_base
<222> LOCATION: (2385)..(2385)
<223> OTHER INFORMATION: a, c, g, t, unknown or other
<220> FEATURE:
<221> NAME/KEY: modified_base
<222> LOCATION: (2388)..(2388)
<223> OTHER INFORMATION: a, c, g, t, unknown or other
<220> FEATURE:
<221> NAME/KEY: modified_base
<222> LOCATION: (2391)..(2391)
<223> OTHER INFORMATION: a, c, g, t, unknown or other
<220> FEATURE:
<221> NAME/KEY: modified_base
<222> LOCATION: (2397)..(2397)
<223> OTHER INFORMATION: a, c, g, t, unknown or other
<220> FEATURE:
<221> NAME/KEY: modified_base
<222> LOCATION: (2403)..(2403)
<223> OTHER INFORMATION: a, c, g, t, unknown or other
<220> FEATURE:
<221> NAME/KEY: modified_base
<222> LOCATION: (2412)..(2412)
<223> OTHER INFORMATION: a, c, g, t, unknown or other
<220> FEATURE:
<221> NAME/KEY: modified_base
<222> LOCATION: (2415)..(2415)
<223> OTHER INFORMATION: a, c, g, t, unknown or other
<220> FEATURE:
<221> NAME/KEY: modified_base
<222> LOCATION: (2418)..(2418)
<223> OTHER INFORMATION: a, c, g, t, unknown or other
<220> FEATURE:
<221> NAME/KEY: modified_base
<222> LOCATION: (2421)..(2421)
<223> OTHER INFORMATION: a, c, g, t, unknown or other
<220> FEATURE:
<221> NAME/KEY: modified_base
<222> LOCATION: (2427)..(2427)
<223> OTHER INFORMATION: a, c, g, t, unknown or other
<220> FEATURE:
<221> NAME/KEY: modified_base
<222> LOCATION: (2430)..(2430)
<223> OTHER INFORMATION: a, c, g, t, unknown or other
<220> FEATURE:
<221> NAME/KEY: modified_base
<222> LOCATION: (2442)..(2442)
<223> OTHER INFORMATION: a, c, g, t, unknown or other
<220> FEATURE:
<221> NAME/KEY: modified_base
<222> LOCATION: (2445)..(2445)
```

-continued

```
<223> OTHER INFORMATION: a, c, g, t, unknown or other
<220> FEATURE:
<221> NAME/KEY: modified_base
<222> LOCATION: (2448)..(2448)
<223> OTHER INFORMATION: a, c, g, t, unknown or other
<220> FEATURE:
<221> NAME/KEY: modified_base
<222> LOCATION: (2454)..(2454)
<223> OTHER INFORMATION: a, c, g, t, unknown or other
<220> FEATURE:
<221> NAME/KEY: modified_base
<222> LOCATION: (2457)..(2457)
<223> OTHER INFORMATION: a, c, g, t, unknown or other
<220> FEATURE:
<221> NAME/KEY: modified_base
<222> LOCATION: (2460)..(2460)
<223> OTHER INFORMATION: a, c, g, t, unknown or other
<220> FEATURE:
<221> NAME/KEY: modified_base
<222> LOCATION: (2463)..(2463)
<223> OTHER INFORMATION: a, c, g, t, unknown or other
<220> FEATURE:
<221> NAME/KEY: modified_base
<222> LOCATION: (2478)..(2478)
<223> OTHER INFORMATION: a, c, g, t, unknown or other
<220> FEATURE:
<221> NAME/KEY: modified_base
<222> LOCATION: (2481)..(2481)
<223> OTHER INFORMATION: a, c, g, t, unknown or other
<220> FEATURE:
<221> NAME/KEY: modified_base
<222> LOCATION: (2484)..(2484)
<223> OTHER INFORMATION: a, c, g, t, unknown or other
<220> FEATURE:
<221> NAME/KEY: modified_base
<222> LOCATION: (2487)..(2487)
<223> OTHER INFORMATION: a, c, g, t, unknown or other
<220> FEATURE:
<221> NAME/KEY: modified_base
<222> LOCATION: (2499)..(2499)
<223> OTHER INFORMATION: a, c, g, t, unknown or other
<220> FEATURE:
<221> NAME/KEY: modified_base
<222> LOCATION: (2511)..(2511)
<223> OTHER INFORMATION: a, c, g, t, unknown or other
<220> FEATURE:
<221> NAME/KEY: modified_base
<222> LOCATION: (2514)..(2514)
<223> OTHER INFORMATION: a, c, g, t, unknown or other
<220> FEATURE:
<221> NAME/KEY: modified_base
<222> LOCATION: (2520)..(2520)
<223> OTHER INFORMATION: a, c, g, t, unknown or other
<220> FEATURE:
<221> NAME/KEY: modified_base
<222> LOCATION: (2523)..(2523)
<223> OTHER INFORMATION: a, c, g, t, unknown or other
<220> FEATURE:
<221> NAME/KEY: modified_base
<222> LOCATION: (2529)..(2529)
<223> OTHER INFORMATION: a, c, g, t, unknown or other
<220> FEATURE:
<221> NAME/KEY: modified_base
<222> LOCATION: (2538)..(2538)
<223> OTHER INFORMATION: a, c, g, t, unknown or other
<220> FEATURE:
<221> NAME/KEY: modified_base
<222> LOCATION: (2541)..(2541)
<223> OTHER INFORMATION: a, c, g, t, unknown or other
<220> FEATURE:
<221> NAME/KEY: modified_base
<222> LOCATION: (2544)..(2544)
<223> OTHER INFORMATION: a, c, g, t, unknown or other
<220> FEATURE:
<221> NAME/KEY: modified_base
<222> LOCATION: (2547)..(2547)
<223> OTHER INFORMATION: a, c, g, t, unknown or other
<220> FEATURE:
<221> NAME/KEY: modified_base
<222> LOCATION: (2550)..(2550)
```

```
<223> OTHER INFORMATION: a, c, g, t, unknown or other
<220> FEATURE:
<221> NAME/KEY: modified_base
<222> LOCATION: (2553)..(2553)
<223> OTHER INFORMATION: a, c, g, t, unknown or other
<220> FEATURE:
<221> NAME/KEY: modified_base
<222> LOCATION: (2556)..(2556)
<223> OTHER INFORMATION: a, c, g, t, unknown or other
<220> FEATURE:
<221> NAME/KEY: modified_base
<222> LOCATION: (2562)..(2562)
<223> OTHER INFORMATION: a, c, g, t, unknown or other
<220> FEATURE:
<221> NAME/KEY: modified_base
<222> LOCATION: (2565)..(2565)
<223> OTHER INFORMATION: a, c, g, t, unknown or other
<220> FEATURE:
<221> NAME/KEY: modified_base
<222> LOCATION: (2568)..(2568)
<223> OTHER INFORMATION: a, c, g, t, unknown or other
<220> FEATURE:
<221> NAME/KEY: modified_base
<222> LOCATION: (2574)..(2574)
<223> OTHER INFORMATION: a, c, g, t, unknown or other
<220> FEATURE:
<221> NAME/KEY: modified_base
<222> LOCATION: (2577)..(2577)
<223> OTHER INFORMATION: a, c, g, t, unknown or other
<220> FEATURE:
<221> NAME/KEY: modified_base
<222> LOCATION: (2583)..(2583)
<223> OTHER INFORMATION: a, c, g, t, unknown or other
<220> FEATURE:
<221> NAME/KEY: modified_base
<222> LOCATION: (2589)..(2589)
<223> OTHER INFORMATION: a, c, g, t, unknown or other
<220> FEATURE:
<221> NAME/KEY: modified_base
<222> LOCATION: (2604)..(2604)
<223> OTHER INFORMATION: a, c, g, t, unknown or other
<220> FEATURE:
<221> NAME/KEY: modified_base
<222> LOCATION: (2607)..(2607)
<223> OTHER INFORMATION: a, c, g, t, unknown or other
<220> FEATURE:
<221> NAME/KEY: modified_base
<222> LOCATION: (2610)..(2610)
<223> OTHER INFORMATION: a, c, g, t, unknown or other
<220> FEATURE:
<221> NAME/KEY: modified_base
<222> LOCATION: (2613)..(2613)
<223> OTHER INFORMATION: a, c, g, t, unknown or other
<220> FEATURE:
<221> NAME/KEY: modified_base
<222> LOCATION: (2625)..(2625)
<223> OTHER INFORMATION: a, c, g, t, unknown or other
<220> FEATURE:
<221> NAME/KEY: modified_base
<222> LOCATION: (2628)..(2628)
<223> OTHER INFORMATION: a, c, g, t, unknown or other
<220> FEATURE:
<221> NAME/KEY: modified_base
<222> LOCATION: (2631)..(2631)
<223> OTHER INFORMATION: a, c, g, t, unknown or other
<220> FEATURE:
<221> NAME/KEY: modified_base
<222> LOCATION: (2634)..(2634)
<223> OTHER INFORMATION: a, c, g, t, unknown or other
<220> FEATURE:
<221> NAME/KEY: modified_base
<222> LOCATION: (2643)..(2643)
<223> OTHER INFORMATION: a, c, g, t, unknown or other
<220> FEATURE:
<221> NAME/KEY: modified_base
<222> LOCATION: (2649)..(2649)
<223> OTHER INFORMATION: a, c, g, t, unknown or other
<220> FEATURE:
<221> NAME/KEY: modified_base
<222> LOCATION: (2664)..(2664)
```

-continued

```
<223> OTHER INFORMATION: a, c, g, t, unknown or other
<220> FEATURE:
<221> NAME/KEY: modified_base
<222> LOCATION: (2670)..(2670)
<223> OTHER INFORMATION: a, c, g, t, unknown or other
<220> FEATURE:
<221> NAME/KEY: modified_base
<222> LOCATION: (2676)..(2676)
<223> OTHER INFORMATION: a, c, g, t, unknown or other
<220> FEATURE:
<221> NAME/KEY: modified_base
<222> LOCATION: (2682)..(2682)
<223> OTHER INFORMATION: a, c, g, t, unknown or other
<220> FEATURE:
<221> NAME/KEY: modified_base
<222> LOCATION: (2688)..(2688)
<223> OTHER INFORMATION: a, c, g, t, unknown or other
<220> FEATURE:
<221> NAME/KEY: modified_base
<222> LOCATION: (2691)..(2691)
<223> OTHER INFORMATION: a, c, g, t, unknown or other
<220> FEATURE:
<221> NAME/KEY: modified_base
<222> LOCATION: (2694)..(2694)
<223> OTHER INFORMATION: a, c, g, t, unknown or other
<220> FEATURE:
<221> NAME/KEY: modified_base
<222> LOCATION: (2697)..(2697)
<223> OTHER INFORMATION: a, c, g, t, unknown or other
<220> FEATURE:
<221> NAME/KEY: modified_base
<222> LOCATION: (2700)..(2700)
<223> OTHER INFORMATION: a, c, g, t, unknown or other
<220> FEATURE:
<221> NAME/KEY: modified_base
<222> LOCATION: (2712)..(2712)
<223> OTHER INFORMATION: a, c, g, t, unknown or other
<220> FEATURE:
<221> NAME/KEY: modified_base
<222> LOCATION: (2715)..(2715)
<223> OTHER INFORMATION: a, c, g, t, unknown or other
<220> FEATURE:
<221> NAME/KEY: modified_base
<222> LOCATION: (2718)..(2718)
<223> OTHER INFORMATION: a, c, g, t, unknown or other
<220> FEATURE:
<221> NAME/KEY: modified_base
<222> LOCATION: (2721)..(2721)
<223> OTHER INFORMATION: a, c, g, t, unknown or other
<220> FEATURE:
<221> NAME/KEY: modified_base
<222> LOCATION: (2733)..(2733)
<223> OTHER INFORMATION: a, c, g, t, unknown or other
<220> FEATURE:
<221> NAME/KEY: modified_base
<222> LOCATION: (2736)..(2736)
<223> OTHER INFORMATION: a, c, g, t, unknown or other
<220> FEATURE:
<221> NAME/KEY: modified_base
<222> LOCATION: (2742)..(2742)
<223> OTHER INFORMATION: a, c, g, t, unknown or other
<220> FEATURE:
<221> NAME/KEY: modified_base
<222> LOCATION: (2745)..(2745)
<223> OTHER INFORMATION: a, c, g, t, unknown or other
<220> FEATURE:
<221> NAME/KEY: modified_base
<222> LOCATION: (2754)..(2754)
<223> OTHER INFORMATION: a, c, g, t, unknown or other
<220> FEATURE:
<221> NAME/KEY: modified_base
<222> LOCATION: (2763)..(2763)
<223> OTHER INFORMATION: a, c, g, t, unknown or other
<220> FEATURE:
<221> NAME/KEY: modified_base
<222> LOCATION: (2766)..(2766)
<223> OTHER INFORMATION: a, c, g, t, unknown or other
<220> FEATURE:
<221> NAME/KEY: modified_base
<222> LOCATION: (2769)..(2769)
```

-continued

```
<223> OTHER INFORMATION: a, c, g, t, unknown or other
<220> FEATURE:
<221> NAME/KEY: modified_base
<222> LOCATION: (2772)..(2772)
<223> OTHER INFORMATION: a, c, g, t, unknown or other
<220> FEATURE:
<221> NAME/KEY: modified_base
<222> LOCATION: (2781)..(2781)
<223> OTHER INFORMATION: a, c, g, t, unknown or other
<220> FEATURE:
<221> NAME/KEY: modified_base
<222> LOCATION: (2787)..(2787)
<223> OTHER INFORMATION: a, c, g, t, unknown or other
<220> FEATURE:
<221> NAME/KEY: modified_base
<222> LOCATION: (2790)..(2790)
<223> OTHER INFORMATION: a, c, g, t, unknown or other
<220> FEATURE:
<221> NAME/KEY: modified_base
<222> LOCATION: (2793)..(2793)
<223> OTHER INFORMATION: a, c, g, t, unknown or other
<220> FEATURE:
<221> NAME/KEY: modified_base
<222> LOCATION: (2811)..(2811)
<223> OTHER INFORMATION: a, c, g, t, unknown or other
<220> FEATURE:
<221> NAME/KEY: modified_base
<222> LOCATION: (2814)..(2814)
<223> OTHER INFORMATION: a, c, g, t, unknown or other
<220> FEATURE:
<221> NAME/KEY: modified_base
<222> LOCATION: (2823)..(2823)
<223> OTHER INFORMATION: a, c, g, t, unknown or other
<220> FEATURE:
<221> NAME/KEY: modified_base
<222> LOCATION: (2832)..(2832)
<223> OTHER INFORMATION: a, c, g, t, unknown or other
<220> FEATURE:
<221> NAME/KEY: modified_base
<222> LOCATION: (2838)..(2838)
<223> OTHER INFORMATION: a, c, g, t, unknown or other
<220> FEATURE:
<221> NAME/KEY: modified_base
<222> LOCATION: (2841)..(2841)
<223> OTHER INFORMATION: a, c, g, t, unknown or other
<220> FEATURE:
<221> NAME/KEY: modified_base
<222> LOCATION: (2847)..(2847)
<223> OTHER INFORMATION: a, c, g, t, unknown or other
<220> FEATURE:
<221> NAME/KEY: modified_base
<222> LOCATION: (2850)..(2850)
<223> OTHER INFORMATION: a, c, g, t, unknown or other
<220> FEATURE:
<221> NAME/KEY: modified_base
<222> LOCATION: (2853)..(2853)
<223> OTHER INFORMATION: a, c, g, t, unknown or other
<220> FEATURE:
<221> NAME/KEY: modified_base
<222> LOCATION: (2856)..(2856)
<223> OTHER INFORMATION: a, c, g, t, unknown or other
<220> FEATURE:
<221> NAME/KEY: modified_base
<222> LOCATION: (2862)..(2862)
<223> OTHER INFORMATION: a, c, g, t, unknown or other
<220> FEATURE:
<221> NAME/KEY: modified_base
<222> LOCATION: (2883)..(2883)
<223> OTHER INFORMATION: a, c, g, t, unknown or other
<220> FEATURE:
<221> NAME/KEY: modified_base
<222> LOCATION: (2886)..(2886)
<223> OTHER INFORMATION: a, c, g, t, unknown or other
<220> FEATURE:
<221> NAME/KEY: modified_base
<222> LOCATION: (2889)..(2889)
<223> OTHER INFORMATION: a, c, g, t, unknown or other
<220> FEATURE:
<221> NAME/KEY: modified_base
<222> LOCATION: (2892)..(2892)
```

-continued

```
<223> OTHER INFORMATION: a, c, g, t, unknown or other
<220> FEATURE:
<221> NAME/KEY: modified_base
<222> LOCATION: (2895)..(2895)
<223> OTHER INFORMATION: a, c, g, t, unknown or other
<220> FEATURE:
<221> NAME/KEY: modified_base
<222> LOCATION: (2898)..(2898)
<223> OTHER INFORMATION: a, c, g, t, unknown or other
<220> FEATURE:
<221> NAME/KEY: modified_base
<222> LOCATION: (2907)..(2907)
<223> OTHER INFORMATION: a, c, g, t, unknown or other
<220> FEATURE:
<221> NAME/KEY: modified_base
<222> LOCATION: (2916)..(2916)
<223> OTHER INFORMATION: a, c, g, t, unknown or other
<220> FEATURE:
<221> NAME/KEY: modified_base
<222> LOCATION: (2919)..(2919)
<223> OTHER INFORMATION: a, c, g, t, unknown or other
<220> FEATURE:
<221> NAME/KEY: modified_base
<222> LOCATION: (2922)..(2922)
<223> OTHER INFORMATION: a, c, g, t, unknown or other
<220> FEATURE:
<221> NAME/KEY: modified_base
<222> LOCATION: (2925)..(2925)
<223> OTHER INFORMATION: a, c, g, t, unknown or other
<220> FEATURE:
<221> NAME/KEY: modified_base
<222> LOCATION: (2946)..(2946)
<223> OTHER INFORMATION: a, c, g, t, unknown or other
<220> FEATURE:
<221> NAME/KEY: modified_base
<222> LOCATION: (2949)..(2949)
<223> OTHER INFORMATION: a, c, g, t, unknown or other
<220> FEATURE:
<221> NAME/KEY: modified_base
<222> LOCATION: (2952)..(2952)
<223> OTHER INFORMATION: a, c, g, t, unknown or other
<220> FEATURE:
<221> NAME/KEY: modified_base
<222> LOCATION: (2958)..(2958)
<223> OTHER INFORMATION: a, c, g, t, unknown or other
<220> FEATURE:
<221> NAME/KEY: modified_base
<222> LOCATION: (2961)..(2961)
<223> OTHER INFORMATION: a, c, g, t, unknown or other
<220> FEATURE:
<221> NAME/KEY: modified_base
<222> LOCATION: (2973)..(2973)
<223> OTHER INFORMATION: a, c, g, t, unknown or other
<220> FEATURE:
<221> NAME/KEY: modified_base
<222> LOCATION: (2991)..(2991)
<223> OTHER INFORMATION: a, c, g, t, unknown or other
<220> FEATURE:
<221> NAME/KEY: modified_base
<222> LOCATION: (2994)..(2994)
<223> OTHER INFORMATION: a, c, g, t, unknown or other
<220> FEATURE:
<221> NAME/KEY: modified_base
<222> LOCATION: (2997)..(2997)
<223> OTHER INFORMATION: a, c, g, t, unknown or other
<220> FEATURE:
<221> NAME/KEY: modified_base
<222> LOCATION: (3000)..(3000)
<223> OTHER INFORMATION: a, c, g, t, unknown or other
<220> FEATURE:
<221> NAME/KEY: modified_base
<222> LOCATION: (3003)..(3003)
<223> OTHER INFORMATION: a, c, g, t, unknown or other
<220> FEATURE:
<221> NAME/KEY: modified_base
<222> LOCATION: (3006)..(3006)
<223> OTHER INFORMATION: a, c, g, t, unknown or other
<220> FEATURE:
<221> NAME/KEY: modified_base
<222> LOCATION: (3009)..(3009)
```

-continued

```
<223> OTHER INFORMATION: a, c, g, t, unknown or other
<220> FEATURE:
<221> NAME/KEY: modified_base
<222> LOCATION: (3012)..(3012)
<223> OTHER INFORMATION: a, c, g, t, unknown or other
<220> FEATURE:
<221> NAME/KEY: modified_base
<222> LOCATION: (3015)..(3015)
<223> OTHER INFORMATION: a, c, g, t, unknown or other
<220> FEATURE:
<221> NAME/KEY: modified_base
<222> LOCATION: (3018)..(3018)
<223> OTHER INFORMATION: a, c, g, t, unknown or other
<220> FEATURE:
<221> NAME/KEY: modified_base
<222> LOCATION: (3039)..(3039)
<223> OTHER INFORMATION: a, c, g, t, unknown or other
<220> FEATURE:
<221> NAME/KEY: modified_base
<222> LOCATION: (3042)..(3042)
<223> OTHER INFORMATION: a, c, g, t, unknown or other
<220> FEATURE:
<221> NAME/KEY: modified_base
<222> LOCATION: (3051)..(3051)
<223> OTHER INFORMATION: a, c, g, t, unknown or other
<220> FEATURE:
<221> NAME/KEY: modified_base
<222> LOCATION: (3060)..(3060)
<223> OTHER INFORMATION: a, c, g, t, unknown or other
<220> FEATURE:
<221> NAME/KEY: modified_base
<222> LOCATION: (3063)..(3063)
<223> OTHER INFORMATION: a, c, g, t, unknown or other
<220> FEATURE:
<221> NAME/KEY: modified_base
<222> LOCATION: (3072)..(3072)
<223> OTHER INFORMATION: a, c, g, t, unknown or other
<220> FEATURE:
<221> NAME/KEY: modified_base
<222> LOCATION: (3078)..(3078)
<223> OTHER INFORMATION: a, c, g, t, unknown or other
<220> FEATURE:
<221> NAME/KEY: modified_base
<222> LOCATION: (3084)..(3084)
<223> OTHER INFORMATION: a, c, g, t, unknown or other
<220> FEATURE:
<221> NAME/KEY: modified_base
<222> LOCATION: (3087)..(3087)
<223> OTHER INFORMATION: a, c, g, t, unknown or other
<220> FEATURE:
<221> NAME/KEY: modified_base
<222> LOCATION: (3090)..(3090)
<223> OTHER INFORMATION: a, c, g, t, unknown or other
<220> FEATURE:
<221> NAME/KEY: modified_base
<222> LOCATION: (3093)..(3093)
<223> OTHER INFORMATION: a, c, g, t, unknown or other
<220> FEATURE:
<221> NAME/KEY: modified_base
<222> LOCATION: (3096)..(3096)
<223> OTHER INFORMATION: a, c, g, t, unknown or other
<220> FEATURE:
<221> NAME/KEY: modified_base
<222> LOCATION: (3102)..(3102)
<223> OTHER INFORMATION: a, c, g, t, unknown or other
<220> FEATURE:
<221> NAME/KEY: modified_base
<222> LOCATION: (3105)..(3105)
<223> OTHER INFORMATION: a, c, g, t, unknown or other
<220> FEATURE:
<221> NAME/KEY: modified_base
<222> LOCATION: (3108)..(3108)
<223> OTHER INFORMATION: a, c, g, t, unknown or other
<220> FEATURE:
<221> NAME/KEY: modified_base
<222> LOCATION: (3111)..(3111)
<223> OTHER INFORMATION: a, c, g, t, unknown or other
<220> FEATURE:
<221> NAME/KEY: modified_base
<222> LOCATION: (3117)..(3117)
```

-continued

```
<223> OTHER INFORMATION: a, c, g, t, unknown or other
<220> FEATURE:
<221> NAME/KEY: modified_base
<222> LOCATION: (3120)..(3120)
<223> OTHER INFORMATION: a, c, g, t, unknown or other
<220> FEATURE:
<221> NAME/KEY: modified_base
<222> LOCATION: (3123)..(3123)
<223> OTHER INFORMATION: a, c, g, t, unknown or other
<220> FEATURE:
<221> NAME/KEY: modified_base
<222> LOCATION: (3129)..(3129)
<223> OTHER INFORMATION: a, c, g, t, unknown or other
<220> FEATURE:
<221> NAME/KEY: modified_base
<222> LOCATION: (3141)..(3141)
<223> OTHER INFORMATION: a, c, g, t, unknown or other
<220> FEATURE:
<221> NAME/KEY: modified_base
<222> LOCATION: (3144)..(3144)
<223> OTHER INFORMATION: a, c, g, t, unknown or other
<220> FEATURE:
<221> NAME/KEY: modified_base
<222> LOCATION: (3156)..(3156)
<223> OTHER INFORMATION: a, c, g, t, unknown or other
<220> FEATURE:
<221> NAME/KEY: modified_base
<222> LOCATION: (3168)..(3168)
<223> OTHER INFORMATION: a, c, g, t, unknown or other
<220> FEATURE:
<221> NAME/KEY: modified_base
<222> LOCATION: (3171)..(3171)
<223> OTHER INFORMATION: a, c, g, t, unknown or other
<220> FEATURE:
<221> NAME/KEY: modified_base
<222> LOCATION: (3174)..(3174)
<223> OTHER INFORMATION: a, c, g, t, unknown or other
<220> FEATURE:
<221> NAME/KEY: modified_base
<222> LOCATION: (3180)..(3180)
<223> OTHER INFORMATION: a, c, g, t, unknown or other
<220> FEATURE:
<221> NAME/KEY: modified_base
<222> LOCATION: (3192)..(3192)
<223> OTHER INFORMATION: a, c, g, t, unknown or other
<220> FEATURE:
<221> NAME/KEY: modified_base
<222> LOCATION: (3198)..(3198)
<223> OTHER INFORMATION: a, c, g, t, unknown or other
<220> FEATURE:
<221> NAME/KEY: modified_base
<222> LOCATION: (3201)..(3201)
<223> OTHER INFORMATION: a, c, g, t, unknown or other
<220> FEATURE:
<221> NAME/KEY: modified_base
<222> LOCATION: (3204)..(3204)
<223> OTHER INFORMATION: a, c, g, t, unknown or other
<220> FEATURE:
<221> NAME/KEY: modified_base
<222> LOCATION: (3207)..(3207)
<223> OTHER INFORMATION: a, c, g, t, unknown or other
<220> FEATURE:
<221> NAME/KEY: modified_base
<222> LOCATION: (3210)..(3210)
<223> OTHER INFORMATION: a, c, g, t, unknown or other
<220> FEATURE:
<221> NAME/KEY: modified_base
<222> LOCATION: (3213)..(3213)
<223> OTHER INFORMATION: a, c, g, t, unknown or other
<220> FEATURE:
<221> NAME/KEY: modified_base
<222> LOCATION: (3216)..(3216)
<223> OTHER INFORMATION: a, c, g, t, unknown or other
<220> FEATURE:
<221> NAME/KEY: modified_base
<222> LOCATION: (3219)..(3219)
<223> OTHER INFORMATION: a, c, g, t, unknown or other
<220> FEATURE:
<221> NAME/KEY: modified_base
<222> LOCATION: (3222)..(3222)
```

-continued

```
<223> OTHER INFORMATION: a, c, g, t, unknown or other
<220> FEATURE:
<221> NAME/KEY: modified_base
<222> LOCATION: (3225)..(3225)
<223> OTHER INFORMATION: a, c, g, t, unknown or other
<220> FEATURE:
<221> NAME/KEY: modified_base
<222> LOCATION: (3234)..(3234)
<223> OTHER INFORMATION: a, c, g, t, unknown or other
<220> FEATURE:
<221> NAME/KEY: modified_base
<222> LOCATION: (3237)..(3237)
<223> OTHER INFORMATION: a, c, g, t, unknown or other
<220> FEATURE:
<221> NAME/KEY: modified_base
<222> LOCATION: (3243)..(3243)
<223> OTHER INFORMATION: a, c, g, t, unknown or other
<220> FEATURE:
<221> NAME/KEY: modified_base
<222> LOCATION: (3246)..(3246)
<223> OTHER INFORMATION: a, c, g, t, unknown or other
<220> FEATURE:
<221> NAME/KEY: modified_base
<222> LOCATION: (3252)..(3252)
<223> OTHER INFORMATION: a, c, g, t, unknown or other
<220> FEATURE:
<221> NAME/KEY: modified_base
<222> LOCATION: (3255)..(3255)
<223> OTHER INFORMATION: a, c, g, t, unknown or other
<220> FEATURE:
<221> NAME/KEY: modified_base
<222> LOCATION: (3258)..(3258)
<223> OTHER INFORMATION: a, c, g, t, unknown or other
<220> FEATURE:
<221> NAME/KEY: modified_base
<222> LOCATION: (3261)..(3261)
<223> OTHER INFORMATION: a, c, g, t, unknown or other
<220> FEATURE:
<221> NAME/KEY: modified_base
<222> LOCATION: (3267)..(3267)
<223> OTHER INFORMATION: a, c, g, t, unknown or other
<220> FEATURE:
<221> NAME/KEY: modified_base
<222> LOCATION: (3279)..(3279)
<223> OTHER INFORMATION: a, c, g, t, unknown or other
<220> FEATURE:
<221> NAME/KEY: modified_base
<222> LOCATION: (3285)..(3285)
<223> OTHER INFORMATION: a, c, g, t, unknown or other
<220> FEATURE:
<221> NAME/KEY: modified_base
<222> LOCATION: (3291)..(3291)
<223> OTHER INFORMATION: a, c, g, t, unknown or other
<220> FEATURE:
<221> NAME/KEY: modified_base
<222> LOCATION: (3297)..(3297)
<223> OTHER INFORMATION: a, c, g, t, unknown or other
<220> FEATURE:
<221> NAME/KEY: modified_base
<222> LOCATION: (3303)..(3303)
<223> OTHER INFORMATION: a, c, g, t, unknown or other
<220> FEATURE:
<221> NAME/KEY: modified_base
<222> LOCATION: (3321)..(3321)
<223> OTHER INFORMATION: a, c, g, t, unknown or other
<220> FEATURE:
<221> NAME/KEY: modified_base
<222> LOCATION: (3324)..(3324)
<223> OTHER INFORMATION: a, c, g, t, unknown or other
<220> FEATURE:
<221> NAME/KEY: modified_base
<222> LOCATION: (3327)..(3327)
<223> OTHER INFORMATION: a, c, g, t, unknown or other
<220> FEATURE:
<221> NAME/KEY: modified_base
<222> LOCATION: (3330)..(3330)
<223> OTHER INFORMATION: a, c, g, t, unknown or other
<220> FEATURE:
<221> NAME/KEY: modified_base
<222> LOCATION: (3333)..(3333)
```

-continued

```
<223> OTHER INFORMATION: a, c, g, t, unknown or other
<220> FEATURE:
<221> NAME/KEY: modified_base
<222> LOCATION: (3339)..(3339)
<223> OTHER INFORMATION: a, c, g, t, unknown or other
<220> FEATURE:
<221> NAME/KEY: modified_base
<222> LOCATION: (3348)..(3348)
<223> OTHER INFORMATION: a, c, g, t, unknown or other
<220> FEATURE:
<221> NAME/KEY: modified_base
<222> LOCATION: (3351)..(3351)
<223> OTHER INFORMATION: a, c, g, t, unknown or other
<220> FEATURE:
<221> NAME/KEY: modified_base
<222> LOCATION: (3354)..(3354)
<223> OTHER INFORMATION: a, c, g, t, unknown or other
<220> FEATURE:
<221> NAME/KEY: modified_base
<222> LOCATION: (3357)..(3357)
<223> OTHER INFORMATION: a, c, g, t, unknown or other
<220> FEATURE:
<221> NAME/KEY: modified_base
<222> LOCATION: (3366)..(3366)
<223> OTHER INFORMATION: a, c, g, t, unknown or other
<220> FEATURE:
<221> NAME/KEY: modified_base
<222> LOCATION: (3369)..(3369)
<223> OTHER INFORMATION: a, c, g, t, unknown or other
<220> FEATURE:
<221> NAME/KEY: modified_base
<222> LOCATION: (3372)..(3372)
<223> OTHER INFORMATION: a, c, g, t, unknown or other
<220> FEATURE:
<221> NAME/KEY: modified_base
<222> LOCATION: (3378)..(3378)
<223> OTHER INFORMATION: a, c, g, t, unknown or other
<220> FEATURE:
<221> NAME/KEY: modified_base
<222> LOCATION: (3381)..(3381)
<223> OTHER INFORMATION: a, c, g, t, unknown or other
<220> FEATURE:
<221> NAME/KEY: modified_base
<222> LOCATION: (3390)..(3390)
<223> OTHER INFORMATION: a, c, g, t, unknown or other
<220> FEATURE:
<221> NAME/KEY: modified_base
<222> LOCATION: (3393)..(3393)
<223> OTHER INFORMATION: a, c, g, t, unknown or other
<220> FEATURE:
<221> NAME/KEY: modified_base
<222> LOCATION: (3396)..(3396)
<223> OTHER INFORMATION: a, c, g, t, unknown or other
<220> FEATURE:
<221> NAME/KEY: modified_base
<222> LOCATION: (3399)..(3399)
<223> OTHER INFORMATION: a, c, g, t, unknown or other
<220> FEATURE:
<221> NAME/KEY: modified_base
<222> LOCATION: (3402)..(3402)
<223> OTHER INFORMATION: a, c, g, t, unknown or other
<220> FEATURE:
<221> NAME/KEY: modified_base
<222> LOCATION: (3411)..(3411)
<223> OTHER INFORMATION: a, c, g, t, unknown or other
<220> FEATURE:
<221> NAME/KEY: modified_base
<222> LOCATION: (3414)..(3414)
<223> OTHER INFORMATION: a, c, g, t, unknown or other
<220> FEATURE:
<221> NAME/KEY: modified_base
<222> LOCATION: (3417)..(3417)
<223> OTHER INFORMATION: a, c, g, t, unknown or other
<220> FEATURE:
<221> NAME/KEY: modified_base
<222> LOCATION: (3423)..(3423)
<223> OTHER INFORMATION: a, c, g, t, unknown or other
<220> FEATURE:
<221> NAME/KEY: modified_base
<222> LOCATION: (3429)..(3429)
```

-continued

```
<223> OTHER INFORMATION: a, c, g, t, unknown or other
<220> FEATURE:
<221> NAME/KEY: modified_base
<222> LOCATION: (3432)..(3432)
<223> OTHER INFORMATION: a, c, g, t, unknown or other
<220> FEATURE:
<221> NAME/KEY: modified_base
<222> LOCATION: (3435)..(3435)
<223> OTHER INFORMATION: a, c, g, t, unknown or other
<220> FEATURE:
<221> NAME/KEY: modified_base
<222> LOCATION: (3450)..(3450)
<223> OTHER INFORMATION: a, c, g, t, unknown or other
<220> FEATURE:
<221> NAME/KEY: modified_base
<222> LOCATION: (3453)..(3453)
<223> OTHER INFORMATION: a, c, g, t, unknown or other
<220> FEATURE:
<221> NAME/KEY: modified_base
<222> LOCATION: (3459)..(3459)
<223> OTHER INFORMATION: a, c, g, t, unknown or other
<220> FEATURE:
<221> NAME/KEY: modified_base
<222> LOCATION: (3465)..(3465)
<223> OTHER INFORMATION: a, c, g, t, unknown or other
<220> FEATURE:
<221> NAME/KEY: modified_base
<222> LOCATION: (3468)..(3468)
<223> OTHER INFORMATION: a, c, g, t, unknown or other
<220> FEATURE:
<221> NAME/KEY: modified_base
<222> LOCATION: (3474)..(3474)
<223> OTHER INFORMATION: a, c, g, t, unknown or other
<220> FEATURE:
<221> NAME/KEY: modified_base
<222> LOCATION: (3477)..(3477)
<223> OTHER INFORMATION: a, c, g, t, unknown or other
<220> FEATURE:
<221> NAME/KEY: modified_base
<222> LOCATION: (3483)..(3483)
<223> OTHER INFORMATION: a, c, g, t, unknown or other
<220> FEATURE:
<221> NAME/KEY: modified_base
<222> LOCATION: (3489)..(3489)
<223> OTHER INFORMATION: a, c, g, t, unknown or other
<220> FEATURE:
<221> NAME/KEY: modified_base
<222> LOCATION: (3498)..(3498)
<223> OTHER INFORMATION: a, c, g, t, unknown or other
<220> FEATURE:
<221> NAME/KEY: modified_base
<222> LOCATION: (3501)..(3501)
<223> OTHER INFORMATION: a, c, g, t, unknown or other
<220> FEATURE:
<221> NAME/KEY: modified_base
<222> LOCATION: (3504)..(3504)
<223> OTHER INFORMATION: a, c, g, t, unknown or other
<220> FEATURE:
<221> NAME/KEY: modified_base
<222> LOCATION: (3507)..(3507)
<223> OTHER INFORMATION: a, c, g, t, unknown or other
<220> FEATURE:
<221> NAME/KEY: modified_base
<222> LOCATION: (3516)..(3516)
<223> OTHER INFORMATION: a, c, g, t, unknown or other
<220> FEATURE:
<221> NAME/KEY: modified_base
<222> LOCATION: (3519)..(3519)
<223> OTHER INFORMATION: a, c, g, t, unknown or other
<220> FEATURE:
<221> NAME/KEY: modified_base
<222> LOCATION: (3522)..(3522)
<223> OTHER INFORMATION: a, c, g, t, unknown or other
<220> FEATURE:
<221> NAME/KEY: modified_base
<222> LOCATION: (3525)..(3525)
<223> OTHER INFORMATION: a, c, g, t, unknown or other
<220> FEATURE:
<221> NAME/KEY: modified_base
<222> LOCATION: (3528)..(3528)
```

-continued

```
<223> OTHER INFORMATION: a, c, g, t, unknown or other
<220> FEATURE:
<221> NAME/KEY: modified_base
<222> LOCATION: (3531)..(3531)
<223> OTHER INFORMATION: a, c, g, t, unknown or other
<220> FEATURE:
<221> NAME/KEY: modified_base
<222> LOCATION: (3537)..(3537)
<223> OTHER INFORMATION: a, c, g, t, unknown or other
<220> FEATURE:
<221> NAME/KEY: modified_base
<222> LOCATION: (3540)..(3540)
<223> OTHER INFORMATION: a, c, g, t, unknown or other
<220> FEATURE:
<221> NAME/KEY: modified_base
<222> LOCATION: (3549)..(3549)
<223> OTHER INFORMATION: a, c, g, t, unknown or other
<220> FEATURE:
<221> NAME/KEY: modified_base
<222> LOCATION: (3552)..(3552)
<223> OTHER INFORMATION: a, c, g, t, unknown or other
<220> FEATURE:
<221> NAME/KEY: modified_base
<222> LOCATION: (3561)..(3561)
<223> OTHER INFORMATION: a, c, g, t, unknown or other
<220> FEATURE:
<221> NAME/KEY: modified_base
<222> LOCATION: (3564)..(3564)
<223> OTHER INFORMATION: a, c, g, t, unknown or other
<220> FEATURE:
<221> NAME/KEY: modified_base
<222> LOCATION: (3567)..(3567)
<223> OTHER INFORMATION: a, c, g, t, unknown or other
<220> FEATURE:
<221> NAME/KEY: modified_base
<222> LOCATION: (3573)..(3573)
<223> OTHER INFORMATION: a, c, g, t, unknown or other
<220> FEATURE:
<221> NAME/KEY: modified_base
<222> LOCATION: (3576)..(3576)
<223> OTHER INFORMATION: a, c, g, t, unknown or other
<220> FEATURE:
<221> NAME/KEY: modified_base
<222> LOCATION: (3579)..(3579)
<223> OTHER INFORMATION: a, c, g, t, unknown or other
<220> FEATURE:
<221> NAME/KEY: modified_base
<222> LOCATION: (3582)..(3582)
<223> OTHER INFORMATION: a, c, g, t, unknown or other
<220> FEATURE:
<221> NAME/KEY: modified_base
<222> LOCATION: (3588)..(3588)
<223> OTHER INFORMATION: a, c, g, t, unknown or other
<220> FEATURE:
<221> NAME/KEY: modified_base
<222> LOCATION: (3591)..(3591)
<223> OTHER INFORMATION: a, c, g, t, unknown or other
<220> FEATURE:
<221> NAME/KEY: modified_base
<222> LOCATION: (3594)..(3594)
<223> OTHER INFORMATION: a, c, g, t, unknown or other
<220> FEATURE:
<221> NAME/KEY: modified_base
<222> LOCATION: (3597)..(3597)
<223> OTHER INFORMATION: a, c, g, t, unknown or other
<220> FEATURE:
<221> NAME/KEY: modified_base
<222> LOCATION: (3603)..(3603)
<223> OTHER INFORMATION: a, c, g, t, unknown or other
<220> FEATURE:
<221> NAME/KEY: modified_base
<222> LOCATION: (3606)..(3606)
<223> OTHER INFORMATION: a, c, g, t, unknown or other
<220> FEATURE:
<221> NAME/KEY: modified_base
<222> LOCATION: (3615)..(3615)
<223> OTHER INFORMATION: a, c, g, t, unknown or other
<220> FEATURE:
<221> NAME/KEY: modified_base
<222> LOCATION: (3618)..(3618)
```

-continued

```
<223> OTHER INFORMATION: a, c, g, t, unknown or other
<220> FEATURE:
<221> NAME/KEY: modified_base
<222> LOCATION: (3630)..(3630)
<223> OTHER INFORMATION: a, c, g, t, unknown or other
<220> FEATURE:
<221> NAME/KEY: modified_base
<222> LOCATION: (3633)..(3633)
<223> OTHER INFORMATION: a, c, g, t, unknown or other
<220> FEATURE:
<221> NAME/KEY: modified_base
<222> LOCATION: (3636)..(3636)
<223> OTHER INFORMATION: a, c, g, t, unknown or other
<220> FEATURE:
<221> NAME/KEY: modified_base
<222> LOCATION: (3639)..(3639)
<223> OTHER INFORMATION: a, c, g, t, unknown or other
<220> FEATURE:
<221> NAME/KEY: modified_base
<222> LOCATION: (3645)..(3645)
<223> OTHER INFORMATION: a, c, g, t, unknown or other
<220> FEATURE:
<221> NAME/KEY: modified_base
<222> LOCATION: (3648)..(3648)
<223> OTHER INFORMATION: a, c, g, t, unknown or other
<220> FEATURE:
<221> NAME/KEY: modified_base
<222> LOCATION: (3651)..(3651)
<223> OTHER INFORMATION: a, c, g, t, unknown or other
<220> FEATURE:
<221> NAME/KEY: modified_base
<222> LOCATION: (3654)..(3654)
<223> OTHER INFORMATION: a, c, g, t, unknown or other
<220> FEATURE:
<221> NAME/KEY: modified_base
<222> LOCATION: (3660)..(3660)
<223> OTHER INFORMATION: a, c, g, t, unknown or other
<220> FEATURE:
<221> NAME/KEY: modified_base
<222> LOCATION: (3669)..(3669)
<223> OTHER INFORMATION: a, c, g, t, unknown or other
<220> FEATURE:
<221> NAME/KEY: modified_base
<222> LOCATION: (3672)..(3672)
<223> OTHER INFORMATION: a, c, g, t, unknown or other
<220> FEATURE:
<221> NAME/KEY: modified_base
<222> LOCATION: (3678)..(3678)
<223> OTHER INFORMATION: a, c, g, t, unknown or other
<220> FEATURE:
<221> NAME/KEY: modified_base
<222> LOCATION: (3684)..(3684)
<223> OTHER INFORMATION: a, c, g, t, unknown or other
<220> FEATURE:
<221> NAME/KEY: modified_base
<222> LOCATION: (3687)..(3687)
<223> OTHER INFORMATION: a, c, g, t, unknown or other
<220> FEATURE:
<221> NAME/KEY: modified_base
<222> LOCATION: (3693)..(3693)
<223> OTHER INFORMATION: a, c, g, t, unknown or other
<220> FEATURE:
<221> NAME/KEY: modified_base
<222> LOCATION: (3699)..(3699)
<223> OTHER INFORMATION: a, c, g, t, unknown or other
<220> FEATURE:
<221> NAME/KEY: modified_base
<222> LOCATION: (3705)..(3705)
<223> OTHER INFORMATION: a, c, g, t, unknown or other
<220> FEATURE:
<221> NAME/KEY: modified_base
<222> LOCATION: (3726)..(3726)
<223> OTHER INFORMATION: a, c, g, t, unknown or other
<220> FEATURE:
<221> NAME/KEY: modified_base
<222> LOCATION: (3729)..(3729)
<223> OTHER INFORMATION: a, c, g, t, unknown or other
<220> FEATURE:
<221> NAME/KEY: modified_base
<222> LOCATION: (3735)..(3735)
```

-continued

```
<223> OTHER INFORMATION: a, c, g, t, unknown or other
<220> FEATURE:
<221> NAME/KEY: modified_base
<222> LOCATION: (3738)..(3738)
<223> OTHER INFORMATION: a, c, g, t, unknown or other
<220> FEATURE:
<221> NAME/KEY: modified_base
<222> LOCATION: (3744)..(3744)
<223> OTHER INFORMATION: a, c, g, t, unknown or other
<220> FEATURE:
<221> NAME/KEY: modified_base
<222> LOCATION: (3747)..(3747)
<223> OTHER INFORMATION: a, c, g, t, unknown or other
<220> FEATURE:
<221> NAME/KEY: modified_base
<222> LOCATION: (3750)..(3750)
<223> OTHER INFORMATION: a, c, g, t, unknown or other
<220> FEATURE:
<221> NAME/KEY: modified_base
<222> LOCATION: (3753)..(3753)
<223> OTHER INFORMATION: a, c, g, t, unknown or other
<220> FEATURE:
<221> NAME/KEY: modified_base
<222> LOCATION: (3756)..(3756)
<223> OTHER INFORMATION: a, c, g, t, unknown or other
<220> FEATURE:
<221> NAME/KEY: modified_base
<222> LOCATION: (3759)..(3759)
<223> OTHER INFORMATION: a, c, g, t, unknown or other
<220> FEATURE:
<221> NAME/KEY: modified_base
<222> LOCATION: (3765)..(3765)
<223> OTHER INFORMATION: a, c, g, t, unknown or other
<220> FEATURE:
<221> NAME/KEY: modified_base
<222> LOCATION: (3768)..(3768)
<223> OTHER INFORMATION: a, c, g, t, unknown or other
<220> FEATURE:
<221> NAME/KEY: modified_base
<222> LOCATION: (3771)..(3771)
<223> OTHER INFORMATION: a, c, g, t, unknown or other
<220> FEATURE:
<221> NAME/KEY: modified_base
<222> LOCATION: (3777)..(3777)
<223> OTHER INFORMATION: a, c, g, t, unknown or other
<220> FEATURE:
<221> NAME/KEY: modified_base
<222> LOCATION: (3780)..(3780)
<223> OTHER INFORMATION: a, c, g, t, unknown or other
<220> FEATURE:
<221> NAME/KEY: modified_base
<222> LOCATION: (3783)..(3783)
<223> OTHER INFORMATION: a, c, g, t, unknown or other
<220> FEATURE:
<221> NAME/KEY: modified_base
<222> LOCATION: (3786)..(3786)
<223> OTHER INFORMATION: a, c, g, t, unknown or other
<220> FEATURE:
<221> NAME/KEY: modified_base
<222> LOCATION: (3789)..(3789)
<223> OTHER INFORMATION: a, c, g, t, unknown or other
<220> FEATURE:
<221> NAME/KEY: modified_base
<222> LOCATION: (3792)..(3792)
<223> OTHER INFORMATION: a, c, g, t, unknown or other
<220> FEATURE:
<221> NAME/KEY: modified_base
<222> LOCATION: (3798)..(3798)
<223> OTHER INFORMATION: a, c, g, t, unknown or other
<220> FEATURE:
<221> NAME/KEY: modified_base
<222> LOCATION: (3801)..(3801)
<223> OTHER INFORMATION: a, c, g, t, unknown or other
<220> FEATURE:
<221> NAME/KEY: modified_base
<222> LOCATION: (3804)..(3804)
<223> OTHER INFORMATION: a, c, g, t, unknown or other
<220> FEATURE:
<221> NAME/KEY: modified_base
<222> LOCATION: (3810)..(3810)
```

-continued

```
<223> OTHER INFORMATION: a, c, g, t, unknown or other
<220> FEATURE:
<221> NAME/KEY: modified_base
<222> LOCATION: (3819)..(3819)
<223> OTHER INFORMATION: a, c, g, t, unknown or other
<220> FEATURE:
<221> NAME/KEY: modified_base
<222> LOCATION: (3822)..(3822)
<223> OTHER INFORMATION: a, c, g, t, unknown or other
<220> FEATURE:
<221> NAME/KEY: modified_base
<222> LOCATION: (3825)..(3825)
<223> OTHER INFORMATION: a, c, g, t, unknown or other
<220> FEATURE:
<221> NAME/KEY: modified_base
<222> LOCATION: (3828)..(3828)
<223> OTHER INFORMATION: a, c, g, t, unknown or other
<220> FEATURE:
<221> NAME/KEY: modified_base
<222> LOCATION: (3840)..(3840)
<223> OTHER INFORMATION: a, c, g, t, unknown or other
<220> FEATURE:
<221> NAME/KEY: modified_base
<222> LOCATION: (3843)..(3843)
<223> OTHER INFORMATION: a, c, g, t, unknown or other
<220> FEATURE:
<221> NAME/KEY: modified_base
<222> LOCATION: (3846)..(3846)
<223> OTHER INFORMATION: a, c, g, t, unknown or other
<220> FEATURE:
<221> NAME/KEY: modified_base
<222> LOCATION: (3852)..(3852)
<223> OTHER INFORMATION: a, c, g, t, unknown or other
<220> FEATURE:
<221> NAME/KEY: modified_base
<222> LOCATION: (3855)..(3855)
<223> OTHER INFORMATION: a, c, g, t, unknown or other
<220> FEATURE:
<221> NAME/KEY: modified_base
<222> LOCATION: (3861)..(3861)
<223> OTHER INFORMATION: a, c, g, t, unknown or other
<220> FEATURE:
<221> NAME/KEY: modified_base
<222> LOCATION: (3864)..(3864)
<223> OTHER INFORMATION: a, c, g, t, unknown or other
<220> FEATURE:
<221> NAME/KEY: modified_base
<222> LOCATION: (3870)..(3870)
<223> OTHER INFORMATION: a, c, g, t, unknown or other
<220> FEATURE:
<221> NAME/KEY: modified_base
<222> LOCATION: (3873)..(3873)
<223> OTHER INFORMATION: a, c, g, t, unknown or other
<220> FEATURE:
<221> NAME/KEY: modified_base
<222> LOCATION: (3879)..(3879)
<223> OTHER INFORMATION: a, c, g, t, unknown or other
<220> FEATURE:
<221> NAME/KEY: modified_base
<222> LOCATION: (3888)..(3888)
<223> OTHER INFORMATION: a, c, g, t, unknown or other
<220> FEATURE:
<221> NAME/KEY: modified_base
<222> LOCATION: (3894)..(3894)
<223> OTHER INFORMATION: a, c, g, t, unknown or other
<220> FEATURE:
<221> NAME/KEY: modified_base
<222> LOCATION: (3897)..(3897)
<223> OTHER INFORMATION: a, c, g, t, unknown or other
<220> FEATURE:
<221> NAME/KEY: modified_base
<222> LOCATION: (3903)..(3903)
<223> OTHER INFORMATION: a, c, g, t, unknown or other
<220> FEATURE:
<221> NAME/KEY: modified_base
<222> LOCATION: (3909)..(3909)
<223> OTHER INFORMATION: a, c, g, t, unknown or other
<220> FEATURE:
<221> NAME/KEY: modified_base
<222> LOCATION: (3912)..(3912)
```

<223> OTHER INFORMATION: a, c, g, t, unknown or other
<220> FEATURE:
<221> NAME/KEY: modified_base
<222> LOCATION: (3921)..(3921)
<223> OTHER INFORMATION: a, c, g, t, unknown or other
<220> FEATURE:
<221> NAME/KEY: modified_base
<222> LOCATION: (3930)..(3930)
<223> OTHER INFORMATION: a, c, g, t, unknown or other
<220> FEATURE:
<221> NAME/KEY: modified_base
<222> LOCATION: (3939)..(3939)
<223> OTHER INFORMATION: a, c, g, t, unknown or other
<220> FEATURE:
<221> NAME/KEY: modified_base
<222> LOCATION: (3951)..(3951)
<223> OTHER INFORMATION: a, c, g, t, unknown or other
<220> FEATURE:
<221> NAME/KEY: modified_base
<222> LOCATION: (3963)..(3963)
<223> OTHER INFORMATION: a, c, g, t, unknown or other
<220> FEATURE:
<221> NAME/KEY: modified_base
<222> LOCATION: (3966)..(3966)
<223> OTHER INFORMATION: a, c, g, t, unknown or other
<220> FEATURE:
<221> NAME/KEY: modified_base
<222> LOCATION: (3969)..(3969)
<223> OTHER INFORMATION: a, c, g, t, unknown or other
<220> FEATURE:
<221> NAME/KEY: modified_base
<222> LOCATION: (3972)..(3972)
<223> OTHER INFORMATION: a, c, g, t, unknown or other
<220> FEATURE:
<221> NAME/KEY: modified_base
<222> LOCATION: (3975)..(3975)
<223> OTHER INFORMATION: a, c, g, t, unknown or other
<220> FEATURE:
<221> NAME/KEY: modified_base
<222> LOCATION: (3978)..(3978)
<223> OTHER INFORMATION: a, c, g, t, unknown or other
<220> FEATURE:
<221> NAME/KEY: modified_base
<222> LOCATION: (3981)..(3981)
<223> OTHER INFORMATION: a, c, g, t, unknown or other
<220> FEATURE:
<221> NAME/KEY: modified_base
<222> LOCATION: (3987)..(3987)
<223> OTHER INFORMATION: a, c, g, t, unknown or other

<400> SEQUENCE: 13
atggcngcng cntggcargg ntggytnytn tgggcnytny tnytnaayws ngcncarggn 60
garytntaya cnccnacnca yaargcnggn ttytgyacnt tytaygarga rtgyggnaar 120
aayccngary tnwsnggngg nytnacnwsn ytnwsnaaya thwsntgyyt nwsnaayacn 180
ccngcnmgnc aygtnacngg ngaycayytn gcnytnytnc armgngtntg yccnmgnytn 240
tayaayggnc cnaaygayac ntaygcntgy tgywsnacna arcarytngt nwsnytngay 300
wsnwsnytnw snathacnaa rgcnytnytn acnmgntgyc cngcntgyws ngaraaytty 360
gtnwsnathc aytgycayaa yacntgywsn ccngaycarw snytnttyat haaygtnacn 420
mgngtngtnc armgngaycc nggncarytn ccngcngtng tngcntayga rgcnttytay 480
carmgnwsnt tygcngaraa rgcntaygar wsntgywsnm gngtnmgnat hccngcngcn 540
gcnwsnytng cngtnggnws natgtgyggn gtntayggnw sngcnytntg yaaygcncar 600
mgntggytna ayttycargg ngayacnggn aayggnytng cnccnytnga yathacntty 660
cayytnytng arccnggnca rgcnytngcn gayggnatga arccnytnga yggnaarath 720
acnccntgya aygarwsnca rggngargay wsngcngcnt gywsntgyca rgaytgygcn 780
gcnwsntgyc cngtnathcc nccnccnccn gcnytnmgnc cnwsnttyta yatgggnmgn 840

-continued

```
atgccnggnt ggytngcnyt nathathath ttyacngcng tnttygtnyt nytnwsngtn    900
gtnytngtnt ayytnmgngt ngcnwsnaay mgnaayaara ayaaracngc nggnwsncar    960
gargcnccna ayytnccnmg naarmgnmgn ttywsnccnc ayacngtnyt nggnmgntty   1020
ttygarwsnt ggggnacnmg ngtngcnwsn tggccnytna cngtnytngc nytnwsntty   1080
athgtngtna thgcnytnws ngtnggnytn acnttyathg arytnacnac ngayccngtn   1140
garytntggw sngcnccnaa rwsncargcn mgnaargara argcnttyca ygaygarcay   1200
ttyggnccnt tyttymgnac naaycarath ttygtnacng cnaaraaymg nwsnwsntay   1260
aartaygayw snytnytnyt nggnccnaar aayttywsng gnathytnws nytngayytn   1320
ytncargary tnytngaryt ncargarmgn ytnmgncayy tncargtntg gwsncaygar   1380
gcncarmgna ayathwsnyt ncargayath tgytaygcnc cnytnaaycc ncayaayacn   1440
wsnytnacng aytgytgygt naaywsnytn ytncartayt tycaraayaa ycayacnytn   1500
ytnytnytna cngcnaayca racnytnaay ggncaracnw snytngtnga ytggaargay   1560
cayttyytnt aytgygcnaa ygcnccnytn acntayaarg ayggnacngc nytngcnytn   1620
wsntgyathg cngaytaygg ngcnccngtn ttyccnttyy tngcngtngg nggntaycar   1680
ggnacngayt aywsngargc ngargcnytn athathacnt tywsnathaa yaaytayccn   1740
gcngaygayc cnmgnatggc ncaygcnaar ytntgggarg argcnttyyt naargaratg   1800
carwsnttyc armgnwsnac ngcngayaar ttycarathg cnttywsngc ngarmgnwsn   1860
ytngargayg arathaaymg nacnacnath cargayytnc cngtnttygc nathwsntay   1920
ytnathgtnt tyytntayat hwsnytngcn ytnggnwsnt aywsnmgntg gwsnmgngtn   1980
gcngtngayw snaargcnac nytnggnytn ggnggngtng cngtngtnyt nggngcngtn   2040
gtngcngcna tgggnttyta ywsntayytn ggngtnccnw snwsnytngt nathathcar   2100
gtngtnccnt tyytngtnyt ngcngtnggn gcngayaaya thttyathtt ygtnytngar   2160
taycarmgny tnccnmgnat gccnggngar carmgngarg cncayathgg nmgnacnytn   2220
ggnwsngtng cnccnwsnat gytnytntgy wsnytnwsng argcnathtg yttyttyytn   2280
ggngcnytna cnwsnatgcc ngcngtnmgn acnttygcny tnacnwsngg nytngcnath   2340
athttygayt tyytnytnca ratgacngcn ttygtngcny tnytnwsnyt ngaywsnaar   2400
mgncargarg cnwsnmgncc ngaygtngtn tgytgyttyw snwsnmgnaa yytnccnccn   2460
ccnaarcara argarggnyt nytnytntgy ttyttymgna arathtayac nccnttyytn   2520
ytncaymgnt tyathmgncc ngtngtnytn ytnytntty tngtnytntt yggngcnaay   2580
ytntayytna tgtgyaayat hwsngtnggn ytngaycarg ayytngcnyt nccnaargay   2640
wsntayytna thgaytaytt yytnttyytn aaymgntayy tngargtngg nccnccngtn   2700
tayttygaya cnacnwsngg ntayaaytty wsnacngarg cnggnatgaa ygcnathtgy   2760
wsnwsngcng gntgygarws nttywsnytn acncaraara thcartaygc nwsngartty   2820
ccnaaycarw sntaygtngc nathgcngcn wsnwsntggg tngaygaytt yathgaytgg   2880
ytnacnccnw snwsnwsntg ytgymgnath tayacnmgng gnccncayaa rgaygartty   2940
tgyccnwsna cngayacnws nttyaaytgy ytnaaraayt gyatgaaymg nacnytnggn   3000
ccngtnmgnc cnacnacnga rcarttycay aartayytnc cntggttyyt naaygayacn   3060
ccnaayathm gntgyccnaa rggnggnytn gcngcntaym gnacnwsngt naayytnwsn   3120
wsngayggnc arathathgc nwsncartty atggcntayc ayaarccnyt nmgnaaywsn   3180
cargayttya cngargcnyt nmgngcnwsn mgnytnytng cngcnaayat hacngcngar   3240
```
ytnmgnaarg tnccnggnac ngayccnaay ttygargtnt tyccntayac nathwsnaay 3300
gtnttytayc arcartayyt nacngtnytn ccngarggna thttyacnyt ngcnytntgy 3360
ttygtnccna cnttygtngt ntgytayytn ytnytnggny tngayathmg nwsnggnath 3420
ytnaayytny tnwsnathat hatgathytn gtngayacna thggnytnat ggcngtntgg 3480
ggnathwsnt ayaaygcngt nwsnytnath aayytngtna cngcngtngg natgwsngtn 3540
garttygtnw sncayathac nmgnwsntty gcngtnwsna cnaarccnac nmgnytngar 3600
mgngcnaarg aygcnacnat httyatgggn wsngcngtnt tygcnggngt ngcnatgacn 3660
aayttyccng gnathytnat hytnggntty gcncargcnc arytnathca rathttytty 3720
ttymgnytna ayytnytnat hacnytnytn ggnytnytnc ayggnytngt nttyytnccn 3780
gtngtnytnw sntayytngg nccngaygtn aaycargcny tngtnytnga rgaraarytn 3840
gcnacngarg cngcnatggt nwsngarccn wsntgyccnc artayccntt yccngcngay 3900
gcnaayacnw sngaytaygt naaytayggn ttyaayccng arttyathcc ngarathaay 3960
gcngcnwsnw snwsnytncc naarwsngay caraartty 3999

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tcttcaccct tgctctttgc 20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
aatgatggag agtaggttga ggat 24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tgcccacctt tgttgtctgc tacc 24

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
atcgctgaca ggatgcagaa g 21

<210> SEQ ID NO 18

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcaggaggag caatgatctt ga                                              22

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agattactgc cctggctcct agcaccat                                        28

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atcctcatcc tgggctttgc                                                 20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcaaggtgat caggaggttg a                                               21

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cccagcttat ccagattttc ttcttccgc                                       29

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcttcaccct tgctctttgc                                                 20

<210> SEQ ID NO 24
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 24
aatgatggag agtaggttga ggat                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgcccacctt tgttgtctgc tacc                                          24

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agcacctgtc cactgaagat ttc                                           23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggacgctga gcttcagttc t                                             21

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cttctctgcg ctgcctcgat ggaa                                          24

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agtaaaaagg gctcgcagga t                                             21

<210> SEQ ID NO 30
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 30
ggcagctggt gacatcagag a                                               21

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aggaggccat gcaggcctac tctga                                           25

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gagtccacgg tcagtccatg t                                               21

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttatgaacaa caatgccaag caa                                             23

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agtccttagg tagtggctta gtccctggaa gctc                                 34

<210> SEQ ID NO 35
<211> LENGTH: 52
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
gtaatacgac tcactatagg gccctgacgg tccttcctga gggaatcttc ac             52

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 36
gtaatacgac tcactatagg gcctgggaag ttggtcatgg ccactccagc          50

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Tyr Lys Asp Asp Asp Asp Lys
1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Gln Arg Leu
1

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Gln Phe His Lys Tyr Leu Pro Trp Phe Leu Asn Asp Pro Pro Asn
1               5                   10                  15

Ile Arg Cys

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Ala Phe Tyr Gln Arg Ser Phe Ala Glu Lys Ala Tyr Glu Ser Cys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gln Thr Ser Leu Val Asp Trp Lys Asp His Phe Leu Tyr Cys
1               5                   10                  15

<210> SEQ ID NO 42
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Ala Asn Ala Pro Leu Thr Phe Lys Asp Gly Thr Ala Leu Ala Leu
1               5                   10                  15

Ser

<210> SEQ ID NO 43
<211> LENGTH: 5092
<212> TYPE: DNA
<213> ORGANISM: Homo sapiens
<220> FEATURE:
<221> NAME/KEY: CDS
<222> LOCATION: (57)..(4136)

<400> SEQUENCE: 43
cttggctgtt cctgaggcct ggcctggctc ccgctgacc ccttcccaga cctggg atg      59
                                                            Met
                                                            1 gcg gag gcc ggc ctg agg ggc tgg ctg ctg tgg gcc ctg ctc ctg cgc      107
Ala Glu Ala Gly Leu Arg Gly Trp Leu Leu Trp Ala Leu Leu Leu Arg
                5                   10                  15 ttg gcc cag agt gag cct tac aca acc atc cac cag cct ggc tac tgc      155
Leu Ala Gln Ser Glu Pro Tyr Thr Thr Ile His Gln Pro Gly Tyr Cys
            20                  25                  30 gcc ttc tat gac gaa tgt ggg aag aac cca gag ctg tct gga agc ctc      203
Ala Phe Tyr Asp Glu Cys Gly Lys Asn Pro Glu Leu Ser Gly Ser Leu
        35                  40                  45 atg aca ctc tcc aac gtg tcc tgc ctg tcc aac acg ccg gcc cgc aag      251
Met Thr Leu Ser Asn Val Ser Cys Leu Ser Asn Thr Pro Ala Arg Lys
50                  55                  60                  65 atc aca ggt gat cac ctg atc cta tta cag aag atc tgc ccc cgc ctc      299
Ile Thr Gly Asp His Leu Ile Leu Leu Gln Lys Ile Cys Pro Arg Leu
                70                  75                  80 tac acc ggc ccc aac acc caa gcc tgc tgc tcc gcc aag cag ctg gta      347
Tyr Thr Gly Pro Asn Thr Gln Ala Cys Cys Ser Ala Lys Gln Leu Val
            85                  90                  95 tca ctg gaa gcg agt ctg tcg atc acc aag gcc ctc ctc acc cgc tgc      395
Ser Leu Glu Ala Ser Leu Ser Ile Thr Lys Ala Leu Leu Thr Arg Cys
        100                 105                 110 cca gcc tgc tct gac aat ttt gtg aac ctg cac tgc cac aac acg tgc      443
Pro Ala Cys Ser Asp Asn Phe Val Asn Leu His Cys His Asn Thr Cys
    115                 120                 125 agc ccc aat cag agc ctc ttc atc aat gtg acc cgc gtg gcc cag cta      491
Ser Pro Asn Gln Ser Leu Phe Ile Asn Val Thr Arg Val Ala Gln Leu
130                 135                 140                 145 ggg gct gga caa ctc cca gct gtg gtg gcc tat gag gcc ttc tac cag      539
Gly Ala Gly Gln Leu Pro Ala Val Val Ala Tyr Glu Ala Phe Tyr Gln
                150                 155                 160 cat agc ttt gcc gag cag agc tat gac tcc tgc agc cgt gtg cgc gtc      587
His Ser Phe Ala Glu Gln Ser Tyr Asp Ser Cys Ser Arg Val Arg Val
            165                 170                 175 cct gca gct gcc acg ctg gct gtg ggc acc atg tgt ggc gtg tat ggc      635
Pro Ala Ala Ala Thr Leu Ala Val Gly Thr Met Cys Gly Val Tyr Gly
        180                 185                 190 tct gcc ctt tgc aat gcc cag cgc tgg ctc aac ttc cag gga gac aca      683
Ser Ala Leu Cys Asn Ala Gln Arg Trp Leu Asn Phe Gln Gly Asp Thr
    195                 200                 205
```

```
ggc aat ggt ctg gcc cca ctg gac atc acc ttc cac ctc ttg gag cct      731
Gly Asn Gly Leu Ala Pro Leu Asp Ile Thr Phe His Leu Leu Glu Pro
210             215                 220                 225 ggc cag gcc gtg ggg agt ggg att cag cct ctg aat gag ggg gtt gca      779
Gly Gln Ala Val Gly Ser Gly Ile Gln Pro Leu Asn Glu Gly Val Ala
                    230                 235                 240 cgt tgc aat gag tcc caa ggt gac gac gtg gcg acc tgc tcc tgc caa      827
Arg Cys Asn Glu Ser Gln Gly Asp Asp Val Ala Thr Cys Ser Cys Gln
                245                 250                 255 gac tgt gct gca tcc tgt cct gcc ata gcc cgc ccc cag gcc ctc gac      875
Asp Cys Ala Ala Ser Cys Pro Ala Ile Ala Arg Pro Gln Ala Leu Asp
            260                 265                 270 tcc acc ttc tac ctg ggc cag atg ccg ggc agt ctg gtc ctc atc atc      923
Ser Thr Phe Tyr Leu Gly Gln Met Pro Gly Ser Leu Val Leu Ile Ile
        275                 280                 285 atc ctc tgc tct gtc ttc gct gtg gtc acc atc ctg ctt gtg gga ttc      971
Ile Leu Cys Ser Val Phe Ala Val Val Thr Ile Leu Leu Val Gly Phe
290                 295                 300                 305 cgt gtg gcc ccc gcc agg gac aaa agc aag atg gtg gac ccc aag aag     1019
Arg Val Ala Pro Ala Arg Asp Lys Ser Lys Met Val Asp Pro Lys Lys
                    310                 315                 320 ggc acc agc ctc tct gac aag ctc agc ttc tcc acc cac acc ctc ctt     1067
Gly Thr Ser Leu Ser Asp Lys Leu Ser Phe Ser Thr His Thr Leu Leu
                325                 330                 335 ggc cag ttc ttc cag ggc tgg ggc acg tgg gtg gct tcg tgg cct ctg     1115
Gly Gln Phe Phe Gln Gly Trp Gly Thr Trp Val Ala Ser Trp Pro Leu
            340                 345                 350 acc atc ttg gtg cta tct gtc atc ccg gtg gtg gcc ttg gca gcg ggc     1163
Thr Ile Leu Val Leu Ser Val Ile Pro Val Val Ala Leu Ala Ala Gly
        355                 360                 365 ctg gtc ttt aca gaa ctc act acg gac ccc gtg gag ctg tgg tcg gcc     1211
Leu Val Phe Thr Glu Leu Thr Thr Asp Pro Val Glu Leu Trp Ser Ala
370                 375                 380                 385 ccc aac agc caa gcc cgg agt gag aaa gct ttc cat gac cag cat ttc     1259
Pro Asn Ser Gln Ala Arg Ser Glu Lys Ala Phe His Asp Gln His Phe
                    390                 395                 400 ggc ccc ttc ttc cga acc aac cag gtg atc ctg acg gct cct aac cgg     1307
Gly Pro Phe Phe Arg Thr Asn Gln Val Ile Leu Thr Ala Pro Asn Arg
                405                 410                 415 tcc agc tac agg tat gac tct ctg ctg ctg ggg ccc aag aac ttc agc     1355
Ser Ser Tyr Arg Tyr Asp Ser Leu Leu Leu Gly Pro Lys Asn Phe Ser
            420                 425                 430 gga atc ctg gac ctg gac ttg ctg ctg gag ctg cta gag ctg cag gag     1403
Gly Ile Leu Asp Leu Asp Leu Leu Leu Glu Leu Leu Glu Leu Gln Glu
        435                 440                 445 agg ctg cgg cac ctc cag gta tgg tcg ccc gaa gca cag cgc aac atc     1451
Arg Leu Arg His Leu Gln Val Trp Ser Pro Glu Ala Gln Arg Asn Ile
450                 455                 460                 465 tcc ctg cag gac atc tgc tac gcc ccc ctc aat ccg gac aat acc agt     1499
Ser Leu Gln Asp Ile Cys Tyr Ala Pro Leu Asn Pro Asp Asn Thr Ser
                    470                 475                 480 ctc tac gac tgc tgc atc aac agc ctg ctg cag tat ttc cag aac aac     1547
Leu Tyr Asp Cys Cys Ile Asn Ser Leu Leu Gln Tyr Phe Gln Asn Asn
                485                 490                 495 cgc acg ctc ctg ctc ctc aca gcc aac cag aca ctg atg ggg cag acc     1595
Arg Thr Leu Leu Leu Leu Thr Ala Asn Gln Thr Leu Met Gly Gln Thr
            500                 505                 510 tcc caa gtc gac tgg aag gac cat ttt ctg tac tgt gcc aat gcc ccg     1643
Ser Gln Val Asp Trp Lys Asp His Phe Leu Tyr Cys Ala Asn Ala Pro
        515                 520                 525
```

```
ctc acc ttc aag gat ggc aca gcc ctg gcc ctg agc tgc atg gct gac    1691
Leu Thr Phe Lys Asp Gly Thr Ala Leu Ala Leu Ser Cys Met Ala Asp
530                 535                 540                 545 tac ggg gcc cct gtc ttc ccc ttc ctt gcc att ggg ggg tac aaa gga    1739
Tyr Gly Ala Pro Val Phe Pro Phe Leu Ala Ile Gly Gly Tyr Lys Gly
                    550                 555                 560 aag gac tat tct gag gca gag gcc ctg atc atg acg ttc tcc ctc aac    1787
Lys Asp Tyr Ser Glu Ala Glu Ala Leu Ile Met Thr Phe Ser Leu Asn
                565                 570                 575 aat tac cct gcc ggg gac ccc cgt ctg gcc cag gcc aag ctg tgg gag    1835
Asn Tyr Pro Ala Gly Asp Pro Arg Leu Ala Gln Ala Lys Leu Trp Glu
            580                 585                 590 gag gcc ttc tta gag gaa atg cga gcc ttc cag cgt cgg atg gct ggc    1883
Glu Ala Phe Leu Glu Glu Met Arg Ala Phe Gln Arg Arg Met Ala Gly
595                 600                 605 atg ttc cag gtc acg ttc atg gct gag cgc tct ctg gaa gac gag atc    1931
Met Phe Gln Val Thr Phe Met Ala Glu Arg Ser Leu Glu Asp Glu Ile
610                 615                 620                 625 aat cgc acc aca gct gaa gac ctg ccc atc ttt gcc acc agc tac att    1979
Asn Arg Thr Thr Ala Glu Asp Leu Pro Ile Phe Ala Thr Ser Tyr Ile
                630                 635                 640 gtc ata ttc ctg tac atc tct ctg gcc ctg ggc agc tat tcc agc tgg    2027
Val Ile Phe Leu Tyr Ile Ser Leu Ala Leu Gly Ser Tyr Ser Ser Trp
                645                 650                 655 agc cga gtg atg gtg gac tcc aag gcc acg ctg ggc ctc ggc ggg gtg    2075
Ser Arg Val Met Val Asp Ser Lys Ala Thr Leu Gly Leu Gly Gly Val
                660                 665                 670 gcc gtg gtc ctg gga gca gtc atg gct gcc atg ggc ttc ttc tcc tac    2123
Ala Val Val Leu Gly Ala Val Met Ala Ala Met Gly Phe Phe Ser Tyr
675                 680                 685 ttg ggt atc cgc tcc tcc ctg gtc atc ctg caa gtg gtt cct ttc ctg    2171
Leu Gly Ile Arg Ser Ser Leu Val Ile Leu Gln Val Val Pro Phe Leu
690                 695                 700                 705 gtg ctg tcc gtg ggg gct gat aac atc ttc atc ttt gtt ctc gag tac    2219
Val Leu Ser Val Gly Ala Asp Asn Ile Phe Ile Phe Val Leu Glu Tyr
                    710                 715                 720 cag agg ctg ccc cgg agg cct ggg gag cca cga gag gtc cac att ggg    2267
Gln Arg Leu Pro Arg Arg Pro Gly Glu Pro Arg Glu Val His Ile Gly
                725                 730                 735 cga gcc cta ggc agg gtg gct ccc agc atg ctg ttg tgc agc ctc tct    2315
Arg Ala Leu Gly Arg Val Ala Pro Ser Met Leu Leu Cys Ser Leu Ser
            740                 745                 750 gag gcc atc tgc ttc ttc cta ggg gcc ctg acc ccc atg cca gct gtg    2363
Glu Ala Ile Cys Phe Phe Leu Gly Ala Leu Thr Pro Met Pro Ala Val
755                 760                 765 cgg acc ttt gcc ctg acc tct ggc ctt gca gtg atc ctt gac ttc ctc    2411
Arg Thr Phe Ala Leu Thr Ser Gly Leu Ala Val Ile Leu Asp Phe Leu
770                 775                 780                 785 ctg cag atg tca gcc ttt gtg gcc ctg ctc tcc ctg gac agc aag agg    2459
Leu Gln Met Ser Ala Phe Val Ala Leu Leu Ser Leu Asp Ser Lys Arg
                    790                 795                 800 cag gag gcc tcc cgg ttg gac gtc tgc tgc tgt gtc aag ccc cag gag    2507
Gln Glu Ala Ser Arg Leu Asp Val Cys Cys Cys Val Lys Pro Gln Glu
                805                 810                 815 ctg ccc ccg cct ggc cag gga gag ggg ctc ctg ctt ggc ttc ttc caa    2555
Leu Pro Pro Pro Gly Gln Gly Glu Gly Leu Leu Leu Gly Phe Phe Gln
            820                 825                 830 aag gct tat gcc ccc ttc ctg ctg cac tgg atc act cga ggt gtt gtg    2603
Lys Ala Tyr Ala Pro Phe Leu Leu His Trp Ile Thr Arg Gly Val Val
835                 840                 845
```

```
ctg ctg ctg ttt ctc gcc ctg ttc gga gtg agc ctc tac tcc atg tgc    2651
Leu Leu Leu Phe Leu Ala Leu Phe Gly Val Ser Leu Tyr Ser Met Cys
850                 855                 860                 865 cac atc agc gtg gga ctg gac cag gag ctg gcc ctg ccc aag gac tcg    2699
His Ile Ser Val Gly Leu Asp Gln Glu Leu Ala Leu Pro Lys Asp Ser
                870                 875                 880 tac ctg ctt gac tat ttc ctc ttt ctg aac cgc tac ttc gag gtg ggg    2747
Tyr Leu Leu Asp Tyr Phe Leu Phe Leu Asn Arg Tyr Phe Glu Val Gly
            885                 890                 895 gcc ccg gtg tac ttt gtt acc acc ttg ggc tac aac ttc tcc agc gag    2795
Ala Pro Val Tyr Phe Val Thr Thr Leu Gly Tyr Asn Phe Ser Ser Glu
        900                 905                 910 gct ggg atg aat gcc atc tgc tcc agt gca ggc tgc aac aac ttc tcc    2843
Ala Gly Met Asn Ala Ile Cys Ser Ser Ala Gly Cys Asn Asn Phe Ser
    915                 920                 925 ttc acc cag aag atc cag tat gcc aca gag ttc cct gag cag tct tac    2891
Phe Thr Gln Lys Ile Gln Tyr Ala Thr Glu Phe Pro Glu Gln Ser Tyr
930                 935                 940                 945 ctg gcc atc cct gcc tcc tcc tgg gtg gat gac ttc att gac tgg ctg    2939
Leu Ala Ile Pro Ala Ser Ser Trp Val Asp Asp Phe Ile Asp Trp Leu
                950                 955                 960 acc ccg tcc tcc tgc tgc cgc ctt tat ata tct ggc ccc aat aag gac    2987
Thr Pro Ser Ser Cys Cys Arg Leu Tyr Ile Ser Gly Pro Asn Lys Asp
            965                 970                 975 aag ttc tgc ccc tcg acc gtc aac tct ctg aac tgc cta aag aac tgc    3035
Lys Phe Cys Pro Ser Thr Val Asn Ser Leu Asn Cys Leu Lys Asn Cys
        980                 985                 990 atg agc atc acg atg ggc tct gtg agg ccc tcg gtg gag cag ttc cat    3083
Met Ser Ile Thr Met Gly Ser Val Arg Pro Ser Val Glu Gln Phe His
    995                 1000                1005 aag tat ctt ccc tgg ttc ctg aac gac cgg ccc aac atc aaa tgt        3128
Lys Tyr Leu Pro Trp Phe Leu Asn Asp Arg Pro Asn Ile Lys Cys
1010                1015                1020 ccc aaa ggc ggc ctg gca gca tac agc acc tct gtg aac ttg act        3173
Pro Lys Gly Gly Leu Ala Ala Tyr Ser Thr Ser Val Asn Leu Thr
1025                1030                1035 tca gat ggc cag gtt tta gac aca gtt gcc att ctg tca ccc agg        3218
Ser Asp Gly Gln Val Leu Asp Thr Val Ala Ile Leu Ser Pro Arg
1040                1045                1050 ctg gag tac agt ggc aca atc tcg gct cac tgc aac ctc tac ctc        3263
Leu Glu Tyr Ser Gly Thr Ile Ser Ala His Cys Asn Leu Tyr Leu
1055                1060                1065 ctg gat tca gcc tcc agg ttc atg gcc tat cac aag ccc ctg aaa        3308
Leu Asp Ser Ala Ser Arg Phe Met Ala Tyr His Lys Pro Leu Lys
1070                1075                1080 aac tca cag gat tac aca gaa gct ctg cgg gca gct cga gag ctg        3353
Asn Ser Gln Asp Tyr Thr Glu Ala Leu Arg Ala Ala Arg Glu Leu
1085                1090                1095 gca gcc aac atc act gct gac ctg cgg aaa gtg cct gga aca gac        3398
Ala Ala Asn Ile Thr Ala Asp Leu Arg Lys Val Pro Gly Thr Asp
1100                1105                1110 ccg gct ttt gag gtc ttc ccc tac acg atc acc aat gtg ttt tat        3443
Pro Ala Phe Glu Val Phe Pro Tyr Thr Ile Thr Asn Val Phe Tyr
1115                1120                1125 gag cag tac ctg acc atc ctc cct gag ggg ctc ttc atg ctc agc        3488
Glu Gln Tyr Leu Thr Ile Leu Pro Glu Gly Leu Phe Met Leu Ser
1130                1135                1140 ctc tgc ctt gtg ccc acc ttc gct gtc tcc tgc ctc ctg ctg ggc        3533
Leu Cys Leu Val Pro Thr Phe Ala Val Ser Cys Leu Leu Leu Gly
1145                1150                1155
```

```
ctg gac ctg cgc tcc ggc ctc ctc aac ctg ctc tcc att gtc atg      3578
Leu Asp Leu Arg Ser Gly Leu Leu Asn Leu Leu Ser Ile Val Met
1160                1165                1170 atc ctc gtg gac act gtc ggc ttc atg gcc ctg tgg ggc atc agt      3623
Ile Leu Val Asp Thr Val Gly Phe Met Ala Leu Trp Gly Ile Ser
1175                1180                1185 tac aat gct gtg tcc ctc atc aac ctg gtc tcg gcg gtg ggc atg      3668
Tyr Asn Ala Val Ser Leu Ile Asn Leu Val Ser Ala Val Gly Met
1190                1195                1200 tct gtg gag ttt gtg tcc cac att acc cgc tcc ttt gcc atc agc      3713
Ser Val Glu Phe Val Ser His Ile Thr Arg Ser Phe Ala Ile Ser
1205                1210                1215 acc aag ccc acc tgg ctg gag agg gcc aaa gag gcc acc atc tct      3758
Thr Lys Pro Thr Trp Leu Glu Arg Ala Lys Glu Ala Thr Ile Ser
1220                1225                1230 atg gga agt gcg gtg ttt gca ggt gtg gcc atg acc aac ctg cct      3803
Met Gly Ser Ala Val Phe Ala Gly Val Ala Met Thr Asn Leu Pro
1235                1240                1245 ggc atc ctt gtc ctg ggc ctc gcc aag gcc cag ctc att cag atc      3848
Gly Ile Leu Val Leu Gly Leu Ala Lys Ala Gln Leu Ile Gln Ile
1250                1255                1260 ttc ttc ttc cgc ctc aac ctg atc act ctg ctg ggc ctg ctg          3893
Phe Phe Phe Arg Leu Asn Leu Leu Ile Thr Leu Leu Gly Leu Leu
1265                1270                1275 cat ggc ttg gtc ttc ctg ccc gtc atc ctc agc tac gtg ggg cct      3938
His Gly Leu Val Phe Leu Pro Val Ile Leu Ser Tyr Val Gly Pro
1280                1285                1290 gac gtt aac ccg gct ctg gca ctg gag cag aag cgg gct gag gag      3983
Asp Val Asn Pro Ala Leu Ala Leu Glu Gln Lys Arg Ala Glu Glu
1295                1300                1305 gcg gtg gca gca gtc atg gtg gcc tct tgc cca aat cac ccc tcc      4028
Ala Val Ala Ala Val Met Val Ala Ser Cys Pro Asn His Pro Ser
1310                1315                1320 cga gtc tcc aca gct gac aac atc tat gtc aac cac agc ttt gaa      4073
Arg Val Ser Thr Ala Asp Asn Ile Tyr Val Asn His Ser Phe Glu
1325                1330                1335 ggt tct atc aaa ggt gct ggt gcc atc agc aac ttc ttg ccc aac      4118
Gly Ser Ile Lys Gly Ala Gly Ala Ile Ser Asn Phe Leu Pro Asn
1340                1345                1350 aat ggg cgg cag ttc tga tacagccaga ggccctgtct aggctctatg         4166
Asn Gly Arg Gln Phe
1355 gccctgaacc aaagggttat ggggatcttc cttgtgactg ccccttgaca cacgccctcc    4226 tcaaatccta ggggaggcca ttcccatgag actgcctgtc actggaggat ggcctgctct    4286 tgaggtatcc aggcagcacc actgatggct cctctgctcc catagtgggt ccccagtttc    4346 caagtcacct aggccttggg cagtgcctcc tcctgggcct gggtctggaa gttggcagga    4406 acagacacac tccatgtttg tcccacactc actcactttc ctaggagccc acttctcatc    4466 caacttttcc cttctcagtt cctctctcga aagtcttaat tctgtgtcag taagtcttta    4526 acacgtagca gtgtccctga gaacacagac aatgaccact accctgggtg tgatatcaca    4586 ggaggccaga gagaggcaaa ggctcaggcc aagagccaac gctgtgggag gccggtcggc    4646 agccactccc tccagggcgc acctgcaggt ctgccatcca cggccttttc tggcaagaga    4706 agggcccagg aaggatgctc tcataaggcc caggaaggat gctctcataa gcaccttggt    4766 catggattag cccctcctgg aaaatggtgt tgggtttggt ctccagctcc aatacttatt    4826 aaggctgttg ctgccagtca aggccaccca ggagtctgaa ggctgggagc tcttggggct    4886
```

```
gggctggtcc tcccatcttc acctcgggcc tggatcccag gcctcaaacc agcccaaccc    4946
gagcttttgg acagctctcc agaagcatga actgcagtgg agatgaagat cctggctctg    5006
tgctgtgcac ataggtgttt aataaacatt tgttggcaga aaaaaaaaaa aaaaaaaaa     5066 aaaaaaaaaa aaaaaaaaaa aaaaa                                          5092
```

<210> SEQ ID NO 44
<211> LENGTH: 1359
<212> TYPE: PRT
<213> ORGANISM: Homo sapiens

<400> SEQUENCE: 44

```
Met Ala Glu Ala Gly Leu Arg Gly Trp Leu Leu Trp Ala Leu Leu Leu
1               5                   10                  15

Arg Leu Ala Gln Ser Glu Pro Tyr Thr Thr Ile His Gln Pro Gly Tyr
            20                  25                  30

Cys Ala Phe Tyr Asp Glu Cys Gly Lys Asn Pro Glu Leu Ser Gly Ser
        35                  40                  45

Leu Met Thr Leu Ser Asn Val Ser Cys Leu Ser Asn Thr Pro Ala Arg
    50                  55                  60

Lys Ile Thr Gly Asp His Leu Ile Leu Leu Gln Lys Ile Cys Pro Arg
65                  70                  75                  80

Leu Tyr Thr Gly Pro Asn Thr Gln Ala Cys Cys Ser Ala Lys Gln Leu
                85                  90                  95

Val Ser Leu Glu Ala Ser Leu Ser Ile Thr Lys Ala Leu Leu Thr Arg
            100                 105                 110

Cys Pro Ala Cys Ser Asp Asn Phe Val Asn Leu His Cys His Asn Thr
        115                 120                 125

Cys Ser Pro Asn Gln Ser Leu Phe Ile Asn Val Thr Arg Val Ala Gln
    130                 135                 140

Leu Gly Ala Gly Gln Leu Pro Ala Val Val Ala Tyr Glu Ala Phe Tyr
145                 150                 155                 160

Gln His Ser Phe Ala Glu Gln Ser Tyr Asp Ser Cys Ser Arg Val Arg
                165                 170                 175

Val Pro Ala Ala Ala Thr Leu Ala Val Gly Thr Met Cys Gly Val Tyr
            180                 185                 190

Gly Ser Ala Leu Cys Asn Ala Gln Arg Trp Leu Asn Phe Gln Gly Asp
        195                 200                 205

Thr Gly Asn Gly Leu Ala Pro Leu Asp Ile Thr Phe His Leu Leu Glu
    210                 215                 220

Pro Gly Gln Ala Val Gly Ser Gly Ile Gln Pro Leu Asn Glu Gly Val
225                 230                 235                 240

Ala Arg Cys Asn Glu Ser Gln Gly Asp Asp Val Ala Thr Cys Ser Cys
                245                 250                 255

Gln Asp Cys Ala Ala Ser Cys Pro Ala Ile Ala Arg Pro Gln Ala Leu
            260                 265                 270

Asp Ser Thr Phe Tyr Leu Gly Gln Met Pro Gly Ser Leu Val Leu Ile
        275                 280                 285

Ile Ile Leu Cys Ser Val Phe Ala Val Val Thr Ile Leu Leu Val Gly
    290                 295                 300

Phe Arg Val Ala Pro Ala Arg Asp Lys Ser Lys Met Val Asp Pro Lys
305                 310                 315                 320

Lys Gly Thr Ser Leu Ser Asp Lys Leu Ser Phe Ser Thr His Thr Leu
                325                 330                 335

Leu Gly Gln Phe Phe Gln Gly Trp Gly Thr Trp Val Ala Ser Trp Pro
```

340                 345                 350
Leu Thr Ile Leu Val Leu Ser Val Ile Pro Val Val Ala Leu Ala Ala
            355                 360                 365

Gly Leu Val Phe Thr Glu Leu Thr Thr Asp Pro Val Glu Leu Trp Ser
            370                 375                 380

Ala Pro Asn Ser Gln Ala Arg Ser Glu Lys Ala Phe His Asp Gln His
385                 390                 395                 400

Phe Gly Pro Phe Phe Arg Thr Asn Gln Val Ile Leu Thr Ala Pro Asn
                405                 410                 415

Arg Ser Ser Tyr Arg Tyr Asp Ser Leu Leu Gly Pro Lys Asn Phe
            420                 425                 430

Ser Gly Ile Leu Asp Leu Asp Leu Leu Glu Leu Glu Leu Gln
            435                 440                 445

Glu Arg Leu Arg His Leu Gln Val Trp Ser Pro Glu Ala Gln Arg Asn
            450                 455                 460

Ile Ser Leu Gln Asp Ile Cys Tyr Ala Pro Leu Asn Pro Asp Asn Thr
465                 470                 475                 480

Ser Leu Tyr Asp Cys Cys Ile Asn Ser Leu Leu Gln Tyr Phe Gln Asn
                485                 490                 495

Asn Arg Thr Leu Leu Leu Leu Thr Ala Asn Gln Thr Leu Met Gly Gln
            500                 505                 510

Thr Ser Gln Val Asp Trp Lys Asp His Phe Leu Tyr Cys Ala Asn Ala
            515                 520                 525

Pro Leu Thr Phe Lys Asp Gly Thr Ala Leu Ala Leu Ser Cys Met Ala
            530                 535                 540

Asp Tyr Gly Ala Pro Val Phe Pro Phe Leu Ala Ile Gly Gly Tyr Lys
545                 550                 555                 560

Gly Lys Asp Tyr Ser Glu Ala Glu Ala Leu Ile Met Thr Phe Ser Leu
                565                 570                 575

Asn Asn Tyr Pro Ala Gly Asp Pro Arg Leu Ala Gln Ala Lys Leu Trp
            580                 585                 590

Glu Glu Ala Phe Leu Glu Glu Met Arg Ala Phe Gln Arg Arg Met Ala
            595                 600                 605

Gly Met Phe Gln Val Thr Phe Met Ala Glu Arg Ser Leu Glu Asp Glu
            610                 615                 620

Ile Asn Arg Thr Thr Ala Glu Asp Leu Pro Ile Phe Ala Thr Ser Tyr
625                 630                 635                 640

Ile Val Ile Phe Leu Tyr Ile Ser Leu Ala Leu Gly Ser Tyr Ser Ser
                645                 650                 655

Trp Ser Arg Val Met Val Asp Ser Lys Ala Thr Leu Gly Leu Gly Gly
            660                 665                 670

Val Ala Val Val Leu Gly Ala Val Met Ala Ala Met Gly Phe Phe Ser
            675                 680                 685

Tyr Leu Gly Ile Arg Ser Ser Leu Val Ile Leu Gln Val Val Pro Phe
            690                 695                 700

Leu Val Leu Ser Val Gly Ala Asp Asn Ile Phe Ile Phe Val Leu Glu
705                 710                 715                 720

Tyr Gln Arg Leu Pro Arg Arg Pro Gly Glu Pro Arg Glu Val His Ile
                725                 730                 735

Gly Arg Ala Leu Gly Arg Val Ala Pro Ser Met Leu Leu Cys Ser Leu
            740                 745                 750

Ser Glu Ala Ile Cys Phe Phe Leu Gly Ala Leu Thr Pro Met Pro Ala
            755                 760                 765

-continued

```
Val Arg Thr Phe Ala Leu Thr Ser Gly Leu Ala Val Ile Leu Asp Phe
770             775             780

Leu Leu Gln Met Ser Ala Phe Val Ala Leu Leu Ser Leu Asp Ser Lys
785             790             795             800

Arg Gln Glu Ala Ser Arg Leu Asp Val Cys Cys Val Lys Pro Gln
            805             810             815

Glu Leu Pro Pro Pro Gly Gln Gly Glu Gly Leu Leu Leu Gly Phe Phe
            820             825             830

Gln Lys Ala Tyr Ala Pro Phe Leu Leu His Trp Ile Thr Arg Gly Val
            835             840             845

Val Leu Leu Leu Phe Leu Ala Leu Phe Gly Val Ser Leu Tyr Ser Met
850             855             860

Cys His Ile Ser Val Gly Leu Asp Gln Glu Leu Ala Leu Pro Lys Asp
865             870             875             880

Ser Tyr Leu Leu Asp Tyr Phe Leu Phe Leu Asn Arg Tyr Phe Glu Val
            885             890             895

Gly Ala Pro Val Tyr Phe Val Thr Thr Leu Gly Tyr Asn Phe Ser Ser
            900             905             910

Glu Ala Gly Met Asn Ala Ile Cys Ser Ser Ala Gly Cys Asn Asn Phe
            915             920             925

Ser Phe Thr Gln Lys Ile Gln Tyr Ala Thr Glu Phe Pro Glu Gln Ser
    930             935             940

Tyr Leu Ala Ile Pro Ala Ser Ser Trp Val Asp Asp Phe Ile Asp Trp
945             950             955             960

Leu Thr Pro Ser Ser Cys Cys Arg Leu Tyr Ile Ser Gly Pro Asn Lys
            965             970             975

Asp Lys Phe Cys Pro Ser Thr Val Asn Ser Leu Asn Cys Leu Lys Asn
            980             985             990

Cys Met Ser Ile Thr Met Gly Ser Val Arg Pro Ser Val Glu Gln Phe
    995             1000            1005

His Lys Tyr Leu Pro Trp Phe Leu Asn Asp Arg Pro Asn Ile Lys
    1010            1015            1020

Cys Pro Lys Gly Gly Leu Ala Ala Tyr Ser Thr Ser Val Asn Leu
    1025            1030            1035

Thr Ser Asp Gly Gln Val Leu Asp Thr Val Ala Ile Leu Ser Pro
    1040            1045            1050

Arg Leu Glu Tyr Ser Gly Thr Ile Ser Ala His Cys Asn Leu Tyr
    1055            1060            1065

Leu Leu Asp Ser Ala Ser Arg Phe Met Ala Tyr His Lys Pro Leu
    1070            1075            1080

Lys Asn Ser Gln Asp Tyr Thr Glu Ala Leu Arg Ala Ala Arg Glu
    1085            1090            1095

Leu Ala Ala Asn Ile Thr Ala Asp Leu Arg Lys Val Pro Gly Thr
    1100            1105            1110

Asp Pro Ala Phe Glu Val Phe Pro Tyr Thr Ile Thr Asn Val Phe
    1115            1120            1125

Tyr Glu Gln Tyr Leu Thr Ile Leu Pro Glu Gly Leu Phe Met Leu
    1130            1135            1140

Ser Leu Cys Leu Val Pro Thr Phe Ala Val Ser Cys Leu Leu Leu
    1145            1150            1155

Gly Leu Asp Leu Arg Ser Gly Leu Leu Asn Leu Leu Ser Ile Val
    1160            1165            1170

Met Ile Leu Val Asp Thr Val Gly Phe Met Ala Leu Trp Gly Ile
    1175            1180            1185
```

| | | | | | | | | | |
|---|---|---|---|---|---|---|---|---|---|
|Ser|Tyr|Asn|Ala|Val|Ser|Leu|Ile|Asn|Leu|Val|Ser|Ala|Val|Gly|
| |1190| | | |1195| | | |1200|

Ser Tyr Asn Ala Val Ser Leu Ile Asn Leu Val Ser Ala Val Gly
    1190                1195                1200

Met Ser Val Glu Phe Val Ser His Ile Thr Arg Ser Phe Ala Ile
    1205                1210                1215

Ser Thr Lys Pro Thr Trp Leu Glu Arg Ala Lys Glu Ala Thr Ile
    1220                1225                1230

Ser Met Gly Ser Ala Val Phe Ala Gly Val Ala Met Thr Asn Leu
    1235                1240                1245

Pro Gly Ile Leu Val Leu Gly Leu Ala Lys Ala Gln Leu Ile Gln
    1250                1255                1260

Ile Phe Phe Phe Arg Leu Asn Leu Leu Ile Thr Leu Leu Gly Leu
    1265                1270                1275

Leu His Gly Leu Val Phe Leu Pro Val Ile Leu Ser Tyr Val Gly
    1280                1285                1290

Pro Asp Val Asn Pro Ala Leu Ala Leu Glu Gln Lys Arg Ala Glu
    1295                1300                1305

Glu Ala Val Ala Ala Val Met Val Ala Ser Cys Pro Asn His Pro
    1310                1315                1320

Ser Arg Val Ser Thr Ala Asp Asn Ile Tyr Val Asn His Ser Phe
    1325                1330                1335

Glu Gly Ser Ile Lys Gly Ala Gly Ala Ile Ser Asn Phe Leu Pro
    1340                1345                1350

Asn Asn Gly Arg Gln Phe
    1355

<210> SEQ ID NO 45
<211> LENGTH: 4471
<212> TYPE: DNA
<213> ORGANISM: Mus musculus

<400> SEQUENCE: 45

```
ggatcacttc ctggctctgg gatggcagct gcctggcagg gatggctgct ctgggccctg    60
ctcctgaatt cggcccaggg tgagctctac acaccccactc acaaagctgg cttctgcacc   120
ttttatgaag agtgtgggaa gaacccagag ctttctggag gcctcacatc actatccaat   180
atctcctgct tgtctaatac cccagccccg ccatgtcaca ggtgaccacc tggctcttct   240
ccagcgcgtc tgtccccgcc tatacaatgg ccccaatgac acctatgcct gttgctctac   300
caagcagctg gtgtcattag acagtagcct gtctatcacc aaggccctcc ttacacgctg   360
cccggcatgc tctgaaaatt ttgtgagcat acactgtcat aatacctgca gccctgacca   420
gagcctcttc atcaatgtta ctcgcgtggt tcagcgggac cctggacagc ttcctgctgt   480
ggtggcctat gaggcctttt atcaacgcag ttttgcagag aaggcctatg agtcctgtag   540
ccgggtgcgc atccctgcag ctgcctcgct ggctgtgggc agcatgtgtg gagtgtatgg   600
ctctgccctc tgcaatgctc agcgcctggc tcaacttcca aggagacaca gggaatggcc   660
tggctccgct ggacatcacc ttccaccctct tggagcctgg ccaggccctg gcagatggga   720
tgaagccact ggatgggaag atcaaaccct gcaatgagtc ccagggtgaa gactcggcag   780
cctgttcctg ccaggactgt gcagcatcct gccctgtcat ccctccgccc ccggccctgc   840
gcccttcttt ctacatgggt cgaatgccag gctggctggc tctcatcatc atcttcactg   900
ctgtctttgt attgctctct gttgtccttg tgtatctccg agtggcttcc aacaggaaca   960
agaacaagac agcaggctcc caggaagccc ccaacctccc tcgtaagcgc agattctcac  1020
ctcacactgt ccttggccgg ttcttcgaga gctggggaac aatggtggcc tcatggccac  1080
```

```
tcactgtctt ggcactgtcc ttcatagttg tgatagcctt gtcagtaggc ctgaccttta    1140
tagaactcac cacagaccct gtggaactgt ggtcggcccc taaaagccaa gcccggaaag    1200
aaaaggcttt ccatgacgag cattttggcc ccttcttccg aaccaaccag attttgtga    1260
cagctaagaa caggtccagc tacaagtacg actccctgct gctagggccc aagaacttca    1320
gtgggatcct atccctggac ttgctgcagg agctgttgga gctacaggag agacttcgac    1380
acctgcaagt gtggtcccat gaggcacagc gcaacatctc cctccaggac atctgctatg    1440
ctcccctcaa accgcataac accagcctca ctgactgctg tgtcaacagc ctccttcaat    1500
acttccagaa caaccacaca ctcctgctgc tcacagccaa ccagactctg aatggccaga    1560
cctccctggt ggactggaag gaccatttcc tctactgtgc caatgcccct ctcacgtaca    1620
aagatggcac agccctggcc ctgagctgca tagctgacta cggggcgcct gtcttcccct    1680
tccttgctgt tggggctac caagggacgg actactcgga ggcagaagcc ctgatcataa    1740
ccttctctat caataactac cccgctgatg atccccgcat ggcccacgcc aagctctggg    1800
aggaggcttt cttgaaggaa atgcaatcct tccagagaag cacagctgac aagttccaga    1860
ttgcgttctc agctgagcgt tctctggagg acgagatcaa tcgcactacc atccaggacc    1920
tgcctgtctt tgccatcagc taccttatcg tcttcctgta catctccctg gccctgggca    1980
gctactccag atggagccga gttgcggtgg attccaaggc tactctgggc ctaggtgggg    2040
tggctgttgt gctgggagca gtcgtggctg ccatgggctt ctactcctac ctgggtgtcc    2100
cctcctctct ggtcatcatt caagtggtac ctttcctggt gctggctgtg ggagctgaca    2160
acatcttcat ctttgttctt gagtaccaga ggctgcctag gatgcccggg gagcagcgag    2220
aggctcacat tggccgcacc ctgggtagtg tggcccccag catgctgctg tgcagcctct    2280
ctgaggccat ctgcttcttt ctaggggccc tgacctccat gccagctgtg aggacctttg    2340
ccttgacctc tggcttagca atcatctttg acttcctgct ccagatgaca gcctttgtgg    2400
ccctgctctc cctggatagc aagaggcagg aggcctctcg ccccgacgtc gtgtgctgct    2460
tttcaagccg aaatctgccc ccaccgaaac aaaaagaagg cctcttactt tgcttcttcc    2520
gcaagatata cactcccttc ctgctgcaca gattcatccg ccctgttgtg ctgctgctct    2580
ttctggtcct gtttggagca aacctctact taatgtgcaa catcagcgtg gggctggacc    2640
aggatctggc tctgcccaag gattcctacc tgatagacta cttcctcttt ctgaaccggt    2700
acttggaagt ggggcctcca gtgtactttg acaccacctc aggctacaac ttttccaccg    2760
aggcaggcat gaacgccatt tgctctagtg caggctgtga gagcttctcc ctaacccaga    2820
aaatccagta tgccagtgaa ttccctaatc agtcttatgt ggctattgct gcatcctcct    2880
gggtagatga cttcatcgac tggctgaccc catcctcctc ctgctgccgc atttataccc    2940
gtggccccca taaagatgag ttctgtccct caacggatac ttccttcaac tgtctcaaaa    3000
actgcatgaa ccgcactctg ggtccgtga gacccacaac agaacagttt cataagtacc    3060
tgccctggtt cctgaatgat acgcccaaca tcagatgtct taaggggggc ctagcagcgt    3120
atagaacctc tgtgaatttg atctcagatg gccagattat agcctcccag ttcatggcct    3180
accacaagcc cttacggaac tcacaggact ttacagaagc tctccgggca tcccggttgc    3240
tagcagccaa catcacagct gaactacgga aggtgcctgg gacagatccc aactttgagg    3300
tcttccctta cacgatctcc aatgtgttct accagcaata cctgacggtt ctccctgagg    3360
gaatcttcac tcttgctctc tgcttcgtgc ccacctttgt ggtctgctac ctcctactgg    3420
gcctggacat acgctcaggc atcctcaacc tgctctccat cattatgatc ctcgtggaca    3480
```

-continued

```
ccatcggcct catggctgtg tggggtatca gctacaatgc tgtgtccctc atcaaccttg    3540
tcacggcagt gggcatgtct gtggagttcg tgtcccacat tacccggtcc tttgctgtaa    3600
gcaccaagcc tacccggctg agagagccaa aagatgctac tatcttcatg ggcagtgcgg    3660
tgtttgctgg agtggccatg accaacttcc cgggcatcct catcctgggc tttgctcagg    3720
cccagcttat ccagattttc ttcttccgcc tcaacctcct gatcaccttg ctgggtctgc    3780
tacacggcct ggtcttcctg cccgttgtcc tcagctatct ggggccagat gttaaccaag    3840
ctctggtact ggaggagaaa ctagccactg aggcagccat ggtctcagag ccttcttgcc    3900
cacagtaccc cttcccggct gatgcaaaca ccagtgacct atgttaacta aggctttaat    3960
ccagaattta tccctgaaat taatgctgct agcagctctc tgcccaaaag tgaccaaaag    4020
ttctaatgga gtaggagctt gtccaggctc catggttctt gctgataagg ggccacgagg    4080
gtcttccctc tggttgtttc caaggcctgg ggaaagttgt tccagaaaaa aattgctggc    4140
attcttgtcc tgaggcagcc agcactggcc actttgttgt cataggtccc cgaggccatg    4200
atcagattac ctcctctgta aagagaatat cttgagtatt gtatgggatg tatcacatgt    4260
caattaaaaa ggccatggcc tatggcttag gcaggaaata gggtgtggaa catccaggag    4320
aagaaaggat tctgggataa aggacacttg ggaacgtgtg gcagtggtac ctgagcacag    4380
gtaattagcc atgtggcgaa atgtagatta atataaatgc atatctaagt tatgattcta    4440
gtctagctat atggccaagg tatttataaa t                                   4471
```

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atgttaggtg agtctgaacc taccc                                            25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggattgcatt tccttcaaga aagcc                                            25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tatggctctg ccctctgcaa tgctc                                            25

<210> SEQ ID NO 49
<211> LENGTH: 28
<212> TYPE: DNA
<213> ORGANISM: Artificial Sequence
<220> FEATURE:

-continued

```
<223> OTHER INFORMATION: Description of Artificial Sequence: Synthetic
      primer

<400> SEQUENCE: 49
tcagcagcct ctgttccaca tacacttc                                          28

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gttccacagg gtctgtggtg agttc                                             25

<210> SEQ ID NO 51
<211> LENGTH: 3996
<212> TYPE: DNA
<213> ORGANISM: Homo sapiens
<220> FEATURE:
<221> NAME/KEY: CDS
<222> LOCATION: (1)..(3996)
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (30)..(30)
<223> OTHER INFORMATION: a, c, g, t, unknown or other
<220> FEATURE:
<221> NAME/KEY: modified_base
<222> LOCATION: (33)..(33)
<223> OTHER INFORMATION: a, c, g, t, unknown or other
<220> FEATURE:
<221> NAME/KEY: modified_base
<222> LOCATION: (39)..(39)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (45)..(45)
<223> OTHER INFORMATION: a, c, g, t, unknown or other
<220> FEATURE:
<221> NAME/KEY: modified_base
<222> LOCATION: (48)..(48)
<223> OTHER INFORMATION: a, c, g, t, unknown or other
<220> FEATURE:
<221> NAME/KEY: modified_base
<222> LOCATION: (51)..(51)
<223> OTHER INFORMATION: a, c, g, t, unknown or other
```

```
<220> FEATURE:
<221> NAME/KEY: modified_base
<222> LOCATION: (54)..(54)
<223> OTHER INFORMATION: a, c, g, t, unknown or other
<220> FEATURE:
<221> NAME/KEY: modified_base
<222> LOCATION: (57)..(57)
<223> OTHER INFORMATION: a, c, g, t, unknown or other
<220> FEATURE:
<221> NAME/KEY: modified_base
<222> LOCATION: (63)..(63)
<223> OTHER INFORMATION: a, c, g, t, unknown or other
<220> FEATURE:
<221> NAME/KEY: modified_base
<222> LOCATION: (69)..(69)
<223> OTHER INFORMATION: a, c, g, t, unknown or other
<220> FEATURE:
<221> NAME/KEY: modified_base
<222> LOCATION: (75)..(75)
<223> OTHER INFORMATION: a, c, g, t, unknown or other
<220> FEATURE:
<221> NAME/KEY: modified_base
<222> LOCATION: (78)..(78)
<223> OTHER INFORMATION: a, c, g, t, unknown or other
<220> FEATURE:
<221> NAME/KEY: modified_base
<222> LOCATION: (90)..(90)
<223> OTHER INFORMATION: a, c, g, t, unknown or other
<220> FEATURE:
<221> NAME/KEY: modified_base
<222> LOCATION: (93)..(93)
<223> OTHER INFORMATION: a, c, g, t, unknown or other
<220> FEATURE:
<221> NAME/KEY: modified_base
<222> LOCATION: (102)..(102)
<223> OTHER INFORMATION: a, c, g, t, unknown or other
<220> FEATURE:
<221> NAME/KEY: modified_base
<222> LOCATION: (120)..(120)
<223> OTHER INFORMATION: a, c, g, t, unknown or other
<220> FEATURE:
<221> NAME/KEY: modified_base
<222> LOCATION: (129)..(129)
<223> OTHER INFORMATION: a, c, g, t, unknown or other
<220> FEATURE:
<221> NAME/KEY: modified_base
<222> LOCATION: (135)..(135)
<223> OTHER INFORMATION: a, c, g, t, unknown or other
<220> FEATURE:
<221> NAME/KEY: modified_base
<222> LOCATION: (138)..(138)
<223> OTHER INFORMATION: a, c, g, t, unknown or other
<220> FEATURE:
<221> NAME/KEY: modified_base
<222> LOCATION: (141)..(141)
<223> OTHER INFORMATION: a, c, g, t, unknown or other
<220> FEATURE:
<221> NAME/KEY: modified_base
<222> LOCATION: (144)..(144)
<223> OTHER INFORMATION: a, c, g, t, unknown or other
<220> FEATURE:
<221> NAME/KEY: modified_base
<222> LOCATION: (147)..(147)
<223> OTHER INFORMATION: a, c, g, t, unknown or other
<220> FEATURE:
<221> NAME/KEY: modified_base
<222> LOCATION: (153)..(153)
<223> OTHER INFORMATION: a, c, g, t, unknown or other
<220> FEATURE:
<221> NAME/KEY: modified_base
<222> LOCATION: (156)..(156)
<223> OTHER INFORMATION: a, c, g, t, unknown or other
<220> FEATURE:
<221> NAME/KEY: modified_base
<222> LOCATION: (159)..(159)
<223> OTHER INFORMATION: a, c, g, t, unknown or other
<220> FEATURE:
<221> NAME/KEY: modified_base
<222> LOCATION: (165)..(165)
<223> OTHER INFORMATION: a, c, g, t, unknown or other
```

```
<220> FEATURE:
<221> NAME/KEY: modified_base
<222> LOCATION: (168)..(168)
<223> OTHER INFORMATION: a, c, g, t, unknown or other
<220> FEATURE:
<221> NAME/KEY: modified_base
<222> LOCATION: (174)..(174)
<223> OTHER INFORMATION: a, c, g, t, unknown or other
<220> FEATURE:
<221> NAME/KEY: modified_base
<222> LOCATION: (177)..(177)
<223> OTHER INFORMATION: a, c, g, t, unknown or other
<220> FEATURE:
<221> NAME/KEY: modified_base
<222> LOCATION: (183)..(183)
<223> OTHER INFORMATION: a, c, g, t, unknown or other
<220> FEATURE:
<221> NAME/KEY: modified_base
<222> LOCATION: (186)..(186)
<223> OTHER INFORMATION: a, c, g, t, unknown or other
<220> FEATURE:
<221> NAME/KEY: modified_base
<222> LOCATION: (189)..(189)
<223> OTHER INFORMATION: a, c, g, t, unknown or other
<220> FEATURE:
<221> NAME/KEY: modified_base
<222> LOCATION: (192)..(192)
<223> OTHER INFORMATION: a, c, g, t, unknown or other
<220> FEATURE:
<221> NAME/KEY: modified_base
<222> LOCATION: (201)..(201)
<223> OTHER INFORMATION: a, c, g, t, unknown or other
<220> FEATURE:
<221> NAME/KEY: modified_base
<222> LOCATION: (204)..(204)
<223> OTHER INFORMATION: a, c, g, t, unknown or other
<220> FEATURE:
<221> NAME/KEY: modified_base
<222> LOCATION: (213)..(213)
<223> OTHER INFORMATION: a, c, g, t, unknown or other
<220> FEATURE:
<221> NAME/KEY: modified_base
<222> LOCATION: (219)..(219)
<223> OTHER INFORMATION: a, c, g, t, unknown or other
<220> FEATURE:
<221> NAME/KEY: modified_base
<222> LOCATION: (222)..(222)
<223> OTHER INFORMATION: a, c, g, t, unknown or other
<220> FEATURE:
<221> NAME/KEY: modified_base
<222> LOCATION: (237)..(237)
<223> OTHER INFORMATION: a, c, g, t, unknown or other
<220> FEATURE:
<221> NAME/KEY: modified_base
<222> LOCATION: (240)..(240)
<223> OTHER INFORMATION: a, c, g, t, unknown or other
<220> FEATURE:
<221> NAME/KEY: modified_base
<222> LOCATION: (243)..(243)
<223> OTHER INFORMATION: a, c, g, t, unknown or other
<220> FEATURE:
<221> NAME/KEY: modified_base
<222> LOCATION: (249)..(249)
<223> OTHER INFORMATION: a, c, g, t, unknown or other
<220> FEATURE:
<221> NAME/KEY: modified_base
<222> LOCATION: (252)..(252)
<223> OTHER INFORMATION: a, c, g, t, unknown or other
<220> FEATURE:
<221> NAME/KEY: modified_base
<222> LOCATION: (255)..(255)
<223> OTHER INFORMATION: a, c, g, t, unknown or other
<220> FEATURE:
<221> NAME/KEY: modified_base
<222> LOCATION: (261)..(261)
<223> OTHER INFORMATION: a, c, g, t, unknown or other
<220> FEATURE:
<221> NAME/KEY: modified_base
<222> LOCATION: (267)..(267)
<223> OTHER INFORMATION: a, c, g, t, unknown or other
```

-continued

```
<220> FEATURE:
<221> NAME/KEY: modified_base
<222> LOCATION: (276)..(276)
<223> OTHER INFORMATION: a, c, g, t, unknown or other
<220> FEATURE:
<221> NAME/KEY: modified_base
<222> LOCATION: (279)..(279)
<223> OTHER INFORMATION: a, c, g, t, unknown or other
<220> FEATURE:
<221> NAME/KEY: modified_base
<222> LOCATION: (288)..(288)
<223> OTHER INFORMATION: a, c, g, t, unknown or other
<220> FEATURE:
<221> NAME/KEY: modified_base
<222> LOCATION: (291)..(291)
<223> OTHER INFORMATION: a, c, g, t, unknown or other
<220> FEATURE:
<221> NAME/KEY: modified_base
<222> LOCATION: (294)..(294)
<223> OTHER INFORMATION: a, c, g, t, unknown or other
<220> FEATURE:
<221> NAME/KEY: modified_base
<222> LOCATION: (297)..(297)
<223> OTHER INFORMATION: a, c, g, t, unknown or other
<220> FEATURE:
<221> NAME/KEY: modified_base
<222> LOCATION: (303)..(303)
<223> OTHER INFORMATION: a, c, g, t, unknown or other
<220> FEATURE:
<221> NAME/KEY: modified_base
<222> LOCATION: (306)..(306)
<223> OTHER INFORMATION: a, c, g, t, unknown or other
<220> FEATURE:
<221> NAME/KEY: modified_base
<222> LOCATION: (309)..(309)
<223> OTHER INFORMATION: a, c, g, t, unknown or other
<220> FEATURE:
<221> NAME/KEY: modified_base
<222> LOCATION: (312)..(312)
<223> OTHER INFORMATION: a, c, g, t, unknown or other
<220> FEATURE:
<221> NAME/KEY: modified_base
<222> LOCATION: (318)..(318)
<223> OTHER INFORMATION: a, c, g, t, unknown or other
<220> FEATURE:
<221> NAME/KEY: modified_base
<222> LOCATION: (324)..(324)
<223> OTHER INFORMATION: a, c, g, t, unknown or other
<220> FEATURE:
<221> NAME/KEY: modified_base
<222> LOCATION: (327)..(327)
<223> OTHER INFORMATION: a, c, g, t, unknown or other
<220> FEATURE:
<221> NAME/KEY: modified_base
<222> LOCATION: (330)..(330)
<223> OTHER INFORMATION: a, c, g, t, unknown or other
<220> FEATURE:
<221> NAME/KEY: modified_base
<222> LOCATION: (333)..(333)
<223> OTHER INFORMATION: a, c, g, t, unknown or other
<220> FEATURE:
<221> NAME/KEY: modified_base
<222> LOCATION: (336)..(336)
<223> OTHER INFORMATION: a, c, g, t, unknown or other
<220> FEATURE:
<221> NAME/KEY: modified_base
<222> LOCATION: (342)..(342)
<223> OTHER INFORMATION: a, c, g, t, unknown or other
<220> FEATURE:
<221> NAME/KEY: modified_base
<222> LOCATION: (345)..(345)
<223> OTHER INFORMATION: a, c, g, t, unknown or other
<220> FEATURE:
<221> NAME/KEY: modified_base
<222> LOCATION: (351)..(351)
<223> OTHER INFORMATION: a, c, g, t, unknown or other
<220> FEATURE:
<221> NAME/KEY: modified_base
<222> LOCATION: (363)..(363)
<223> OTHER INFORMATION: a, c, g, t, unknown or other
```

-continued

```
<220> FEATURE:
<221> NAME/KEY: modified_base
<222> LOCATION: (369)..(369)
<223> OTHER INFORMATION: a, c, g, t, unknown or other
<220> FEATURE:
<221> NAME/KEY: modified_base
<222> LOCATION: (384)..(384)
<223> OTHER INFORMATION: a, c, g, t, unknown or other
<220> FEATURE:
<221> NAME/KEY: modified_base
<222> LOCATION: (390)..(390)
<223> OTHER INFORMATION: a, c, g, t, unknown or other
<220> FEATURE:
<221> NAME/KEY: modified_base
<222> LOCATION: (393)..(393)
<223> OTHER INFORMATION: a, c, g, t, unknown or other
<220> FEATURE:
<221> NAME/KEY: modified_base
<222> LOCATION: (402)..(402)
<223> OTHER INFORMATION: a, c, g, t, unknown or other
<220> FEATURE:
<221> NAME/KEY: modified_base
<222> LOCATION: (405)..(405)
<223> OTHER INFORMATION: a, c, g, t, unknown or other
<220> FEATURE:
<221> NAME/KEY: modified_base
<222> LOCATION: (417)..(417)
<223> OTHER INFORMATION: a, c, g, t, unknown or other
<220> FEATURE:
<221> NAME/KEY: modified_base
<222> LOCATION: (420)..(420)
<223> OTHER INFORMATION: a, c, g, t, unknown or other
<220> FEATURE:
<221> NAME/KEY: modified_base
<222> LOCATION: (423)..(423)
<223> OTHER INFORMATION: a, c, g, t, unknown or other
<220> FEATURE:
<221> NAME/KEY: modified_base
<222> LOCATION: (426)..(426)
<223> OTHER INFORMATION: a, c, g, t, unknown or other
<220> FEATURE:
<221> NAME/KEY: modified_base
<222> LOCATION: (429)..(429)
<223> OTHER INFORMATION: a, c, g, t, unknown or other
<220> FEATURE:
<221> NAME/KEY: modified_base
<222> LOCATION: (435)..(435)
<223> OTHER INFORMATION: a, c, g, t, unknown or other
<220> FEATURE:
<221> NAME/KEY: modified_base
<222> LOCATION: (438)..(438)
<223> OTHER INFORMATION: a, c, g, t, unknown or other
<220> FEATURE:
<221> NAME/KEY: modified_base
<222> LOCATION: (441)..(441)
<223> OTHER INFORMATION: a, c, g, t, unknown or other
<220> FEATURE:
<221> NAME/KEY: modified_base
<222> LOCATION: (444)..(444)
<223> OTHER INFORMATION: a, c, g, t, unknown or other
<220> FEATURE:
<221> NAME/KEY: modified_base
<222> LOCATION: (450)..(450)
<223> OTHER INFORMATION: a, c, g, t, unknown or other
<220> FEATURE:
<221> NAME/KEY: modified_base
<222> LOCATION: (453)..(453)
<223> OTHER INFORMATION: a, c, g, t, unknown or other
<220> FEATURE:
<221> NAME/KEY: modified_base
<222> LOCATION: (456)..(456)
<223> OTHER INFORMATION: a, c, g, t, unknown or other
<220> FEATURE:
<221> NAME/KEY: modified_base
<222> LOCATION: (459)..(459)
<223> OTHER INFORMATION: a, c, g, t, unknown or other
<220> FEATURE:
<221> NAME/KEY: modified_base
<222> LOCATION: (462)..(462)
<223> OTHER INFORMATION: a, c, g, t, unknown or other
```

-continued

```
<220> FEATURE:
<221> NAME/KEY: modified_base
<222> LOCATION: (465)..(465)
<223> OTHER INFORMATION: a, c, g, t, unknown or other
<220> FEATURE:
<221> NAME/KEY: modified_base
<222> LOCATION: (474)..(474)
<223> OTHER INFORMATION: a, c, g, t, unknown or other
<220> FEATURE:
<221> NAME/KEY: modified_base
<222> LOCATION: (489)..(489)
<223> OTHER INFORMATION: a, c, g, t, unknown or other
<220> FEATURE:
<221> NAME/KEY: modified_base
<222> LOCATION: (495)..(495)
<223> OTHER INFORMATION: a, c, g, t, unknown or other
<220> FEATURE:
<221> NAME/KEY: modified_base
<222> LOCATION: (504)..(504)
<223> OTHER INFORMATION: a, c, g, t, unknown or other
<220> FEATURE:
<221> NAME/KEY: modified_base
<222> LOCATION: (513)..(513)
<223> OTHER INFORMATION: a, c, g, t, unknown or other
<220> FEATURE:
<221> NAME/KEY: modified_base
<222> LOCATION: (519)..(519)
<223> OTHER INFORMATION: a, c, g, t, unknown or other
<220> FEATURE:
<221> NAME/KEY: modified_base
<222> LOCATION: (522)..(522)
<223> OTHER INFORMATION: a, c, g, t, unknown or other
<220> FEATURE:
<221> NAME/KEY: modified_base
<222> LOCATION: (525)..(525)
<223> OTHER INFORMATION: a, c, g, t, unknown or other
<220> FEATURE:
<221> NAME/KEY: modified_base
<222> LOCATION: (528)..(528)
<223> OTHER INFORMATION: a, c, g, t, unknown or other
<220> FEATURE:
<221> NAME/KEY: modified_base
<222> LOCATION: (531)..(531)
<223> OTHER INFORMATION: a, c, g, t, unknown or other
<220> FEATURE:
<221> NAME/KEY: modified_base
<222> LOCATION: (534)..(534)
<223> OTHER INFORMATION: a, c, g, t, unknown or other
<220> FEATURE:
<221> NAME/KEY: modified_base
<222> LOCATION: (537)..(537)
<223> OTHER INFORMATION: a, c, g, t, unknown or other
<220> FEATURE:
<221> NAME/KEY: modified_base
<222> LOCATION: (540)..(540)
<223> OTHER INFORMATION: a, c, g, t, unknown or other
<220> FEATURE:
<221> NAME/KEY: modified_base
<222> LOCATION: (543)..(543)
<223> OTHER INFORMATION: a, c, g, t, unknown or other
<220> FEATURE:
<221> NAME/KEY: modified_base
<222> LOCATION: (546)..(546)
<223> OTHER INFORMATION: a, c, g, t, unknown or other
<220> FEATURE:
<221> NAME/KEY: modified_base
<222> LOCATION: (549)..(549)
<223> OTHER INFORMATION: a, c, g, t, unknown or other
<220> FEATURE:
<221> NAME/KEY: modified_base
<222> LOCATION: (552)..(552)
<223> OTHER INFORMATION: a, c, g, t, unknown or other
<220> FEATURE:
<221> NAME/KEY: modified_base
<222> LOCATION: (555)..(555)
<223> OTHER INFORMATION: a, c, g, t, unknown or other
<220> FEATURE:
<221> NAME/KEY: modified_base
<222> LOCATION: (558)..(558)
<223> OTHER INFORMATION: a, c, g, t, unknown or other
```

-continued

```
<220> FEATURE:
<221> NAME/KEY: modified_base
<222> LOCATION: (561)..(561)
<223> OTHER INFORMATION: a, c, g, t, unknown or other
<220> FEATURE:
<221> NAME/KEY: modified_base
<222> LOCATION: (570)..(570)
<223> OTHER INFORMATION: a, c, g, t, unknown or other
<220> FEATURE:
<221> NAME/KEY: modified_base
<222> LOCATION: (573)..(573)
<223> OTHER INFORMATION: a, c, g, t, unknown or other
<220> FEATURE:
<221> NAME/KEY: modified_base
<222> LOCATION: (579)..(579)
<223> OTHER INFORMATION: a, c, g, t, unknown or other
<220> FEATURE:
<221> NAME/KEY: modified_base
<222> LOCATION: (582)..(582)
<223> OTHER INFORMATION: a, c, g, t, unknown or other
<220> FEATURE:
<221> NAME/KEY: modified_base
<222> LOCATION: (585)..(585)
<223> OTHER INFORMATION: a, c, g, t, unknown or other
<220> FEATURE:
<221> NAME/KEY: modified_base
<222> LOCATION: (588)..(588)
<223> OTHER INFORMATION: a, c, g, t, unknown or other
<220> FEATURE:
<221> NAME/KEY: modified_base
<222> LOCATION: (597)..(597)
<223> OTHER INFORMATION: a, c, g, t, unknown or other
<220> FEATURE:
<221> NAME/KEY: modified_base
<222> LOCATION: (603)..(603)
<223> OTHER INFORMATION: a, c, g, t, unknown or other
<220> FEATURE:
<221> NAME/KEY: modified_base
<222> LOCATION: (609)..(609)
<223> OTHER INFORMATION: a, c, g, t, unknown or other
<220> FEATURE:
<221> NAME/KEY: modified_base
<222> LOCATION: (621)..(621)
<223> OTHER INFORMATION: a, c, g, t, unknown or other
<220> FEATURE:
<221> NAME/KEY: modified_base
<222> LOCATION: (627)..(627)
<223> OTHER INFORMATION: a, c, g, t, unknown or other
<220> FEATURE:
<221> NAME/KEY: modified_base
<222> LOCATION: (630)..(630)
<223> OTHER INFORMATION: a, c, g, t, unknown or other
<220> FEATURE:
<221> NAME/KEY: modified_base
<222> LOCATION: (636)..(636)
<223> OTHER INFORMATION: a, c, g, t, unknown or other
<220> FEATURE:
<221> NAME/KEY: modified_base
<222> LOCATION: (639)..(639)
<223> OTHER INFORMATION: a, c, g, t, unknown or other
<220> FEATURE:
<221> NAME/KEY: modified_base
<222> LOCATION: (642)..(642)
<223> OTHER INFORMATION: a, c, g, t, unknown or other
<220> FEATURE:
<221> NAME/KEY: modified_base
<222> LOCATION: (645)..(645)
<223> OTHER INFORMATION: a, c, g, t, unknown or other
<220> FEATURE:
<221> NAME/KEY: modified_base
<222> LOCATION: (648)..(648)
<223> OTHER INFORMATION: a, c, g, t, unknown or other
<220> FEATURE:
<221> NAME/KEY: modified_base
<222> LOCATION: (657)..(657)
<223> OTHER INFORMATION: a, c, g, t, unknown or other
<220> FEATURE:
<221> NAME/KEY: modified_base
<222> LOCATION: (666)..(666)
<223> OTHER INFORMATION: a, c, g, t, unknown or other
```

```
<220> FEATURE:
<221> NAME/KEY: modified_base
<222> LOCATION: (669)..(669)
<223> OTHER INFORMATION: a, c, g, t, unknown or other
<220> FEATURE:
<221> NAME/KEY: modified_base
<222> LOCATION: (675)..(675)
<223> OTHER INFORMATION: a, c, g, t, unknown or other
<220> FEATURE:
<221> NAME/KEY: modified_base
<222> LOCATION: (678)..(678)
<223> OTHER INFORMATION: a, c, g, t, unknown or other
<220> FEATURE:
<221> NAME/KEY: modified_base
<222> LOCATION: (684)..(684)
<223> OTHER INFORMATION: a, c, g, t, unknown or other
<220> FEATURE:
<221> NAME/KEY: modified_base
<222> LOCATION: (687)..(687)
<223> OTHER INFORMATION: a, c, g, t, unknown or other
<220> FEATURE:
<221> NAME/KEY: modified_base
<222> LOCATION: (690)..(690)
<223> OTHER INFORMATION: a, c, g, t, unknown or other
<220> FEATURE:
<221> NAME/KEY: modified_base
<222> LOCATION: (693)..(693)
<223> OTHER INFORMATION: a, c, g, t, unknown or other
<220> FEATURE:
<221> NAME/KEY: modified_base
<222> LOCATION: (696)..(696)
<223> OTHER INFORMATION: a, c, g, t, unknown or other
<220> FEATURE:
<221> NAME/KEY: modified_base
<222> LOCATION: (705)..(705)
<223> OTHER INFORMATION: a, c, g, t, unknown or other
<220> FEATURE:
<221> NAME/KEY: modified_base
<222> LOCATION: (708)..(708)
<223> OTHER INFORMATION: a, c, g, t, unknown or other
<220> FEATURE:
<221> NAME/KEY: modified_base
<222> LOCATION: (717)..(717)
<223> OTHER INFORMATION: a, c, g, t, unknown or other
<220> FEATURE:
<221> NAME/KEY: modified_base
<222> LOCATION: (720)..(720)
<223> OTHER INFORMATION: a, c, g, t, unknown or other
<220> FEATURE:
<221> NAME/KEY: modified_base
<222> LOCATION: (723)..(723)
<223> OTHER INFORMATION: a, c, g, t, unknown or other
<220> FEATURE:
<221> NAME/KEY: modified_base
<222> LOCATION: (726)..(726)
<223> OTHER INFORMATION: a, c, g, t, unknown or other
<220> FEATURE:
<221> NAME/KEY: modified_base
<222> LOCATION: (738)..(738)
<223> OTHER INFORMATION: a, c, g, t, unknown or other
<220> FEATURE:
<221> NAME/KEY: modified_base
<222> LOCATION: (744)..(744)
<223> OTHER INFORMATION: a, c, g, t, unknown or other
<220> FEATURE:
<221> NAME/KEY: modified_base
<222> LOCATION: (753)..(753)
<223> OTHER INFORMATION: a, c, g, t, unknown or other
<220> FEATURE:
<221> NAME/KEY: modified_base
<222> LOCATION: (756)..(756)
<223> OTHER INFORMATION: a, c, g, t, unknown or other
<220> FEATURE:
<221> NAME/KEY: modified_base
<222> LOCATION: (759)..(759)
<223> OTHER INFORMATION: a, c, g, t, unknown or other
<220> FEATURE:
<221> NAME/KEY: modified_base
<222> LOCATION: (765)..(765)
<223> OTHER INFORMATION: a, c, g, t, unknown or other
```

-continued

```
<220> FEATURE:
<221> NAME/KEY: modified_base
<222> LOCATION: (780)..(780)
<223> OTHER INFORMATION: a, c, g, t, unknown or other
<220> FEATURE:
<221> NAME/KEY: modified_base
<222> LOCATION: (783)..(783)
<223> OTHER INFORMATION: a, c, g, t, unknown or other
<220> FEATURE:
<221> NAME/KEY: modified_base
<222> LOCATION: (786)..(786)
<223> OTHER INFORMATION: a, c, g, t, unknown or other
<220> FEATURE:
<221> NAME/KEY: modified_base
<222> LOCATION: (792)..(792)
<223> OTHER INFORMATION: a, c, g, t, unknown or other
<220> FEATURE:
<221> NAME/KEY: modified_base
<222> LOCATION: (795)..(795)
<223> OTHER INFORMATION: a, c, g, t, unknown or other
<220> FEATURE:
<221> NAME/KEY: modified_base
<222> LOCATION: (801)..(801)
<223> OTHER INFORMATION: a, c, g, t, unknown or other
<220> FEATURE:
<221> NAME/KEY: modified_base
<222> LOCATION: (804)..(804)
<223> OTHER INFORMATION: a, c, g, t, unknown or other
<220> FEATURE:
<221> NAME/KEY: modified_base
<222> LOCATION: (807)..(807)
<223> OTHER INFORMATION: a, c, g, t, unknown or other
<220> FEATURE:
<221> NAME/KEY: modified_base
<222> LOCATION: (813)..(813)
<223> OTHER INFORMATION: a, c, g, t, unknown or other
<220> FEATURE:
<221> NAME/KEY: modified_base
<222> LOCATION: (816)..(816)
<223> OTHER INFORMATION: a, c, g, t, unknown or other
<220> FEATURE:
<221> NAME/KEY: modified_base
<222> LOCATION: (822)..(822)
<223> OTHER INFORMATION: a, c, g, t, unknown or other
<220> FEATURE:
<221> NAME/KEY: modified_base
<222> LOCATION: (825)..(825)
<223> OTHER INFORMATION: a, c, g, t, unknown or other
<220> FEATURE:
<221> NAME/KEY: modified_base
<222> LOCATION: (834)..(834)
<223> OTHER INFORMATION: a, c, g, t, unknown or other
<220> FEATURE:
<221> NAME/KEY: modified_base
<222> LOCATION: (837)..(837)
<223> OTHER INFORMATION: a, c, g, t, unknown or other
<220> FEATURE:
<221> NAME/KEY: modified_base
<222> LOCATION: (846)..(846)
<223> OTHER INFORMATION: a, c, g, t, unknown or other
<220> FEATURE:
<221> NAME/KEY: modified_base
<222> LOCATION: (849)..(849)
<223> OTHER INFORMATION: a, c, g, t, unknown or other
<220> FEATURE:
<221> NAME/KEY: modified_base
<222> LOCATION: (852)..(852)
<223> OTHER INFORMATION: a, c, g, t, unknown or other
<220> FEATURE:
<221> NAME/KEY: modified_base
<222> LOCATION: (855)..(855)
<223> OTHER INFORMATION: a, c, g, t, unknown or other
<220> FEATURE:
<221> NAME/KEY: modified_base
<222> LOCATION: (858)..(858)
<223> OTHER INFORMATION: a, c, g, t, unknown or other
<220> FEATURE:
<221> NAME/KEY: modified_base
<222> LOCATION: (861)..(861)
<223> OTHER INFORMATION: a, c, g, t, unknown or other
```

-continued

```
<220> FEATURE:
<221> NAME/KEY: modified_base
<222> LOCATION: (873)..(873)
<223> OTHER INFORMATION: a, c, g, t, unknown or other
<220> FEATURE:
<221> NAME/KEY: modified_base
<222> LOCATION: (879)..(879)
<223> OTHER INFORMATION: a, c, g, t, unknown or other
<220> FEATURE:
<221> NAME/KEY: modified_base
<222> LOCATION: (882)..(882)
<223> OTHER INFORMATION: a, c, g, t, unknown or other
<220> FEATURE:
<221> NAME/KEY: modified_base
<222> LOCATION: (888)..(888)
<223> OTHER INFORMATION: a, c, g, t, unknown or other
<220> FEATURE:
<221> NAME/KEY: modified_base
<222> LOCATION: (891)..(891)
<223> OTHER INFORMATION: a, c, g, t, unknown or other
<220> FEATURE:
<221> NAME/KEY: modified_base
<222> LOCATION: (894)..(894)
<223> OTHER INFORMATION: a, c, g, t, unknown or other
<220> FEATURE:
<221> NAME/KEY: modified_base
<222> LOCATION: (897)..(897)
<223> OTHER INFORMATION: a, c, g, t, unknown or other
<220> FEATURE:
<221> NAME/KEY: modified_base
<222> LOCATION: (903)..(903)
<223> OTHER INFORMATION: a, c, g, t, unknown or other
<220> FEATURE:
<221> NAME/KEY: modified_base
<222> LOCATION: (906)..(906)
<223> OTHER INFORMATION: a, c, g, t, unknown or other
<220> FEATURE:
<221> NAME/KEY: modified_base
<222> LOCATION: (909)..(909)
<223> OTHER INFORMATION: a, c, g, t, unknown or other
<220> FEATURE:
<221> NAME/KEY: modified_base
<222> LOCATION: (912)..(912)
<223> OTHER INFORMATION: a, c, g, t, unknown or other
<220> FEATURE:
<221> NAME/KEY: modified_base
<222> LOCATION: (918)..(918)
<223> OTHER INFORMATION: a, c, g, t, unknown or other
<220> FEATURE:
<221> NAME/KEY: modified_base
<222> LOCATION: (921)..(921)
<223> OTHER INFORMATION: a, c, g, t, unknown or other
<220> FEATURE:
<221> NAME/KEY: modified_base
<222> LOCATION: (924)..(924)
<223> OTHER INFORMATION: a, c, g, t, unknown or other
<220> FEATURE:
<221> NAME/KEY: modified_base
<222> LOCATION: (927)..(927)
<223> OTHER INFORMATION: a, c, g, t, unknown or other
<220> FEATURE:
<221> NAME/KEY: modified_base
<222> LOCATION: (930)..(930)
<223> OTHER INFORMATION: a, c, g, t, unknown or other
<220> FEATURE:
<221> NAME/KEY: modified_base
<222> LOCATION: (933)..(933)
<223> OTHER INFORMATION: a, c, g, t, unknown or other
<220> FEATURE:
<221> NAME/KEY: modified_base
<222> LOCATION: (942)..(942)
<223> OTHER INFORMATION: a, c, g, t, unknown or other
<220> FEATURE:
<221> NAME/KEY: modified_base
<222> LOCATION: (951)..(951)
<223> OTHER INFORMATION: a, c, g, t, unknown or other
<220> FEATURE:
<221> NAME/KEY: modified_base
<222> LOCATION: (957)..(957)
<223> OTHER INFORMATION: a, c, g, t, unknown or other
```

-continued

```
<220> FEATURE:
<221> NAME/KEY: modified_base
<222> LOCATION: (966)..(966)
<223> OTHER INFORMATION: a, c, g, t, unknown or other
<220> FEATURE:
<221> NAME/KEY: modified_base
<222> LOCATION: (969)..(969)
<223> OTHER INFORMATION: a, c, g, t, unknown or other
<220> FEATURE:
<221> NAME/KEY: modified_base
<222> LOCATION: (972)..(972)
<223> OTHER INFORMATION: a, c, g, t, unknown or other
<220> FEATURE:
<221> NAME/KEY: modified_base
<222> LOCATION: (975)..(975)
<223> OTHER INFORMATION: a, c, g, t, unknown or other
<220> FEATURE:
<221> NAME/KEY: modified_base
<222> LOCATION: (978)..(978)
<223> OTHER INFORMATION: a, c, g, t, unknown or other
<220> FEATURE:
<221> NAME/KEY: modified_base
<222> LOCATION: (987)..(987)
<223> OTHER INFORMATION: a, c, g, t, unknown or other
<220> FEATURE:
<221> NAME/KEY: modified_base
<222> LOCATION: (990)..(990)
<223> OTHER INFORMATION: a, c, g, t, unknown or other
<220> FEATURE:
<221> NAME/KEY: modified_base
<222> LOCATION: (996)..(996)
<223> OTHER INFORMATION: a, c, g, t, unknown or other
<220> FEATURE:
<221> NAME/KEY: modified_base
<222> LOCATION: (999)..(999)
<223> OTHER INFORMATION: a, c, g, t, unknown or other
<220> FEATURE:
<221> NAME/KEY: modified_base
<222> LOCATION: (1005)..(1005)
<223> OTHER INFORMATION: a, c, g, t, unknown or other
<220> FEATURE:
<221> NAME/KEY: modified_base
<222> LOCATION: (1008)..(1008)
<223> OTHER INFORMATION: a, c, g, t, unknown or other
<220> FEATURE:
<221> NAME/KEY: modified_base
<222> LOCATION: (1011)..(1011)
<223> OTHER INFORMATION: a, c, g, t, unknown or other
<220> FEATURE:
<221> NAME/KEY: modified_base
<222> LOCATION: (1014)..(1014)
<223> OTHER INFORMATION: a, c, g, t, unknown or other
<220> FEATURE:
<221> NAME/KEY: modified_base
<222> LOCATION: (1029)..(1029)
<223> OTHER INFORMATION: a, c, g, t, unknown or other
<220> FEATURE:
<221> NAME/KEY: modified_base
<222> LOCATION: (1035)..(1035)
<223> OTHER INFORMATION: a, c, g, t, unknown or other
<220> FEATURE:
<221> NAME/KEY: modified_base
<222> LOCATION: (1038)..(1038)
<223> OTHER INFORMATION: a, c, g, t, unknown or other
<220> FEATURE:
<221> NAME/KEY: modified_base
<222> LOCATION: (1044)..(1044)
<223> OTHER INFORMATION: a, c, g, t, unknown or other
<220> FEATURE:
<221> NAME/KEY: modified_base
<222> LOCATION: (1047)..(1047)
<223> OTHER INFORMATION: a, c, g, t, unknown or other
<220> FEATURE:
<221> NAME/KEY: modified_base
<222> LOCATION: (1050)..(1050)
<223> OTHER INFORMATION: a, c, g, t, unknown or other
<220> FEATURE:
<221> NAME/KEY: modified_base
<222> LOCATION: (1056)..(1056)
<223> OTHER INFORMATION: a, c, g, t, unknown or other
```

-continued

```
<220> FEATURE:
<221> NAME/KEY: modified_base
<222> LOCATION: (1059)..(1059)
<223> OTHER INFORMATION: a, c, g, t, unknown or other
<220> FEATURE:
<221> NAME/KEY: modified_base
<222> LOCATION: (1062)..(1062)
<223> OTHER INFORMATION: a, c, g, t, unknown or other
<220> FEATURE:
<221> NAME/KEY: modified_base
<222> LOCATION: (1068)..(1068)
<223> OTHER INFORMATION: a, c, g, t, unknown or other
<220> FEATURE:
<221> NAME/KEY: modified_base
<222> LOCATION: (1071)..(1071)
<223> OTHER INFORMATION: a, c, g, t, unknown or other
<220> FEATURE:
<221> NAME/KEY: modified_base
<222> LOCATION: (1074)..(1074)
<223> OTHER INFORMATION: a, c, g, t, unknown or other
<220> FEATURE:
<221> NAME/KEY: modified_base
<222> LOCATION: (1077)..(1077)
<223> OTHER INFORMATION: a, c, g, t, unknown or other
<220> FEATURE:
<221> NAME/KEY: modified_base
<222> LOCATION: (1080)..(1080)
<223> OTHER INFORMATION: a, c, g, t, unknown or other
<220> FEATURE:
<221> NAME/KEY: modified_base
<222> LOCATION: (1086)..(1086)
<223> OTHER INFORMATION: a, c, g, t, unknown or other
<220> FEATURE:
<221> NAME/KEY: modified_base
<222> LOCATION: (1089)..(1089)
<223> OTHER INFORMATION: a, c, g, t, unknown or other
<220> FEATURE:
<221> NAME/KEY: modified_base
<222> LOCATION: (1092)..(1092)
<223> OTHER INFORMATION: a, c, g, t, unknown or other
<220> FEATURE:
<221> NAME/KEY: modified_base
<222> LOCATION: (1095)..(1095)
<223> OTHER INFORMATION: a, c, g, t, unknown or other
<220> FEATURE:
<221> NAME/KEY: modified_base
<222> LOCATION: (1098)..(1098)
<223> OTHER INFORMATION: a, c, g, t, unknown or other
<220> FEATURE:
<221> NAME/KEY: modified_base
<222> LOCATION: (1101)..(1101)
<223> OTHER INFORMATION: a, c, g, t, unknown or other
<220> FEATURE:
<221> NAME/KEY: modified_base
<222> LOCATION: (1104)..(1104)
<223> OTHER INFORMATION: a, c, g, t, unknown or other
<220> FEATURE:
<221> NAME/KEY: modified_base
<222> LOCATION: (1107)..(1107)
<223> OTHER INFORMATION: a, c, g, t, unknown or other
<220> FEATURE:
<221> NAME/KEY: modified_base
<222> LOCATION: (1110)..(1110)
<223> OTHER INFORMATION: a, c, g, t, unknown or other
<220> FEATURE:
<221> NAME/KEY: modified_base
<222> LOCATION: (1113)..(1113)
<223> OTHER INFORMATION: a, c, g, t, unknown or other
<220> FEATURE:
<221> NAME/KEY: modified_base
<222> LOCATION: (1119)..(1119)
<223> OTHER INFORMATION: a, c, g, t, unknown or other
<220> FEATURE:
<221> NAME/KEY: modified_base
<222> LOCATION: (1125)..(1125)
<223> OTHER INFORMATION: a, c, g, t, unknown or other
<220> FEATURE:
<221> NAME/KEY: modified_base
<222> LOCATION: (1128)..(1128)
<223> OTHER INFORMATION: a, c, g, t, unknown or other
```

```
<220> FEATURE:
<221> NAME/KEY: modified_base
<222> LOCATION: (1131)..(1131)
<223> OTHER INFORMATION: a, c, g, t, unknown or other
<220> FEATURE:
<221> NAME/KEY: modified_base
<222> LOCATION: (1137)..(1137)
<223> OTHER INFORMATION: a, c, g, t, unknown or other
<220> FEATURE:
<221> NAME/KEY: modified_base
<222> LOCATION: (1140)..(1140)
<223> OTHER INFORMATION: a, c, g, t, unknown or other
<220> FEATURE:
<221> NAME/KEY: modified_base
<222> LOCATION: (1146)..(1146)
<223> OTHER INFORMATION: a, c, g, t, unknown or other
<220> FEATURE:
<221> NAME/KEY: modified_base
<222> LOCATION: (1152)..(1152)
<223> OTHER INFORMATION: a, c, g, t, unknown or other
<220> FEATURE:
<221> NAME/KEY: modified_base
<222> LOCATION: (1155)..(1155)
<223> OTHER INFORMATION: a, c, g, t, unknown or other
<220> FEATURE:
<221> NAME/KEY: modified_base
<222> LOCATION: (1158)..(1158)
<223> OTHER INFORMATION: a, c, g, t, unknown or other
<220> FEATURE:
<221> NAME/KEY: modified_base
<222> LOCATION: (1164)..(1164)
<223> OTHER INFORMATION: a, c, g, t, unknown or other
<220> FEATURE:
<221> NAME/KEY: modified_base
<222> LOCATION: (1170)..(1170)
<223> OTHER INFORMATION: a, c, g, t, unknown or other
<220> FEATURE:
<221> NAME/KEY: modified_base
<222> LOCATION: (1173)..(1173)
<223> OTHER INFORMATION: a, c, g, t, unknown or other
<220> FEATURE:
<221> NAME/KEY: modified_base
<222> LOCATION: (1176)..(1176)
<223> OTHER INFORMATION: a, c, g, t, unknown or other
<220> FEATURE:
<221> NAME/KEY: modified_base
<222> LOCATION: (1185)..(1185)
<223> OTHER INFORMATION: a, c, g, t, unknown or other
<220> FEATURE:
<221> NAME/KEY: modified_base
<222> LOCATION: (1206)..(1206)
<223> OTHER INFORMATION: a, c, g, t, unknown or other
<220> FEATURE:
<221> NAME/KEY: modified_base
<222> LOCATION: (1209)..(1209)
<223> OTHER INFORMATION: a, c, g, t, unknown or other
<220> FEATURE:
<221> NAME/KEY: modified_base
<222> LOCATION: (1218)..(1218)
<223> OTHER INFORMATION: a, c, g, t, unknown or other
<220> FEATURE:
<221> NAME/KEY: modified_base
<222> LOCATION: (1221)..(1221)
<223> OTHER INFORMATION: a, c, g, t, unknown or other
<220> FEATURE:
<221> NAME/KEY: modified_base
<222> LOCATION: (1230)..(1230)
<223> OTHER INFORMATION: a, c, g, t, unknown or other
<220> FEATURE:
<221> NAME/KEY: modified_base
<222> LOCATION: (1236)..(1236)
<223> OTHER INFORMATION: a, c, g, t, unknown or other
<220> FEATURE:
<221> NAME/KEY: modified_base
<222> LOCATION: (1239)..(1239)
<223> OTHER INFORMATION: a, c, g, t, unknown or other
<220> FEATURE:
<221> NAME/KEY: modified_base
<222> LOCATION: (1242)..(1242)
<223> OTHER INFORMATION: a, c, g, t, unknown or other
```

-continued

```
<220> FEATURE:
<221> NAME/KEY: modified_base
<222> LOCATION: (1245)..(1245)
<223> OTHER INFORMATION: a, c, g, t, unknown or other
<220> FEATURE:
<221> NAME/KEY: modified_base
<222> LOCATION: (1251)..(1251)
<223> OTHER INFORMATION: a, c, g, t, unknown or other
<220> FEATURE:
<221> NAME/KEY: modified_base
<222> LOCATION: (1254)..(1254)
<223> OTHER INFORMATION: a, c, g, t, unknown or other
<220> FEATURE:
<221> NAME/KEY: modified_base
<222> LOCATION: (1257)..(1257)
<223> OTHER INFORMATION: a, c, g, t, unknown or other
<220> FEATURE:
<221> NAME/KEY: modified_base
<222> LOCATION: (1263)..(1263)
<223> OTHER INFORMATION: a, c, g, t, unknown or other
<220> FEATURE:
<221> NAME/KEY: modified_base
<222> LOCATION: (1272)..(1272)
<223> OTHER INFORMATION: a, c, g, t, unknown or other
<220> FEATURE:
<221> NAME/KEY: modified_base
<222> LOCATION: (1275)..(1275)
<223> OTHER INFORMATION: a, c, g, t, unknown or other
<220> FEATURE:
<221> NAME/KEY: modified_base
<222> LOCATION: (1278)..(1278)
<223> OTHER INFORMATION: a, c, g, t, unknown or other
<220> FEATURE:
<221> NAME/KEY: modified_base
<222> LOCATION: (1281)..(1281)
<223> OTHER INFORMATION: a, c, g, t, unknown or other
<220> FEATURE:
<221> NAME/KEY: modified_base
<222> LOCATION: (1284)..(1284)
<223> OTHER INFORMATION: a, c, g, t, unknown or other
<220> FEATURE:
<221> NAME/KEY: modified_base
<222> LOCATION: (1287)..(1287)
<223> OTHER INFORMATION: a, c, g, t, unknown or other
<220> FEATURE:
<221> NAME/KEY: modified_base
<222> LOCATION: (1299)..(1299)
<223> OTHER INFORMATION: a, c, g, t, unknown or other
<220> FEATURE:
<221> NAME/KEY: modified_base
<222> LOCATION: (1302)..(1302)
<223> OTHER INFORMATION: a, c, g, t, unknown or other
<220> FEATURE:
<221> NAME/KEY: modified_base
<222> LOCATION: (1308)..(1308)
<223> OTHER INFORMATION: a, c, g, t, unknown or other
<220> FEATURE:
<221> NAME/KEY: modified_base
<222> LOCATION: (1314)..(1314)
<223> OTHER INFORMATION: a, c, g, t, unknown or other
<220> FEATURE:
<221> NAME/KEY: modified_base
<222> LOCATION: (1320)..(1320)
<223> OTHER INFORMATION: a, c, g, t, unknown or other
<220> FEATURE:
<221> NAME/KEY: modified_base
<222> LOCATION: (1323)..(1323)
<223> OTHER INFORMATION: a, c, g, t, unknown or other
<220> FEATURE:
<221> NAME/KEY: modified_base
<222> LOCATION: (1326)..(1326)
<223> OTHER INFORMATION: a, c, g, t, unknown or other
<220> FEATURE:
<221> NAME/KEY: modified_base
<222> LOCATION: (1332)..(1332)
<223> OTHER INFORMATION: a, c, g, t, unknown or other
<220> FEATURE:
<221> NAME/KEY: modified_base
<222> LOCATION: (1335)..(1335)
<223> OTHER INFORMATION: a, c, g, t, unknown or other
```

-continued

```
<220> FEATURE:
<221> NAME/KEY: modified_base
<222> LOCATION: (1341)..(1341)
<223> OTHER INFORMATION: a, c, g, t, unknown or other
<220> FEATURE:
<221> NAME/KEY: modified_base
<222> LOCATION: (1350)..(1350)
<223> OTHER INFORMATION: a, c, g, t, unknown or other
<220> FEATURE:
<221> NAME/KEY: modified_base
<222> LOCATION: (1353)..(1353)
<223> OTHER INFORMATION: a, c, g, t, unknown or other
<220> FEATURE:
<221> NAME/KEY: modified_base
<222> LOCATION: (1356)..(1356)
<223> OTHER INFORMATION: a, c, g, t, unknown or other
<220> FEATURE:
<221> NAME/KEY: modified_base
<222> LOCATION: (1362)..(1362)
<223> OTHER INFORMATION: a, c, g, t, unknown or other
<220> FEATURE:
<221> NAME/KEY: modified_base
<222> LOCATION: (1368)..(1368)
<223> OTHER INFORMATION: a, c, g, t, unknown or other
<220> FEATURE:
<221> NAME/KEY: modified_base
<222> LOCATION: (1374)..(1374)
<223> OTHER INFORMATION: a, c, g, t, unknown or other
<220> FEATURE:
<221> NAME/KEY: modified_base
<222> LOCATION: (1377)..(1377)
<223> OTHER INFORMATION: a, c, g, t, unknown or other
<220> FEATURE:
<221> NAME/KEY: modified_base
<222> LOCATION: (1383)..(1383)
<223> OTHER INFORMATION: a, c, g, t, unknown or other
<220> FEATURE:
<221> NAME/KEY: modified_base
<222> LOCATION: (1389)..(1389)
<223> OTHER INFORMATION: a, c, g, t, unknown or other
<220> FEATURE:
<221> NAME/KEY: modified_base
<222> LOCATION: (1398)..(1398)
<223> OTHER INFORMATION: a, c, g, t, unknown or other
<220> FEATURE:
<221> NAME/KEY: modified_base
<222> LOCATION: (1401)..(1401)
<223> OTHER INFORMATION: a, c, g, t, unknown or other
<220> FEATURE:
<221> NAME/KEY: modified_base
<222> LOCATION: (1419)..(1419)
<223> OTHER INFORMATION: a, c, g, t, unknown or other
<220> FEATURE:
<221> NAME/KEY: modified_base
<222> LOCATION: (1422)..(1422)
<223> OTHER INFORMATION: a, c, g, t, unknown or other
<220> FEATURE:
<221> NAME/KEY: modified_base
<222> LOCATION: (1425)..(1425)
<223> OTHER INFORMATION: a, c, g, t, unknown or other
<220> FEATURE:
<221> NAME/KEY: modified_base
<222> LOCATION: (1431)..(1431)
<223> OTHER INFORMATION: a, c, g, t, unknown or other
<220> FEATURE:
<221> NAME/KEY: modified_base
<222> LOCATION: (1440)..(1440)
<223> OTHER INFORMATION: a, c, g, t, unknown or other
<220> FEATURE:
<221> NAME/KEY: modified_base
<222> LOCATION: (1443)..(1443)
<223> OTHER INFORMATION: a, c, g, t, unknown or other
<220> FEATURE:
<221> NAME/KEY: modified_base
<222> LOCATION: (1446)..(1446)
<223> OTHER INFORMATION: a, c, g, t, unknown or other
<220> FEATURE:
<221> NAME/KEY: modified_base
<222> LOCATION: (1467)..(1467)
<223> OTHER INFORMATION: a, c, g, t, unknown or other
```

-continued

```
<220> FEATURE:
<221> NAME/KEY: modified_base
<222> LOCATION: (1470)..(1470)
<223> OTHER INFORMATION: a, c, g, t, unknown or other
<220> FEATURE:
<221> NAME/KEY: modified_base
<222> LOCATION: (1473)..(1473)
<223> OTHER INFORMATION: a, c, g, t, unknown or other
<220> FEATURE:
<221> NAME/KEY: modified_base
<222> LOCATION: (1494)..(1494)
<223> OTHER INFORMATION: a, c, g, t, unknown or other
<220> FEATURE:
<221> NAME/KEY: modified_base
<222> LOCATION: (1497)..(1497)
<223> OTHER INFORMATION: a, c, g, t, unknown or other
<220> FEATURE:
<221> NAME/KEY: modified_base
<222> LOCATION: (1500)..(1500)
<223> OTHER INFORMATION: a, c, g, t, unknown or other
<220> FEATURE:
<221> NAME/KEY: modified_base
<222> LOCATION: (1503)..(1503)
<223> OTHER INFORMATION: a, c, g, t, unknown or other
<220> FEATURE:
<221> NAME/KEY: modified_base
<222> LOCATION: (1506)..(1506)
<223> OTHER INFORMATION: a, c, g, t, unknown or other
<220> FEATURE:
<221> NAME/KEY: modified_base
<222> LOCATION: (1509)..(1509)
<223> OTHER INFORMATION: a, c, g, t, unknown or other
<220> FEATURE:
<221> NAME/KEY: modified_base
<222> LOCATION: (1512)..(1512)
<223> OTHER INFORMATION: a, c, g, t, unknown or other
<220> FEATURE:
<221> NAME/KEY: modified_base
<222> LOCATION: (1515)..(1515)
<223> OTHER INFORMATION: a, c, g, t, unknown or other
<220> FEATURE:
<221> NAME/KEY: modified_base
<222> LOCATION: (1524)..(1524)
<223> OTHER INFORMATION: a, c, g, t, unknown or other
<220> FEATURE:
<221> NAME/KEY: modified_base
<222> LOCATION: (1527)..(1527)
<223> OTHER INFORMATION: a, c, g, t, unknown or other
<220> FEATURE:
<221> NAME/KEY: modified_base
<222> LOCATION: (1533)..(1533)
<223> OTHER INFORMATION: a, c, g, t, unknown or other
<220> FEATURE:
<221> NAME/KEY: modified_base
<222> LOCATION: (1539)..(1539)
<223> OTHER INFORMATION: a, c, g, t, unknown or other
<220> FEATURE:
<221> NAME/KEY: modified_base
<222> LOCATION: (1542)..(1542)
<223> OTHER INFORMATION: a, c, g, t, unknown or other
<220> FEATURE:
<221> NAME/KEY: modified_base
<222> LOCATION: (1548)..(1548)
<223> OTHER INFORMATION: a, c, g, t, unknown or other
<220> FEATURE:
<221> NAME/KEY: modified_base
<222> LOCATION: (1569)..(1569)
<223> OTHER INFORMATION: a, c, g, t, unknown or other
<220> FEATURE:
<221> NAME/KEY: modified_base
<222> LOCATION: (1578)..(1578)
<223> OTHER INFORMATION: a, c, g, t, unknown or other
<220> FEATURE:
<221> NAME/KEY: modified_base
<222> LOCATION: (1584)..(1584)
<223> OTHER INFORMATION: a, c, g, t, unknown or other
<220> FEATURE:
<221> NAME/KEY: modified_base
<222> LOCATION: (1587)..(1587)
<223> OTHER INFORMATION: a, c, g, t, unknown or other
```

```
<220> FEATURE:
<221> NAME/KEY: modified_base
<222> LOCATION: (1590)..(1590)
<223> OTHER INFORMATION: a, c, g, t, unknown or other
<220> FEATURE:
<221> NAME/KEY: modified_base
<222> LOCATION: (1593)..(1593)
<223> OTHER INFORMATION: a, c, g, t, unknown or other
<220> FEATURE:
<221> NAME/KEY: modified_base
<222> LOCATION: (1605)..(1605)
<223> OTHER INFORMATION: a, c, g, t, unknown or other
<220> FEATURE:
<221> NAME/KEY: modified_base
<222> LOCATION: (1608)..(1608)
<223> OTHER INFORMATION: a, c, g, t, unknown or other
<220> FEATURE:
<221> NAME/KEY: modified_base
<222> LOCATION: (1611)..(1611)
<223> OTHER INFORMATION: a, c, g, t, unknown or other
<220> FEATURE:
<221> NAME/KEY: modified_base
<222> LOCATION: (1614)..(1614)
<223> OTHER INFORMATION: a, c, g, t, unknown or other
<220> FEATURE:
<221> NAME/KEY: modified_base
<222> LOCATION: (1617)..(1617)
<223> OTHER INFORMATION: a, c, g, t, unknown or other
<220> FEATURE:
<221> NAME/KEY: modified_base
<222> LOCATION: (1620)..(1620)
<223> OTHER INFORMATION: a, c, g, t, unknown or other
<220> FEATURE:
<221> NAME/KEY: modified_base
<222> LOCATION: (1623)..(1623)
<223> OTHER INFORMATION: a, c, g, t, unknown or other
<220> FEATURE:
<221> NAME/KEY: modified_base
<222> LOCATION: (1632)..(1632)
<223> OTHER INFORMATION: a, c, g, t, unknown or other
<220> FEATURE:
<221> NAME/KEY: modified_base
<222> LOCATION: (1641)..(1641)
<223> OTHER INFORMATION: a, c, g, t, unknown or other
<220> FEATURE:
<221> NAME/KEY: modified_base
<222> LOCATION: (1644)..(1644)
<223> OTHER INFORMATION: a, c, g, t, unknown or other
<220> FEATURE:
<221> NAME/KEY: modified_base
<222> LOCATION: (1647)..(1647)
<223> OTHER INFORMATION: a, c, g, t, unknown or other
<220> FEATURE:
<221> NAME/KEY: modified_base
<222> LOCATION: (1650)..(1650)
<223> OTHER INFORMATION: a, c, g, t, unknown or other
<220> FEATURE:
<221> NAME/KEY: modified_base
<222> LOCATION: (1656)..(1656)
<223> OTHER INFORMATION: a, c, g, t, unknown or other
<220> FEATURE:
<221> NAME/KEY: modified_base
<222> LOCATION: (1662)..(1662)
<223> OTHER INFORMATION: a, c, g, t, unknown or other
<220> FEATURE:
<221> NAME/KEY: modified_base
<222> LOCATION: (1665)..(1665)
<223> OTHER INFORMATION: a, c, g, t, unknown or other
<220> FEATURE:
<221> NAME/KEY: modified_base
<222> LOCATION: (1671)..(1671)
<223> OTHER INFORMATION: a, c, g, t, unknown or other
<220> FEATURE:
<221> NAME/KEY: modified_base
<222> LOCATION: (1674)..(1674)
<223> OTHER INFORMATION: a, c, g, t, unknown or other
<220> FEATURE:
<221> NAME/KEY: modified_base
<222> LOCATION: (1683)..(1683)
<223> OTHER INFORMATION: a, c, g, t, unknown or other
```

```
-continued

<220> FEATURE:
<221> NAME/KEY: modified_base
<222> LOCATION: (1695)..(1695)
<223> OTHER INFORMATION: a, c, g, t, unknown or other
<220> FEATURE:
<221> NAME/KEY: modified_base
<222> LOCATION: (1701)..(1701)
<223> OTHER INFORMATION: a, c, g, t, unknown or other
<220> FEATURE:
<221> NAME/KEY: modified_base
<222> LOCATION: (1707)..(1707)
<223> OTHER INFORMATION: a, c, g, t, unknown or other
<220> FEATURE:
<221> NAME/KEY: modified_base
<222> LOCATION: (1710)..(1710)
<223> OTHER INFORMATION: a, c, g, t, unknown or other
<220> FEATURE:
<221> NAME/KEY: modified_base
<222> LOCATION: (1719)..(1719)
<223> OTHER INFORMATION: a, c, g, t, unknown or other
<220> FEATURE:
<221> NAME/KEY: modified_base
<222> LOCATION: (1725)..(1725)
<223> OTHER INFORMATION: a, c, g, t, unknown or other
<220> FEATURE:
<221> NAME/KEY: modified_base
<222> LOCATION: (1728)..(1728)
<223> OTHER INFORMATION: a, c, g, t, unknown or other
<220> FEATURE:
<221> NAME/KEY: modified_base
<222> LOCATION: (1740)..(1740)
<223> OTHER INFORMATION: a, c, g, t, unknown or other
<220> FEATURE:
<221> NAME/KEY: modified_base
<222> LOCATION: (1743)..(1743)
<223> OTHER INFORMATION: a, c, g, t, unknown or other
<220> FEATURE:
<221> NAME/KEY: modified_base
<222> LOCATION: (1746)..(1746)
<223> OTHER INFORMATION: a, c, g, t, unknown or other
<220> FEATURE:
<221> NAME/KEY: modified_base
<222> LOCATION: (1752)..(1752)
<223> OTHER INFORMATION: a, c, g, t, unknown or other
<220> FEATURE:
<221> NAME/KEY: modified_base
<222> LOCATION: (1755)..(1755)
<223> OTHER INFORMATION: a, c, g, t, unknown or other
<220> FEATURE:
<221> NAME/KEY: modified_base
<222> LOCATION: (1758)..(1758)
<223> OTHER INFORMATION: a, c, g, t, unknown or other
<220> FEATURE:
<221> NAME/KEY: modified_base
<222> LOCATION: (1761)..(1761)
<223> OTHER INFORMATION: a, c, g, t, unknown or other
<220> FEATURE:
<221> NAME/KEY: modified_base
<222> LOCATION: (1767)..(1767)
<223> OTHER INFORMATION: a, c, g, t, unknown or other
<220> FEATURE:
<221> NAME/KEY: modified_base
<222> LOCATION: (1773)..(1773)
<223> OTHER INFORMATION: a, c, g, t, unknown or other
<220> FEATURE:
<221> NAME/KEY: modified_base
<222> LOCATION: (1785)..(1785)
<223> OTHER INFORMATION: a, c, g, t, unknown or other
<220> FEATURE:
<221> NAME/KEY: modified_base
<222> LOCATION: (1791)..(1791)
<223> OTHER INFORMATION: a, c, g, t, unknown or other
<220> FEATURE:
<221> NAME/KEY: modified_base
<222> LOCATION: (1803)..(1803)
<223> OTHER INFORMATION: a, c, g, t, unknown or other
<220> FEATURE:
<221> NAME/KEY: modified_base
<222> LOCATION: (1806)..(1806)
<223> OTHER INFORMATION: a, c, g, t, unknown or other
```

```
<220> FEATURE:
<221> NAME/KEY: modified_base
<222> LOCATION: (1815)..(1815)
<223> OTHER INFORMATION: a, c, g, t, unknown or other
<220> FEATURE:
<221> NAME/KEY: modified_base
<222> LOCATION: (1818)..(1818)
<223> OTHER INFORMATION: a, c, g, t, unknown or other
<220> FEATURE:
<221> NAME/KEY: modified_base
<222> LOCATION: (1824)..(1824)
<223> OTHER INFORMATION: a, c, g, t, unknown or other
<220> FEATURE:
<221> NAME/KEY: modified_base
<222> LOCATION: (1827)..(1827)
<223> OTHER INFORMATION: a, c, g, t, unknown or other
<220> FEATURE:
<221> NAME/KEY: modified_base
<222> LOCATION: (1839)..(1839)
<223> OTHER INFORMATION: a, c, g, t, unknown or other
<220> FEATURE:
<221> NAME/KEY: modified_base
<222> LOCATION: (1842)..(1842)
<223> OTHER INFORMATION: a, c, g, t, unknown or other
<220> FEATURE:
<221> NAME/KEY: modified_base
<222> LOCATION: (1848)..(1848)
<223> OTHER INFORMATION: a, c, g, t, unknown or other
<220> FEATURE:
<221> NAME/KEY: modified_base
<222> LOCATION: (1851)..(1851)
<223> OTHER INFORMATION: a, c, g, t, unknown or other
<220> FEATURE:
<221> NAME/KEY: modified_base
<222> LOCATION: (1857)..(1857)
<223> OTHER INFORMATION: a, c, g, t, unknown or other
<220> FEATURE:
<221> NAME/KEY: modified_base
<222> LOCATION: (1860)..(1860)
<223> OTHER INFORMATION: a, c, g, t, unknown or other
<220> FEATURE:
<221> NAME/KEY: modified_base
<222> LOCATION: (1863)..(1863)
<223> OTHER INFORMATION: a, c, g, t, unknown or other
<220> FEATURE:
<221> NAME/KEY: modified_base
<222> LOCATION: (1881)..(1881)
<223> OTHER INFORMATION: a, c, g, t, unknown or other
<220> FEATURE:
<221> NAME/KEY: modified_base
<222> LOCATION: (1884)..(1884)
<223> OTHER INFORMATION: a, c, g, t, unknown or other
<220> FEATURE:
<221> NAME/KEY: modified_base
<222> LOCATION: (1887)..(1887)
<223> OTHER INFORMATION: a, c, g, t, unknown or other
<220> FEATURE:
<221> NAME/KEY: modified_base
<222> LOCATION: (1890)..(1890)
<223> OTHER INFORMATION: a, c, g, t, unknown or other
<220> FEATURE:
<221> NAME/KEY: modified_base
<222> LOCATION: (1899)..(1899)
<223> OTHER INFORMATION: a, c, g, t, unknown or other
<220> FEATURE:
<221> NAME/KEY: modified_base
<222> LOCATION: (1902)..(1902)
<223> OTHER INFORMATION: a, c, g, t, unknown or other
<220> FEATURE:
<221> NAME/KEY: modified_base
<222> LOCATION: (1911)..(1911)
<223> OTHER INFORMATION: a, c, g, t, unknown or other
<220> FEATURE:
<221> NAME/KEY: modified_base
<222> LOCATION: (1914)..(1914)
<223> OTHER INFORMATION: a, c, g, t, unknown or other
<220> FEATURE:
<221> NAME/KEY: modified_base
<222> LOCATION: (1917)..(1917)
<223> OTHER INFORMATION: a, c, g, t, unknown or other
```

```
<220> FEATURE:
<221> NAME/KEY: modified_base
<222> LOCATION: (1926)..(1926)
<223> OTHER INFORMATION: a, c, g, t, unknown or other
<220> FEATURE:
<221> NAME/KEY: modified_base
<222> LOCATION: (1935)..(1935)
<223> OTHER INFORMATION: a, c, g, t, unknown or other
<220> FEATURE:
<221> NAME/KEY: modified_base
<222> LOCATION: (1944)..(1944)
<223> OTHER INFORMATION: a, c, g, t, unknown or other
<220> FEATURE:
<221> NAME/KEY: modified_base
<222> LOCATION: (1947)..(1947)
<223> OTHER INFORMATION: a, c, g, t, unknown or other
<220> FEATURE:
<221> NAME/KEY: modified_base
<222> LOCATION: (1950)..(1950)
<223> OTHER INFORMATION: a, c, g, t, unknown or other
<220> FEATURE:
<221> NAME/KEY: modified_base
<222> LOCATION: (1953)..(1953)
<223> OTHER INFORMATION: a, c, g, t, unknown or other
<220> FEATURE:
<221> NAME/KEY: modified_base
<222> LOCATION: (1956)..(1956)
<223> OTHER INFORMATION: a, c, g, t, unknown or other
<220> FEATURE:
<221> NAME/KEY: modified_base
<222> LOCATION: (1959)..(1959)
<223> OTHER INFORMATION: a, c, g, t, unknown or other
<220> FEATURE:
<221> NAME/KEY: modified_base
<222> LOCATION: (1965)..(1965)
<223> OTHER INFORMATION: a, c, g, t, unknown or other
<220> FEATURE:
<221> NAME/KEY: modified_base
<222> LOCATION: (1968)..(1968)
<223> OTHER INFORMATION: a, c, g, t, unknown or other
<220> FEATURE:
<221> NAME/KEY: modified_base
<222> LOCATION: (1974)..(1974)
<223> OTHER INFORMATION: a, c, g, t, unknown or other
<220> FEATURE:
<221> NAME/KEY: modified_base
<222> LOCATION: (1977)..(1977)
<223> OTHER INFORMATION: a, c, g, t, unknown or other
<220> FEATURE:
<221> NAME/KEY: modified_base
<222> LOCATION: (1980)..(1980)
<223> OTHER INFORMATION: a, c, g, t, unknown or other
<220> FEATURE:
<221> NAME/KEY: modified_base
<222> LOCATION: (1986)..(1986)
<223> OTHER INFORMATION: a, c, g, t, unknown or other
<220> FEATURE:
<221> NAME/KEY: modified_base
<222> LOCATION: (1992)..(1992)
<223> OTHER INFORMATION: a, c, g, t, unknown or other
<220> FEATURE:
<221> NAME/KEY: modified_base
<222> LOCATION: (1998)..(1998)
<223> OTHER INFORMATION: a, c, g, t, unknown or other
<220> FEATURE:
<221> NAME/KEY: modified_base
<222> LOCATION: (2001)..(2001)
<223> OTHER INFORMATION: a, c, g, t, unknown or other
<220> FEATURE:
<221> NAME/KEY: modified_base
<222> LOCATION: (2004)..(2004)
<223> OTHER INFORMATION: a, c, g, t, unknown or other
<220> FEATURE:
<221> NAME/KEY: modified_base
<222> LOCATION: (2007)..(2007)
<223> OTHER INFORMATION: a, c, g, t, unknown or other
<220> FEATURE:
<221> NAME/KEY: modified_base
<222> LOCATION: (2010)..(2010)
<223> OTHER INFORMATION: a, c, g, t, unknown or other
```

-continued

```
<220> FEATURE:
<221> NAME/KEY: modified_base
<222> LOCATION: (2013)..(2013)
<223> OTHER INFORMATION: a, c, g, t, unknown or other
<220> FEATURE:
<221> NAME/KEY: modified_base
<222> LOCATION: (2016)..(2016)
<223> OTHER INFORMATION: a, c, g, t, unknown or other
<220> FEATURE:
<221> NAME/KEY: modified_base
<222> LOCATION: (2019)..(2019)
<223> OTHER INFORMATION: a, c, g, t, unknown or other
<220> FEATURE:
<221> NAME/KEY: modified_base
<222> LOCATION: (2022)..(2022)
<223> OTHER INFORMATION: a, c, g, t, unknown or other
<220> FEATURE:
<221> NAME/KEY: modified_base
<222> LOCATION: (2025)..(2025)
<223> OTHER INFORMATION: a, c, g, t, unknown or other
<220> FEATURE:
<221> NAME/KEY: modified_base
<222> LOCATION: (2028)..(2028)
<223> OTHER INFORMATION: a, c, g, t, unknown or other
<220> FEATURE:
<221> NAME/KEY: modified_base
<222> LOCATION: (2031)..(2031)
<223> OTHER INFORMATION: a, c, g, t, unknown or other
<220> FEATURE:
<221> NAME/KEY: modified_base
<222> LOCATION: (2034)..(2034)
<223> OTHER INFORMATION: a, c, g, t, unknown or other
<220> FEATURE:
<221> NAME/KEY: modified_base
<222> LOCATION: (2037)..(2037)
<223> OTHER INFORMATION: a, c, g, t, unknown or other
<220> FEATURE:
<221> NAME/KEY: modified_base
<222> LOCATION: (2040)..(2040)
<223> OTHER INFORMATION: a, c, g, t, unknown or other
<220> FEATURE:
<221> NAME/KEY: modified_base
<222> LOCATION: (2046)..(2046)
<223> OTHER INFORMATION: a, c, g, t, unknown or other
<220> FEATURE:
<221> NAME/KEY: modified_base
<222> LOCATION: (2049)..(2049)
<223> OTHER INFORMATION: a, c, g, t, unknown or other
<220> FEATURE:
<221> NAME/KEY: modified_base
<222> LOCATION: (2055)..(2055)
<223> OTHER INFORMATION: a, c, g, t, unknown or other
<220> FEATURE:
<221> NAME/KEY: modified_base
<222> LOCATION: (2064)..(2064)
<223> OTHER INFORMATION: a, c, g, t, unknown or other
<220> FEATURE:
<221> NAME/KEY: modified_base
<222> LOCATION: (2070)..(2070)
<223> OTHER INFORMATION: a, c, g, t, unknown or other
<220> FEATURE:
<221> NAME/KEY: modified_base
<222> LOCATION: (2073)..(2073)
<223> OTHER INFORMATION: a, c, g, t, unknown or other
<220> FEATURE:
<221> NAME/KEY: modified_base
<222> LOCATION: (2079)..(2079)
<223> OTHER INFORMATION: a, c, g, t, unknown or other
<220> FEATURE:
<221> NAME/KEY: modified_base
<222> LOCATION: (2082)..(2082)
<223> OTHER INFORMATION: a, c, g, t, unknown or other
<220> FEATURE:
<221> NAME/KEY: modified_base
<222> LOCATION: (2085)..(2085)
<223> OTHER INFORMATION: a, c, g, t, unknown or other
<220> FEATURE:
<221> NAME/KEY: modified_base
<222> LOCATION: (2088)..(2088)
<223> OTHER INFORMATION: a, c, g, t, unknown or other
```

```
<220> FEATURE:
<221> NAME/KEY: modified_base
<222> LOCATION: (2091)..(2091)
<223> OTHER INFORMATION: a, c, g, t, unknown or other
<220> FEATURE:
<221> NAME/KEY: modified_base
<222> LOCATION: (2097)..(2097)
<223> OTHER INFORMATION: a, c, g, t, unknown or other
<220> FEATURE:
<221> NAME/KEY: modified_base
<222> LOCATION: (2103)..(2103)
<223> OTHER INFORMATION: a, c, g, t, unknown or other
<220> FEATURE:
<221> NAME/KEY: modified_base
<222> LOCATION: (2106)..(2106)
<223> OTHER INFORMATION: a, c, g, t, unknown or other
<220> FEATURE:
<221> NAME/KEY: modified_base
<222> LOCATION: (2109)..(2109)
<223> OTHER INFORMATION: a, c, g, t, unknown or other
<220> FEATURE:
<221> NAME/KEY: modified_base
<222> LOCATION: (2115)..(2115)
<223> OTHER INFORMATION: a, c, g, t, unknown or other
<220> FEATURE:
<221> NAME/KEY: modified_base
<222> LOCATION: (2118)..(2118)
<223> OTHER INFORMATION: a, c, g, t, unknown or other
<220> FEATURE:
<221> NAME/KEY: modified_base
<222> LOCATION: (2121)..(2121)
<223> OTHER INFORMATION: a, c, g, t, unknown or other
<220> FEATURE:
<221> NAME/KEY: modified_base
<222> LOCATION: (2124)..(2124)
<223> OTHER INFORMATION: a, c, g, t, unknown or other
<220> FEATURE:
<221> NAME/KEY: modified_base
<222> LOCATION: (2127)..(2127)
<223> OTHER INFORMATION: a, c, g, t, unknown or other
<220> FEATURE:
<221> NAME/KEY: modified_base
<222> LOCATION: (2130)..(2130)
<223> OTHER INFORMATION: a, c, g, t, unknown or other
<220> FEATURE:
<221> NAME/KEY: modified_base
<222> LOCATION: (2133)..(2133)
<223> OTHER INFORMATION: a, c, g, t, unknown or other
<220> FEATURE:
<221> NAME/KEY: modified_base
<222> LOCATION: (2154)..(2154)
<223> OTHER INFORMATION: a, c, g, t, unknown or other
<220> FEATURE:
<221> NAME/KEY: modified_base
<222> LOCATION: (2157)..(2157)
<223> OTHER INFORMATION: a, c, g, t, unknown or other
<220> FEATURE:
<221> NAME/KEY: modified_base
<222> LOCATION: (2169)..(2169)
<223> OTHER INFORMATION: a, c, g, t, unknown or other
<220> FEATURE:
<221> NAME/KEY: modified_base
<222> LOCATION: (2172)..(2172)
<223> OTHER INFORMATION: a, c, g, t, unknown or other
<220> FEATURE:
<221> NAME/KEY: modified_base
<222> LOCATION: (2175)..(2175)
<223> OTHER INFORMATION: a, c, g, t, unknown or other
<220> FEATURE:
<221> NAME/KEY: modified_base
<222> LOCATION: (2178)..(2178)
<223> OTHER INFORMATION: a, c, g, t, unknown or other
<220> FEATURE:
<221> NAME/KEY: modified_base
<222> LOCATION: (2181)..(2181)
<223> OTHER INFORMATION: a, c, g, t, unknown or other
<220> FEATURE:
<221> NAME/KEY: modified_base
<222> LOCATION: (2184)..(2184)
<223> OTHER INFORMATION: a, c, g, t, unknown or other
```

```
-continued

<220> FEATURE:
<221> NAME/KEY: modified_base
<222> LOCATION: (2187)..(2187)
<223> OTHER INFORMATION: a, c, g, t, unknown or other
<220> FEATURE:
<221> NAME/KEY: modified_base
<222> LOCATION: (2193)..(2193)
<223> OTHER INFORMATION: a, c, g, t, unknown or other
<220> FEATURE:
<221> NAME/KEY: modified_base
<222> LOCATION: (2196)..(2196)
<223> OTHER INFORMATION: a, c, g, t, unknown or other
<220> FEATURE:
<221> NAME/KEY: modified_base
<222> LOCATION: (2202)..(2202)
<223> OTHER INFORMATION: a, c, g, t, unknown or other
<220> FEATURE:
<221> NAME/KEY: modified_base
<222> LOCATION: (2211)..(2211)
<223> OTHER INFORMATION: a, c, g, t, unknown or other
<220> FEATURE:
<221> NAME/KEY: modified_base
<222> LOCATION: (2214)..(2214)
<223> OTHER INFORMATION: a, c, g, t, unknown or other
<220> FEATURE:
<221> NAME/KEY: modified_base
<222> LOCATION: (2217)..(2217)
<223> OTHER INFORMATION: a, c, g, t, unknown or other
<220> FEATURE:
<221> NAME/KEY: modified_base
<222> LOCATION: (2220)..(2220)
<223> OTHER INFORMATION: a, c, g, t, unknown or other
<220> FEATURE:
<221> NAME/KEY: modified_base
<222> LOCATION: (2223)..(2223)
<223> OTHER INFORMATION: a, c, g, t, unknown or other
<220> FEATURE:
<221> NAME/KEY: modified_base
<222> LOCATION: (2226)..(2226)
<223> OTHER INFORMATION: a, c, g, t, unknown or other
<220> FEATURE:
<221> NAME/KEY: modified_base
<222> LOCATION: (2229)..(2229)
<223> OTHER INFORMATION: a, c, g, t, unknown or other
<220> FEATURE:
<221> NAME/KEY: modified_base
<222> LOCATION: (2232)..(2232)
<223> OTHER INFORMATION: a, c, g, t, unknown or other
<220> FEATURE:
<221> NAME/KEY: modified_base
<222> LOCATION: (2235)..(2235)
<223> OTHER INFORMATION: a, c, g, t, unknown or other
<220> FEATURE:
<221> NAME/KEY: modified_base
<222> LOCATION: (2238)..(2238)
<223> OTHER INFORMATION: a, c, g, t, unknown or other
<220> FEATURE:
<221> NAME/KEY: modified_base
<222> LOCATION: (2244)..(2244)
<223> OTHER INFORMATION: a, c, g, t, unknown or other
<220> FEATURE:
<221> NAME/KEY: modified_base
<222> LOCATION: (2247)..(2247)
<223> OTHER INFORMATION: a, c, g, t, unknown or other
<220> FEATURE:
<221> NAME/KEY: modified_base
<222> LOCATION: (2253)..(2253)
<223> OTHER INFORMATION: a, c, g, t, unknown or other
<220> FEATURE:
<221> NAME/KEY: modified_base
<222> LOCATION: (2256)..(2256)
<223> OTHER INFORMATION: a, c, g, t, unknown or other
<220> FEATURE:
<221> NAME/KEY: modified_base
<222> LOCATION: (2259)..(2259)
<223> OTHER INFORMATION: a, c, g, t, unknown or other
<220> FEATURE:
<221> NAME/KEY: modified_base
<222> LOCATION: (2265)..(2265)
<223> OTHER INFORMATION: a, c, g, t, unknown or other
```

-continued

```
<220> FEATURE:
<221> NAME/KEY: modified_base
<222> LOCATION: (2280)..(2280)
<223> OTHER INFORMATION: a, c, g, t, unknown or other
<220> FEATURE:
<221> NAME/KEY: modified_base
<222> LOCATION: (2283)..(2283)
<223> OTHER INFORMATION: a, c, g, t, unknown or other
<220> FEATURE:
<221> NAME/KEY: modified_base
<222> LOCATION: (2286)..(2286)
<223> OTHER INFORMATION: a, c, g, t, unknown or other
<220> FEATURE:
<221> NAME/KEY: modified_base
<222> LOCATION: (2289)..(2289)
<223> OTHER INFORMATION: a, c, g, t, unknown or other
<220> FEATURE:
<221> NAME/KEY: modified_base
<222> LOCATION: (2292)..(2292)
<223> OTHER INFORMATION: a, c, g, t, unknown or other
<220> FEATURE:
<221> NAME/KEY: modified_base
<222> LOCATION: (2295)..(2295)
<223> OTHER INFORMATION: a, c, g, t, unknown or other
<220> FEATURE:
<221> NAME/KEY: modified_base
<222> LOCATION: (2301)..(2301)
<223> OTHER INFORMATION: a, c, g, t, unknown or other
<220> FEATURE:
<221> NAME/KEY: modified_base
<222> LOCATION: (2304)..(2304)
<223> OTHER INFORMATION: a, c, g, t, unknown or other
<220> FEATURE:
<221> NAME/KEY: modified_base
<222> LOCATION: (2307)..(2307)
<223> OTHER INFORMATION: a, c, g, t, unknown or other
<220> FEATURE:
<221> NAME/KEY: modified_base
<222> LOCATION: (2310)..(2310)
<223> OTHER INFORMATION: a, c, g, t, unknown or other
<220> FEATURE:
<221> NAME/KEY: modified_base
<222> LOCATION: (2313)..(2313)
<223> OTHER INFORMATION: a, c, g, t, unknown or other
<220> FEATURE:
<221> NAME/KEY: modified_base
<222> LOCATION: (2319)..(2319)
<223> OTHER INFORMATION: a, c, g, t, unknown or other
<220> FEATURE:
<221> NAME/KEY: modified_base
<222> LOCATION: (2322)..(2322)
<223> OTHER INFORMATION: a, c, g, t, unknown or other
<220> FEATURE:
<221> NAME/KEY: modified_base
<222> LOCATION: (2325)..(2325)
<223> OTHER INFORMATION: a, c, g, t, unknown or other
<220> FEATURE:
<221> NAME/KEY: modified_base
<222> LOCATION: (2328)..(2328)
<223> OTHER INFORMATION: a, c, g, t, unknown or other
<220> FEATURE:
<221> NAME/KEY: modified_base
<222> LOCATION: (2331)..(2331)
<223> OTHER INFORMATION: a, c, g, t, unknown or other
<220> FEATURE:
<221> NAME/KEY: modified_base
<222> LOCATION: (2334)..(2334)
<223> OTHER INFORMATION: a, c, g, t, unknown or other
<220> FEATURE:
<221> NAME/KEY: modified_base
<222> LOCATION: (2337)..(2337)
<223> OTHER INFORMATION: a, c, g, t, unknown or other
<220> FEATURE:
<221> NAME/KEY: modified_base
<222> LOCATION: (2340)..(2340)
<223> OTHER INFORMATION: a, c, g, t, unknown or other
<220> FEATURE:
<221> NAME/KEY: modified_base
<222> LOCATION: (2346)..(2346)
<223> OTHER INFORMATION: a, c, g, t, unknown or other
```

-continued

```
<220> FEATURE:
<221> NAME/KEY: modified_base
<222> LOCATION: (2355)..(2355)
<223> OTHER INFORMATION: a, c, g, t, unknown or other
<220> FEATURE:
<221> NAME/KEY: modified_base
<222> LOCATION: (2358)..(2358)
<223> OTHER INFORMATION: a, c, g, t, unknown or other
<220> FEATURE:
<221> NAME/KEY: modified_base
<222> LOCATION: (2367)..(2367)
<223> OTHER INFORMATION: a, c, g, t, unknown or other
<220> FEATURE:
<221> NAME/KEY: modified_base
<222> LOCATION: (2370)..(2370)
<223> OTHER INFORMATION: a, c, g, t, unknown or other
<220> FEATURE:
<221> NAME/KEY: modified_base
<222> LOCATION: (2376)..(2376)
<223> OTHER INFORMATION: a, c, g, t, unknown or other
<220> FEATURE:
<221> NAME/KEY: modified_base
<222> LOCATION: (2379)..(2379)
<223> OTHER INFORMATION: a, c, g, t, unknown or other
<220> FEATURE:
<221> NAME/KEY: modified_base
<222> LOCATION: (2382)..(2382)
<223> OTHER INFORMATION: a, c, g, t, unknown or other
<220> FEATURE:
<221> NAME/KEY: modified_base
<222> LOCATION: (2385)..(2385)
<223> OTHER INFORMATION: a, c, g, t, unknown or other
<220> FEATURE:
<221> NAME/KEY: modified_base
<222> LOCATION: (2388)..(2388)
<223> OTHER INFORMATION: a, c, g, t, unknown or other
<220> FEATURE:
<221> NAME/KEY: modified_base
<222> LOCATION: (2391)..(2391)
<223> OTHER INFORMATION: a, c, g, t, unknown or other
<220> FEATURE:
<221> NAME/KEY: modified_base
<222> LOCATION: (2397)..(2397)
<223> OTHER INFORMATION: a, c, g, t, unknown or other
<220> FEATURE:
<221> NAME/KEY: modified_base
<222> LOCATION: (2403)..(2403)
<223> OTHER INFORMATION: a, c, g, t, unknown or other
<220> FEATURE:
<221> NAME/KEY: modified_base
<222> LOCATION: (2412)..(2412)
<223> OTHER INFORMATION: a, c, g, t, unknown or other
<220> FEATURE:
<221> NAME/KEY: modified_base
<222> LOCATION: (2415)..(2415)
<223> OTHER INFORMATION: a, c, g, t, unknown or other
<220> FEATURE:
<221> NAME/KEY: modified_base
<222> LOCATION: (2418)..(2418)
<223> OTHER INFORMATION: a, c, g, t, unknown or other
<220> FEATURE:
<221> NAME/KEY: modified_base
<222> LOCATION: (2421)..(2421)
<223> OTHER INFORMATION: a, c, g, t, unknown or other
<220> FEATURE:
<221> NAME/KEY: modified_base
<222> LOCATION: (2427)..(2427)
<223> OTHER INFORMATION: a, c, g, t, unknown or other
<220> FEATURE:
<221> NAME/KEY: modified_base
<222> LOCATION: (2439)..(2439)
<223> OTHER INFORMATION: a, c, g, t, unknown or other
<220> FEATURE:
<221> NAME/KEY: modified_base
<222> LOCATION: (2445)..(2445)
<223> OTHER INFORMATION: a, c, g, t, unknown or other
<220> FEATURE:
<221> NAME/KEY: modified_base
<222> LOCATION: (2454)..(2454)
<223> OTHER INFORMATION: a, c, g, t, unknown or other
```

```
<220> FEATURE:
<221> NAME/KEY: modified_base
<222> LOCATION: (2457)..(2457)
<223> OTHER INFORMATION: a, c, g, t, unknown or other
<220> FEATURE:
<221> NAME/KEY: modified_base
<222> LOCATION: (2460)..(2460)
<223> OTHER INFORMATION: a, c, g, t, unknown or other
<220> FEATURE:
<221> NAME/KEY: modified_base
<222> LOCATION: (2463)..(2463)
<223> OTHER INFORMATION: a, c, g, t, unknown or other
<220> FEATURE:
<221> NAME/KEY: modified_base
<222> LOCATION: (2466)..(2466)
<223> OTHER INFORMATION: a, c, g, t, unknown or other
<220> FEATURE:
<221> NAME/KEY: modified_base
<222> LOCATION: (2472)..(2472)
<223> OTHER INFORMATION: a, c, g, t, unknown or other
<220> FEATURE:
<221> NAME/KEY: modified_base
<222> LOCATION: (2478)..(2478)
<223> OTHER INFORMATION: a, c, g, t, unknown or other
<220> FEATURE:
<221> NAME/KEY: modified_base
<222> LOCATION: (2481)..(2481)
<223> OTHER INFORMATION: a, c, g, t, unknown or other
<220> FEATURE:
<221> NAME/KEY: modified_base
<222> LOCATION: (2484)..(2484)
<223> OTHER INFORMATION: a, c, g, t, unknown or other
<220> FEATURE:
<221> NAME/KEY: modified_base
<222> LOCATION: (2487)..(2487)
<223> OTHER INFORMATION: a, c, g, t, unknown or other
<220> FEATURE:
<221> NAME/KEY: modified_base
<222> LOCATION: (2490)..(2490)
<223> OTHER INFORMATION: a, c, g, t, unknown or other
<220> FEATURE:
<221> NAME/KEY: modified_base
<222> LOCATION: (2505)..(2505)
<223> OTHER INFORMATION: a, c, g, t, unknown or other
<220> FEATURE:
<221> NAME/KEY: modified_base
<222> LOCATION: (2511)..(2511)
<223> OTHER INFORMATION: a, c, g, t, unknown or other
<220> FEATURE:
<221> NAME/KEY: modified_base
<222> LOCATION: (2514)..(2514)
<223> OTHER INFORMATION: a, c, g, t, unknown or other
<220> FEATURE:
<221> NAME/KEY: modified_base
<222> LOCATION: (2520)..(2520)
<223> OTHER INFORMATION: a, c, g, t, unknown or other
<220> FEATURE:
<221> NAME/KEY: modified_base
<222> LOCATION: (2523)..(2523)
<223> OTHER INFORMATION: a, c, g, t, unknown or other
<220> FEATURE:
<221> NAME/KEY: modified_base
<222> LOCATION: (2535)..(2535)
<223> OTHER INFORMATION: a, c, g, t, unknown or other
<220> FEATURE:
<221> NAME/KEY: modified_base
<222> LOCATION: (2538)..(2538)
<223> OTHER INFORMATION: a, c, g, t, unknown or other
<220> FEATURE:
<221> NAME/KEY: modified_base
<222> LOCATION: (2541)..(2541)
<223> OTHER INFORMATION: a, c, g, t, unknown or other
<220> FEATURE:
<221> NAME/KEY: modified_base
<222> LOCATION: (2544)..(2544)
<223> OTHER INFORMATION: a, c, g, t, unknown or other
<220> FEATURE:
<221> NAME/KEY: modified_base
<222> LOCATION: (2547)..(2547)
<223> OTHER INFORMATION: a, c, g, t, unknown or other
```

-continued

```
<220> FEATURE:
<221> NAME/KEY: modified_base
<222> LOCATION: (2550)..(2550)
<223> OTHER INFORMATION: a, c, g, t, unknown or other
<220> FEATURE:
<221> NAME/KEY: modified_base
<222> LOCATION: (2553)..(2553)
<223> OTHER INFORMATION: a, c, g, t, unknown or other
<220> FEATURE:
<221> NAME/KEY: modified_base
<222> LOCATION: (2556)..(2556)
<223> OTHER INFORMATION: a, c, g, t, unknown or other
<220> FEATURE:
<221> NAME/KEY: modified_base
<222> LOCATION: (2562)..(2562)
<223> OTHER INFORMATION: a, c, g, t, unknown or other
<220> FEATURE:
<221> NAME/KEY: modified_base
<222> LOCATION: (2565)..(2565)
<223> OTHER INFORMATION: a, c, g, t, unknown or other
<220> FEATURE:
<221> NAME/KEY: modified_base
<222> LOCATION: (2568)..(2568)
<223> OTHER INFORMATION: a, c, g, t, unknown or other
<220> FEATURE:
<221> NAME/KEY: modified_base
<222> LOCATION: (2574)..(2574)
<223> OTHER INFORMATION: a, c, g, t, unknown or other
<220> FEATURE:
<221> NAME/KEY: modified_base
<222> LOCATION: (2577)..(2577)
<223> OTHER INFORMATION: a, c, g, t, unknown or other
<220> FEATURE:
<221> NAME/KEY: modified_base
<222> LOCATION: (2580)..(2580)
<223> OTHER INFORMATION: a, c, g, t, unknown or other
<220> FEATURE:
<221> NAME/KEY: modified_base
<222> LOCATION: (2583)..(2583)
<223> OTHER INFORMATION: a, c, g, t, unknown or other
<220> FEATURE:
<221> NAME/KEY: modified_base
<222> LOCATION: (2589)..(2589)
<223> OTHER INFORMATION: a, c, g, t, unknown or other
<220> FEATURE:
<221> NAME/KEY: modified_base
<222> LOCATION: (2604)..(2604)
<223> OTHER INFORMATION: a, c, g, t, unknown or other
<220> FEATURE:
<221> NAME/KEY: modified_base
<222> LOCATION: (2607)..(2607)
<223> OTHER INFORMATION: a, c, g, t, unknown or other
<220> FEATURE:
<221> NAME/KEY: modified_base
<222> LOCATION: (2610)..(2610)
<223> OTHER INFORMATION: a, c, g, t, unknown or other
<220> FEATURE:
<221> NAME/KEY: modified_base
<222> LOCATION: (2613)..(2613)
<223> OTHER INFORMATION: a, c, g, t, unknown or other
<220> FEATURE:
<221> NAME/KEY: modified_base
<222> LOCATION: (2625)..(2625)
<223> OTHER INFORMATION: a, c, g, t, unknown or other
<220> FEATURE:
<221> NAME/KEY: modified_base
<222> LOCATION: (2628)..(2628)
<223> OTHER INFORMATION: a, c, g, t, unknown or other
<220> FEATURE:
<221> NAME/KEY: modified_base
<222> LOCATION: (2631)..(2631)
<223> OTHER INFORMATION: a, c, g, t, unknown or other
<220> FEATURE:
<221> NAME/KEY: modified_base
<222> LOCATION: (2634)..(2634)
<223> OTHER INFORMATION: a, c, g, t, unknown or other
<220> FEATURE:
<221> NAME/KEY: modified_base
<222> LOCATION: (2643)..(2643)
<223> OTHER INFORMATION: a, c, g, t, unknown or other
```

```
<220> FEATURE:
<221> NAME/KEY: modified_base
<222> LOCATION: (2649)..(2649)
<223> OTHER INFORMATION: a, c, g, t, unknown or other
<220> FEATURE:
<221> NAME/KEY: modified_base
<222> LOCATION: (2652)..(2652)
<223> OTHER INFORMATION: a, c, g, t, unknown or other
<220> FEATURE:
<221> NAME/KEY: modified_base
<222> LOCATION: (2664)..(2664)
<223> OTHER INFORMATION: a, c, g, t, unknown or other
<220> FEATURE:
<221> NAME/KEY: modified_base
<222> LOCATION: (2670)..(2670)
<223> OTHER INFORMATION: a, c, g, t, unknown or other
<220> FEATURE:
<221> NAME/KEY: modified_base
<222> LOCATION: (2676)..(2676)
<223> OTHER INFORMATION: a, c, g, t, unknown or other
<220> FEATURE:
<221> NAME/KEY: modified_base
<222> LOCATION: (2688)..(2688)
<223> OTHER INFORMATION: a, c, g, t, unknown or other
<220> FEATURE:
<221> NAME/KEY: modified_base
<222> LOCATION: (2691)..(2691)
<223> OTHER INFORMATION: a, c, g, t, unknown or other
<220> FEATURE:
<221> NAME/KEY: modified_base
<222> LOCATION: (2694)..(2694)
<223> OTHER INFORMATION: a, c, g, t, unknown or other
<220> FEATURE:
<221> NAME/KEY: modified_base
<222> LOCATION: (2697)..(2697)
<223> OTHER INFORMATION: a, c, g, t, unknown or other
<220> FEATURE:
<221> NAME/KEY: modified_base
<222> LOCATION: (2700)..(2700)
<223> OTHER INFORMATION: a, c, g, t, unknown or other
<220> FEATURE:
<221> NAME/KEY: modified_base
<222> LOCATION: (2709)..(2709)
<223> OTHER INFORMATION: a, c, g, t, unknown or other
<220> FEATURE:
<221> NAME/KEY: modified_base
<222> LOCATION: (2712)..(2712)
<223> OTHER INFORMATION: a, c, g, t, unknown or other
<220> FEATURE:
<221> NAME/KEY: modified_base
<222> LOCATION: (2715)..(2715)
<223> OTHER INFORMATION: a, c, g, t, unknown or other
<220> FEATURE:
<221> NAME/KEY: modified_base
<222> LOCATION: (2718)..(2718)
<223> OTHER INFORMATION: a, c, g, t, unknown or other
<220> FEATURE:
<221> NAME/KEY: modified_base
<222> LOCATION: (2721)..(2721)
<223> OTHER INFORMATION: a, c, g, t, unknown or other
<220> FEATURE:
<221> NAME/KEY: modified_base
<222> LOCATION: (2733)..(2733)
<223> OTHER INFORMATION: a, c, g, t, unknown or other
<220> FEATURE:
<221> NAME/KEY: modified_base
<222> LOCATION: (2736)..(2736)
<223> OTHER INFORMATION: a, c, g, t, unknown or other
<220> FEATURE:
<221> NAME/KEY: modified_base
<222> LOCATION: (2742)..(2742)
<223> OTHER INFORMATION: a, c, g, t, unknown or other
<220> FEATURE:
<221> NAME/KEY: modified_base
<222> LOCATION: (2745)..(2745)
<223> OTHER INFORMATION: a, c, g, t, unknown or other
<220> FEATURE:
<221> NAME/KEY: modified_base
<222> LOCATION: (2754)..(2754)
<223> OTHER INFORMATION: a, c, g, t, unknown or other
```

-continued

```
<220> FEATURE:
<221> NAME/KEY: modified_base
<222> LOCATION: (2763)..(2763)
<223> OTHER INFORMATION: a, c, g, t, unknown or other
<220> FEATURE:
<221> NAME/KEY: modified_base
<222> LOCATION: (2766)..(2766)
<223> OTHER INFORMATION: a, c, g, t, unknown or other
<220> FEATURE:
<221> NAME/KEY: modified_base
<222> LOCATION: (2769)..(2769)
<223> OTHER INFORMATION: a, c, g, t, unknown or other
<220> FEATURE:
<221> NAME/KEY: modified_base
<222> LOCATION: (2772)..(2772)
<223> OTHER INFORMATION: a, c, g, t, unknown or other
<220> FEATURE:
<221> NAME/KEY: modified_base
<222> LOCATION: (2787)..(2787)
<223> OTHER INFORMATION: a, c, g, t, unknown or other
<220> FEATURE:
<221> NAME/KEY: modified_base
<222> LOCATION: (2793)..(2793)
<223> OTHER INFORMATION: a, c, g, t, unknown or other
<220> FEATURE:
<221> NAME/KEY: modified_base
<222> LOCATION: (2811)..(2811)
<223> OTHER INFORMATION: a, c, g, t, unknown or other
<220> FEATURE:
<221> NAME/KEY: modified_base
<222> LOCATION: (2814)..(2814)
<223> OTHER INFORMATION: a, c, g, t, unknown or other
<220> FEATURE:
<221> NAME/KEY: modified_base
<222> LOCATION: (2823)..(2823)
<223> OTHER INFORMATION: a, c, g, t, unknown or other
<220> FEATURE:
<221> NAME/KEY: modified_base
<222> LOCATION: (2832)..(2832)
<223> OTHER INFORMATION: a, c, g, t, unknown or other
<220> FEATURE:
<221> NAME/KEY: modified_base
<222> LOCATION: (2838)..(2838)
<223> OTHER INFORMATION: a, c, g, t, unknown or other
<220> FEATURE:
<221> NAME/KEY: modified_base
<222> LOCATION: (2841)..(2841)
<223> OTHER INFORMATION: a, c, g, t, unknown or other
<220> FEATURE:
<221> NAME/KEY: modified_base
<222> LOCATION: (2847)..(2847)
<223> OTHER INFORMATION: a, c, g, t, unknown or other
<220> FEATURE:
<221> NAME/KEY: modified_base
<222> LOCATION: (2850)..(2850)
<223> OTHER INFORMATION: a, c, g, t, unknown or other
<220> FEATURE:
<221> NAME/KEY: modified_base
<222> LOCATION: (2853)..(2853)
<223> OTHER INFORMATION: a, c, g, t, unknown or other
<220> FEATURE:
<221> NAME/KEY: modified_base
<222> LOCATION: (2856)..(2856)
<223> OTHER INFORMATION: a, c, g, t, unknown or other
<220> FEATURE:
<221> NAME/KEY: modified_base
<222> LOCATION: (2862)..(2862)
<223> OTHER INFORMATION: a, c, g, t, unknown or other
<220> FEATURE:
<221> NAME/KEY: modified_base
<222> LOCATION: (2883)..(2883)
<223> OTHER INFORMATION: a, c, g, t, unknown or other
<220> FEATURE:
<221> NAME/KEY: modified_base
<222> LOCATION: (2886)..(2886)
<223> OTHER INFORMATION: a, c, g, t, unknown or other
<220> FEATURE:
<221> NAME/KEY: modified_base
<222> LOCATION: (2889)..(2889)
<223> OTHER INFORMATION: a, c, g, t, unknown or other
```

```
<220> FEATURE:
<221> NAME/KEY: modified_base
<222> LOCATION: (2892)..(2892)
<223> OTHER INFORMATION: a, c, g, t, unknown or other
<220> FEATURE:
<221> NAME/KEY: modified_base
<222> LOCATION: (2895)..(2895)
<223> OTHER INFORMATION: a, c, g, t, unknown or other
<220> FEATURE:
<221> NAME/KEY: modified_base
<222> LOCATION: (2904)..(2904)
<223> OTHER INFORMATION: a, c, g, t, unknown or other
<220> FEATURE:
<221> NAME/KEY: modified_base
<222> LOCATION: (2907)..(2907)
<223> OTHER INFORMATION: a, c, g, t, unknown or other
<220> FEATURE:
<221> NAME/KEY: modified_base
<222> LOCATION: (2916)..(2916)
<223> OTHER INFORMATION: a, c, g, t, unknown or other
<220> FEATURE:
<221> NAME/KEY: modified_base
<222> LOCATION: (2919)..(2919)
<223> OTHER INFORMATION: a, c, g, t, unknown or other
<220> FEATURE:
<221> NAME/KEY: modified_base
<222> LOCATION: (2922)..(2922)
<223> OTHER INFORMATION: a, c, g, t, unknown or other
<220> FEATURE:
<221> NAME/KEY: modified_base
<222> LOCATION: (2943)..(2943)
<223> OTHER INFORMATION: a, c, g, t, unknown or other
<220> FEATURE:
<221> NAME/KEY: modified_base
<222> LOCATION: (2946)..(2946)
<223> OTHER INFORMATION: a, c, g, t, unknown or other
<220> FEATURE:
<221> NAME/KEY: modified_base
<222> LOCATION: (2949)..(2949)
<223> OTHER INFORMATION: a, c, g, t, unknown or other
<220> FEATURE:
<221> NAME/KEY: modified_base
<222> LOCATION: (2952)..(2952)
<223> OTHER INFORMATION: a, c, g, t, unknown or other
<220> FEATURE:
<221> NAME/KEY: modified_base
<222> LOCATION: (2958)..(2958)
<223> OTHER INFORMATION: a, c, g, t, unknown or other
<220> FEATURE:
<221> NAME/KEY: modified_base
<222> LOCATION: (2961)..(2961)
<223> OTHER INFORMATION: a, c, g, t, unknown or other
<220> FEATURE:
<221> NAME/KEY: modified_base
<222> LOCATION: (2970)..(2970)
<223> OTHER INFORMATION: a, c, g, t, unknown or other
<220> FEATURE:
<221> NAME/KEY: modified_base
<222> LOCATION: (2985)..(2985)
<223> OTHER INFORMATION: a, c, g, t, unknown or other
<220> FEATURE:
<221> NAME/KEY: modified_base
<222> LOCATION: (2991)..(2991)
<223> OTHER INFORMATION: a, c, g, t, unknown or other
<220> FEATURE:
<221> NAME/KEY: modified_base
<222> LOCATION: (2997)..(2997)
<223> OTHER INFORMATION: a, c, g, t, unknown or other
<220> FEATURE:
<221> NAME/KEY: modified_base
<222> LOCATION: (3000)..(3000)
<223> OTHER INFORMATION: a, c, g, t, unknown or other
<220> FEATURE:
<221> NAME/KEY: modified_base
<222> LOCATION: (3003)..(3003)
<223> OTHER INFORMATION: a, c, g, t, unknown or other
<220> FEATURE:
<221> NAME/KEY: modified_base
<222> LOCATION: (3006)..(3006)
<223> OTHER INFORMATION: a, c, g, t, unknown or other
```

-continued

```
<220> FEATURE:
<221> NAME/KEY: modified_base
<222> LOCATION: (3009)..(3009)
<223> OTHER INFORMATION: a, c, g, t, unknown or other
<220> FEATURE:
<221> NAME/KEY: modified_base
<222> LOCATION: (3012)..(3012)
<223> OTHER INFORMATION: a, c, g, t, unknown or other
<220> FEATURE:
<221> NAME/KEY: modified_base
<222> LOCATION: (3015)..(3015)
<223> OTHER INFORMATION: a, c, g, t, unknown or other
<220> FEATURE:
<221> NAME/KEY: modified_base
<222> LOCATION: (3036)..(3036)
<223> OTHER INFORMATION: a, c, g, t, unknown or other
<220> FEATURE:
<221> NAME/KEY: modified_base
<222> LOCATION: (3039)..(3039)
<223> OTHER INFORMATION: a, c, g, t, unknown or other
<220> FEATURE:
<221> NAME/KEY: modified_base
<222> LOCATION: (3048)..(3048)
<223> OTHER INFORMATION: a, c, g, t, unknown or other
<220> FEATURE:
<221> NAME/KEY: modified_base
<222> LOCATION: (3057)..(3057)
<223> OTHER INFORMATION: a, c, g, t, unknown or other
<220> FEATURE:
<221> NAME/KEY: modified_base
<222> LOCATION: (3060)..(3060)
<223> OTHER INFORMATION: a, c, g, t, unknown or other
<220> FEATURE:
<221> NAME/KEY: modified_base
<222> LOCATION: (3075)..(3075)
<223> OTHER INFORMATION: a, c, g, t, unknown or other
<220> FEATURE:
<221> NAME/KEY: modified_base
<222> LOCATION: (3081)..(3081)
<223> OTHER INFORMATION: a, c, g, t, unknown or other
<220> FEATURE:
<221> NAME/KEY: modified_base
<222> LOCATION: (3084)..(3084)
<223> OTHER INFORMATION: a, c, g, t, unknown or other
<220> FEATURE:
<221> NAME/KEY: modified_base
<222> LOCATION: (3087)..(3087)
<223> OTHER INFORMATION: a, c, g, t, unknown or other
<220> FEATURE:
<221> NAME/KEY: modified_base
<222> LOCATION: (3090)..(3090)
<223> OTHER INFORMATION: a, c, g, t, unknown or other
<220> FEATURE:
<221> NAME/KEY: modified_base
<222> LOCATION: (3093)..(3093)
<223> OTHER INFORMATION: a, c, g, t, unknown or other
<220> FEATURE:
<221> NAME/KEY: modified_base
<222> LOCATION: (3099)..(3099)
<223> OTHER INFORMATION: a, c, g, t, unknown or other
<220> FEATURE:
<221> NAME/KEY: modified_base
<222> LOCATION: (3102)..(3102)
<223> OTHER INFORMATION: a, c, g, t, unknown or other
<220> FEATURE:
<221> NAME/KEY: modified_base
<222> LOCATION: (3105)..(3105)
<223> OTHER INFORMATION: a, c, g, t, unknown or other
<220> FEATURE:
<221> NAME/KEY: modified_base
<222> LOCATION: (3108)..(3108)
<223> OTHER INFORMATION: a, c, g, t, unknown or other
<220> FEATURE:
<221> NAME/KEY: modified_base
<222> LOCATION: (3114)..(3114)
<223> OTHER INFORMATION: a, c, g, t, unknown or other
<220> FEATURE:
<221> NAME/KEY: modified_base
<222> LOCATION: (3117)..(3117)
<223> OTHER INFORMATION: a, c, g, t, unknown or other
```

```
-continued

<220> FEATURE:
<221> NAME/KEY: modified_base
<222> LOCATION: (3120)..(3120)
<223> OTHER INFORMATION: a, c, g, t, unknown or other
<220> FEATURE:
<221> NAME/KEY: modified_base
<222> LOCATION: (3126)..(3126)
<223> OTHER INFORMATION: a, c, g, t, unknown or other
<220> FEATURE:
<221> NAME/KEY: modified_base
<222> LOCATION: (3132)..(3132)
<223> OTHER INFORMATION: a, c, g, t, unknown or other
<220> FEATURE:
<221> NAME/KEY: modified_base
<222> LOCATION: (3135)..(3135)
<223> OTHER INFORMATION: a, c, g, t, unknown or other
<220> FEATURE:
<221> NAME/KEY: modified_base
<222> LOCATION: (3138)..(3138)
<223> OTHER INFORMATION: a, c, g, t, unknown or other
<220> FEATURE:
<221> NAME/KEY: modified_base
<222> LOCATION: (3141)..(3141)
<223> OTHER INFORMATION: a, c, g, t, unknown or other
<220> FEATURE:
<221> NAME/KEY: modified_base
<222> LOCATION: (3144)..(3144)
<223> OTHER INFORMATION: a, c, g, t, unknown or other
<220> FEATURE:
<221> NAME/KEY: modified_base
<222> LOCATION: (3153)..(3153)
<223> OTHER INFORMATION: a, c, g, t, unknown or other
<220> FEATURE:
<221> NAME/KEY: modified_base
<222> LOCATION: (3165)..(3165)
<223> OTHER INFORMATION: a, c, g, t, unknown or other
<220> FEATURE:
<221> NAME/KEY: modified_base
<222> LOCATION: (3168)..(3168)
<223> OTHER INFORMATION: a, c, g, t, unknown or other
<220> FEATURE:
<221> NAME/KEY: modified_base
<222> LOCATION: (3177)..(3177)
<223> OTHER INFORMATION: a, c, g, t, unknown or other
<220> FEATURE:
<221> NAME/KEY: modified_base
<222> LOCATION: (3189)..(3189)
<223> OTHER INFORMATION: a, c, g, t, unknown or other
<220> FEATURE:
<221> NAME/KEY: modified_base
<222> LOCATION: (3195)..(3195)
<223> OTHER INFORMATION: a, c, g, t, unknown or other
<220> FEATURE:
<221> NAME/KEY: modified_base
<222> LOCATION: (3198)..(3198)
<223> OTHER INFORMATION: a, c, g, t, unknown or other
<220> FEATURE:
<221> NAME/KEY: modified_base
<222> LOCATION: (3201)..(3201)
<223> OTHER INFORMATION: a, c, g, t, unknown or other
<220> FEATURE:
<221> NAME/KEY: modified_base
<222> LOCATION: (3204)..(3204)
<223> OTHER INFORMATION: a, c, g, t, unknown or other
<220> FEATURE:
<221> NAME/KEY: modified_base
<222> LOCATION: (3207)..(3207)
<223> OTHER INFORMATION: a, c, g, t, unknown or other
<220> FEATURE:
<221> NAME/KEY: modified_base
<222> LOCATION: (3210)..(3210)
<223> OTHER INFORMATION: a, c, g, t, unknown or other
<220> FEATURE:
<221> NAME/KEY: modified_base
<222> LOCATION: (3216)..(3216)
<223> OTHER INFORMATION: a, c, g, t, unknown or other
<220> FEATURE:
<221> NAME/KEY: modified_base
<222> LOCATION: (3219)..(3219)
<223> OTHER INFORMATION: a, c, g, t, unknown or other
```

```
<220> FEATURE:
<221> NAME/KEY: modified_base
<222> LOCATION: (3222)..(3222)
<223> OTHER INFORMATION: a, c, g, t, unknown or other
<220> FEATURE:
<221> NAME/KEY: modified_base
<222> LOCATION: (3231)..(3231)
<223> OTHER INFORMATION: a, c, g, t, unknown or other
<220> FEATURE:
<221> NAME/KEY: modified_base
<222> LOCATION: (3234)..(3234)
<223> OTHER INFORMATION: a, c, g, t, unknown or other
<220> FEATURE:
<221> NAME/KEY: modified_base
<222> LOCATION: (3240)..(3240)
<223> OTHER INFORMATION: a, c, g, t, unknown or other
<220> FEATURE:
<221> NAME/KEY: modified_base
<222> LOCATION: (3243)..(3243)
<223> OTHER INFORMATION: a, c, g, t, unknown or other
<220> FEATURE:
<221> NAME/KEY: modified_base
<222> LOCATION: (3249)..(3249)
<223> OTHER INFORMATION: a, c, g, t, unknown or other
<220> FEATURE:
<221> NAME/KEY: modified_base
<222> LOCATION: (3252)..(3252)
<223> OTHER INFORMATION: a, c, g, t, unknown or other
<220> FEATURE:
<221> NAME/KEY: modified_base
<222> LOCATION: (3255)..(3255)
<223> OTHER INFORMATION: a, c, g, t, unknown or other
<220> FEATURE:
<221> NAME/KEY: modified_base
<222> LOCATION: (3258)..(3258)
<223> OTHER INFORMATION: a, c, g, t, unknown or other
<220> FEATURE:
<221> NAME/KEY: modified_base
<222> LOCATION: (3264)..(3264)
<223> OTHER INFORMATION: a, c, g, t, unknown or other
<220> FEATURE:
<221> NAME/KEY: modified_base
<222> LOCATION: (3267)..(3267)
<223> OTHER INFORMATION: a, c, g, t, unknown or other
<220> FEATURE:
<221> NAME/KEY: modified_base
<222> LOCATION: (3276)..(3276)
<223> OTHER INFORMATION: a, c, g, t, unknown or other
<220> FEATURE:
<221> NAME/KEY: modified_base
<222> LOCATION: (3282)..(3282)
<223> OTHER INFORMATION: a, c, g, t, unknown or other
<220> FEATURE:
<221> NAME/KEY: modified_base
<222> LOCATION: (3288)..(3288)
<223> OTHER INFORMATION: a, c, g, t, unknown or other
<220> FEATURE:
<221> NAME/KEY: modified_base
<222> LOCATION: (3294)..(3294)
<223> OTHER INFORMATION: a, c, g, t, unknown or other
<220> FEATURE:
<221> NAME/KEY: modified_base
<222> LOCATION: (3300)..(3300)
<223> OTHER INFORMATION: a, c, g, t, unknown or other
<220> FEATURE:
<221> NAME/KEY: modified_base
<222> LOCATION: (3318)..(3318)
<223> OTHER INFORMATION: a, c, g, t, unknown or other
<220> FEATURE:
<221> NAME/KEY: modified_base
<222> LOCATION: (3321)..(3321)
<223> OTHER INFORMATION: a, c, g, t, unknown or other
<220> FEATURE:
<221> NAME/KEY: modified_base
<222> LOCATION: (3327)..(3327)
<223> OTHER INFORMATION: a, c, g, t, unknown or other
<220> FEATURE:
<221> NAME/KEY: modified_base
<222> LOCATION: (3330)..(3330)
<223> OTHER INFORMATION: a, c, g, t, unknown or other
```

```
<220> FEATURE:
<221> NAME/KEY: modified_base
<222> LOCATION: (3336)..(3336)
<223> OTHER INFORMATION: a, c, g, t, unknown or other
<220> FEATURE:
<221> NAME/KEY: modified_base
<222> LOCATION: (3339)..(3339)
<223> OTHER INFORMATION: a, c, g, t, unknown or other
<220> FEATURE:
<221> NAME/KEY: modified_base
<222> LOCATION: (3348)..(3348)
<223> OTHER INFORMATION: a, c, g, t, unknown or other
<220> FEATURE:
<221> NAME/KEY: modified_base
<222> LOCATION: (3351)..(3351)
<223> OTHER INFORMATION: a, c, g, t, unknown or other
<220> FEATURE:
<221> NAME/KEY: modified_base
<222> LOCATION: (3354)..(3354)
<223> OTHER INFORMATION: a, c, g, t, unknown or other
<220> FEATURE:
<221> NAME/KEY: modified_base
<222> LOCATION: (3360)..(3360)
<223> OTHER INFORMATION: a, c, g, t, unknown or other
<220> FEATURE:
<221> NAME/KEY: modified_base
<222> LOCATION: (3363)..(3363)
<223> OTHER INFORMATION: a, c, g, t, unknown or other
<220> FEATURE:
<221> NAME/KEY: modified_base
<222> LOCATION: (3366)..(3366)
<223> OTHER INFORMATION: a, c, g, t, unknown or other
<220> FEATURE:
<221> NAME/KEY: modified_base
<222> LOCATION: (3369)..(3369)
<223> OTHER INFORMATION: a, c, g, t, unknown or other
<220> FEATURE:
<221> NAME/KEY: modified_base
<222> LOCATION: (3375)..(3375)
<223> OTHER INFORMATION: a, c, g, t, unknown or other
<220> FEATURE:
<221> NAME/KEY: modified_base
<222> LOCATION: (3378)..(3378)
<223> OTHER INFORMATION: a, c, g, t, unknown or other
<220> FEATURE:
<221> NAME/KEY: modified_base
<222> LOCATION: (3381)..(3381)
<223> OTHER INFORMATION: a, c, g, t, unknown or other
<220> FEATURE:
<221> NAME/KEY: modified_base
<222> LOCATION: (3387)..(3387)
<223> OTHER INFORMATION: a, c, g, t, unknown or other
<220> FEATURE:
<221> NAME/KEY: modified_base
<222> LOCATION: (3390)..(3390)
<223> OTHER INFORMATION: a, c, g, t, unknown or other
<220> FEATURE:
<221> NAME/KEY: modified_base
<222> LOCATION: (3393)..(3393)
<223> OTHER INFORMATION: a, c, g, t, unknown or other
<220> FEATURE:
<221> NAME/KEY: modified_base
<222> LOCATION: (3396)..(3396)
<223> OTHER INFORMATION: a, c, g, t, unknown or other
<220> FEATURE:
<221> NAME/KEY: modified_base
<222> LOCATION: (3399)..(3399)
<223> OTHER INFORMATION: a, c, g, t, unknown or other
<220> FEATURE:
<221> NAME/KEY: modified_base
<222> LOCATION: (3405)..(3405)
<223> OTHER INFORMATION: a, c, g, t, unknown or other
<220> FEATURE:
<221> NAME/KEY: modified_base
<222> LOCATION: (3408)..(3408)
<223> OTHER INFORMATION: a, c, g, t, unknown or other
<220> FEATURE:
<221> NAME/KEY: modified_base
<222> LOCATION: (3411)..(3411)
<223> OTHER INFORMATION: a, c, g, t, unknown or other
```

-continued

```
<220> FEATURE:
<221> NAME/KEY: modified_base
<222> LOCATION: (3414)..(3414)
<223> OTHER INFORMATION: a, c, g, t, unknown or other
<220> FEATURE:
<221> NAME/KEY: modified_base
<222> LOCATION: (3417)..(3417)
<223> OTHER INFORMATION: a, c, g, t, unknown or other
<220> FEATURE:
<221> NAME/KEY: modified_base
<222> LOCATION: (3420)..(3420)
<223> OTHER INFORMATION: a, c, g, t, unknown or other
<220> FEATURE:
<221> NAME/KEY: modified_base
<222> LOCATION: (3426)..(3426)
<223> OTHER INFORMATION: a, c, g, t, unknown or other
<220> FEATURE:
<221> NAME/KEY: modified_base
<222> LOCATION: (3429)..(3429)
<223> OTHER INFORMATION: a, c, g, t, unknown or other
<220> FEATURE:
<221> NAME/KEY: modified_base
<222> LOCATION: (3432)..(3432)
<223> OTHER INFORMATION: a, c, g, t, unknown or other
<220> FEATURE:
<221> NAME/KEY: modified_base
<222> LOCATION: (3438)..(3438)
<223> OTHER INFORMATION: a, c, g, t, unknown or other
<220> FEATURE:
<221> NAME/KEY: modified_base
<222> LOCATION: (3447)..(3447)
<223> OTHER INFORMATION: a, c, g, t, unknown or other
<220> FEATURE:
<221> NAME/KEY: modified_base
<222> LOCATION: (3450)..(3450)
<223> OTHER INFORMATION: a, c, g, t, unknown or other
<220> FEATURE:
<221> NAME/KEY: modified_base
<222> LOCATION: (3456)..(3456)
<223> OTHER INFORMATION: a, c, g, t, unknown or other
<220> FEATURE:
<221> NAME/KEY: modified_base
<222> LOCATION: (3459)..(3459)
<223> OTHER INFORMATION: a, c, g, t, unknown or other
<220> FEATURE:
<221> NAME/KEY: modified_base
<222> LOCATION: (3462)..(3462)
<223> OTHER INFORMATION: a, c, g, t, unknown or other
<220> FEATURE:
<221> NAME/KEY: modified_base
<222> LOCATION: (3471)..(3471)
<223> OTHER INFORMATION: a, c, g, t, unknown or other
<220> FEATURE:
<221> NAME/KEY: modified_base
<222> LOCATION: (3474)..(3474)
<223> OTHER INFORMATION: a, c, g, t, unknown or other
<220> FEATURE:
<221> NAME/KEY: modified_base
<222> LOCATION: (3486)..(3486)
<223> OTHER INFORMATION: a, c, g, t, unknown or other
<220> FEATURE:
<221> NAME/KEY: modified_base
<222> LOCATION: (3495)..(3495)
<223> OTHER INFORMATION: a, c, g, t, unknown or other
<220> FEATURE:
<221> NAME/KEY: modified_base
<222> LOCATION: (3498)..(3498)
<223> OTHER INFORMATION: a, c, g, t, unknown or other
<220> FEATURE:
<221> NAME/KEY: modified_base
<222> LOCATION: (3501)..(3501)
<223> OTHER INFORMATION: a, c, g, t, unknown or other
<220> FEATURE:
<221> NAME/KEY: modified_base
<222> LOCATION: (3504)..(3504)
<223> OTHER INFORMATION: a, c, g, t, unknown or other
<220> FEATURE:
<221> NAME/KEY: modified_base
<222> LOCATION: (3513)..(3513)
<223> OTHER INFORMATION: a, c, g, t, unknown or other
```

```
-continued

<220> FEATURE:
<221> NAME/KEY: modified_base
<222> LOCATION: (3516)..(3516)
<223> OTHER INFORMATION: a, c, g, t, unknown or other
<220> FEATURE:
<221> NAME/KEY: modified_base
<222> LOCATION: (3519)..(3519)
<223> OTHER INFORMATION: a, c, g, t, unknown or other
<220> FEATURE:
<221> NAME/KEY: modified_base
<222> LOCATION: (3522)..(3522)
<223> OTHER INFORMATION: a, c, g, t, unknown or other
<220> FEATURE:
<221> NAME/KEY: modified_base
<222> LOCATION: (3525)..(3525)
<223> OTHER INFORMATION: a, c, g, t, unknown or other
<220> FEATURE:
<221> NAME/KEY: modified_base
<222> LOCATION: (3528)..(3528)
<223> OTHER INFORMATION: a, c, g, t, unknown or other
<220> FEATURE:
<221> NAME/KEY: modified_base
<222> LOCATION: (3534)..(3534)
<223> OTHER INFORMATION: a, c, g, t, unknown or other
<220> FEATURE:
<221> NAME/KEY: modified_base
<222> LOCATION: (3537)..(3537)
<223> OTHER INFORMATION: a, c, g, t, unknown or other
<220> FEATURE:
<221> NAME/KEY: modified_base
<222> LOCATION: (3546)..(3546)
<223> OTHER INFORMATION: a, c, g, t, unknown or other
<220> FEATURE:
<221> NAME/KEY: modified_base
<222> LOCATION: (3549)..(3549)
<223> OTHER INFORMATION: a, c, g, t, unknown or other
<220> FEATURE:
<221> NAME/KEY: modified_base
<222> LOCATION: (3558)..(3558)
<223> OTHER INFORMATION: a, c, g, t, unknown or other
<220> FEATURE:
<221> NAME/KEY: modified_base
<222> LOCATION: (3561)..(3561)
<223> OTHER INFORMATION: a, c, g, t, unknown or other
<220> FEATURE:
<221> NAME/KEY: modified_base
<222> LOCATION: (3564)..(3564)
<223> OTHER INFORMATION: a, c, g, t, unknown or other
<220> FEATURE:
<221> NAME/KEY: modified_base
<222> LOCATION: (3570)..(3570)
<223> OTHER INFORMATION: a, c, g, t, unknown or other
<220> FEATURE:
<221> NAME/KEY: modified_base
<222> LOCATION: (3576)..(3576)
<223> OTHER INFORMATION: a, c, g, t, unknown or other
<220> FEATURE:
<221> NAME/KEY: modified_base
<222> LOCATION: (3579)..(3579)
<223> OTHER INFORMATION: a, c, g, t, unknown or other
<220> FEATURE:
<221> NAME/KEY: modified_base
<222> LOCATION: (3585)..(3585)
<223> OTHER INFORMATION: a, c, g, t, unknown or other
<220> FEATURE:
<221> NAME/KEY: modified_base
<222> LOCATION: (3588)..(3588)
<223> OTHER INFORMATION: a, c, g, t, unknown or other
<220> FEATURE:
<221> NAME/KEY: modified_base
<222> LOCATION: (3594)..(3594)
<223> OTHER INFORMATION: a, c, g, t, unknown or other
<220> FEATURE:
<221> NAME/KEY: modified_base
<222> LOCATION: (3600)..(3600)
<223> OTHER INFORMATION: a, c, g, t, unknown or other
<220> FEATURE:
<221> NAME/KEY: modified_base
<222> LOCATION: (3603)..(3603)
<223> OTHER INFORMATION: a, c, g, t, unknown or other
```

```
<220> FEATURE:
<221> NAME/KEY: modified_base
<222> LOCATION: (3612)..(3612)
<223> OTHER INFORMATION: a, c, g, t, unknown or other
<220> FEATURE:
<221> NAME/KEY: modified_base
<222> LOCATION: (3615)..(3615)
<223> OTHER INFORMATION: a, c, g, t, unknown or other
<220> FEATURE:
<221> NAME/KEY: modified_base
<222> LOCATION: (3621)..(3621)
<223> OTHER INFORMATION: a, c, g, t, unknown or other
<220> FEATURE:
<221> NAME/KEY: modified_base
<222> LOCATION: (3627)..(3627)
<223> OTHER INFORMATION: a, c, g, t, unknown or other
<220> FEATURE:
<221> NAME/KEY: modified_base
<222> LOCATION: (3630)..(3630)
<223> OTHER INFORMATION: a, c, g, t, unknown or other
<220> FEATURE:
<221> NAME/KEY: modified_base
<222> LOCATION: (3633)..(3633)
<223> OTHER INFORMATION: a, c, g, t, unknown or other
<220> FEATURE:
<221> NAME/KEY: modified_base
<222> LOCATION: (3636)..(3636)
<223> OTHER INFORMATION: a, c, g, t, unknown or other
<220> FEATURE:
<221> NAME/KEY: modified_base
<222> LOCATION: (3642)..(3642)
<223> OTHER INFORMATION: a, c, g, t, unknown or other
<220> FEATURE:
<221> NAME/KEY: modified_base
<222> LOCATION: (3645)..(3645)
<223> OTHER INFORMATION: a, c, g, t, unknown or other
<220> FEATURE:
<221> NAME/KEY: modified_base
<222> LOCATION: (3648)..(3648)
<223> OTHER INFORMATION: a, c, g, t, unknown or other
<220> FEATURE:
<221> NAME/KEY: modified_base
<222> LOCATION: (3651)..(3651)
<223> OTHER INFORMATION: a, c, g, t, unknown or other
<220> FEATURE:
<221> NAME/KEY: modified_base
<222> LOCATION: (3657)..(3657)
<223> OTHER INFORMATION: a, c, g, t, unknown or other
<220> FEATURE:
<221> NAME/KEY: modified_base
<222> LOCATION: (3663)..(3663)
<223> OTHER INFORMATION: a, c, g, t, unknown or other
<220> FEATURE:
<221> NAME/KEY: modified_base
<222> LOCATION: (3666)..(3666)
<223> OTHER INFORMATION: a, c, g, t, unknown or other
<220> FEATURE:
<221> NAME/KEY: modified_base
<222> LOCATION: (3669)..(3669)
<223> OTHER INFORMATION: a, c, g, t, unknown or other
<220> FEATURE:
<221> NAME/KEY: modified_base
<222> LOCATION: (3675)..(3675)
<223> OTHER INFORMATION: a, c, g, t, unknown or other
<220> FEATURE:
<221> NAME/KEY: modified_base
<222> LOCATION: (3678)..(3678)
<223> OTHER INFORMATION: a, c, g, t, unknown or other
<220> FEATURE:
<221> NAME/KEY: modified_base
<222> LOCATION: (3681)..(3681)
<223> OTHER INFORMATION: a, c, g, t, unknown or other
<220> FEATURE:
<221> NAME/KEY: modified_base
<222> LOCATION: (3684)..(3684)
<223> OTHER INFORMATION: a, c, g, t, unknown or other
<220> FEATURE:
<221> NAME/KEY: modified_base
<222> LOCATION: (3687)..(3687)
<223> OTHER INFORMATION: a, c, g, t, unknown or other
```

-continued

```
<220> FEATURE:
<221> NAME/KEY: modified_base
<222> LOCATION: (3690)..(3690)
<223> OTHER INFORMATION: a, c, g, t, unknown or other
<220> FEATURE:
<221> NAME/KEY: modified_base
<222> LOCATION: (3696)..(3696)
<223> OTHER INFORMATION: a, c, g, t, unknown or other
<220> FEATURE:
<221> NAME/KEY: modified_base
<222> LOCATION: (3702)..(3702)
<223> OTHER INFORMATION: a, c, g, t, unknown or other
<220> FEATURE:
<221> NAME/KEY: modified_base
<222> LOCATION: (3723)..(3723)
<223> OTHER INFORMATION: a, c, g, t, unknown or other
<220> FEATURE:
<221> NAME/KEY: modified_base
<222> LOCATION: (3726)..(3726)
<223> OTHER INFORMATION: a, c, g, t, unknown or other
<220> FEATURE:
<221> NAME/KEY: modified_base
<222> LOCATION: (3732)..(3732)
<223> OTHER INFORMATION: a, c, g, t, unknown or other
<220> FEATURE:
<221> NAME/KEY: modified_base
<222> LOCATION: (3735)..(3735)
<223> OTHER INFORMATION: a, c, g, t, unknown or other
<220> FEATURE:
<221> NAME/KEY: modified_base
<222> LOCATION: (3741)..(3741)
<223> OTHER INFORMATION: a, c, g, t, unknown or other
<220> FEATURE:
<221> NAME/KEY: modified_base
<222> LOCATION: (3744)..(3744)
<223> OTHER INFORMATION: a, c, g, t, unknown or other
<220> FEATURE:
<221> NAME/KEY: modified_base
<222> LOCATION: (3747)..(3747)
<223> OTHER INFORMATION: a, c, g, t, unknown or other
<220> FEATURE:
<221> NAME/KEY: modified_base
<222> LOCATION: (3750)..(3750)
<223> OTHER INFORMATION: a, c, g, t, unknown or other
<220> FEATURE:
<221> NAME/KEY: modified_base
<222> LOCATION: (3753)..(3753)
<223> OTHER INFORMATION: a, c, g, t, unknown or other
<220> FEATURE:
<221> NAME/KEY: modified_base
<222> LOCATION: (3756)..(3756)
<223> OTHER INFORMATION: a, c, g, t, unknown or other
<220> FEATURE:
<221> NAME/KEY: modified_base
<222> LOCATION: (3762)..(3762)
<223> OTHER INFORMATION: a, c, g, t, unknown or other
<220> FEATURE:
<221> NAME/KEY: modified_base
<222> LOCATION: (3765)..(3765)
<223> OTHER INFORMATION: a, c, g, t, unknown or other
<220> FEATURE:
<221> NAME/KEY: modified_base
<222> LOCATION: (3768)..(3768)
<223> OTHER INFORMATION: a, c, g, t, unknown or other
<220> FEATURE:
<221> NAME/KEY: modified_base
<222> LOCATION: (3774)..(3774)
<223> OTHER INFORMATION: a, c, g, t, unknown or other
<220> FEATURE:
<221> NAME/KEY: modified_base
<222> LOCATION: (3777)..(3777)
<223> OTHER INFORMATION: a, c, g, t, unknown or other
<220> FEATURE:
<221> NAME/KEY: modified_base
<222> LOCATION: (3780)..(3780)
<223> OTHER INFORMATION: a, c, g, t, unknown or other
<220> FEATURE:
<221> NAME/KEY: modified_base
<222> LOCATION: (3786)..(3786)
<223> OTHER INFORMATION: a, c, g, t, unknown or other
```

-continued

```
<220> FEATURE:
<221> NAME/KEY: modified_base
<222> LOCATION: (3789)..(3789)
<223> OTHER INFORMATION: a, c, g, t, unknown or other
<220> FEATURE:
<221> NAME/KEY: modified_base
<222> LOCATION: (3795)..(3795)
<223> OTHER INFORMATION: a, c, g, t, unknown or other
<220> FEATURE:
<221> NAME/KEY: modified_base
<222> LOCATION: (3798)..(3798)
<223> OTHER INFORMATION: a, c, g, t, unknown or other
<220> FEATURE:
<221> NAME/KEY: modified_base
<222> LOCATION: (3801)..(3801)
<223> OTHER INFORMATION: a, c, g, t, unknown or other
<220> FEATURE:
<221> NAME/KEY: modified_base
<222> LOCATION: (3807)..(3807)
<223> OTHER INFORMATION: a, c, g, t, unknown or other
<220> FEATURE:
<221> NAME/KEY: modified_base
<222> LOCATION: (3813)..(3813)
<223> OTHER INFORMATION: a, c, g, t, unknown or other
<220> FEATURE:
<221> NAME/KEY: modified_base
<222> LOCATION: (3816)..(3816)
<223> OTHER INFORMATION: a, c, g, t, unknown or other
<220> FEATURE:
<221> NAME/KEY: modified_base
<222> LOCATION: (3819)..(3819)
<223> OTHER INFORMATION: a, c, g, t, unknown or other
<220> FEATURE:
<221> NAME/KEY: modified_base
<222> LOCATION: (3822)..(3822)
<223> OTHER INFORMATION: a, c, g, t, unknown or other
<220> FEATURE:
<221> NAME/KEY: modified_base
<222> LOCATION: (3825)..(3825)
<223> OTHER INFORMATION: a, c, g, t, unknown or other
<220> FEATURE:
<221> NAME/KEY: modified_base
<222> LOCATION: (3837)..(3837)
<223> OTHER INFORMATION: a, c, g, t, unknown or other
<220> FEATURE:
<221> NAME/KEY: modified_base
<222> LOCATION: (3840)..(3840)
<223> OTHER INFORMATION: a, c, g, t, unknown or other
<220> FEATURE:
<221> NAME/KEY: modified_base
<222> LOCATION: (3849)..(3849)
<223> OTHER INFORMATION: a, c, g, t, unknown or other
<220> FEATURE:
<221> NAME/KEY: modified_base
<222> LOCATION: (3852)..(3852)
<223> OTHER INFORMATION: a, c, g, t, unknown or other
<220> FEATURE:
<221> NAME/KEY: modified_base
<222> LOCATION: (3855)..(3855)
<223> OTHER INFORMATION: a, c, g, t, unknown or other
<220> FEATURE:
<221> NAME/KEY: modified_base
<222> LOCATION: (3858)..(3858)
<223> OTHER INFORMATION: a, c, g, t, unknown or other
<220> FEATURE:
<221> NAME/KEY: modified_base
<222> LOCATION: (3861)..(3861)
<223> OTHER INFORMATION: a, c, g, t, unknown or other
<220> FEATURE:
<221> NAME/KEY: modified_base
<222> LOCATION: (3867)..(3867)
<223> OTHER INFORMATION: a, c, g, t, unknown or other
<220> FEATURE:
<221> NAME/KEY: modified_base
<222> LOCATION: (3870)..(3870)
<223> OTHER INFORMATION: a, c, g, t, unknown or other
<220> FEATURE:
<221> NAME/KEY: modified_base
<222> LOCATION: (3873)..(3873)
<223> OTHER INFORMATION: a, c, g, t, unknown or other
```

```
<220> FEATURE:
<221> NAME/KEY: modified_base
<222> LOCATION: (3879)..(3879)
<223> OTHER INFORMATION: a, c, g, t, unknown or other
<220> FEATURE:
<221> NAME/KEY: modified_base
<222> LOCATION: (3888)..(3888)
<223> OTHER INFORMATION: a, c, g, t, unknown or other
<220> FEATURE:
<221> NAME/KEY: modified_base
<222> LOCATION: (3891)..(3891)
<223> OTHER INFORMATION: a, c, g, t, unknown or other
<220> FEATURE:
<221> NAME/KEY: modified_base
<222> LOCATION: (3894)..(3894)
<223> OTHER INFORMATION: a, c, g, t, unknown or other
<220> FEATURE:
<221> NAME/KEY: modified_base
<222> LOCATION: (3897)..(3897)
<223> OTHER INFORMATION: a, c, g, t, unknown or other
<220> FEATURE:
<221> NAME/KEY: modified_base
<222> LOCATION: (3900)..(3900)
<223> OTHER INFORMATION: a, c, g, t, unknown or other
<220> FEATURE:
<221> NAME/KEY: modified_base
<222> LOCATION: (3903)..(3903)
<223> OTHER INFORMATION: a, c, g, t, unknown or other
<220> FEATURE:
<221> NAME/KEY: modified_base
<222> LOCATION: (3906)..(3906)
<223> OTHER INFORMATION: a, c, g, t, unknown or other
<220> FEATURE:
<221> NAME/KEY: modified_base
<222> LOCATION: (3921)..(3921)
<223> OTHER INFORMATION: a, c, g, t, unknown or other
<220> FEATURE:
<221> NAME/KEY: modified_base
<222> LOCATION: (3930)..(3930)
<223> OTHER INFORMATION: a, c, g, t, unknown or other
<220> FEATURE:
<221> NAME/KEY: modified_base
<222> LOCATION: (3939)..(3939)
<223> OTHER INFORMATION: a, c, g, t, unknown or other
<220> FEATURE:
<221> NAME/KEY: modified_base
<222> LOCATION: (3942)..(3942)
<223> OTHER INFORMATION: a, c, g, t, unknown or other
<220> FEATURE:
<221> NAME/KEY: modified_base
<222> LOCATION: (3951)..(3951)
<223> OTHER INFORMATION: a, c, g, t, unknown or other
<220> FEATURE:
<221> NAME/KEY: modified_base
<222> LOCATION: (3954)..(3954)
<223> OTHER INFORMATION: a, c, g, t, unknown or other
<220> FEATURE:
<221> NAME/KEY: modified_base
<222> LOCATION: (3957)..(3957)
<223> OTHER INFORMATION: a, c, g, t, unknown or other
<220> FEATURE:
<221> NAME/KEY: modified_base
<222> LOCATION: (3960)..(3960)
<223> OTHER INFORMATION: a, c, g, t, unknown or other
<220> FEATURE:
<221> NAME/KEY: modified_base
<222> LOCATION: (3966)..(3966)
<223> OTHER INFORMATION: a, c, g, t, unknown or other
<220> FEATURE:
<221> NAME/KEY: modified_base
<222> LOCATION: (3975)..(3975)
<223> OTHER INFORMATION: a, c, g, t, unknown or other
<220> FEATURE:
<221> NAME/KEY: modified_base
<222> LOCATION: (3978)..(3978)
<223> OTHER INFORMATION: a, c, g, t, unknown or other
<220> FEATURE:
<221> NAME/KEY: modified_base
<222> LOCATION: (3987)..(3987)
<223> OTHER INFORMATION: a, c, g, t, unknown or other
```

-continued

<220> FEATURE:
<221> NAME/KEY: modified_base
<222> LOCATION: (3990)..(3990)
<223> OTHER INFORMATION: a, c, g, t, unknown or other

<400> SEQUENCE: 51

```
atggcngarg cnggnytnmg nggntggytn ytntgggcny tnytnytnmg nytngcncar      60
wsngarccnt ayacnacnat hcaycarccn ggntaytgyg cnttytayga ygartgyggn     120
aaraayccng arytnwsngg nwsnytnatg acnytnwsna aygtnwsntg yytnwsnaay     180
acnccngcnm gnaarathac nggngaycay ytnathytny tncaraarat htgyccnmgn     240
ytntayacng gnccnaayac ncargcntgy tgywsngcna arcarytngt nwsnytngar     300
gcnwsnytnw snathacnaa rgcnytnytn acnmgntgyc cngcntgyws ngayaaytty     360
gtnaayytnc aytgycayaa yacntgywsn ccnaaycarw snytnttyat haaygtnacn     420
mgngtngcnc arytnggngc nggncarytn ccngcngtng tngcntayga rgcnttytay     480
carcaywsnt tygcngarca rwsntaygay wsntgywsnm gngtnmgngt nccngcngcn     540
gcnacnytng cngtnggnac natgtgyggn gtntayggnw sngcnytntg yaaygcncar     600
mgntggytna ayttycargg ngayacnggn aayggnytng cnccnytnga yathacntty     660
cayytnytng arccnggnca rgcngtnggn wsnggnathc arccnytnaa ygarggngtn     720
gcnmgntgya aygarwsnca rggngaygay gtngcnacnt gywsntgyca rgaytgygcn     780
gcnwsntgyc cngcnathgc nmgnccncar gcnytngayw snacnttyta yytnggncar     840
atgccnggnw snytngtnyt nathathath ytntgywsng tnttygcngt ngtnacnath     900
ytnytngtng gnttymgngt ngcnccngcn mgngayaarw snaaratggt ngayccnaar     960
aarggnacnw snytnwsnga yaarytnwsn ttywsnacnc ayacnytnyt nggncartty    1020
ttycarggnt ggggnacntg ggtngcnwsn tggccnytna cnathytngt nytnwsngtn    1080
athccngtng tngcnytngc ngcnggnytn gtnttyacng arytnacnac ngayccngtn    1140
garytntggw sngcnccnaa ywsncargcn mgnwsngara argcnttyca ygaycarcay    1200
ttyggnccnt tyttymgnac naaycargtn athytnacng cnccnaaymg nwsnwsntay    1260
mgntaygayw snytnytnyt nggnccnaar aayttywsng gnathytnga yytngayytn    1320
ytnytngary tnytngaryt ncargarmgn ytnmgncayy tncargtntg gwsnccngar    1380
gcncarmgna ayathwsnyt ncargayath tgytaygcnc cnytnaaycc ngayaayacn    1440
wsnytntayg aytgytgyat haaywsnytn ytncartayt tycaraayaa ymgnacnytn    1500
ytnytnytna cngcnaayca racnytnatg ggncaracnw sncargtnga ytggaargay    1560
cayttyytnt aytgygcnaa ygcnccnytn acnttyaarg ayggnacngc nytngcnytn    1620
wsntgyatgg cngaytaygg ngcnccngtn ttyccnttyy tngcnathgg nggntayaar    1680
ggnaargayt aywsngargc ngargcnytn athatgacnt tywsnytnaa yaaytayccn    1740
gcnggngayc cnmgnytngc ncargcnaar ytntgggarg argcnttyyt ngargaratg    1800
mgngcnttyc armgnmgnat ggcnggnatg ttycargtna cnttyacngc ngarmgnwsn    1860
ytngargayg arathaaymg nacnacngcn gargayytnc cnathttygc nacnwsntay    1920
athgtnatht tyytntayat hwsnytngcn ytnggnwsnt aywsnwsntg gwsnmgngtn    1980
atggtngayw snaargcnac nytnggnytn ggnggngtng cngtngtnyt nggngcngtn    2040
atggcngcna tgggnttytt ywsntayytn ggnathmgnw snwsnytngt nathytncar    2100
gtngtnccnt tyytngtnyt nwsngtnggn gcngayaaya thttyathtt ygtnytngar    2160
taycarmgny tnccnmgnmg nccnggngar ccnmgngarg tncayathgg nmgngcnytn    2220
```

```
ggnmgngtng cnccnwsnat gytnytntgy wsnytnwsng argcnathtg yttyttyytn    2280
ggngcnytna cnccnatgcc ngcngtnmgn acnttygcny tnacnwsngg nytngcngtn    2340
athytngayt tyytnytnca ratgwsngcn ttygtngcny tnytnwsnyt ngaywsnaar    2400
mgncargarg cnwsnmgnyt ngaygtntgy tgytgygtna arccncarga rytnccnccn    2460
ccnggncarg gngarggnyt nytnytnggn ttyttycara argcntaygc nccnttyytn    2520
ytncaytgga thacnmgngg ngtngtnytn ytnytnttyy tngcnytntt yggngtnwsn    2580
ytntaywsna tgtgycayat hwsngtnggn ytngaycarg arytngcnyt nccnaargay    2640
wsntayytny tngaytaytt yytnttyytn aaymgntayt tygargtngg ngcnccngtn    2700
tayttygtna cnacnytngg ntayaaytty wsnwsngarg cnggnatgaa ygcnathtgy    2760
wsnwsngcng gntgyaayaa yttywsntty acncaraara thcartaygc nacngartty    2820
ccngarcarw sntayytngc nathccngcn wsnwsntggg tngaygaytt yathgaytgg    2880
ytnacnccnw snwsntgytg ymgnytntay athwsnggnc cnaayaarga yaarttytgy    2940
ccnwsnacng tnaaywsnyt naaytgyytn aaraaytgya tgwsnathac natgggnwsn    3000
gtnmgnccnw sngtngarca rttycayaar tayytnccnt ggttyytnaa ygaymgnccn    3060
aayathaart gyccnaargg nggnytngcn gcntaywsna cnwsngtnaa yytnacnwsn    3120
gayggncarg tnytngcnws nmgnttyatg gcntaycaya arccnytnaa raaywsncar    3180
gaytayacng argcnytnmg ngcngcnmgn garytngcng cnaayathac ngcngayytn    3240
mgnaargtnc cnggnacnga yccngcntty gargtnttyc cntayacnat hacnaaygtn    3300
ttytaygarc artayytnac nathytnccn garggnytnt tyatgytnws nytntggytn    3360
gtnccnacnt tygcngtnws ntgyytnytn ytnggnytng ayytnmgnws nggnytnytn    3420
aayytnytnw snathgtnat gathytngtn gayacngtng gnttyatggc nytntgggay    3480
athwsntaya aygcngtnws nytnathaay ytngtnwsng cngtnggnat gwsngtngar    3540
ttygtnwsnc ayathacnmg nwsnttygcn athwsnacna arccnacntg gytngarmgn    3600
gcnaargarg cnacnathws natgggnwsn gcngtnttyg cnggngtngc natgacnaay    3660
ytnccnggna thytngtnyt nggnytngcn aargcncary tnathcarat httyttytty    3720
mgnytnaayy tnytnathac nytnytnggn ytnytncayg gnytngtntt yytnccngtn    3780
athytnwsnt aygtnggncc ngaygtnaay ccngcnytng cnytngarca raarmgngcn    3840
gargargcng tngcngcngt natggtngcn wsntgyccna aycayccnws nmgngtnwsn    3900
acngcngaya ayathtaygt naaycaywsn ttygarggnw snathaargg ngcnggngcn    3960
athwsnaayt tyytnccnaa yaayggnmgn cartty                             3996

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 52

His His His His His His
1               5
```